US007491827B2

(12) United States Patent
Dai et al.

(10) Patent No.: US 7,491,827 B2
(45) Date of Patent: *Feb. 17, 2009

(54) ARYL SULFONAMIDES USEFUL AS INHIBITORS OF CHEMOKINE RECEPTOR ACTIVITY

(75) Inventors: Mingshi Dai, Billerica, MA (US); Bing Guan, Needham, MA (US); Robert A. Bennett, Milford, MA (US); Douglas F. Burdi, Arlington, MA (US); Shomir Ghosh, Brookline, MA (US); Gang Li, Westborough, MA (US); Charles Minor, Kingston, MA (US); Tracy J. Jenkins, Belmont, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 654 days.

This patent is subject to a terminal disclaimer.

(21) Appl. No.: 10/891,362

(22) Filed: Jul. 14, 2004

(65) Prior Publication Data

US 2005/0085518 A1 Apr. 21, 2005

Related U.S. Application Data

(63) Continuation-in-part of application No. 10/744,236, filed on Dec. 23, 2003, now Pat. No. 7,329,755, which is a continuation-in-part of application No. 10/744,585, filed on Dec. 23, 2003, now Pat. No. 7,378,525.

(51) Int. Cl.
*C07D 211/06* (2006.01)
*C07D 215/38* (2006.01)
*C07D 413/00* (2006.01)
*C07D 239/02* (2006.01)

(52) U.S. Cl. .................. 546/206; 546/158; 546/169; 544/129; 544/298

(58) Field of Classification Search .............. 546/192, 546/195, 206, 158, 169; 544/129, 298
See application file for complete search history.

(56) References Cited

U.S. PATENT DOCUMENTS

| 5,281,626 | A |   | 1/1994  | Oinuma et al.              |
|-----------|---|---|---------|----------------------------|
| 5,354,904 | A | * | 10/1994 | Mayer et al. ........ 564/86 |
| 5,378,715 | A |   | 1/1995  | Stein et al.               |
| 5,530,118 | A |   | 6/1996  | Oinuma et al.              |
| 5,571,898 | A | * | 11/1996 | Schloesser et al. ..... 534/604 |
| 5,663,414 | A |   | 9/1997  | Oinuma et al.              |
| 5,994,398 | A | * | 11/1999 | John et al. ............ 514/485 |
| 6,262,112 | B1 |  | 7/2001  | Mittendorf et al.          |
| 6,417,181 | B1 |  | 7/2002  | Bender et al.              |
| 2003/0130287 | A1 | | 7/2003  | Ackermann et al.           |
| 2004/0209948 | A1 | | 10/2004 | Guan et al.                |
| 2004/0224978 | A1 | | 11/2004 | Dai et al.                 |

FOREIGN PATENT DOCUMENTS

DE    858 551    12/1952

| DE | 100 00 739 A1 | 7/2001 |
| DE | 100 53 796 A1 | 5/2002 |
| EP | 0 618 223 A2 | 10/1994 |
| EP | 1 038 868 A2 | 9/2000 |
| JP | 32002219 | 4/1957 |
| JP | 32005169 | 7/1957 |
| JP | 32008075 | 9/1957 |
| JP | 32008422 | 9/1957 |
| JP | 32009570 | 11/1957 |
| JP | 33007538 | 8/1958 |
| JP | 63017870 A2 | 1/1988 |
| JP | 63208042 A2 | 8/1988 |
| RU | 2051146 C1 | 12/1995 |
| RU | 2051147 C1 | 12/1995 |
| RU | 2053226 C1 | 1/1996 |
| TW | 402606 B | 8/2000 |
| WO | WO 99/29670 A2 | 6/1990 |
| WO | WO 91/12237 A1 | 8/1991 |
| WO | WO 95/26957 A1 | 10/1995 |
| WO | WO 96/40641 A1 | 12/1996 |
| WO | WO 97/20822 A1 | 6/1997 |
| WO | WO 99/37609 A1 | 7/1999 |
| WO | WO 99/62885 A1 | 12/1999 |
| WO | WO 01/07403 A1 | 2/2001 |
| WO | WO 01/58484 A2 | 8/2001 |
| WO | WO 02/072549 A1 | 9/2002 |
| WO | WO 2006/107252 A1 | 10/2006 |
| WO | WO 2006/107253 A1 | 10/2006 |

(Continued)

OTHER PUBLICATIONS

Campos, Kevin R., et al., "Asymmetric synthesis of a prostaglandin D2 receptor antagonist," *Journal of Organic Chemistry*, vol. 70 (2005) pp. 268-274.

(Continued)

*Primary Examiner*—D. Margaret Seaman

(57) ABSTRACT

The present invention provides compounds of general formula I:

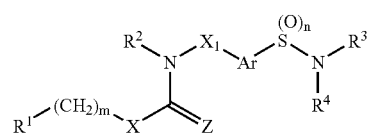

or a pharmaceutically acceptable salt thereof, wherein $R^1$, X, Z, $R^2$, $X_1$, Ar, n, $R^3$ and $R^4$ are defined generally and in subsets herein. Compounds of the invention are inhibitors of CCR8 and accordingly are useful for the treatment of a variety of inflammatory and allergic disorders.

32 Claims, No Drawings

FOREIGN PATENT DOCUMENTS

| | | |
|---|---|---|
| WO | WO 2006/107254 A1 | 10/2006 |
| WO | WO 2007/030061 A1 | 3/2007 |

OTHER PUBLICATIONS

Jenkins, Tracy J., et al., "Design, synthesis, and evaluation of naphthalene-sulfonamide antagonists of human CCR8," *Journal of Medicinal Chemistry,* vol. 50, No. 3 (2007) pp. 566-584.

Jin, Jian, et al., "Oxazolidinones as novel human CCR8 antagonists," *Bioorganic & Medicinal Chemistry Letters,* vol. 17 (2007) pp. 1722-1725.

Data slides (15 pages).

International Search Report dated Jun. 9, 2004 from corresponding PCT Application No. PCT/US03/41360.

Trushkin, et al., "ANSA-analysis. II. Aminonaphthalenesulfonamides as detectable groups for polysubstrate analysis of proteases," *Biokhimiya* (Moscow) 59(10): 1521-1534 (1994).

Nedospasov, A. A., et al., "The Synthesis of N(S)-alkoxyethyl-substituted aminoaphthalenesulfonamides by opening an aziridene ring," *Synlett* (8): 661-662 (1992).

Horstmann, H., et al., "Compounds With Schistosomicide Activity. 1. N4-(N-acyl-N-alkylglycyl)sulfanilamide," *European J. Of Medicinal Chem.,* 12(4): 387-392 (1977).

Database Chemcats 'Online!, Chemical Abstracts Service, Columbus, Ohio, US; XP002280062, Order No. 5242677, 5242739, 5242752 & "Chembridge Product List" Jan. 17, 2002, Chembridge Corporation, 16981 Via Tazon, Suite G, San Diego, CA 92127, USA.

Database Chemcats 'Online!, Chemical Abstracts Service, Columbus, Ohio, US; XP002280063, Order No. BAS 0371287 & Interchim Intermediates, Jul. 9, 2002, Interchim, 213 A Venue Kennedy, BP 1140, Montlucon, Cedex, 03103, France.

\* cited by examiner

ARYL SULFONAMIDES USEFUL AS INHIBITORS OF CHEMOKINE RECEPTOR ACTIVITY

PRIORITY INFORMATION

The present application claims priority under 35 U.S.C. §120, and is a continuation-in-part of U.S. Ser. No. 10/744,236, filed Dec. 23, 2003 now U.S. Pat. No. 7,329,755, entitled "CCR8 Inhibitors" and U.S. Ser. No. 10/744,585, filed Dec. 23, 2003 now U.S. Pat. No. 7,378,525, entitled "CCR8 Inhibitors". The entire teachings of each of the above-referenced applications are incorporated herein by reference.

BACKGROUND OF THE INVENTION

Chemoattractant cytokines or chemokines are a family of proinflammatory mediators that promote recruitment and activation of multiple lineages of leukocytes, such as T lymphocytes. Chemokines can be released by many kinds of tissue cells after activation. Release of chemokines at sites of inflammation mediates the ongoing migration of effector cells during chronic inflammation. The chemokines are related in primary structure and contain four conserved cysteines, which form disulfide bonds. The chemokine family includes the C—X—C chemokines (α-chemokines), and the C—C chemokines (β-chemokines), in which the first two conserved cysteines are separated by an intervening residue, or are adjacent, respectively (Baggiolini, M. and Dahinden, C. A., *Immunology Today*, 15:127-133 (1994)).

Chemokines exert their biological activity by binding to specific G-protein receptors, which then transduce signals important for the development and trafficking of specific leukocyte subsets (Baggiolini, et. al., *Nature* 15:365 (1994)). A number of chemokine receptors have been characterized and each are differentially expressed among leukocyte populations. Significantly, each chemokine binds specifically to a single receptor or to a small group of receptors. Thus, the recruitment and activation of specific classes of leukocytes or lymphocytes can be modulated by agents that selectively act at one chemokine receptor and/or block the activity of a specific chemokine. Agents which selectively block the activity of a specific chemokine or chemokine receptor are therefore useful in treating inflammatory diseases caused by aberrant activation of leukocytes or lymphocytes which express those chemokine receptors (or are activated by the chemokine) and minimally affect immune system cells which express other chemokine receptors.

CCR8 is a chemokine receptor (see WO 99/065561) whose expression is primarily restricted to Th2 cells (Zingoni et al., *J. Immunol.* 161:547 (1998) and D'Ambrosio et al., *J. Immunol.* 161:5111 (1998)). I-309 is a ligand for CCR8 and has shown to be chemotactic for Th2 cells in vitro (D'Ambrosio et al., *J. Immunol.* 161:5111 (1998). CCR8 is also involved in eosinophil recruitment (see WO 99/065561). Thus, antagonists for CCR8 are useful in treating disorders mediated by Th2 and eosinophil cells, e.g., asthma.

SUMMARY OF THE INVENTION

It has now been found that compounds of this invention, and pharmaceutically acceptable compositions thereof, are effective as inhibitors of CCR8 activity. For example, most of the compounds shown in the Tables in the Exemplification Section inhibit CCR8 activity with a $K_i$ less than 30 μM and many with a $K_i$ less than 1.0 μM. Based on this discovery, CCR8 inhibitors, pharmaceutical compositions comprising these inhibitors and methods of treating inflammatory and/or allergic diseases or disorders with these inhibitors are disclosed herein.

These compounds have the general formula I:

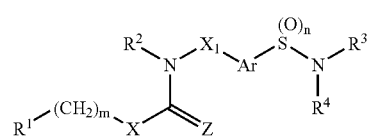

or a pharmaceutically acceptable salt thereof, wherein $R^1$, X, Z, $R^2$, $X_1$, Ar, n, $R^3$ and $R^4$ are defined generally and in subsets herein.

In another embodiment of the present invention a pharmaceutical composition is provided which comprises a pharmaceutically acceptable carrier or diluent and a compound as disclosed herein. The pharmaceutical compositions can be used in therapy, for example, to treat a subject with inflammatory and allergic disorders and diseases including, but not limited to asthma, atopic dermatitis, allergic rhinitis, systemic anaphylaxis or hypersensitivity responses, drug allergies (e.g., to penicillin, cephalosporins), insect sting allergies and dermatoses such as dermatitis, eczema, atopic dermatitis, allergic contact dermatitis, urticaria, rheumatoid arthritis, osteoarthritis, inflammatory bowel disease e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis, disorders of the skin [e.g., psoriasis, erythema, pruritis, and acne], multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease), stroke, cardiac ischemia, mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases, sarcoidosis, vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

In another embodiment, the present invention provides a method of inhibiting CCR8 activity in (a) a subject; or (b) a biological sample; which method comprises administering to said subject, or contacting said biological sample with compounds as described herein, or a pharmaceutically acceptable salt or composition thereof.

Another embodiment of the present invention method is a method of treating a subject with a CCR8 mediated condition or disease, e.g., a subject with asthma. The method comprises the step of administering to the subject an effective amount of a CCR8 inhibitor disclosed herein.

Yet another embodiment of the present invention is the use of one of the disclosed CCR8 inhibitors for the manufacture of a medicament for treating a subject with a CCR8 mediated condition or disease. The medicament comprises an effective amount of the CCR8 inhibitor.

DESCRIPTION OF THE INVENTION

1. General Description of Compounds of the Invention:

The present invention is directed to inhibitors of the chemokine receptor commonly referred to as "CCR8". CCR8 is expressed on monocytes and Th2 lymphocytes and in the brain, spleen and thymus. It is the receptor for the chemokine I-309, which is chemotactic for Th2 cells. I-309 has also shown to be involved in esinophil recruitment. Thus, the disclosed compounds can be used to inhibit CCR8 activity; to inhibit I-309 activity and to inhibit or treat (therapeutically or prophylactically) conditions mediated by CCR8 and/or I-309, including inflammatory disorders and allergic conditions. The disclosed compounds can also be advantageously used to inhibit conditions mediated by esinophils and by monocytes, T lymphocytes and other immune system cells which express CCR8, including inflammatory disorders and allergic conditions mediated by these cells.

The present invention relates to a compound of formula I:

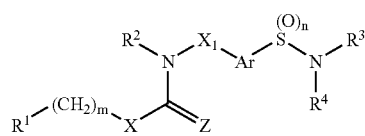

(I)

or a pharmaceutically acceptable salt thereof, wherein:

$X_1$ is a covalent bond, C=O or $CR^aR^b$, wherein $R^a$ and $R^b$ are each independently H or a $C_1$-$C_3$ alkyl group;

m is 0, 1, 2 or 3;

n is 1 or 2;

C=Z is C=O, $CH_2$, C=NH, C=S, or is absent, provided that:
i) when $X_1$ is a covalent bond then C=Z is other than $CH_2$;
ii) when C=Z is absent then X is a covalent bond; and
iii) when X is $NR^5$ and C=Z is C=O, then $R^4$ is other than a substituted or unsubstituted aliphatic group;

$R^1$ is: i) a substituted or unsubstituted aromatic or non-aromatic ring; or
ii) when X is $NR^5$, then for $NR^5(CH_2)_mR^1$, $R^5$ and $(CH_2)_mR^1$ taken together with the nitrogen atom to which they are bound, form a substituted or unsubstituted non-aromatic heterocyclic ring;

$R^2$ is —H or a $C_1$-$C_3$ alkyl group;

$R^3$ is —H;

$R^4$ is a substituted or unsubstituted group selected from an aliphatic group, aromatic ring, a non-aromatic ring, or a bridged bicyclic ring, wherein the aromatic ring, the non-aromatic ring, or the bridged bicyclic ring is bound directly to the nitrogen atom or through a $C_1$-$C_4$ alkyl group; or $R^3$ and $R^4$, taken together with the nitrogen atom to which they are bound, is a substituted or unsubstituted nitrogen-containing non-aromatic heterocyclic ring;

X is a covalent bond, O, or $NR^5$, wherein $R^5$ is —H or a $C_1$-$C_3$ alkyl group;

Ar is a substituted or unsubstituted bicyclic aromatic ring comprising a first six membered aromatic ring A fused to a second six membered aromatic ring or a five or six membered non-aromatic ring B, wherein Ar is optionally substituted at any substitutable carbon or nitrogen atom with p independent occurrences of $R^6$, wherein:

p is 0, 1, 2, or 3; and each occurrence of $R^6$ is independently halogen, —CN, $NO_2$, —$R^1$, or —$OR^7$, wherein each occurrence of $R^7$ is independently hydrogen or a substituted or unsubstituted $C_1$-$C_6$aliphatic group.

In some embodiments for compounds of formula (I):
a) $R^1$ or the non-aromatic heterocyclic ring formed from $NR^5(CH_2)_mR^1$, are each optionally substituted at one or more substitutable aromatic or non-aromatic carbon atoms with q occurrences of $R^8$, and at one or more substitutable nitrogen atoms with t occurrences of $R^9$ wherein:

q is 0, 1, 2, or 3, t is 0 or 1, provided that the sum of q and t is not greater than 4, each occurrence of $R^8$ is independently halogen, —$R^{10}$, —$OR^{10}$, —$SR^{10}$, —$NO_2$, —CN, —$N(R^{11})_2$, —$NR^{11}CO_2R^{10}$, —$NR^{11}C(O)R^{10}$, —$NR^{11}NR^{11}C(O)R^{10}$, —$N(R^{11})C(O)N(R^{11})_2$, —$NR^{11}NR^{11}C(O)N(R^{11})_2$, —$NR^{11}NR^{11}CO_2R^{10}$, —$C(O)C(O)R^{10}$, —$C(O)CH_2C(O)R^{10}$, —$CO_2R^{10}$, —$C(O)R^{10}$, —$C(O)N(R^{11})_2$, —$OC(O)R^{10}$, —$OC(O)N(R^{11})_2$, —$S(O)_2R^{10}$, —$SO_2N(R^{11})_2$, —$S(O)R^{10}$, —$NR^{11}SO_2N(R^{11})_2$, —$NR^{11}SO_2R^{10}$, —C(=S)N$(R^{11})_2$, —C(=NH)—N$(R^{11})_2$, -V-$R^{10}$, -V-OH, -V-O$R^{10}$, -V-SH, -V-S$R^{10}$, -V-$NO_2$, -V-CN, -V-N$(R^{11})_2$, -V-NR$^{11}$CO$_2$R$^{10}$, -V-NR$^{11}$C(O)R$^{10}$, -V-NR$^{11}$NR$^{11}$C(O)R$^{10}$, -V-N(R$^{11}$)C(O)N(R$^{11}$)$_2$, -V-NR$^{11}$NR$^{11}$C(O)N(R$^{11}$)$_2$, -V-R$^{11}$NR$^{11}$CO$_2$R$^{10}$, -V-C(O)C(O)R$^{10}$, -V-C(O)CH$_2$C(O)R$^{10}$, -V-CO$_2$R$^{10}$, -V-C(O)R$^{10}$, -V-C(O)N(R$^{10}$)$_2$, -V-OC(O)R$^{10}$, -V-OC(O)N(R$^{11}$)$_2$, -V-S(O)$_2$R$^{10}$, -V-SO$_2$N(R$^{11}$)$_2$, -V-S(O)R$^{10}$, —V-NR$^{11}$SO$_2$N(R$^{11}$)$_2$, -V-NR$^{11}$SO$_2$R$^{10}$, -V-C(=S)N(R$^{11}$)$_2$, or -V-C(=NH)—N(R$^{11}$)$_2$, or two occurrences of $R^8$, taken together with the atom(s) to which they are bound form a substituted or unsubstituted cycloaliphatic or substituted or unsubstituted non-aromatic heterocyclic ring, and when $R^1$ is a non-aromatic ring, any occurrence of $R^8$ is also selected from: =O, =S, =NNHR*, =NN(R*)$_2$, =NNHC(O)R*, =NNHCO$_2$(alkyl), =NNHSO$_2$(alkyl), or =NR*;

V is a substituted or unsubstituted $C_1$-$C_6$alkylene group;

each occurrence of $R^{10}$ is independently hydrogen or a substituted or unsubstituted aliphatic group, a substituted or unsubstituted cycloaliphatic ring, a substituted or unsubstituted non-aromatic heterocyclic ring, or a substituted or unsubstituted aromatic ring;

each occurrence of $R^{11}$ is independently —$R^{10}$, —$CO_2R^{10}$, —$SO_2R^{10}$ or —$C(O)R^{10}$, or two occurrences of $R^{11}$, taken together with the nitrogen atom to which they are bound form a substituted or unsubstituted non-aromatic heterocyclic ring;

each occurrence of R* is independently hydrogen, or a substituted or unsubstituted aliphatic group; and each occurrence of $R^9$ is independently —$R^{12}$, —C(O)$R^{12}$, —$CO_2R^{12}$, —$C(O)C(O)R^{12}$, —$C(O)CH_2C(O)R^{12}$, —$SO_2R^{12}$, —$SO_2N(R^{12})_2$, —C(=S)N(R$^{12}$)$_2$, —C(=NH)—N(R$^{12}$)$_2$, —C(O)—N(R$^{12}$)$_2$, —C(O)—CH[N(R$^{12}$)$_2$]R$^{12}$ or —C(O)—CH[OR$^{12}$]R$^{12}$;

wherein each occurrence of $R^{12}$ is independently hydrogen, a substituted or unsubstituted group selected from heteroaryl, aliphatic, cycloaliphatic, non-aromatic heterocyclic, phenyl or benzyl, or two occurrences of $R^{12}$, taken together with the nitrogen atom, form a substituted or unsubstituted non-aromatic heterocyclic ring, wherein each substitutable carbon atom of the heteroaryl, aliphatic, cycloaliphatic, non-aromatic heterocyclic, phenyl or benzyl group is optionally and independently substituted with amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl; and each substitutable nitrogen atom of the non-aromatic heterocyclic group is optionally and independently substituted with alkyl, alkoxycarbonyl, alkylcarbonyl, alkylaminocarbonyl or dialkylaminocarbonyl;

b) $R^4$ or the non-aromatic heterocyclic ring formed from $R^3$ and $R^4$, taken together with the nitrogen atom to which they are bound are each optionally and independently substituted at one or more substitutable aromatic or non-aromatic carbon atoms with s occurrences of $R^{13}$, and at one or more substitutable nitrogen atoms with r occurrences of $R^{14}$ wherein:

s is 0, 1, 2, or 3, r is 0 or 1, provided that the sum of s and r is not greater than 4, each occurrence of $R^{13}$ is independently halogen, $-R^{15}$, $-OR^{15}$, $-SR^{15}$, $-NO_2$, $-CN$, $-N(R^{16})_2$, $-NR^{16}CO_2R^{15}$, $-NR^{16}C(O)R^{15}$, $-NR^{16}NR^{16}C(O)R^{15}$, $-N(R^{15})C(O)N(R^{16})_2$, $-NR^{16}NR^{16}C(O)N(R^{16})_2$, $-NR^{16}NR^{16}CO_2R^{15}$, $-C(O)C(O)R^{15}$, $-C(O)CH_2C(O)R^{15}$, $-CO_2R^{15}$, $-C(O)R^{15}$, $-C(O)N(R^{16})_2$, $-OC(O)R^{15}$, $-OC(O)N(R^{16})_2$, $-S(O)_2R^{15}$, $-SO_2N(R^{16})_2$, $-S(O)R^{15}$, $-NR^{16}SO_2N(R^{16})_2$, $-NR^{16}SO_2R^{15}$, $-C(=S)N(R^{16})_2$, $-C(=NH)-N(R^{16})_2$, $-W-R^{15}$, $-W-OH$, $-W-OR^{15}$, $-W-SH$, $-W-SR$, $-W-NO_2$, $-W-CN$, $-W-N(R^{16})_2$, $-W-NR^{16}CO_2R^{15}$, $-W-NR^{16}C(O)R^{15}$, $-W-NR^{16}NR^{16}C(O)R^{15}$, $-W-N(R^{16})C(O)N(R^{16})_2$, $-W-NR^{16}NR^{16}C(O)N(R^{16})_2$, $-W-NR^{16}NR^{16}CO_2R^{15}$, $-W-C(O)C(O)R^{15}$, $-W-C(O)CH_2C(O)R^{15}$, $-W-CO_2R^{15}$, $-W-C(O)R^{15}$, $-W-C(O)N(R^{16})_2$, $-W-OC(O)R^{15}$, $-W-OC(O)N(R^{16})_2$, $-W-S(O)_2R^{15}$, $-W-SO_2N(R^{16})_2$, $-W-S(O)R^{15}$, $-W-NR^{16}SO_2N(R^{16})_2$, $-W-NR^{16}SO_2R^{15}$, $-W-C(=S)N(R^{16})_2$, or $-W-C(=NH)-N(R^{16})_2$, or two occurrences of $R^{13}$, taken together with the atom(s) to which they are bound form a substituted or unsubstituted cycloaliphatic or substituted or unsubstituted non-aromatic heterocyclic ring, and when $R^4$ is a non-aromatic ring, any occurrence of $R^{13}$ is also selected from:

=O, =S, =NNHR$^+$, =NN(R$^+$)$_2$, =NNHC(O)R$^+$, =NNHCO$_2$(alkyl), =NNHSO$_2$ (alkyl), or W is a substituted or unsubstituted $C_1$-$C_6$alkylene group;

each occurrence of $R^{15}$ is independently hydrogen or a substituted or unsubstituted aliphatic group, a substituted or unsubstituted cycloaliphatic, a substituted or unsubstituted non-aromatic heterocyclic ring, or a substituted or unsubstituted aromatic ring, each occurrence of $R^{16}$ is independently $R^{15}$, $-CO_2R^{15}$, $-SO_2R^{15}$ or $-C(O)R^{15}$, or two occurrences of $R^{16}$, taken together with the nitrogen atom, form a substituted or unsubstituted non-aromatic heterocyclic ring;

each occurrence of $R^+$ is independently hydrogen, or a substituted or unsubstituted aliphatic group; and each occurrence of $R^{14}$ is independently $-R^{17}$, -L-N(R$^{17}$)$_2$, $-C(O)R^{17}$, $-C(O)$-L-R$^{17}$, -L-C(O)R$^{17}$, $-CO_2R^{17}$, -L-CO$_2R^{17}$, $-C(O)C(O)R^{17}$, -L-C(O)C(O)R$^{17}$, $-C(O)$-L-C(O)R$^{17}$, $-SO_2R^{17}$, L-SO$_2R^{17}$, $-SO_2N(R^{17})_2$, -L-SO$_2N(R^{17})_2$, $-C(=S)N(R^{17})_2$, $-C(=NH)-N(R^{17})_2$, L-NR$^{17}SO_2R^{17}$, $-C(O)-N(R^{17})_2$, -L-C(O)-N(R$^{17}$)$_2$, $-C(O)$-L-N(R$^{17}$)$_2$ or $-C(O)$-L-OR$^{17}$;

wherein L is a substituted or unsubstituted $C_1$-$C_6$alkylene group; and each occurrence of $R^{17}$ is independently hydrogen, a substituted or unsubstituted group selected from an aliphatic, aromatic, cycloaliphatic, or non-aromatic heterocyclic group, or two occurrences of $R^{17}$, taken together with the nitrogen atom, form a substituted or unsubstituted non-aromatic heterocyclic ring.

In certain other embodiments, the present invention is directed to a compound represented by any of the structural formulas disclosed herein provided that one or more, or all of, the following apply:

a. when $R^1$ is a substituted aromatic group, then the aromatic group represented by $R^1$ is substituted with a group other than pyrazole;

b. when $R^4$ is a substituted phenyl, substituted benzyl or substituted phenethyl group, then the phenyl, benzyl or phenethyl group represented by $R^4$ is substituted with a group other than $-NO_2$, $-N(R^{16})_2$, $-CON(R^{16})_2$, $-NR^{16}COR^{15}$, or an aliphatic group substituted with $-NO_2$, $-N(R^{16})_2$, $-CON(R^{16})_2$, $-NR^{16}COR^{15}$, wherein $R^{15}$ and $R^{16}$ are each independently H, an aliphatic group, a substituted aliphatic group, an aryl group, a substituted aryl group, a non-aromatic ring or a substituted non-aromatic ring;

c. compounds disclosed herein are other than:
  i) N-[4-[[(4-methoxyphenyl)amino]sulfonyl]-1-naphthalenyl]-benzamide,
  ii) N-[4-[(2-propenylamino)sulfonyl]-1-naphthalenyl]-benzamide,
  iii) N-[4-(4-morpholinylsulfonyl)-1-naphthalenyl]-benzamide, or
  iv) N-[4-(1-piperidinylsulfonyl)-1-naphthalenyl]-benzamide.

In still other embodiments, the present invention is directed to a compound represented by any of the structural formulas disclosed herein provided that one or more, or all of, the following apply:

a. when Ar is naphthyl, $X_1$ is NH, C=Z is C=O, X is NH, m is 0, and $R^1$ is a phenyl group, then the phenyl group represented by $R^1$ is substituted with a group other than substituted or unsubstituted pyrazole;

b. when Ar is naphthyl, $R^4$ is a substituted phenyl group, then the phenyl group represented by $R^4$ is substituted with a group other than $-NR^{16}COR^{15}$, wherein $R^{15}$ and $R^{16}$ are each independently H, an aliphatic group, or a substituted aliphatic group;

c. when Ar is naphthyl, $X_1$ is NH, C=Z is C=O, X is O, m is 1, and $R^1$ is unsubstituted phenyl, then $R^3$ and $R^4$, taken together with the nitrogen atom to which they are bound form a group other than unsubstituted piperidinyl or unsubstituted azetidinyl;

d. when Ar is naphthyl, $X_1$ is NH, C=Z is C=S, X is NH, m is 0, $R^1$ is unsubstituted phenyl, and $R^3$ is hydrogen, then $R^4$ is a group other than substituted or unsubstituted isoxazolyl;

e. when Ar is naphthyl, $X_1$ is N—CH$_3$, C=Z is C=O, X is O, m is 1, $R^1$ is unsubstituted phenyl, and $R^3$ is hydrogen, then $R^4$ is a group other than substituted or unsubstituted pyrazinyl; and f. when R is a non-aromatic ring, then the non-aromatic ring is substituted with a group other than —COOH, —SO$_2$NH$_2$, or —SO$_3$H; and g. compounds disclosed herein are other than:

i) N-[4-[[(4-methoxyphenyl)amino]sulfonyl]-1-naphthalenyl]-benzamide, ii) N-[4-[(2-propenylamino)sulfonyl]-1-naphthalenyl]-benzamide, iii) N-[4-(4-morpholinylsulfonyl)-1-naphthalenyl]-benzamide, or iv) N-[4-(1-piperidinylsulfonyl)-1-naphthalenyl]-benzamide.

In yet other embodiments, R$^4$ is a group other than a substituted or unsubstituted aliphatic group.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. The terms "alkenyl" and "alkynyl" used alone or as part of a larger moiety shall include both straight and branched chains containing two to eight carbon atoms and one or more double and/or triple bonds, respectively. The terms "alkyl", "alkoxy", "hydroxyalkyl", "alkoxyalkylene", and "alkoxycarbonyl" used alone or as part of larger moiety includes both straight and branched saturated chains containing one to eight carbon atoms. In some embodiments, "cycloaliphatic" (or "carbocycle" or "cycloalkyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "haloalkyl" means an alkyl group substituted with one or more halogens.

The term "non-aromatic bridged bicyclic group", used alone or as part of a larger moiety, shall include bicyclic ring systems comprising from seven to fifteen ring atoms in which at least three adjacent ring atoms in the bicyclic ring system are shared by both rings. The ring systems can be carbocyclic, in which all ring atoms are carbon, or heterocyclic ("bridged bicyclic non-aromatic heterocyclic groups"), in which one or more ring carbons are replaced with nitrogen, oxygen, sulfur and the like. Examples are shown below:

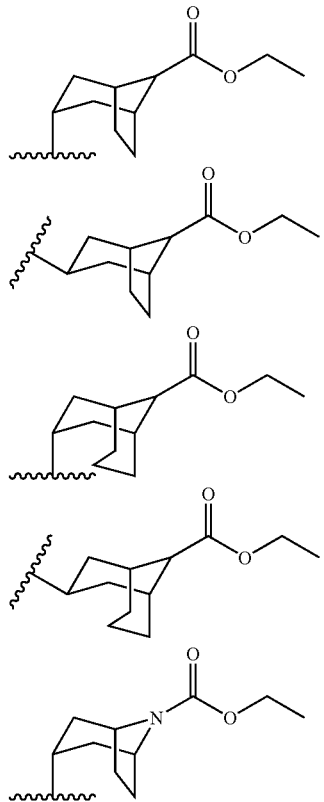

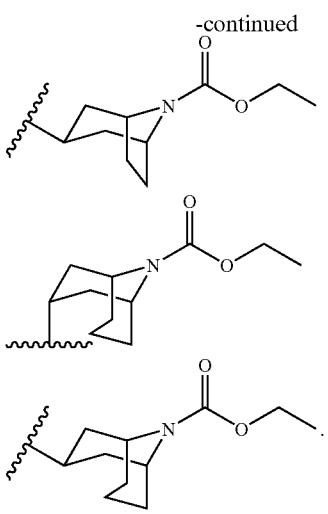

Suitable substituents for substitutable carbon atoms of a non-aromatic bridged bicyclic group are as described generally and in specific embodiments herein for non-aromatic heterocyclic groups. Suitable substituents for substitutable nitrogen atoms of a non-aromatic bridged bicyclic group are as described generally and in specific embodiments herein for non-aromatic heterocyclic groups.

"Alkoxy" means (alkyl)-O—; "alkoxyalkylene" means (alkyl)-O-(alkylene) such as methoxymethylene ($CH_3OCH_2$); "hydroxyalkyl" means hydroxy substituted alkyl group; "alkoxy carbonyl means a carbonyl substituted with a carbonyl as in (alkyl)-O—C(O)—; and "aralkyl" mean alkyl substituted with an aromatic group. A "$C_1$-$C_4$ aralkyl group", for example, has a $C_1$-$C_4$ alkyl group substituted with an aromatic group.

The term "heteroatom" means nitrogen, oxygen, or sulfur and includes any oxidized form of nitrogen and sulfur, and the quatemized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aromatic group" used alone or as part of a larger moiety as in "aralkyl", "aralkoxy", or "aryloxyalkyl", includes carbocyclic aromatic ring groups and heteroaryl rings groups. The term "aromatic group" may be used interchangeably with the terms "aryl", "aryl ring" or "aromatic ring".

Carbocyclic aromatic ring groups have only carbon ring atoms and include monocyclic aromatic rings such as phenyl and fused polycyclic aromatic ring systems in which two or more carbocyclic aromatic rings are fused to one another. Examples of fused polycyclic aromatic carbocyclic aromatic ring groups include, but are not limited to, 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (aliphatic or heterocyclic), including, but not limited to, indanyl, phthalimidyl, naphthimidyl, phenantriidinyl, or tetrahydronaphthyl, where the radical or point of attachment is on the aromatic ring. Additional carbocyclic aromatic ring groups are described herein and suitable substituents are described generally and in specific embodiments, herein.

The term "heteroaryl", "heteroaromatic" or "heteroaryl ring", used alone or as part of a larger moiety as in "heteroaralkyl" or "heteroarylalkoxy", refers to heteroaromatic ring groups having five to fourteen members, including monocyclic heteraromatic rings and polycyclic aromatic rings in which a monocyclic aromatic ring is fused to one or more other carbocyclic or heteroaromatic aromatic rings. Examples of heteroaryl groups include, but are not limited to, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, quinolinyl, quinazolinyl, benzotriazolyl, benzothiazolyl, benzooxazolyl, benzimidazolyl, isoquinolinyl, indolyl, isoindolyl, acridinyl, or benzoisazolyl. Also included within the scope of the term "heteroaryl", as it is used herein, is a group in which a heteroaryl ring is fused to one or more cycloaliphatic or non-aromatic heterocyclic groups where the radical or point of attachment is on the heteroaromatic ring. Examples include, but are not limited to tetrahydroquinolinyl, tetrahydroisoquinolinyl, and pyrido [3, 4-d] pyrimidinyl. Additional heteroaryl ring groups are described herein and suitable substituents are described generally and in specific embodiments, herein.

The term "non-aromatic ring", used alone or as part of a larger moiety, includes non-aromatic heterocyclic groups and cycloaliphatic groups.

The term "non-aromatic heterocyclic ring", used alone or as part of a larger moiety as in "hetercyclylalkyl", refers to non-aromatic ring systems typically having five to fourteen members, preferably five to ten, in which one or more ring carbons, preferably one to four, are each replaced by a heteroatom such as N, O, or S. Examples of non-aromatic heterocyclic rings include, but are not limited to 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl. Additional non-aromatic heterocyclic ring groups are described herein and suitable substituents are described generally and in specific embodiments, herein.

The term "alkylene chain" refers to a straight or branched substituted or unsubstituted carbon chain that may be fully saturated or have one or more units of unsaturation and has two points of attachment to the rest of the molecule.

As detailed above, in some embodiments, two independent occurrences of a particular substituent (shown as R° directly below for a general description) taken together with the atom (s) to which they are bound to form a substituted or unsubstituted non-aromatic heterocyclic group.

Exemplary rings that are formed when two independent occurrences of R° (or any other variable similarly defined herein), are taken together with the atom(s) to which each variable is bound include, but are not limited to the following: a) two independent occurrences of R° (or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or any other variable similarly defined herein) that are bound to different atoms and are taken together with both of those atoms to form a fused or bridged ring. For example, where a phenyl group is substituted with two occurrences

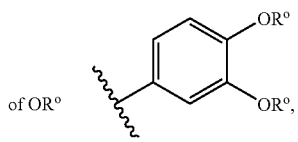

these two occurrences of R° are taken together with the oxygen atoms to which they are bound to form a fused 6-membered oxygen containing ring:

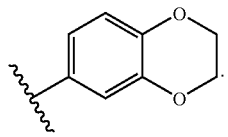

It will be appreciated that a variety of other rings can be formed when two independent occurrences of R° (or any other variable similarly defined herein) are taken together with the atom(s) to which each variable is bound and that the examples detailed above are not intended to be limiting.

An "electron donating group" is a substituent which results in a phenyl ring that has more electron density when the group is present than when it is absent. Electron donating groups have a Hammet sigma value greater than one (see, for example, C. Hansch, A. Leo and D. Hoeckman, "Exploring QSAR Hydrophobic, Electronic and Steric Constants", American Chemical Society (1995), pages 217-32). Examples of electron donating groups include alkoxy groups, alkyl groups, amine, alkylamine and dialkylamine.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Some of the disclosed compounds contain one or more chiral centers. The presence of chiral centers in a molecule gives rise to stereoisomers. For example, a pair of optical isomers, referred to as "enantiomers", exist for every chiral center in a molecule; and a pair of diastereomers exist for every chiral center in a compound having two or more chiral centers.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diastereomeric pairs, mixtures of diasteromers, mistures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95% 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

In certain instances compounds of the present invention may associated in isolated form with solvent or water, as in a "solvate" or "hydrate". References to the disclosed compounds or structural formulas depicting the disclosed compounds are meant to include such solvates and hydrates.

In general, suitable values for the substituents described in more detail herein that form part(s) of the compounds are those which do not significantly reduce the compounds ability to antagonize the activity of CCR8 and/or which do not significantly increase toxicity to the subject.

3. Description of Exemplary Compounds:

As described generally above for compounds of Formula I Ar is an optionally substituted bicyclic aromatic group comprising a first six membered aromatic group A fused to a second six membered aromatic group or a five or six membered non-aromatic ring B, wherein Ar is optionally additionally substituted with p occurrences of $R^6$, wherein: p is 0, 1, 2, or 3; and each occurrence of $R^6$ is independently halogen, —CN, $NO_2$, —$R^7$, or —$OR^7$, wherein each occurrence of $R^7$ is independently hydrogen or an optionally substituted $C_1$-$C_6$ aliphatic group.

In certain embodiments, Ar in Structural Formula (I) is a group selected from:

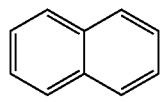

A

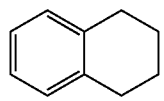

B

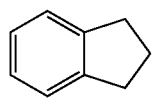

C

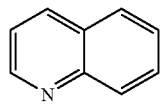

D

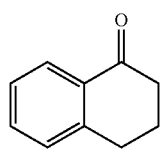

E

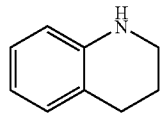

F

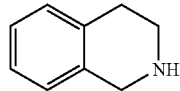

G

In certain other embodiments, Ar in Structural Formula (I) is a naphthyl (A) or tetrahydronaphthyl (B) group. It will be appreciated that the invention is not limited to any particular substitution pattern on the groups represented by Ar. For example, compounds of the invention may have 1,3-, 1,4-, 1,5-, 1,6- and 1,7-substitution patterns, or, in the case of certain heteroaromatic groups (e.g., quinolinyl as depicted above or quinazolinyl), compounds of the invention may have 3,8-, 4,8-, 5,8-, or 6,8- or other relevant substitution patterns.

In certain exemplary embodiments, compounds have substitution patterns as shown by formulas A-i, A-ii, B-i, B-ii, C-i, C-ii, D-i, D-ii, E-I, F-I, and G-I depicted below:

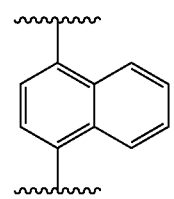

A-i

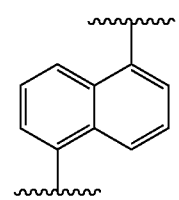

A-ii

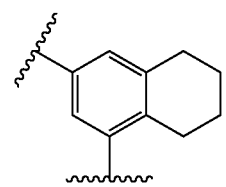

B-i

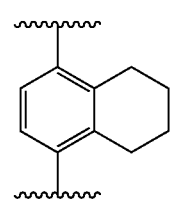

B-ii

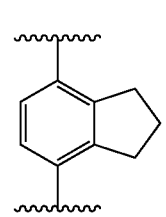

C-i

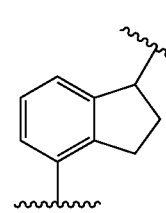

C-ii

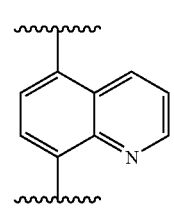

D-i

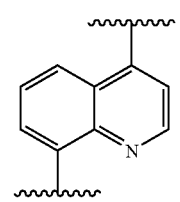

D-ii

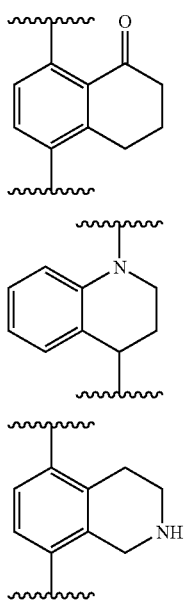

E-i

F-i or

G-i

As described generally above, Ar is optionally additionally substituted at any substitutable carbon or nitrogen atom with p occurrences of $R^6$, wherein: p is 0, 1, 2, or 3; and each occurrence of $R^6$ is independently halogen, —CN, —NO$_2$, —$R^7$, or —O$R^7$, wherein each occurrence of $R^7$ is independently hydrogen or an optionally substituted $C_1$-$C_6$aliphatic group. In some embodiments, each occurrence of $R^6$ is independently alkyl, haloalkyl, cyano, nitro, hydroxy, haloalkoxy, or alkoxy. In certain embodiments, p is 0, 1, or 2, and $R^6$, when present, is halogen, $C_1$-$C_3$alkyl, or —O($C_1$-$C_3$alkyl), wherein the $C_1$-$C_3$alkyl group is optionally substituted with up to three halogen atoms. In certain other embodiments, p is 0 or 1, and $R^6$, when present is —Cl, —F, —Br, —CH$_3$, —CH$_2$CH$_3$, —CF$_3$, —OCH$_3$, or —OCF$_3$. In other embodiments, p is 0. In still other embodiments, when Ar is substituted at a substitutable nitrogen atom (e.g., the nitrogen atom in G-i above), —$R^6$ is —$R^7$, where $R^7$ is $C_1$-$C_4$alkyl.

As described generally above, $X_1$ is a covalent bond, C=O or CR$^a$R$^b$, wherein R$^a$ and R$^b$ are each independently H or a $C_1$-$C_3$ alkyl group. In other embodiments, $X_1$ is —CH$_2$—, CHR$^a$, or CR$^a$R$^b$, wherein R$^a$ and R$^b$ are each independently $C_1$-$C_3$alkyl. In still other embodiments, $X_1$ is a covalent bond. In yet other embodiments, $X_1$ is —CH$_2$—.

As described generally above, X is a covalent bond, O, or NR$^5$, wherein R$^5$ is —H or a $C_1$-$C_3$ alkyl group. In certain exemplary embodiments, X is a covalent bond.

As described generally above, C=Z is C=O, CH$_2$, C=NH, C=S, or is absent, provided that: i) when $X_1$ is a covalent bond then C=Z is other than CH$_2$; ii) when C=Z is absent then X is a covalent bond; and iii) when X is NR$^5$ and C=Z is C=O, then $R^4$ is other than a substituted or unsubstituted aliphatic group. In certain exemplary embodiments, C=Z is C=O, C=S, or —CH$_2$—. In other embodiments C=Z is C=O. In still other embodiments, C=Z is CH$_2$.

In still other embodiments, X—(C=Z)—NH group is replaced with a carbamate (—O—C(O)NH—), a thiocarbamate (—O—C(S)NH—), a urethane (NH—C(O)—NH—) or a thiourethane group (NH—C(S)—NH—).

As described generally above, m is 0, 1, 2, or 3 and n is 1 or 2. In certain exemplary embodiments, m is 0 or 1, and n is 2. In still other embodiments, m is 0 and n is 2.

In yet other embodiments, for compounds of the invention described generally above and in subsets described herein, $X_1$ is a bond, C=Z is C=O, X is a bond, m is 0 or 1, and n is 2. In still other embodiments, $X_1$ is CR$^a$R$^b$, C=Z is absent or is C=O, X is a bond, m is 0 or 1, and n is 2. In yet other embodiments, $X_1$ is C=O, C=Z is absent, X is a bond, m is 0 and n is 2.

As described generally above, $R^1$ is: i) a substituted or unsubstituted aromatic or non-aromatic ring; or ii) when X is NR$^5$, then for NR$^5$(CH$_2$)$_m$R$^1$, R$^5$ and (CH$_2$)$_m$R$^1$ taken together with the nitrogen atom to which they are bound, form a substituted or unsubstituted non-aromatic heterocyclic ring. In certain exemplary embodiments, $R^1$ is a ring selected from:

i

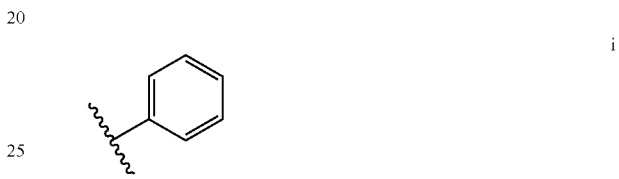

ii

iii iv

v

vi

vii

viii ix

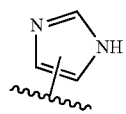 x
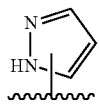 xi
 xii
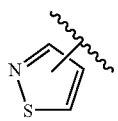 xiii
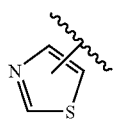 xiv
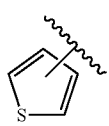 xv
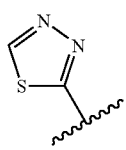 xvi
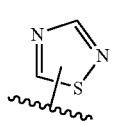 xvii
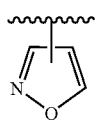 xviii
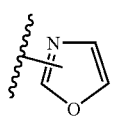 xix
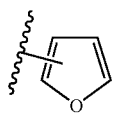 xx
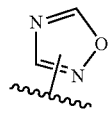 xxi
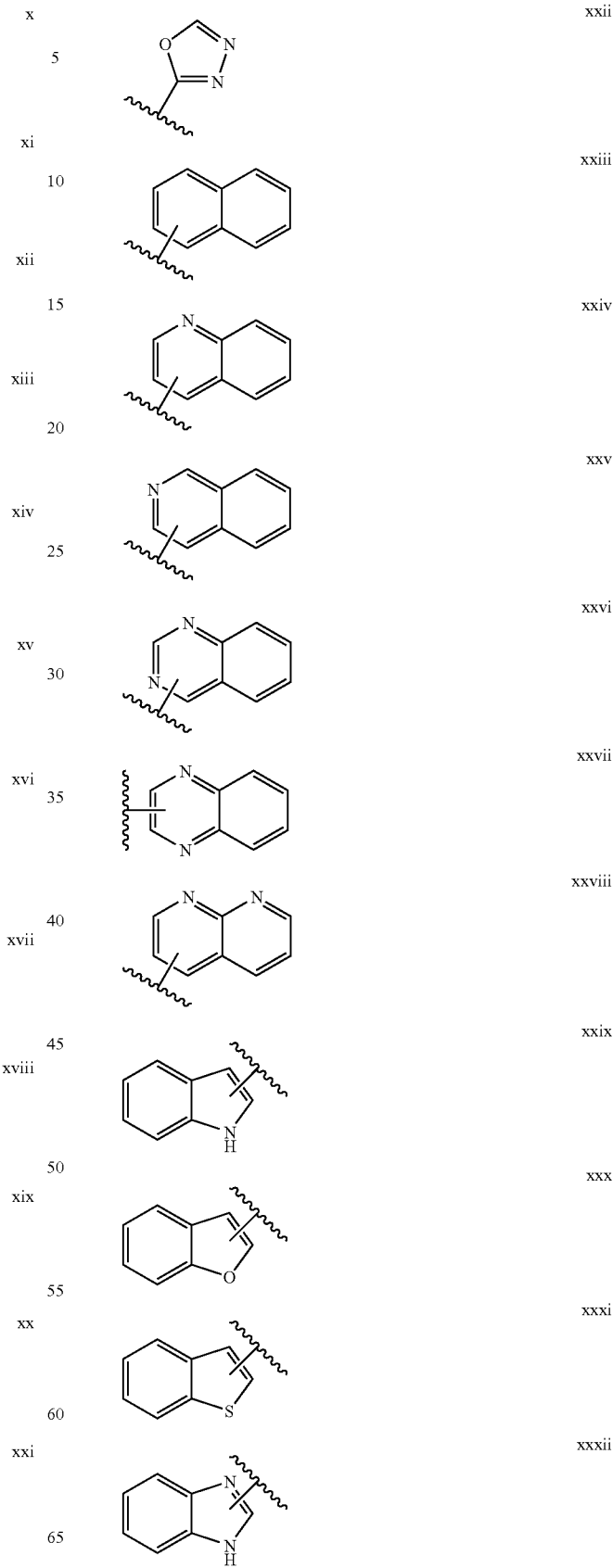

-continued xxxiii 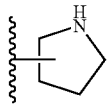

xxxiv 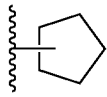

xxxv 

xxxvi 

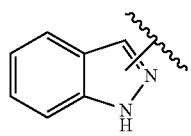 xxxiii

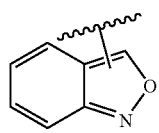 xxxiv

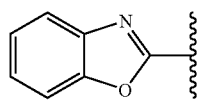 xxxv

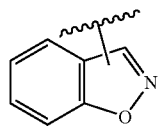 xxxvi

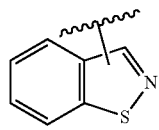 xxxvii

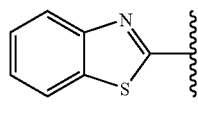 xxxviii

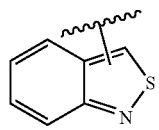 xxxix

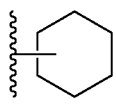 xL

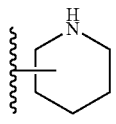 xLi

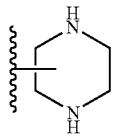 xLii

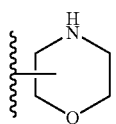 xLiii

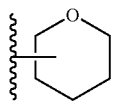 xLiv xLv 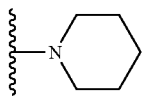

xLvi 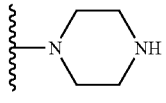

xLvii 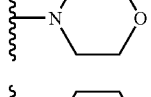

xLviii 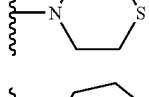

In some embodiments, $R^1$ is a substituted or unsubstituted ring selected from phenyl (i), pyridyl (ii), imidazolyl (x), thiophene (xv), furyl (xx), benzthiophene (xxxi), cyclohexyl (xL), piperidinyl (xLi), tetrahydropyran (xLiv), cyclopentyl (xLvi), cyclobutyl (xLvii), or cyclopropyl (xLviii). In still other embodiments, $R^1$ is a substituted or unsubstituted ring selected from phenyl (i) or pyridyl (ii). In yet other embodiments, $R^1$ is substituted or unsubstituted phenyl (i).

In other embodiments, $R^5$ and $-(CH_2)_m R^1$ are taken together with the nitrogen atom to which they are bound and form a substituted or unsubstituted non-aromatic heterocyclic group. In certain embodiments, the non-aromatic heterocyclic group is selected from:

xLix 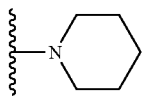

L 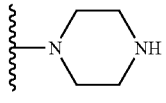

Li 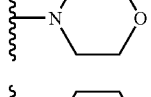

Lii 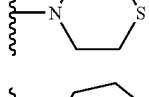

Liii 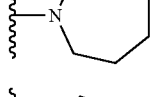

Liv 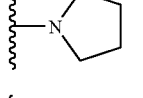

Lv 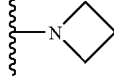

Lvi

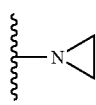

As described generally above, R¹ or the non-aromatic heterocyclic group formed from NR⁵(CH₂)ₘR¹, are each optionally substituted at one or more substitutable aromatic or non-aromatic carbon atoms with q occurrences of R⁸, and at one or more substitutable nitrogen atoms with t occurrences of R⁹. In certain embodiments, q is 0, 1, or 2 and each occurrence of R⁸, when present is halogen, —CN, —NO₂, —C₁-C₆alkyl, -OH, -O(C₁-C₆alkyl), —NH₂, —NH(C₁-C₆alkyl), —N(C₁-C₆alkyl)₂, —SH, —S(C₁-C₆alkyl), wherein C₁-C₆alkyl is substituted or unsubstituted. In certain other embodiments, q is 0, 1, or 2 and each occurrence of R⁸, when present is —Cl, —F, —Br, —CH₃, —CH₂CH₃, —CH₂CH₂CH₃, —OCH₃, —OCH₂CH₃, —OCH₂CH₂CH₃, —CF₃, —OCF₃, —NO₂, or —CN. In still other embodiments, q is 0. In yet other embodiments, when R¹ is phenyl, q is 1 and R⁸ is substituted in the ortho position of the phenyl ring. In still other embodiments, when R¹ is phenyl, q is 1 and R⁸ is C₁-C₃alkyl, halogen, or —CN and is substituted in the ortho position of the phenyl ring. In yet other embodiments, when R¹ is phenyl, q is 1 and R⁸ is substituted in the meta position of the phenyl ring. In still other embodiments, when R¹ is phenyl, q is 1 and R⁸ is C₁-C₃alkyl, halogen, or —CN and is substituted in the meta position of the phenyl ring. In yet other embodiments, when R¹ is phenyl, q is 2 and R⁸ is disubstituted in the ortho and meta positions of the phenyl ring. In still other embodiments, when R¹ is phenyl, q is 2 and R⁸ is C₁-C₃alkyl, halogen, or —CN and is disubstituted in the ortho and meta positions of the phenyl ring.

In still other embodiments, R¹ is preferably a substituted or unsubstituted cyclohexyl group, a substituted or substituted phenyl group, a substituted or substituted benzyl group, a substituted or substituted pyridyl group or a substituted or a substituted —CH₂—(pyridyl) group, and more preferably is an unsubstituted phenyl group, an unsubstituted benzyl group or a phenyl or benzyl group substituted with an electron donating group. In certain other embodiments, R¹ is a phenyl group substituted in the ortho or meta position with an electron donating group.

As described generally above, R⁴ is a substituted or unsubstituted group selected from an aliphatic group, an aromatic ring, a non-aromatic ring, or a bridged bicyclic ring, wherein the aromatic ring, the non-aromatic ring, or the bridged bicyclic ring is bound directly to the nitrogen atom or through a C₁-C₄alkyl group; or R³ and R⁴, taken together with the nitrogen atom to which they are bound, is a substituted or unsubstituted nitrogen-containing non-aromatic heterocyclic ring. In certain embodiments, R³ is hydrogen, and R⁴ is a substituted or unsubstituted ring selected from:

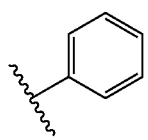

a

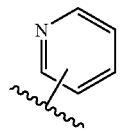

b

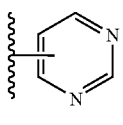

c

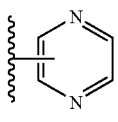

d

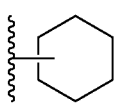

e

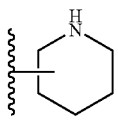

f

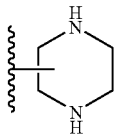

g

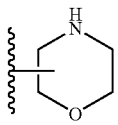

h

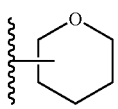

i

j

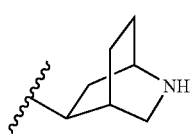

k

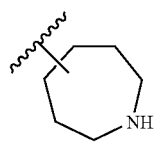

l

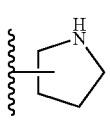

m

-continued

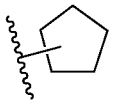
n wherein the ring is bound directly to the nitrogen atom or through a $C_1$-$C_4$ alkyl group.

Accordingly, in certain embodiments, $R^4$ is a substituted or unsubstituted ring selected from: phenyl, —(CH$_2$)phenyl, cyclohexyl, —(CH$_2$)cyclohexyl, —(CH$_2$)$_2$cyclohexyl, —(CH$_2$)$_3$cyclohexyl, cyclopentyl, —(CH$_2$)cyclopentyl, —(CH$_2$)$_2$cyclopentyl, —(CH$_2$)$_3$cyclopentyl, pyridyl, —(CH$_2$)pyridyl, —(CH$_2$)$_2$pyridyl, —(CH$_2$)$_3$pyridyl, tetrahydrofuryl, —(CH$_2$)tetrahydrofuryl, —(CH$_2$)$_2$tetrahydrofuryl, —(CH$_2$)$_3$tetrahydrofuryl, piperidinyl, —(CH$_2$)piperidinyl, —(CH$_2$)$_2$piperidinyl, —(CH$_2$)$_3$piperidinyl, aza-bicyclo[3.2.1]octane, morpholinyl, —(CH$_2$)morpholinyl, —(CH$_2$)$_2$ morpholinyl, —(CH$_2$)$_3$ morpholinyl, piperazinyl, —(CH$_2$)piperazinyl, —(CH$_2$)$_2$piperazinyl, —(CH$_2$)$_3$piperazinyl, pyrrolidinyl, —(CH$_2$)pyrrolidinyl, —(CH$_2$)$_2$pyrrolidinyl, or —(CH$_2$)$_3$pyrrolidinyl. In still other embodiments, $R^4$ is a substituted or unsubstituted ring selected from: phenyl, benzyl, cyclohexyl, —CH$_2$cyclohexyl, cyclopentyl, —CH$_2$pyrid-4-yl, pyrid-4-yl, pyrid-3-yl, pyrid-2-yl, piperidin-3-yl, piperidin-4-yl, —CH$_2$piperidin-4-yl, aza-bicyclo[3.2.1]octane, or —(CH$_2$)$_3$-morpholinyl. In other embodiments, $R^3$ is hydrogen, and $R^4$ is a ring selected from:

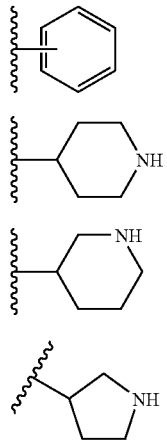

In still other embodiments, $R^3$ is hydrogen, and $R^4$ is a ring selected from:

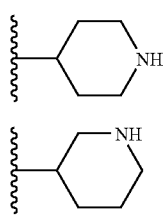

In still other embodiments, $R^3$ is hydrogen, and $R^4$ is piperidin-4-yl (f-i).

In other embodiments, $R^3$ and $R^4$, taken together with the nitrogen atom to which they are bound, is a substituted or unsubstituted nitrogen-containing non-aromatic heterocyclic group. In certain embodiments, the non-aromatic heterocyclic group is selected from:

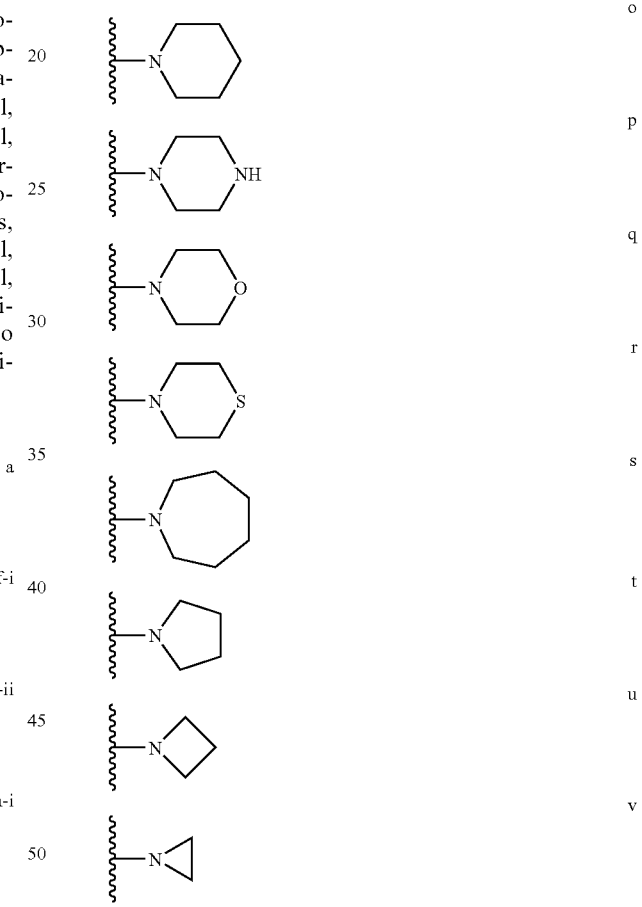

In some embodiments, the non-aromatic heterocyclic group is piperazinyl (p).

As described generally above, $R^4$ or the non-aromatic heterocyclic ring formed from $R^3$ and $R^4$, taken together with the nitrogen atom to which they are bound are each optionally and independently substituted at one or more substitutable aromatic or non-aromatic carbon atoms with s occurrences of $R^{13}$, and at one or more substitutable nitrogen atoms with r occurrences of $R^{14}$.

In certain embodiments, s is 0, 1, or 2, and each occurrence of $R^{13}$ is halogen, —$R^{15}$, —COR$^{15}$, —CO$_2$H, or —CO$_2$R$^{15}$, wherein $R^{15}$ is phenyl or a $C_1$-$C_4$alkyl group optionally substituted with halogen, —OH, O($C_{1-3}$alkyl), —SH, —S($C_1$-

$C_3$alkyl), $NH_2$, $NH(C_1$-$C_3$alkyl), or —$N(C_1$-$C_3$alkyl)$_2$. In certain exemplary embodiments, s is 0, 1, or 2, and each occurrence of $R^{13}$ is —F, —Cl, —Br, phenyl, —$CH_3$, —$OCH_3$, —$CH_2CH_3$, —$CH(CH_3)_2$, —$CH_2CH(CH_3)_2$, —$OCH_2CH_3$, —$CO_2H$, $CO_2CH_3$, —$CO_2CH_2CH_3$, —OH, —$CH_2OH$, —$CH_2CH_2OH$, or —$CONH_2$, or two occurrences of $R^{13}$, taken together, form a fused 5- or 6-membered cycloaliphatic ring.

In some embodiments, when $R^4$ is a phenyl group, a substituted phenyl group, a benzyl group, or a substituted benzyl group, suitable substituents for phenyl and benzyl groups are preferably electron donating groups. In certain embodiments, these electron donating groups are methoxy, ethoxy, iso-propoxy, methyl, ethyl, propyl, —$NH_2$, —$NHCH_3$, —$N(CH_3)_2$, —$NHCH_2CH_3$, —$N(CH_2CH_3)_2$, —$N(CH_3)(CH_2CH_3)$, —$NH(CH_2CH_2CH_3)$, —$N(CH_2CH_2CH_3)_2$, —$N(CH_3)(CH_2CH_2CH_3)$ or —$N(CH_2CH_3)(CH_2CH_2CH_3)$.

In yet other embodiments, when $R^4$ is a piperidin-4-yl, piperidin-3-yl, or pyrrolidin-3-yl ring that is substituted at one or more substitutable carbon atoms with 1 or 2 occurrences of $R^{13}$, then $R^{13}$ is —$CH_3$, —$CH_2CH_3$, —$CH_2CH(CH_3)_2$, —$CH(CH_3)_2$, $CO_2CH_2CH_3$, —$CH_2OH$, or $CONH_2$ or two occurrences of $R^{13}$, taken together, form a fused 5- or 6-membered cycloaliphatic ring.

In yet other embodiments, $R^4$ is a piperidinyl-4-yl group substituted at one or more carbon atoms and has one of the following structures:

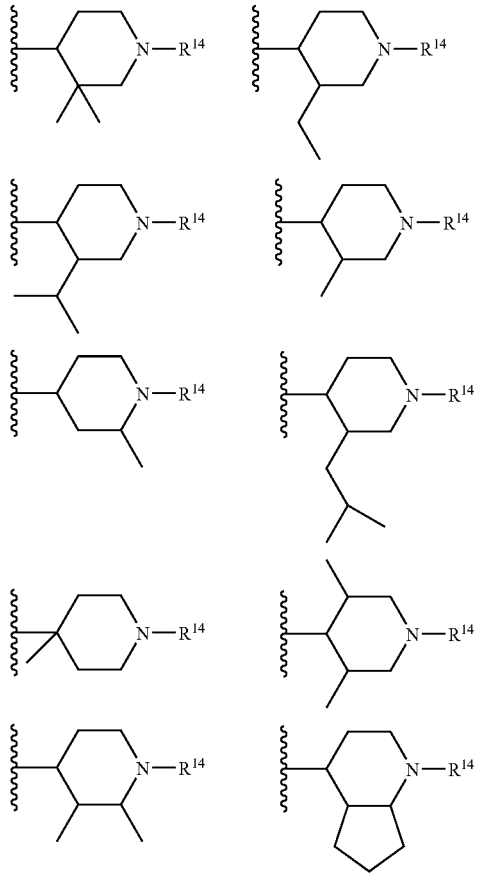

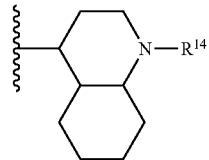

In still other embodiments, $R^4$ is a piperidinyl-4-yl group substituted at one or more carbon atoms and has one of the following structures:

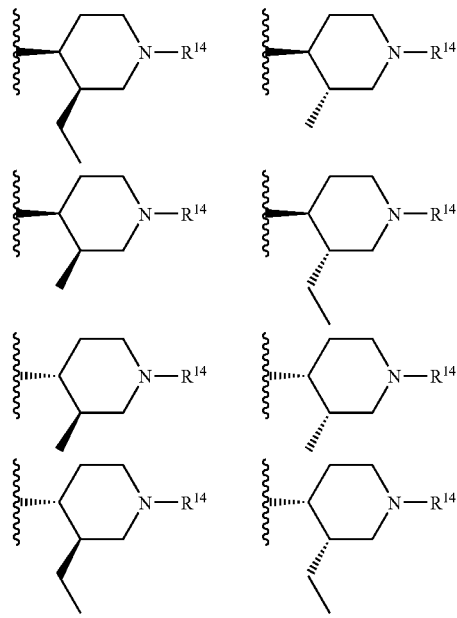

In other embodiments, r is 1 and $R^4$ is additionally substituted at a substitutable nitrogen atom with —$R^{14}$. As described generally above, in some embodiments, $R^{14}$ is independently —$R^{17}$, -L-N($R^{17}$)$_2$, —C(O)$R^{17}$, —C(O)-L-$R^{17}$, -L-C(O)$R^{17}$, —$CO_2R^{17}$, -L-$CO_2R^{17}$, —C(O)C(O)$R^{17}$, —C(O)-L-C(O)$R^{17}$, —$SO_2R^{17}$, -L-$SO_2R^{17}$, —$SO_2N(R^{17})_2$, -L-$SO_2N(R^{17})_2$, —C(=NH)—N($R^{17}$)$_2$, -L-N$R^{17}SO_2R^{17}$, —C(O)—N($R^{17}$)$_2$, -L-C(O)—N($R^{17}$)$_2$, —C(O)-L-N($R^{17}$)$_2$ or —C(O)-L-O$R^{17}$, wherein L is an optionally substituted $C_1$-$C_6$alkylene group, and each occurrence of $R^{17}$ is independently hydrogen, a substituted or unsubstituted group selected from an aliphatic, aromatic, cycloaliphatic, or non-aromatic heterocyclic group, or two occurrences of $R^{17}$, taken together with the nitrogen atom, form a substituted or unsubstituted non-aromatic heterocyclic ring.

In certain embodiments, L is a substituted or unsubstituted $C_1$-$C_4$alkylene chain. In other embodiments, L is a substituted or unsubstituted $C_1$-$C_3$alkylene chain. In still other embodiments, L is a substituted or unsubstituted $C_1$-$C_2$alkylene chain. In yet other embodiments, L is —$(CH_2)_x$—$(CR^{17a}R^{17b})_y$—, wherein x is 0, 1, 2, 3, or 4, and y is 0 or 1, provided that the sum of x and y is at least 1, and wherein each occurrence of $R^{17a}$ and $R^{17b}$ is independently hydrogen, substituted or unsubstituted $C_1$-$C_6$alkyl, substituted or unsubstituted Cy, substituted or unsubstituted —($C_1$-$C_6$alkyl)Cy, where Cy is a ring selected from: substituted or unsubstituted $C_3$-$C_6$cycloalkyl, a substituted or unsubstituted 5- or 6-membered heterocyclic group, a substituted or unsubstituted 5- or 6-membered aromatic group, or $R^{17a}$ and $R^{17b}$ taken together form a substituted or unsubstituted $C_3$-$C_6$ spiro cycloalkyl ring. In some embodiments, $R^{17a}$ and $R^{17b}$, as defined above, are substituted with up to three occurrences of $R^{17c}$, where $R^{17c}$ is halogen, —CN, —$NO_2$, —OH, —O($C_1$-$C_6$alkyl), —SH, —S($C_1$-$C_6$alkyl), —$NH^2$, —NH($C_1$-$C_6$alkyl), —N($C_1$-$C_6$alkyl)$_2$, —CO($C_1$-$C_6$alkyl), —COOH, —COO($C_1$-$C_6$alkyl), —$CONH_2$, —CONH($C_1$-$C_6$alkyl), —CON($C_1$-$C_6$alkyl)$_2$, —NHCO($C_1$-$C_6$alkyl), —$NHSO_2$($C_1$-$C_6$alkyl), —$SO_2NH_2$, or —$SO_2$NH($C_1$-$C_6$alkyl). In certain exemplary embodiments both $R^{17a}$ and $R^{17b}$ are hydrogen. In other embodiments, one of $R^{17a}$ or $R^{17b}$ is hydrogen and the other is substituted or unsubstituted $C_1$-$C_4$alkyl, or a substituted or unsubstituted ring selected from phenyl, cyclohexyl, imidazolyl, thiazolyl, oxazolyl, pyrrolyl, pyrazolyl, thiophene, furyl, —($C_1$-$C_3$alkyl)phenyl, —($C_1$-$C_3$alkyl)cyclohexyl, —($C_1$-$C_3$alkyl)imidazolyl, —($C_1$-$C_3$alkyl)thiazolyl, —($C_1$-$C_3$alkyl)oxazolyl, —($C_1$-$C_3$alkyl)pyrrolyl, —($C_1$-$C_3$alkyl)pyrazolyl, —($C_1$-$C_3$alkyl)thiophene, or —($C_1$-$C_3$alkyl)furyl. In other embodiments, one of $R^{17a}$ or $R^{17b}$ is hydrogen and the other is —$CH_3$, —$CH_2CH_3$, —$CH_2CH_2CH_3$, —$CH_2CH_2CH_2CH_3$, —CH($CH_3$)$_2$, cyclohexyl, phenyl, —C($CH_3$)$_3$, —$CH_2$COOH, —$CH_2$CH($CH_3$)$_2$, —$CH_2$cyclohexyl, —$CH_2$phenyl, —$CH_2$(4-chlorophenyl), —$CH_2CH_2CH_3$, —($CH_2$)$_2$phenyl, -or $CH_2$(1-methyliidazol-5-yl). In still other embodiments, one of $R^{17a}$ or $R^{17b}$ is hydrogen and the other is —$CH_3$. In yet other embodiments, both $R^{17a}$ and $R^{17b}$ are —$CH_3$. In still other embodiments, $R^{17a}$ and $R^{17b}$, taken together form a spiro cyclopropyl ring. In some embodiments, x is 0, 1, or 2 and y is 1. In still other embodiments, x is 0 or 1 and y is 1. In yet other embodiments, x is 0 and y is 1.

In certain embodiments, each occurrence of $R^{17}$ is independently hydrogen, substituted or unsubstituted $C_1$-$C_6$alkyl, or a substituted or unsubstituted ring selected from:

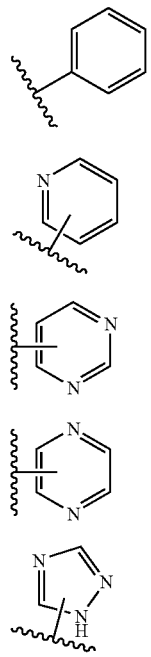
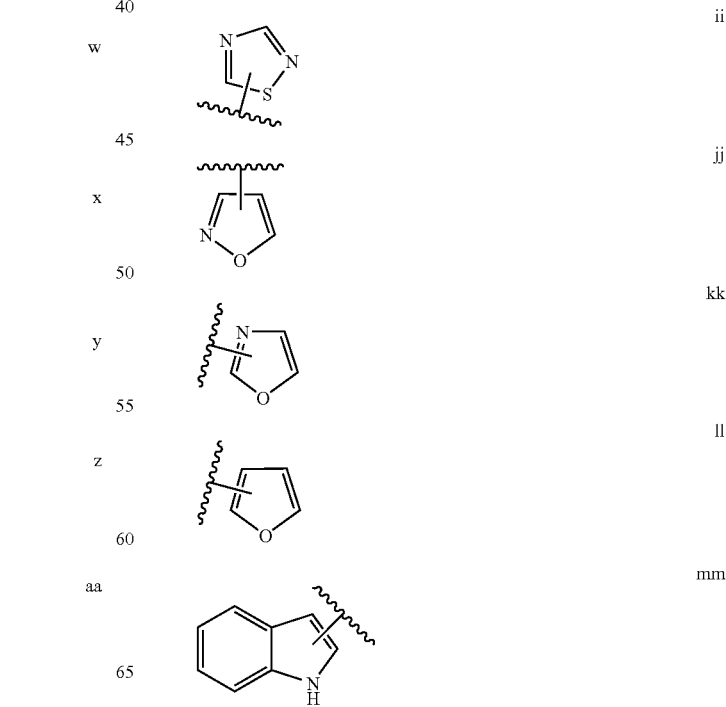

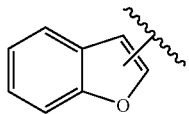
nn

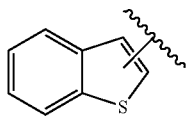
oo

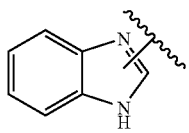
pp

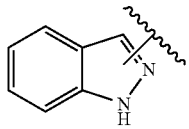
qq

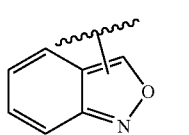
rr

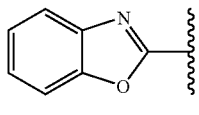
ss

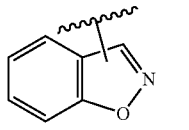
tt

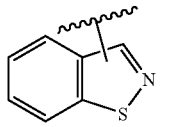
uu

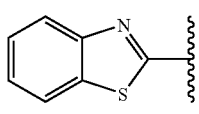
vv

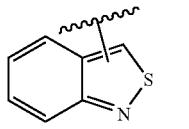
ww

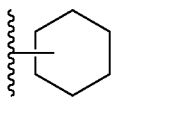
xx

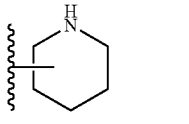
yy

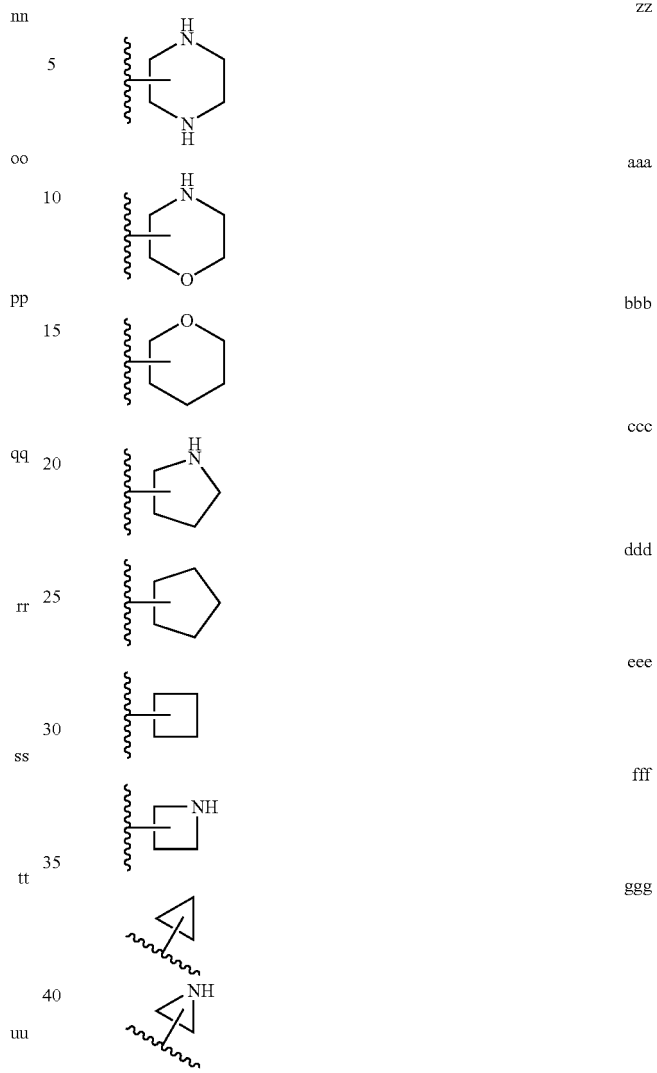

In certain embodiments, one or more substitutable carbon atoms of $R^{17}$ are substituted with w occurrences of $R^{18}$, and one or more substitutable nitrogen atoms are substituted with z occurrences of $R^{19}$, wherein w is 0, 1, 2, or 3, z is 0, 1, or 2, $R^{18}$ is halogen, —CN, —NO$_2$, —$R^{20}$, OR$^{20}$, —SR$^{20}$, —N(R$^{20}$)$_2$, —COR$^{20}$, —COOR$^2$, —NHCOR$^{20}$, —CON(R$^°$)$_2$, —SO$_2$R$^{20}$, —SO$_2$N(R$^{20}$)$_2$, —NHSO$_2$R$^{20}$, =O, =S, or =NR$^{20}$, and R is —R$^{20}$, —COR$^{20}$, —COOR$^{20}$, —CON(R$^{20}$)$_2$, —SO$_2$R$^{20}$, —SO$_2$N(R$^{20}$)$_2$, wherein each occurrence of $R^{20}$ is hydrogen, substituted or unsubstituted C$_1$-C$_6$aliphatic, or is a substituted or unsubstituted ring selected from an aromatic or non-aromatic ring, or two occurrences of $R^{20}$, taken together with the atom(s) to which they are bound form a substituted or unsubstituted fused or spiro aromatic or non-aromatic 5- or 6-membered ring.

In some embodiments, w is 0, 1, or 2, and each occurrence of $R^{18}$, when present, is halogen, —CN, —NO$_2$, —R , —OR$^{20}$, wherein each occurrence of $R^{20}$ is independently hydrogen, substituted or unsubstituted C$_1$-C$_4$alkyl, or is a substituted or unsubstituted monocyclic 5- or 6-membered aromatic or non-aromatic ring optionally having 0-3 heteroatoms selected from nitrogen, oxygen, or sulfur, or two occurrences of $R^{20}$, taken together with the atoms to which are bound form a substituted or unsubstituted 5- or 6-membered fused aromatic or nonaromatic ring. In other embodiments, w is 0, 1, or 2, and each occurrence of $R^{18}$, when present, is —CN, —CH$_3$, —CF$_3$, —CH$_2$CH$_3$, —CH$_2$CH$_2$CH$_3$, —CH(CH$_3$)$_2$, —CH$_2$CH(CH$_3$)$_2$, —OH, —OCH$_3$, —OCF$_3$, —OCH$_2$CH$_3$, phenyl, fused phenyl, —F, —Br, or —Cl.

In other embodiments z is 0 or 1 and $R^{19}$ is —$R^{20}$ or —COR$^{20}$, wherein each occurrence of $R^{20}$ is independently hydrogen, substituted or unsubstituted C$_1$-C$_4$alkyl, or is a substituted or unsubstituted monocyclic 5- or 6-membered aromatic or non-aromatic ring optionally having 0-3 heteroatoms selected from nitrogen, oxygen, or sulfur. In still other embodiments, z is 0 or 1 and $R^{19}$ is —CH$_3$, —CH$_2$CH$_3$, —CH$_2$CH$_2$CH$_3$, —CH(CH$_3$)$_2$, —CH$_2$CH$_2$CH$_2$CH$_3$, substituted or unsubstituted phenyl, —COCH$_3$, —COCH$_2$CH$_3$, —CO(substituted or unsubstituted phenyl), or a substituted or unsubstituted group selected from isoxazolyl, thiazolyl, pyrrolyl, or pyrazolyl. In some embodiments, the phenyl group is substituted with halogen, —OH, —O(C$_1$-C$_4$alkyl), or C$_1$-C$_4$alkyl.

In certain exemplary embodiments, $R^{14}$ is —COR$^{17}$, —C(O)—(CH$_2$)$_x$—(CR$^{17a}$R$^{17b}$)$_y$R$^{17}$, —C(O)—(CH$_2$)$_x$—(CR$^{17a}$R$^{17b}$)$_y$N(R$^{17}$)$_2$, —C(O)N(R$^{17}$)$_2$, or —C(O)OR$^{17}$.

In some embodiments, $R^{14}$ is —COR$^{17}$ or —C(O)—(CH$_2$)$_x$—(CR$^{17a}$R$^{17b}$)$_y$R$^{17}$, wherein x is 0, 1, 2, 3, or 4, and y is 0 or 1, provided that the sum of x and y is at least 1, and wherein each occurrence of $R^{17a}$ and $R^{17b}$ is independently hydrogen, substituted or unsubstituted C$_1$-C$_6$alkyl, substituted or unsubstituted Cy, substituted or unsubstituted —(C$_1$-C$_6$alkyl)Cy, where Cy is a ring selected from: substituted or unsubstituted C$_3$-C$_6$cycloalkyl, a substituted or unsubstituted 5- or 6-membered heterocyclic group, a substituted or unsubstituted 5- or 6-membered aromatic group, or $R^{17a}$ and $R^{17b}$ taken together form a substituted or unsubstituted C$_3$-C$_6$spiro cycloalkyl ring, and $R^{17}$ is hydrogen, C$_1$-C$_4$alkyl, or is a ring selected from:

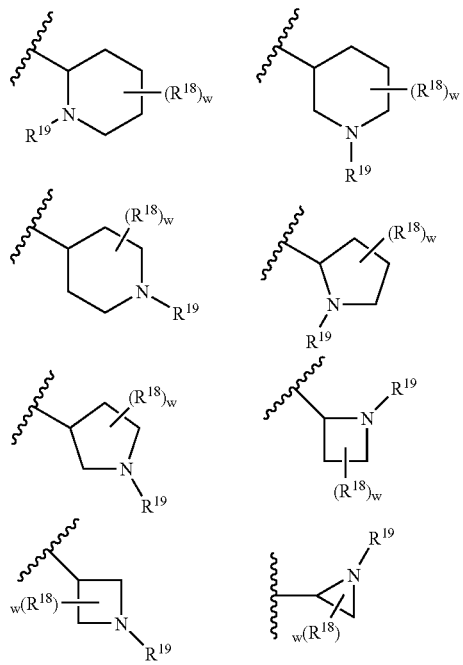

wherein w is 0, 1, 2, or 3, $R^{18}$ is halogen, —CN, —NO$_2$, —R$^{20}$, —OR$^{20}$, —SR$^{20}$, —N(R$^{20}$)$_2$, —COR$^{20}$, —COOR$^{20}$, —NHCOR$^{20}$, —CON(R$^{20}$)$_2$, —SO$_2$R$^{20}$, —SO$_2$N(R$^{20}$)$_2$, —NHSO$_2$R$^{20}$, =O, =S, or =NR$^{20}$, and $R^{19}$ is —R$^{20}$, —COR$^{20}$, —COOR$^{20}$, —CON(R$^{20}$)$_2$, —SO$_2$R$^{20}$, —SO$_2$N(R$^{20}$)$_2$, wherein each occurrence of $R^{20}$ is hydrogen, substituted or unsubstituted C$_1$-C$_6$aliphatic, or is a substituted or unsubstituted ring selected from an aromatic or non-aromatic ring, or two occurrences of $R^{20}$, taken together with the atom(s) to which they are bound form a substituted or unsubstituted fused or spiro aromatic or non-aromatic 5- or 6-membered ring.

In addition to each of the embodiments described above, in certain other embodiments, the compound represented by Structural Formula (I) is characterized by one, two, three or more, or all of, the following features:

(1) C=Z is C=O and X$_1$ is a bond or C=Z is CH$_2$ and X$_1$ is CR$^a$R$^b$;

(2) X is a bond;

(3) $R^1$ is a substituted or unsubstituted cycloalkyl group or an aromatic group optionally substituted with one or more substituent groups, e.g., the substituent groups represented by $R^8$ and $R^9$;

(4) R is —H;

(5) $R^3$ is —H or $R^3$ and $R^4$ taken together with the nitrogen atom to which they are bonded are a substituted or unsubstituted nitrogen-containing non-aromatic heterocyclic group;

(6) $R^4$ is a substituted or unsubstituted non-aromatic ring or a phenyl or benzyl group optionally substituted with one or more substituent groups, e.g., the substituent groups represented by $R^{13}$ and $R^{14}$;

(7) m is 0 or 1; and (8) n is 2.

In other embodiments, the compound is characterized by the features or combination of features: (1); (2); (3); (4); (5); (6); (7); (8); (1) and (4); (I), (2) and (4); (1), (3) and (4); (1), (4) and (5); (1), (4), and (6); (1), (4) and (7); (1), (4) and (8); (1), (4), (7) and (8); (1), (2), (4), (7) and (8); (1), (3), (4), (7) and (8); (1), (4), (5), (7) and (8); (1), (4), (6), (7) and (8); (1), (2), (3), (4), (5), (7) and (8); (1), (2), (4), (5), (6), (7) and (8); and (1), (3), (4), (5), (6), (7) and (8). In certain embodiments, the compound represented by Structural Formula (I) is characterized by all of Features (1)-(8).

Alternatively, the compound represented by Structural Formula (I) is characterized as described in the previous paragraph, except that for feature (1), X$_1$ is C=O and C=Z is absent.

In one embodiment, the compound is represented by any one of Structural Formulas (II)-(VI):

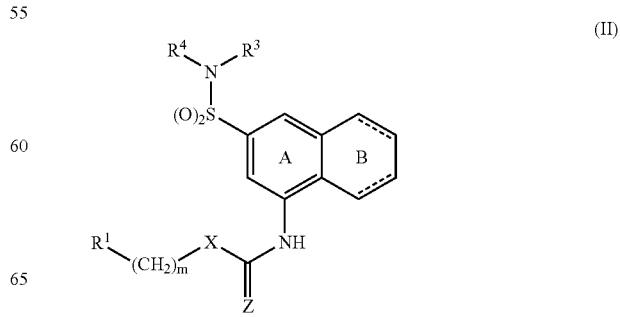

(II)

-continued
(III)
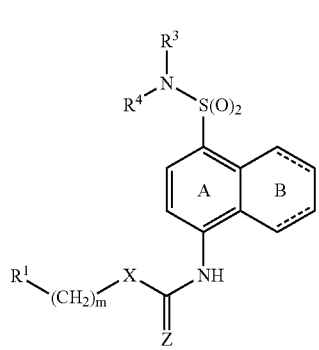
(IV)
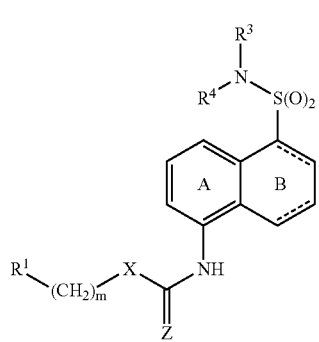
(V)
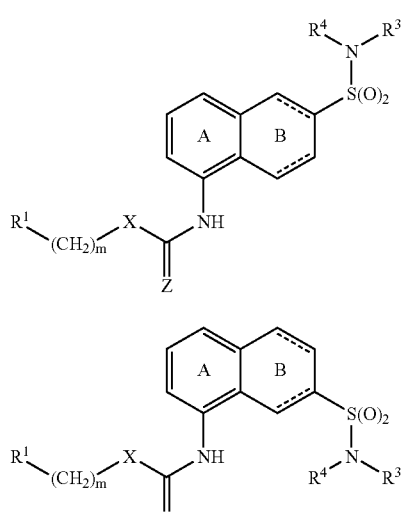
(VI)
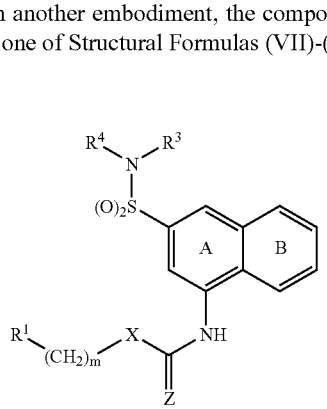
In another embodiment, the compound is represented by any one of Structural Formulas (VII)-(XI):
(VII)
-continued
(VIII)
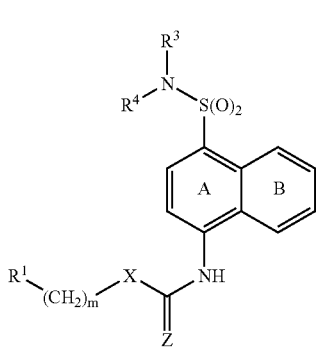
(IX)
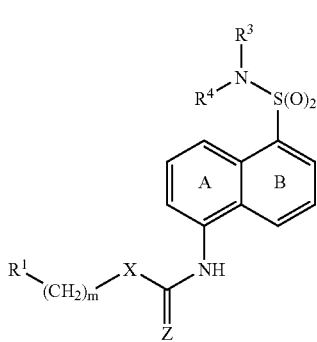
(X)
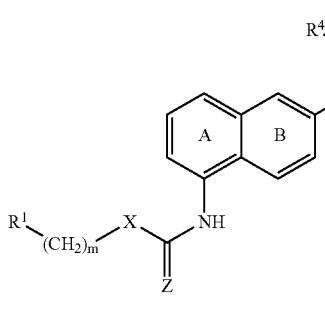
(XI)
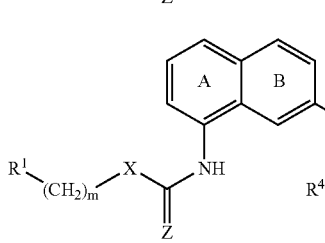
In another embodiment, the compound is represented by any one of structural Formulas (XII)-(XVI):
(XII)
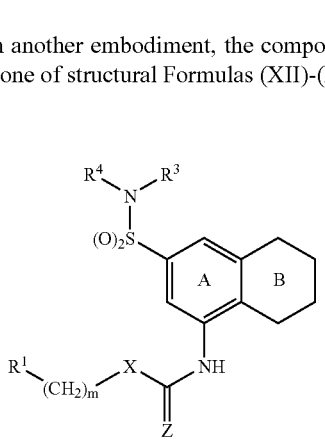

-continued
(XIII)
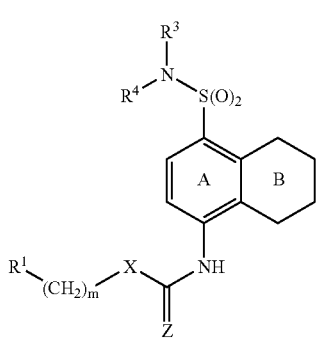
(XIV)
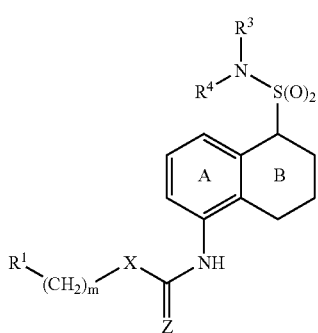
(XV)
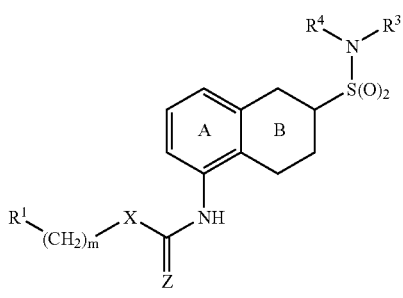
(XVI)
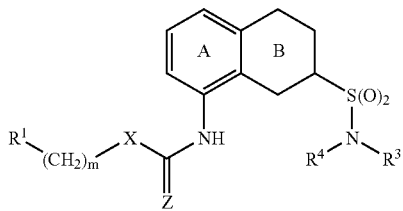
In yet another preferred embodiment, the compound is represented by structural Formulas (XVII) or (XVIII):
(XVII)
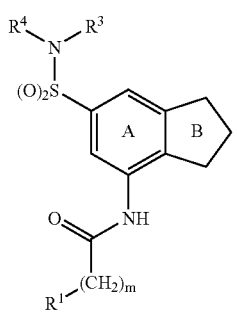
(XVIII)
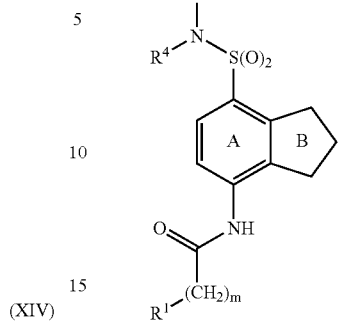
In yet another embodiment, the compound is represented by any one of structural Formulas (XIX)-(XXIII):
(XIX)
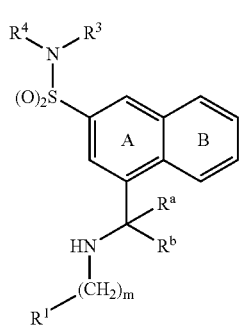
(XX)
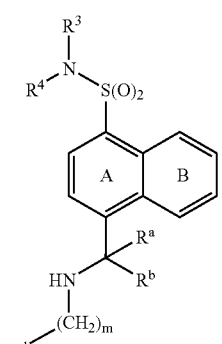
(XXI)
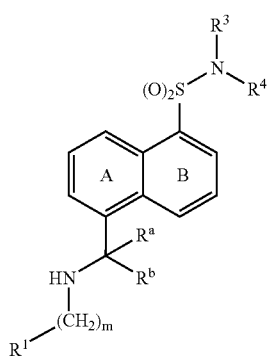

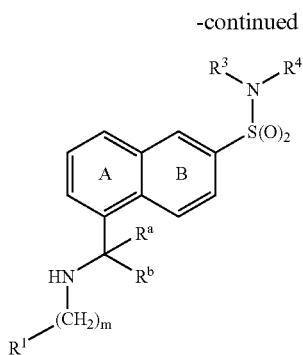
(XXII)
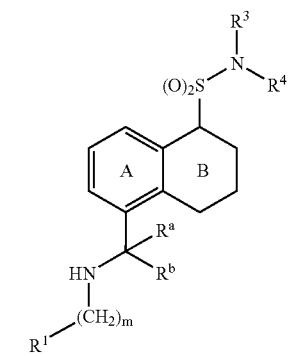
(XXVI)
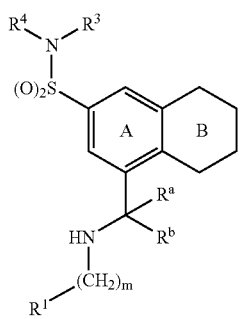
(XXIII)
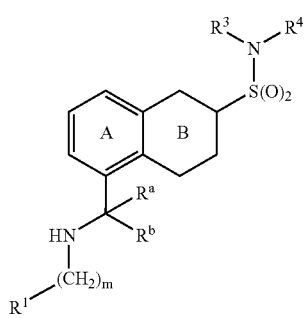
(XXVII)
In yet another preferred embodiment, the compound is represented by any one of structural Formulas (XXIV)-(XXVIII):
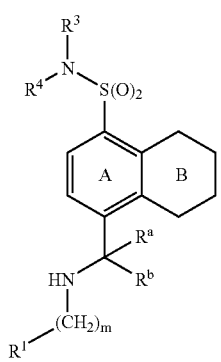
(XXIV)
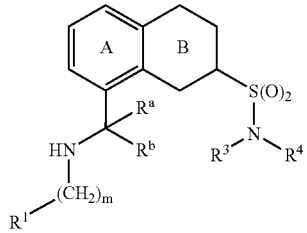
(XXVIII)
In yet another preferred embodiment, the compound is represented by Structural Formulas (XXIX) or (XXX):
(XXV)
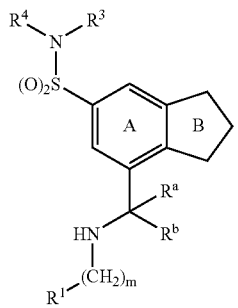
(XXIX)

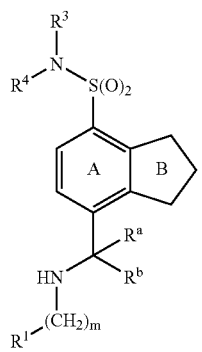
(XXX)

In yet another preferred embodiment, the compound is represented by any one of structural Formulas (XXXI)-(XXXV):

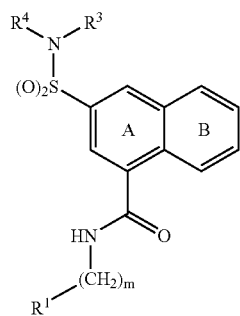
(XXXI)

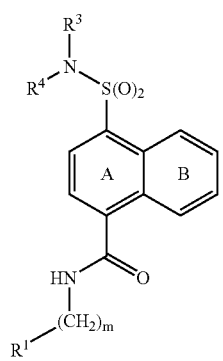
(XXXII)

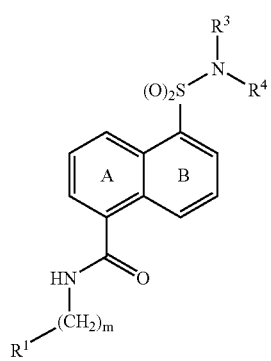
(XXXIII)

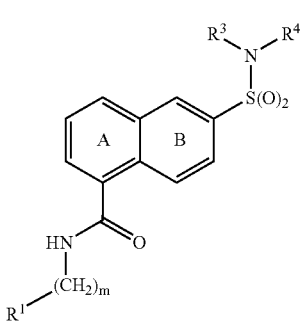
(XXXIV)

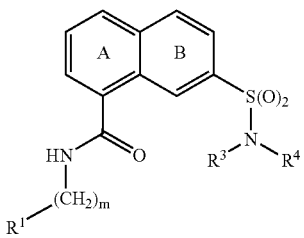
(XXXV)

In yet another preferred embodiment, the compound is represented by Structural Formulas (XXXVI) or (XXXVII):

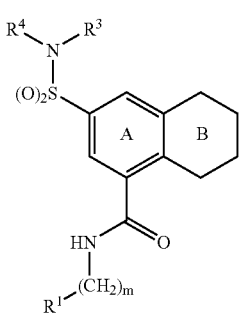
(XXXVI)

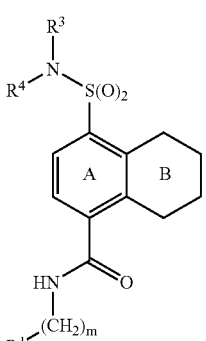
(XXXVII)

In yet another preferred embodiment, the compound is represented by Structural Formulas (XXXVIII) or (XXXIX):

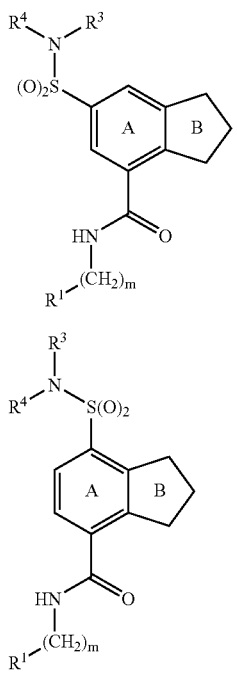

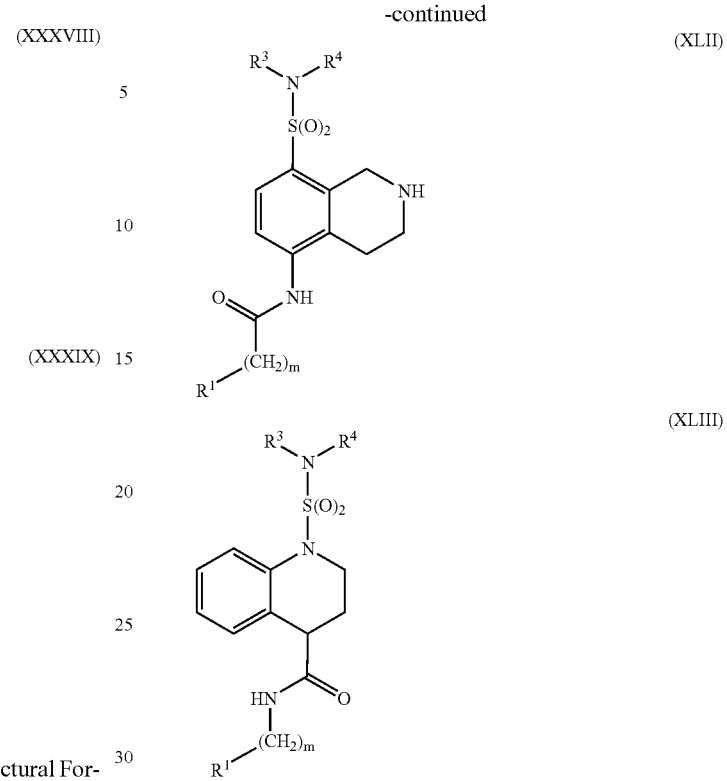

The 1,4- and 1,5-substitution patterns (e.g., Structural Formulas (III), (IV), (VIII), (IX), (XIII), (XIV), (XVIII), (XX), (XXI), (XXV), (XXVI), (XXX), (XXXII), (XXXIII), (XXXVII), and (XXXIX) are preferred.

In yet another preferred embodiment, the compound is represented by Structural Formulas (XL)-(XLIII):

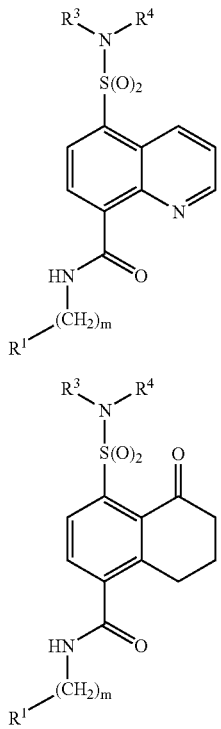

In yet another preferred embodiment, the compound is respresented by one of Structural Formulas (VII), (VIII), (IX), (X), (XI), (XII), (XIII), (XVII), (XVIII), (XIX), (XX), (XXI), (XXII), (XXIII), (XXIV), (XXV), (XXIX), (XXX), (XXXI), (XXXII), (XXXIII), (XXXIV), (XXXV), (XXXVI), (XXXVII), (XXXVIII), (XXXIX), (XL), (XLI), (XLII) or (XLIII):

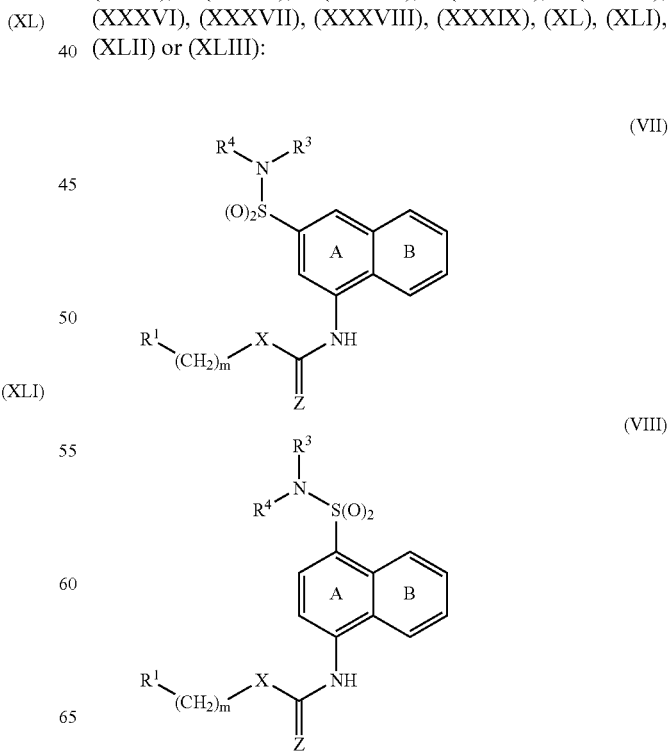

-continued
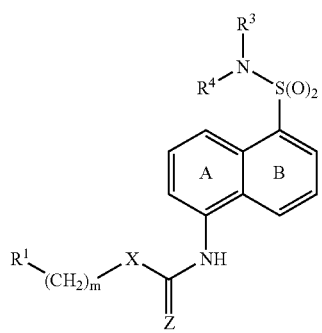
(IX)
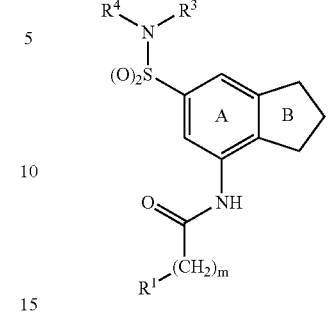
(XVII)
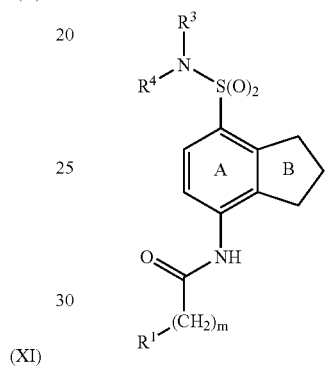
(X)
(XVIII)
(XI)
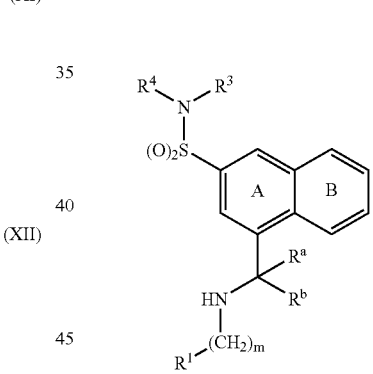
(XIX)
(XII)
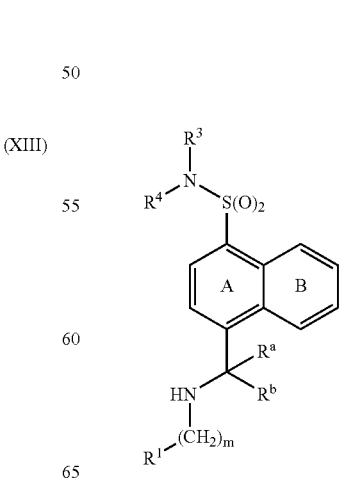
(XX)
(XIII)

-continued
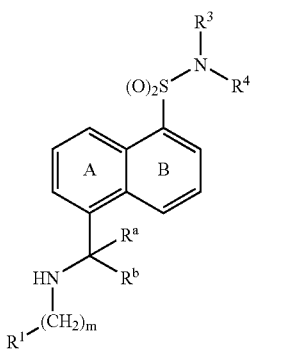
(XXI)
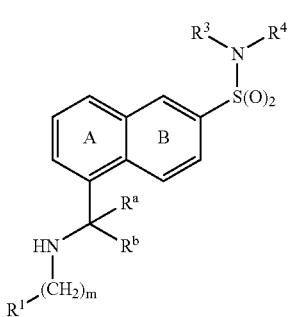
(XXII)
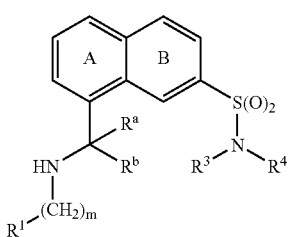
(XXIII)
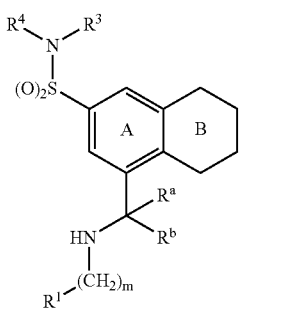
(XXIV)
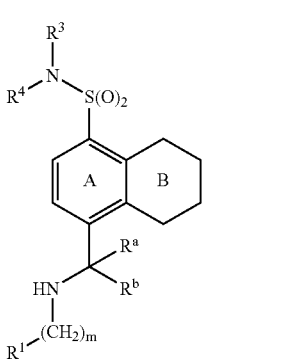
(XXV)
-continued
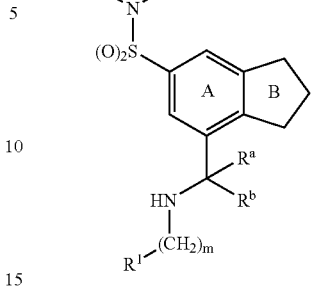
(XXIX)
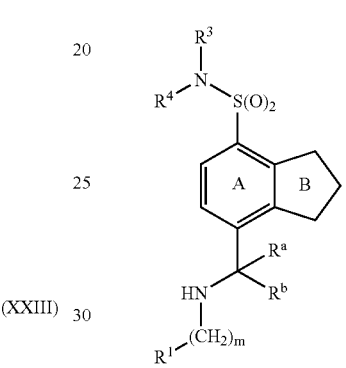
(XXX)
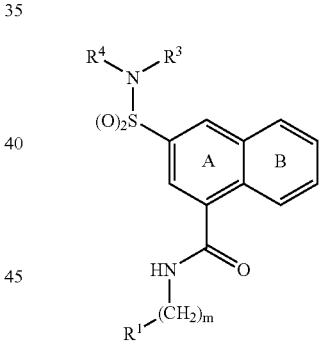
(XXXI)
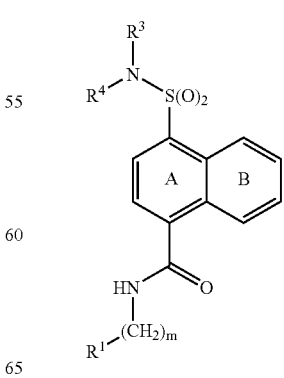
(XXXII)

-continued
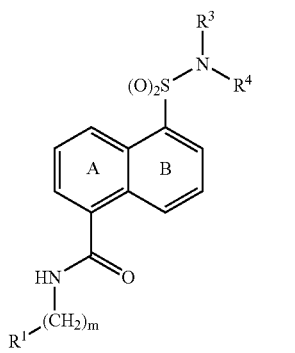
(XXXIII)
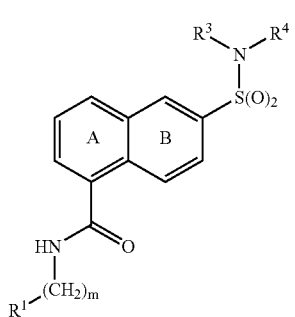
(XXXIV)
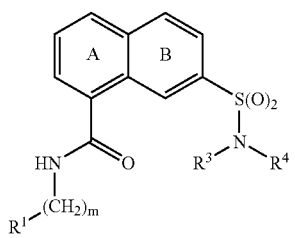
(XXXV)
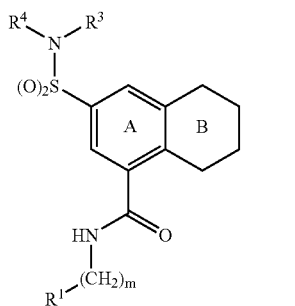
(XXXVI)
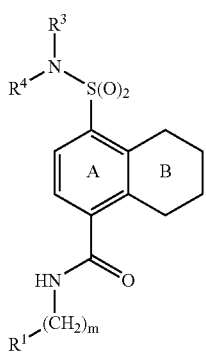
(XXXVII)
-continued
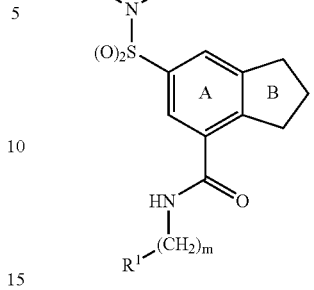
(XXXVIII)
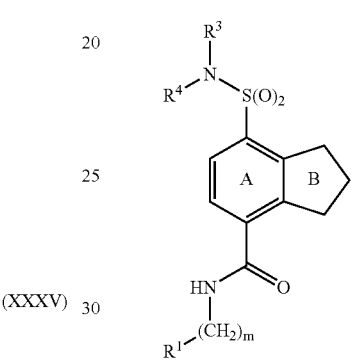
(XXXIX)
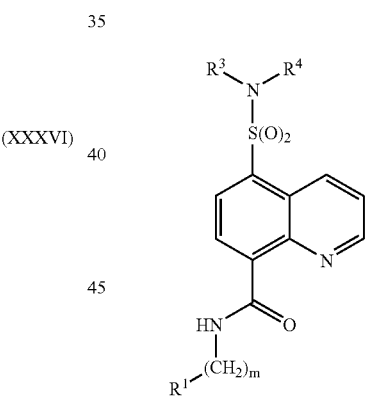
(XL)
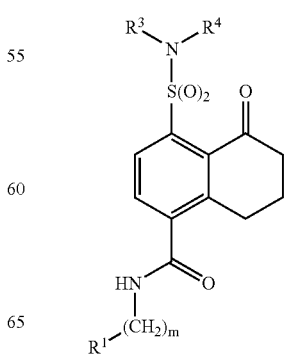
(XLI)

-continued (XLII)

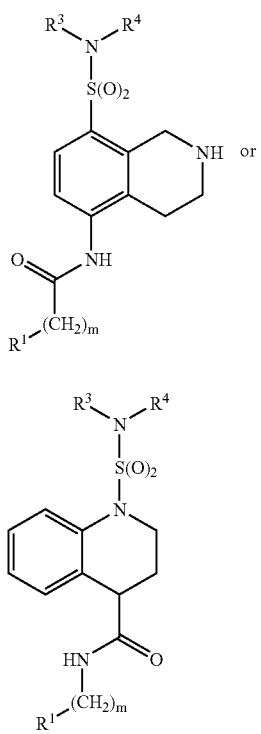

(XLIII)

wherein Ar is optionally substituted at any substitutable carbon or nitrogen atom with p independent occurrences of $R^6$, wherein p is 0, 1, 2, or 3; and each occurrence of $R^6$ is independently halogen, —CN, $NO_2$, —$R^7$, or —$OR^7$, wherein each occurrence of $R^7$ is independently hydrogen or a substituted or unsubstituted $C_1$-$C_6$ aliphatic group.

In some embodiments, for compounds of any one or all of formulas (I)-(XLIII) one or more, or all of the compound variables are selected from:

a) $R^1$ is a ring selected from:

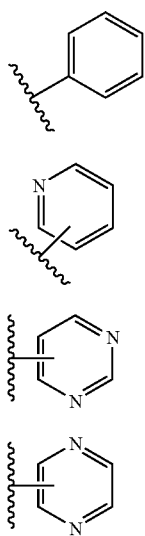

i ii iii iv

-continued

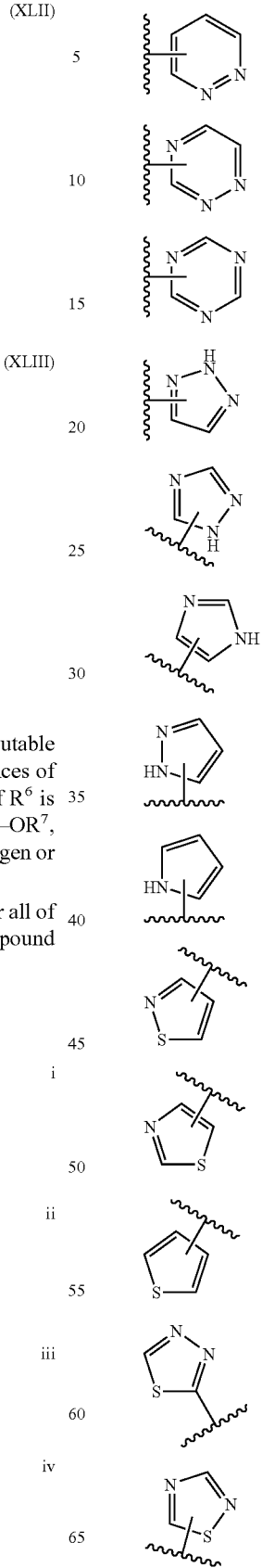

v vi vii viii ix x xi xii xiii xiv xv xvi xvii

-continued
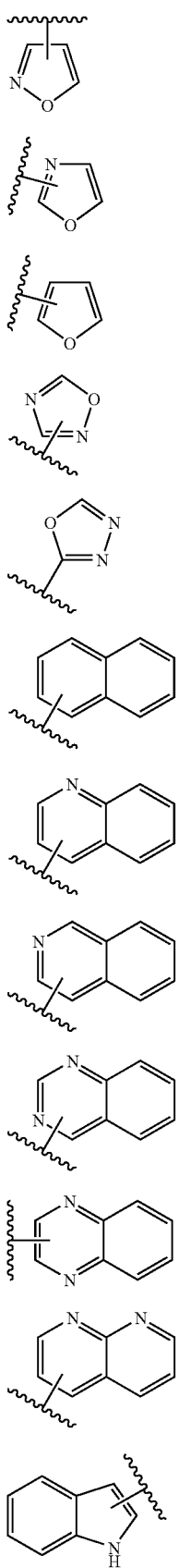
-continued
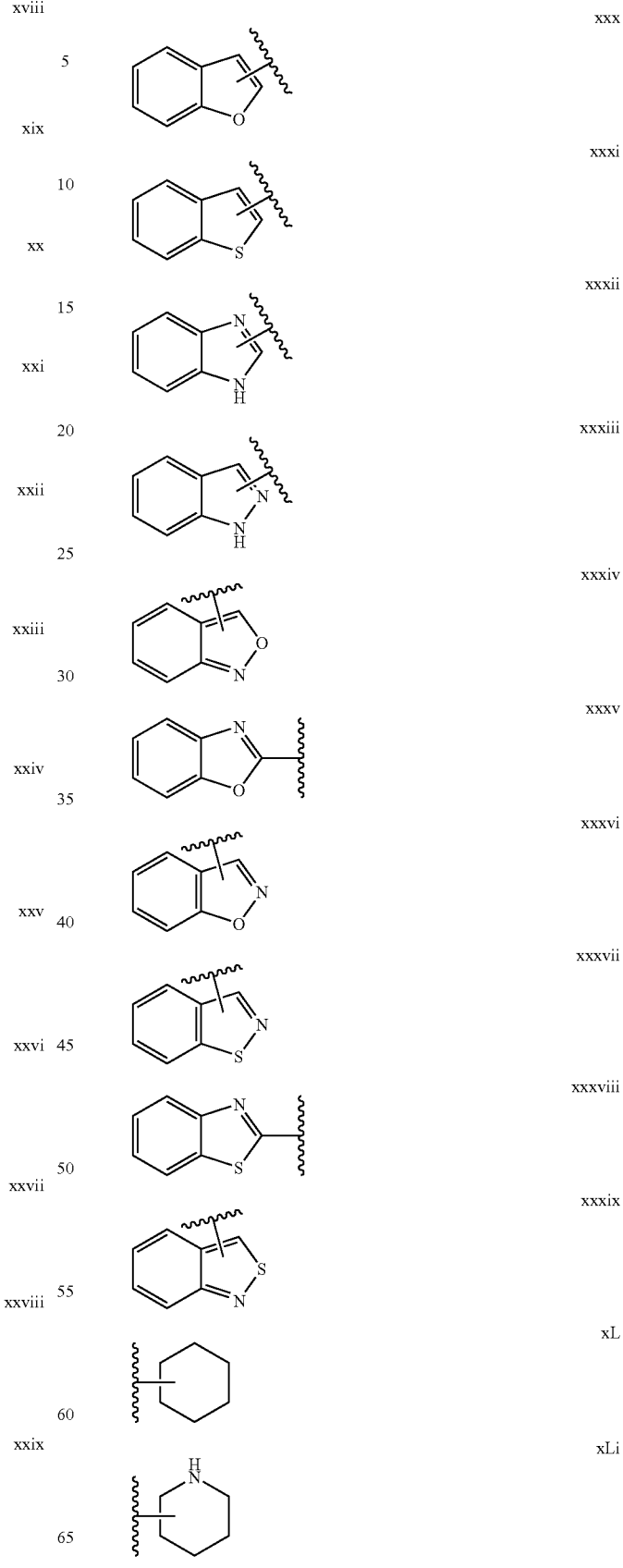

-continued

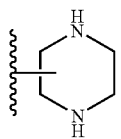 xLii

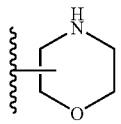 xLiii

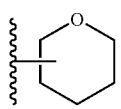 xLiv

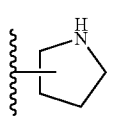 xLv

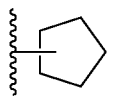 xLvi

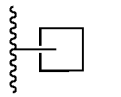 xLvii

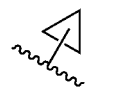 xLviii or $R^5$ and —$(CH_2)_m R^1$ are taken together with the nitrogen atom to which they are bound and form a substituted or unsubstituted non-aromatic heterocyclic ring selected from:

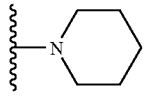 xLix

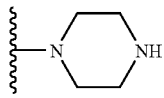 L

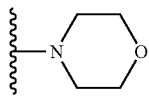 Li

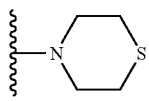 Lii

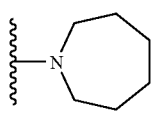 Liii

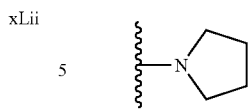 Liv

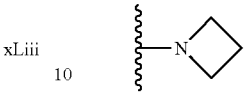 Lv

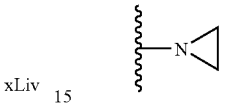 Lvi wherein $R^1$ or the non-aromatic heterocyclic ring formed from $NR^5(CH_2)_m R^1$, are each optionally substituted at one or more substitutable aromatic or non-aromatic carbon atoms with q occurrences of $R^8$, and at one or more substitutable nitrogen atoms with t occurrences of $R^9$;

b) $R^3$ is hydrogen, and $R^4$ is a substituted or unsubstituted ring selected from:

a b c d e f g h

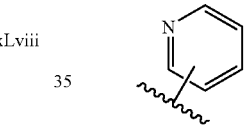
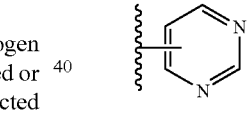
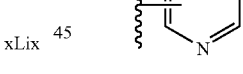
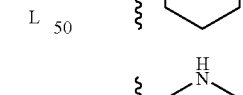
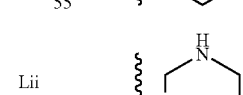
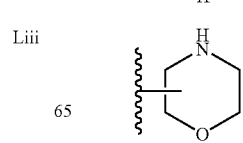

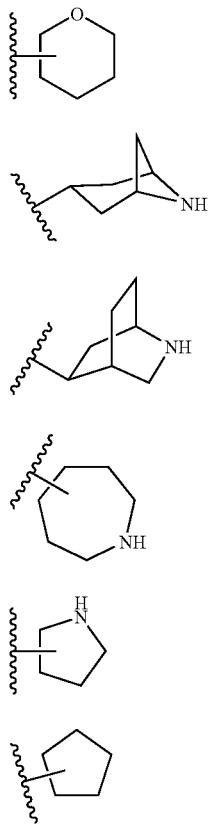
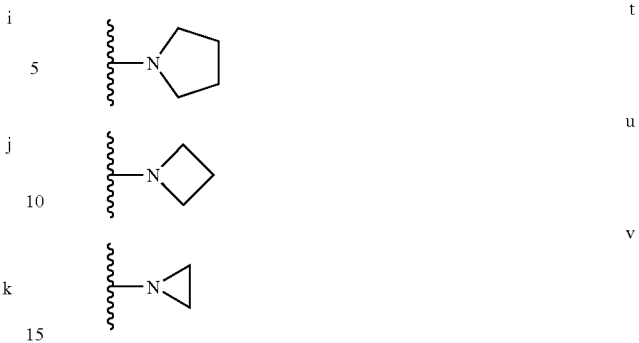

wherein the ring is bound directly to the nitrogen atom or through a $C_1$-$C_4$alkyl group, or:

$R^3$ and $R^4$, taken together with the nitrogen atom to which they are bound, is a substituted or unsubstituted nitrogen-containing non-aromatic heterocyclic ring selected from:

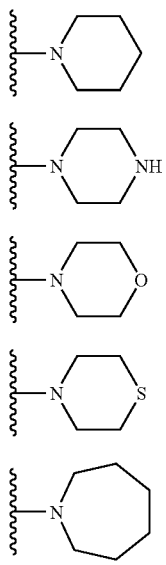

wherein $R^4$ or the non-aromatic heterocyclic ring formed from $R^3$ and $R^4$, taken together with the nitrogen atom to which they are bound are each optionally and independently substituted at one or more substitutable aromatic or non-aromatic carbon atoms with s occurrences of $R^{13}$, and at one or more substitutable nitrogen atoms with r occurrences of $R^{14}$; and c) C=Z is C=O, X is a bond, and m is 0 or 1.

In other embodiments, for compounds of any one or all of formulas (I)-(XLIII) one or more, or all of the compound variables are selected from:

a) $R^1$ is a substituted or unsubstituted ring selected from phenyl (i), pyridyl (ii), imidazolyl (x), thiophene (xv), furyl (xx), benzthiophene (xxxi), cyclohexyl (xL), piperidinyl (xLi), tetrahydropyran (xLiv), cyclopentyl (xLvi), cyclobutyl (xLvii), or cyclopropyl (xLviii), wherein q is 0, 1, or 2 and each occurrence of $R^8$, when present is halogen, —CN, —$NO_2$, —$C_1$-$C_6$alkyl, —OH, —O($C_1$-$C_6$alkyl), —$NH_2$, —NH($C_1$-$C_6$alkyl), —N($C_1$-$C_6$alkyl)$_2$, —SH, —S($C_1$-$C_6$alkyl), wherein $C_1$-$C_6$alkyl is substituted or unsubstituted;

b) $R^3$ is hydrogen and $R^4$ is a substituted or unsubstituted ring selected from: phenyl, —($CH_2$)phenyl, cyclohexyl, —($CH_2$)cyclohexyl, —($CH_2$)$_2$cyclohexyl, —($CH_2$)$_3$cyclohexyl, cyclopentyl, —($CH_2$)cyclopentyl, —($CH_2$)$_2$cyclopentyl, —($CH_2$)$_3$cyclopentyl, pyridyl, —($CH_2$)pyridyl, —($CH_2$)$_2$pyridyl, —($CH_2$)$_3$pyridyl, tetrahydrofuryl, —($CH_2$)tetrahydrofuryl, —($CH_2$)$_2$tetrahydrofuryl, —($CH_2$)$_3$tetrahydrofuryl, piperidinyl, —($CH_2$)piperidinyl, —($CH_2$)$_2$piperidinyl, —($CH_2$)$_3$piperidinyl, aza-bicyclo[3.2.1]octane, morpholinyl, —($CH_2$)morpholinyl, —($CH_2$)$_2$ morpholinyl, —($CH_2$)$_3$ morpholinyl, piperazinyl, —($CH_2$)piperazinyl, —($CH_2$)$_2$ piperazinyl, —($CH_2$)$_3$piperazinyl, pyrrolidinyl, —($CH_2$)pyrrolidinyl, —($CH_2$)$_2$pyrrolidinyl, or —($CH_2$)$_3$pyrrolidinyl, wherein s is 0, 1, or 2, and each occurrence of $R^{13}$ is halogen, —$R^{15}$, —$COR^{15}$, —$CO_2H$, or $O_2R^{15}$, wherein $R^{15}$ is phenyl or a $C_1$-$C_4$alkyl group optionally substituted with halogen, —OH, O($C_{1-3}$alkyl), —SH, —S($C_1$-$C_3$alkyl), $NH_2$, NH($C_1$-$C_3$alkyl), or —N($C_1$-$C_3$alkyl)$_2$;

r is 0 or 1, and $R^{14}$ is independently —$R^{17}$, -L-N($R^{17}$)$_2$, —C(O)$R^{17}$, —C(O)-L-$R^{17}$, -L-C(O)$R^{17}$, —$CO_2R^{17}$, -L-$CO_2R^{17}$, —C(O)C(O)$R^{17}$, -L-C(O)C(O)$R^{17}$, —C(O)-L-C(O)$R^{17}$, —$SO_2R^{17}$, -L-$SO_2R^{17}$, —$SO_2$N($R^{17}$)$_2$, -L-$SO_2$N($R^{17}$)$_2$, —C(=S)N($R^{17}$)$_2$, —C(=NH)—N($R^{17}$)$_2$, -L-$NR^{17}SO_2R^{17}$, —C(O)—N($R^{17}$)$_2$, -L-C(O)—N($R^{17}$)$_2$, —C(O)-L-N($R^{17}$)$_2$ or —C(O)-L-$OR^{17}$, wherein L is —($CH_2$)$_x$—($CR^{17a}R^{17b}$)$_y$—, wherein x is 0, 1, 2, 3, or 4, and y is 0 or 1, provided that the sum of x and y is at least 1, and wherein each occurrence of $R^{17a}$ and $R^{17b}$ is independently hydrogen, substituted or unsubstituted $C_1$-$C_6$alkyl, substituted or unsubstituted Cy, substituted or unsubstituted —($C_1$-$C_6$alkyl)Cy, where Cy is a ring selected from: substituted or unsubstituted $C_3$-$C_6$cycloalkyl, a substituted or unsubstituted 5- or 6-membered heterocyclic ring, a substituted or unsubstituted 5- or 6-membered aromatic ring, or $R^{17a}$ and $R^{17b}$ taken together form a substituted or unsubstituted $C_3$-$C_6$spiro cycloalkyl ring;

each occurrence of $R^{17}$ is independently hydrogen, substituted or unsubstituted $C_1$-$C_6$alkyl, or a substituted or unsubstituted ring selected from:

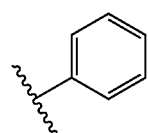

w

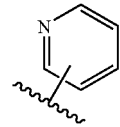

x

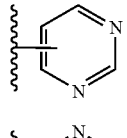

y

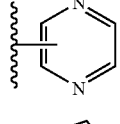

z

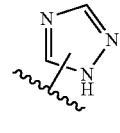

aa

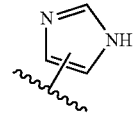

bb

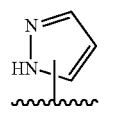

cc

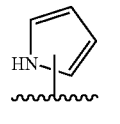

dd

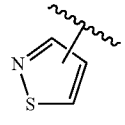

ee

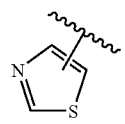

ff

-continued

gg

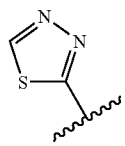

hh

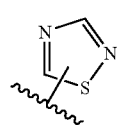

ii

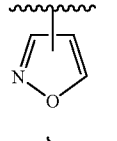

jj

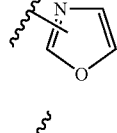

kk

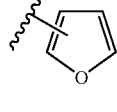

ll

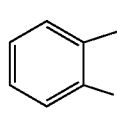

mm

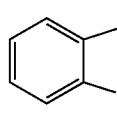

nn

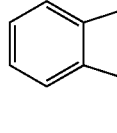

oo

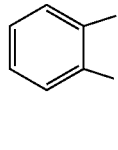

pp

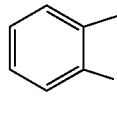

qq

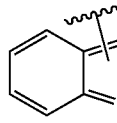

rr

-continued ss 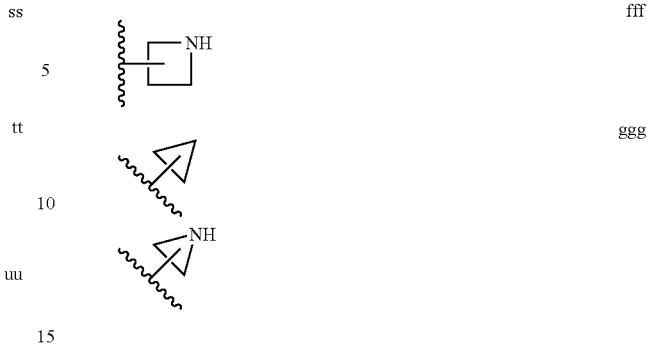

tt uu vv ww xx 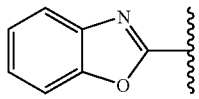

yy 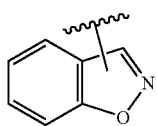

zz 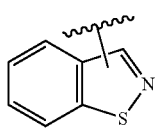

aaa 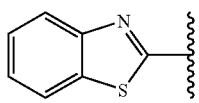

bbb 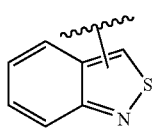

ccc 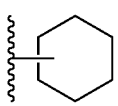

ddd 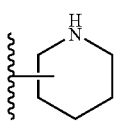

eee 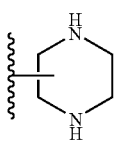

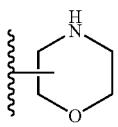

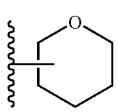


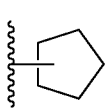

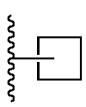

wherein one or more substitutable carbon atoms of $R^{17}$ are substituted with w occurrences of $R^{18}$, and one or more substitutable nitrogen atoms are substituted with z occurrences of $R^{19}$, wherein w is 0, 1, 2, or 3, z is 0, 1, or 2, $R^{18}$ is halogen, —CN, —NO$_2$, —$R^{20}$, —O$R^{20}$, —S$R^{20}$, —N($R^{20}$)$_2$, —CO$R^{20}$, —COO$R^{20}$, —NH-CO$R^{20}$, —CON($R^{20}$)$_2$, —SO$_2$$R^{20}$, —SO$_2$N($R^{20}$)$_2$, —NHSO$_2$$R^{20}$, =O, =S, or =N$R^{20}$, and R is —$R^{20}$, —CO$R^{20}$, —COO$R^{20}$, —CON($R^{20}$)$_2$, —SO$_2$$R^{20}$, —SO$_2$N($R^{20}$)$_2$, wherein each occurrence of $R^{20}$ is hydrogen, substituted or unsubstituted C$_1$-C$_6$aliphatic, or is a substituted or unsubstituted ring selected from an aromatic or non-aromatic ring, or two occurrences of $R^{20}$, taken together with the atom(s) to which they are bound form a substituted or unsubstituted fused or spiro aromatic or non-aromatic 5- or 6-membered ring; and c) C=Z is C=O, X is a bond, and m is 0 or 1.

In still other embodiments, for compounds of any one or all of formulas (I)-(XLIII) one or more, or all of the compound variables are selected from:

a) $R^1$ is substituted or unsubstituted phenyl (i), and q is 0, 1, or 2 and each occurrence of $R^8$, when present is —Cl, —F, —Br, —CH$_3$, —CH$_2$CH$_3$, —OCH$_3$, —OCH$_2$CH$_3$, —CF$_3$, —OCF$_3$, —NO$_2$, or —CN;

b) $R^3$ is hydrogen, and $R^4$ is a ring selected from:

fff ggg f-i f-ii m-i

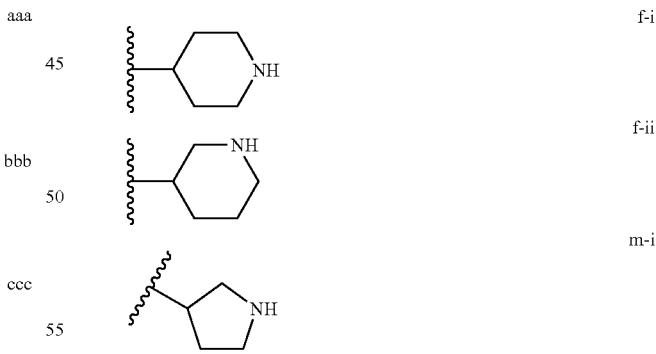

wherein s is 0, 1, or 2, and each occurrence of $R^{13}$ is —F, —Cl, —Br, phenyl, —CH$_3$, —OCH$_3$, —CH$_2$CH$_3$, —CH(CH$_3$)$_2$, —CH$_2$CH(CH$_3$)$_2$, —OCH$_2$CH$_3$, —CO$_2$H, CO$_2$CH$_3$, —CO$_2$CH$_2$CH$_3$, —OH, —CH$_2$OH, or —CH$_2$CH$_2$OH, r is 0 or 1 and $R^{14}$ is —CO$R^{17}$, —C(O)—(CH$_2$)$_x$—(C$R^{17a}$$R^{17b}$)$_y$$R^{17}$, —C(O)—(CH$_2$)$_x$—(C$R^{17a}$$R^{17b}$)$_y$N($R^{17}$)$_2$, —C(O)N($R^{17}$)$_2$, or —C(O)O$R^{17}$, and x is 0 or 1, and y is 0 or 1, $R^{17}$ is hydrogen, C$_1$-C$_4$alkyl, or is a ring selected from:

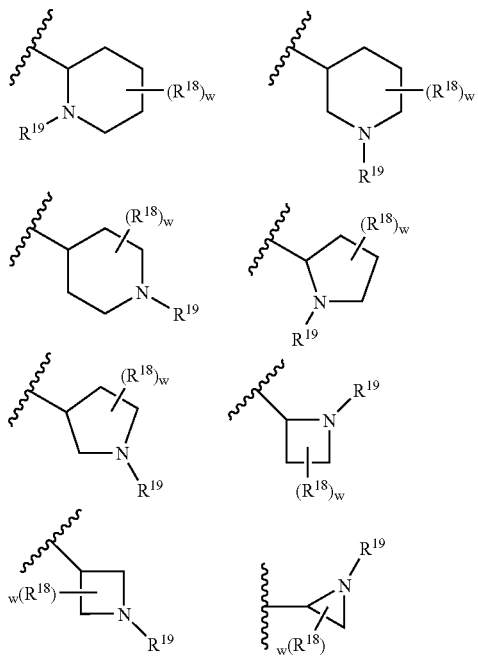

wherein w is 0, 1, or 2, and each occurrence of $R^{18}$, when present, is halogen, —CN, —NO$_2$, —$R^{20}$, —$OR^{20}$, wherein each occurrence of $R^{20}$ is independently hydrogen, substituted or unsubstituted $C_1$-$C_4$alkyl, or is a substituted or unsubstituted monocyclic 5- or 6-membered aromatic or nonaromatic ring optionally having 0-3 heteroatoms selected from nitrogen, oxygen, or sulfur, or two occurrences of $R^{20}$, taken together with the atoms to which they are bound form a substituted or unsubstituted 5- or 6-membered fused aromatic or nonaromatic ring, and z is 0 or 1 and $R^{19}$ is —$R^{20}$ or —$COR^{20}$, wherein each occurrence of $R^{20}$ is independently hydrogen, substituted or unsubstituted $C_1$-$C_4$alkyl, or is a substituted or unsubstituted monocyclic 5- or 6-membered aromatic or non-aromatic ring optionally having 0-3 heteroatoms selected from nitrogen, oxygen, or sulfur; and c) C=Z is C=O, X is a bond, and m is 0 or 1.

In still other embodiments, for compounds of any one of or all of formulas (I)-(XLIII) one or more, or all of the compound variables are selected from:

a) $R^1$ is phenyl, q is 1 and $R^8$ is $C_1$-$C_3$alkyl, halogen, or —CN and is substituted in the ortho position of the phenyl ring, or q is 2 and each occurrence of $R^8$ is $C_1$-$C_3$alkyl, halogen, or —CN and is substituted in the ortho and meta positions of the phenyl ring;

b) $R^3$ is hydrogen, and $R^4$ is piperidin-4-yl (f-i), wherein the piperidin-4-yl ring is either unsubstituted or is substituted at one or more substitutable carbon atoms with 1 or 2 occurrences of $R^{13}$ and at any substitutable nitrogen atom with $R^{14}$ wherein:

$R^{13}$ is —CH$_3$, —CH$_2$CH$_3$, —CH$_2$CH(CH$_3$)$_2$, —CH(CH$_3$)$_2$, CO$_2$CH$_2$CH$_3$, —CH$_2$OH, or CONH$_2$ or two occurrences of $R^{13}$, taken together, form a fused 5- or 6-membered cycloaliphatic ring;

$R^{14}$ is —COR$^{17}$, —C(O)—(CH$_2$)$_x$—(CR$^{17a}$R$^{17b}$)$_y$R$^{17}$, (O)—(CH$_2$)$_x$—(CR$^{17a}$R$^{17b}$)$_y$N(R$^{17}$)$_2$, —C(O)N(R$^{17}$)$_2$, or —C(O)OR$^{17}$, and x is 0 or 1, and y is 0 or 1, $R^{17a}$ or $R^{17b}$ are each independently selected from hydrogen, substituted or unsubstituted $C_1$-$C_4$alkyl, or a substituted or unsubstituted ring selected from phenyl, cyclohexyl, imidazolyl, thiazolyl, oxazolyl, pyrrolyl, pyrazolyl, thiophene, furyl, —($C_1$-$C_3$alkyl)phenyl, —($C_1$-$C_3$alkyl)cyclohexyl, —($C_1$-$C_3$alkyl)imidazolyl, —($C_1$-$C_3$alkyl)thiazolyl, —($C_1$-$C_3$alkyl)oxazolyl, —($C_1$-$C_3$alkyl)pyrrolyl, —($C_1$-$C_3$alkyl)pyrazolyl, —($C_1$-$C_3$alkyl)thiophene, or —($C_1$-$C_3$alkyl)furyl, wherein $R^{17a}$ and $R^{17b}$ are optionally substituted with up to three occurrences of $R^{17c}$, where $R^{17c}$ is halogen, —CN, —NO$_2$, —OH, —O($C_1$-$C_6$alkyl), —SH, —S($C_1$-$C_6$alkyl), —NH$_2$, —NH($C_1$-$C_6$alkyl), —N($C_1$-$C_6$alkyl)$_2$, —CO($C_1$-$C_6$alkyl), —COOH, —COO($C_1$-$C_6$alkyl), —CONH$_2$, —CONH($C_1$-$C_6$alkyl), —CON($C_1$-$C_6$alkyl)$_2$, —NHCO($C_1$-$C_6$alkyl), —NHSO$_2$($C_1$-$C_6$alkyl), —SO$_2$NH$_2$, —SO$_2$NH($C_1$-$C_6$alkyl);

$R^{17}$ is hydrogen, $C_1$-$C_4$alkyl, or is a ring selected from:

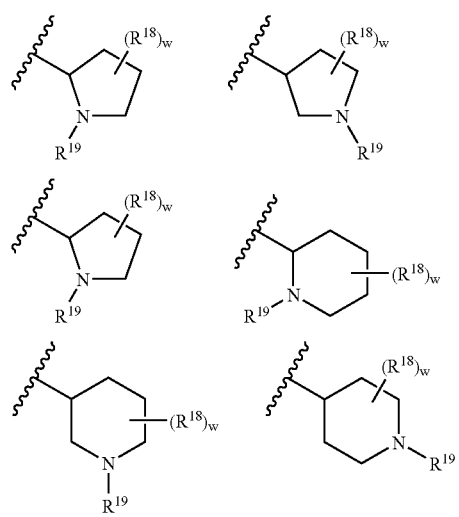

w is 0, 1, or 2, and each occurrence of $R^{18}$, when present, is N, —CH$_3$, —CF$_3$, —CH$_2$CH$_3$, —CH$_2$CH$_2$CH$_3$, —CH(CH$_3$)$_2$, —CH$_2$CH(CH$_3$)$_2$, —OH, —OCH$_3$, —OCF$_3$, —OCH$_2$CH$_3$, phenyl, fused phenyl, —F, —Br, or —Cl, and z is 0 or 1 and $R^{19}$ is —CH$_3$, —CH$_2$CH$_3$, —CH$_2$CH$_2$CH$_3$, —CH(CH$_3$)$_2$, —CH$_2$CH$_2$CH$_2$CH$_3$, substituted or unsubstituted phenyl, —COCH$_3$, —COCH$_2$CH$_3$, —CO(substituted or unsubstituted phenyl), or a substituted r unsubstituted ring selected from isoxazolyl, thiazolyl, pyrrolyl, or pyrazolyl; and c) C=Z is C=O, Xis a bond, and mis 0 or 1.

Yet another preferred embodiment of the present invention is a compound represented by Structural Formulas (XLIV), (XLV), (XLVI), or (XLVII):

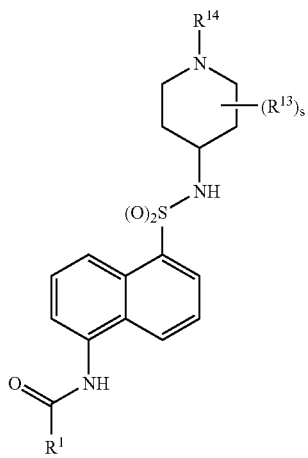

(XLIV)

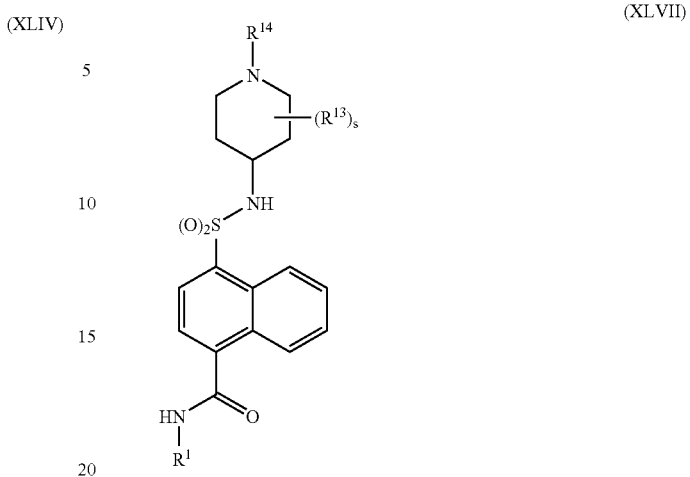

(XLV)

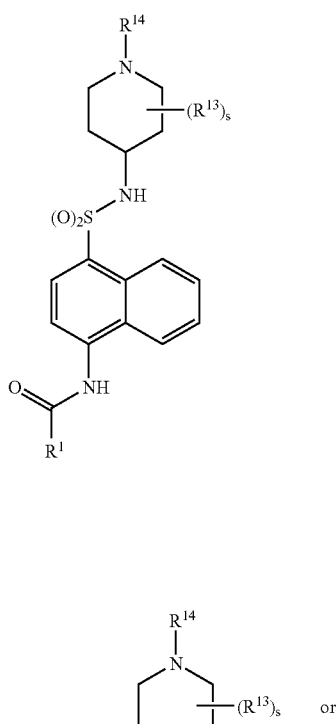

The variables in Structural Formulas (XLIV), (XLV), (XLVI), or (XLVII) are as defined generally and in subsets above.

In other embodiments for compounds of formulas (XLIV), (XLV), (XLVI), or (XLVII), compound variables are:

a) $R^1$ is phenyl (i), pyridyl (ii), imidazolyl (x), thiophene (xv), furyl (xx), benzthiophene (xxxi), cyclohexyl (xL), piperidinyl (xLi), tetrahydropyran (xLiv), cyclopentyl (xLvi), cyclobutyl (xLvii), or cyclopropyl (xLviii), wherein q is 0, 1, or 2 and each occurrence of $R^8$, when present is halogen, —CN, —NO$_2$, —C$_1$-C$_6$alkyl, —OH, —O(C$_1$-C$_6$alkyl), —NH$_2$, —NH(C$_1$-C$_6$alkyl), —N(C$_1$-C$_6$alkyl)$_2$, —SH, —S(C$_1$-C$_6$alkyl), wherein C$_1$-C$_6$alkyl is substituted or unsubstituted; and b) s is 0 and the piperidin-4-yl group is not substituted with $R^{13}$, or s is 1 or 2 and piperidin-4-yl group has one of the following structures:

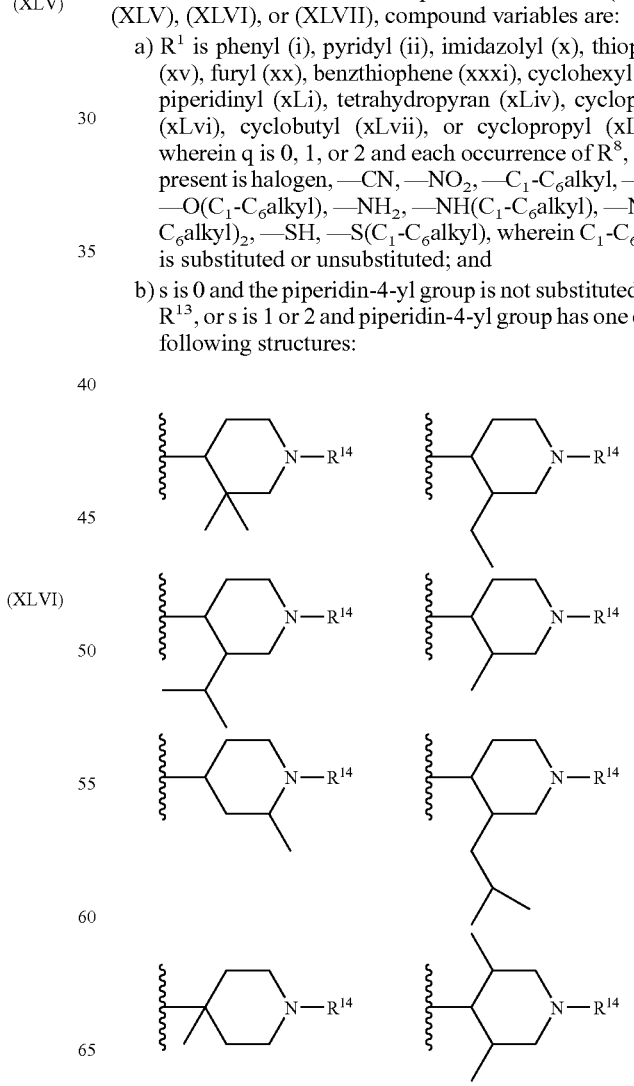

(XLVI) or

-continued

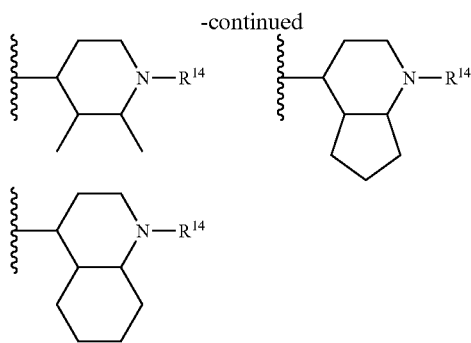

c) $R^{14}$ is —$COR^{17}$, —C(O)—(CH$_2$)—(CR$^{17a}$R$^{17b}$)$_y$R$^{17}$—C(O)—(CH$_2$)$_x$—(CR$^{17a}$R$^{17b}$)$_y$N(R$^{17}$)$_2$, —C(O)N(R$^{17}$)$_2$, or —C(O)OR$^{17}$, and x is 0 or 1, and y is 0 or 1; $R^{17a}$ or $R^{17b}$ are each independently selected from hydrogen, substituted or unsubstituted C$_1$-C$_4$alkyl, or a substituted or unsubstituted ring selected from phenyl, cyclohexyl, imidazolyl, thiazolyl, oxazolyl, pyrrolyl, pyrazolyl, thiophene, furyl, —(C$_1$-C$_3$alkyl)phenyl, —(C$_1$-C$_3$alkyl)cyclohexyl, —(C$_1$-C$_3$alkyl)imidazolyl, —(C$_1$-C$_3$alkyl)thiazolyl, —(C$_1$-C$_3$alkyl)oxazolyl, —(C$_1$-C$_3$alkyl)pyrrolyl, —(C$_1$-C$_3$alkyl)pyrazolyl, —(C$_1$-C$_3$alkyl)thiophene, or —(C$_1$-C$_3$alkyl)furyl, wherein $R^{17a}$ and $R^{17b}$ are optionally substituted with up to three occurrences of $R^{17c}$, where $R^{17c}$ is halogen, —CN, —NO$_2$, —OH, —O(C$_1$-C$_6$alkyl), —SH, —S(C,-C$_6$alkyl), —NH$_2$, —NH(C$_1$-C$_6$alkyl), —N(C$_1$-C$_6$alkyl)$_2$, —CO(C$_1$-C$_6$alkyl), —COOH, —COO(C$_1$-C$_6$alkyl), —CONH$_2$, —CONH(C$_1$-C$_6$alkyl), —CON(C$_1$-C$_6$alkyl)$_2$, —NHCO(C$_1$-C$_6$alkyl), —NHSO$_2$(C$_1$-C$_6$alkyl), —SO$_2$NH$_2$, —SO$_2$NH(C$_1$-C$_6$alkyl);
$R^{17}$ is hydrogen, C$_1$-C$_4$alkyl, or is a ring selected from:

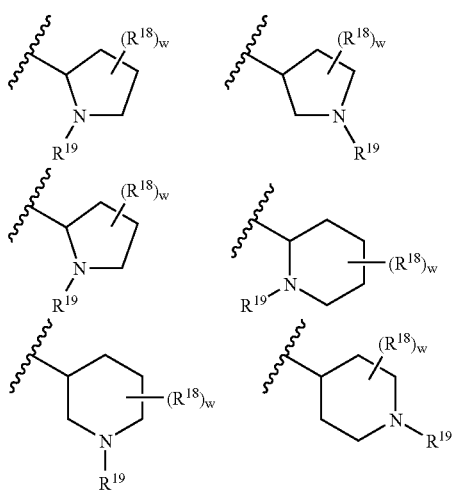

w is 0, 1, or 2, and each occurrence of $R^{18}$, when present, is N, —CH$_3$, —CF$_3$, —CH$_2$CH$_3$, —CH$_2$CH$_2$CH$_3$, —CH(CH$_3$)$_2$, —CH$_2$CH(CH$_3$)$_2$, —OH, —OCH$_3$, —OCF$_3$, —OCH$_2$CH$_3$, phenyl, fused phenyl, —F, —Br, or —Cl, and z is 0 or 1 and $R^{19}$ is —CH$_3$, —CH$_2$CH$_3$, —CH$_2$CH$_2$CH$_3$, —CH(CH$_3$)$_2$, —CH$_2$CH$_2$CH$_3$, substituted or unsubstituted phenyl, —COCH$_3$, —COCH$_2$CH$_3$, —CO(substituted or unsubstituted phenyl), or a substituted or unsubstituted ring selected from isoxazolyl, thiazolyl, pyrrolyl, or pyrazolyl.

In still other embodiments, for compounds described directly above, $R^1$ is a substituted or unsubstituted ring selected from phenyl or pyridyl. In yet other embodiments, $R^1$ is substituted or unsubstituted phenyl. In still other embodiments, $R^1$ is phenyl, q is 1 and $R^8$ is —C$_3$alkyl, halogen, or —CN and is substituted in the ortho position of the phenyl ring. In still other embodiments, $R^1$ is phenyl, q is 2 and each occurrence of $R^8$ is C$_1$-C$_3$alkyl, halogen, or —CN and is substituted at the ortho and meta positions of the phenyl ring.

In yet other embodiments, for compounds described directly above, the piperidinyl-4-yl group is substituted at one carbon atom with —CH$_3$ or —CH$_2$CH$_3$ and has one of the following structures:

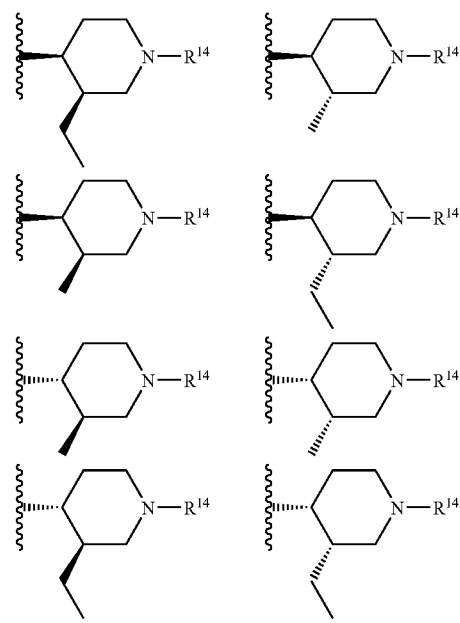

In other embodiments for compounds of formulas (XLIV), (XLV), (XLVI), or (XLVII) compound variables are:
$R^1$ is cyclohexyl or phenyl, furanyl, thienyl or pyridyl optionally substituted with C$_1$-C$_4$ alkyl, C$_1$-C$_4$ alkoxy, C$_1$-C$_4$ haloalkyl, C$_1$-C$_4$ haloalkoxy, methylenedioxy, ethylenedioxy, halogen, cyano, or nitro;
$R^{14}$ is —C(O)R$^{17}$,

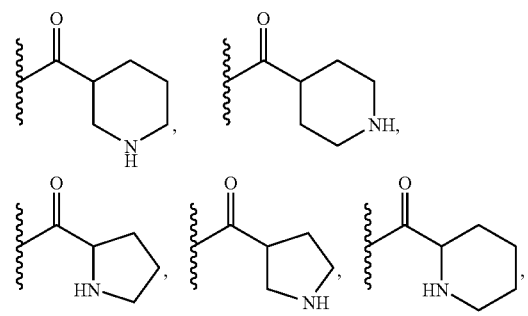

—C(O)OR$^{17}$, —C(O)—NHR$^{17}$, —C(O)—N(R$^{17}$)$_2$ or —C(O)CR$^{17a}$R$^{17b}$N(R$^{17}$)$_2$;

$R^{13}$ is methyl, ethyl 2-hydroxyethyl or iso-propyl, wherein the piperidinyl groups in Structural Formulas (XLIV), (XLV), (XLVI), or (XLVII) are optionally substituted at up to four substitutable carbon atoms with $R^{13}$, and a substitutable methylene group in the piperidinyl rings can optionally be substituted with up to two independently selected $R^{13}$s;

$R^{17}$ is —H or $C_1$-$C_4$ alkyl or —N$(R^{17})_2$ taken together is N-pyrrolidinyl or N-piperidinyl, provided that $R^{17}$ is not —H when $R^{14}$ is —COOR$^{17}$;

when $R^{14}$ is —C(O)CR$^{17a}$R$^{17b}$N$(R^{17})_2$, $R^{17}$ is —H, methyl or ethyl; and $R^{17a}$ and $R^{17b}$ are each independently —H, methyl, ethyl, phenyl, benzyl, 4-hydroxyphenyl or 4-hydroxybenzyl.

4. Uses, Formulation and Administration

Pharmaceutically Acceptable Compositions

As discussed above, the present invention provides compounds that are inhibitors of CCR8, and thus the present compounds are useful for the treatment of diseases, disorders, and conditions including, but not limited to asthma, atopic dermatitis, allergic rhinitis, systemic anaphylaxis or hypersensitivity responses, drug allergies (e.g., to penicillin, cephalosporins), insect sting allergies and dermatoses such as dermatitis, eczema, atopic dermatitis, allergic contact dermatitis, urticaria, rheumatoid arthritis, osteoarthritis, inflammatory bowel disease e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis, disorders of the skin [e.g., psoriasis, erythema, pruritis, and acne], multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease), stroke, cardiac ischemia, mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases, sarcoidosis, vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of CCR8.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_1$-$C_4$alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives: and antioxidants can also be present in the composition, according to the judgment of the formulator.

The disclosed compounds, pharmaceutical compositions and methods can be used to inhibit CCR8 activity, to inhibit I-309 activity and to inhibit or treat (therapeutically or prophylactically) conditions mediated by CCR8 and/or I-309, including inflammatory disorders and allergic conditions. The disclosed compounds can also be advantageously used to inhibit conditions mediated by esinophils and monocytes, T lymphocytes and other immune system cells which express CCR8, including inflammatory disorders and allergic mediated by these cells.

Examples of allergic conditions for which the disclosed compounds, pharmaceutical compositions and methods are particularly effective include asthma. Other allergic conditions which are expected to be treatable by inhibiting CCR8 activity include, atopic dermatitis, allergic rhinitis, systemic anaphylaxis or hypersensitivity responses, drug allergies (e.g., to penicillin, cephalosporins), insect sting allergies and dermatoses such as dermatitis, eczema, atopic dermatitis, allergic contact dermatitis and urticaria.

Examples of diseases with an inflammatory component for which the disclosed compounds, pharmaceutical composition and methods are effective include rheumatoid arthritis, osteoarthritis, inflammatory bowel disease [e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis] and disorders of the skin [e.g., psoriasis, erythema, pruritis, and acne].

Many autoimmune diseases also have an inflammatory component. Examples include multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease). The inflammatory component of these disorders is believed to be mediated, at least in part, by CCR8.

Diseases characterized by repurfusion have an inflammatory component that is believed to be mediated, at least in part by CCR8. Examples include stroke, cardiac ischemia, and the like. The disclosed compounds and compositions also can be used to treat these disorders.

Other diseases and conditions with an inflammatory component believed to be mediated by CCR8 include mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases and sarcoidosis. Yet other diseases or conditions with inflammatory components which are amendable to treatment according to methods disclosed herein include vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

A "subject" is preferably a bird or mammal, such as a human (*Homo sapiens*), but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of the disclosed CCR8 inhibitors is the quantity which inhibits CCR8 activity in a subject in need of such inhibition, or which, when administered to a subject with a CCR8 mediated disease, ameliorates the symptoms of the disease or condition, delays the onset of the symptoms and/or increases longevity. The precise amount of CCR8 inhibitor administered to the subject will depend on the type and severity of the disease or condition and on the characteristics of the subject, such as general health, age, sex, body weight and tolerance to drugs. The dosage may also vary according to the route of administration, which includes oral, aerosol, rectal, transdermal, subcutaneous, intravenous, intramuscular, intraperitoneal and intranasal.

The skilled artisan will be able to determine appropriate dosages depending on these and other factors. An "effective amount" typically ranges between about 0.01 mg/kg/day to about 100 mg/kg/day, preferably between about 0.5 mg/kg/day to about 50 mglkg/day.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. An antagonist of chemokine receptor function can also be administered in combination with one or more additional therapeutic agents, such as, theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFN-β-1a, IFNβ-1b)) and the like.

When a compound of the invention is administered in combination with another therapeutic agent, the compound and agent can be administered in a manner that afford overlap of pharmacological activity, for example, concurrently or sequentially.

The compound can be administered by any suitable route, including, for example, orally in capsules, suspensions or tablets or by parenteral administration. Parenteral administration can include, for example, systemic administration, such as by intramuscular, intravenous, subcutaneous or intraperitoneal injection. The compound can also be administered orally (e.g., dietary), transdermally, topically, by inhalation (e.g., intrabronchial, intranasal, oral inhalation or intranasal drops), or rectally, depending on the disease or condition to be treated. Oral or parenteral administration are preferred modes of administration. The compound can be administered to the individual as part of a pharmaceutical or physiological composition.

Uses of Compounds and Pharmaceutically Acceptable Compositions

In yet another aspect, a method for the treatment or lessening the severity of inflammatory and allergic disorders is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of an inflammatory or allergic disorder. The compounds and compositions, according to the method of the present invention, may be administered using any amount and any route of administration effective for treating or lessening the severity of an inflammatory or allergic disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a). fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of CCR8, and thus, without wishing to be bound by any particular theory, the compounds and compositions are particularly useful for treating or lessening the severity of a disease, condition, or disorder where activation of CCR8 is implicated in the disease, condition, or disorder. When activation of CCR8 is implicated in a particular disease, condition, or disorder, the disease, condition, or disorder may also be referred to as "a CCR8-mediated disease" or disease symptom. Accordingly, in another aspect, the present invention provides a method for treating or lessening the severity of a disease, condition, or disorder where activation of CCR8 is implicated in the disease state.

The terms "CCR8-mediated disease" or "CCR8-mediated condition", as used herein, mean any disease or other deleterious condition in which CCR8 is known to play a role. The terms "CCR8-mediated disease" or "CCR8-mediated condition" also mean those diseases or conditions that are alleviated by treatment with a CCR8 inhibitor. CCR8-mediated diseases or conditions include, but are not limited to, asthma, atopic dermatitis, allergic rhinitis, systemic anaphylaxis or hypersensitivity responses, drug allergies (e.g., to penicillin, cephalosporins), insect sting allergies and dermatoses such as dermatitis, eczema, atopic dermatitis, allergic contact dermatitis, urticaria, rheumatoid arthritis, osteoarthritis, inflammatory bowel disease e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis, disorders of the skin [e.g., psoriasis, erythema, pruritis, and acne], multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease), stroke, cardiac ischemia, mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or 11D associated with rheumatoid arthritis, or other autoimmune conditions), hypersensitivity pneumonitis, collagen diseases, sarcoidosis, vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting CCR8 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of CCR8 activity in a biological sample is useful for a variety of purposes that are known to one of skill in the art. Examples of such purposes include, but are not limited to, blood transfusion, organ-transplantation, biological specimen storage, and biological assays.

While this invention has been particularly shown and described with references to preferred embodiments thereof, it will be understood by those skilled in the art that various changes in form and details may be made therein without departing from the scope of the invention encompassed by the appended claims.

EXPERIMENTALS

General

All reactions involving air-sensitive reagents were performed under a nitrogen atmosphere. Reagents were used as received from commercial suppliers unless otherwise noted. Anhydrous solvents such as dimethylformamide (DMF), tetrahydrofuran (THF), dichloromethane ($CH_2Cl_2$), and dioxane were obtained from Aldrich Chemical Company in Sure/Seal bottles. $^1$H NMR data were recorded using the Bruker UltraShield 300 MHz/54 mm instrument equipped with Bruker B-ACS60 Auto Sampler or the Varian 300 MHz instrument. Chemical shifts are expressed in ppm downfield from internal tetramethylsilane. Significant $^1$H NMR data are reported in the following order: ppm, multiplicity (s, singlet; d, doublet; t, triplet; q, quartet; m, multiplet; quin, quintet), and number of protons. Intermediates and final compounds were purified by flash chromatography using one of the following instruments: 1. Biotage 4-channel Quad UV Flash Collector equipped with a Quad 1 Pump Module and the Quad 12/25 Cartridge module. 2. Biotage 12-channel Quad UV Flash Collector equipped with a Quad 3 Pump Module and a Quad 3 Cartridge module. 3. Flash column combi-flash chromatography instrument. LC/MS spectra were obtained using a MicroMass Platform LC (Phenomenx C18 column, 5 micron, 50×4.6 mm) equipped with a Gilson 215 Liquid Handler.

Standard LC/MS conditions are as follows:

Formic acid-Standard conditions:

LC-MS data were acquired using the "Formic acid-Standard" method unless otherwise noted.

| | |
|---|---|
| % C (Water) | 95.0 |
| % D (Acetonitrile) | 5.0 |
| % Formic Acid | 0.1 |
| Flow (mL/min) | 3.500 |
| Stop Time (mins) | 4.4 |
| Min Pressure (bar) | 0 |
| Max Pressure (bar) | 400 |
| Oven Temperature Left (° C.) | 25.0 |
| Oven Temperature Right (° C.) | 25.0 |

HP1100 LC Pump Gradient Timetable
The gradient Timetable contains 5 entries which are:

| Time | A % | B % | C % | D % | Flow | Pressure |
|---|---|---|---|---|---|---|
| 0.00 | 0.0 | 0.0 | 95.0 | 5.0 | 3.500 | 400 |
| 3.50 | 0.0 | 0.0 | 0.0 | 100.0 | 3.500 | 400 |
| 4.30 | 0.0 | 0.0 | 0.0 | 100.0 | 3.500 | 400 |
| 4.40 | 0.0 | 0.0 | 95.0 | 5.0 | 4.000 | 400 |
| 5.00 | 0.0 | 0.0 | 95.0 | 5.0 | 4.000 | 400 |

Scheme 1: Preparation of amine intermediates

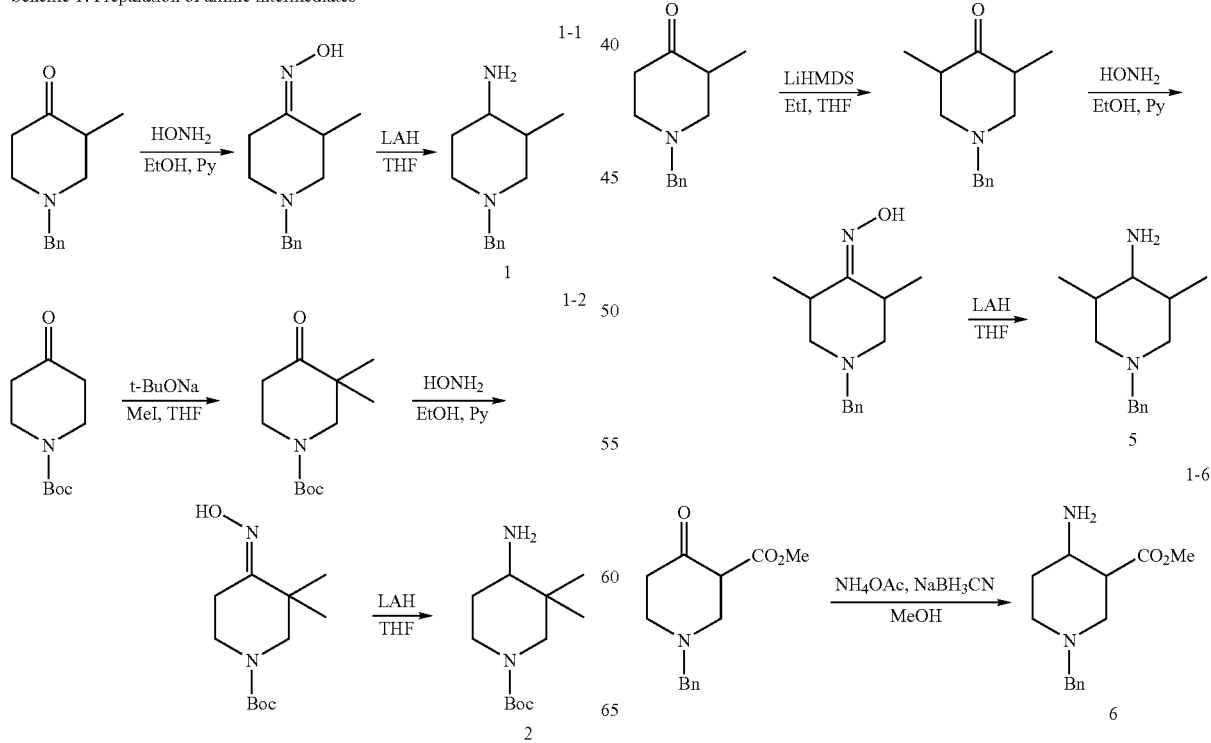

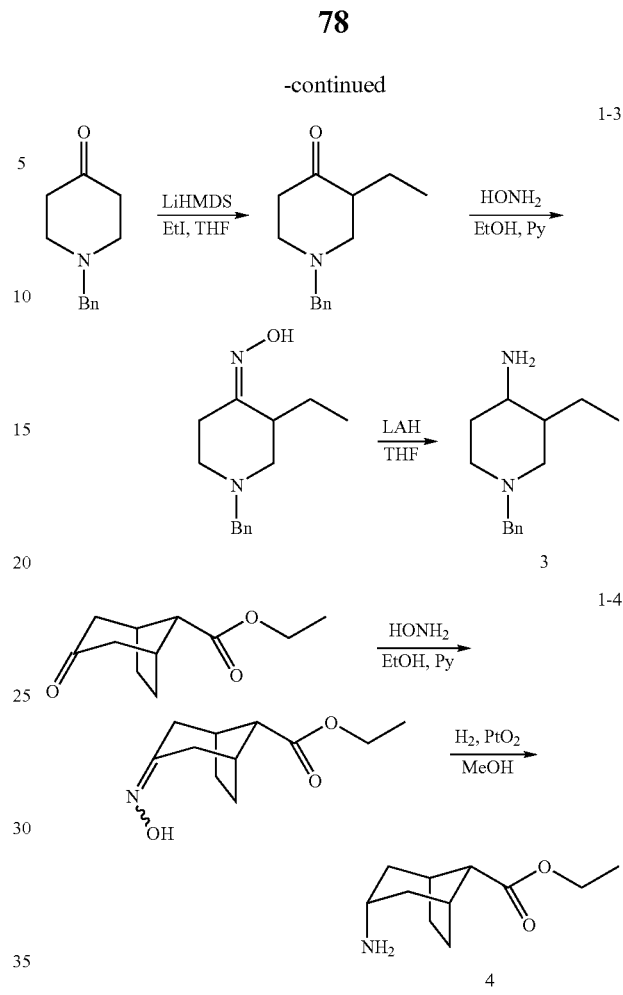

-continued

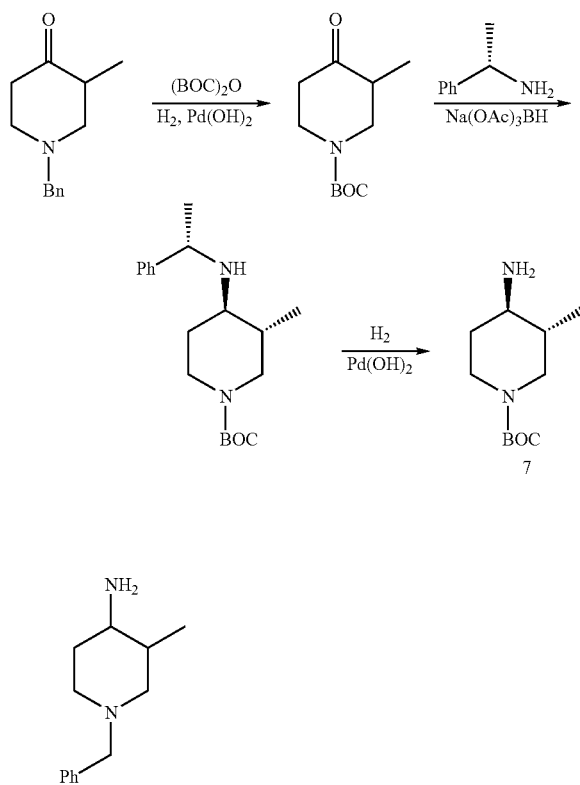

1-Benzyl-3-methyl-piperidin-4-ylamine (1)

To a solution of 1-benzyl-3-methyl-piperidin-4-one (2.04 g, 10 mmol) in EtOH (20 mL), was added pyridine (20 mL, 0.25 mol) and hydroxylamine hydrochloride (0.70 g, 10 mmol). After being stirred at 90+ C. overnight, the resultant solution was concentrated in vacuo to give the crude product 1-benzyl-3-methyl-piperidin-4-one oxime. LC/MS m/z: 219 (M+H)$^+$. This material was used without further purification.

To a 25° C. solution of 1-benzyl-3-methyl-piperidin-4-one oxime in anhydrous THF (20 mL) was added LAH (1.0 M solution TBF), (15 mL, 15 mmol). After being stirred at 50° C. overnight, the resultant mixture was quenched with 20% KOH solution. The aqueous layer was extracted with CH$_2$Cl$_2$. The organic extracts were combined, washed with brine and dried over MgSO$_4$. The solution was filtered and concentrated in vacuo to give the crude mixture ((±)-cis: (±)-trans=1:1) 1-benzyl-3-methyl-piperidin-4-ylamine (1). LC/MS m/z: 205 (M+H)$^+$. This material was used without further purification.

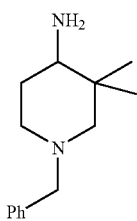

(±)-1-Benzyl-3,3-dimethyl-piperidin-4-one (2)

To a solution of 1-benzyl-3-methyl-piperidin-4-one (7.0 g, 34 mmol) and MeI (2.4 mL) in THF (100 mL) was added NaOt-Bu (4.2 g, 44 mmol) at 0° C. The reaction was slowly allowed to warm to room temperature and stirred overnight. The aqueous layer was extracted with CH$_2$Cl$_2$. The organic extracts were combined, washed with brine and dried over MgSO$_4$. The solution was filtered and concentrated in vacuo to give the crude product. Flash column chromatography (Hexane/EtOAc, gradient) of the residue gave 1-benzyl-3,3-dimethyl-piperidin-4-one, which was converted into 1-benzyl-3,3-dimethyl-piperidin-4-ylamine (2) using the same procedure as in Scheme 1-1. LC/MS m/z: 220 (M+H)$^+$. This material was used without further purification.

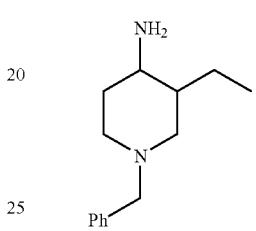

1-Benzyl-3-ethyl-piperidin-4-one (3)

To a −78° C. solution of 1-benzyl-piperidin-4-one (3.79 g, 20 mmol) in anhydrous THF (20 mL) was added lithium hexamethyldisilazide (21 mL, 21 mmol of a 1.0 M solution in THF). After being stirred at −78° C. for 30 min, a solution of iodoethane (1.7 mL, 21 mmol) in THF (5 mL) was added to the reaction mixture. The resultant solution was stirred at 25° C. for 2 h and quenched with water. The aqueous layer was extracted with CH$_2$Cl$_2$. The organic extracts were combined, washed with brine and dried over MgSO$_4$. The solution was filtered and concentrated in vacuo to give the crude product. The crude material was purified by flash column chromatography (hexane/EtOAc) to provide 0.51 g (11.5% yield) of 1-benzyl-3-ethyl-piperidin-4-one, which was converted into 1-benzyl-3-ethyl-piperidin-4-ylamine (3) using the same procedure as in Scheme 1-1. ((±)-cis:(±)-trans=1:1) LC/MS m/z : 219 (M+H)$^+$. This material was used without further purification.

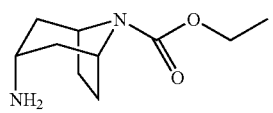

cis-3-Amino-8-aza-bicyclo[3.2.1]octane-8-carboxylic acid ethyl ester (4)

The titled compound was made following the procedure in Scheme 1-1. The oxime (prepared as detailed in Scheme 1-1) (2.5 g) was dissolved in MeOH (10 mL) and AcOH (2 mL) and PtO$_2$ (100 mg) were added at the resultant mixture stirred at room temperature. The reaction mixture was shaken for 2 days at 60 psi under an atmosphere of H$_2$. The resultant solution was filtered and concentrated to give the crude product of racemic 3-amino-8-aza-bicyclo[3.2.1]octane-8-carboxylic acid ethyl ester. It was used without further purification.

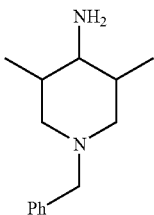

1-Benzyl-3,5-dimethyl-piperidin-4-ylamine (5)

To a −78° C. solution of 1-benzyl-3-methyl-piperidin-4-one (4.06 g, 20 mmol) in anhydrous THF (20 mL) was added lithium hexamethyldisilazide (21 mL, 21 mmol of a 1.0 M solution THF). After being stirred at −78° C. for 30 min, a solution of iodomethane (1.31 mL, 21 mmol) in THF (5 mL) was added into the reaction mixture. The resultant solution was stirred at 25° C. for 2 h and quenched with water. The aqueous layer was extracted with $CH_2Cl_2$. The organic extracts were combined, washed with brine and dried over $MgSO_4$. The solution was filtered and concentrated in vacuo to give the crude product. The crude material was purified by flash column chromatography (hexane/EtOAc) to provide 1.37 g (31.5% yield) of 1-benzyl-3,5-dimethyl-piperidin-4-one.

Following the same procedure as in Scheme 1-1, the crude product 1-benzyl-3,5-dimethyl-piperidin-4-ylamine (5) was prepared as a mixture of diastereomers. LC/MS m/z: 219 (M+H)$^+$. This material was used without further purification.

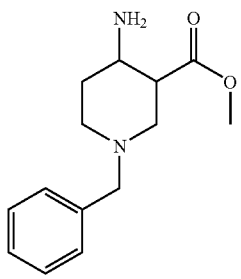

4-Amino-1-benzyl-piperidine-3-carboxylic acid methyl ester (6)

To a 25° C. solution of 1-benzyl-4-oxo-piperidine-3-carboxylic acid methyl ester hydrochloride (2.97 g, 10 mmol) in MeOH (10 mL) was added MP-Carbonate (12 g, 30 mmol, 2.54 mmol/g). After shaking at 25° C. for 1 h, the solution was filtered. To the resultant solution was added ammonium acetate (7.71 g, 100 mmol). After stirring at 65° C. overnight, sodium cyanoborohydride (610 mg, 10 mmol) was added into the resultant mixture and the mixture further stirred for 2 h at 50° C. The solution was then concentrated in vacuo to give a solid. The resultant solid was dissolved in water (100 mL) and the aqueous layer was extracted with $CH_2Cl_2$. The organic extracts were combined, washed with brine and dried over $MgSO_4$. The solution was filtered and concentrated in vacuo to give the crude product 4-amino-1-benzyl-piperidine-3-carboxylic acid methyl ester (6) as a mixture of diastereomers. LC/MS showed m/z: 249 (M+H)$^+$. This material was used without further purification.

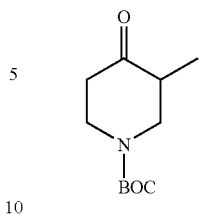

(±)-3-Methyl-4-oxo-piperidine-1-carboxylic acid tert-butyl ester

1-Benzyl-3-methyl-piperidin-4-one (6.5 g, 32.0 mmol) was dissolved in methanol (30 mL). Di-tert-butyl dicarbonate (10.46 g, 48.0 mmol) was added followed by palladium hydroxide (20%, 100 mg) and the reaction shaken overnight at 55 psi under a hydrogen atmosphere. The reaction was filtered and concentrated in vacuo to give a clear oil. Flash column chromatography (75:25 hexanes/ethyl acetate) afforded the title compound as a white solid. Wt.: 5.5 g (81%). $^1$H NMR (300 MHz, CDCl$_3$) δ 4.18 (m, 2H), 3.25 (m, 1H), 2.84 (m, 1H), 2.53 (m, 1H), 2.43 (m, 2H), 1.50 (s, 9H), 1.05 (d, 3H).

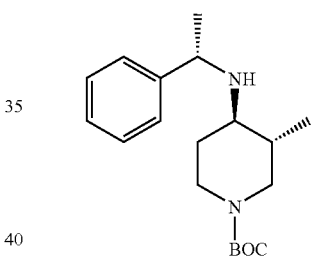

(3R, 4R)-3-methyl-4-(1-(S)-phenyl-ethylamino)-piperidine-1-carboxylic acid tert-butyl ester (±)-3-Methyl-4-oxo-piperidine-1-carboxylic acid tert-butyl ester (5.4 g, 25.3 mmol) was dissolved in dichloromethane (75 mL). S-(−)-α-Methylbenzylamine (3.1 g, 3.2 mL, 25.3 mmol) was added followed by sodium triacetoxyborohydride (10.7 g, 50.6 mmol). The reaction was stirred at room temperature overnight. LC/MS analysis revealed four components, with only one component clearly separated. The reaction was diluted with dichloromethane (150 mL) and extracted water (2×), brine and dried over $MgSO_4$. The solution was filtered and concentrated in vacuo to afford a white foam that was purified by flash column chromatography (84.5:15:0.5 dichloromethane:acetonitrile:NH$_4$OH) to afford a clear oil. This material was rechromatographed (89.5:10:0.5 dichloromethane:acetonitrile:NH$_4$OH) to afford the title compound as a clear oil. Wt.: 820 mg (10%). $^1$H NMR (300 MHz, CDCl$_3$) δ 7.31 (m, 3H), 7.22 (m, 2H), 3.85 (m, 3H), 2.68 (m, 1H), 2.46 (m. 1H), 2.17 (m, 1H), 1.67 (m, 1H), 1.40 (s, 9H), 1.30 (d, 3H), 1.08 (m, 2H), 0.97 (d, 3H); LC/MS m/z 319 (M+H)$^+$.

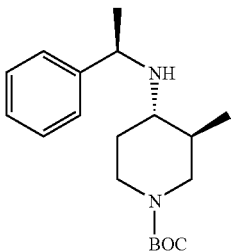

(3S, 4S)-3-methyl-4-(1-(R)-phenyl-ethylamino)-piperidine-1-carboxylic acid tert-butyl ester (±)-3-Methyl-4-oxo-piperidine-1-carboxylic acid tert-butyl ester (5.4 g, 25.3 mmol) was dissolved in dichloromethane (75 mL). R-(+)-α-Methylbenzylamine (3.1 g, 3.2 mL, 25.3 mmol) was added followed by sodium triacetoxyborohydride (10.7 g, 50.6 mmol). The reaction was stirred overnight at room temperature. LC/MS analysis revealed four components, with only one component clearly separated. The reaction was diluted with dichloromethane (150 mL) and extracted twice with water, once with brine and dried over MgSO$_4$. Filtration and concentration in vacuo afforded a white foam that was purified by flash column chromatography (84.5:15:0.5 CH$_2$Cl$_2$:acetonitrile:NH$_4$OH) to afford a clear oil. The material was rechromatographed (89.5:10:0.5 CH$_2$Cl$_2$:acetonitrile:NH$_4$OH) to afford the title compound as a clear oil. Wt.: 547 mg (7%). $^1$H NMR (300 MHz, CDCl$_3$) δ 7.31 (m, 3H), 7.22 (m, 2H), 3.85 (m, 3H), 2.68 (m, 1H), 2.46 (m. 1H), 2.17 (m, 1H), 1.67 (m, 1H), 1.40 (s, 9H), 1.30 (d, 3H), 1.08 (m, 2H), 0.97 (d, 3H); LC/MS m/z 319 (M+H)$^+$.

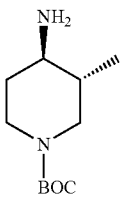

(3R, 4R)-4-amino-3-methyl-piperidine-1-carboxylic acid tert-butyl ester (7)

(3R, 4R)-3-Methyl-4-(1-(S)-phenyl-ethylamino)-piperidine-1-carboxylic acid tert-butyl ester (810 mg, 2.55 mmol) was dissolved in methanol (15 mL). Palladium hydroxide (20%, 100 mg) was added and the mixture was shaken under a hydrogen atmosphere overnight at 55 psi. The reaction was filtered and concentrated in vacuo to give the title compound as a clear oil. Wt.: 500 mg (92%). NMR (300 MHz, CDCl$_3$) δ 4.06 (m, 1H), 3.96 (m, 1H), 2.73 (m, 1H), 2.34 (m, 2H), 1.77 (m, 1H), 1.43 (s, 9H), 1.27 (m, 2H), 0.94 (d, 3H); LC/MS m/z 215 (M+H)$^+$.

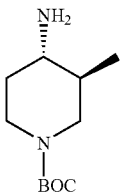

(3S, 4S)-4-amino-3-methyl-piperidine-1-carboxylic acid tert-butyl ester (single enantiomer, absolute configuration undetermined)

(3S, 4S)-3-Methyl-4-(1-(R)-phenyl-ethylamino)-piperidine-1-carboxylic acid tert-butyl ester (510 mg, 1.60 mmol) was dissolved in methanol (15 mL). Palladium hydroxide (20%, 100 mg) was added and the mixture was shaken under a hydrogen atmosphere overnight at 55 psi. The reaction was filtered and concentrated in vacuo to provide the title compound as a clear oil. Wt.: 320 mg (88%). NMR (300 MHz, CDCl$_3$) δ 4.06 (m, 1H), 3.96 (m, 1H), 2.73 (m, 1H), 2.34 (m, 2H), 1.77 (m, 1H), 1.43 (s, 9H), 1.27 (m, 2H), 0.94 (d, 3H); LC/MS m/z 215 (M+H)$^+$.

Scheme 2

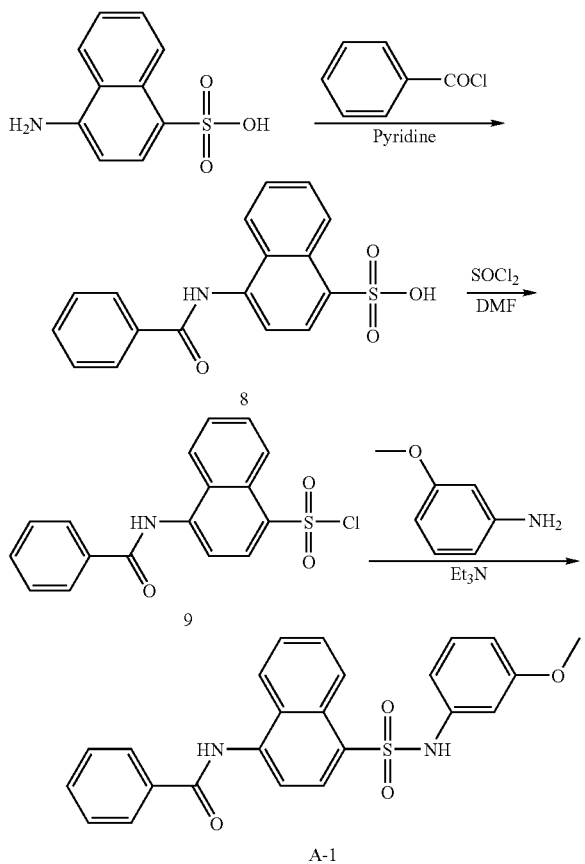

4-Benzoylamino-naphthalene-1-sulfonic acid (8)

To a solution of 4-amino-naphthalene-1-sulfonic acid (2.3 g, 10.0 mmol) in pyridine (15 mL), was added benzoyl chloride (1.4 mL, 12.0 mmol) and the resultant solution was heated at 100° C. and stirred overnight. The solvent was removed in vacuo and the crude material was recrystallized from MeOH (2×) to give the pyridinium salt of 4-benzoylamino-naphthalene-1-sulfonic acid (2.0 g) as a gray colored solid. $^1$H NMR (300 MHz, DMSO) δ 8.92 (m, 3H), 8.60 (t, 1H), 8.00 (m, 6H), 7.55 (m, 6H); LC/MS m/z 327 (M–H)$^-$.

4-Benzoylamino-naphthalene-1-sulfonyl chloride (9)

To a solution of the pyridinium salt of 4-benzoylamino-napthalene-1-sulfonic acid (2.4 g, 5.9 mmol) in DMF (10 mL), was added thionyl chloride (0.6 mL, 8.8 mmol). The resultant solution was stirred at 25° C. for 3 hours. The reaction mixture was quenched by pouring into ice water and filtered to give the title compound (1.8 g) a pale white solid. This material was used without further purification. $^1$H NMR (300 MHz, DMSO) δ 8.88 (d, 1H), 8.09 (d, 2H), 7.97 (d, 2H), 7.55 (m, 6H).

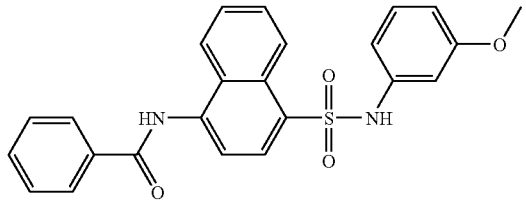

N-[4-(3-Methoxy-phenylsulfamoyl)-naphthalen-1-yl]-benzamide (A-1)

To a solution of 4-benzoylamino-naphthalene-1-sulfonyl chloride (320 mg, 0.93 mmol) in CH$_2$Cl$_2$ (20 mL) was added triethylamine (0.26 mL, 1.85 mmol) and m-anisidine (137 mg, 1.11 mmol). The resultant solution was stirred at 25° C. overnight. The reaction mixture was quenched with water and extracted with CH$_2$Cl$_2$. The organic extracts were combined, washed with brine, dried over Na$_2$SO$_4$, filtered and concentrated to provide the crude product as yellow viscous oil. HPLC purification of the residue gave the title compound (190 mg) as a pale white solid. $^1$H NMR (300 MHz, DMSO) δ 8.72 (d, 1H), 8.26 (d, 1H), 8.15 (d, 1H), 8.02 (d, 2H), 7.78 (d, 1H), 7.60 (m, 5H), 7.00 (t, 1H), 6.55 (m, 2H), 6.46 (d, 1H), 3.56 (s, 3H); LC/MS m/z 433 (M+H)$^+$.

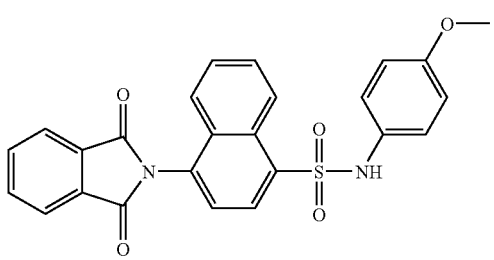

4-(1,3-Dioxo-1,3-dihydro-isoindol-2-yl)-naphthalene-1-sulfonic acid (4-methoxyphenyl)-amide (A-2)

The title compound was made following the general procedure detailed in Scheme 2, substituting phthalic anhydride for benzoyl chloride and benzylamine for m-anisidine. $^1$H NMR (300 MHz, CDCl$_3$) δ 8.75 (d, 1H), 8.20 (d, 1H), 8.02 (m, 2H), 7.87 (m, 2H), 7.66 (m, 3H), 7.42 (d, 1H), 6.86 (d, 2H), 6.69 (d, 2H), 3.72 (s, 3H); LC/MS m/z 459 (M+H)$^+$.

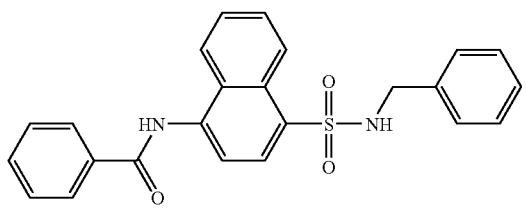

N-(4-Benzylsulfamoyl-naphthalen-1-yl)-benzamide (A-3)

The title compound was made following the general procedure in Scheme 2, substituting benzylamine for m-anisidine. $^1$H NMR (300 MHz, DMSO) δ 8.71 (d, 1H), 8.18 (m, 2H), 8.11 (d, 2H), 7.90 (d, 1H), 7.60 (m, 5H), 7.40 (m, 5H), 4.05 (s, 2H); LC/MS m/z 417 (M+H)$^+$.

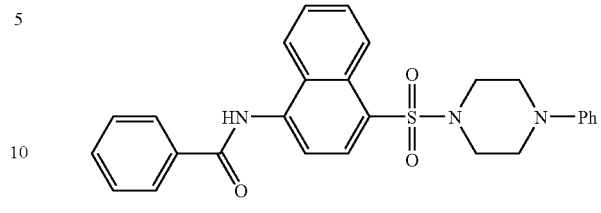

N-[4-(4-Phenyl-piperazine-1-sulfonyl)-naphthalen-1-yl]-benzamide (A-5)

The title compound was made following general procedure in Scheme 2, substituting 1-phenyl-pyrazine for m-anisidine. $^1$H NMR (300 MHz, DMSO) δ 8.68 (d, 1H), 8.22 (d, 1H), 8.05 (d, 1H), 7.87 (d, 1H), 7.60 (m, 5H), 7.15 (m, 2H), 6.85 (d, 2H), 6.72 (t, 1H), 3.17 (m, 4H), 3.11 (m, 4H); LC/MS m/z 472 (M+H)$^+$.

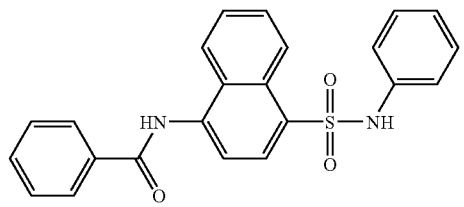

N-(4-Phenylsulfamoyl-naphthalen-1-yl)-benzamide (A-7)

The title compound was made following the general procedure in Scheme 2, substituting aniline for m-anisidine. $^1$H NMR (300 MHz, MeOD) δ 8.76 (d, 1H), 8.16 (d, 1H), 8.05 (d, 1H), 7.96 (d, 2H), 7.60 (m, 6H), 7.00 (m, 5H), LC/MS m/z 403 (M+H)$^+$.

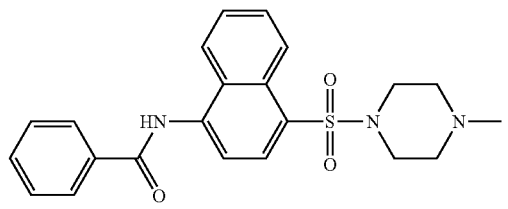

N-[4-(4-Methyl-piperazine-1-sulfonyl)-naphthalen-1-yl]-benzamide (A-8)

The title compound was made following general procedure in Scheme 2, substituting 1-methyl-pyrazine for p-anisidine. $^1$H NMR (300 MHz, MeOD) δ 8.74 (d, 1H), 8.37 (d, 1H), 8.15 (m, 2H), 8.08 (d, 2H), 7.86 (d, 1H), 7.55 (m, 5H), 3.36 (m, 4H), 2.86 (m, 4H), 2.50 (s, 3H); LC/MS m/z 410 (M+H)$^+$.

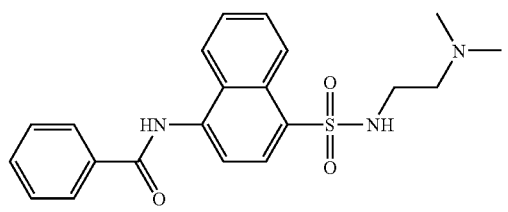

N-[4-(2-Dimethylamino-ethylsulfamoyl)-naphthalen-1-yl]-benzamide (A-9)

The title compound was made following general procedure in Scheme 2, substituting 2-dimethylamino-ethylamine for m-anisidine. $^1$H NM (300 MHz, MeOD) δ 8.74 (d, 1H), 8.45 (s, 1H), 8.30 (d, 1H), 8.22 (d, 1H), 8.08 (d, 2H), 7.85 (d, 1H), 7.65 (m, 5H), 3.10 (m, 4H), 2.74 (s, 6H); LC/MS m/z 398 (M+H)$^+$.

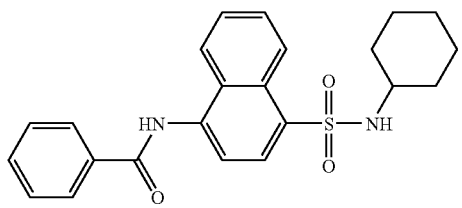

N-(4-Cyclohexylsulfamoyl-naphthalen-1-yl)-benzamide (A-10)

The title compound was made following general procedure in Scheme 2, substituting cyclohexylamine for m-anisidine. $^1$H NMR (300 MHz, MeOD) δ 8.80 (d, 1H), 8.33 (d, 1H), 8.20 (d, 1H), 8.08 (d, 2H), 7.85 (d, 1H), 7.66 (m, 5H), 3.05 (br s, 1H), 1.60 (m, 3H), 1.48 (m, 1H), 1.35 (m, 1H), 1.25 (m, 5H); LC/MS m/z 409 (M+H)$^+$.

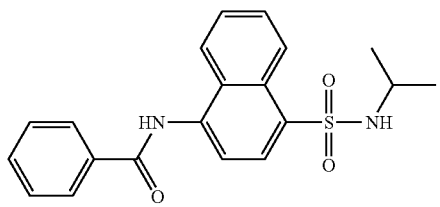

N-(4-Isopropylsulfamoyl-naphthalen-1-yl)-benzamide (A-11)

The title compound was made following general procedure in Scheme 2, substituting isopropylamine for m-anisidine. $^1$H NMR (300 MHz, DMSO) δ 8.69 (d, 1H), 8.19 (d, 2H), 8.09 (d, 2H), 8.02 (d, 2H), 7.81 (d, 1H), 7.60 (m, 5H), 3.07 (m, 1H), 0.88 (m, 6H); LC/MS m/z 369 (M+H)$^+$.

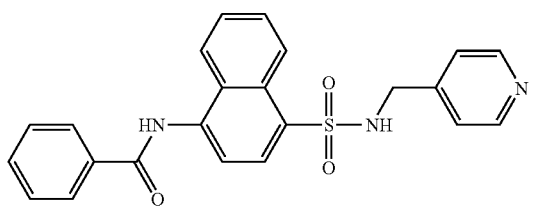

N-{4-[(Pyridin-4-ylmethyl)-sulfamoyl]-naphthalen-1-yl}-benzamide (A-13)

The title compound was made following general procedure in Scheme 2, substituting 4-aminomethyl pyridine for m-anisidine. $^1$H NMR (300 MHz, MeOD) δ 8.76 (d, 1H), 8.22 (d, 2H), 8.14 (d, 1H), 8.09 (d, 2H), 7.74 (d, 1H), 7.60 (m, 5H), 7.08 (d, 2H), 4.10 (s, 2H); LC/MS m/z 418 (M+H)$^+$.

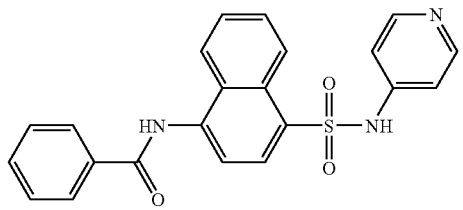

N-[4-(Pyridin-4-ylsulfamoyl)-naphthalen-1-yl]-benzamide (A-14)

The title compound was made following general procedure in Scheme 2, substituting 4-aminopyridine for m-anisidine. $^1$H NMR (300 MHz, DMSO) δ 8.83 (d, 1H), 8.26 (d, 1H), 8.08 (m, 3H), 7.93 (d, 2H), 7.75 (d, 1H), 7.60 (m, 5H), 6.91 (d, 2H); LC/MS m/z 404 (M+H)$^+$.

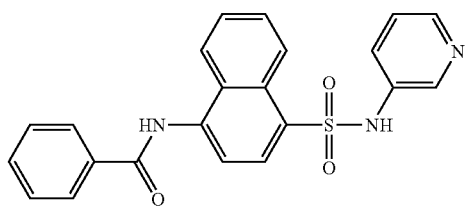

N-[4-(Pyridin-3-ylsulfamoyl)-naphthalen-1-yl]-benzamide (A-16)

The title compound was made following general procedure in Scheme 2, substituting 3-aminopyridine for m-anisidine. $^1$H NMR (300 MHz, DMSO) δ 8.85 (d, 1H), 8.34 (d, 1H), 8.10 (m, 3H), 7.82 (m, 1H), 7.76 (d, 1H), 7.58 (m, 6H), 7.18 (d, 1H), 6.71 (t, 1H); LC/MS m/z 404 (M+H)$^+$.

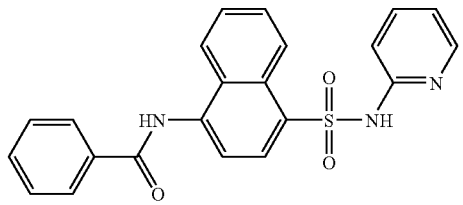

N-[4-(Pyridin-3-ylsulfamoyl)-naphthalen-1-yl]-benzamide (A-17)

The title compound was made following the general procedure in Scheme 2, substituting 2-aminopyridine for m-anisidine. $^1$H NMR (300 MHz, DMSO) δ 8.76 (d, 1H), 8.28 (d, 1H), 8.20 (d, 1H), 8.10 (d, 2H), 8.06 (d, 2H), 7.65 (m, 6H), 7.41 (d, 1H), 7.10 (dd, 1H); LC/MS m/z 404 (M+H)$^+$.

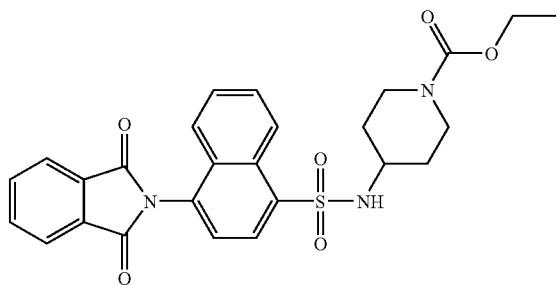

4-[4-(1,3-Dioxo-1,3-dihydro-isoindol-2-yl)-naphthalene-1-sulfonylamino]-piperidine-1-carboxylic acid ethyl ester (A-18)

The title compound was made following the general procedure in Scheme 2, substituting phthalic anhydride for benzoyl chloride, and 4-amino-piperidine-1-carboxylic acid ethyl ester for m-anisidine. $^1$H NMR (300 MHz, MeOD) δ 8.71 (d, 1H), 8.39 (d, 1H), 8.03 (m, 2H), 7.89 (m, 2H), 7.58 (m, 4H), 5.10 (br s, 1H), 4.07 (q, 2H), 3.94 (m, 2H), 3.36 (br s, 1H), 3.08 (m, 1H), 2.78 (m, 2H), 1.75 (m, 2H), 1,33 (m, 2H), 1.21 (t, 3H); LC/MS m/z 508 (M+H)$^+$.

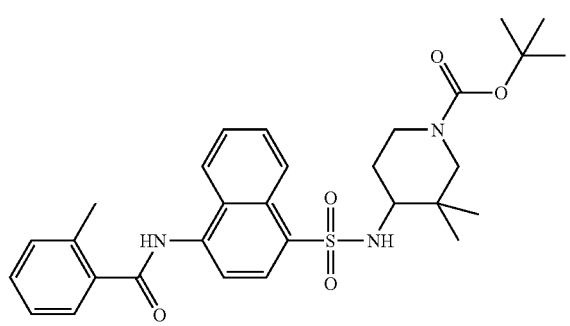

(±)-3,3-Dimethyl-4-[4-(2-methyl-benzoylamino)-naphthalene-0-sulfonylamino]-piperidine-1-carboxylic acid tert-butyl ester (A-19)

The title compound was made following general procedure in Scheme 2, substituting 2-methyl-benzoyl chloride for benzoyl chloride and 4-amino-3,3-dimethyl-piperidine-1-carboxylic acid tert-butyl ester for m-anisidine.IH NMR (300 MHz, MeOD) δ 8.83 (d, 1H), 8.30 (d, 1H), 8.23 (d, 1H), 7.93 (d, 1H), 7.40 (m, 3H), 3.76 (d, 1H), 3.55 (d, 1H), 2.97 (m, 1H), 2.54 (s, 6H); 1.38 (s, 3H), 1.14 (m, 1H), 0.77 (s, 3H), 0.61 (s, 3H); LC/MS m/z 552 (M+H)$^+$.

N-[4-(1-Benzyl-3-methyl-piperidin-4-ylsulfamoyl)-naphthalen-1-yl]-2-methyl-benzamide (A-20)

The title compounds (1:1 mixture) were made following general procedure in Scheme 2, substituting 2-methyl-benzoyl chloride for benzoyl chloride and 4-amino-1-benzyl-3-methyl-piperidine for m-anisidine. LC/MS m/z 528 (M+H)$^+$.

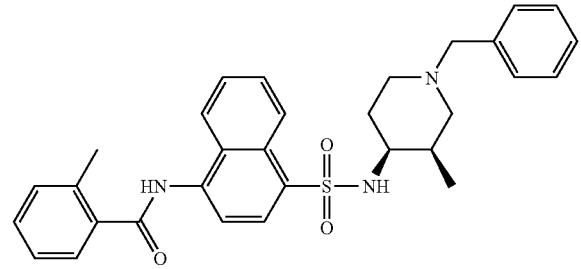

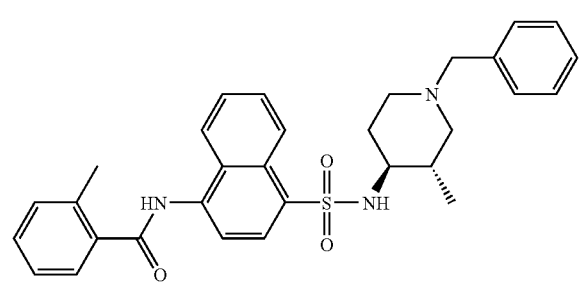

(±)-cis-N-[4-(1-Benzyl-3-methyl-piperidin-4-ylsulfamoyl)-naphthalen-1-yl]-2-methyl-benzamide (A-21) and (±)-trans-N-[4-(1-Benzyl-3-methyl-piperidin-4-ylsulfamoyl)-naphthalen-1-yl]-2-methyl-benzamide (A-23)

The title compounds were made following general procedure in Scheme 2, substituting 2-methyl-benzoyl chloride for benzoyl chloride and 4-amino-1-benzyl-3-methyl-piperidine for m-anisidine. Flash column chromatography of the mixture gave both title compounds respectively. A-21: $^1$H NMR (300 MHz, CDCl$_3$) δ 8.73 (d, 1H), 8.35 (m, 2H), 8.11 (s, 1H), 7.93 (d, 1H), 7.65 (m, 3H), 7.44 (m, 1H), 7.33 (d, 2H), 7.23(m, 5H), 4.70 (d, 1H), 3.38 (q, 2H), 3.29 (m, 1H), 2.58 (s, 3H), 2.25 (br s, 2H), 1.75 (m, 1H), 1.48 (m, 2H), 0.97 (d, 1H); 0.65 (d, 3H); LC/MS m/z 528 (M+H)$^+$. A-23: $^1$H NMR (300 MHz, CDCl$_3$) δ 8.70 (d, 1H), 8.32 (s, 1H), 8.25 (s, 2H), 7.93 (d, 1H), 7.60 (m, 3H), 7.40 (m, 1H), 7.25 (m, 6H), 4.78 (d, 1H), 3.38 (q, 2H), 2.72 (m, 2H), 2.55 (s, 3H), 2.24 (m, 1H), 1.86 (m, 1H), 1.63 (m, 3H), 1.35 (m, 2H); 0.57 (d, 3H); LC/MS m/z 528 (M+H)$^+$.

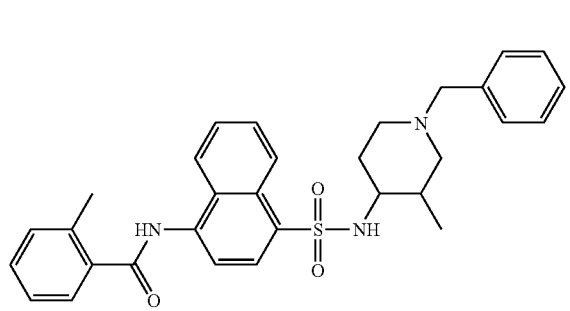

4-Methyl-4-[4-(2-methyl-benzoylamino)-naphthalene-1-sulfonylamino]-piperidine-1-carboxylic acid isopropyl ester (A-22)

The title compound was made following general procedure in Scheme 2, substituting 2-methyl-benzoyl chloride for benzoyl chloride and 4-amino-4-methyl-piperidine-1-carboxylic acid tert-butyl ester for m-anisidine. $^1$H NMR (300 MHz, MeOD) δ 8.78 (d, 1H), 8.380 (m, 2H), 8.19 (d, 1H), 7.95 (d, 2H), 7.68 (m, 3H), 7.44 (m, 1H), 7.35 (m, 2H), 4.78 (s, 1H), 3.40 (m, 2H), 3.03 (m, 2H), 2.68 (s, 3H), 1.72 (m, 2H), 1.470 (m, 2H), 1.38 (s, 9H), 1.18 (s, 3H); LC/MS m/z 524 (M+H)$^+$.

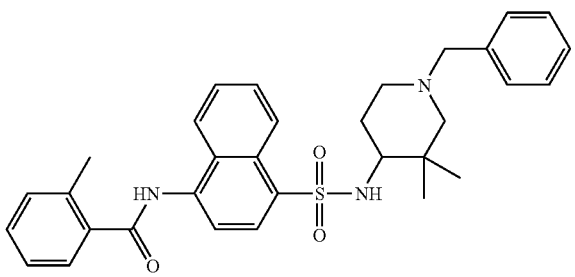

(±)-N-[4-(1-Benzyl-3,3-dimethyl-piperidin-4-ylsulfamoyl)-naphthalen-1-yl]-2-methyl-benzamide (A-24)

The title compound was made following general procedure in Scheme 2, substituting 2-methyl-benzoyl chloride for benzoyl chloride and 4-amino-1-benzyl-3,3-dimethyl-piperidine-1-carboxylic acid tert-butyl ester for m-anisidine. $^1$H NMR (300 MHz, DMSO) δ 8.77 (d, 1H), 8.22 (dd, 2H), 7.91 (d, 1H), 7.70 (m, 4H), 7.35 (m, 3H), 7.22 (m, 5H), 3.30 (q, 2H), 2.67 (m, 1H), 2.57 (m, 1H), 2.47 (s, 3H), 2.25 (d, 1H), 1.68 (t, 1H), 1.56 (d, 1H), 1.47 (m, 1H), 1.04 (m, 1H); 0.85 (s, 3H), 0.45(s, 3H); LC/MS m/z 542 (M+H)$^+$.

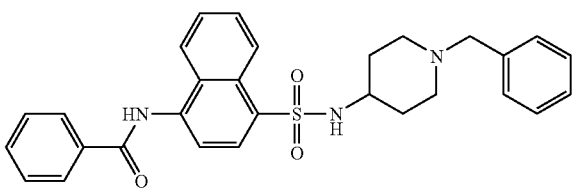

N-[4-(1-Benzyl-piperidin-4-ylsulfamoyl)-naphthalen-1-yl]-benzamide (A-25)

The title compound was prepared following the general procedure in Scheme 2, substituting 4-amino-1-benzyl-piperidine for m-anisidine.

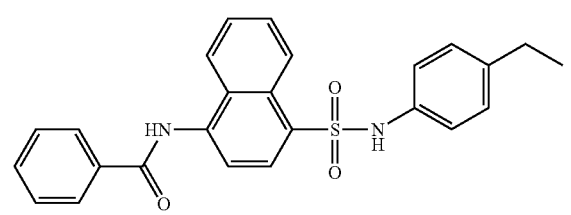

N-[4-(4-Ethyl-phenylsulfamoyl)-naphthalen-1-yl]-benzamide (A-26)

The title compound was prepared following the general procedure in Scheme 2, substituting 4-ethyl-phenylamine for m-anisidine. $^1$H NMR (300 MHz, DMSO) δ 8.76 (d, 1H), 8.21 (d, 1H), 8.16 (d, 1H), 8.07 (s, 1H), 8.04 (m, 1H), 7.78 (d, 1H), 7.76 (m, 5H), 6.94 (m, 4H), 2.4 (m, 2H), 1.03 (t, 3H); LC/MS (M+H)$^+$ m/z 431.

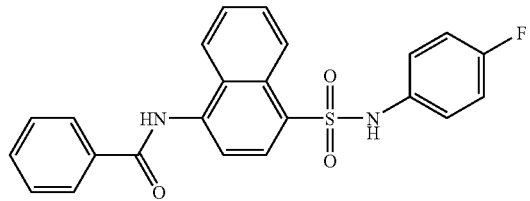

2-Methyl-penta-2,4-dienoic acid [4-(4-fluoro-phenylsulfamoyl)-naphthalen-1-yl]-amide (A-27)

The title compound was prepared following the general procedure in Scheme 2, substituting 4-fluoro-phenyl-amine for m-anisidine. $^1$H NMR (300 MHz, DMSO) δ 8.74 (d, 1H), 8.18 (m, 3H), 8.06 (d, 2H), 7.67 (m, 7H), 7.0 (m, 4H); LC/MS (M+H)$^+$ m/z 421.

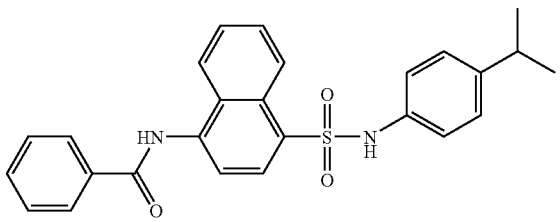

N-[4-(4-Isopropyl-phenylsulfamoyl)-naphthalene-1-yl]-benzamide (A-28)

The title compound was prepared following the general procedure in Scheme 2, substituting 4-isopropyl-phenylamine for m-anisidine. $^1$H NMR (300 MHz, DMSO) δ 8.76 (d, 1H), 8.25 (d, 1H), 8.18 (d, 1H), 8.05 (m, 2H), 7.8 (d, 1H), 7.65 (m, 5H), 6.95 (m, 4H), 2.7 (m, 1H), 1.05 (d, 6H); LC/MS (M+H)$^+$ m/z 445.

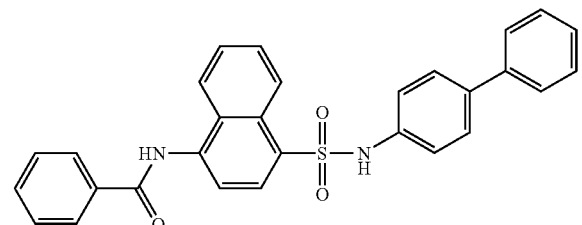

N-[Biphenyl-4-yl sulfamoyl)-naphthalen-1-yl]-benzamide (A-29)

The title compound was prepared following the general procedure in Scheme 2, substituting biphenyl-4-yl amine for m-anisidine. $^1$H NMR (300 MHz, DMSO) δ 8.79 (d, 1H), 8.31 (d, 1H), 8.18 (d, 1H), 8.05 (s, 1H), 8.03 (s, 1H), 7.82 (d, 1H), 7.76 (m, 1H), 7.6 (m, 8H), 7.36 (t, 2H), 7.26 (m, 1H), 7.13 (s, 1H), 7.11 (s, 1H); LC/MS (M+H)$^+$ m/z 479.

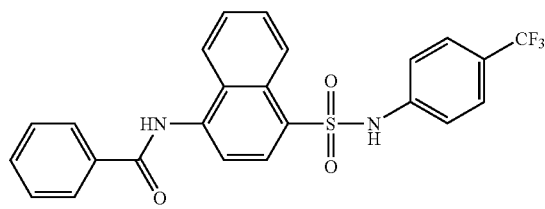

N-[4-(4-Trifluoromethyl-phenylsulfamoyl)-naphthalen-1-yl]-benzamide (A-30)

The title compound was prepared following the general procedure in Scheme 2, substituting 4-trifluoromethyl-phenylamine for m-anisidine. $^1$H NMR (300 MHz, DMSO) δ 8.27 (d, 1H), 8.11 (d, 1H), 8.08 (s, 1H), 8.05 (d, 2H), 7.77 (d, 1H), 7.58 (m, 5H), 7.42 (d, 2H), 7.12 (d, 2H); LC/MS (M+H)$^+$ m/z 469.

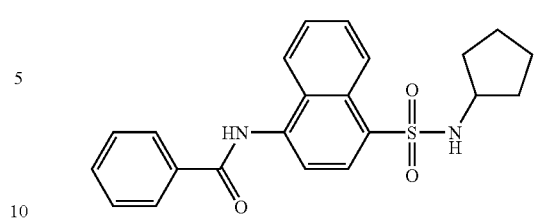

N-(4-Cyclopentysulfamoyl-naphthalen-1-yl)-benzamide (A-35)

The title compound was prepared following the general procedure in Scheme 2, substituting cyclopentylamine for m-anisidine. $^1$H NMR (300 MHz, MeOD) δ 8.29 (d, 1H), 8.19 (d, 1H), 8.10 (m, 1H), 8.07 (m, 1H), 7.82 (d, 1H), 7.65 (m, 5H), 3.51 (m, 1H), 1.56 (m, 4H), 1.34 (m, 5H); LC/MS (M+H)$^+$ m/z 395.

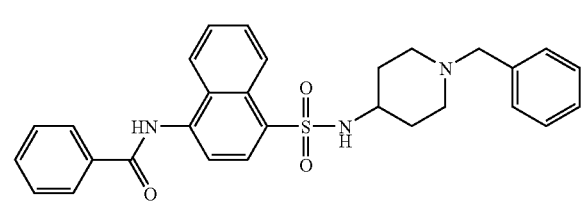

N-[4-(1-Benzyl-piperidin-4-ylsulfamoyl)-naphthalen-1-yl]-benzamide (A-31)

The title compound was prepared following the general procedure in Scheme 2, substituting 1-benzyl-piperidin-4-yl amine for m-anisidine. $^1$H NMR (300 MHz, MeOD) δ 8.73 (d, 1H), 8.30 (d, 1H), 8.18 (d, 1H), 8.09 (s, 1H), 8.07 (m, 1H), 7.80 (d, 1H), 7.65 (m, 5H), 7.42 (m, 5H), 4.17 (s, 2H), 3.34 (m, 2H), 2.92 (m, 2H), 1.86 (d, 3H), 1.64 (m, 2H); LC/MS (M+H)$^+$ m/z 500.

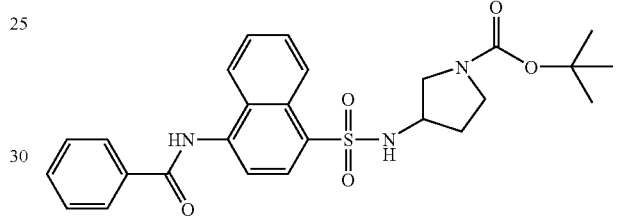

3-(4-Benzoylamino-naphthalene-1-sulfonylamino)-pyrrolidine-1-carboxylic acid tert-butyl ester (A-37)

The title compound was prepared following the general procedure in Scheme 2, substituting 3-amino-pyrrolidine-1-carboxylic acid tert-butyl ester for m-anisidine. $^1$H NMR (300 MHz, MeOD) δ 8.79 (d, 1H), 8.35 (d, 1H), 8.25 (d, 1H), 8.11 (d, 2H), 7.89 (m, 1H), 7.69 (m, 5H), 3.78 (m, 1H), 3.03 (m, 1H), 1.88 (m, 1H), 1.71 (m, 1H), 1.41 (d, 9H); LC/MS (M+H)$^+$ m/z 496.

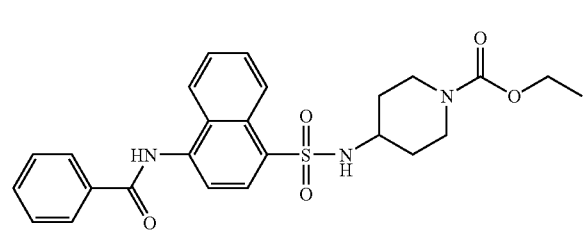

4-(4-Benzoylamino-naphthalene-1-sulfonylamino)-piperidine-1-carboxylic acid ethyl ester (A-34)

The title compound was prepared following the general procedure in Scheme 2, substituting 4-amino-piperidine-1-carboxylic acid ethyl ester for m-anisidine. $^1$H NMR (300 MHz, MeOD) δ 8.75 (d, 1H), 8.31 (d, 1H), 8.11 (m, 1H), 8.09 (m, 1H), 8.07 (m, 1H), 7.82 (d, 1H), 7.65 (m, 5H), 4.03 (m, 2H), 3.82 (m, 2H), 2.78 (m, 2H), 1.56 (m, 2H), 1.28 (m, 2H), 1.19 (t, 3H); LC/MS (M+H)$^+$ m/z 480.

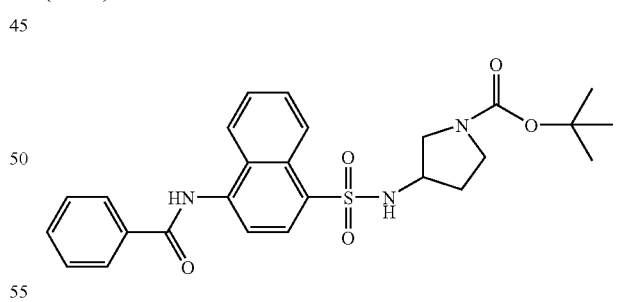

4-(4-Benzoylamino-naphthalene-1-sulfonylamino)-piperidine-1-carboxylic acid tert-butyl ester (A-38)

The title compound was prepared following the general procedure in Scheme 2, substituting 4-amino-piperidine-1-carboxylic acid tert-butyl ester for m-anisidine. $^1$H NMR (300 MHz, MeOD) δ 8.75 (d, 1H), 8.31 (d, 1H), 8.19 (d, 1H), 8.09 (m, 1H), 8.07 (m, 1H), 7.82 (d, 1H), 7.65 (m, 5H), 3.78 (m, 2H), 2.73 (m, 2H), 1.52 (m, 3H), 1.39 (s, 9H), 1.28 (m, 2H); LC/MS (M+H)$^+$ m/z 510.

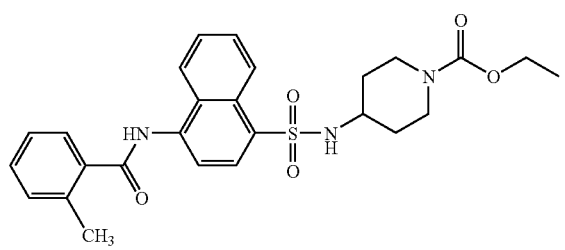

4-[4-(2-Methyl-benzoylamino)-naphthalene-1-sulfonylamino]-piperidine-1-carboxylic acid ethyl ester (A-40)

The title compound was prepared following the general procedure in Scheme 2, substituting 4-amino-piperidine-1-carboxylic acid ethyl ester for m-anisidine and 2-methyl benzoyl chloride for benzoyl chloride. $^1$H NMR (300 MHz, MeOD) δ 8.74 (d, 1H), 8.31 (d, 1H), 8.23 (d, 1H), 7.92 (d, 1H), 7.72 (m, 3H), 7.39 (m, 3H), 4.04 (q, 2H), 3.83 (m, 2H), 3.25 (m, 1H), 2.78 (m, 2H), 2.55 (s, 3H), 1.56 (m, 2H), 1.28 (m, 2H), 1.18 (t, 3H); LC/MS (M+H)$^+$ m/z 496.

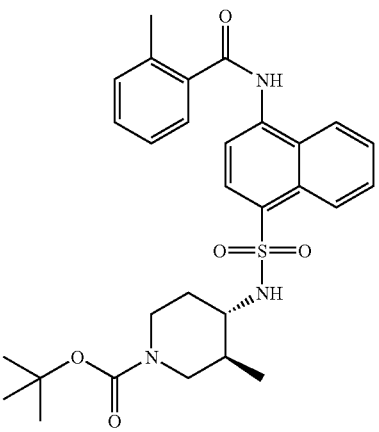

(3S, 4S)-3-Methyl-4-[4-(2-methyl-benzoylamino)-naphthalene-1-sulfonylamino]-piperidine-1-carboxylic acid tert-butyl ester (A-42)

The title compound was prepared according to the general procedure in Scheme 2, substituting (3S, 4S)-4-amino-3-methyl-piperidine-1-carboxylic acid tert-butyl ester for m-anisidine, and 2-methylbenzoyl chloride for benzoyl chloride. $^1$H NMR (300 MHz, CDCl$_3$) δ 8.69 (d, 1H), 8.40 (m, 1H), 8.32 (m, 1H), 8.12 (s, 1H), 7.69 (m, 1H), 7.63 (m, 2H), 7.43 (m, 1H), 7.32 (m, 2H), 4.48 (d, 1H), 3.87 (m, 2H), 2.82 (m, 1H), 2.57 (s, 3H), 2.28 (m, 1H), 1.64 (m, 1H), 1.17 (m, 2H), 0.58 (m, 3H); LC/MS nvz 538 (M+H)$^+$.

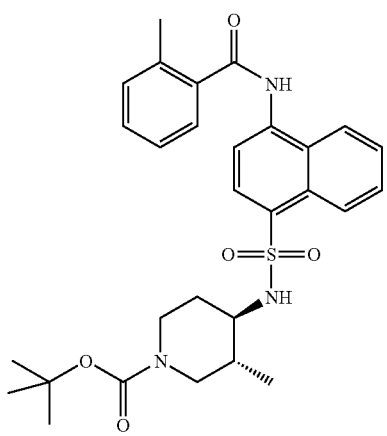

(3R, 4R)-3-Methyl-4-[4-(2-methyl-benzoylamino)-naphthalene-1-sulfonylamino]-piperidine-1-carboxylic acid tert-butyl ester (A-41)

The title compound was prepared according to the general procedure in Scheme 2, substituting (3R, 4R)-4-amino-3-methyl-piperidine-1-carboxylic acid tert-butyl ester for m-anisidine, and 2-methylbenzoyl chloride for benzoyl chloride. $^1$H NMR (300 MHz, CDCl$_3$) δ 8.69 (d, 1H), 8.40 (m, 1H), 8.32 (m, 1H), 8.12 (s, 1H), 7.69 (m, 1H), 7.63 (m, 2H), 7.43 (m, 1H), 7.32 (m, 2H), 4.48 (d, 1H), 3.87 (m, 2H), 2.82 (m, 1H), 2.57 (s, 3H), 2.28 (m, 1H), 1.64 (m, 1H), 1.17 (m, 2H), 0.58 (m, 3H); LC/MS m/z 538 (M+H)$^+$.

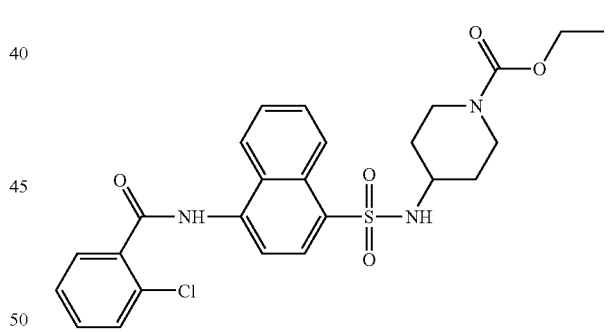

4-[4-(2-Chloro-benzoylamino)-naphthalene-1-sulfonylamino]-piperidine-1-carboxylic acid ethyl ester (A-43)

The title compound was made following general procedure in Scheme 2, substituting 4-(2-chloro-benzoylamino)-naphthalene-1-sulfonyl chloride for 4-benzoylamino-naphthalene-1-sulfonyl chloride benzylamine and substituting 4-amino-piperidine-1-carboxylic acid ethyl ester for m-anisidine. $^1$H NMR (300 MHz, MeOD) δ 8.75 (d, 1H), 8.31 (d, 2H), 7.98 (d, 2H), 7.73 (m, 3H), 7.53 (m, 3H), 4.02 (q, 2H), 3.72 (d, 2H), 3.42 (m, 1H), 2.75 (m, 2H), 1.55 (m, 2H), 1.25 (m, 2H), 1.15 (t, 3H); LC/MS m/z 516 (M+H)$^+$

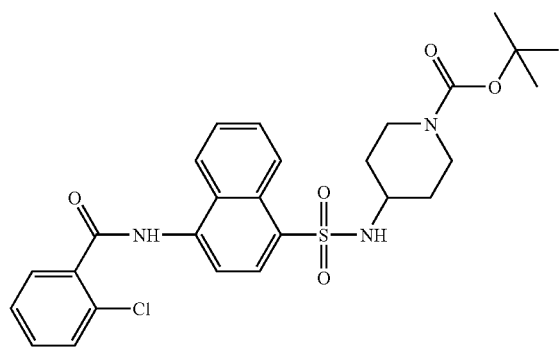

4-[4-(2-Chloro-benzoylamino)-naphthalene-1-sulfonylamino]-piperidine-1-carboxylic acid tert-butyl ester (A-44)

The title compound was made following general procedure in Scheme 2, substituting 4-(2-chloro-benzoylamino)-naphthalene-1-sulfonyl chloride for 4-benzoylamino-naphthalene-1-sulfonyl chloride benzylamine and substituting 4-amino-piperidine-1-carboxylic acid tert-butyl ester for m-anisidine. $^1$H NMR (300 MHz, CDCl$_3$) δ 8.70 (m, 2H), 8.36 (m, 2H), 8.08 (d, 1H), 7.90 (m, 1H), 7.67 (m, 2H), 7.48 (m, 3H), 4.80 (d, 1H), 3.82 (m, 2H), 3.25 (m, 1H), 2.70 (t, 2H), 1.65 (m, 3H), 1.35 (s, 9H), 1.20 (m, 2H); LC/MS m/z 544 (M+H)$^+$

(±)-(cis, trans)-N-[4-(1-Benzyl-3,5-dimethyl-piperidin-4-ylsulfamoyl)-naphthalen-1-yl]-2-methyl-benzamide (A-45) and (±)-(cis, cis)-N-[4-(1-Benzyl-3,5-dimethyl-piperidin-4-ylsulfamoyl)-naphthalen-1-yl]-2-methyl-benzamide (A-46)

The title compounds were made following general procedure in Scheme 2, substituting 4-(2-methyl-benzoylamino)-naphthalene-1-sulfonyl chloride for 4-benzoylamino-naphthalene-1-sulfonyl chloride benzylamine and substituting 1-benzyl-3,5-dimethyl-piperidin-4-ylamine 6 for m-anisidine. After flash column separation, A-45 and A-46 were obtained. A-45: $^1$H NMR (300 MHz, CDCl$_3$) δ 8.77 (d, 1H), 8.36 (m, 2H), 8.10 (s, 1H), 7.92 (d, 1H), 7.66 (m, 3H), 7.44 (m, 1H), 7.34 (m, 1H), 7.22 (m, 6H), 4.65 (d, 1H), 3.34 (dd, 2H), 2.90 (m, 1H), 2.59 (s, 3H), 2.35 (m, 1H), 2.05 (d, 1H), 1.70 (s, br, 3H), 1.57 (s, 1H), 0.75 (d, 3H), 0.60 (d, 3H); LC/MS m/z 543 (M+H)$^+$; A-46: $^1$H NMR (300 MHz, CDCl$_3$) δ 8.25(d, 1H), 8.34 (m, 4H), 7.98 (d, 1H), 7.64 (m, 3H), 7.43 (m, 1H), 7.31 (m, 6H), 6.15 (d, 1H), 3.84 (s, 2H), 3.40 (d, 1H), 2.80 (d, 3H), 2.56 (s, 3H), 2.30 (t, 2H), 2.10 (s, br, 2H), 0.42 (d, 6H); LC/MS m/z 543 (M+H)$^+$

(±)-(cis)-1-Benzyl-4-[4-(2-methyl-benzoylamino)-naphthalene-1-sulfonylamino]-piperidine-3-carboxylic acid ethyl ester (A-47) and (±)-(trans)-1-Benzyl-4-[4-(2-methyl-benzoylamino)-naphthalene-1-sulfonylamino]-piperidine-3-carboxylic acid ethyl ester (A-48)

The title compounds were made following general procedure in Scheme 2, substituting 4-(2-methyl-benzoylamino)-naphthalene-1-sulfonyl chloride for 4-benzoylamino-naphthalene-1-sulfonyl chloride benzylamine and substituting 4-amino-1-benzyl-piperidine-3-carboxylic acid ethyl ester 5 for m-anisidine. After flash column separation, A-47 and A-48 were obtained. A47: $^1$H NMR (300 MHz, CDCl$_3$) δ 8.65 (d, 1H), 8.32 (m, 2H), 8.30 (s, 1H), 7.88 (d, 1H), 7.64 (m, 3H), 7.42 (t, 1H), 7.32 (m, 2H), 7.20 (m, 5H), 6.18 (d, 1H), 3.85 (m, 2H), 3.45 (m, 1H), 3.25 (m, 2H), 3.00 (d, 1H), 2.65 (s, 1H), 2.55 (s, 3H), 2.35 (s, 1H), 1.80 (m, 3H), 1.42 (m, 1H), 1.00 (t, 3H); LC/MS m/z 586 (M+H)$^+$; A-48: $^1$H NMR (300 MHz, CDCl$_3$) δ 8.64 (d, 1H), 8.36 (m, 2H), 8.10 (s, 1H), 7.90 (d, 1H), 7.65 (m, 3H), 7.42 (t, 1H), 7.32 (m, 2H), 7.24 (m, 5H), 4.95 (d, 1H), 3.50 (m, 4H), 2.86 (d, 1H), 2.70 (m, 2H), 2.51 (s, 3H), 2.20 (t, 1H), 2.02 (t, 1H), 1.88 (m, 3H), 1.48 (m, 1H), 1.00 (t, 3H); LC/MS m/z 586 (M+H)$^+$

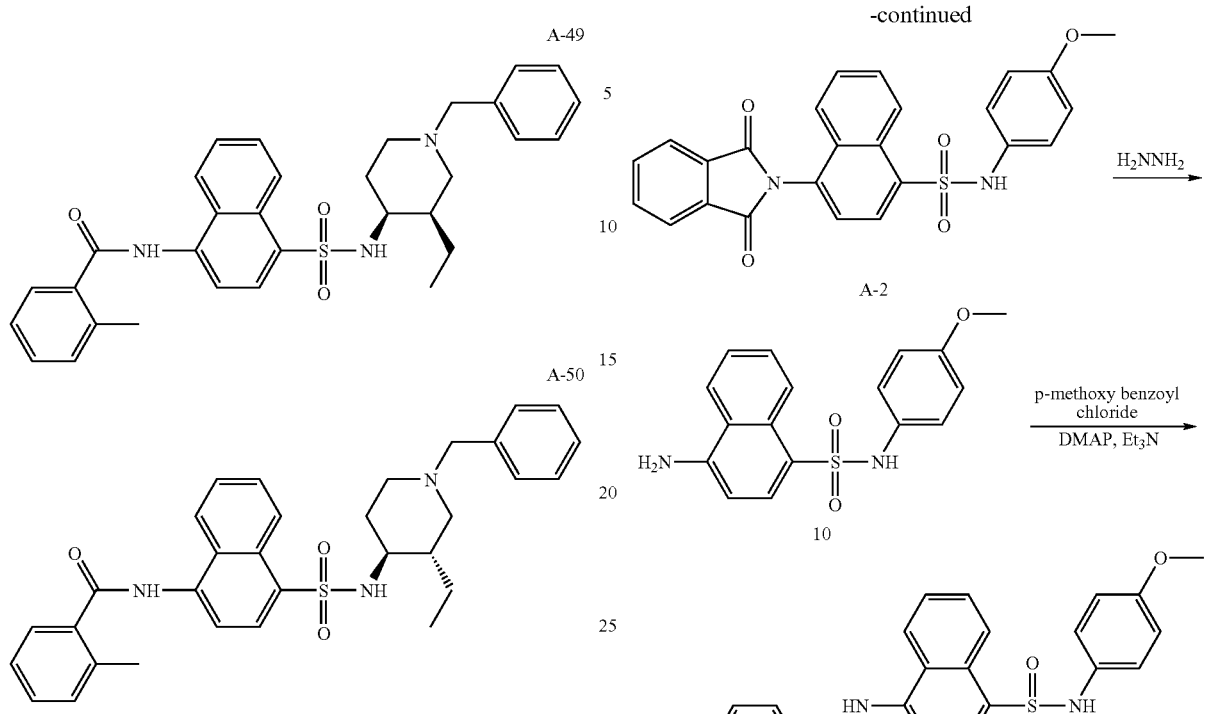

(±)-(cis)-N-[4-(1-Benzyl-3-ethyl-piperidin-4-ylsulfamoyl)-naphthalen-1-yl]-2-methyl-benzamide (A-49) and (±)-(trans)-N-[4-(1-Benzyl-3-ethyl-piperidin-4-ylsulfamoyl)-naphthalen-1-yl]-2-methyl-benzamide (A-50)

The title compounds were made following general procedure in Scheme 2, substituting 4-(2-methyl-benzoylamino)-naphthalene-1-sulfonyl chloride for 4-benzoylamino-naphthalene-1-sulfonyl chloride benzylaamine and substituting 1-benzyl-3-ethyl-piperidin-4-ylamine 3 for m-anisidine. After flash column separation and further HPLC purification, A-49 and A-50 formic acid salts were obtained. A-49: $^1$H NMR (300 MHz, CDCl$_3$) δ 8.42 (d, 1H), 8.18 (s, 1H), 8.00 (d, 2H), 7.65 (d, 1H), 7.30 (m, 3H), 7.05 (t, 1H), 6.95 (m, 8H), 5.30 (s, br, 1H), 3.50 (s, br, 1H), 3.20 (q, 2H), 3.08 (s, 1H), 2.21 (s, 3H), 2.05 (m, 3H), 1.20 (m, 3H), 0.60 (m, 2H), 0.05 (t, 3H); LC/MS m/z 542 (M+H)$^+$; $^{A-}$50: $^1$H NMR (300 MHz, CDCl$_3$) δ 8.70 (d, 1H), 8.30 (m, 2H), 8.20 (s, 1H), 7.90 (d, 1H), 7.60 (m, 3H), 7.42 (t, 1H), 7.25 (m, 8H), 4.75 (d, 1H), 3.45 (dd, 2H), 2.85 (m, 2H), 2.60 (m, 1H), 2.55 (s, 3H), 1.85 (t, 1H), 1.75 (t, 1H), 1.40 (m, 4H), 0.85 (m, 1H), 0.55 (t, 3H); LC/MS m/z 542 (M+H)$^+$ Scheme 3

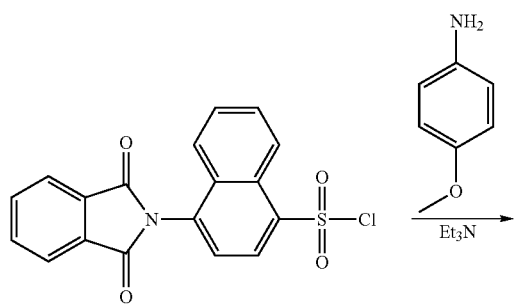

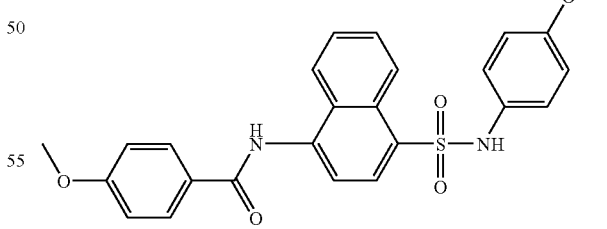

4-Amino-naphthalene-1-sulfonic acid (4-methoxy-phenyl)-amide (10)

To a solution of sulfonamide (A-2) (0.75 g, 1.64 mmol) in methanol (10 mL) was added hydrazine (1 mL). The resultant solution was stirred at 55° C. for 2 hr. A precipitate formed which was filtered and washed with a small amount of methanol. The filtrate was collected and solvent was removed in vacuo to give the title compound as white solid (0.7 g). $^1$H NMR (300 MHz, DMSO) δ 9.84 (br s, 1H), 8.55 (d, 1H), 8.16 (d, 1H), 7.80 (d, 1H), 7.60 (t, 1H), 7.47 (t, 1H), 6.82 (d, 2H), 6.71 (m, 3H), 6.53 (d, 1H), 3.58 (s, 3H); LC/MS m/z 329 (M+H)$^+$.

4-Methoxy-N-[4-(4-methoxy-phenylsulfamoyl)-naphthalen-1-yl]-benzamide (B-2)

To a solution of naphthalenyl amine (10) (65 mg, 0.2 mmol) in CH$_2$Cl$_2$ (5 mL) was added p-methoxybenzoyl chloride (45 μL, 0.24 mmol) and Et$_3$N (50 μL, 0.4 mmol). The resultant solution was stirred at 25° C. overnight. The solvent was removed in vacuo and the residue was purified using HPLC to give the title compound (30 mg) as pale yellow solid.

$^1$H NMR (300 MHz, MeOD) δ 8.73 (d, 1H), 8.08 (m, 4H), 7.70 (m, 3H), 7.10 (d, 2H), 6.90 (d, 2H), 6.70 (d, 2H), 3.84 (s, 3H), 3.60 (s, 3H); LC/MS m/z 463 (M+H)$^+$.

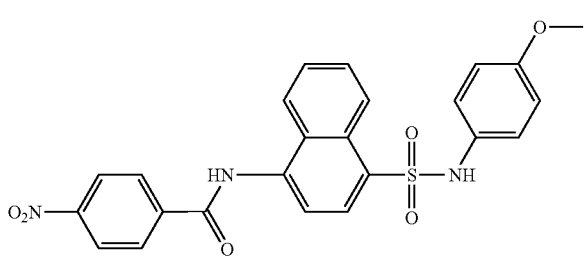

N-[4-(4-Methoxy-phenylsulfamoyl)-naphthalen-1-yl]-4-nitro-benzamide (B-3)

The title compound was made following general procedure in scheme 3, substituting p-nitrobenzoyl chloride for p-methoxy-benzoyl chloride. $^1$H NMR (300 MHz, DMSO) δ 8.24 (d, 2H), 8.02 (m, 3H), 7.55 (d, 2H), 7.48 (m, 1H), 7.18 (d, 2H), 6.83 (d, 2H), 6.69 (d, 1H), 3.69 (s, 3H); LC/MS m/z 478 (M+H)$^+$.

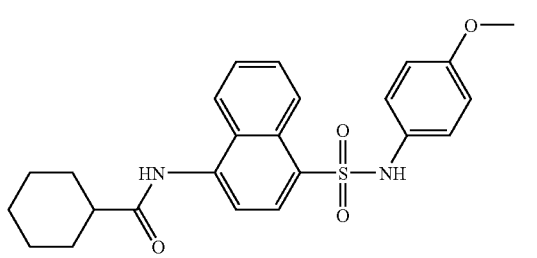

Cyclohexanecarboxylic acid [4-(4-methoxy-phenylsulfamoyl)-naphthalen-1-yl]-amide (B-4)

The title compound was made following general procedure in Scheme 3, substituting cyclohexyl carboxyl chloride for p-methoxy-benzoyl chloride. $^1$H NMR (300 MHz, DMSO) δ 10.28 (s, 1H), 10.05 (s, 1H), 8.74 (d, 1H), 8.25 (d, 1H), 8.08 (d, 1H), 7.85 (d, 1H), 7.70 (m, 2H), 6.86 (d, 2H), 6.67 (d, 2H), 3.60 (s, 3H), 2.60 (m, 1H), 1.50 (m, 1OH); LC/MS m/z 439 (M+H)$^+$.

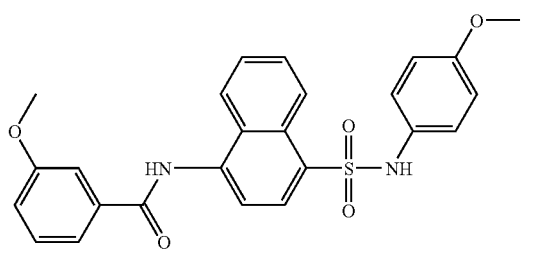

3-Methoxy-N-[4-(4-methoxy-phenylsulfamoyl)-naphthalen-1-yl]-benzamide (B-5)

The title compound was made following general procedure in Scheme 3, substituting 3-methoxy-benzoyl chloride for p-methoxy-benzoyl chloride. $^1$H NMR (300 MHz, DMSO) δ 10.67 (s, 1H), 10.32 (br s, 1H), 8.79 (d, 1H), 8.22 (d, 1H), 8.19 (s, 2H), 7.90 (d, 1H), 7.79 (d, 1H), 7.62 (t, 1H), 7.31 (m, 1H), 7.18 (t, 1H), 6.92 (d, 2H), 6.76 (d, 2H), 3.63 (s, 3H), 3.37 (s, 3H); LC/MS m/z 463 (M+H)$^+$.

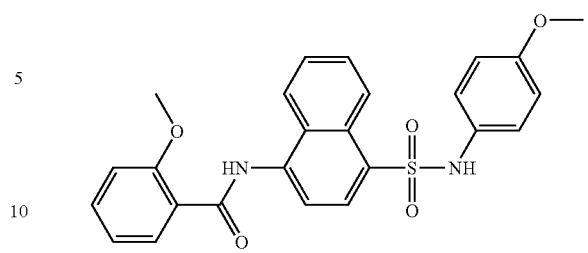

2-Methoxy-N-[4-(4-methoxy-phenylsulfamoyl)-naphthalen-1-yl]-benzamide (B-6)

The title compound was made following general procedure in Scheme 3, substituting 2-methoxy benzoyl chloride for p-methoxy-benzoyl chloride. $^1$H NMR (300 MHz, DMSO) δ 10.60 (s, 1H), 10.2 (br s, 1H), 8.87 (d, 1H), 8.40 (d, 1H), 8.11 (s, 2H), 7.84 (d, 1H), 7.76 (d, 2H), 7.55 (t, 1H), 7.45 (d, 1H), 7.12 (t, 1H), 6.88 (d, 2H), 6.70 (d, 2H), 3.60 (s, 3H), 3.34 (s, 3H); LC/MS m/z 463 (M+H)$^+$.

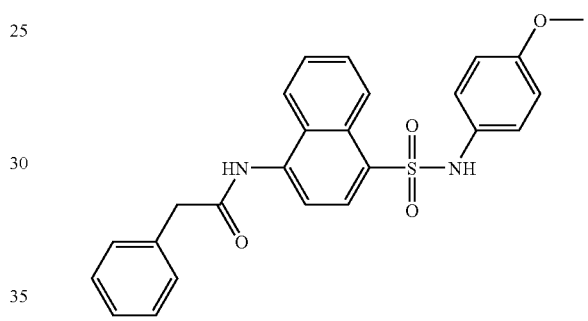

N-[4-(4-Methoxy-phenylsulfamoyl)-naphthalen-1-yl]-2-phenyl-acetamide (B-7)

The title compound was made following general procedure in Scheme 3, substituting phenylacetyl chloride for p-methoxy-benzoyl chloride. $^1$H NMR (300 MHz, DMSO) δ 10.30 (s, 1H), 10.18 (s, 1H), 8.67 (d, 1H), 8.24 (d, 1H), 8.05 (s, 1H), 7.84 (d, 1H), 7.66 (m, 2H), 7.30 (m, 5H), 6.82 (d, 2H), 6.67 (d, 2H), 3.81 (s, 2H), 3.55 (s, 3H), 3.29 (s, 3H); LC/MS m/z 447 (M+H)$^+$.

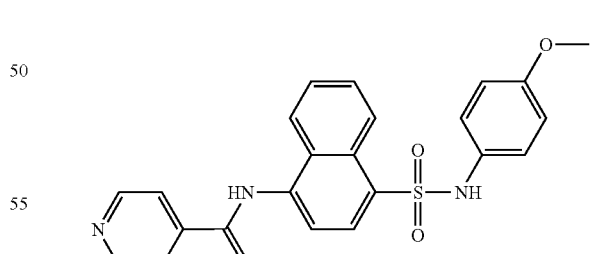

N-[4-(4-Methoxy-phenylsulfamoyl)-naphthalen-1-yl]-isonicotinamide (B-8)

The title compound was made following general procedure in Scheme 3, substituting isonicotinoyl chloride for p-methoxy-benzoyl chloride. $^1$H NMR (300 MHz, DMSO) δ 8.82 (d, 2H), 8.78 (d, 1H), 8.22 (d, 1H), 8.17 (d, 1H), 7.98 (d, 2H), 7.80 (d, 2H), 7.72 (m, 1H), 6.92 (d, 2H), 6.74 (d, 2H), 3.62 (s, 3H); LC/MS m/z 434 (M+H)$^+$.

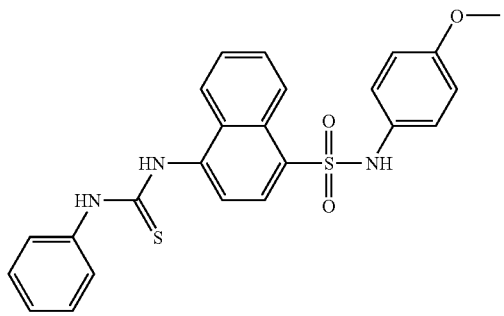

4-(3-Phenyl-thioureido)-naphthalene-1-sulfonic acid (4-methoxy-phenyl)-amide (B-9)

The title compound was made following general procedure in Scheme 3, substituting phenyl isothionitrile for p-methoxy-benzoyl chloride. $^1$H NM (300 MHz, DMSO) δ 8.73 (d, 1H), 8.10 (d, 1H), 8.08 (d, 1H), 7.70 (m, 3H), 7.50 (d, 2H), 7.32 (t, 2H), 7.13 (t, 1H), 6.90 (d, 2H), 6.70 (d, 2H), 3.60 (s, 3H); LC/MS m/z 464 (M+H)$^+$.

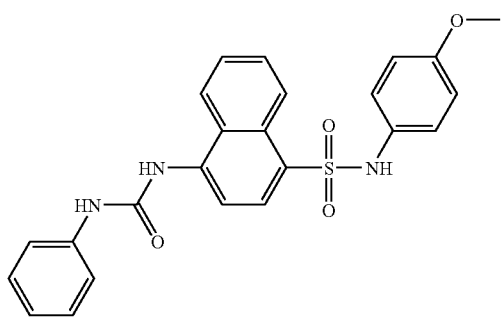

4-(3-Phenyl-ureido)-naphthalene-1-sulfonic acid (4-methoxy-phenyl)-amide (B-10)

The title compound was made following general procedure in Scheme 3, substituting phenyl isocyanate for p-methoxy-benzoyl chloride. $^1$H NMR (300 MHz, DMSO) δ 8.58 (d, 1H), 8.05 (m, 3H), 7.48 (m, 2H), 7.40 (d, 2H), 7.22 (m, 2H), 6.96 (t, 1H), 6.75 (d, 2H), 6.65 (d, 2H), 3.58 (s, 3H); LC/MS m/z 448 (M+H)$^+$.

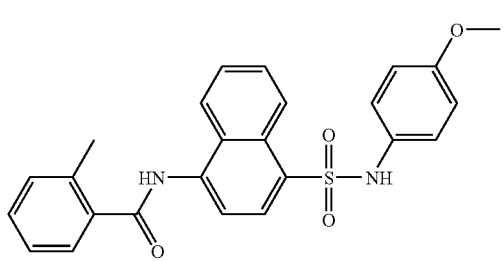

N-[4-(4-Methoxy-phenylsulfamoyl)-naphthalen-1-yl]-2-methyl-benzamide (B-11)

The title compound was made following general procedure in Scheme 3, substituting o-tolyl chloride for p-methoxy-benzoyl chloride. $^1$H NMR (300 MHz, DMSO) δ 8.75 (d, 1H), 8.24 (d, 1H), 8.14 (d, 1H), 7.86 (d, 1H), 7.71 (m, 3H), 7.42 (m, 1H), 7.36 (m, 2H), 6.90 (d, 2H), 6.70 (d, 2H); 3.60 (s, 3H), 2.45 (s, 3H); LC/MS m/z 447 (M+H)$^+$.

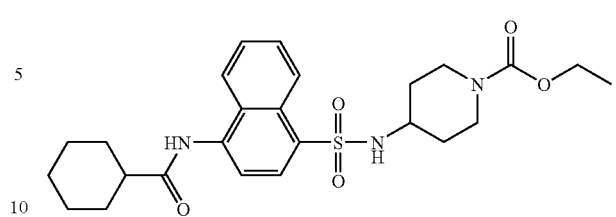

4-[4-(Cyclohexanecarbonyl-amino)-naphthalene-1-sulfonylamino]-piperidine-1-carboxylic acid ethyl ester (B-12)

The title compound was prepared following the general procedure in Scheme 3, substituting 4-amino-piperidine-1-carboxylic acid ethyl ester for p-anisidine and cyclohexane carbonyl chloride for p-methoxy-benzoyl chloride. $^1$H NMR (300 MHz, DMSO) δ 10.05 (s, 1H), 8.65 (d, 1H), 8.26 (d, 1H), 8.14 (d, 1H), 8.04 (d, 1H), 7.92 (d, 1H), 7.71 (m, 2H), 3.95 (m, 3H), 3.68 (m, 2H), 1.93 (m, 2H), 1.80 (m, 2H), 1.31 (m, 13H), 1.13 (t, 3H); LC/MS (M+H)$^+$ m/z 488.

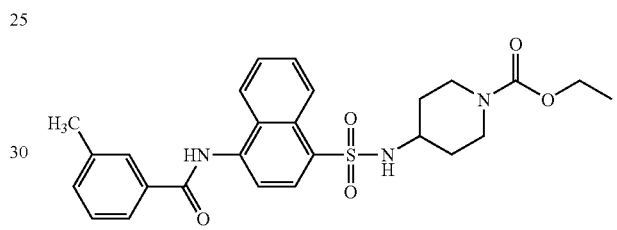

4-[4-(3-Methyl-benzoylamino)-naphthalene-1-sulfonylamino]-piperidine-1-carboxylic acid ethyl ester (B-13)

The title compound was prepared following the general procedure in Scheme 3, substituting 4-amino-piperidine-1-carboxylic acid ethyl ester for p-anisidine and 3-methyl benzoyl chloride for p-methoxy-benzoyl chloride. $^1$H NMR (300 MHz, MeOD) δ 8.75 (d, 1H), 8.30 (d, 1H), 8.18 (d, 1H), 7.80 (m, 5H), 7.46 (m, 2H), 4.03 (q, 2H), 3.83 (d, 2H), 3.23 (m, 1H), 2.78 (m, 2H), 2.47 (s, 3H), 1.56 (m, 2H), 1.28 (m, 2H), 1.19 (t, 3H); LC/MS (M+H)$^+$ m/z 496.

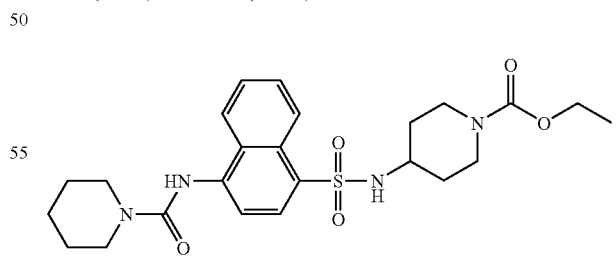

4-{4-[(Piperidine-1-carbonyl)-amino]-naphthalene-1-sulfonylamino}-piperidine-1-carboxylic acid ethyl ester (B-14)

The title compound was prepared following the general procedure in Scheme 3, substituting 4-amino-piperidine-1-carboxylic acid ethyl ester for p-anisidine and 1-piperidine carbonyl chloride for p-methoxy-benzoyl chloride.

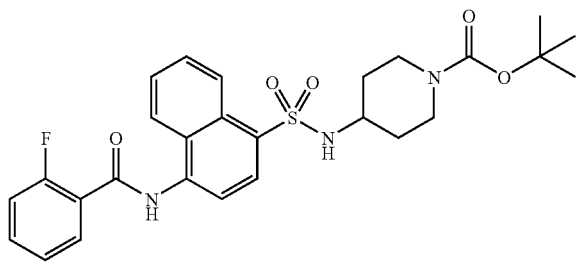

4-[4-(2-Fluoro-benzoylamino)-naphthalene-1-sulfonylamino]-piperidine-1-carboxylic acid tert-butyl ester (B-15)

The title compound was made following the general procedure in Scheme 3, substituting 4-amino-piperidine-1-carboxylic acid tert-butyl ester for p-anisidine and 2-fluorobenzoyl chloride for p-methoxy-benzoyl chloride. $^1$H NMR (300 MHz, DMSO) δ 10.72(s, 1H), 8.67(d, 1H), 8.30(d, 1H), 8.20 (d, 1H), 8.10(d, 1H), 8.01(d, 1H), 7.83(t, 1H), 7.74(t, 2H), 7.65(m, 1H), 7.41(q, 2H), 3.67(d, 2H), 3.18(m, 1H), 2.70(m, 2H), 1.43(m, 2H), 1.33(s, 9H), δ 1.18(m, 2H). LC/MS nmz 527 (M−H)⁻˙ 529 (M+H)⁺

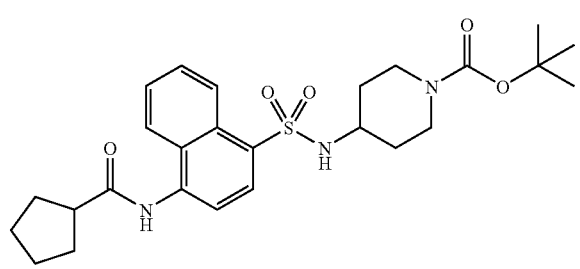

4-[4-(Cyclopentanecarbonyl-amino)-naphthalene-1-sulfonylamino]-piperidine-1-carboxylic acid tert-butyl ester (B-16)

The title compound was made following the general procedure in Scheme 3, substituting 4-amino-piperidine-1-carboxylic acid tert-butyl ester for p-anisidine, and cyclopentanecarbonyl chloride for p-methoxy-benzoyl chloride. $^1$H NMR (300 MHz, DMSO) δ 10.11(s, 1H), 8.64(d, 1H), 8.25(d, 1H), 8.13(d, 1H), 8.01(d, 1H), 7.92(d, 1H), 7.89(m, 1H), 7.70(m, 2H), 3.61(d, 2H), 3.11(m, 2H), 1.94(m, 2H), 1.84-1.60 (m, 7H), 1.38(d, 2H), 1.33(s, 9H), 1.12(m, 2H). LC/MS m/z 500 (M−H)⁻, 502 (M+H)⁺

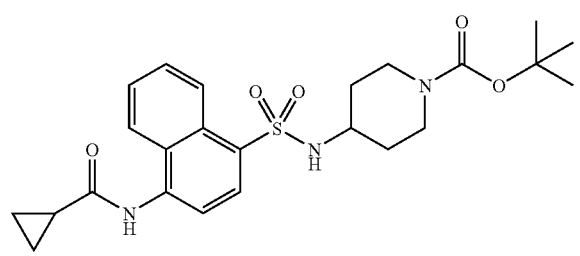

4-[4-(Cyclopropanecarbonyl-amino)-naphthalene-1-sulfonylamino]-piperidine-1-carboxylic acid tert-butyl ester (B-17)

The title compound was made following the general procedure in Scheme 3, substituting 4-amino-piperidine-1-carboxylic acid tert-butyl ester for p-anisidine, and cyclopropanecarbonyl chloride for p-methoxy-benzoyl chloride. $^1$H NMR (300 MHz, DMSO) δ 10.43 (s, 1H), 8.65 (d, 1H), 8.34 (d, 1H), 8.12 (d, 1H), 7.99(t, 2H), 7.73 (m, 2H), 3.61 (d, 2H), 3.13 (m, 1H), 2.68 (m, 2H), 2.16 (m, 2H), 2.16 (m, 1H), 1.39 (d, 2H), 1.33 (s, 9H), 1.12 (m, 2H), 0.88 (d, 4H); LC/MS m/z 472 (M−H)⁻, 474 (M+H)⁺

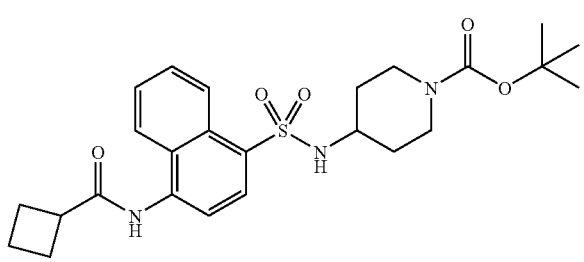

4-[4-(Cyclobutanecarbonyl-amino)-naphthalene-1-sulfonylamino]-piperidine-1-carboxylic acid tert-butyl ester (B-18)

The title compound was made following the general procedure in Scheme 3, substituting 4-amino-piperidine-1-carboxylic acid tert-butyl ester for p-anisidine, and cyclobutanecarbonyl chloride for p-methoxy-benzoyl chloride. $^1$H NMR (300 MHz, DMSO) δ 9.98 (s, 1H), 8.62 (d, 1H), 8.21 (d, 1H), 8.12 (d, 1H), 7.99 (d, 1H), 7.95 (d, 1H), 7.70 (m, 2H), 3.59 (d, 2H), 3.51 (t, 1H), 3.13 (m, 1H), 2.67 (m, 2H), 2.32-2.16 (m, 4H), 1.99 (m, 1H), 1.84 (m, 1H), 1.37 (d, 2H), 1.31 (s, 9H), 1.10(m, 2H); LC/MS m/z 486 (M−H)⁻, 488 (M+H)⁺

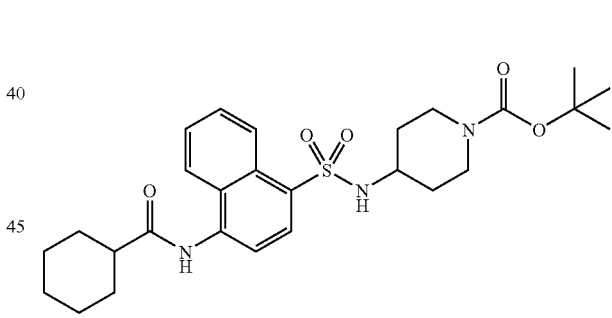

4-[4-(Cyclohexanecarbonyl-amno)-naphthalene-1-sulfonylamino]-piperidine-1-carboxylic acid tert-butyl ester (B-19)

The title compound was made following the general procedure in Scheme 3, substituting 4-amino-piperidine-1-carboxylic acid tert-butyl ester for p-anisidine and cyclohexanecarbonyl chloride for p-methoxy-benzoyl chloride. $^1$H NMR (300 MHz, DMSO) δ 10.05 (s, 1H), 8.64 (d, 1H), 8.25 (d, 1H), 8.12 (d, 1H), 8.00 (d, 1H), 7.91 (d, 1H), 7.71 (m, 2H), 3.61 (d, 2H), 3.43 (m, 1H), 3.15 (m, 1H), 2.65 (m, 2H), 1.90 (d, 2H), 1.77 (d, 2H), 1.69 (m, 1H), 1.54-1.33 (m, 5H), 1.32 (s, 9H), 1.30-1.12 (m, 4H); LC/MS m/z 486 (M−H)⁻, 488 (M+H)⁺

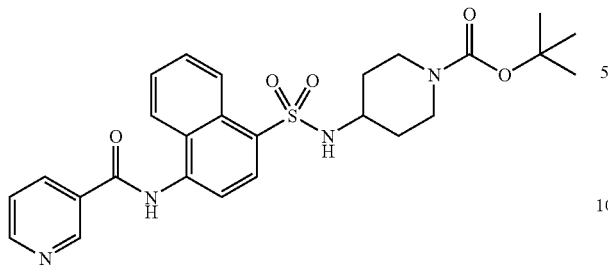

4-{4-[(Pyridine-3-carbonyl)-amino]-naphthalene-1-sulfonylamino}-piperidine-1-carboxylic acid tert-butyl ester (B-20)

The title compound was made following the general procedure in Scheme 3, substituting 4-amino-piperidine-1-carboxylic acid tert-butyl ester for p-anisidine, and nicotinoyl chloride hydrochloride for p-methoxy-benzoyl chloride. $^1$H NMR (300 MHz, DMSO) δ 10.83 (s, 1H), 9.23 (d, 1H), 8.81 (d, 1H), 8.67 (dd, 1H), 8.11 (dt, 1H), 8.27 (dd,1 H), 8.27 (dd, 1H), 8.20 (d, 1H), 8.09 (d, 1H), 7.85 (d, 1H), 7.75 (m, 2H), 7.6 (m, 1H), 3.62 (d, 2H), 3.18 (m, 1H), 2.69 (m, 2H), 1.45-1.37 (m, 2H), 1.30 (s, 9H), 1.14 (m, 2H); LC/MS nmz 509 (M−H)$^-$, 511 (M+H)$^+$

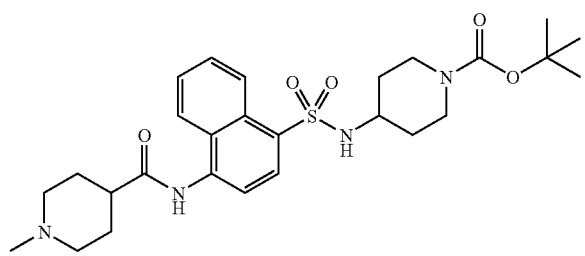

4-{4-[(1-Methyl-piperidine-4-carbonyl)-amino]-naphthalene-1-sulfonylamino}-piperidine-1-carboxylic acid tert-butyl ester (B-21)

The title compound was made following the general procedure in Scheme 3, substituting 4-amino-piperidine-1-carboxylic acid tert-butyl ester for p-anisidine, N-methyl-piperidine-4-carboxylic acid hydrochloride for p-methoxy-benzoyl chloride and reagents 1-(3-dimethylaminopropyl)-3-ethyl-carbodiimide hydrochloride (EDCI), 1-hydroxybenzotriazole hydrate (HOBt) and pyridine for dimethylamino pyridine (DMAP) and triethylamine. $^1$H NMR (300 MHz, DMSO) δ 10.39 (s, 1H), 8.64 (dd, 1H), 8.29 (dd, 1H), 8.14 (d, 1H), 8.05 (d, 1H), 7.89 (d, 1H), 7.72 (m, 2H), 3.62 (d, 2H), 3.40 (m, 2H), 3.15 (m, 1H), 2.95 (m, 2H), 2.78-2.67 (m, 6H), 2.09 (m, 2H), 2.0 (m, 2H), 1.84 (m, 1H), 1.39 (m, 1H), 1.32 (s, 9H), 1.18 (m, 2H); LC/MS m/z 484 (M−H)$^-$, 486 (M+H)$^+$

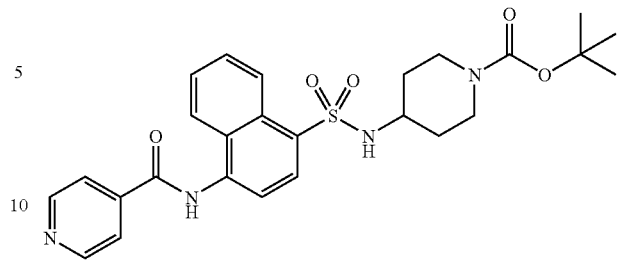

4-{4-[(Pyridine-4-carbonyl)-amino]-naphthalene-1-sulfonylamino}-piperidine-1-carboxylic acid tert-butyl ester (B-22)

The title compound was made following the general procedure in Scheme 3, substituting 4-amino-piperidine-1-carboxylic acid tert-butyl ester for p-anisidine and isonicotinoyl-chloride hydrochloride for p-methoxy-benzoyl chloride. LC/MS m/z 511 (M+H)$^+$

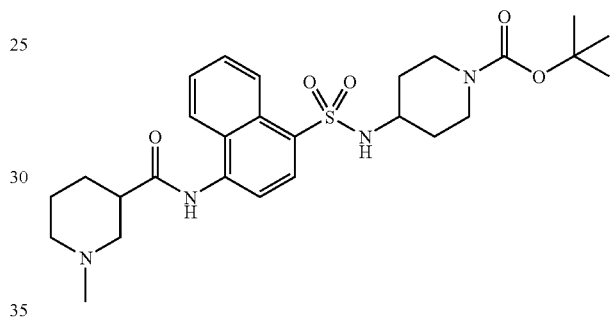

4-14-[(1-Methyl-piperidine-3-carbonyl)-amino]-naphthalene-4-sulfonylamino)-piperidine-1-carboxylic acid tert-butyl ester (B-23)

The title compound was made following the general procedure in Scheme 3, substituting 4-amino-piperidine-1-carboxylic acid tert-butyl ester for p-anisidine, N-methyl-piperidine-3-carbonyl chloride (prepared in situ from N-methyl-piperidine-3-carboxylic acid, oxalyl chloride (1.2 eq) and triethylamine (1 eq)) for p-methoxy-benzoyl chloride. LC/MS m/z 531 (M+H)$^+$

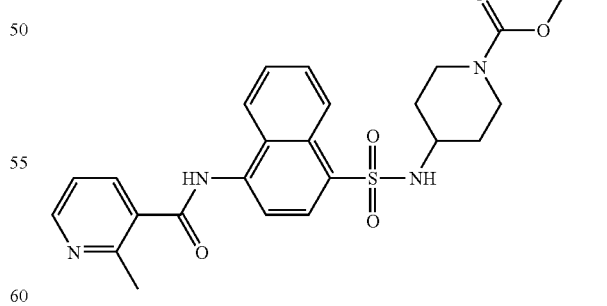

4-14-[(2-Methyl-pyridine-3-carbonyl)-amino]-naphthalene-0-sulfonylamino]-piperidine-1-carboxylic acid ethyl ester (B-24):

To a suspension of 4-(4-Amino-naphthalene-1-sulfonylarnino)-piperidine-1-carboxylic acid ethyl ester (0.26 g, 0.71 mmol) (prepared following the general procedure in Scheme 3, substituting 4-amino-piperidine-1-carboxylic acid ethyl ester for p-anisidine) in CH₂Cl₂ (10 mL) and aqueous saturated sodium bicarbonate solution (4 mL) was added 2-methyl nicotinic chloride (0.16 g, 1.07 mmol) and the resulting mixture was stirred at room temperature overnight. The organic layer was separated, dried over sodium sulfate and concentrated. Purification of the residue by column chromatography (2-5% MeOHI/CH₂Cl₂) provided the B-24 (0.09 g, 26%). ¹H NMR (300 MHz, CDCl₃) δ 8.61-8.66 (m, 2H), 8.34 (s, 1H), 8.19-8.28 (m, 1H), 7.94 (d, 2H), 7.60-7.70 (m, 2H), 7.28-7.31(m, 1H), 4.91(d, 1H), 4.03 (q, 2H), 3.85 (d, 2H), 3.20-3.32 (m, 1H), 2.80 (s, 2H), 2.63-2.74 (m, 2H), 1.67 (br s, 4H), 1.16-1.21 (m, 5H). LC/MS m/z 497 (M+H)⁺.

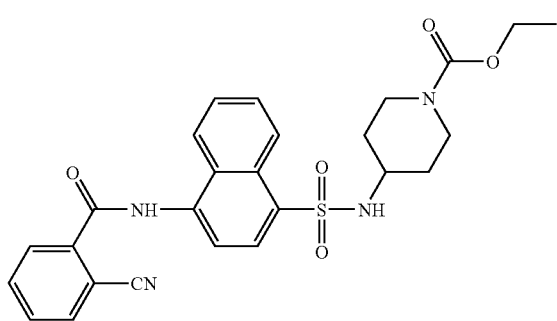

4-[4-(2-Cyano-benzoylamino)-naphthalene-1-sulfonylamino]-piperidine-1-carboxylic acid ethyl ester (B-26)

A solution of 2-cyano-benzoic acid (294 mg, 2 mmol) in thionyl chloride (5 mL) was heated to reflux where the mixture was stirred for 3 h and then concentrated in vacuo. The crude material, 2-cyano-benzoyl chloride was used without purification. The title compound was made following the general procedure in scheme 3, substituting 4-(4-amino-naphthalene-1-sulfonylamino)-piperidine-1-carboxylic acid ethyl ester for 4-amino-naphthalene-1-sulfonic acid (4-methoxy-phenyl)-amide and substituting 2-cyano-benzoyl chloride for p-methoxy-benzoyl chloride. ¹H NMR (300 MHz, MeOD) δ 8.05 (dd, 1H), 8.36 (d, 1H), 8.05 (m, 2H), 7.92 (m, 2H), 7.83 (m, 1H), 7.75 (m, 1H), 7.64 (d, 2H), 6.89 (td, 1H), 4.05 (q, 2H), 3.85 (d, 2H), 3.30 (m, 1H), 2.80 (m, 2H), 1.60 (m, 2H), 1.30 (m, 2H), 1.20 (t, 3H); LC/MS m/z 508 (M+H)⁺

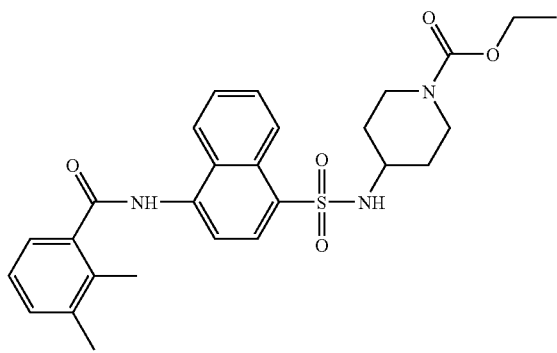

4-[4-[4-(2,3-Dimethyl-benzoylamino]-naphthalene-1-sulfonylamino]-piperidine-1-carboxylic acid ethyl ester (B-27)

The title compound was made following general procedure in Scheme 3, substituting 4-(4-amino-naphthalene-1-sulfonylamino)-piperidine-1-carboxylic acid ethyl ester for 4-amino-naphthalene-1-sulfonic acid (4-methoxy-phenyl)-amide and substituting 2,3-dimethyl-benzoyl chloride for p-methoxy-benzoyl chloride. ¹H NMR (300 MHz, MeOD/CDCl₃) δ 8.63 (d, 1H), 8.24 (m, 2H), 7.97 (d, 1H), 7.60 (m, 2H), 7.38 (m, 1H), 7.30 (m, 2H), 4.00 (q, 2H), 3.81 (d, 2H), 3.20 (m, 1H), 2.75 (m, 2H), 2.40 (s, 3H), 2.30 (s, 3H), 1.58 (m, 2H), 1.20 (m, 2H), 1.12 (t, 3H); LC/MS m/z 510 (M+H)⁺

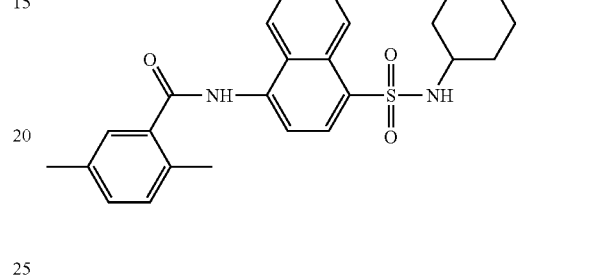

4-[4-(2,5-Dimethyl-benzoylamino)-naphthalene-1-sulfonylamino]-piperidine-1-carboxylic acid ethyl ester (B-28)

A solution of 2,5-dimethyl-benzoic acid (300 mg, 2 mmol) in thionyl chloride (5 mL) was refluxed for 3 h and then concentrated in vacuo. The crude material was used without purification as 2,5-dimethyl-benzoyl chloride. The title compound was made following general procedure in Scheme 3, substituting 4-(4-amino-naphthalene-1-sulfonylamino)-piperidine-1-carboxylic acid ethyl ester for 4-amino-naphthalene-1-sulfonic acid (4-methoxy-phenyl)-amide and substituting 2,5-dimethyl-benzoyl chloride for p-methoxy-benzoyl chloride. ¹H NMR (300 MHz, MeOD/CDCl₃) δ 8.60 (dd, 1H), 8.22 (d, 1H), 8.10 (m, 1H), 7.98 (m, 1H), 7.58 (m, 2H), 7.35 (s, 1H), 7.14 (m, 2H), 3.98 (q, 2H), 3.78 (d, 2H), 3.15 (m, 1H), 2.68 (m, 2H), 2.42 (s, 3H), 2.32 (s, 3H), 1.55 (m, 2H), 1.20 (m, 2H), 1.12 (t, 3H); LC/MS m/z 510 (M+H)⁺

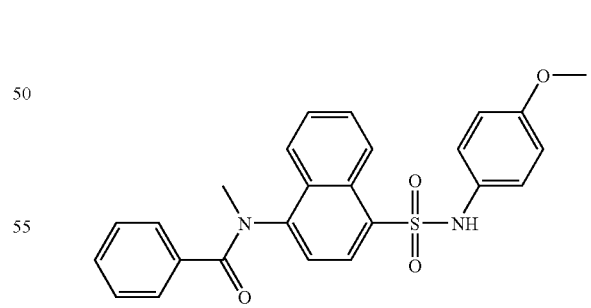

N-[4-(4-Methoxy-phenylsulfamoyl)-naphthalen-1-yl]-N-methyl-benzamide (B-33)

The title compound was made from B-30 following the general procedure in Scheme 3. ¹H NMR (300 MHz, DMSO) δ 8.23 (t, 2H), 8.10 (d, 3H), 7.87 (d, 1H), 7.60 (m, 5H), 7.03 (d, 2H), 6.82 (d, 2H), 3.72 (s, 3H), 3.18 (s, 3H); LC/MS m/z 445 (M−H)⁻.

Scheme 4: General procedures for amine deprotections

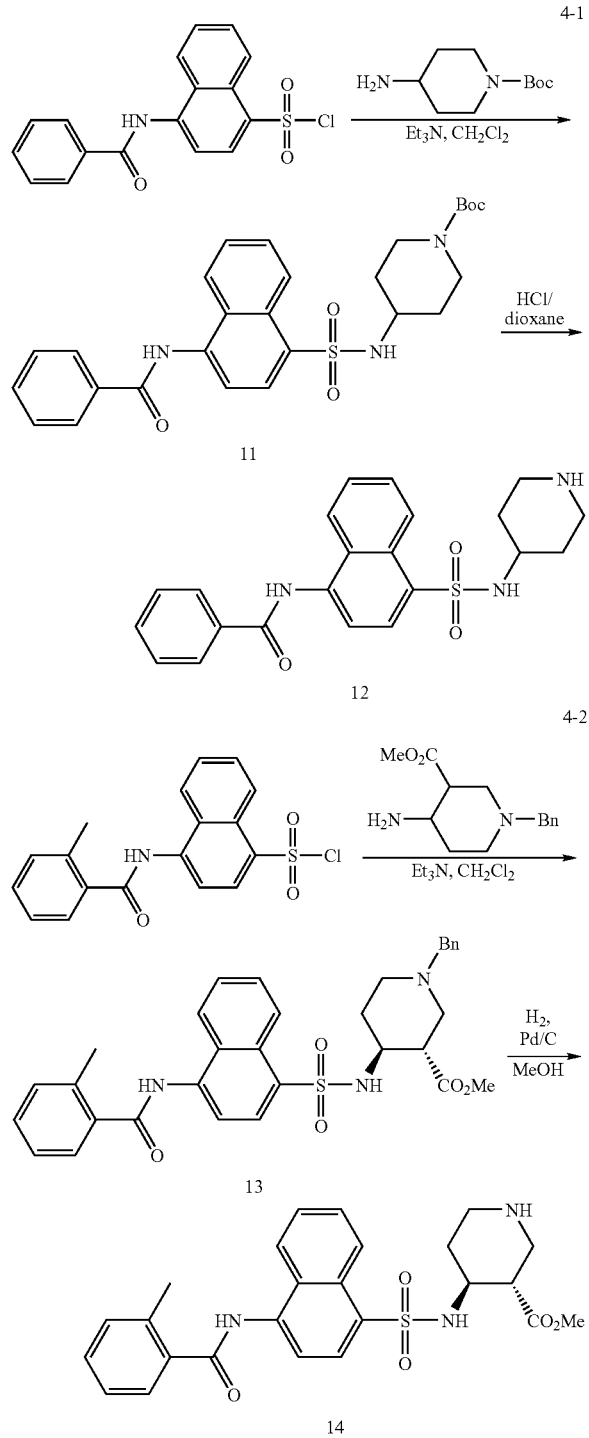

was stirred at 25° C. for 5 h and then concentrated in vacuo. The crude material was purified by reverse phase HPLC to provide the title compound. $^1$H NMR (300 MHz, MeOH) δ 8.75 (d, 1H), 8.46 (s, 1H), 8.33 (d, 1H), 8.21 (d, 1H), 8.10 (m, 1H), 8.07 (m, 1H), 7.83 (d, 1H), 7.69 (m, 5H), 3.21 (m, 3H), 2.92 (m, 2H), 1.82 (m, 2H), 1.60 (m, 2H); LC/MS (M+H)$^+$ m/z 410.

(±)-(trans)-4-[4-(2-Methyl-benzoylamino)naphthalene-1sulfonylamino]-piperidine-3-carboxylic acid ethyl ester (14)

(±)-(trans)-1-Benzyl-4-[4-(2-methyl-benzoylamino)-naphthalene-1-sulfonylamino]-piperidine-3-carboxylic acid methyl ester 13 was made following general procedure in Scheme 2, substituting (±)-4-amino-1-benzyl-piperidine-3-carboxylic acid ethyl ester (5) for m-anisidine and 4-(2-methyl-benzoylamino)-naphthalene-1-sulfonyl chloride for 4-benzoylamino-naphthalene-1-sulfonyl chloride benzyl amine.

To a solution of 1-benzyl-4-[4-(2-methyl-benzoylamino)-naphthalene-1-sulfonylamino]-piperidine-3-carboxylic acid methyl ester 13 (170 mg, 0.29 mmol) in MeOH was added Pd(OH)$_2$/C 20% wet (8 mg). The reaction mixture was stirred at 25° C. under an hydrogen atmosphere overnight. The resultant mixture was filtered and the solvent was concentrated in vacuo to provide the title compound 14. This material was not further purified and used directly in the next reaction.

Scheme 5

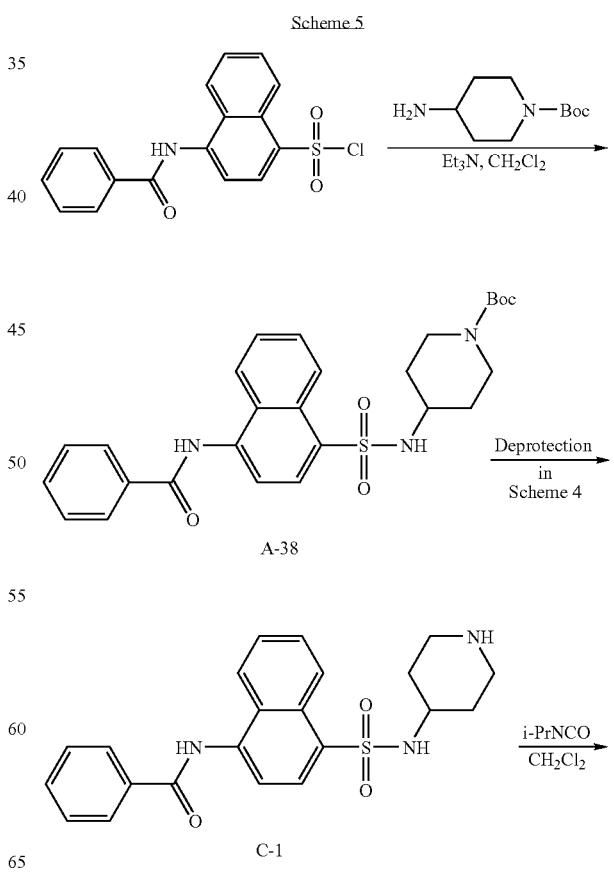

N-[4-(Piperidin-4-ylsulfamoyl]-naphthalen-1-yl)-benzamide (12)

4-(4-Benzoylamino-naphthalene-1-sulfonylamino)-piperidine-1-carboxylic acid tert-butyl ester (11) was prepared following the general procedure in Scheme 2. To a solution of 4-(4-benzoylamino-naphthalene-1-sulfonylamino)-piperidine-1-carboxylic acid tert-butyl ester (11) in MeOH was added a solution of 4 N HCl in dioxane. The reaction mixture

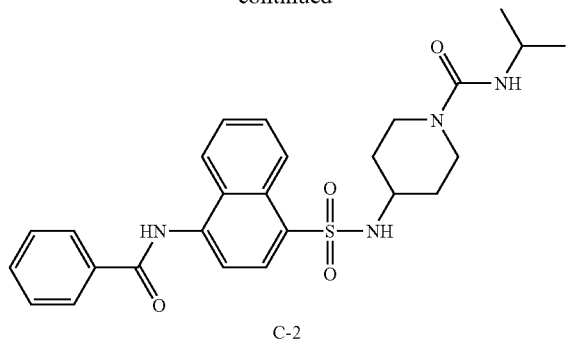

C-2

N-[4-(Piperidin-4-ylsulfamoyl)-naphthalen-1-yl]-benzamide (C-1)

4-(4-Benzoylamino-naphthalene-1-sulfonylamino)-piperidine-1-carboxylic acid tert-butyl ester (A-38) was prepared following the general procedure in Scheme 2. Deprotection was achieved following the procedure in Scheme 4-1. The reaction mixture was stirred at 25° C. for 5 h and then concentrated in vacuo. The crude material was purified by reverse phase HPLC to provide the title compound. $^1$H NMR (300 MHz, MeOH) δ 8.75 (d, 1H), 8.46 (s, 1H), 8.33 (d, 1H), 8.21 (d, 1H), 8.10 (m, 1H), 8.07 (m, 1H), 7.83 (d, 1H), 7.69 (m, 5H), 3.21 (m, 3H), 2.92 (m, 2H), 1.82 (m, 2H), 1.60 (m, 2H); LC/MS (M+H)$^+$ m/z 410.

4-(4-Benzoylamino-naphthalene-1-sulfonylamino)-piperidine-1-carboxylic acid isopropyl amide (C-2)

To a 25° C. solution of N-[4-(piperidin-4-yl sulfamoyl)-naphthalen-1-yl]-benzamide (C-1) in CH$_2$Cl$_2$ was added Et$_3$N followed by 2-isocyanato-propane. The reaction mixture was stirred at 25° C. overnight. Aqueous work-up followed by purification using reverse phase HPLC provided the title compound. $^1$H NMR (300 MHz, MeOD) δ 8.74 (d, 1H), 8.29 (d, 1H), 8.17 (d, 1H), 8.07 (s, 1H), 8.05 (s, 1H), 7.81 (d, 1H), 7.63 (m, 5H), 3.75 (m, 3H), 3.21 (m, 1H), 2.68 (t, 2H), 1.51 (m, 2H), 1.26 (m, 2H), 1.05 (d, 6H); LC/MS (M+H)$^+$ m/z 495.

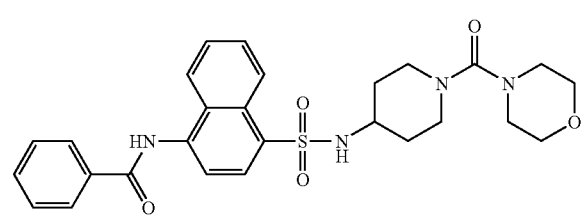

N-{4-[1-(Morpholine-4-carbonyl)-piperidin-4-ylsulfamoyl]-naphthalen-1-yl}-benzamide (C-4)

The title compound was made following general procedure in Scheme 5, substituting 4-isocyanato-tetrahydro-pyran for 2-isocyanato-propane. $^1$H NMR (300 MHz, MeOD) δ 8.74 (d, 1H), 8.29 (d, 1H), 8.17 (d, 1H), 8.07 (m, 1H), 8.05 (m, 1H), 7.81 (d, 1H), 7.63 (m, 5H), 3.57 (m, 4H), 3.48 (m, 2H), 3.13 (m, 3H), 2.73 (t, 2H), 2.54 (m, 2H), 1.32 (m, 2H); LC/MS (M+H)$^+$ m/z 523.

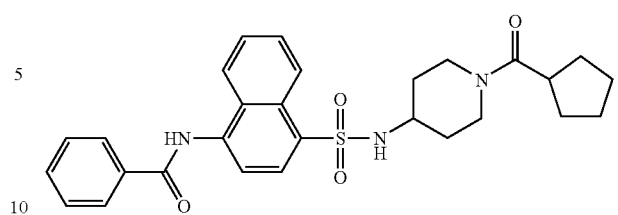

N-[4-(1-Cyclopentanecarbonyl-piperidin-4-ylsulfamoyl)-naphthalen-1-yl]-benzamide (C-5)

The title compound was prepared following general procedure in Scheme 5, substituting cyclopentanecarbonyl chloride for 2-isocyanato-propane to afford the title compound as a cream colored solid. $^1$H NMR (300 MHz, MeOD) δ 8.75 (d, 1H), 8.31 (d, 1H), 8.19 (d, 1H), 8.09 (m, 1H), 8.07 (d, 1H), 7.82 (d, 1H), 7.65 (m, 6H), 4.17 (d, 1H), 3.83 (d, 1H), 2.97 (m, 2H), 2.65 (m, 1H), 1.65 (m, H), 1.29 (m, 2H); LC/MS (M+H)$^+$ m/z 506.

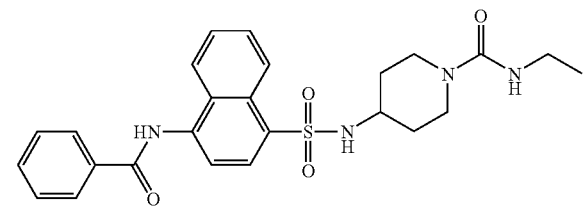

4-(4-Benzoylamino-naphthalene-1-sulfonylamino)-piperidine-1-carboxylic acid ethylamide (C-7)

The title compound was prepared following general procedure in Scheme 5, substituting isocyanato-ethane for 2-isocyanato-propane. $^1$H NMR (300 MHz, MeOD) δ 8.75 (d, 1H), 8.30 (d, 1H), 8.19 (d, 1H 8.08 (d, 2H), 7.82 (d, 1H), 7.65 (m, 5H), 3.74 (d, 2H), 3.23 (m, 1H), 3.10 (m, 2H), 2.70 (t, 2H), 1.53 (m, 2H), 1.28 (m, 2H), 1.04 (t, 3H); LC/MS (M+H)$^+$ m/z 481.

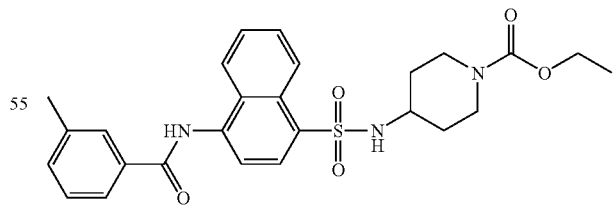

4-[4-(3-Methyl-benzoylamino)-naphthalene-1-sulfonylamino]-piperidine-1-carboxylic acid ethyl ester (C-9)

The title compound was made following general procedure in Scheme 5, substituting 4-aminopiperidine-1-carboxylic acid ethyl ester for 4-aminopiperidine-1-carboxylic acid tert-butyl ester and m-tolyl chloride for benzoyl chloride.

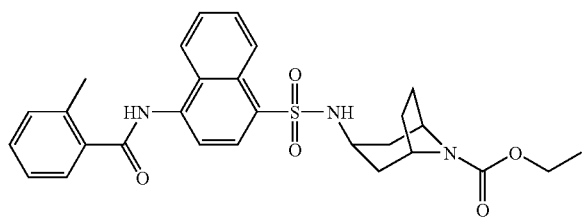

cis-3-[4-(2-Methyl-benzoylamino)-naphthalene-1-sulfonylamino]-8-aza-bicyclo[3.2.1]octane-8-carboxylic acid ethyl ester (C-10)

The title compound was made following general procedure in Scheme 5, substituting cis-3-amino-8-aza-bicyclo[3.2.1]octane-8-carboxylic acid ethyl ester for 4-aminopiperidine-1-carboxylic acid tert-butyl ester. $^1$H NMR (300 MHz, DMSO) δ 8.75 (d, 1H), 8.27 (d, 1H), 8.14 (d, 1H), 7.75 (d, 1H), 7.65 (m, 4H), 7.41 (m, 1H), 7.35 (m, 2H), 3.94 (m, 4H), 3.25 (br s, 1H); 2.50 (s, 3H), 1.92 (d, 2H), 1.67 (m, 4H), 1.07 (t, 3H); LC/MS nlvz 523 (M+H)$^+$.

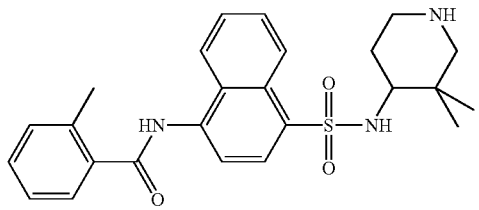

(±)-N-[4-(3,3-Dimethyl-piperidin-4-ylsulfamoyl)-naphthalen-1-yl]-2-methyl-benzamide (C-11)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride and 4-amino-3,3-dimethyl-piperidine-1-carboxylic acid tert-butyl ester for 4-amino-piperidine-1-carboxylic acid tert-butyl ester. $^1$H NMR (300 MHz, MeOD) δ 8.82 (d, 1H), 8.33 (d, 1H), 8.23 (d, 1H), 7.93 (d, 1H), 7.68 (m, 3H), 7.40 (m, 3H), 3.18 (m, 3H), 3.00 (d, 1H), 2.85 (m, 2H); 2.54 (s, 3H), 1.60 (m, 3H), 0.95 (s, 3H), 0.70 (s, 3H); LC/MS m/z 452 (M+H)$^+$.

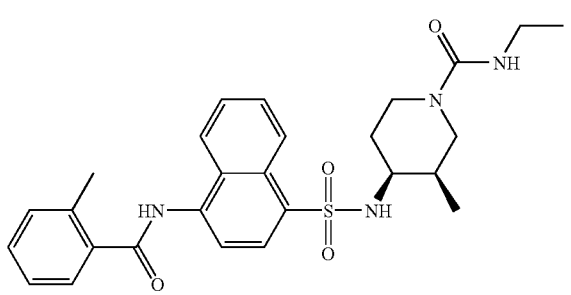

(±)-cis-3-Methyl-4-[4-(2-methyl-benzoylamino)-naphthalene-3-sulfonylamino]-piperidine-1-carboxylic acid ethylamide (C-12)

The title compounds were made following general procedure in Scheme 5 and deprotection in scheme 4-1, substituting 4-(2-methyl-benzoylamino)-naphthalene-1-sulfonyl chloride for 4-benzoylamino-naphthalene-1-sulfonyl chloride, 4-amino-1-benzyl-3-methyl-piperidine for 4-amino-piperidine-1-carboxylic acid tert-butyl ester and ethyl isocyanate for 2-isocyanato-propane. $^1$H NMR (300 MHz, CDCl$_3$) δ 8.71 (d, 1H), 8.40 (s, 1H), 8.28 (s, 2H), 7.98 (d, 1H), 7.68 (m, 3H), 7.41 (m, 1H), 7.30 (m, 2H), 5.21(d, 1H), 4.36 (m, 1H), 3.35 (m, 2H), 3.15 (m, 4H), 2.98 (m, 2H), 2.57 (s, 3H), 1.71 (m, 2H), 1.40 (m, 2H), 1.10 (m, 1H), 1.03 (t, 3H) 0.63 (d, 3H); LC/MS m/z 509 (M+H)$^+$.

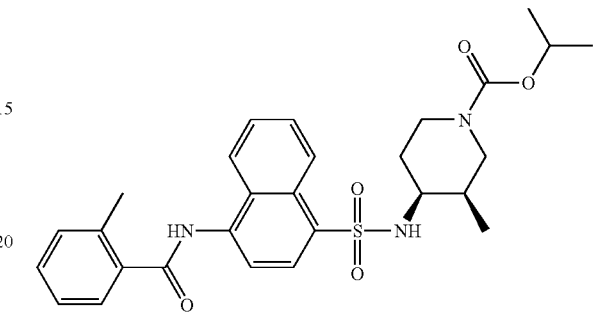

(±)-cis-3-Methyl-4-[4-(2-methyl-benzoylamino)-naphthalene-1-sulfonylamino]-piperidine-1-carboxylic acid isopropyl ester (C-13)

The title compounds were made following the general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (p)-4-amino-1-benzyl-3-methyl-piperidine for 4-amino-piperidine-1-carboxylic acid tert-butyl ester and isopropyl chloroformate for 2-isocyanato-propane. $^1$H NMR (300 MHz, CDCl$_3$) δ 8.72 (d, 1H), 8.43 (d, 1H), 8.35 (d, 1H), 8.12 (d, 1H), 7.95 (d, 2H), 7.72 (m, 3H), 7.46 (m, 1H), 7.35(d, 2H), 4.85 (m, 1H), 4.66 (d, 1H), 3.55 (m, 1H), 3.37 (m, 1H), 3.17 (m, 2H), 2.59 (s, 3H), 1.74 (m, 1H), 1.58 (m, 1H), 1.40 (m, 2H) 1.18 (dd, 6H), 0.67 (m, 3H); LC/MS m/z 524 (M+H)$^+$.

(±)-trans-2-MethylN-[4-(3-methyl-piperidin-4-ylsulfamoyl)-naphthalen-1-yl]-benzamide (C-14)

The title compound was made following general procedure in Scheme 5 and flash column chromatography (Hexane/EtOAc, gradient) followed by deprotection in Scheme 4-1, substituting 4-(2-methyl-benzoylamino)-naphthalene-1-sulfonyl chloride for 4-benzoylamino-naphthalene-1-sulfonyl chloride and (±)-4-amino-1-benzyl-3-methyl-piperidine for 4-amino-piperidine-1-carboxylic acid tert-butyl ester. $^1$H NMR (300 MHz, MeOD) δ 8.77 (d, 1H), 8.48 (s, 1H), 8.32 (d, 1H), 8.24 (d, 1H), 7.94 (d, 1H), 7.75 (m, 3H), 7.40 (m, 3H), 3.25 (m, 1H), 2.90 (m, 2H), 2.55 (s, 3H), 1.60 (m, 3H), 0.65 (d, 3H); LC/MS m/z 438 (M+H)$^+$.

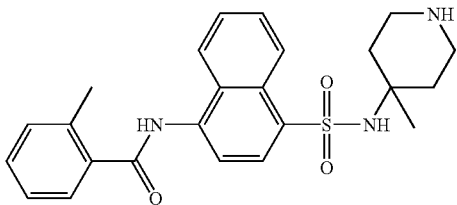

2-Methyl-N-[4-(4-methyl-piperidin-4-ylsulfamoyl)-naphthalen-1-yl]-benzamide (C-15)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride and 4-amino-4-methyl-piperidine-1-carboxylic acid tert-butyl ester for 4-amino-piperidine-1-carboxylic acid tert-butyl ester. $^1$H NMR (300 MHz, DMSO) δ 8.73 (d, 1H), 8.68 (br s, 1H), 8.28 (d, 1H), 8.23 (d, 1H), 7.95 (d, 1H), 7.70 (m, 3H), 7.40 (m, 3H), 2.90 (m, 4H), 2.48 (s, 3H), 2.00 (m, 2H), 1.58 (m, 2H), 0.95 (s, 3H); LC/MS m/z 438 (M+H)$^+$.

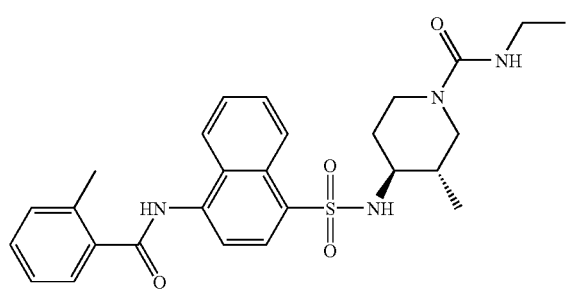

(±)-trans-3-Methyl-4-[4-(2-methyl-benzoylanlino)-naphthalene-1-sulfonylamino]-piperidine-1-carboxylic acid ethylaiide (C-16)

The title compounds were made following general procedure in Scheme 5 and deprotection in scheme 4-1, substituting 4-(2-methyl-benzoylamino)-naphthalene-1-sulfonyl chloride for 4-benzoylamino-naphthalene-1-sulfonyl chloride, 4-amino-1-benzyl-3-methyl-piperidine for 4-amino-piperidine-1-carboxylic acid tert-butyl ester and ethyl isocyanate for 2-isocyanato-propane. $^1$H NMR (300 MHz, DMSO) δ 8.77 (d, 1H), 8.29 (d, 1H), 8.23 (d, 1H), 7.91 (d, 1H), 7.70 (m, 3H), 7.36 (m, 3H), 3.82 (m, 2H), 3.12 (q, 2H), 2.82 (m, 1H), 2.58 (m, 1H), 2.55 (s, 3H), 2.31 (t, 1H), 1.40 (m, 2H), 1.20 (m, 1H), 1.03 (t, 3H), 0.59 (d, 3H); LC/MS m/z 509 (M+H)$^+$.

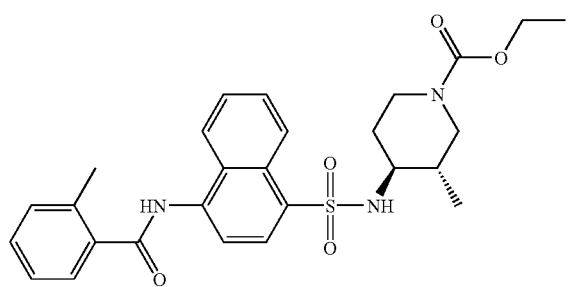

(±)-trans-3-Methyl-4-[4-(2-methyl-benzoylaminno)-naphthalene-1-sulfonylaminno]-piperidine-1-carboxylic acid ethyl ester (C-17)

The title compound was made following general procedure in scheme 5 and deprotection in scheme 4, substituting 4-(2-methyl-benzoylamino)-naphthalene-1-sulfonyl chloride for 4-benzoylarnino-naphthalene-1-sulfonyl chloride, (±)4-amino-1-benzyl-3-methyl-piperidine for 4-amino-piperidine-1-carboxylic acid tert-butyl ester and ethyl chloroformate for 2-isocyanato-propane. Flash column chromatography (Hexane/EtOAc, gradient) of the mixture gave C-17. $^1$H NMR (300 MHz, CDCl$_3$) δ 8.77 (d, 1H), 8.30 (d, 1H), 8.23 (d, 1H), 7.92 (d, 1H), 7.73 (m, 3H), 7.35 (m, 3H), 4.03 (q, 2H), 3.94 (t, 2H), 2.85 (dt, 1H), 2.64 (m, 1H), 2.55 (s, 3H), 2.40 (m, 1H), 1.48 (m, 1H), 1.38 (m, 1H), 1.20 (t, 3H), 0.59 (d, 3H); LC/MS m/z 510 (M+H)$^+$.

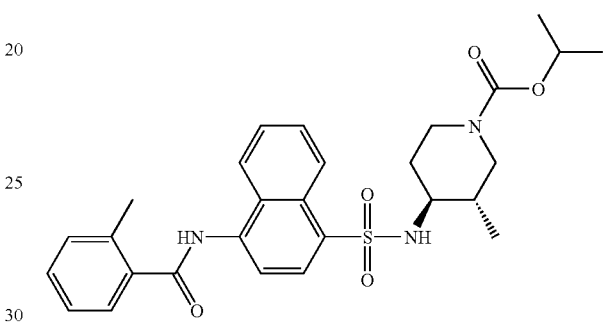

(±)-trans-3-methyl-4-[4-(2-methyl-benzoylalino)-naphthalene-1-sulfonylamino]-piperidine-1-carboxylic acid isopropyl ester (C-18)

The title compounds were made following the general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3-methyl-piperidine for 4-amino-piperidine-1-carboxylic acid tert-butyl ester and isopropyl chloroformate for 2-isocyanato-propane. C-18: $^1$H NMR (300 MHz, CDCl$_3$) δ 8.70 (d, 1H), 8.40 (m, 2H), 8.17 (s, 1H), 7.95 (d, 1H), 7.70 (m, 3H), 7.44 (m, 1H), 7.34 (m, 2H), 4.80 (m, 1H), 4.58 (d, 1H), 3.90 (d, 2H), 2.87 (m, 1H), 2.60 (m, 1H), 2.59 (s, 3H), 2.33 (m, 1H), 1.65 (m, 1H), 1.32 (m, 1H), 1.18(d, 6H), 0.60 (br s, 3H); LC/MS m/z 524 (M+H)$^+$.

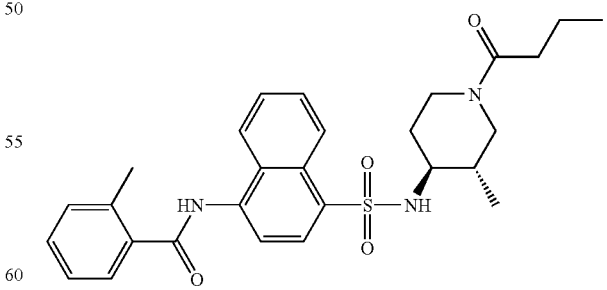

(±)-trans-N-[4-(1-Butyryl-3-methyl-piperidin-4-ylsulfamoyl)-naphthalen-1-yl]-2-methyl-benzamide (C-19)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3-methyl-piperidine for 4-amino-piperidine-1-carboxylic acid tert-butyl ester and butyryl chloride for 2-isocyanato-propane. Flash column chromatography (Hexane/EtOAc, gradient) of the mixture gave C-19. $^1$H NMR (300 MHz, CDCl$_3$) δ 8.70 (t, 1H), 8.33 (m, 3H), 7.95 (d, 1H), 7.62 (m, 3H), 7.40 (m, 1H), 7.34 (m, 2H), 5.00 (d, 1H), 4.30 (dd, 1H), 3.63 (m, 1H), 2.85 (m, 1.5H), 2.57 (s, 3H), 2.40 (t, 0.5H), 2.15 (m, 1.5H), 2.09 (m, 0.5H), 1.83 (m, 0.5H), 1.50 (m, 1.5H); LC/MS m/z 508 (M+H)$^+$.

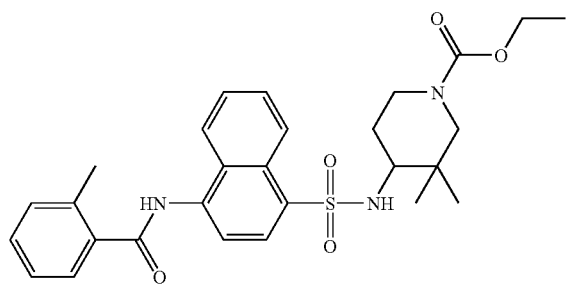

(±)-3,3-Dimethyl-4-[4-(2-methyl-benzoylamino)-naphthalene-1-sulfonylamino]-piperidine-1-carboxylic acid ethyl ester (C-20)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3,3-dimethyl-piperidine for 4-amino-piperidine-1-carboxylic acid tert-butyl ester and ethyl chloroformate for 2-isocyanato-propane. $^1$H NMR (300 MHz, DMSO) δ 8.75 (d, 1H), 8.24 (m, 2H), 7.93 (d, 1H), 7.77 (d, 1H), 7.66 (m, 3H), 7.40 (m, 3H), 3.98 (q, 2H), 3.69 (m, 1H), 3.43 (d, 1H), 2.96 (m, 1H), 2.60 (m, 1H), 2.48 (s, 3H), 1.33 (m, 1H), 1.15 (m, 1H), 1.10 (t, 3H), 0.68 (s, 3H), 0.50 (s, 3H); LC/MS m/z 524 (M+H)$^+$.

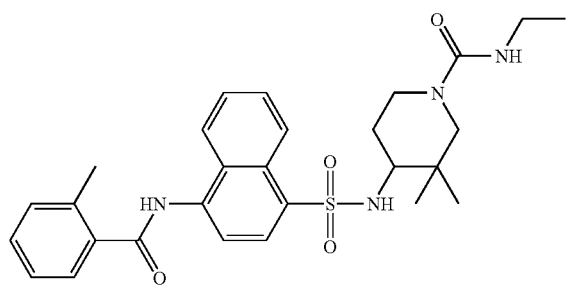

(±)-3,3-Dimethyl-4-[4-(2-methyl-benzoylamino)-naphthalene-1-sulfonylamino]-piperidine-1-carboxylic acid ethylamide (C-21)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (:)-4-amino-1-benzyl-3,3-dimethyl-piperidine for 4-amino-piperidine-1-carboxylic acid tert-butyl ester and ethyl isocyanate for 2-isocyanato-propane. $^1$H NMR (300 MHz, DMSO) δ 8.76 (d, 1H), 8.26 (m, 2H), 7.92 (d, 1H), 7.65 (m, 4H), 7.38 (m, 3H), 6.24 (m, 1H), 3.65 (d, 1H), 3.48 (d, 1H), 3.48 (d, 1H), 2.90 (m, 3H), 2.47 (s, 3H), 2.42 (m, 3H), 1.25 (m, 1H), 1.00 (m, 1H), 0.91 (t, 3H), 0.68 (s, 3H), 0.53 (s, 3H); LC/MS m/z 523 (M+H)$^+$.

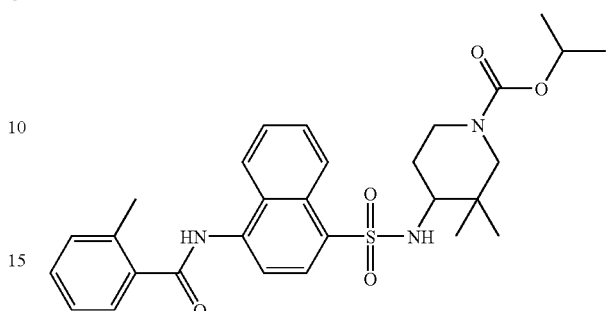

(±)-3,3-Dimethyl-4-[4-(2-methyl-benzoylamino)-naphthalene-1-sulfonylamino]-piperidine-1-carboxylic acid isopropyl ester (C-22)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (:)-4-amino-1-benzyl-3,3-dimethyl-piperidine for 4-amino-piperidine-1-carboxylic acid tert-butyl ester and isopropyl chloroformate for 2-isocyanato-propane. $^1$H NMR (300 MHz, DMSO) δ 8.75 (d, 1H), 8.25 (m, 2H), 7.93 (d, 1H), 7.70 (m, 3H), 7.38 (m, 3H), 4.66 (m, 1H), 3.68 (m, 1H), 3.43 (d, 1H), 2.94 (m, 1H), 2.55 (m, 2H), 2.47 (s, 3H), 1.30 (m, 1H), 1.10 (d, 6H), 0.67 (s, 3H), 0.50 (s, 3H); LC/MS m/z 538 (M+H)$^+$.

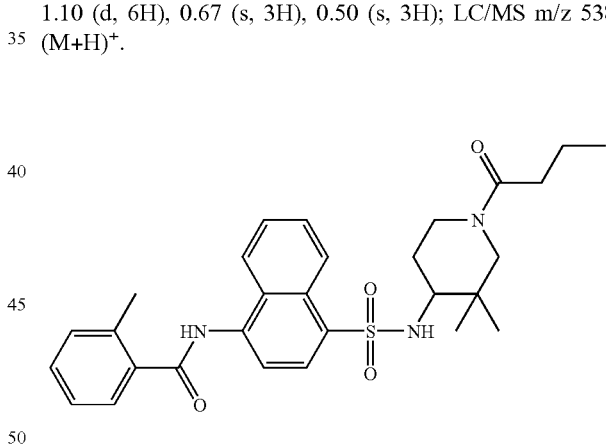

(±)-N-[4-(1-Butyryl-3,3-dimethyl-piperidin-4-ylsulfamoyl)-naphthalen-1-yl]-2-methyl-benzamide (C-23)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3,3-dimethyl-piperidine for 4-amino-piperidine-1-carboxylic acid tert-butyl ester and butyryl chloride for 2-isocyanato-propane. $^1$H NMR (300 MHz, DMSO) δ 8.77 (dd, 1H), 8.25 (m, 2H), 7.93 (d, 1H), 7.70 (m, 4H), 7.38 (m, 3H), 4.06 (d, 0.5H), 3.85 (d, 0.5H), 3.60 (d, 0.5H), 3.37 (d, 0.5H), 2.98 (m, 1H), 2.77 (m, 1H), 2.47 (s, 3H), 2.35 (d, 0.5H), 2.16 (m, 2H), 1.40 (m, 2H), 1.24 (m, 0.5H), 1.11 (m, 0.5H), 0.80 (t, 3H), 0.70 (s, 1.5H), 0.64 (s, 1.5H), 0.55 (s, 3H); LC/MS m/z 522 (M+H)$^+$.

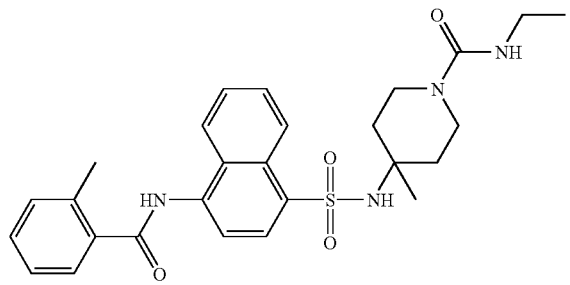

4-Methyl-4-[4-(2-methyl-benzoylamino)-naphthalene-1-sulfonylamino]-piperidine-1-carboxylic acid ethylamide (C-24)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, and 4-amino-4-methyl-piperidine-1-carboxylic acid tert-butyl ester for 4-amino-piperidine-1-carboxylic acid tert-butyl ester and ethyl isocyanate for 2-isocyanato-propane. $^1$H NMR (300 MHz, DMSO) δ 8.76 (d, 1H), 8.24 (m, 2H), 7.93 (d, 1H), 7.38 (m, 3H), 7.70 (m, 4H), 6.26 (t, 1H), 3.18 (m, 2H), 2.93 (m, 2H), 2.78 (m, 2H), 2.47 (s, 3H), 1.69 (m, 2H), 1.24 (m, 2H), 1.09 (s, 3H), 0.90 (t, 3H); LC/MS m/z 509 (M+H)$^+$.

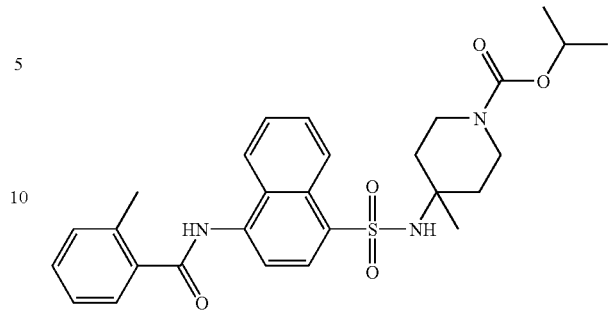

4-Methyl-4-[4-(2-methyl-benzoylaminno)-naphthalene-1-sulfonylamino]-piperidine-1-carboxylic acid isopropyl ester (C-26)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, 4-amino-4-methyl-piperidine-1-carboxylic acid tert-butyl ester for 4-amino-piperidine-1-carboxylic acid tert-butyl ester. $^1$H NMR (300 MHz, MeOD) δ 8.80 (d, 1H), 8.30 (d, 1H), 8.23 (d, 1H), 7.93 (d, 1H), 7.75 (m, 3H), 7.35 (m, 3H), 4.79 (q, 2H), 3.40 (m, 2H), 2.88 (t, 2H), 1.86 (m, 2H), 1.37 (m, 6H), 1.10 (m, 9H); LC/MS m/z 524 (M+H)$^+$.

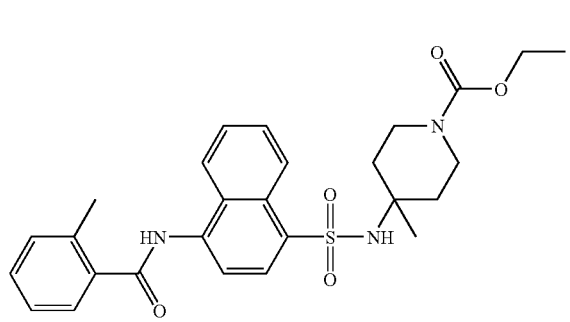

4-Methyl-4-[4-(2-methyl-benzoylamino)-naphthalene-1-sulfonylamino]-piperidine-1-carboxylic acid ethyl ester (C-25)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, 4-amino-4-methyl-piperidine-1-carboxylic acid tert-butyl ester for 4-amino-piperidine-1-carboxylic acid tert-butyl ester and ethyl chloroformate for 2-isocyanato-propane. $^1$H NMR (300 MHz, MeOD) δ 8.80 (d, 1H), 8.29 (m, 1H), 8.23 (d, 1H), 7.93 (d, 1H), 7.65 (m, 3H), 7.38 (m, 3H), 4.02 (q, 2H), 3.43 (m, 2H), 2.90 (m, 2H), 2.54 (s, 3H), 1.87 (m, 2H), 1.15 (m, 6H); LC/MS m/z 510 (M+H)$^+$.

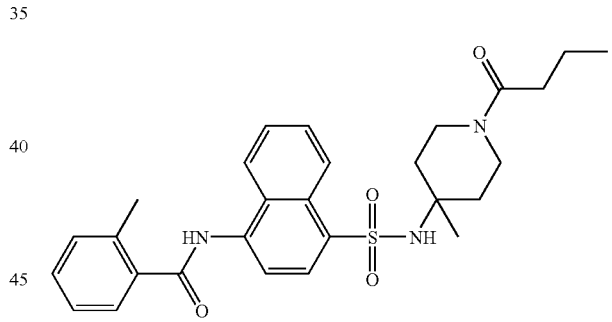

N-[4-(1-Butyryl-4-methyl-piperidin-4-ylsulfamoyl)-naphthalen-1-yl]-2-methyl-benzamide (C-27)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, 4-amino-4-methyl-piperidine-1-carboxylic acid tert-butyl ester for 4-amino-piperidine-1-carboxylic acid tert-butyl ester and butyryl chloride for 2-isocyanato-propane. $^1$H NMR (300 MHz, DMSO) δ 8.76 (d, 1H), 8.26 (m, 2H), 7.95 (d, 1H), 7.70 (m, 3H), 7.34 (m, 3H), 3.54 (m, 1H), 3.31 (m, 1H), 3.04 (m, 1H), 2.76 (m, 1H), 2.47 (s, 3H), 2.09 (t, 3H), 1.82 (m, 2H), 1.30 (m, 6H), 1.07 (s, 3H), 0.77 (t, 3H); LC/MS m/z 508 (M+H)$^+$.

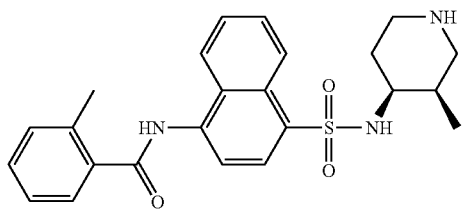

(±)-cis-2-Methyl-N-[4-(3-methyl-piperidin-4-ylsulfamoyl)-naphthalen-1-yl]-benzamide (C-28)

The title compound was made following general procedure in Scheme 5, substituting 4-(2-methyl-benzoylamino)-naphthalene-1-sulfonyl chloride for 4-benzoylamino-naphthalene-1-sulfonyl chloride and (±)-4-amino-1-benzyl-3-methyl-piperidine for 4-amino-piperidine-1-carboxylic acid tert-butyl ester. Purification of the benzyl-protected intermediate by Flash column chromatography (Hexane/EtOAc, gradient) followed by deprotection according to Scheme 4-2 gave C-28. $^1$H NMR (300 MHz, MeOD) δ 8.82 (d, 1H), 8.52 (s, 1H), 8.32 (d, 1H), 8.24 (d, 2H), 7.94 (d, 2H), 7.70 (m, 3H), 7.4 (m, 3H), 3.46 (m, 1H), 3.00 (m, 2H), 2.97 (m, 1H), 2.55 (s, 3H), 1.93 (m, 1H), 1.64 (m, 2H), 0.63 (d, 3H); LC/MS m/z 438 (M+H)$^+$.

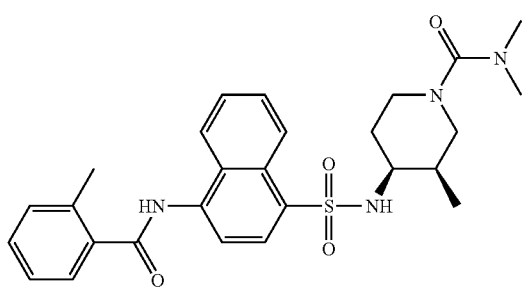

(±)-cis-3-Methyl-4-[4-(2-methyl-benzoylandno)-naphthalene-1-sulfonylamio]-piperidine-1-carboxylic acid dimethylamide (C-29)

The title compound was made following general procedure in Scheme 5 and deprotection in Scheme 4-2, substituting 4-(2-methyl-benzoylamino)-naphthalene-1-sulfonyl chloride for 4-benzoylamino-naphthalene-1-sulfonyl chloride, 4-amino-1-benzyl-3-methyl-piperidine for 4-amino-piperidine-1-carboxylic acid tert-butyl ester and dimethylcarbamyl chloride for 2-isocyanato-propane. $^1$H NMR (300 MHz, CDCl$_3$) δ 8.71 (d, 1H), 8.41 (s, 1H), 8.28 (s, 1H), 7.97 (d, 1H), 7.62 (m, 3H), 7.41 (m, 1H), 7.28 (m, 2H), 5.27 (d, 1H), 3.38 (m, 1H), 3.11 (m, 1H), 2.99 (dd, 1H), 2.88 (m, 2H), 2.70 (s, 6H), 2.56 (s, 3H), 1.46 (m, 1H), 1.42 (m, 2H), 0.63 (d, 3H); LC/MS m/z 509 (M+H)$^+$.

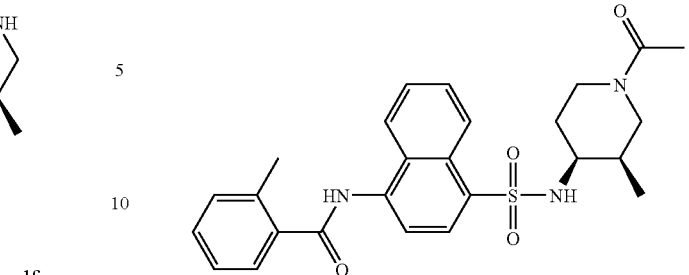

(±)-cis-N-[4-(1-Acetl-3-methyl-piperidin-4-ylsulfamoyl)-naphthalen-1-yl]-2-methyl-benzamide (C-30)

The title compound was made following general procedure in Scheme 5 and deprotection in Scheme 4-2, substituting 4-(2-methyl-benzoylamino)-naphthalene-1-sulfonyl chloride for 4-benzoylamino-naphthalene-1-sulfonyl chloride, 4-amino-1-benzyl-3-methyl-piperidine for 4-amino-piperidine-1-carboxylic acid tert-butyl ester and acetyl chloride for 2-isocyanato-propane. 1H NMR (300 MHz, CDCl$_3$) δ 8.74 (m, 1H), 8.33 (br s, 3H), 7.98 (d, 1H), 7.63 (m, 3H), 7.42 (m, 1H), 7.26 (m, 2H), 5.29 (d, 1H), 3.78 (m, 0.5H), 3.38 (m, 1.5H), 3.20 (m, 1.5H), 2.97 (m, 0.5H), 2.57 (s, 3H), 2.08 (m, 1.5H), 1.96 (d, 3H), 1.83 (m, 0.5H), 1.45 (m, 2H), 0.72 (d, 1.5H), 0.56 (d, 1.5H); LC/MS m/z 480 (M+H)$^+$.

(±)-(trans)-N-[4-(1-Acetyl-3-methyl-piperidin-4-ylsulfamoyl)-naphthalen-1-yl]-2-methyl-benzamide (C-31)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, 4-amino-4-methyl-piperidine-1-carboxylic acid tert-butyl ester for 4-amino-piperidine-1-carboxylic acid tert-butyl ester and acetyl chloride for 2-isocyanato-propane. $^1$H NMR (300 MHz, CDCl$_3$) δ 8.70 (m, 1H), 8.35 (m, 3H), 7.95 (d, 1H), 7.65 (m, 3H), 7.40 (m, 1H), 7.26 (m, 2H), 5.02 (d, 1H), 4.30 (m, 1H), 3.58 (m, 1H), 2.95 (m, 2H), 2.62 (m, 0.5H), 2.58 (s, 3H), 2.45 (m, 0.5H), 1.98 (s, 3H), 1.75 (m, 1H), 1.25 (m, 2H), 0.70 (d, 1.5H), 0.51 (d, 1.5H); LC/MS m/z 480 (M+H)$^+$.

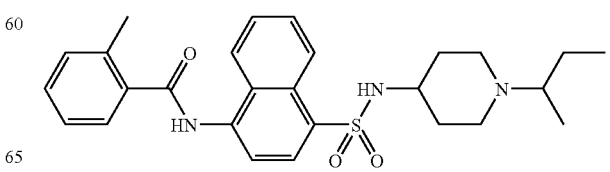

(±)-N-[4-(1-sec-Butyl-piperidin-4-ylsulfamoyl)-naphthalen-1-yl]-2-methyl-benzamide (C-32)

The title compound was made following general procedure in Scheme 5, substituting 4-(2-methyl-benzoylamino)-naphthalene-1-sulfonyl chloride for 4-benzoylamino-naphthalene-1-sulfonyl chloride, and butan-2-one/sodium triacetoxyborohydride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 3.39 (m, 1H), 3.15 (m, 3H), 2.98 (m, 2H), 2.55 (s, 3H), 1.88 (m, 2H), 1.72 (m, 3H), 1.43 (m, 1H), 1.19 (d, 3H), 0.95 (t, 3H); LC/MS (M+H)$^+$ m/z 480.

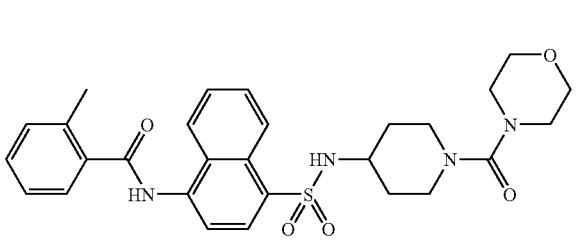

2-Methyl-N-{4-[1-(morpholine-4-carbonyl)-piperidin-4-ylsulfamoyl]-naphthalen-1-yl}-benzamide (C-33)

The title compound was made following general procedure in Scheme 5, substituting 4-(2-methyl-benzoylamino)-naphthalene-1-sulfonyl chloride for 4-benzoylamino-naphthalene-1-sulfonyl chloride, and morpholine-4-carbonyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.59 (t, 4H), 3.50 (m, 2H), 3.27 (m, 1H), 3.19 (t, 4H), 2.76 (m, 2H), 2.54 (s, 3H), 1.59 (m, 2H), 1.27 (m, 2H); LC/MS (M+H)$^+$ m/z 537.

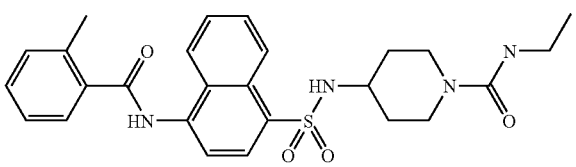

4-[4-(2-Methyl-benzoylamino)-naphthalene-1-sulfonylamino]-piperidine-1-carboxylic acid ethylamide (C-34)

The title compound was made following general procedure in Scheme 5, substituting 4-(2-methyl-benzoylamino)-naphthalene-1-sulfonyl chloride for 4-benzoylamino-naphthalene-1-sulfonyl chloride, and isocyanato-ethane for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.73 (m, 2H), 3.23 (m, 1H), 3.11 (q, 2H), 2.69 (m, 2H), 2.54 (s, 3H), 1.53 (m, 2H), 1.29 (m, 2H), 1.04 (t, 3H); LC/MS (M+H)$^+$ m/z 495.

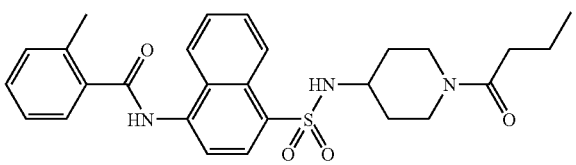

N-[4-(1-Butyryl-piperidin-4-ylsulfamoyl)-naphthalen-1-yl]-2-methyl-benzamide (C-35)

The title compound was made following general procedure in Scheme 5, substituting 4-(2-methyl-benzoylamino)-naphthalene-1-sulfonyl chloride for 4-benzoylamino-naphthalene-1-sulfonyl chloride, and butyryl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 4.19 (m, 1H), 3.74 (m, 1H), 3.33 (m, 1H), 3.01 (m, 1H), 2.64 (m, 1H), 2.54 (s, 3H), 2.74 (t, 2H), 1.62 (m, 2H), 1.55 (m, 2H), 1.29 (m, 21H), 0.89 (t, 3H); LC/MS (M+H)$^+$ m/z 496.

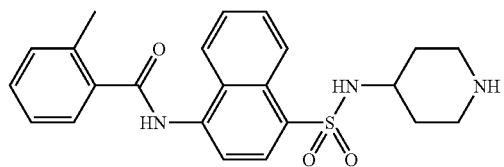

2-Methyl-N-[4-(piperidin-4-ylsulfamoyl)-naphthalen-1-yl]-benzamide (C-36)

The title compound was made following general procedure in Scheme 5, substituting 4-(2-methyl-benzoylamino)-naphthalene-1-sulfonyl chloride for 4-benzoylamino-naphthalene-1-sulfonyl chloride. $^1$H NMR (300 MHz, MeOD) δ 8.75 (d, 1H), 8.33 (d, 1H), 8.23 (d, 1H), 7.94 (d, 1H), 7.71 (m, 3H), 7.39 (m, 3H), 3.49 (m, 1H), 3.15 (m, 2H), 2.90 (m, 2H), 2.50 (s, 3H), 2.21 (m, 1H), 1.82 (m, 2H), 1.59 (m, 1H)); LC/MS (M+H)$^+$ m/z 424.

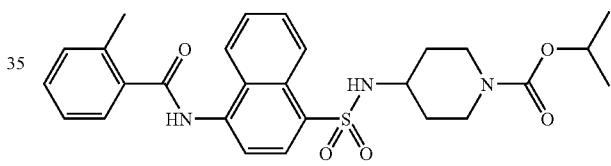

4-[4-(2-Methyl-benzoylamino)-naphthalene-1-sulfonylamino]-piperidine-1-carboxylic acid isopropyl ester (C-37)

The title compound was made following general procedure in Scheme 5, substituting 4-(2-methyl-benzoylamino)-naphthalene-1-sulfonyl chloride for 4-benzoylamino-naphthalene-1-sulfonyl chloride, and isopropyl chloroformate for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 4.80 (m, 1H), 3.83 (m, 2H), 3.25 (m, 1H), 2.79 (m, 2H), 2.54 (s, 3H), 1.58 (m, 2H), 1.29 (m, 2H), 1.20 (t, 3H); LC/MS (M+H)$^+$ m/z 510.

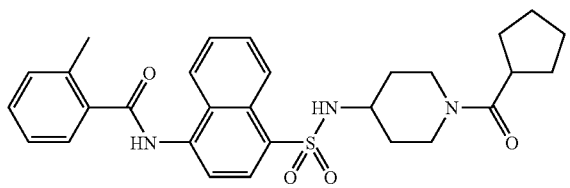

N-[4-(1-Cyclopentanecarbonyl-piperidin-4-ylsulfamoyl)-naphthalen-1-yl]-2-methyl-benzamide (C-38)

The title compound was made following general procedure in Scheme 5, substituting 4-(2-methyl-benzoylamino)-naphthalene-1-sulfonyl chloride for 4-benzoylamino-naphthalene-1-sulfonyl chloride, and cyclopentanecarbonyl chloride for 2-isocyanato-propane. ¹H NMR (300 MHz, MeOD) δ 8.78 (d, 1H), 8.33 (d, 1H), 8.25 (d, 1H), 7.94 (d, 1H), 7.71 (m, 3H), 7.41 (m, 3H), 4.19 (m, 1H), 3.88 (m, 1H), 3.00 (m, 2H), 2.68 (m, 2llH), 2.54 (s, 3H), 1.65 (m, 11lH), 1.29 (m, 3H); LC/MS (M+H)⁺ m/z 520.

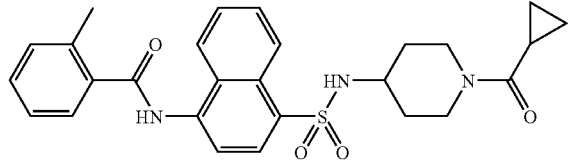

N-[4-(1-Cyclopropanecarbonyl-piperidin-4-ylsulfamoyl)-naphthalen-1-yl]-2-methyl-benzamide (C-39)

The title compound was made following general procedure in Scheme 5, substituting 4-(2-methyl-benzoylamino)-naphthalene-1-sulfonyl chloride for 4-benzoylamino-naphthalene-1-sulfonyl chloride, and cyclopropanecarbonyl chloride for 2-isocyanato-propane. ¹H NMR (300 MHz, MeOD) δ 8.78 (d, 1H), 8.33 (d, 1H), 8.25 (d, 1H), 7.94 (d, 1H), 7.71 (m, 3H), 7.41 (m, 3H), 4.17 (m, 2H), 3.13 (m, 1H), 2.71 (m, 2H), 2.54 (s, 3H), 1.84 (m, 1H), 1.71 (m, 1H), 1.59 (m, 1H), 1.29 (m, 2H), 0.79 (m, 4H); LC/MS (M+H)⁺ m/z 492.

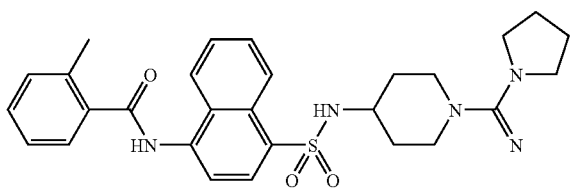

N-{4-[1-(Imino-pyrrolidin-1-yl-methyl)-piperidin-4-ylsulfamoyl]-naphthalen-1-yl}-2-methyl-benzamide (C-40)

The title compound was made following general procedure in Scheme 5, substituting 4-(2-methyl-benzoylamino)-naphthalene-1-sulfonyl chloride for 4-benzoylamino-naphthalene-1-sulfonyl chloride, and pyrrolidine-1-carbonitrile for 2-isocyanato-propane. ¹H NMR (300 MHz, DMSO) δ 8.70 (d, 1H), 8.49 (s, 1H), 8.28 (d, 1H), 8.21 (d, 1H), 7.93 (d, 1H), 7.71 (m, 3H), 7.39 (m, 3H), 3.40 (m, 9H), 2.98 (m, 2H), 2.54 (s, 3H), 1.82 (m, 4H), 1.60 (m, 1H), 1.39 (m, 1H); LC/MS (M+H)⁺ m/z 520.

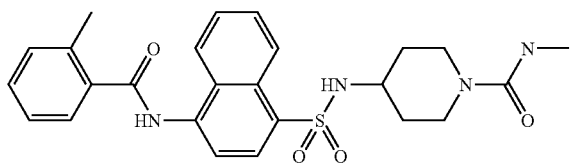

4-[4-(2-Methyl-benzoylamino)-naphthalene-1-sulfonylamino]-piperidine-1-carboxylic acid methylamide (C-41)

The title compound was made following general procedure in Scheme 5, substituting 4-(2-methyl-benzoylamino)-naphthalene-1-sulfonyl chloride for 4-benzoylamino-naphthalene-1-sulfonyl chloride, and isocyanatomethane for 2-isocyanato-propane. ¹H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.73 (m, 2H), 3.25 (m, 1H), 2.72 (m, 2H), 2.65 (s, 3H), 2.56 (s, 3H), 1.53 (m, 2H), 1.28 (m, 2H); LC/MS (M+H)⁺ m/z 481.

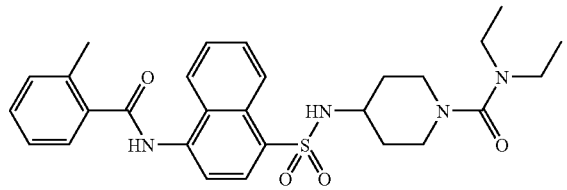

4-[4-(2-Methyl-benzoylamino)-naphthalene-1-sulfonylamino]-piperidine-1-carboxylic acid diethylamide (C-42)

The title compound was made following general procedure in Scheme 5, substituting 4-(2-methyl-benzoylamino)-naphthalene-1-sulfonyl chloride for 4-benzoylamino-naphthalene-1-sulfonyl chloride, and diethylcarbamyl chloride for 2-isocyanato-propane.

¹H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.41 (m, 2H), 3.23 (m, 1H), 3.15 (q, 4H), 2.72 (m, 2H), 2.56 (s, 3H), 1.53 (m, 2H), 1.40 (m, 2H), 1.07 (t, 6H); LC/MS (M+H)⁺ m/z 523.

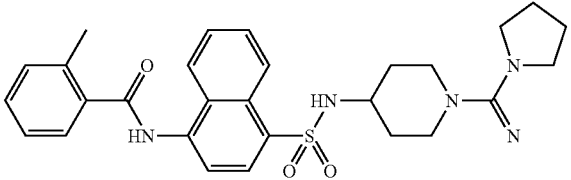

2-Methyl-N-{4-[1-(pyrrolidine-1-carbonyl)-piperidin-4-ylsulfamoyl]-naphthalen-1-yl}-benzamide (C-43)

The title compound was made following general procedure in Scheme 5, substituting 4-(2-methyl-benzoylamino)-naphthalene-1-sulfonyl chloride for 4-benzoylamino-naphthalene-1-sulfonyl chloride, and pyrrolidine-1-carbonyl chloride for 2-isocyanato-propane. ¹H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.55 (m, 2H), 3.25 (m, 5H), 2.72 (m, 2H), 2.56 (s, 3H), 1.72 (m, 4H), 1.59 (m, 2H), 1.38 (m, 2H); LC/MS (M+H)⁺ m/z 521.

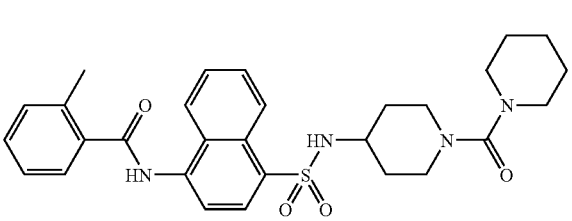

2-Methyl-N-{4-[1-(piperidine-1-carbonyl)-piperidin-4-ylsulfamoyl]-naphthalen-1-yl}-benzamide (C-44)

The title compound was made following general procedure in Scheme 5, substituting 4-(2-methyl-benzoylamino)-naphthalene-1-sulfonyl chloride for 4-benzoylamino-naphthalene-1-sulfonyl chloride, and piperidine-1-carbonyl chloride for 2-isocyanato-propane. ¹H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.41 (m, 4H), 3.15 (m, 5H), 2.72 (m,2H), 2.56 (s, 3H), 1.58 (m, 8H); LC/MS (M+H)+ m/z 535.

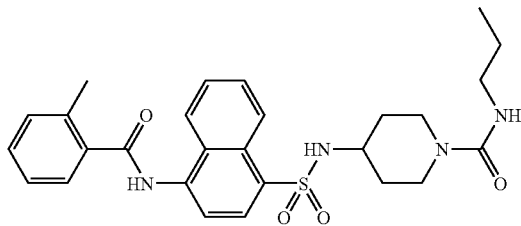

4-[4-(2-Methyl-benzoylamino)-naphthalene-1-sulfonylamino]-piperidine-1-carboxylic acid propylamide (C-45)

The title compound was made following general procedure in Scheme 5, substituting 4-(2-methyl-benzoylamino)-naphthalene-1-sulfonyl chloride for 4-benzoylamino-naphthalene-1-sulfonyl chloride, and 1-isocyanato-propane for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 3.75 (m, 2H), 3.25 (m, 1H), 3.06 (t, 2H), 2.74 (m, 2H), 2.59 (s, 3H), 1.59 (m, 2H), 1.49 (m, 2H), 1.30 (m, 2H), 0.89 (t, 31H); LCtMS (M+H)+ m/z 509.

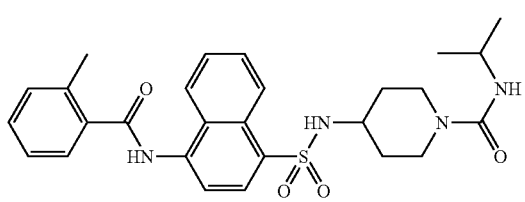

4-[4-(2-Methyl-benzoylamino)-naphthalene-1-sulfonylamino]-piperidine-1-carboxylic acid isopropylamide (C-46)

The title compound was made following general procedure in Scheme 5, substituting 4-(2-methyl-benzoylamino)-naphthalene-1-sulfonyl chloride for 4-benzoylamino-naphthalene-1-sulfonyl chloride. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H ), 7.38 (m, 2H), 3.76 (m, 2H), 3.25 (m, 2H), 2.71 (m, 2H), 2.57 (s, 3H), 1.59 (m, 2H), 1.30 (m, 2H), 1.05 (d, 6H); LC/MS (M+H)+ m/z 509.

4-[4-(2-Methyl-benzoylamino)-naphthalene-1-sulfonylamino]-piperidine-1-carboxylic acid dimethylamide (C-47)

The title compound was made following general procedure in Scheme 5, substituting 4-(2-methyl-benzoylamino)-naphthalene-1-sulfonyl chloride for 4-benzoylamino-naphthalene-1-sulfonyl chloride, and dimethylcarbamyl chloride for 2-isocyanato-propane. 1H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 3.54 (m, 2H), 3.25 (m, 1H), 2.75 (s, 6H), 2.71 (m, 2H), 2.55 (s, 3H), 1.59 (m, 2H), 1.35 (m, 211); LC/MS (M+H)+ m/z 495.

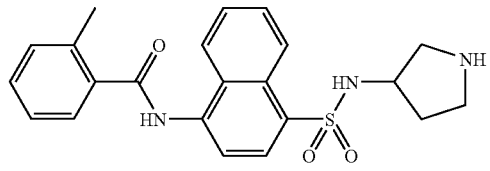

(±)-2-Methyl-N-[4-(pyrrolidin-3-ylsulfamoyl)-naphthalen-1-yl]-benzamide (C-48)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-pyrrolidine-1-carboxylic acid tert-butyl ester for 4-amino-piperidine-1-carboxylic acid tert-butyl ester. $^1$H NMR (300 MHz, DMSO) δ 8.78 (d, 1H), 8.33 (m, 2H), 8.23 (d, 1H), 7.94 (d, 1H), 7.71 (m, 3H), 7.43 (m, 1H ), 7.38 (m, 2H), 3.69 (m, 1H), 3.88 (m, 3H), 2.61 (m, 1H ), 2.48 (s, 3H), 1.74 (m, 1H), 1.49 (m, 1H); LC/MS (M+H)+ m/z 410.

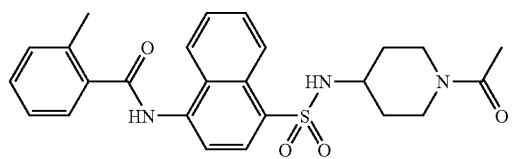

N-[4-(1-Acetyl-piperidin-4-ylsulfamoyl)-naphthalen-1-yl]-2-methyl-benzamide (C-49)

The title compound was made following general procedure in Scheme 5, substituting 4-(2-methyl-benzoylamino)-naphthalene-1-sulfonyl chloride for 4-benzoylamino-naphthalene-1-sulfonyl chloride, and acetyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 4.15 (m, 1H), 3.69 (m, 1H), 3.25 (m, 1H), 3.03 (m, 1H ), 2.69 (m, 1H), 2.55 (s, 3H), 1.98 (s, 3H), 1.59 (m, 2H), 1.31 (m, 2H); LC/MS (M+H)+ m/z 466.

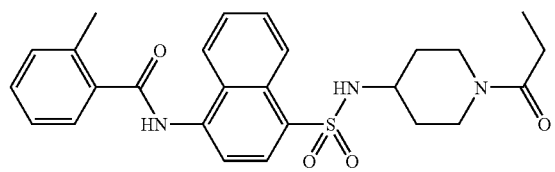

2-Methyl-N-[4-(1-propionyl-piperidin-4-ylsulfamoyl)-naphthalen-1-yl]-benzamide (C-50)

The title compound was made following general procedure in Scheme 5, substituting 4-(2-methyl-benzoylamino)-naphthalene-1-sulfonyl chloride for 4-benzoylamino-naphthalene-1-sulfonyl chloride, and propionyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H ), 7.38 (m, 2H), 4.19 (m, 1H), 3.72 (m, 1H), 3.25 (m, 1H), 3.01 (m, 1H), 2.69 (m, 1H), 2.55 (s, 3H), 2.41 (q, 2H), 1.61 (m, 2H), 1.31 (m, 2H), 1.02 (t, 3Hj; LC/MS (M+H)+ m/z 480.

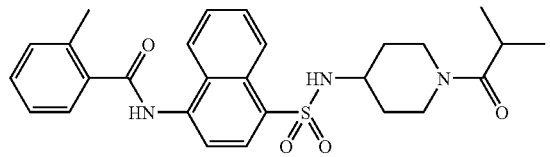

N-[4-(1-Isobutyryl-piperidin-4-ylsuffamoyl)-naphthalen-1-yl]-2-methyl-benzamide (C-51)

The title compound was made following general procedure in Scheme 5, substituting 4-(2-methyl-benzoylamino)-naphthalene-1-sulfonyl chloride for 4-benzoylamino-naphthalene-1-sulfonyl chloride, and isobutyryl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 4.20 (m, 1H), 3.72.

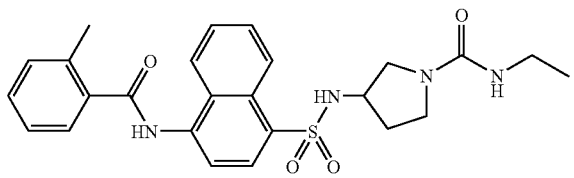

(±)-3-[4-(2-Methyl-benzoylamino)-naphthalene-1-sulfonylamino]-pyrrolidine-1-carboxylic acid ethylamide (C-52)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-pyrrolidine-1-carboxylic acid tert-butyl ester for 4-amino-piperidine-1-carboxylic acid tert-butyl ester and isocyanato-ethane for 2-isocyanato-propane. $^1$H NMR (300 MHz, MeOD) δ 8.78 (d, 1H), 8.33 (m, 2H), 8.23 (d, 1H), 7.94 (d, 1H), 7.71 (m, 3H), 7.43 (m, 1H), 7.38 (m, 2H), 3.80 (m, 1H), 3.19 (m, 1H), 3.11 (q, 2H), 3.09 (m, 3H), 2.55 (s, 3H), 1.89 (m, 1H), 1.73 (m, 1H), 1.03 (t, 3H); LC/MS (M+H)$^+$ m/z 481.

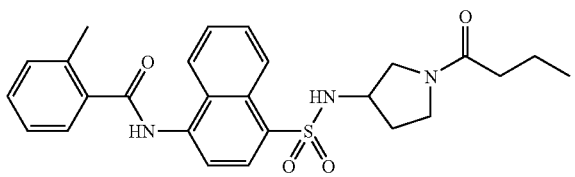

(±)-3-[4-(2-Methyl-benzoylandno)-naphthalene-1-sulfonylamino]-pyrrolidine-1-carboxylic acid ethylarnide (C-53)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-pyrrolidine-1-carboxylic acid tert-butyl ester for 4-amino-piperidine-1-carboxylic acid tert-butyl ester and butyryl chloride for 2-isocyanato-propane. $^1$H NMR (300 MHz, MeOD) δ 8.78 (d, 1H), 8.33 (m, 2H), 8.23 (d, 1H), 7.94 (d, 1H), 7.71 (m, 3H), 7.43 (m, 1H), 7.38 (m, 2H), 3.85 (m, 1H), 3.40 (m, 3H), 3.15 (m, 1H), 2.53 (s, 3H), 2.19 (t, 1H), 1.95 (t, 1H), 1.85 (m, 2H), 1.50 (m, 2H), 0.88 (m, 3H); LC/MS (M+H)$^+$ m/z 480.

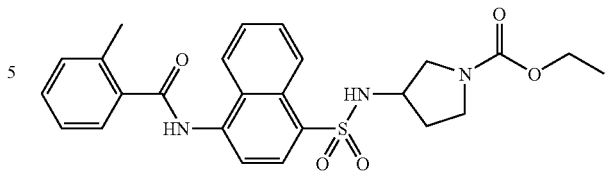

(±)-3-[4-(2-Methyl-benzoylamino)-naphthalene-2-sulfonylamino]-pyrrolidine-1-carboxylic acid ethyl ester (C-54)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-pyrrolidine-1-carboxylic acid tert-butyl ester for 4-amino-piperidine-1-carboxylic acid tert-butyl ester and ethyl chlorofomate for 2-isocyanato-propane. $^1$H NMR (300 MHz, MeOD) δ 8.78 (d, 1H), 8.33 (m, 2H), 8.23 (d, 1H), 7.94 (d, 1H), 7.71 (m, 3H), 7.43 (m, 1H ), 7.38 (m, 2H), 4.06 (m, 2H), 3.80 (m, 1H), 3.38 (m, 1H), 3.25 (m, 1H ), 3.09 (m, 2H), 2.55 (s, 3H), 1.89 (m, 1H), 1.73 (m, 1H), 1.20 (m, 3H); LC/MS (M+H)$^+$ m/z 483.

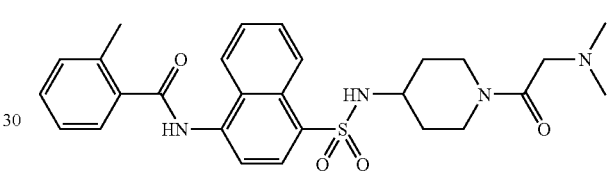

N-{4-[1-(2-Dimethylamino-acetl)-piperidin-4-ylsulfamoyl]-naphthalen-1-yl}-2-methyl-benzamide (C-55)

The title compound was made following general procedure in Scheme 5, substituting 4-(2-methyl-benzoylamino)-naphthalene-1-sulfonyl chloride for 4-benzoylamino-naphthalene-1-sulfonyl chloride, and dimethylamino-acetyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 4.18 (m, 1 H), 3.94 (d, 2H), 3.54 (m, 11H), 3.34 (m, 1H), 3.03 (m, 1H ), 2.80 (m, 1H), 2.77 (s, 6H), 2.55 (s, 3H), 1.68 (m, 2H), 1.39 (m, 2H); LC/MS (M+H)$^+$ m/z 509.

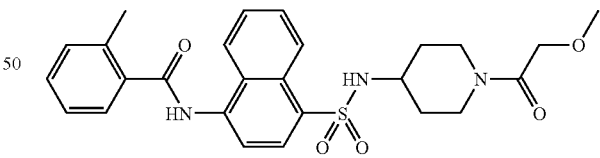

N{4-[1-(2-Methoxy-acetyl)-piperidin-4-ylsulfamoyl]-naphthalen-1-yl}-2-methyl-benzamide (C-56)

The title compound was made following general procedure in Scheme 5, substituting 4-(2-methyl-benzoylamino)-naphthalene-1-sulfonyl chloride for 4-benzoylamino-naphthalene-1-sulfonyl chloride, and methoxy-acetyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H ), 7.38 (m, 2H), 4.15 (m, 1H), 4.04 (d, 2H), 3.94 (d, 2H), 3.63 (m, 1H), 3.34 (s, 3H), 3.32 (m, 1H), 3.01 (m, 1H ), 2.71 (m, 1H), 2.55 (s, 3H), 1.63 (m, 2H), 1.41 (m, 2H); LC/MS (M+H)$^+$ m/z 496.

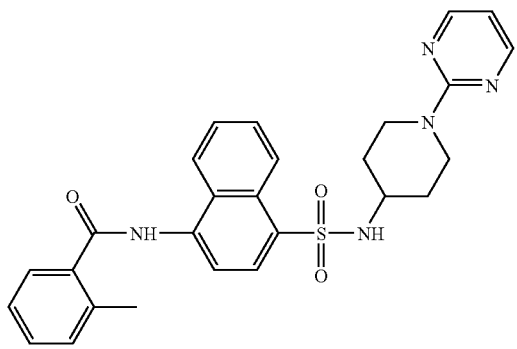

2-Methyl-N-[4-(1-pyrimidin-2-yl-piperidin-4-ylsulfamoyl)-naphthalen-1-yl]-benzamide (C-57)

The title compound was made following general procedure in Scheme 5, substituting 4-[4-(2-methyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting 2-bromo-pyrimidine for 2-isocyanato-propane. $^1$H NMR (300 MHz, CDCl$_3$/MeOD) δ 8.57 (d, 1H), 8.19 (d, 2H), 8.08 (d, 2H), 7.97 (d, 2H), 7.52 (m, 3H), 7.27 (t, 1H), 7.18 (d, 2H), 6.32 (t, 1H), 4.30 (d, 2H), 3.93 (s, 3H), 3.21 (m, 1H), 2.79 (dt, 2H), 2.43 (s, 3H), 1.58 (m, 2H), 1.20 (m, 3H); LC/MS m/z 500 (M−H)$^-$

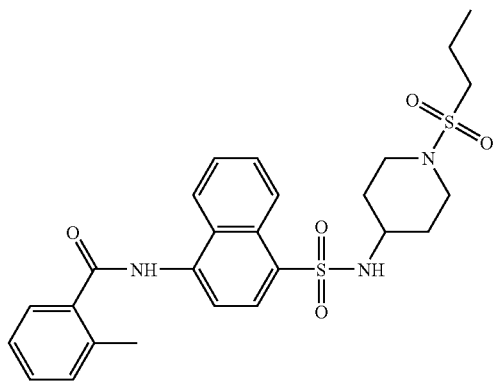

2-Methyl-N-{4-[1-(propane-1-sulfonyl)-piperidin-4-ylsulfamoyl]-naphthalen-1-yl}-benzamide (C-59)

The title compound was made following general procedure in Scheme 5, substituting 4-[4-(2-methyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting propane-1-sulfonyl chloride for 2-isocyanato-propane. $^1$H NMR (300 MHz, MeOD/CDCl$_3$) δ 8.69 (d, 1H), 8.27 (d, 1H), 8.17 (d, 1H), 7.97 (m, 1H), 7.62 (m, 4H), 7.34 (m, 2H), 3.50 (d, 2H), 3.15 (m, 1H), 2.75 (m, 4H), 2.54 (s, 3H), 1.68 (m, 4H), 1.45 (m, 2H), 1.00 (s, 3H); LC/MS m/z 528 (M−H)$^-$

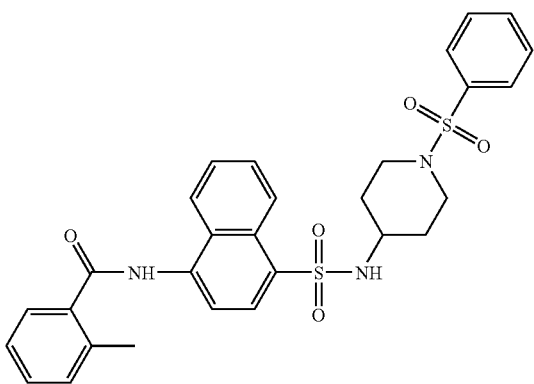

N-[4-(1-Benzenesulfonyl-piperidin-4-ylsulfamoyl)-naphthalen-1-yl]-2-methyl-benzamide (C-58)

The title compound was made following general procedure in Scheme 5, substituting 4-[4-(2-methyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting benzenesulfonyl chloride for 2-isocyanato-propane. $^1$H NMR (300 MHz, CDCl$_3$) δ 8.60 (d, 1H), 8.22 (m, 3H), 7.94 (d, 1H), 7.48 (m, 1H), 4.57 (d, 1H), 3.49 (m, 2H), 3.02 (s, br, 1H), 2.55 (s, 3H), 2.28 (t, 2H), 1.60 (m, 2H), 1.40 (m, 2H); LC/MS m/z 564 (M+H)$^+$

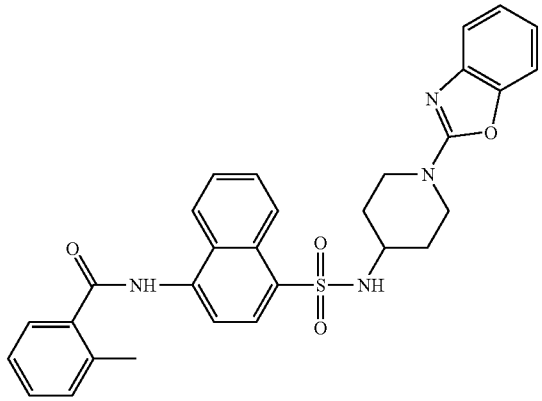

N-[4-(1-Benzooxazol-2-yl-piperidin-4-ylsulfamoyl)-naphthalen-1-yl]-2-methyl-benzamide (C-60)

The title compound was made following general procedure in Scheme 5, substituting 4-[4-(2-Methyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting 2-chloro-benzooxazole for 2-isocyanato-propane. $^1$H NMR (300 MHz, MeOD/CDCl$_3$) δ 8.47 (dd, 1H), 8.08 (d, 1H), 8.94 (m, 1H), 7.80 (m, 1H), 7.44 (m, 3H), 7.12 (m, 3H), 6.98 (t, 2H), 6.89 (td, 1H), 6.76 (td, 1H), 3.75 (d, 2H), 3.10 (m, 1H), 2.75 (td, 2H), 2.30 (s, 3H), 1.50 (m, 2H), 1.25 (m, 2H); LC/MS m/z 528 (M+H)$^+$

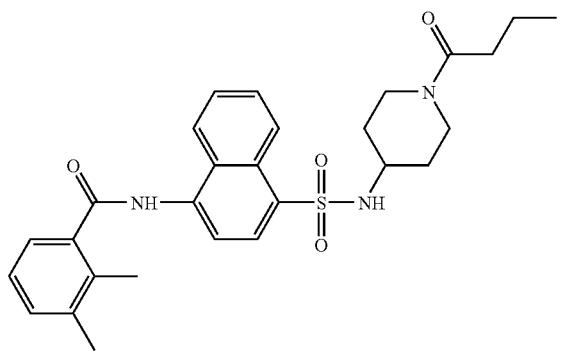

N-[4-(1-Butyryl-piperidin-4-ylsulfamoyl)-naphthalen-1-yl]-2,3-dimethyl-benzamide (C-61)

The title compound was made following general procedure in Scheme 5, substituting 4-[4-(2,3-dimethyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting butyl chloride for 2-isocyanato-propane. $^1$H NMR (300 MHz, MeOD) δ 8.75 (d, 1H), 8.32 (d, 1H), 8.22 (d, 1H), 7.96 (m, 1H), 7.71 (m, 2H), 7.46 (m, 1H), 7.29 (m, 2H), 4.35 (d, 1H), 3.75 (d, 1H), 3.02 (t, 1H), 2.65 (m, 1H), 2.45 (s, 3H), 2.35 (s, 3H), 2.25 (m, 1H), 1.60 (m, 4H), 1.28 (m, 2H), 2.75 (m, 2H), 0.90 (m, 5H); LC/MS m/z 508 (M+H)$^+$

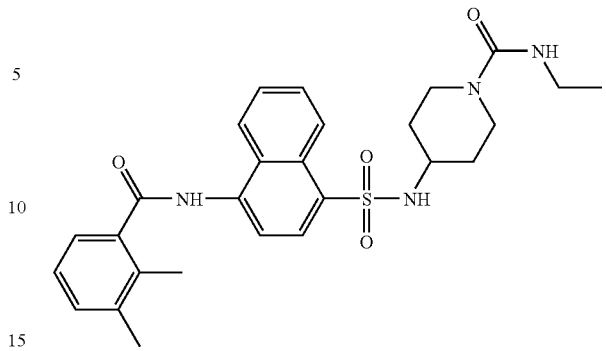

4-[4-(2,3-Dimethyl-benzoylamino)-naphthalene-1-sulfonylamino]-piperidine-1-carboxylic acid ethylamide (C-63)

The title compound was made following general procedure in Scheme 5, substituting 4-[4-(2,3-dimethyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting isocyanato-ethane for 2-isocyanato-propane. $^1$H NMR (300 MHz, MeOD) δ 8.75 (d, 1H), 8.31 (d, 1H), 8.22 (d, 1H), 7.96 (m, 1H), 7.71 (m, 2H), 7.46 (m, 1H), 7.29 (m, 2H), 3.75 (d, 2H), 3.82 (d, 2H), 3.25 (m, 1H), 3.10 (q, 2H), 2.72 (t, 2H), 2.45 (s, 3H), 2.35 (s, 3H), 1.55 (m, 2H), 1.25 (m, 2H), 1.05 (t, 3H); LC/MS m/z 509 (M+H)$^+$

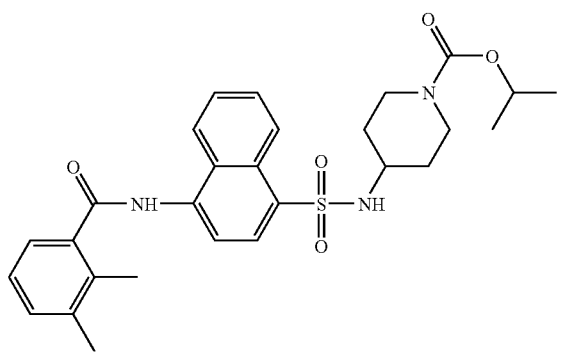

4-[4-(2,3-Dimethyl-benzoylamino)-naphthalene-1-sulfonylamino]-piperidine-1-carboxylic acid isopropyl ester (C-62)

The title compound was made following general procedure in Scheme 5, substituting 4-[4-(2,3-dimethyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting isopropyl chloroformate for 2-isocyanato-propane. $^1$H NMR (300 MHz, MeOD) δ 8.75 (d, 1H), 8.31 (d, 1H), 8.22 (d, 1H), 7.96 (m, 1H), 7.71 (m, 2H), 7.46 (m, 1H), 7.29 (m, 2H), 4.78 (m, 1H), 3.82 (d, 2H), 3.25 (m, 1H), 2.75 (m, 2H), 2.45 (s, 3H), 2.35 (s, 3H), 1.50 (m, 2H), 1.25 (m, 2H), 1.15 (d, 6H); LC/MS m/z 524 (M+H)$^+$

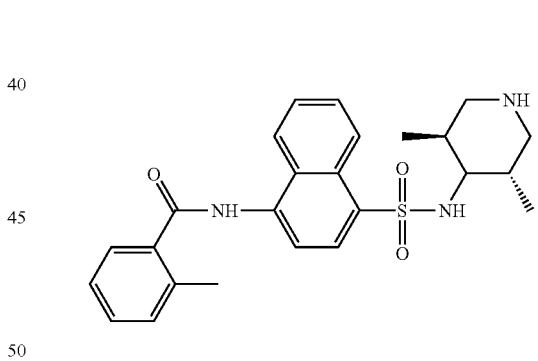

(±)-(cistrans)-N-[4-(3,5-Dimethyl-piperidin-4-ylsulfamoyl)-naphthalen-1-yl]-2-methyl-benzamide (C-64)

The title compound was made following general procedure in scheme 4-2, substituting (±)-1-benzyl-3,5-dimethyl-piperidin-4-ylamine (5) for (±)-4-amino-1-benzyl-piperidine-3-carboxylic acid ethyl ester (6). $^1$H NMR (300 MHz, CDCl$_3$) δ 8.65 (d, 1H), 8.35 (s, 1H), 8.18 (d, 1H), 8.05 (m, 2H), 7.55 (m, 3H), 7.30 (m, 1H), 7.20 (m, 2H), 3.85 (s, br, 1H), 3.05 (m, 2H), 2.80 (m, 2H), 2.50 (s, 3H), 2.40 (m, 1H), 1.85 (m, 2H), 0.63 (dd, 6H); LC/MS m/z 453 (M+H)$^+$

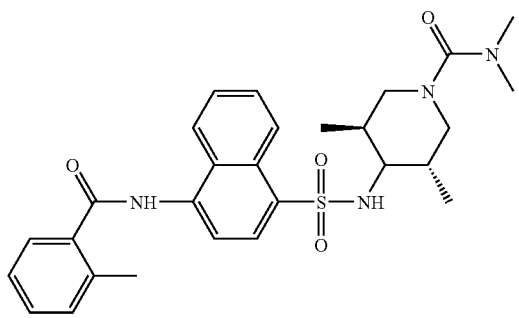

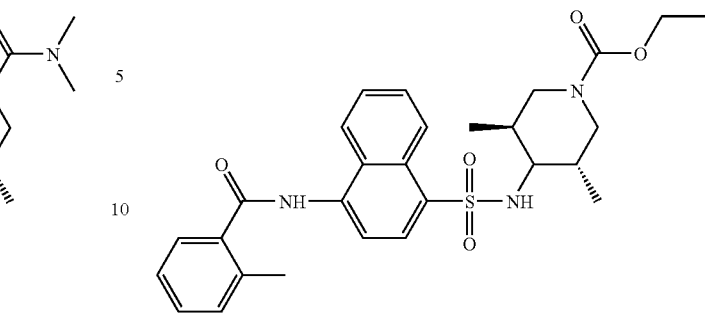

(±)-(cisstrans)-3,5-Dimethyl-4-[4-(2-methyl-benzoylamino)-naphthalene-1-sulfonylainno]-piperidine-1-carboxylic acid dimethylamide (C-65)

The title compound was made following general procedure in Scheme 5, substituting (±)-(cis, trans)-N-[4-(3,5-dimethyl-piperidin-4-ylsulfamoyl)-naphthalen-1-yl]-2-methyl-benzamide (C-64) for N-[4-(piperidin-4-ylsulfamoyl)-naphthalen-1-yl]-benzamide (C-1) and substituting dimethylcarbamyl chloride for 2-isocyanato-propane. $^1$H NMR (300 MHz, CDCl$_3$) δ 8.75 (d, 1H), 8.34 (m, 2H), 8.21 (s, 1H), 7.95 (d, 1H), 7.65 (m, 3H), 7.43 (m, 1H), 7.34 (m, 2H), 4.85 (m, 1H), 3.44 (d, 1H), 3.18 (d, 1H), 2.90 (m, 2H), 2.73 (s, 6H), 2.56 (s, 3H), 2.37 (dd, 1H), 1.74 (m, 2H), 0.71 (d, 3H), 0.59 (d, 3H); LC/MS m/z 524 (M+H)$^+$ (±)-(cistrans)-3,5-Dimethyl-4-[4-(2-methyl-benzoylamino)-naphthalene-1-sulfonylamino]-piperidine-1-carboxylic acid ethyl ester (C-67)

The title compound was made following general procedure in Scheme 5, substituting (±)-(cis, trans)-N-[4-(3,5-dimethyl-piperidin-4-ylsulfamoyl)-naphthalen-1-yl]-2-methyl-benzamide (C-64) for N-[4-(piperidin-4-ylsulfamoyl)-naphthalen-1-yl]-benzamide (C-1) and substituting ethyl chloroformate for 2-isocyanato-propane. $^1$H NMR (300 MHz, CDCl$_3$) δ 8.75 (d, 1H), 8.35 (m, 2H), 8.19 (s, 1H), 7.95 (d, 1H), 7.66 (m, 3H), 7.38 (m, 3H), 4.79 (d, 1H), 4.05 (m, 2H), 3.74 (m, 2H), 2.95 (m, 2H), 2.59 (s, 3H), 2.40 (m, 1H), 1.80 (s, br, 2H), 1.18 (t, 3H), 0.62 (m, 6H); LC/MS m/z 525 (M+H)$^+$

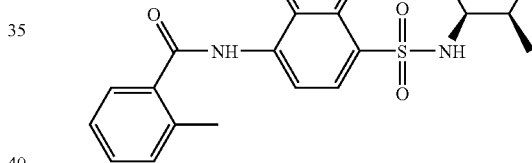

(±)-(cisscis)-N-[4-(3,5-Dimethyl-piperidin-4-ylsulfamoyl)-naphthalen-1-yl]-2-methyl-benzamide (C-68)

The title compound was made following general procedure in Scheme 4-2, substituting (±)-1-benzyl-3,5-dimethyl-piperidin-4-ylamine (5) for (±)-4-amino-1-benzyl-piperidine-3-carboxylic acid ethyl ester (6). $^1$H NMR (300 MHz, CDCl$_3$) δ 8.75 (d, 1H), 8.39 (s, 1H), 8.16 (d, 1H), 8.05 (m, 2H), 7.58 (m, 3H), 7.32 (m, 1H), 7.20 (m, 2H), 3.75 (s, br, 1H), 3.45 (s, 1H), 2.75 (m, 2H), 2.56 (m, 2H), 2.45 (s, 3H), 1.82 (m, 2H), 0.40 (d, 6H); LC/MS m/z 453 (M+H)$^+$

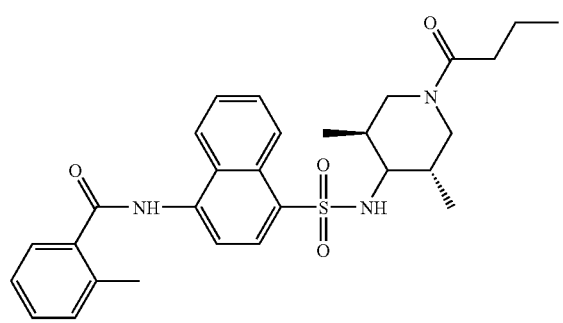

(±)-(cistrans)-N-[4-(1-Butyryl-3,5-dimethyl-piperidin-4-ylsulfamoyl)-naphthalen-1-yl]-2-methyl-benzamide (C-66)

The title compound was made following general procedure in Scheme 5, substituting (±)-(cis, trans)-N-[4-(3,5-dimethyl-piperidin-4-ylsulfamoyl)-naphthalen-1-yl]-2-methyl-benzamide (C-64) for N-[4-(piperidin-4-ylsulfamoyl)-naphthalen-1-yl]-benzamide (C-1) and substituting butyl chloride for 2-isocyanato-propane. $^1$H NMR (300 MHz, CDCl$_3$) δ 8.74(d, 1H), 8.33 (m, 3H), 7.96 (m, 1H), 7.64 (m, 3H), 7.42 (m, 1H), 7.31 (m, 2H), 5.12 (m, 1H), 3.60 (m, 2H), 3.18 (d, 1H), 3.00 (m, 2H), 2.56 (s, 3H), 2.15 (m, 2H), 1.80 (m, 2H), 1.55 (m, 3H), 0.86 (m, 3H), 0.68 (m, 3H), 0.49 (m, 3H); LC/MS m/z 523 (M+H)$^+$

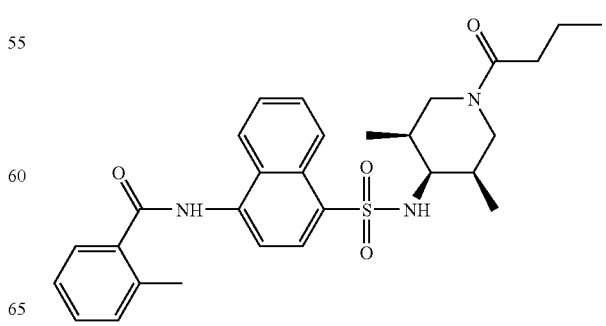

(±)-(cisscis)-N-[4-(1-Butyryl-3,5-dimethyl-piperidin-4-ylsulfamoyl)-naphthalen-1-yl]-2-methyl-benzamide (C-69)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting butyl chloride for 2-isocyanato-propane. $^1$H NMR (300 MHz, CDCl$_3$) δ 8.80 (d, 1H), 8.28 (m, 3H), 7.96 (d, 1H), 7.64 (m, 3H), 7.42 (m, 1H), 7.32 (m, 2H), 5.16 (d, 1H), 4.18 (dd, 1H), 3.51 (d, 1H), 3.38 (d, 1H), 2.68 (t, 1H), 2.55 (s, 3H), 2.18 (m, 3H), 1.62 (m, 4H), 0.90 (t, 3H), 0.63 (d, 3H), 0.36 (d, 3H); LC/MS m/z 523 (M+H)$^+$

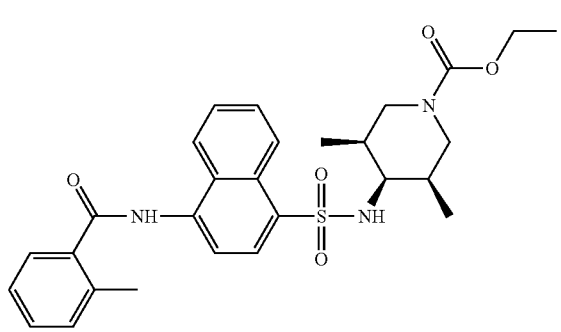

(±)-(cis,cis)-3,5-Dimethyl-4-[4-(2-methyl-benzoylamino)-naphthalene-1-sulfonylamino]-piperidine-1-carboxylic acid ethyl ester (C-70)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting ethyl chloroformate for 2-isocyanato-propane. $^1$H NMR (300 MHz, CDCl$_3$) δ 8.77 (d, 1H), 8.33 (m, 2H), 8.15 (s, 1H), 7.94 (d, 1H), 7.67 (m, 3H), 7.37 (m, 3H), 4.77 (d, 1H), 4.07 (q, 2H), 3.75 (s, br, 2H), 3.48 (m, 2H), 2.58 (s, 3H), 2.37 (m, 1H), 1.72 (m, 2H), 1.22 (t, 3H), 0.48 (s, br, 6H); LC/MS m/z 525 (M+H)$^+$

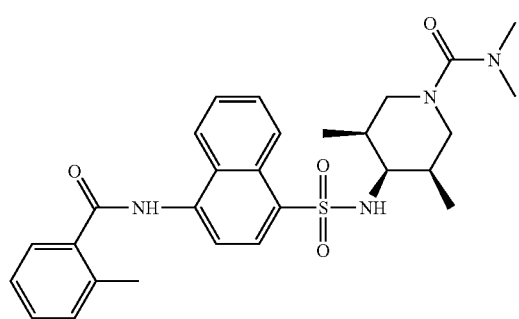

(±)-(cis,cis)-3,5-Dimethyl-4-[4-(2-methyl-benzoylamino)-naphthalene-1-sulfonylamino]-piperidine-1-carboxylic acid dimethylamide (C-71)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting dimethylcarbamyl chloride for 2-isocyanato-propane. $^1$H NMR (300 MHz, CDCl$_3$) δ 8.76 (d, 1H), 8.26 (m, 3H), 7.95 (d, 1H), 7.65 (m, 3H), 7.34 (m, 3H), 5.20 (d, 1H), 3.51 (m, 1H), 3.20 (d, 2H), 2.76 (s, 6H), 2.56 (s, 3H), 2.40 (t, 2H), 1.78 (m, 2H), 0.44 (dd, 6H); LC/MS m/z 524 (M+H)$^+$

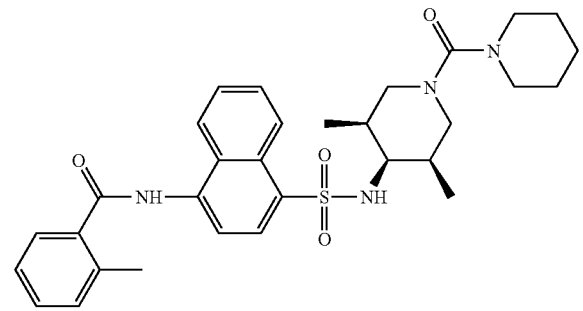

(±)-(cis,cis)-N-{4-[3,5-Dimethyl-1-(piperidine-1-carbonyl)-piperidin-4-ylsulfamoyl]-naphthalen-1-yl}-2-methyl-benzamide (C-72)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting piperidine-1-carbonyl chloride for 2-isocyanato-propane. $^1$H NM (300 MHz, CDCl$_3$) δ 8.75 (d, 1H), 8.33 (s, 1H), 8.25 (m, 2H), 7.95 (d, 1H), 7.63 (m, 3H), 7.32 (m, 3H), 5.08 (d, 1H), 3.49 (d, 1H), 3.18 (dd, 2H), 3.07 (s, br, 4H), 2.55 (s, 3H), 2.39 (t, 2H), 1.75 (m, 2H), 1.50 (s, br, 5H), 0.43 (dd, 6H); LC/MS m/z 564 (M+H)$^+$

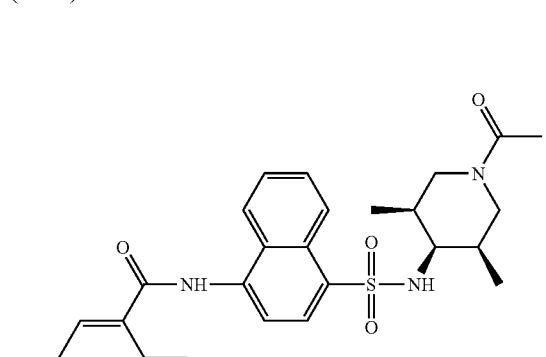

(±)-(cis,cis)-N-[4-(1-Acetyl-3,5-dimethyl-piperidin-4-ylsulfamoyl)-naphthalen-1-yl]-2-methyl-benzamide (C-73)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting acetyl chloride for 2-isocyanato-propane. $^1$H NMR (300 MHz, CDCl$_3$) δ 8.80 (d, 1H), 8.28 (m, 3H), 7.76 (d, 1H), 7.64 (m, 3H), 7.35 (m, 3H), 5.26 (d, 1H), 4.16 (dd, 1H), 3.51 (dd, 1H), 3.32 (dd, 1H), 3.32 (dd, 1H), 2.74 (t, 1H), 2.56 (s, 3H), 2.18 (t, 1H), 1.99 (s, 3H), 1.70 (m, 2H), 0.60 (d, 3H), 0.38 (d, 3H); LC/MS m/z 495 (M+H)$^+$

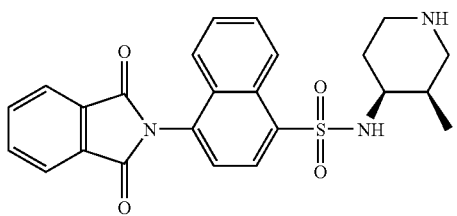

(±)-(cis)-4-(1,3-Dioxo-1,3-dihydro-isoindol-2-yl)-naphthalene-1-sulfonic acid (3-methyl-piperidin-4-yl)-amide (C-74)

The title compound was made as its formate salt following general procedure in Scheme 4-2, substituting (±)-1-benzyl-3-methyl-piperidin-4-ylamine (1) for (±)4-amino-1-benzyl-piperidine-3-carboxylic acid ethyl ester (6) and substituting 4-(1,3-dioxo-1,3-dihydro-isoindol-2-yl)-naphthalene-1-sulfonyl chloride for 4-(2-methyl-benzoylamino)-naphthalene-1-sulfonyl chloride. $^1$H NMR (300 MHz, MeOD) δ 8.88 (d, 1H), 8.45 (s, 1H), 8.39 (d, 1H), 8.02 (m, 2H), 7.93 (m, 2H), 7.80 (m, 2H), 7.67 (d, 2H), 3.50 (m, 1H), 3.05 (m, 3H), 2.80 (t, 1H), 1.95 (m, 1H), 1.65 (m, 2H), 0.60 (d, 3H); LC/MS m/z 451 (M+H)$^+$

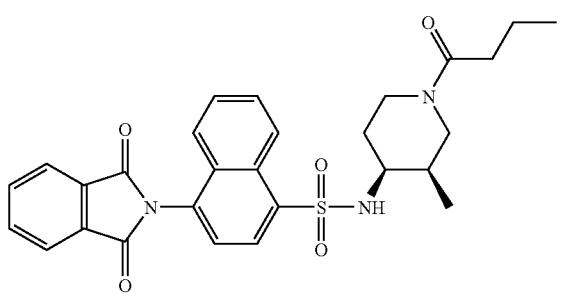

(±)-(cis)-4-(1,3-Dioxo-1,3-dihydro-isoindol-2-yl)-naphthalene-1-sulfonic acid (1-butyryl-3-methyl-piperidin-4-yl)-amide (C-75)

The title compound was made following general procedure in Scheme 5, substituting (±)-(cis)-4-( 1,3-dioxo-1,3-dihydro-isoindol-2-yl)-naphthalene-1-sulfonic acid (3-methyl-piperidin-4-yl)-amide (C-74) for N -[4-(piperidin-4-ylsulfamoyl)-naphthalen-1-yl]-benzamide (C-1) and substituting butyl chloride for 2-isocyanato-propane. $^1$H NMR (300 MHz, CDCl$_3$) δ 8.76 (dd, 1H), 8.41 (dd, 1H), 8.03 (dd, 2H), 7.88 (m, 2H), 7.74 (m, 2H), 7.58 (m, 2H), 5.25 (dd, 1H), 3.30 (m, 4H), 2.22 (m, 2H), 1.65 (m, 6H), 0.90 (t, 3H), 0.70 (dd, 3H); LC/MS m/z 521 (M+H)$^+$

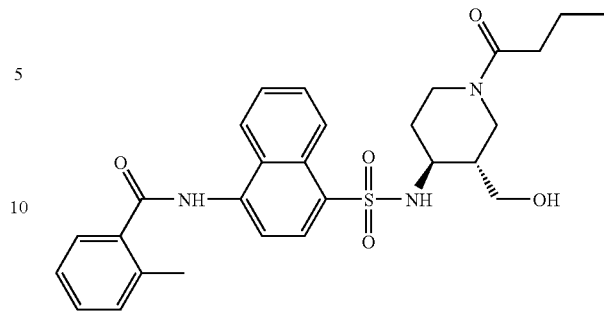

(±)-(trans)-N-[4-(1-butyryl-3-hydroxymethyl-piperidin-4-ylsulfamoyl)-naphthalen-1-yl]-2-methyl-benzamide (C-76)

(±)-(trans)-1-Butyryl-4-[4-(2-methyl-benzoylamino)-naphthalene-1-sulfonylamino]-piperidine-3-carboxylic acid ethyl ester was made following general procedure in Scheme 5, substituting (±)4-amino-1-benzyl-piperidine-3-carboxylic acid ethyl ester (5) for 4-amino-piperidine-1-carboxylic acid tert-butyl ester and substituting butyl chloride for 2-isocyanato-propane. To the solution of (±)-(trans)-1-butyryl-4-[4-(2-methyl-benzoylamino)-naphthalene-1-sulfonylamino]-piperidine-3-carboxylic acid ethyl ester (121 mg, 0.21 mmol) in THF (5 mL), was added lithium borohydride in THF solution (1.07 mL, 2.1 mmol) and the resultant solution was stired at 0° C. for 2 h. The solvent was removed in vacuo and the crude material was purified by HPLC to give the title compound. $^1$H NMR (300 MHz, MeOD) δ 8.75 (d, 1H), 8.32 (dd, 1H), 8.24 (d, 1H), 7.93 (d, 1H), 7.70 (m, 3H), 7.38 (m, 3H), 4.00 (m, 3H), 3.20 (m, 2H), 2.88 (m, 1H), 2.55 (s, 3H), 2.46 (m, 1H), 2.28 (m, 2H), 1.50 (m, 3H), 1.24 (m, 2H), 0.90 (dd, 3H); LC/MS m/z 525 (M+H)$^+$

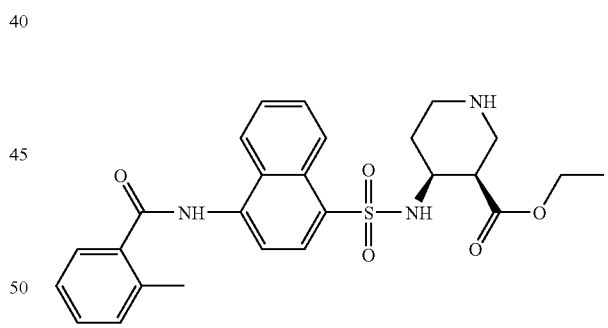

(±)-(cis)-4-[4-(2-Methyl-benzoylamino)-naphthalene-1-sulfonylamino]-piperidine-3-carboxylic acid ethyl ester (C-77)

The title compound was prepared as its formate salt following general procedure in Scheme 4-2. $^1$H NMR (300 MHz, MeOD) δ 8.75 (d, 1H), 8.52 (s, 1H), 8.34 (d, 1H), 8.25 (d, 3H), 7.97 (d, 1H), 7.71 (m, 3H), 7.40 (m, 3H), 3.93 (m, 1H), 3.70 (m, 2H), 3.28 (m, 2H), 3.07 (m, 2H), 2.90 (m, 1H), 2.56 (s, 3H), 1.82 (m, 2H), 0.98 (t, 3H); LC/MS m/z 497 (M+H)$^+$

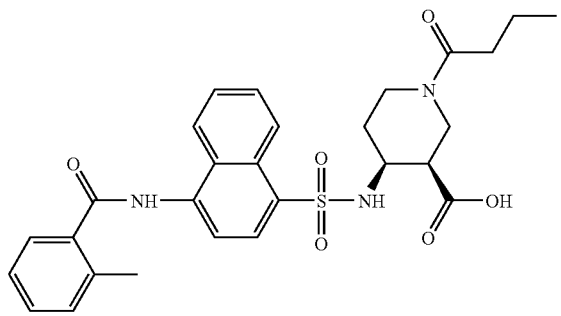

(±)-(cis)-1-Butyryl-4-[4-(2-methyl-benzoylamino)-naphthalene-1-sulfonylamino]-piperidine-3-carboxylic acid (C-78)

(±)-(cis)-1-Butyryl-4-[4-(2-methyl-benzoylamino)-naphthalene-1-sulfonylamino]-piperidine-3-carboxylic acid ethyl ester was made following general procedure in Scheme 5, substituting (±)4-amino-1-benzyl-piperidine-3-carboxylic acid ethyl ester (5) for 4-amino-piperidine-1-carboxylic acid tert-butyl ester and substituting butyl chloride for 2-isocyanato-propane. To the solution of (±)-(cis)-1-butyryl-4-[4-(2-methyl-benzoylamino)-naphthalene-1-sulfonylamino]-piperidine-3-carboxylic acid ethyl ester (70 mg, 0.12 mmol) in THF (5 mL), was added lithium hydroxide in water solution (6 mg, 0.25 mmol) and the resultant solution was stired at 25° C. for 2 h. The reaction mixture was extracted with CH$_2$Cl$_2$. The organic extracts were washed with brine, dried over Na$_2$SO$_4$, filtered and concentrated to provide the crude product. HPLC purification of the residue gave the title compound. $^1$H NMR (300 MHz, DMSO) δ 10.62 (s, 1H), 8.77 (t, 1H), 8.24 (m, 3H), 7.95 (d, 1H), 7.70 (m, 3H), 7.38 (m, 3H), 3.72 (m, 2H), 3.35 (m, 6H), 3.12 (m, 1H), 2.60 (m, 1H), 2.15 (m, 2H), 1.32 (m, 4H), 0.80 (dd, 3H); LC/MS nm/z 539 (M+H)$^+$

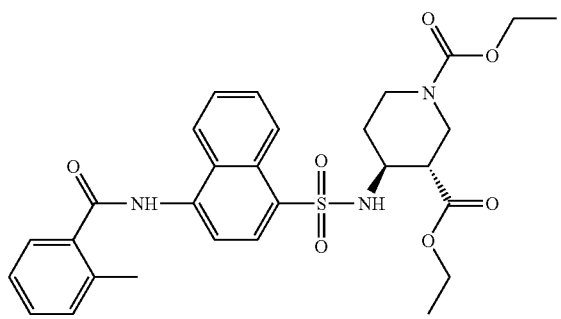

(±)-(trans)-4-[4-(2-Methyl-benzoylamino)-naphthalene-1-sulfonylamino]-piperidine-1,3-dicarboxylic acid diethyl ester (C-79)

The title compound was made following general procedure in Scheme 5, substituting (±)-4-amino-1-benzyl-piperidine-3-carboxylic acid ethyl ester (5) for 4-amino-piperidine-1-carboxylic acid tert-butyl ester and substituting ethyl chloroformate for 2-isocyanato-propane. $^1$H NMR (300 MHz, MeOD) δ 8.68 (d, 1H), 8.30 (d, 1H), 8.23 (d, 1H), 7.93 (d, 1H), 7.70 (m, 3H), 7.38 (m, 3H), 4.00 (m, 4H), 3.48 (m, 3H), 2.85 (m, 2H), 2.55 (s, 3H), 2.36 (dt, 1H), 1.75 (d, 1H), 1.32 (d, 1H), 1.21 (t, 3H), 0.96 (t, 3H); LC/MS m/z 568 (M+H)$^+$

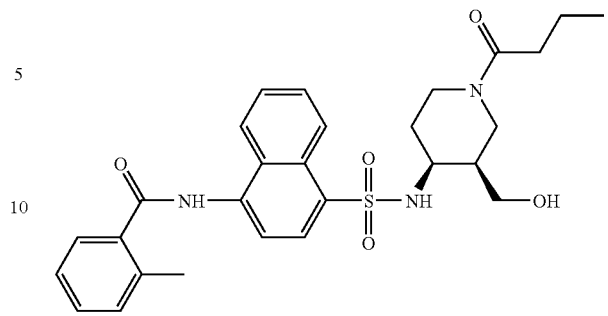

(±)-(cis)-N-[4-(1-Butryl-3-hydroxymethyl-piperidin-4-ylsulfamoyl)-naphthalen-1-yl]-2-methyl-benzamide (C-80)

(±)-(cis)-1-Butyryl-4-[4-(2-methyl-benzoylamino)-naphthalene-1-sulfonylamino]-piperidine-3-carboxylic acid ethyl ester was made following general procedure in Scheme 5, substituting (±)4-amino-1-benzyl-piperidine-3-carboxylic acid ethyl ester (5) for 4-amino-piperidine-1-carboxylic acid tert-butyl ester and substituting butyl chloride for 2-isocyanato-propane. To the solution of (±)-(cis)-1-butyryl-4-[4-(2-methyl-benzoylamino)-naphthalene-1-sulfonylamino]-piperidine-3-carboxylic acid ethyl ester (48 mg, 0.085 mmol) in THF (5 mL), was added lithium borohydride in THF solution (0.5 mL, 0.25 mmol) and the resultant solution was stired at 0° C. for 2 h. The solvent was removed in vacuo and the crude material was purified by HPLC to give the title compound. $^1$H NMR (300 MHz, MeOD) δ 8.81 (d, 1H), 8.34 (d, 1H), 8.25 (d, 1H), 7.95 (d, 1H), 7.72 (m, 3H), 7.40 (m, 3H), 3.46 (m, 7H), 2.56 (s, 3H), 2.32 (m, 2H), 2.55 (s, 3H), 1.52 (m, 5H), 0.92 (m, 3H); LC/MS m/z 525 (M+H)$^+$

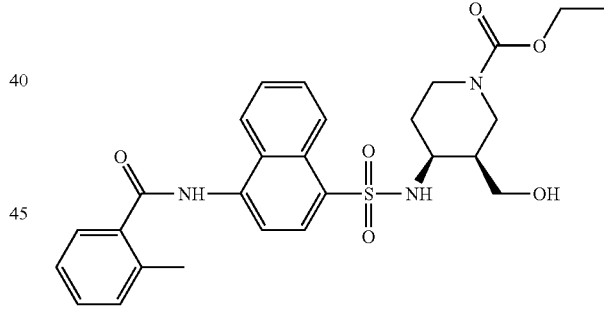

(±)-(cis)-3—Hydroxymethyl-4-[4-(2-methyl-benzoylamino)-naphthalene-1-sulfonylamino]-piperidine-1-carboxylic acid ethyl ester (C-81)

(±)-(cis)-4-[4-(2-Methyl-benzoylamino)-naphthalene-1-sulfonylamino]-piperidine-1,3-dicarboxylic acid diethyl ester was made following general procedure in Scheme 5, substituting (±)-4-amino-1-benzyl-piperidine-3-carboxylic acid ethyl ester (5) for 4-amino-piperidine-1-carboxylic acid tert-butyl ester, and substituting ethyl chloroformate for 2-isocyanato-propane. To the solution of (±)-(cis)-4-[4-(2-Methyl-benzoylamino)-naphthalene-1-sulfonylamino]-piperidine-1,3-dicarboxylic acid diethyl ester (57 mg, 0.1 mmol) in THF (5 mL), was added lithium borohydride in THF solution (0.5 mL, 0.25 mmol) and the resultant solution was stired at 0° C. for 2 h. The solvent was removed in vacuo and the crude material was purified by HPLC to give the title compound. $^1$H NMR (300 MHz, MeOD) δ 8.81 (d, 1H), 8.33 (d, 1H), 8.24 (d, 1H), 7.94 (d, 1H), 7.72 (m, 3H), 7.40 (m, 3H), 4.06 (q, 2H), 3.55 (m, 2H), 3.32 (m, 5H), 2.56 (s, 3H), 1.75 (m, 1H), 1.30 (m, 2H), 1.20 (t, 3H); LC/MS m/z 526 (M+H)+

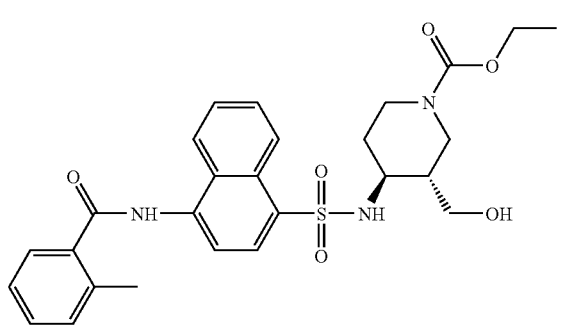

(±)-(trans)-3—Hydroxymethyl-4-[4-(2-methyl-benzoylamino)-naphthalene-1-sulfonylamino]-piperidine-1-carboxylic acid ethyl ester (C-82)

(±)-(trans)-4-[4-(2-Methyl-benzoylamino)-naphthalene-1-sulfonylamino]-piperidine-1,3-dicarboxylic acid diethyl ester was made following general procedure in Scheme 5, substituting (±)-4-amino-1-benzyl-piperidine-3-carboxylic acid ethyl ester (5) for 4-amino-piperidine-1-carboxylic acid tert-butyl ester and substituting ethyl chloroformate for 2-isocyanato-propane. To the solution of (±)-(trans)-4-[4-(2-methyl-benzoylamino)-naphthalene-1-sulfonylamino]-piperidine-1,3-dicarboxylic acid diethyl ester (57 mg, 0.1 mmol) in THF (5 mL), was added lithium borohydride in THF solution (0.5 mL, 0.25 mmol) and the resultant solution was stired at 0° C. for 2 h. The solvent was removed in vacuo and the crude material was purified by HPLC to give the title compound. ¹H NMR (300 MHz, MeOD) δ 8.73 (d, 1H), 8.30 (d, 1H), 8.22 (d, 1H), 7.93 (d, 1H), 7.68 (m, 3H), 7.36 (m, 3H), 4.15 (d, 1H), 4.05 (q, 2H), 3.85 (d, 1H), 3.55 (d, 1H), 3.25 (m, 1H), 3.10 (m, 1H), 2.60 (m, 2H), 2.56 (s, 3H), 1.40 (m, 3H), 1.20 (t, 3H); LC/MS m/z 526 (M+H)+

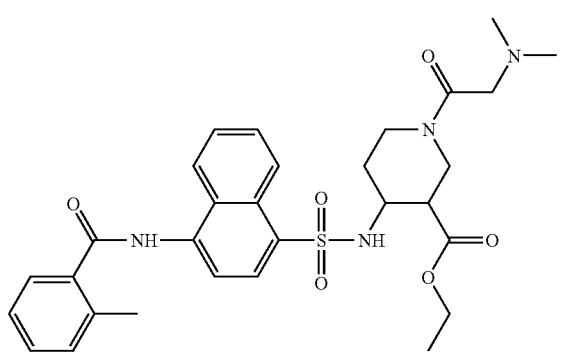

1-(2-Dimethylainino-acetyl)-4-[4-(2-methyl-benzoylamino)-naphthalene-1-sulfonylamino]-piperidine-3-carboxylic acid ethyl ester (C-83)

The title compound was made following general procedure in Scheme 5, substituting (±)4-amino-1-benzyl-piperidine-3-carboxylic acid ethyl ester (5) for 4-amino-piperidine-1-carboxylic acid tert-butyl ester and substituting dimethylamino-acetyl chloride hydrochloride for 2-isocyanato-propane. ¹H NMR (300 MHz, CDCl₃) δ 8.62 (m, 1H), 8.32 (m, 3H), 7.94 (d, 1H), 7.64 (m, 3H), 7.36 (m, 3H), 5.95 (m, 1H), 4.10 (m, 4H), 3.50 (s, br, 1H), 3.05 (m, 6H), 2.56 (m, 3H), 2.25 (dd, 6H), 1.84 (m, 1H), 1.10 (m, 3H); LC/MS m/z 581 (M+H)+

(±)-(cis)-3-Ethyl-4-[4-(2-methyl-benzoylamino)-naphthalene-1-sulfonylamino]-piperidine-1-carboxylic acid ethyl ester (C-84)

The title compound was made following general procedure in Scheme 5, substituting (±)-1-benzyl-3-ethyl-piperidin-4-ylamine (3) for 4-amino-piperidine-1-carboxylic acid tert-butyl ester and substituting ethyl chloroformate for 2-isocyanato-propane. ¹H NMR (300 MHz, CDCl₃) δ 8.71 (d, 1H), 8.37 (m, 2H), 8.13 (s, 1H), 7.93 (d, 1H), 7.66 (m, 3H), 7.43 (m, 1H), 7.33 (m, 2H), 4.78 (d, 1H), 4.05 (m, 2H), 3.42 (m, 1H), 3.22 (m, 4H), 2.58 (s, 3H), 1.35 (s, br, 2H), 1.17 (t, 3H), 1.00 (s, br, 2H), 0.55 (s, br, 3H); LC/MS m/z 524 (M+H)+

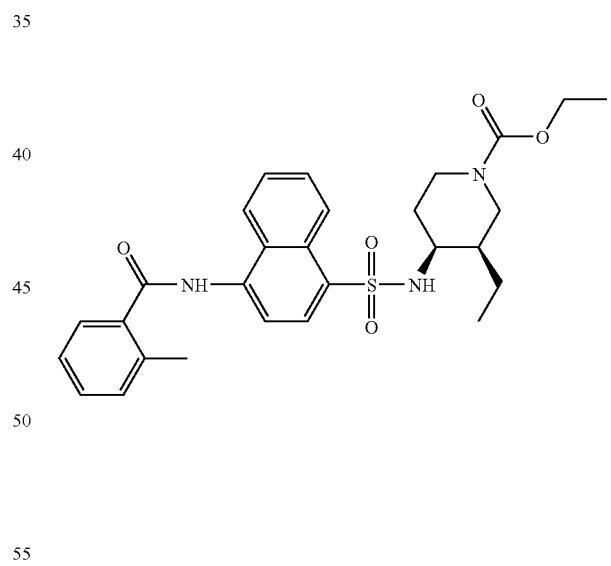

(±)-(cis)-N-[4-(1-Butyryl-3-ethyl-piperidin-4-ylsulfamoyl)-naphthalen-1-yl]-2-methyl-benzamide (C-85)

The title compound was made following general procedure in Scheme 5, substituting (±)-1-benzyl-3-ethyl-piperidin-4-ylamine (3) for 4-amino-piperidine-1-carboxylic acid tert-butyl ester, and substituting butyl chloride for 2-isocyanato-propane. ¹H NMR (300 MHz, CDCl₃) δ 8.72 (d, 1H), 8.37 (m, 2H), 8.16 (s, 1H), 7.94 (d, 1H), 7.66 (m, 3H), 7.43 (m, 1H), 7.33 (m, 2H), 4.90 (m, 1H), 3.32 (m, 5H), 2.58 (s, 3H), 2.18 (m, 2H), 1.45 (m, 6H), 0.87 (t, 3H), 0.50 (m, 3H); LC/MS m/z 522 (M+H)+

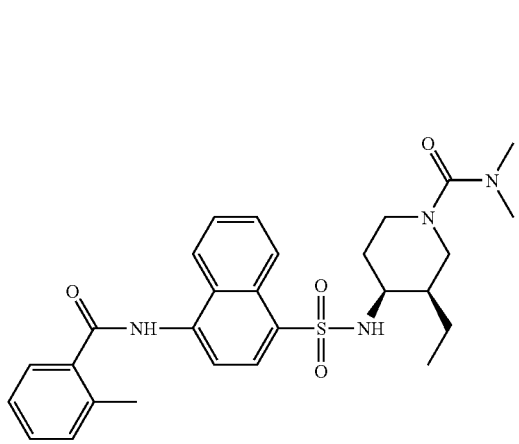

(±)-(cis)-3-Ethyl-4-[4-(2-methyl-benzoylamino)-naphthalene-1-sulfonylamino]-piperidine-1-carboxylic acid dimethylamide (C-86)

The title compound was made following general procedure in Scheme 5, substituting (±)-1-benzyl-3-ethyl-piperidin-4-ylamine (3) for 4-amino-piperidine-1-carboxylic acid tert-butyl ester, and substituting dimethylamino-acetyl chloride hydrochloride for 2-isocyanato-propane. $^1$H NMR (300 MHz, CDCl$_3$) δ 8.72 (d, 1H), 8.36 (m, 2H), 8.16 (s, 1H), 7.93 (d, 1H), 7.65 (m, 3H), 7.42 (m, 1H), 7.32 (m, 2H), 4.88 (d, 1H), 3.45 (m, 1H), 3.20 (m, 1H), 3.00 (m, 2H), 2.80 (m, 1H), 2.70 (s, 6H), 2.50 (s, 3H), 1.40 (m, 3H), 1.00 (m, 2H), 0.52 (t, 3H); LC/MS m/z 523 (M+H)$^+$

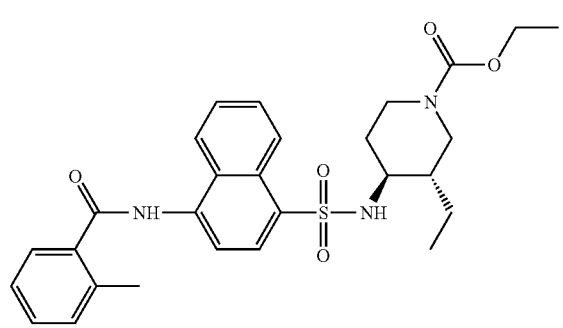

(±)-(trans)-3-Ethyl-4-[4-(2-methyl-benzoylamino)-naphthalene-1-sulfonylamino]-piperidine-1-carboxylic acid ethyl ester (C-87)

The title compound was made following general procedure in Scheme 5, substituting (±)-1-benzyl-3-ethyl-piperidin-4-ylamine (3) for 4-amino-piperidine-1-carboxylic acid tert-butyl ester, and substituting ethyl chloroformate for 2-isocyanato-propane. $^1$H NMR (300 MHz, CDCl$_3$) δ 8.69 (d, 1H), 8.36 (m, 2H), 8.12 (s, 1H), 7.93 (d, 1H), 7.66 (m, 3H), 7.43 (m, 1H), 7.33 (m, 2H), 4.50 (d, 1H), 4.05 (m, 2H), 3.55 (d, 1H), 2.95 (m, 1H), 2.70 (t, 1H), 2.57 (s, 3H), 2.49 (m, 1H), 1.50 (m, 3H), 1.17 (m, 5H), 0.85 (m, 1H), 0.65 (s, br, 3H); LC/MS m/z 524 (M+H)$^+$

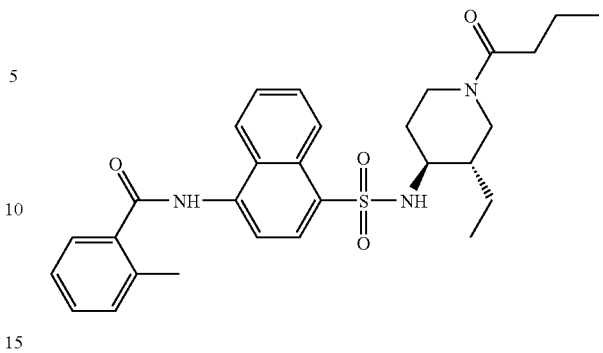

(±)-(trans)-N-[4-(1-Butyryl-3-ethyl-piperidin-4-ylsuffamoyl)-naphthalen-1-yl]-2-methyl-benzamide (C-88)

The title compound was made following general procedure in Scheme 5, substituting (±)-1-benzyl-3-ethyl-piperidin-4-ylamine (3) for 4-amino-piperidine-1-carboxylic acid tert-butyl ester and substituting butyl chloride for 2-isocyanato-propane. $^1$H NMR (300 MHz, CDCl$_3$) δ 8.68 (m, 1H), 8.35 (m, 2H), 8.18 (s, 1H), 7.94 (d, 1H), 7.66 (m, 3H), 7.42 (m, 1H), 7.32 (m, 2H), 4.65 (d, 1H), 4.30 (m, 1H), 3.68 (m, 1H), 2.95 (m, 2H), 2.57 (s, 3H), 2.50 (m, 1H), 2.20 (m, 2H), 1.55 (m, 5H), 1.15 (m, 2H), 0.85 (t, 3H), 0.60 (m, 3H); LC/MS m/z 522 (M+H)$^+$

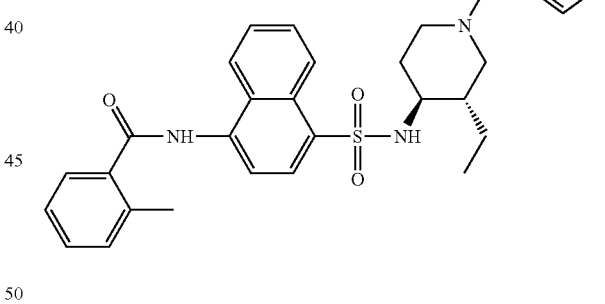

(±)-(trans)-N-{4-[3-Ethyl-1-(3-methyl-3H-imidazole-4-carbonyl)-piperidin-4-ylsulfamoyl]-naphthalen-1-yl}-2-methyl-benzamide (C-89)

The title compound was made following general procedure in Scheme 5, substituting (±)-1-benzyl-3-ethyl-piperidin-4-ylamine (3) for 4-amino-piperidine-1-carboxylic acid tert-butyl ester and substituting 3-methyl-3H-imidazole-4-carbonyl chloride hydrochloride for 2-isocyanato-propane. $^1$H NMR (300 MHz, MeOD) δ 8.79 (d, 1H), 8.33 (d, 1H), 8.25 (d, 1H), 8.15 (s, 1H), 7.94 (d, 1H), 7.70 (m, 4H), 7.43 (m, 1H), 7.36 (m, 2H), 7.14 (s, 1H), 4.20 (m, 2H), 3.75 (s, 3H), 3.05 (m, 2H), 2.70 (m, 1H), 2.55 (s, 3H), 1.55 (m, 3H), 1.30 (m, 1H), 0.85 (m, 1H), 0.62 (m, 3H); LC/MS m/z 560 (M+H)$^+$

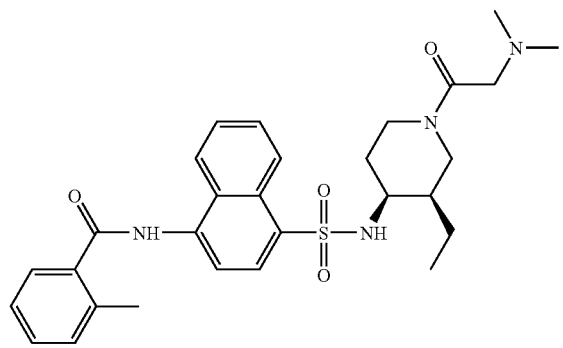

(±)-(cis)-N-{4-[1-(2-Dimethylamino-acetyl)-3-ethyl-piperidin-4-ylsulfamoyl]-naphthalen-1-yl}-2-methyl-benzamide (C-90)

The title compound (formic acid salt) was made following general procedure in Scheme 5, substituting (±)-1-benzyl-3-ethyl-piperidin-4-ylamine (3) for 4-amino-piperidine-1-carboxylic acid tert-butyl ester, and substituting dimethylamino-acetyl chloride hydrochloride for 2-isocyanato-propane. $^1$H NMR (300 MHz, MeOD) δ 8.85 (d, 1H), 8.55 (s, 1H), 8.32 (d, 1H), 8.25 (d, 1H), 7.94 (d, 1H), 7.71 (m, 3H), 7.43 (m, 1H), 7.35 (m, 2H), 3.47 (m, 4H), 3.25 (m, 2H), 2.55 (s, 3H), 2.33 (d, 6H), 1.38 (m, 3H), 1.15 (m, 3H), 0.50 (m, 3H); LC/MS m/z 537 (M+H)$^+$

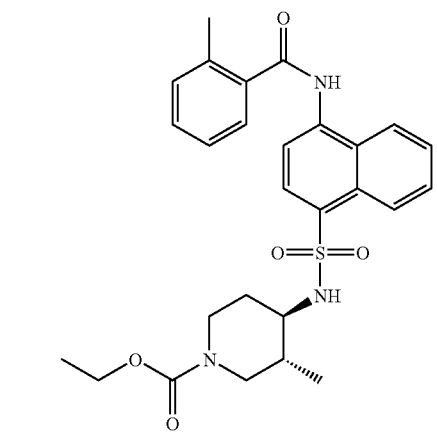

(3R, 4R)-3-Methyl-4-[4-(2-methyl-benzoylamino)-naphthalene-1-sulfonylamino]-piperidine-1-carboxylic acid ethyl ester (C-92)

The title compound was prepared according to the general procedure in Scheme 5, substituting (3R, 4R)-4-amino-3-methyl-piperidine-1-carboxylic acid tert-butyl ester for 4-amino-piperidine-1-carboxylic acid tert-butyl ester, and ethyl chloroformate for 2-isocyanato-propane. $^1$H NMR (300 MHz, CDCl$_3$) δ 8.77 (d, 1H), 8.30 (d, 1H), 8.23 (d, 1H), 7.92 (d, 1H), 7.73 (m, 3H), 7.35 (m, 3H), 4.03 (q, 2H), 3.94 (t, 2H), 2.85 (dt, 1H), 2.64 (m, 1H), 2.55 (s, 3H), 2.40 (m, 1H), 1.48 (m, 1H), 1.38 (m, 1H), 1.20 (t, 3H), 0.59 (d, 3H); LC/MS m/z 510 (M+H)$^+$.

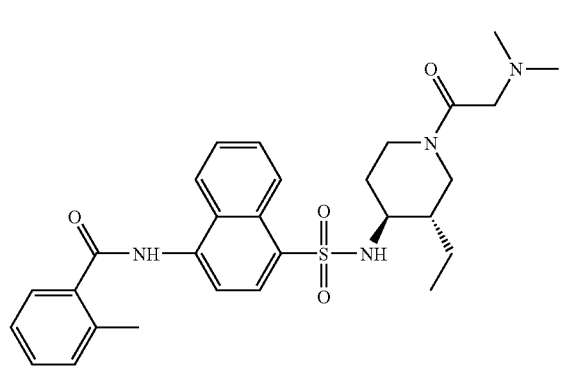

(±)-(trans)-N-{4-[1-(2-Dimethylamino-acetyl)-3-ethyl-piperidin-4-ylsulfamoyl]-naphthalen-1-yl}-2-methyl-benzamide (C-91)

The title compound (formic acid salt) was made following general procedure in Scheme 5, substituting (±)-1-benzyl-3-ethyl-piperidin-4-ylamine (3) for 4-amino-piperidine-1-carboxylic acid tert-butyl ester and substituting dimethylamino-acetyl chloride hydrochloride for 2-isocyanato-propane. $^1$H NMR (300 MHz, MeOD) δ 8.78 (d, 1H), 8.55 (s, 1H), 8.32 (d, 1H), 8.25 (d, 1H), 7.94 (d, 1H), 7.71 (m, 3H), 7.43 (m, 1H), 7.35 (m, 2H), 4.05 (m, 2H), 3.10 (m, 3H), 2.60 (m, 1H), 2.55 (s, 3H), 2.30 (s, 6H), 1.25 (m, 2H), 1.10 (m, 3H), 0.90 (m, 1H), 0.85 (m, 3H); LC/MS m/z 537 (M+H)$^+$

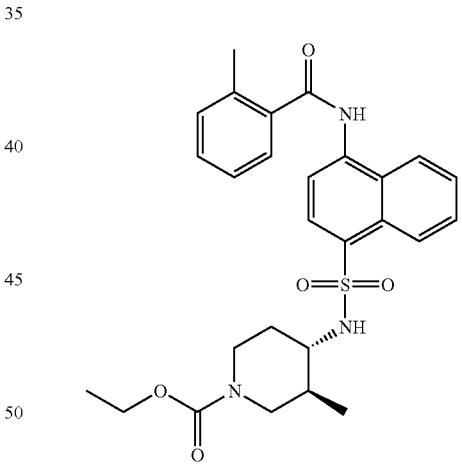

(3S, 4S)-3-Methyl-4-[4-(2-methyl-benzoylainno)-naphthalene-1-sulfonylamino]-piperidine-1-carboxylic acid ethyl ester (C-93)

The title compound was prepared according to the general procedure in Scheme 5, substituting (3S, 4S)-4-amino-3-methyl-piperidine-1-carboxylic acid tert-butyl ester for 4-amino-piperidine-1-carboxylic acid tert-butyl ester, and ethyl chloroformate for 2-isocyanato-propane. $^1$H NMR (300 MHz, CDCl$_3$) δ 8.77 (d, 1H), 8.30 (d, 1H), 8.23 (d, 1H), 7.92 (d, 1H), 7.73 (m, 3H), 7.35 (m, 3H), 4.03 (q, 2H), 3.94 (t, 2H), 2.85 (dt, 1H), 2.64 (m, 1H), 2.55 (s, 3H), 2.40 (m, 1H), 1.48 (m, 1H), 1.38 (m, 1H), 1.20 (t, 3H), 0.59 (d, 3H); LC/MS m/z 510 (M+H)$^+$.

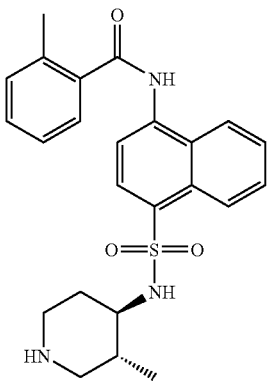

(3R, 4R)-2-Methyl-N-[4-(3-methyl-piperidin-4-ylsulfamoyl)-naphthalen-1-yl]-benzamide (C-94)

The title compound was prepared according to the general procedure in Scheme 5, substituting (3R, 4R)-4-amino-3-methyl-piperidine-1-carboxylic acid tert-butyl ester for 4-amino-piperidine-1-carboxylic acid tert-butyl ester. $^1$H NMR (300 MHz, MeOD) δ 8.78 (dd, 1H), 8.34 (d, 1H), 8.24 (dd, 1H), 7.94 (d, 1H), 7.78 (m, 1H), 7.74 (m, 1H), 7.69 (m, 1H), 7.44 (m, 1H), 7.37 (m, 2H), 3.23 (m, 2H), 3.00 (m, 1H), 2.78 (m, 1H), 2.64 (m, 1H), 2.55 (s, 3H), 1.76 (m, 2H), 1.58 (m, 1H), 0.66 (d, 3H); LC/MS m/z 438 (M+H)$^+$.

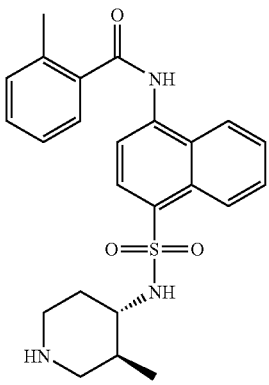

(3S, 4S)-2-Methyl-N-[4-(3-methyl-piperidin-4-ylsulfamoyl)-naphthalen-1-yl]-benzamide (C-95)

The title compound was prepared according to the general procedure in Scheme 5, substituting (3S, 4S)-4-amino-3-methyl-piperidine-1-carboxylic acid tert-butyl ester for 4-amino-piperidine-1-carboxylic acid tert-butyl ester. $^1$H NMR (300 MHz, MeOD) δ 8.78 (dd, 1H), 8.34 (d, 1H), 8.24 (dd, 1H), 7.94 (d, 1H), 7.78 (m, 1H), 7.74 (m, 1H), 7.69 (m, 1H), 7.44 (m, 1H), 7.37 (m, 2H), 3.23 (m, 2H), 3.00 (m, 1H), 2.78 (m, 1H), 2.64 (m, 1H), 2.55 (s, 3H), 1.76 (m, 2H), 1.58 (m, 1H), 0.66 (d, 3H); LC/MS m/z 438 (M+H)$^+$.

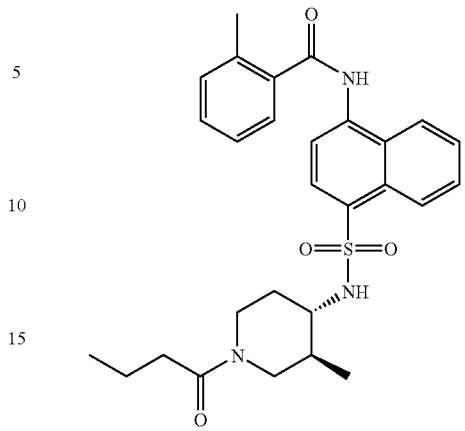

(3S, 4S)-N-[4-(1-Butyryl-3-methyl-piperidin-4-ylsulfamoyl)-naphthalen-1-yl]-2-methyl-benzamide (C-96)

The title compound was prepared according to the general procedure in Scheme 5, substituting (3S, 4S)-4-amino-3-methyl-piperidine-1-carboxylic acid tert-butyl ester for 4-amino-piperidine-1-carboxylic acid tert-butyl ester, and butyryl chloride for 2-isocyanato-propane. $^1$H NMR (300 MHz, CDCl$_3$) δ 8.70 (t, 1H), 8.33 (m, 3H), 7.95 (d, 1H), 7.62 (m, 3H), 7.40 (m, 1H), 7.34 (m, 2H), 5.00 (d, 1H), 4.30 (dd, 1H), 3.63 (m, 1H), 2.85 (m, 1.5H), 2.57 (s, 3H), 2.40 (t, 0.5H), 2.15 (m, 1.5H), 2.09 (m, 0.5H), 1.83 (m, 0.5H), 1.50 (m, 1.5H); LC/MS m/z 508 (M+H)$^+$.

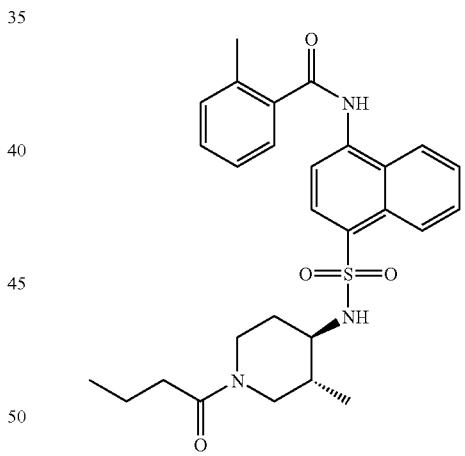

(3R, 4R)-N-[4-(1-Butyryl-3-methyl-piperidin-4-ylsulfamoyl)-naphthalen-1-yl]-2-methyl-benzamide (C-97)

The title compound was prepared according to the general procedure in Scheme 5, substituting (3R, 4R)-4-amino-3-methyl-piperidine-1-carboxylic acid tert-butyl ester for 4-amino-piperidine-1-carboxylic acid tert-butyl ester, and butyryl chloride for 2-isocyanato-propane. $^1$H NMR (300 MHz, CDCl$_3$) δ 8.70 (t, 1H), 8.33 (m, 3H), 7.95 (d, 1H), 7.62 (m, 3H), 7.40 (m, 1H), 7.34 (m, 2H), 5.00 (d, 1H), 4.30 (dd, 1H), 3.63 (m, 1H), 2.85 (m, 1.5H), 2.57 (s, 3H), 2.40 (t, 0.5H), 2.15 (m, 1.5H), 2.09 (m, 0.5H), 1.83 (m, 0.5H), 1.50 (m, 1.5H); LC/MS m/z 508 (M+H)$^+$.

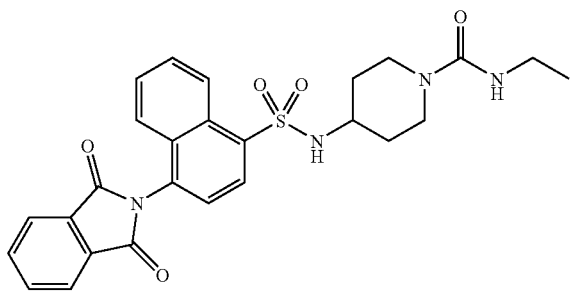

4-[4-(1,3-Dioxo-1,3-dihydro-isoindol-2-yl)-naphthalene-1-sulfonylamino]-piperidine-1-carboxylic acid ethylamide (C-98)

The title compound was prepared following the general procedure in Scheme 5, beginning with 4-(1,3-dioxo-1,3-dihydro-isoindol-2-yl)-naphthalene-1-sulfonyl chloride, and substituting ethyl isocyanate for 2-isocyanato-propane. $^1$H NMR (300 MHz, DMSO) δ 8.75 (d, 1H), 8.29 (d, 1H), 8.23 (d, 1H), 8.03 (m, 5H), 7.83 (d, 1H), 7.80 (t, 1H), 7.67 (t, 1H), 6.36 (t, 1H), 3.69 (d, 2H), 3.27 (m, 1H), 2.97 (p, 211), 2.64 (t, 2H), 1.47 (d, 2H), 1.23 (m, 2H), 0.95 (t, 3H); LC/MS m/z 505 (M–H)$^-$.

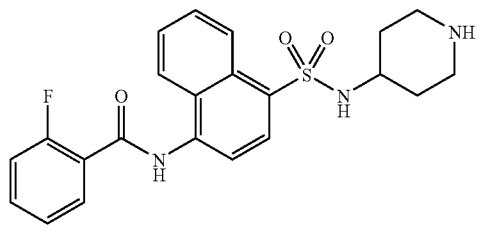

2-Fluoro-N-[4-(piperidin-4-ylsulfamoyl)-naphthalen-1-yl]-benzamide (C-99)

The title compound was prepared following the general procedure in Scheme 5, beginning with 4-(2-fluoro-benzoylamino)-naphthalene-1-sulfonyl chloride. $^1$H NMR (300 MHz, DMSO) δ 10.72 (s, 1H), 8.67 (d, 1H), 8.30 (d, 1H), 8.20 (d, 1H), 8.10 (d, 1H), 8.01 (d, 1H), 7.83 (t, 1H), 7.74 (t, 2H), 7.65 (m, 1H), 7.41 (q, 2H), 3.67 (d, 2H), 3.18 (m, 1H), 2.70 (m, 2H), 1.43 (m, 2H), 1.18 (m, 2H); LC/MS m/z 426 (M–H)$^-$, 428 (M+H)$^+$

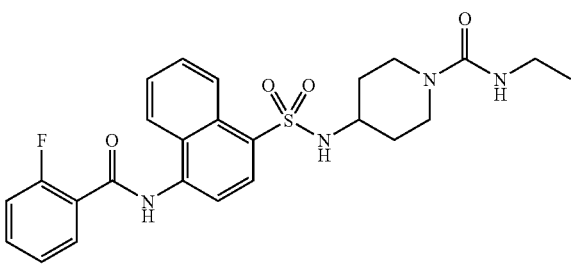

4-[4-(2-Fluoro-benzoylamino)-naphthalene-1-sulfonylamino]-piperidine-1-carboxylic acid ethylamide (C-100)

The title compound was prepared following the general procedure in Scheme 5, beginning with 4-(2-fluoro-benzoylamino)-naphthalene-1-sulfonyl chloride, and substituting ethyl isocyanate for 2-isocyanato-propane. $^1$H NMR (300 MHz, DMSO) δ 10.74 (s, 1H), 8.67 (d, 1H), 8.29 (d, 1H), 8.19 (d, 1H), 8.05 (d, 1H), 7.99 (d, 1H), 7.82 (t, 1H), 7.73 (t, 2H), 7.65 (t, 2H), 7.41 (q, 2H), 6.32 (t, 1H), 3.67 (d, 2H), 3.17 (m, 1H), 2.94 (m, 2H), 2.59 (t, 2H), 1.36 (d, 2H), 1.14 (m, 2H), 0.95 (t, 3H); LC/MS m/z 498 (M–H)$^-$, 500 (M+H)$^+$

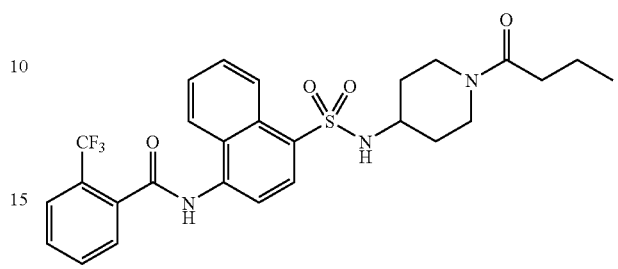

N-[4-(1-Butyryl-piperidin-4-ylsulfamoyl)-naphthalen-1-yl]-2-trifluoromethyl-benzamide (C-101)

The title compound was prepared following the general procedure in Scheme 5, beginning with 4-(2-trifluoromethyl-benzoylamino)-naphthalene-1-sulfonyl chloride and substituting butyryl chloride and triethylamine for 2-isocyanato-propane. $^1$H NMR (300 MHz, DMSO) δ 10.91(s, 1H), 8.68 (d, 1H), 8.25 (m, 2H), 8.11 (d, 1H), 7.85 (m, 4H), 7.76 (m, 3H), 4.06 (m, 1H), 4.01(m, 1H), 3.62 (d, 1H), 2.94 (t, 1H), 2.59 (t, 2H), 1.48 (m, 2H), 1.41 (m, 2H), 1.19 (m, 2H), 0.82 (t, 3H); LC/MS m/z 546 (M–H)$^-$, 548 (M+H)$^+$

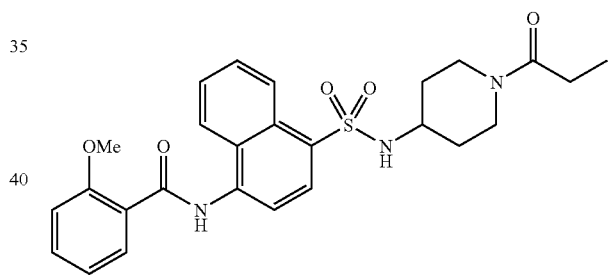

2-Methoxy-N-[4-(1-propionyl-piperidin-4-ylsulfamoyl)-naphthalen-1-yl]-benzamide (C-102)

The title compound was prepared following the general procedure in Scheme 5 beginning with 4-(2-methoxy-benzoylamino)-naphthalene-1-sulfonyl chloride, and substituting propionyl chloride and triethylamine for 2-isocyanato-propane. LC/MS m/z 495 (M–H)$^-$, 497 (M+H)$^+$

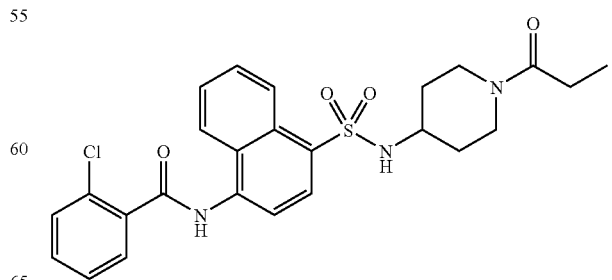

2-Chloro-N-[4-(1-propionyl-piperidin-4-ylsuffamoyl)-naphthalen-1-yl]-benzamide (C-103)

The title compound was prepared following the general procedure in Scheme 5 beginning with 4-(2-chloro-benzoylamino)-naphthalene-1-sulfonyl chloride, and substituting propionyl chloride and triethylamine for 2-isocyanato-propane. $^1$H NMR (300 MHz, DMSO) δ 10.86 (s, 1H), 8.68 (d, 1H), 8.33 (d, 1H), 8.22 (d, 1H), 8.12 (d, 1H), 7.98 (d, 1H), 7.74 (m, 3H), 7.64 (t, 1H), 7.54 (m, 2H), 4.01 (m, 1H), 3.59 (d, 1H), 3.24 (m, 1H), 3.16 (d, 1H), 2.96 (t, 1H), 2.20 (q, 2H), 1.51 (d, 2H), 1.20 (m, 2H), 0.81 (t, 3H); LC/MS m/z 498 (M−H)$^-$, 500 (M+H)$^+$

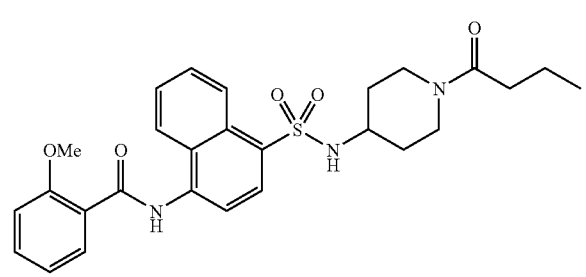

N-[4-(1-Butyryl-piperidin-4-ylsulfamoyl)-naphthalen-1-yl]-2-methoxy-benzamide (C-104)

The title compound was prepared following the general procedure in Scheme 5, beginning with 4-(2-methoxy-benzoylamino)-naphthalene-1-sulfonyl chloride, and substituting butyric chloride and triethylamine for 2-isocyanato-propane. LC/MS m/z 508 (M−H)$^-$, 510 (M+H)$^+$

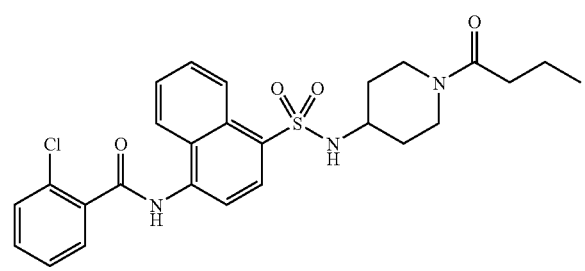

N-[4-(1-Butyryl-piperidin-4-ylsulfamoyl)-naphthalen-1-yl]-2-chloro-benzamide (C-105)

The title compound was prepared following the general procedure in Scheme 5, beginning with 4-(2-chloro-benzoylamino)-naphthalene-1-sulfonyl chloride, and substituting butyryl chloride and triethylamine for 2-isocyanato-propane. $^1$H NMR (300 MHz, DMSO) δ 10.86 (s, 1H), 8.35 (d, 1H), 8.25 (d,1H), 8.13 (d, 1H), 8.0 (m, 1H), 7.74 (m, 3H), 7.64 (m, 3H), 4.00 (d, 1H), 3.60 (d, 1H), 3.26 (m, 1H), 2.93 (t, 1H), 2.59 (m, 2H), 2.17 (t, 2H), 1.46 (m, 2H), 1.43 (q, 2H), 1.17 (m, 1H), 0.82 (t, 3H); LC/MS m/z 512 (M−H)$^-$, 514 (M+H)$^+$

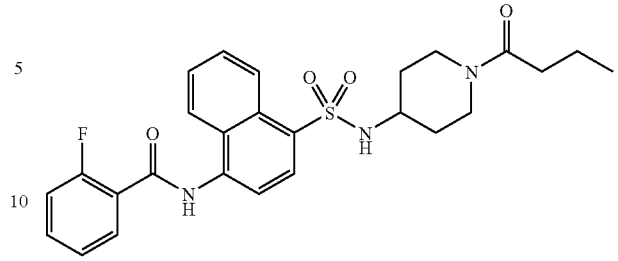

N-[4-(1-Butyryl-piperidin-4-ylsulfamoyl)-naphthalen-1-yl]-2-fluoro-benzamide (C-106)

The title compound was prepared following the general procedure in Scheme 5, beginning with 4-(2-fluoro-benzoylamino)-naphthalene-1-sulfonyl chloride and substituting butyryl chloride and triethylamine for 2-isocyanato-propane. $^1$H NMR (300 MHz, DMSO) δ 10.73 (s, 1H), 8.69 (d, 1H), 8.28 (d, 1H), 8.21 (d, 1H), 8.11 (d, 1H), 7.99 (d, 1H), 7.83 (t, 1H), 7.76 (m, 2H), 7.64 (m, 1H), 7.40 (q, 2H), 4.00 (d, 1H), 3.60 (d, 1H), 3.26 (m, 1H), 2.93 (t, 1H), 2.59 (m, 2H), 2.17 (t, 2H), 1.46 (m, 2H), 1.43 (q, 2H), 1.17 (m, 1H), 0.82 (t, 3H); LC/MS m/z 496 (M−H)$^-$, 498 (M+H)$^+$

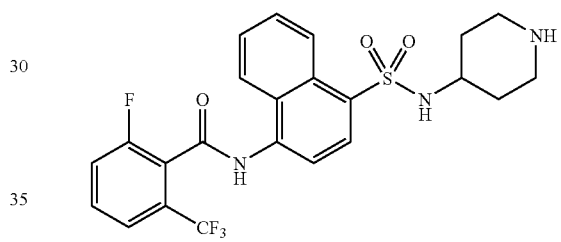

2-Fluoro-N-[4-(piperidin-4-ylsulfamoyl)-naphthalen-1-yl]-6-trifluoromethyl-benzamide (C-107)

The title compound was prepared following the general procedure in Scheme 5, beginning with 4-(2-fluoro-6-trifluoromethyl-benzoylamino)-naphthalene-1-sulfonyl chloride. $^1$H NMR (300 MHz, DMSO) δ 11.15 (s, 1H), 8.70 (d, 1H), 8.32 (d, 1H), 8.29 (m, 1H), 8.01 (d, 1H), 7.77 (m, 1H), 7.65 (m, 1H), 7.32 (m, 1H), 6.94 (m, 1H), 3.08 (d, 1H), 2.85 (m, 1H), 2.54 (m, 5H), 1.64 (m, 1H), 1.51 (m, 1H). LC/MS m/z 494 (M−H)$^-$, 496 (M+H)$^+$

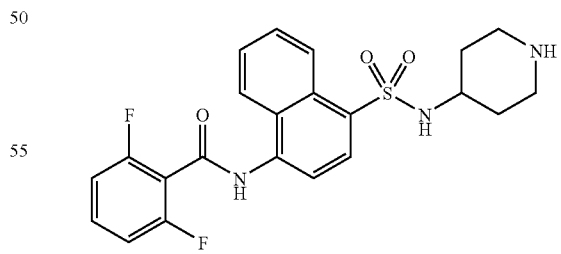

2,6-Difluoro-N-[4-(piperidin-4-ylsuffamoyl)-naphthalen-1-yl]-benzamide (C-108)

The title compound was prepared following the general procedure in Scheme 5, beginning with 4-(2,6-difluoro-benzoylamino)-naphthalene-1-sulfonyl chloride. $^1$H NMR (300 MHz, DMSO) δ 11.15 (s, 1H), 8.70 (d, 1H), 8.32 (d, 1H), 8.29 (m, 1H), 8.01 (d, 1H), 7.77 (m, 1H), 7.65 (m, 1H), 7.32 (m, 1H), 6.94 (m, 1H), 3.08 (d, 1H), 2.85 (m, 1H), 2.54 (m, 5H), 1.64 (m, 1H), 1.51 (m, 1H). LC/MS m/z 444 (M–H)⁻, 446 (M+H)⁺

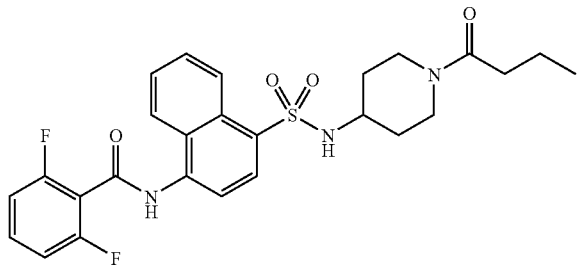

N-[4-(1-Butyryl-piperidin-4-ylsulfamoyl)-naphthalen-1-yl]-2,6-difluoro-benzamide (C-109)

The title compound was prepared following the general procedure in Scheme 5, beginning with 4-(2,6-difluoro-benzoylamino)-naphthalene-1-sulfonyl chloride, and substituting butyryl chloride and triethylamine for 2-isocyanato-propane. ¹H NMR (300 MHz, DMSO) δ 11.12(s, 1H), 8.71 (m, 1H), 8.26 (m, 2H), 8.13 (d, 1H), 7.98 (d, 1H), 7.75 (m, 2H), 7.62 (m, 1H), 7.31 (t, 2H), 4.01 (d, 1H), 3.60 (d, 1H), 2.93 (t, 1H), 2.59 (m, 2H), 2.15 (t, 2H), 1.45 (m, 2H), 1.43 (q, 2H), 1.17 (m, 2H), 0.81 (t, 3H); LC/MS m/z 514 (M–H)⁻, 516 (M+H)⁺

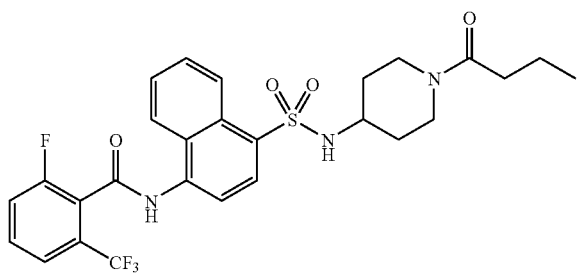

N-[4-(1-Butyryl-piperidin-4-ylsulfamoyl)-naphthalen-1-yl]-2-fluoro-6-trifluoromethyl-benzamide (C-110)

The title compound was prepared following the general procedure in Scheme 5, beginning with 4-(2-fluoro-6-trifluoromethyl-benzoylamino)-naphthalene-1-sulfonyl chloride and substituting butyric chloride and triethylamine for 2-isocyanato-propane. ¹H NMR (300 MHz, DMSO) δ 11.12 (s, 1H), 8.71 (m, 1H), 8.26 (m, 2H), 8.13 (m, 1H), 7.98 (d, 1H), 7.79 (m, 6H), 4.01 (d, 1H), 3.60 (d, 1H), 2.93 (t, 1H), 2.59 (m, 2H), 2.15 (t, 2H), 1.45 (m, 2H), 1.43 (q, 2H), 1.17 (m, 2H), 0.81 (t, 3H). LC/MS m/z 514 (M–H)⁻, 516 (M+H)⁺

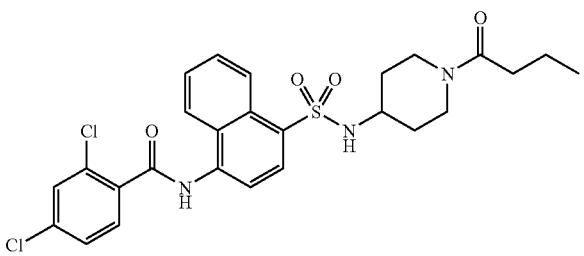

N-[4-(1-Butyryl-piperidin-4-ylsulfamoyl)-naphthalen-1-yl]-2,4-dichloro-benzamide (C-111)

The title compound was prepared following the general procedure in Scheme 5, beginning with 4-(2,4-dichloro-benzoylamino)-naphthalene-1-sulfonyl chloride and substituting butyryl chloride and triethylamine for 2-isocyanato-propane. ¹H NMR (300 MHz, DMSO) δ 10.87 (s, 1H), 8.70 (dd, 1H), 8.34 (dd, 1H), 8.21 (d, 1H), 8.13 (d, 1H), 8.01 (d, 1H), 7.82 (m, 2H), 7.73 (m, 1H), 7.63 (d, 1H), 4.00 (d, 1H), 3.6 (d, 1H), 3.24 (m, 1H), 2.92 (t, 1H), 2.59 (m, 1H), 2.17 (t, 2H), 1.47 (m, 2H), 1.43 (m, 2H), 1.18 (m, 2H), 0.82 (t, 3H). LC/MS m/z 548 (M–H)⁻, 560 (M+H)⁺

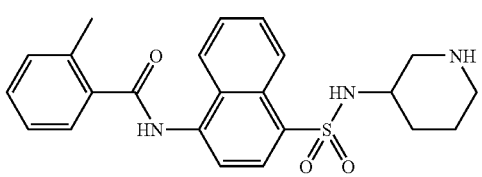

(±)-2-Methyl-N-[4-(piperidin-3-ylsulfamoyl)-naphthalen-1-yl]-benzamide (C-112)

The title compound was made following general procedure in Scheme 5, substituting 4-(2-methyl-benzoylamino)-naphthalene-1-sulfonyl chloride for 4-benzoylamino-naphthalene-1-sulfonyl chloride, and 3-amino-piperidine-1-carboxylic acid tert-butyl ester for 4-amino-piperidine-1-carboxylic acid tert-butyl ester. ¹H NMR (300 MHz, MeOD) δ 8.78 (d, 1H), 8.33 (d, 2H), 8.25 (d, 1H), 7.96 (d, 1H), 7.71 (m, 3H), 7.45 (m, 1H ), 7.38 (m, 2H), 3.33 (m, 1H), 3.19 (m, 2H), 2.70 (m, 2H), 2.57 (s, 3H), 1.83 (m, 1H), 1.55 (m, 3H); LC/MS (M+H)⁺ m/z 424.

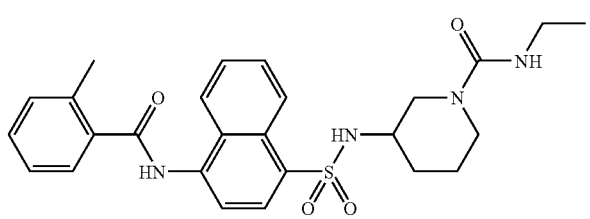

(±)-3-[4-(2-Methyl-benzoylangno)-naphthalene-1-sulfonylamino]-piperidine-1-carboxylic acid ethylamide (C-113)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-piperidine-1-carboxylic acid tert-butyl ester for 4-amino-piperidine-1-carboxylic acid tert-butyl ester and isocyanato-ethane for 2-isocyanato-propane. ¹H NMR (300 MHz, MeOD) δ 8.78 (d, 1H), 8.33 (m, 2H), 8.23 (d, 1H), 7.94 (d, 1H), 7.71 (m, 3H), 7.43 (m, 1H ), 7.38 (m, 2H), 3.79 (m, 1H), 3.55 (m, 1H), 3.12 (q, 2H), 3.10 (m, 1H ), 2.85 (m, 1H), 2.72 (m, 1H), 2.55 (s, 3H), 1.58 (m, 2H), 1.30 (m, 2H), 1.19 (m, 3H); LC/MS (M+H)⁺ m/z 495.

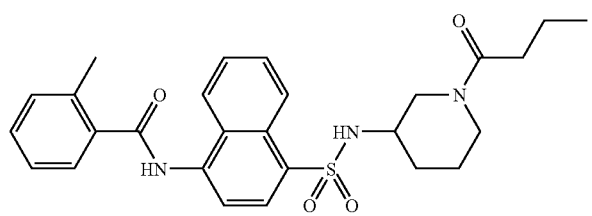

(±)-N-[4-(I-Butyryl-piperidin-3-ylsulfamoyl)-naphthalen-1-yl]-2-methyl-benzamide (C-114)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-piperidine-1-carboxylic acid tert-butyl ester for 4-amino-piperidine-1-carboxylic acid tert-butyl ester and butyryl chloride for 2-isocyanato-propane. $^1$H NMR (300 MHz, MeOD) δ 8.78 (m, 1H), 8.33 (m, 2H), 8.23 (m, 1H), 7.94 (m, 1H), 7.71 (m, 3H), 7.43 (m, 1H), 7.38 (m, 2H), 3.79 (m, 1H), 3.91 (m, 1H), 3.55 (q, 1H), 3.08 (m, 1H), 2.95 (m, 1H), 2.82 (m, 1H), 2.55 (s, 3H), 2.01 (m, 2H), 1.50 (m, 6H), 0.90 (m, 3H); LC/MS (M+H)$^+$ m/z 494.

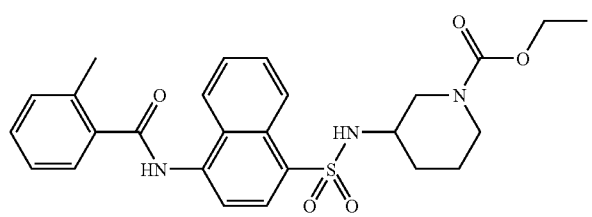

(±)-3-[4-(2-Methyl-benzoylamno)-naphthalene-1-sulfonylamino]-piperidine-1-carboxylic acid ethyl ester (C-115)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-piperidine-1-carboxylic acid tert-butyl ester for 4-amino-piperidine-1-carboxylic acid tert-butyl ester and ethyl chlorofomate for 2-isocyanato-propane. $^1$H NMR (300 MHz, MeOD) δ 8.78 (m, 1H), 8.33 (m, 2H), 8.23 (m, 1H), 7.94 (m, 1H), 7.71 (m, 3H), 7.43 (m, 1H), 7.38 (m, 2H), 4.02 (m, 2H), 3.70 (m, 2H), 3.06 (m, 1H), 2.69 (m, 1H), 2.38 (m, 1H), 2.55 (s, 3H), 1.71 (m, 2H), 1.30 (m, 2H), 1.18 (m, 3H); LC/MS (M+H)$^+$ m/z 496.

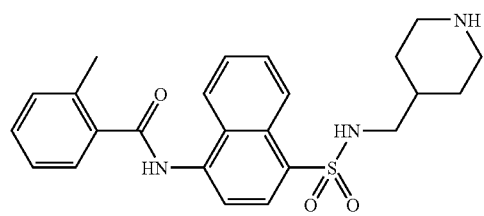

2-Methyl-N-{4-[(piperidin-4-ylmethyl)-sulfamoyl]-naphthalen-1-yl}-benzamide (C-116)

The title compound was made following general procedure in Scheme 5, substituting 4-(2-methyl-benzoylamino)-naphthalene-1-sulfonyl chloride for 4-benzoylamino-naphthalene-1-sulfonyl chloride, and 4-aminomethyl-piperidine-1-carboxylic acid tert-butyl ester for 4-amino-piperidine-1-carboxylic acid tert-butyl ester. $^1$H NMR (300 MHz, MeOD) δ 8.78 (d, 1H), 8.29 (m, 2H), 7.93 (m, 1H), 7.74 (m, 3H), 7.41 (m, 3H), 3.30 (m, 2H), 2.82 (m, 2H), 2.80 (d, 2H), 2.55 (s, 3H), 1.84 (m, 2H), 1.65 (m, 1H), 1.28 (m, 2H); LC/MS (M+H)$^+$ m/z 438.

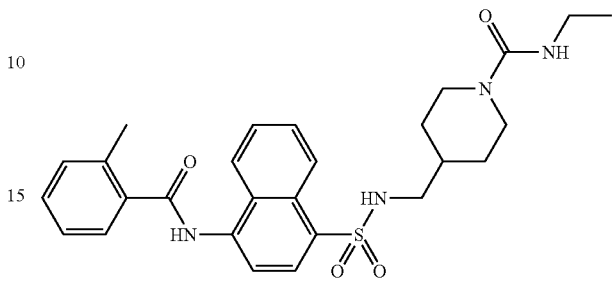

4-{[4-(2-Methyl-benzoylamino)-naphthalene-1-sulfonylamino]-methyl}-piperidine-1-carboxylic acid ethylamide (C-117)

The title compound was made following general procedure in Scheme 5, substituting 4-(2-methyl-benzoylamino)-naphthalene-1-sulfonyl chloride for 4-benzoylamino-naphthalene-1-sulfonyl chloride, 4-aminomethyl-piperidine-1-carboxylic acid tert-butyl ester for 4-amino-piperidine-1-carboxylic acid tert-butyl ester and isocyanato-ethane for 2-isocyanato-propane. $^1$H NMR (300 MHz, MeOD) δ 8.78 (d, 1H), 8.29 (m, 2H), 7.93 (m, 1H), 7.74 (m, 3H), 7.41 (m, 3H), 3.79 (m, 2H), 3.25 (q, 2H), 2.78 (d, 2H), 2.61 (m, 2H), 2.57 (s, 3H), 1.56 (m, 3H), 1.09 (t, 3H), 0.92 (m, 2H); LC/MS (M+H)$^+$ m/z 509.

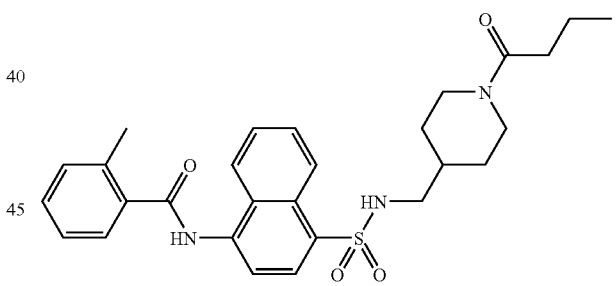

N-{4-[(1-Butyryl-piperidin-4-ylmethyl)-sulfamoyl]-naphthalen-1-yl}-2-methyl-benzamide (C-118)

The title compound was made following general procedure in Scheme 5, substituting 4-(2-methyl-benzoylamino)-naphthalene-1-sulfonyl chloride for 4-benzoylamino-naphthalene-1-sulfonyl chloride, 4-aminomethyl-piperidine-1-carboxylic acid tert-butyl ester for 4-amino-piperidine-1-carboxylic acid tert-butyl ester and butyryl chloride for 2-isocyanato-propane. $^1$H NMR (300 MHz, MeOD) δ 8.78 (d, 1H), 8.29 (m, 2H), 7.93 (m, 1H), 7.74 (m, 3H), 7.41 (m, 3H), 4.49 (m, 1H), 3.85 (m, 1H), 2.89 (m, 1H), 2.78 (d, 2H), 2.57 (s, 3H), 2.41 (m, 1H), 2.30 (t, 2H), 1.61 (m, 5H), 0.96 (t, 3H), 0.93 (m, 2H); LC/MS (M+H)$^+$ m/z 508.

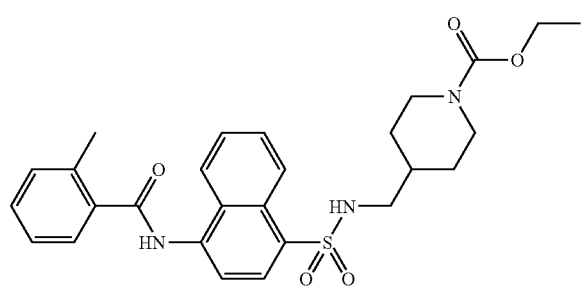

4-{[4-(2-Methyl-benzoylamino)-naphthalene-1-sulfonylamino]-methyl}-piperidine-1-carboxylic acid ethyl ester (C-119)

The title compound was made following general procedure in Scheme 5, substituting 4-(2-methyl-benzoylamino)-naphthalene-1-sulfonyl chloride for 4-benzoylamino-naphthalene-1-sulfonyl chloride, 4-aminomethyl-piperidine-1-carboxylic acid tert-butyl ester for 4-amino-piperidine-1-carboxylic acid tert-butyl ester and ethyl chlorofomate for 2-isocyanato-propane. $^1$H NMR (300 MHz, MeOD) δ 8.78 (d, 1H), 8.29 (m, 2H), 7.93 (m, 1H), 7.74 (m, 3H), 7.41 (m, 3H ), 4.09 (q, 2H), 4.00 (m, 2H), 2.78 (d, 2H), 2.59 (m, 2H), 2.57 (s, 3H), 1.59 (m, 3H), 1.22 (t, 3H), 0.90 (m, 2H); LC/MS (M+H)$^+$ m/z 510.

Scheme 6

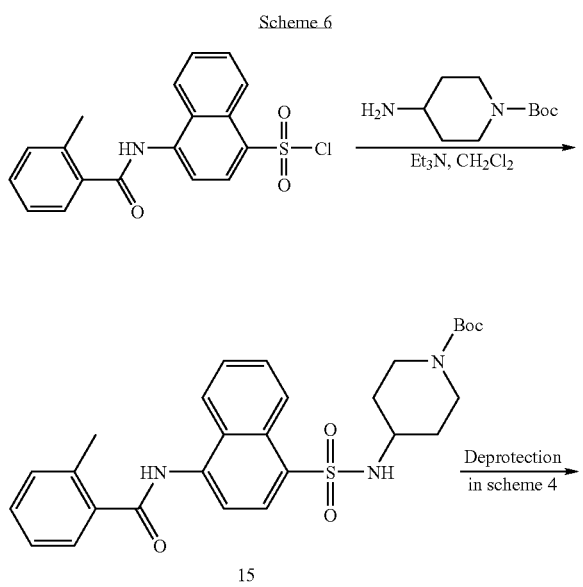

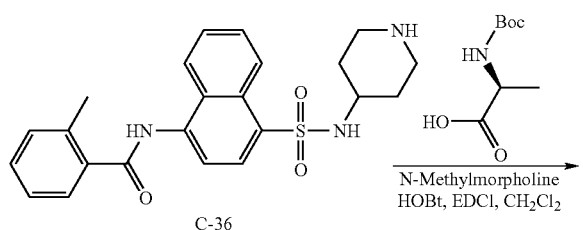

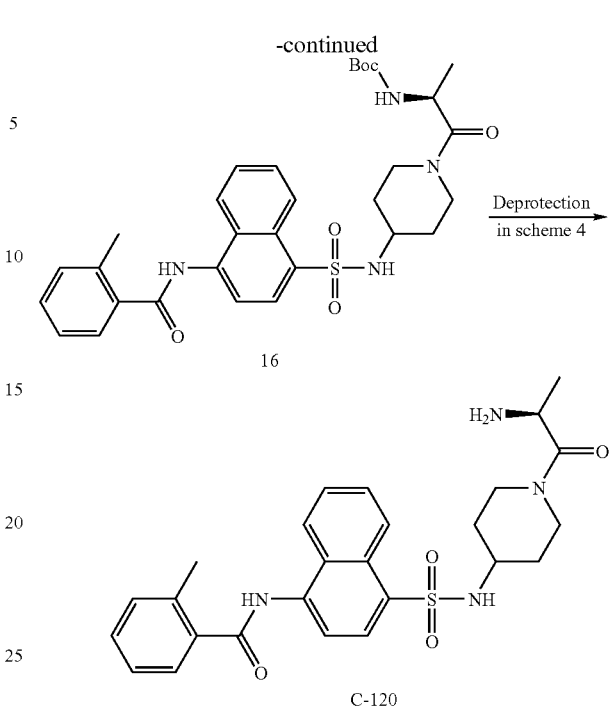

4-[4-(2-methyl-benzoylamino)-naphthalene-1-sulfonylamino]-piperidine-1-carboxylic acid tert-butyl ester (15)

The title compound was prepared following the general procedure in Scheme 2, substituting 4-amino-piperidine-1-carboxylic acid tert-butyl ester for p-anisidine and 2-methyl-benzoyl chloride for benzoyl chloride. LC/MS (M+H)$^+$ m/z 524.

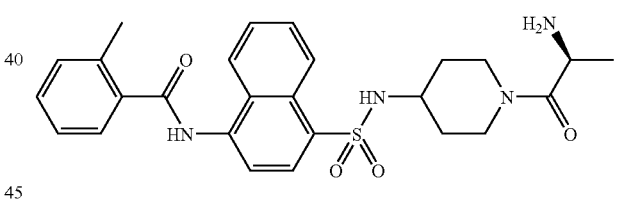

(S)-N-{4-[1-(2-Amino-propionyl)-piperidin-4-ylsulfamoyl]-naphthalen-1-yl}-2-methyl-benzamide (C-120)

2-Methyl-N-[4-(piperidin-4-ylsulfamoyl)-naphthalen-1-yl]-benzamide (C-36) was prepared from 4-[4-(2-methyl-benzoylamino)-naphthalene-1-sulfonylamino]-piperidine-1-carboxylic acid tert-butyl ester 15 via coupling and deprotection as shown in Scheme 4-1. To a 25° C. mixture of 2-methyl-N-[4-(piperidin-4-ylsulfamoyl)-naphthalen-1-yl]-benzamide (C-36) hydrochloride (368 mg, 0.8 mmol) in CH$_2$Cl$_2$ (12 mL), was added 1-hydroxybenzotriazole hydrate (108 mg, 0.8 mmol), 1-(3-dimethylaminopropyl)-3-ethylcarbodiimide hydrochloride (184 mg, 0.96 mmol), N-methylmorpholine (243 mg, 2.4 mmol) and (S)-2-tert-butoxycarbonylamino-propionic acid. After stirring at 25° C. for 20 hours, the reaction mixture was filtered and the filtrate was concentrated to dryness in vacuo to afford 16. A solution of 4N HCl/Dioxane (5 mL) was added and the mixture was stirred for 2 hours. After removing the solvent, the crude product was purified via chromatography. $^1$H NMR (300 MHz, MeOD) δ 8.71 (d, 1H), 8.28 (m, 3H), 7.96 (d, 1H), 7.71 (m, 3H), 7.43 (m, 1H ), 7.38 (m, 2H), 4.00 (m, 2H), 3.60 (m, 2H), 3.01 (m, 1H ), 2.71 (m, 1H), 2.49 (s, 3H), 1.57 (m, 2H), 1.22 (m, 2H), 1.09 (m, 3H); LC/MS (M+H)+ m/z 495.

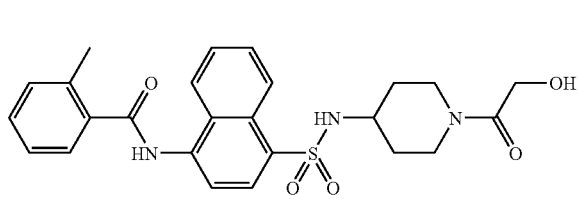

N-{4-[1-(2—Hydroxy-acetyl)-piperidin-4-ylsuffamoyl]-naphthalen-1-yl}-2-methyl-benzamide (C-121)

The title compound was made following general procedure in Scheme 6, substituting hydroxy-acetic acid for (S)-2-tert-butoxycarbonylamino-propionic acid. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 4.16 (m, 1H), 4.13 (s, 2H), 3.55 (m, 1H), 3.34 (m, 1H), 2.95 (m, 1H ), 2.74 (m, 1H), 2.55 (s, 3H), 1.63 (m, 2H), 1.41 (m, 2H); LC/MS (M+H)+ m/z 483.

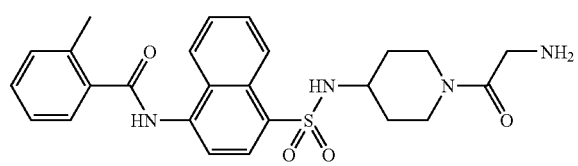

N-{4-[1-(2-Amino-acetyl)-piperidin-4-ylsulfamoyl]-naphthalen-1-yl}-2-methyl-benzamide (C-122)

The title compound was made following general procedure in Scheme 6, substituting tert-butoxycarbonylamino-acetic acid for (S)-2-tert-butoxycarbonylamino-propionic acid. $^1$H NMR (300 MHz, MeOD) δ 8.72 (d, 1H), 8.25 (m, 3H), 7.94 (d, 1H), 7.71 (m, 3H), 7.43 (m, 1H), 7.38 (m, 2H), 4.05 (m, 1H), 3.60 (m, 4H), 2.95 (m, 1H), 2.74 (m, 1H), 2.49 (s, 3H), 1.55 (m, 2H), 1.31 (m, 2H); LC/MS (M+H)+ m/z 481.

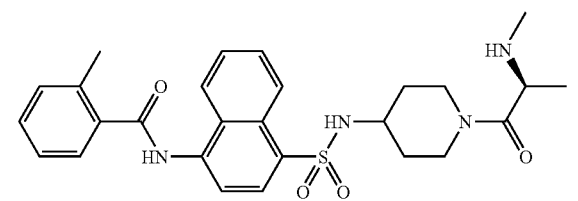

(S)-2-Methyl-N-{4-[1-(2-methylamno-propionyl)-piperidin-4-ylsulfamoyl]-naphthalen-1-yl}-benzamide (C-123)

The title compound was made following general procedure in Scheme 6, substituting (S)-2-(tert-butoxycarbonyl-methyl-amino)-propionic acid for (S)-2-tert-butoxycarbonylamino-propionic acid. $^1$H NMR (300 MHz, MeOD) δ 8.72 (d, 1H), 8.25 (m, 3H), 7.96 (d, 1H), 7.71 (m, 3H), 7.43 (m, 1H ), 7.38 (m, 2H), 4.10 (m, 1H), 3.60 (m, 2H), 3.01 (m, 1H ), 2.71 (m, 1H), 2.49 (s, 3H), 2.19 (d, 3H), 1.57 (m, 2H), 1.22 (m, 2H), 1.05 (m, 3H); LC/MS (M+H)+ m/z 509.

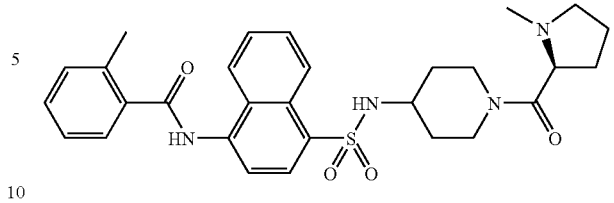

(S)-2-Methyl-N-{4-[1-(1-methyl-pyrrolidine-2-carbonyl)-piperidin-4-ylsulfamoyl]-naphthalen-1-yl}-benzamide (C-124)

The title compound was made following general procedure in Scheme 6, substituting (S)-1-methyl-pyrrolidine-2-carboxylic acid for (S)-2-tert-butoxycarbonylamino-propionic acid. $^1$H NMR (300 MHz, MeOD) δ 8.72 (d, 1H), 8.25 (m, 3H), 7.96 (d, 1H), 7.71 (m, 3H), 7.43 (m, 1H ), 7.38 (m, 2H), 4.03 (m, 2H), 3.40 (m, 5H), 2.99 (m, 1H ), 2.68 (m, 1H), 2.49 (s, 3H), 2.21 (d, 3H), 2.02 (m, 1H), 1.71 (m, 2H), 1.55 (m, 2H), 1.20 (m, 2H); LC/MS (M+H)+ m/z 535.

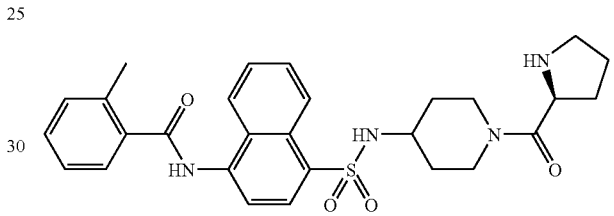

(S)-2-Methyl-N-{4-[1-(pyrrolidine-2-carbonyl)-piperidin-4-ylsulfamoyl]-naphthalen-1-yl}-benzamide (C-125)

The title compound was made following general procedure in Scheme 6, substituting (S)-pyrrolidine-1,2-dicarboxylic acid 1-tert-butyl ester for (S)-2-tert-butoxycarbonylamino-propionic acid. $^1$H NMR (300 MHz, MeOD) δ 8.72 (d, 1H), 8.25 (m, 3H), 7.96 (d, 1H), 7.71 (m, 3H), 7.43 (m, 1H), 7.38 (m, 2H), 4.03 (m, 2H), 3.40 (m, 2H), 3.02 (m, 2H), 2.78 (m, 2H), 2.49 (s, 3H), 2.06 (m, 1H), 1.62 (m, 5H), 1.25 (m, 2H); LC/MS (M+H)+ m/z 521.

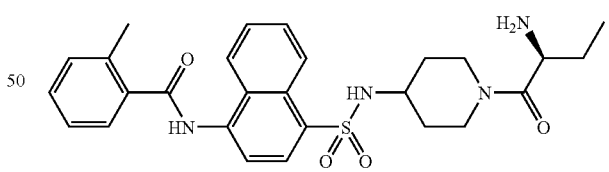

(S)-N-{4-[1-(2-Amino-butyryl)-piperidin-4-ylsulfamoyl]-naphthalen-1-yl}-2-methyl-benzamide (C-126)

The title compound was made following general procedure in Scheme 6, substituting (S)-2-tert-butoxycarbonylamino-butyric acid for (S)-2-tert-butoxycarbonylamino-propionic acid. $^1$H NMR (300 MHz, MeOD) δ 8.71 (d, 1H), 8.28 (m, 3H), 7.96 (d, 1H), 7.71 (m, 3H), 7.43 (m, 1H ), 7.38 (m, 2H), 4.09 (m, 1H), 3.78 (m, 2H), 3.01 (m, 2H ), 2.71 (m, 1H), 2.49 (s, 3H), 1.57 (m, 2H), 1.25 (m, 4H), 0.82 (m, 3H); LC/MS (M+H)+ m/z 509.

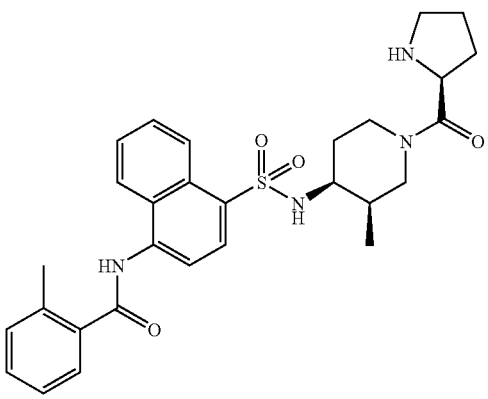

(±)-cis-2-Methyl-N-{4-[3-methyl-1-((s)-pyrrolidine-2-carbonyl)-piperidin-4-ylsulfamoyl]-naphthalen-1-yl}-benzamide (C-127) (mixture of two diastereomers)

The title compound (mixture of disatereomers) was made following general procedure in scheme 6, substituting 1-benzyl-3-methyl-piperidin-4-ylamine for 4-amino-piperidine-1-carboxylic acid tert-butyl ester, and substituting (s)-pyrrolidine-1,2-dicarboxylic acid 1-tert-butyl ester for (s)-2-tert-butoxycarbonylamino-propionic acid. LC/MS (M+H)$^+$ m/z 535.

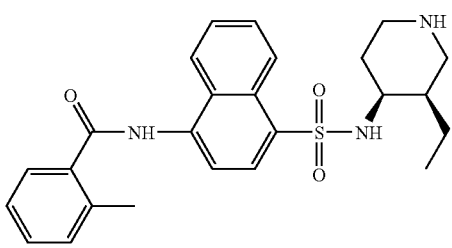

(±)-(cis)-N-[4-(3-Ethyl-piperidin-4-ylsulfamoyl)-naphthalen-1-yl]-2-methyl-benzamide (C-128)

The title compound was prepared as its formate salt following general procedure in scheme 4-2, substituting (±)-1-benzyl-3-ethyl-piperidin-4-ylamine (3) for (±)-4-amino-1-benzyl-piperidine-3-carboxylic acid ethyl ester (6). $^1$H NMR (300 MHz, MeOD) δ 8.84 (d, 1H), 8.53 (s, 1H), 8.35 (d, 1H), 8.26 (d, 1H), 7.96 (d, 1H), 7.73 (m, 3H), 7.38 (m, 3H), 3.55 (m, 1H), 3.05 (m, 3H), 2.92 (m, 1H), 2.55 (s, 3H), 1.68 (m, 3H), 1.00 (m, 2H), 0.42 (t, 3H); LC/MS m/z 452 (M+H)$^+$

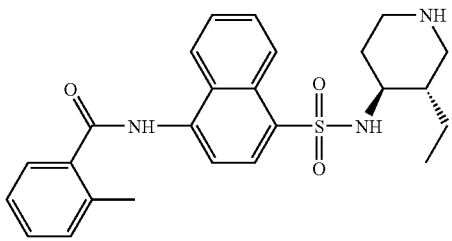

(±)-(trans)-N-[4-(3-Ethyl-piperidin-4-ylsulfamoyl)-naphthalen-1-yl]-2-methyl-benzamide (C-129)

The title compound was prepared as its formate salt following general procedure in scheme 4-2, substituting (±)-1-benzyl-3-ethyl-piperidin-4-ylamine (3) for (±)-4-amino-1-benzyl-piperidine-3-carboxylic acid ethyl ester (6). $^1$H NMR (300 MHz, MeOD) δ 8.78 (d, 1H), 8.53 (s, 1H), 8.33 (d, 1H), 8.25 (d, 1H), 7.94 (d, 1H), 7.72 (m, 3H), 7.40 (m, 3H), 3.35 (m, 1H), 3.20 (m, 2H), 2.85 (m, 1H), 2.60 (m, 1H), 2.56 (s, 3H), 1.75 (m, 1H), 1.52 (m, 3H), 0.90 (m, 1H), 0.58 (t, 3H); LC/MS m/z 452 (M+H)$^+$

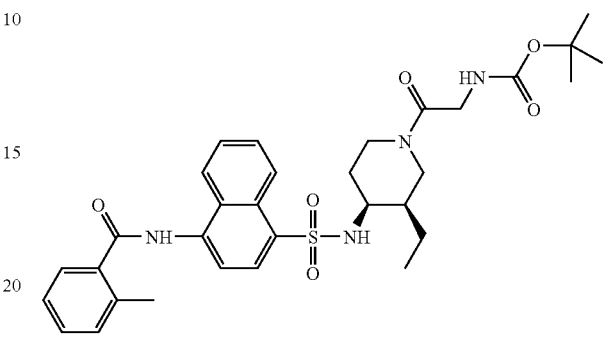

(±)-(cis)-(2-{3-Ethyl-4-[4-(2-methyl-benzoylamino)-naphthalene-1-sulfonylamino]-piperidin-1-yl}-2-oxo-ethyl)-carbamic acid tert-butyl ester (C-130)

The title compound was made following general procedure in Scheme 6, substituting (±)-(cis)-N-[4-(3-ethyl-piperidin-4-ylsulfamoyl)-naphthalen-1-yl]-2-methyl-benzarnide (C-128) for N-[4-(piperidin-4-ylsulfamoyl)-naphthalen-1-yl]-benzamide (C-1) and substituting tert-butoxycarbonylamino-acetic acid for 3-tert-butoxycarbonylamino-butyric acid. $^1$H NMR (300 MHz, MeOD) δ 8.85 (d, 1H), 8.33 (d, 1H), 8.25 (d, 1H), 7.95 (d, 1H), 7.71 (m, 3H), 7.43 (m, 1H), 7.36 (m, 2H), 3.80 (s, 2H), 3.45 (m, 3H), 3.25 (m, 2H), 2.56 (s, 3H), 1.40 (m, 12H), 1.04 (m, 2H), 0.50 (m, 3H); LC/MS m/z 609 (M+H)$^+$

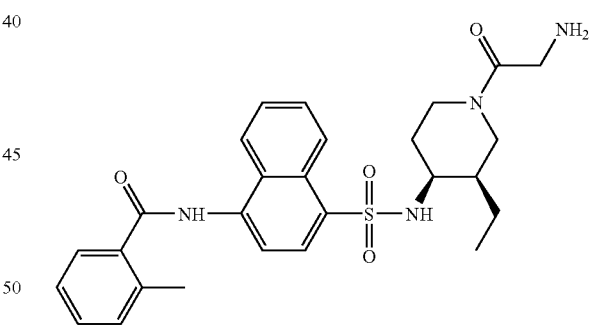

(±)-(cis)-N-{4-[1-(2-Amino-acetl)-3-ethyl-piperidin-4-ylsulfamoyl]-naphthalen-1-yl}-2-methyl-benzamide (C-131)

The title compound was prepared as its formate salt following general procedure in Scheme 6, substituting (±)-(cis)-N-[4-(3-ethyl-piperidin-4-ylsulfamoyl)-naphthalen-1-yl]-2-methyl-benzamide (C-128) for N-[4-(piperidin-4-ylsulfamoyl)-naphthalen-1-yl]-benzamide (C-1), and substituting tert-butoxycarbonylamino-acetic acid for 3-tert-butoxycarbonylarnino-butyric acid. $^1$H NMR (300 MHz, MeOD) δ 8.85 (d, 1H), 8.52 (s, 1H), 8.33 (d, 1H), 8.25 (d, 1H), 7.95 (d, 1H), 7.72 (m, 3H), 7.43 (m, 1H), 7.36 (m, 2H), 3.78 (m, 2H), 3.45 (m, 3H), 3.20 (m, 2H), 2.56 (s, 3H), 1.45 (m, 3H), 1.05 (m, 2H), 0.50 (m, 3H); LC/MS m/z 509 (M+H)$^+$

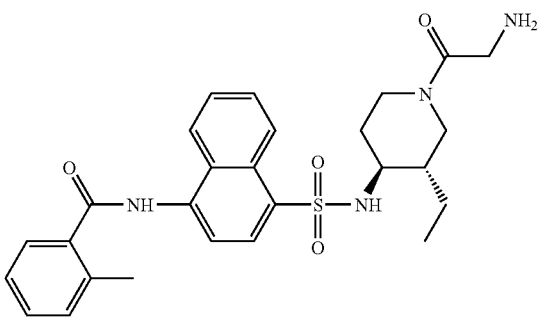

(±)-(trans)-N-{4-[1-(2-Anino-acetyl)-3-ethyl-piperidin-4-ylsulfamoyl]-naphthalen-1-yl}-2-methyl-benzamide (C-132)

The title compound was prepared as its formate salt following general procedure in Scheme 6, substituting (±)-(trans)-N-[4-(3-ethyl-piperidin-4-ylsulfamoyl)-naphthalen-1-yl]-2-methyl-benzamide (C-129) for N-[4-(piperidin-4-ylsulfamoyl)-naphthalen-1-yl]-benzamide (C-1) and substituting tert-butoxycarbonylamino-acetic acid for 3-tert-butoxycarbonylamino-butyric acid. $^1$H NMR (300 MHz, MeOD) δ 8.78 (d, 1H), 8.52 (s, 1H), 8.33 (d, 1H), 8.25 (d, 1H), 7.95 (d, 1H), 7.72 (m, 3H), 7.43 (m, 1H), 7.36 (m, 2H), 4.25 (m, 1H), 3.75 (m, 2H), 3.55 (m, 1H), 3.05 (m, 2H), 2.56 (s, 3H), 2.50 (m, 1H), 1.40 (m, 4H), 0.85 (m, 1H), 0.65 (m, 3H); LC/MS m/z 509 (M+H)$^+$ (±)-(cis)-N-{4-[3-Ethyl-1-(2-ethylamino-acetyl)-piperidin-4-ylsulfamoyl]-naphthalen-1-yl}-2-methyl-benzamide (C-133)

To a 25° C. solution of (±)-(cis)-N-{4-[1-(2-amino-acetyl)-3-ethyl-piperidin-4-ylsulfamoyl]-naphthalen-1-yl}-2-methyl-benzamide (C-131) (65 mg, 0.128 mmol) in MeOH (4 mL) was added acetyl aldehyde (5.62 mg, 0.128 mmol) and sodium cyanoborohydride (40 mg, 0.64 mmol). After stirring for 2 h at 25° C., the solution was concentrated in vacuo to give a solid. The resultant solid was purified by reverse phase HPLC to provide the title compound. $^1$H NMR (300 MHz, MeOD) δ 8.85 (d, 1H), 8.33 (d, 1H), 8.25 (d, 1H), 7.94 (d, 1H), 7.71 (m, 3H), 7.43 (m, 1H), 7.35 (m, 2H), 3.55 (m, 5H), 3.20 (m, 2H), 2.85 (m, 2H), 2.56 (s, 3H), 1.25 (m, 7H), 0.50 (m, 3H); LC/MS m/z 537 (M+H)$^+$ Scheme 7

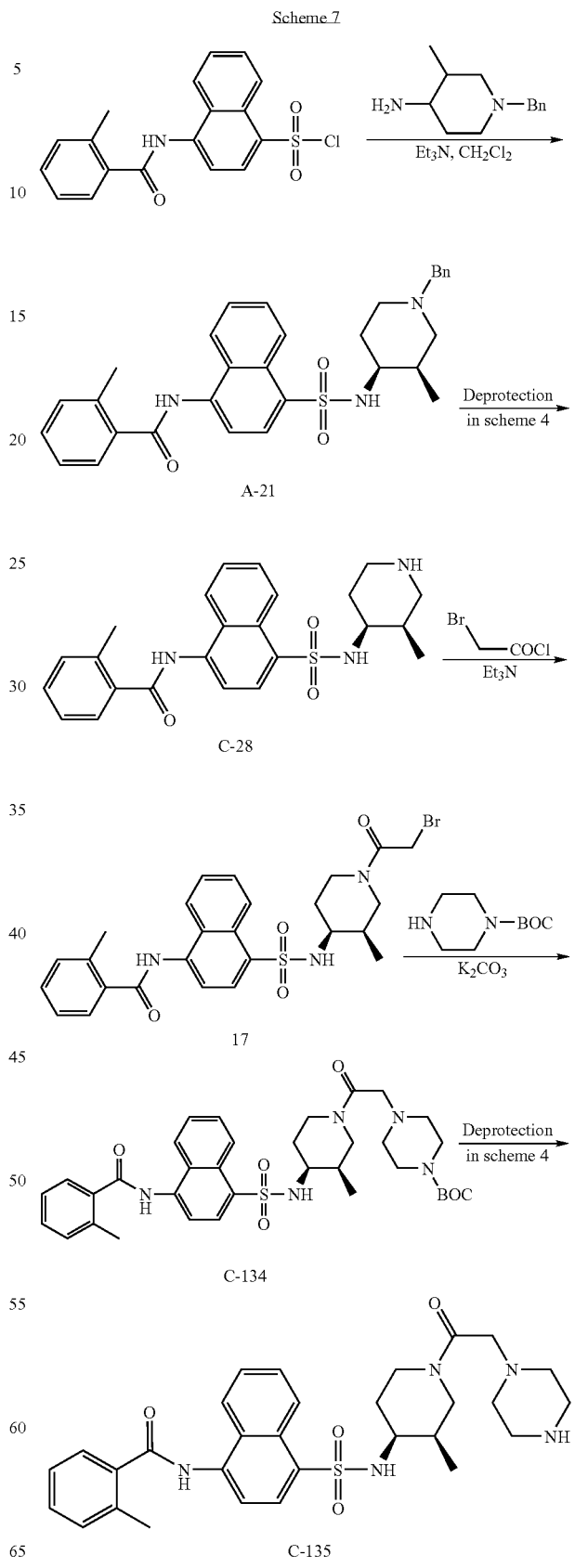

4-[1-{2-bromo-acetyl}-3-cis-methyl-piperidin-4-yl-sulfamoyl]-naphthalen-1-yl}-2-methyl-benzamide (17)

(±)-cis-N-[4-(1-Benzyl-3-methyl-piperidin-4-ylsulfamoyl)-naphthalen-1-yl]-2-methyl-benzamide (A-21) was prepared as described previously according to the general procedure in Scheme 2. Deprotection of A-21 to afford 2-Methyl-N-[4-(3-cis-methyl-piperidin-4-ylsulfamoyl)-naphthalen-1-yl]-benzamide (C-28) was achieved according to the general procedure described in Scheme 4-2. 2-Methyl-N-[4-(3-cis-methyl-piperidin-4-ylsulfamoyl)-naphthalen-1-yl]-benzamide (C-28) (700 mg, 1.6 mmol) was dissolved in dichloromethane (8 mL). Triethylamine (192 mg, 0.26 mL, 1.9 mmol) was added followed by bromoacetyl chloride (378 mg, 0.20 mL, 2.4 mmol). The reaction was stirred for 1 hour at room temperature and then passed through a plug of silica gel. Elution with ethyl acetate followed by evaporation in vacuo afforded the title product (644 mg, 72%) as a white solid. This material was used without further purification. LC/MS m/z 556 (M–H)⁻.

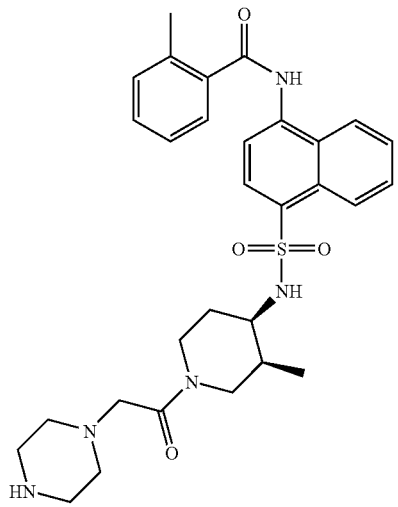

(±)-2-methyl-N-{4-[3-cis-methyl-1-(2-piperazin-1-yl-acetyl)-piperidin-4-ylsulfamoyl]-naphthalen-1-yl}-benzamide (C-135)

(±)-4-(2-{3-cis-Methyl-4-[4-(2-methyl-benzoylamino)-naphthalene-1-sulfonylamino]-piperidin-1-yl}-2-oxo-ethyl)-piperazine-1-carboxylic acid tert-butyl ester (43 mg, 0.07 mmol) was dissolved in a solution of 4N HCl/dioxane (3 mnL). The reaction was left standing for 3 hours at room temperature; concentration in vacuo afforded the titled compound (14 mg, 40%) as its bis-hydrochloride salt. $^1$H NMR (300 MHz, CD$_3$OD) (1:1 mixture of rotamers) δ 8.85 (d, 1H), 8.32 (d, 1H), 8.24 (d, 1H), 7.96 (d, 1H), 7.72 (m, 3H), 7.40 (m, 4H), 4.30 (m, 2H), 3.52 (m, 12H), 3.22 (m, 2H), 2.58 (s, 3H), 1.83 (m, 1H), 1.58 (m, 2H), 0.74 (d, 1.5H), 0.68 (d, 1.5H); LC/MS m/z 564 (M+H)⁺.

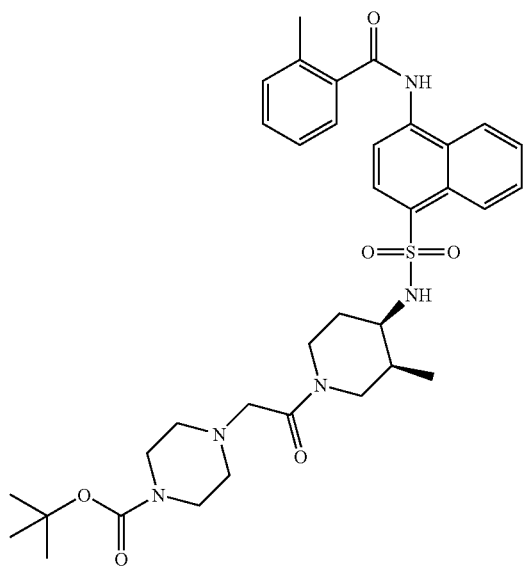

(±)-4-(2-{3-cis-methyl-4-[4-(2-methyl-benzoylamino)-naphthalene-1-sulfonylamino]-piperidin-1-yl}-2-oxo-ethyl)-piperazine-1-carboxylic acid tert-butyl ester (C-134)

N-{4-[1-(2-Bromo-acetyl)-3-cis-methyl-piperidin-4-ylsulfamoyl]-naphthalen-1-yl}-2-methyl-benzamide (100 mg, 0.18 mM) was dissolved in a mixture of acetonitrile (1 mL) and water (0.25 mL). Potassium carbonate (37 mg, 0.27 mmol) was added followed by piperazine-1-carboxylic acid tert-butyl ester (37 mg, 0.2 mM). The reaction was stirred for 1 hour at room temperature before being passed through a plug of silica gel. Elution with ethyl acetate:methanol (90:10) afforded the titled compound (43 mg, 34%) as a yellow solid. $^1$H NMR (300 MHz, CD$_3$OD) (1:1 mixture of rotamers) δ 8.85 (d, 1H), 8.30 (d, 1H), 8.22 (d, 1H), 7.95 (d, 1H), 7.70 (m, 3H), 7.38 (m, 4H), 3.57 (m, 5H), 3.40 (m, 6H), 3.18 (m, 4H), 2.58 (s, 3H), 1.78 (m, 1H), 1.52 (m, 2H), 1.42 (s, 9H), 0.70 (d, 1.5H), 0.65 (d, 1.5H); LC/MS m/z 664 (M+H)⁺.

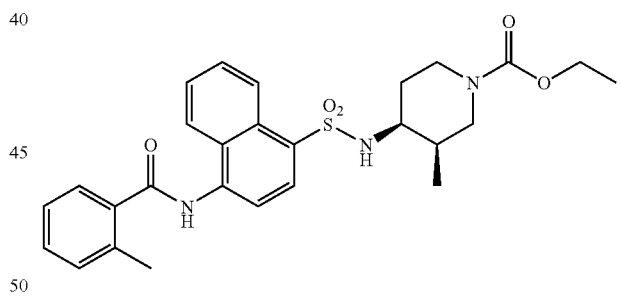

(±)-cis-3-Methyl-4-[4-(2-methyl-benzoylamino)-naphthalene-1-sulfonylamino]-piperidine-1-carboxylic acid ethyl ester (C-136)

The title compound was prepared from A-21 according to the general procedure in Scheme 7. To a solution of A-21 in ethyl acetate was added Pd(OH)$_2$ and diethyl pyrocarbonate (1.0 eq). The vessel was evacuated and pressurized to 50 psi H$_2$ and allowed to agitate on a Parr apparatus overnight. The solution was filtered through a celite plug, washed with hot ethyl acetate and concentrated at 40° C. at reduced pressure. The residue was purified using flash chromatography to provide the title compound. $^1$H NMR (300 MHz, DMSO) δ 10.63 (s, 1H), 8.77 (d, 1H), 8.28 (d, 1H), 8.21 (d, 1H), 8.12 (d, 1H), 7.97 (d, 1H), 7.74 (m, 3H), 7.45 (d, 1H), 7.38 (m, 2H), 3.98 (q, 2H), 3.38 (m, 1H), 3.29 (m, 1H), 3.21 (m, 3H), 2.52 (s, 3H), 1.67 (m, 1H), 1.30 (m, 2H), 1.13 (t, 3H), 0.57 (d, 3H); LC/MS m/z 508 (M−H)⁻, 510 (M+H)⁺

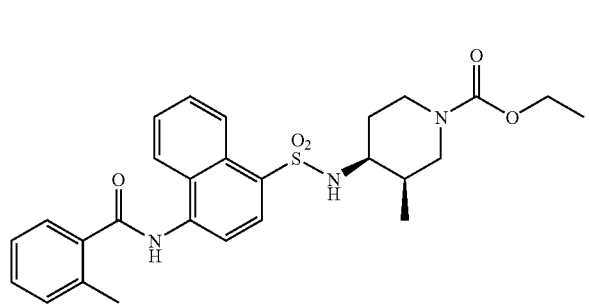

cis-3-Methyl-4-[4-(2-methyl-benzoylamino)-naphthalene-1-sulfonylamino]-piperidine-1-carboxylic acid ethyl ester (single enantiomer, absolute stereochemistry not determined) (C-137)

Compound C-136 was subjected to reverse phase chiral HPLC separation, and the title compound was the first enantiomer to elute from the column. ¹H NMR (300 MHz, DMSO) δ 8.70 (d, 1H), 8.42 (d, 1H), 8.34 (d, 1H), 8.11 (s, 1H), 7.93 (d, 1H), 7.63 (m, 3H), 7.42 (d, 1H), 7.34 (d, 2H), 4.64 (d, 1H), 4.05 (m, 2H), 3.48 (m, 0.5H), 3.38 (m, 1H), 3.21 (m, 2.5H), 2.59 (s, 3H), 1.74 (m, 1H), 1.48 (s, 1H), 1.43 (m, 2H), 1.19 (t, 3H), 0.66 (s, 3H. LC/MS m/z 508 (M−H)⁻, 510 (M+H)⁺

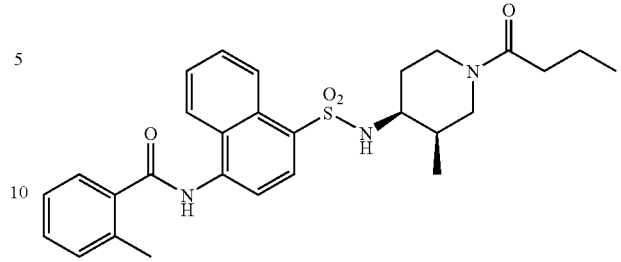

(±)-cis-N-[4-(1-Butryl-3-methyl-piperidin-4-ylsuffamoyl)-naphthalen-1-yl]-2-methyl-benzamide (C-139)

The title compound was prepared from A-21 according to the general procedure in Scheme 7. To a solution of A-21 in ethyl acetate was added Pd(OH)₂ and butyric anhydride (1.0 eq). The vessel was evacuated and pressurized to 50 psi H2 and allowed to agitate on a Parr apparatus overnight. The solution was filtered through a celite plug, washed with hot ethyl acetate and concentrated at 40° C. at reduced pressure. The residue was purified using flash chromatography to provide the title compound. ¹H NMR (300 MHz, DMSO) δ 8.75 (m, 1H), 8.32 (m, 3H), 7.95 (d, 1H), 7.63 (m, 3H), 7.43 (m, 1H), 7.33 (m, 2H), 5.20 (d, 1H), 3.63 (m, 0.5H), 3.40 (m, 2H), 3.20 (m, 2H), 3.01 (m, 0.5H), 2.57 (s, 3H), 2.19 (m, 2H), 1.82 (m, 0.5H), 1.67 (m, 0.5H), 1.56 (m, 3H), 1.30 (m 1H), 0.95 (dt, 3H), 0.73 (d, 0.5H), 0.59 (d, 0.5H). LC/MS m/z 506 (M−H)⁻, 508 (M+H)⁺

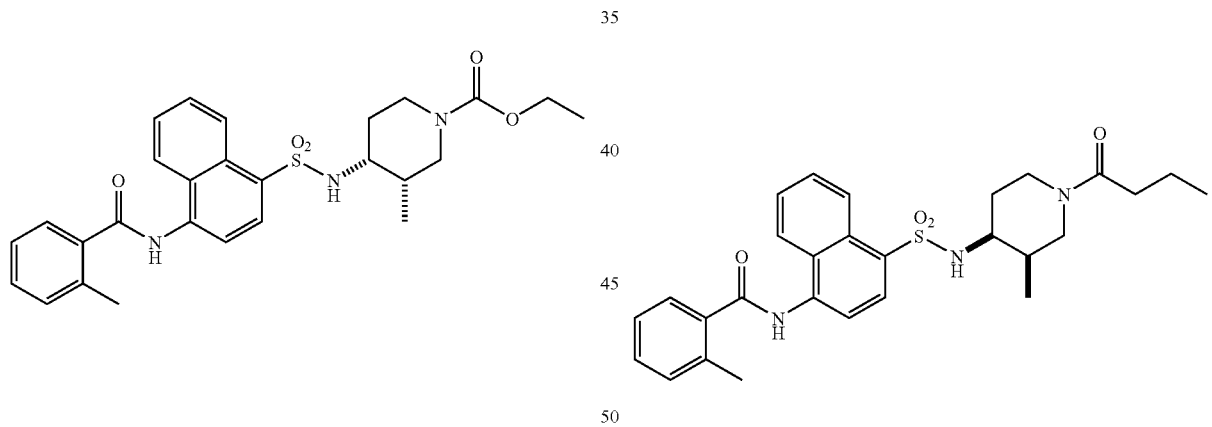

cis-3-Methyl-4-[4-(2-methyl-benzoylamino)-naphthalene-1-sulfonylamino]-piperidine-1-carboxylic acid ethyl ester (single enantiomer, absolute stereochemistry not determined) (C-138)

Compound C-136 was subjected to reverse phase chiral HPLC separation, and the title compound was the second enantiomer to elute from the column. ¹H NMR (300 MHz, DMSO) δ 8.70 (d, 1H), 8.42 (d, 1H), 8.34 (d, 1H), 8.11 (s, 1H), 7.93 (d, 1H), 7.63 (m, 3H), 7.42 (d, 1H), 7.34 (d, 2H), 4.64 (d, 1H), 4.05 (m, 2H), 3.48 (m, 0.5H), 3.38 (m, 1H), 3.21 (m, 2.5H), 2.59 (s, 3H), 1.74 (m, 1H), 1.48 (s, 1H), 1.43(m, 2H), 1.19 (t, 3H), 0.66 (s, 3H). LC/MS m/z 508 (M−H)⁻, 510 (M+H)⁺ cis-N-[4-(1-butyryl-3-methyl-piperidin-4-ylsulfamoyl)-naphthalen-1-yl]-2-methyl-benzamiide (C-140) (single enantiomer, absolute stereochemistry not determined)

Compound C-139 was subjected to reverse phase chiral HPLC separation, and the title compound was the first enantiomer to elute from the column. ¹H NMR (300 MHz, CDCl₃) δ 8.71 (m, 1H), 8.42 (d, 1H), 8.37 (d, 1H), 8.12 (s, 1H), 7.94 (d, 1H), 7.73 (m, 1H), 7.63 (m, 2H), 7.43 (m, 1H), 7.34 (d, 2H), 4.68 (m, 1H), 3.42-3.20 (m, 3H), 2.59 (s, 3H), 2.20 (m, 2H), 1.57 (m, 4H), 1.35 (m, 1H), 1.25 (m, 2H), 0.89 (m, 311), 0.74 (d, 1.5H), 0.55 (d, 1.5H). LC/MS m/z 506 (M−H)⁻, 508 (M+H)⁺

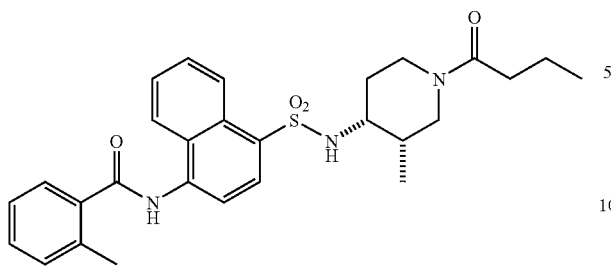

cis-N-[4-(1-butyryl-3-methyl-piperidin-4-ylsulfamoyl)-naphthalen-1-yl]-2-methyl-benzamide (C-141) (single enantiomer, absolute stereochemistry not determined)

Compound C-139 was subjected to reverse phase chiral HPLC separation, and the title compound was the second enantiomer to elute from the column. ¹H NMR (300 MHz, CDCl₃) δ 8.71 (m, 1H), 8.42 (d, 1H), 8.37 (d, 1H), 8.12 (s, 1H), 7.94 (d, 1H), 7.73 (m, 1H), 7.63 (m, 2H), 7.43 (m, 1H), 7.34 (d, 2H), 4.68 (m, 1H), 3.42-3.20 (m, 3H), 2.59 (s, 3H), 2.20 (m, 2H), 1.57 (m, 4H), 1.35 (m, 1H), 1.25 (m, 2H), 0.89 (m, 3H), 0.74 (d, 1.5H), 0.55 (d, 1.5H). LC/MS m/z 506 (M−H)⁻, 508 (M+H)⁺

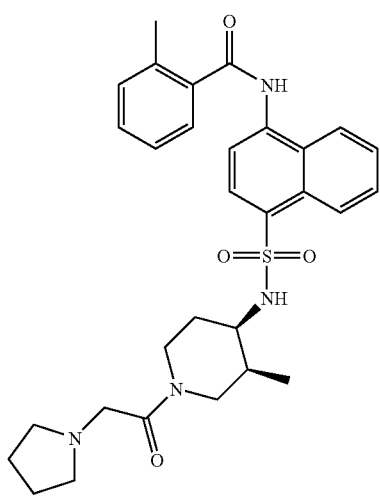

(±)-2-Methyl-N-{4-[cis-3-methyl-1-(2-pyrrolidin-1-yl-acetyl)-piperidin-4-ylsulfamoyl]-naphthalen-1-yl}-benzamide (C-142)

The title compound was prepared as shown in Scheme 7 for the preparation of C-134 except substituting pyrrolidine for piperazine-1-carboxylic acid tert-butyl ester. Reverse phase HPLC purification afforded the title compound as its formate salt. Wt.: 37 mg (38%). ¹H NMR (300 MHz, CD₃OD) (1:1 mixture of rotamers) δ 8.85 (d, 1H), 8.47 (s, 1H), 8.36 (d, 1H), 8.27 (d, 1H), 7.96 (d, 1H), 7.70 (m, 3H), 7.40 (m, 3H), 4.22 (m, 2H), 3.68 (m, 1H), 3.45 (m, 4H), 3.24 (m, 4H), 2.58 (s, 3H), 2.04 (m, 4H), 1.80 (m, 1H), 1.47 (m, 2H), 0.70 (d, 1.5H), 0.65 (d, 1.5H); LC/MS m/z 549 (M+H)⁺.

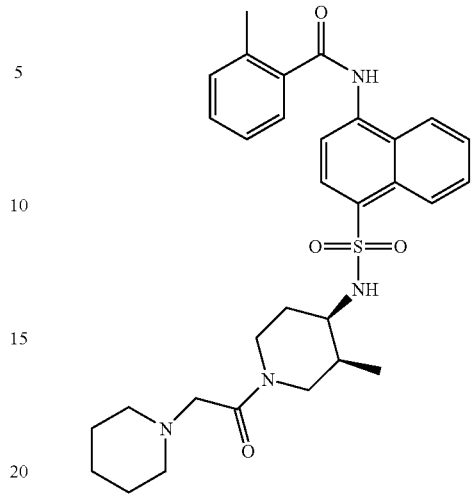

(±)-2-Methyl-N-{4-[cis-3-methyl-1-(2-piperidin-1-yl-acetyl)-piperidin-4-ylsulfamoyl]-naphthalen-1-yl}-benzamide (C-143)

The title compound was prepared as shown in Scheme 7 for the preparation of C-134 except substituting piperidine for piperazine-1-carboxylic acid tert-butyl ester. Reverse phase HPLC purification afforded the title compound as its formate salt. Wt.: 43 mg (43 %). ¹H NMR (300 MHz, CD₃OD) (1:1 mixture of rotamers) δ 8.85 (d, 1H), 8.33 (d, 2H), 8.25 (d, 1H), 7.95 (d, 1H), 7.70 (m, 3H), 7.40 (m, 3H), 4.04 (m, 2H), 3.63 (m, 1H), 3.45 (m, 4H), 3.20 (m, 4H), 2.56 (s, 3H), 1.88 (m, 6H), 1.67 (m, 2H), 1.45 (m, 1H), 0.70 (d, 1.5H), 0.64 (d, 1.5H); LC/MS m/z 563 (M+H)⁺.

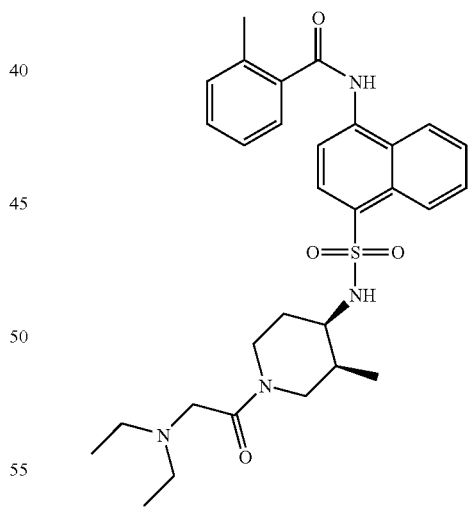

(±)-N-{4-[1-(2-diethylamino-acetyl)-3-cis-methyl-piperidin-4-ylsulfamoyl]-naphthalen-1-yl}-2-methyl-benzamide (C-144)

The title compound was prepared as shown in Scheme 7 for the preparation of C-134 except substituting diethylamine for piperazine-1-carboxylic acid tert-butyl ester. Reverse phase HPLC purification afforded the title compound as its formate salt. Wt.: 49 mg (50%). ¹H NMR (300 MHz, CD₃OD) (1:1 mixture of rotamers) δ 8.85 (d, 1H), 8.46 (s, 1H), 8.38 (d, 1H), 8.28 (d, 1H), 7.95 (d, 1H), 7.70 (m, 3H), 7.40 (m, 3H), 4.16 (m, 2H), 3.65 (m, 1H), 3.44 (m, 4H), 3.19 (m, 4H), 2.56 (s, 3H), 1.80 (m, 1H), 1.52 (m, 2H), 1.25 (t, 6H), 0.70 (d, 1.5H), 0.64 (d, 1.5H); LC/MS m/z 551 (M+H)+.

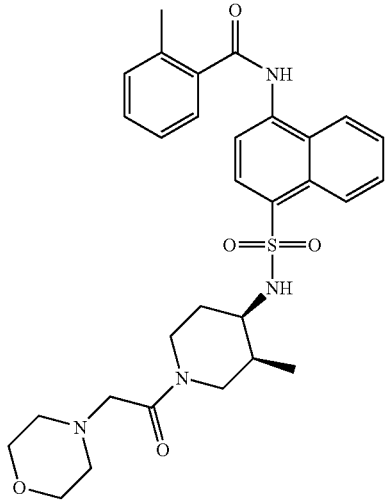

(±)-2-Methyl-N-{4-[3-cis-methyl-1-(2-morpholin-4-yl-acetyl)-piperidin-4-ylsulfamoyl]-naphthalen-1-yl}-benzamide (C-145)

The title compound was prepared as shown in Scheme 7 for the preparation of C-134 except substituting morpholine for piperazine-1-carboxylic acid tert-butyl ester. Wt.: 60 mg (58%). $^1$H NMR (300 MHz, CD$_3$OD) (1:1 mixture of rotamers) δ 8.88 (d, 1H), 8.38 (d, 1H), 8.32 (d, 1H), 8.00 (d, 1H), 7.80 (m, 3H), 7.45 (m, 3H), 4.26 (m, 2H), 4.06 (m, 2H), 3.86 (m, 3H), 3.50 (m, 4H), 3.24 (m, 3H), 2.60 (s, 3H), 1.85 (m, 1H), 1.55 (m, 2H), 0.76 (d, 1.5H), 0.69 (d, 1.5H); LC/MS m/z 565 (M+H)+.

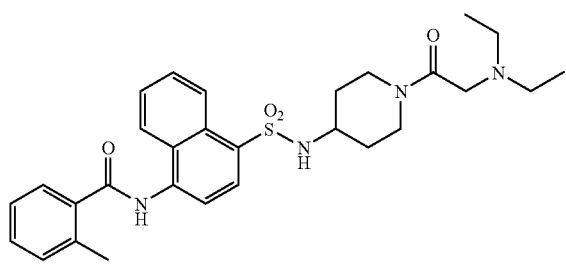

N-{4-[1-(2-Diethylamino-acetyl)-piperidin-4-ylsulfamoyl]-naphthalen-1-yl}-2-methyl-benzamide (C-146)

The title compound was prepared following the general procedure for preparing C-134 in Scheme 7, substituting 4-amino-piperidine-1-carboxylic acid tert-butyl ester for 1-benzyl-3-methyl-piperidin-4-ylamine, and diethyl amine for piperazine-1-carboxylic acid tert-butyl ester. $^1$H NMR (300 MHz, DMSO) δ 10.66 (s, 1H), 9.08 (m, 1H), 8.69 (d, 1H), 8.27 (d, 1H), 8.22 (t, 2H), 7.94 (d, 1H), 7.70 (m, 3H), 7.42 (m, 1H), 7.35 (m, 2H), 4.27-4.02 (m, 2H), 4.03 (d, 1H), 3.40 (m, 3H), 2.98 (m, 3H), 2.83 (m, 1H), 2.56 (s, 3H), 1.92 (m,5 H), 1.58 (m, 2H), 1.30 (m, 2H), 1.11 (t, 2H). LC/MS m/z 536 (M−H)−, 538 (M+H)+

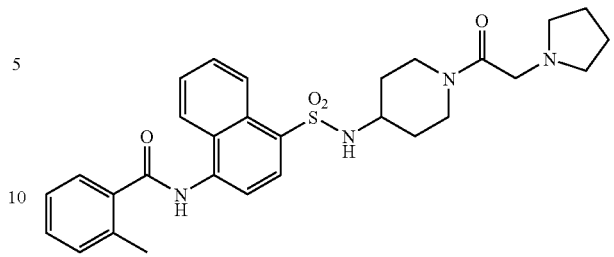

2-Methyl-N-{4-[1-(2-pyrrolidin-1-yl-acetyl)-piperidin-4-ylsulfamoyl]-naphthalen-1-yl}-benzamide (C-147)

The title compound was prepared following the general procedure for preparing C-134 in Scheme 7, substituting 4-amino-piperidine-1-carboxylic acid tert-butyl ester for 1-benzyl-3-methyl-piperidin-4-ylamine, and pyrrole for piperazine-1-carboxylic acid tert-butyl ester. $^1$H NMR (300 MHz, DMSO) δ 10.56 (s, 1H), 9.28 (m, 1H), 8.68 (d, 1H), 8.27 (d, 1H), 8.21 (m, 2H), 7.94 (d, 1H), 7.72 (m, 3H), 7.43 (d, 1H), 7.38 (m, 2H), 4.31 (m, 2H), 4.03 (d, 1H), 3.27 (m, 2H), 2.98 (m, 3H), 2.83 (m, 1H), 2.56 (s, 3H), 1.92 (m, 5H), 1.58 (m, 2H), 1.3 (m, 2H). LC/MS m/z 534 (M−H)−, 535 (M+H)+

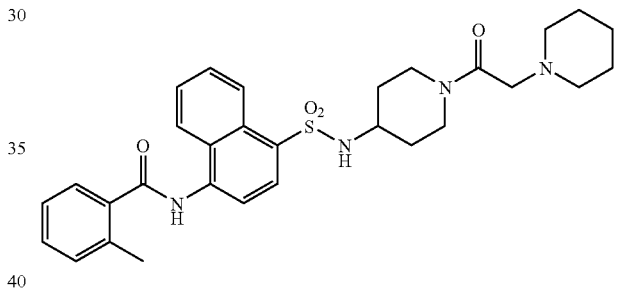

2-Methyl-N-{4-[1-(2-piperidin-1-yl-acetyl)-piperidin-4-ylsulfamoyl]-naphthalen-1-yl}-benzamide (C-148)

The title compound was prepared following the general procedure for preparing C-134 in Scheme 7, substituting 4-amino-piperidine-1-carboxylic acid tert-butyl ester for 1-benzyl-3-methyl-piperidin-4-ylamine, and substituting piperidine for piperazine-1-carboxylic acid tert-butyl ester. $^1$H NMR (300 MHz, DMSO) δ 10.56 (s, 1H), 9.28 (m, 1H), 8.68 (d, 1H), 8.27 (d, 1H), 8.21 (m, 2H), 7.94 (d, 1H), 7.72 (m, 3H), 7.43 (d, 1H), 7.38 (m, 2H), 4.15 (m, 3H), 3.36 (m, 3H), 2.99 (m, 1H), 2.80 (m, 3H), 2.56 (s, 3H), 1.74 (m, 3H), 1.58 (m, 4H), 1.27 (m, 3H). LC/MS m/z 548 (M−H)−, 549 (M+H)+

Scheme 8

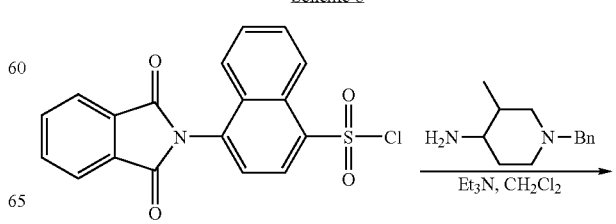

-continued

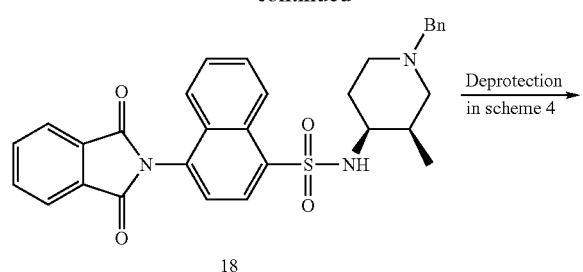

18

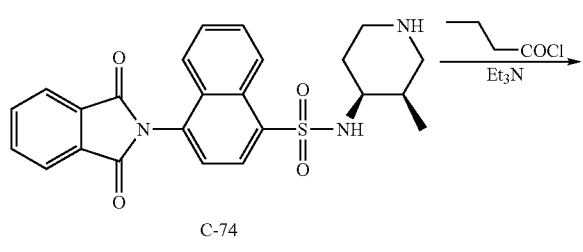

C-74

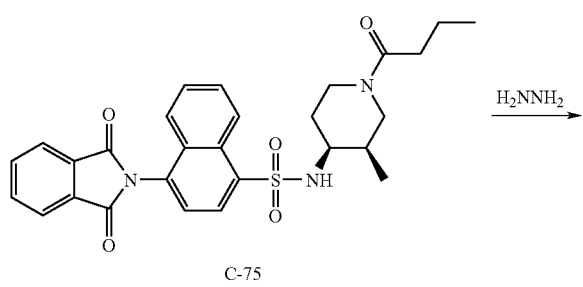

C-75

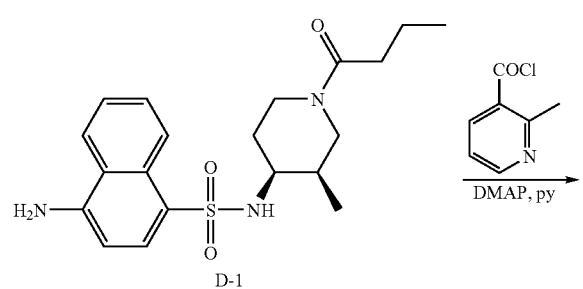

D-1

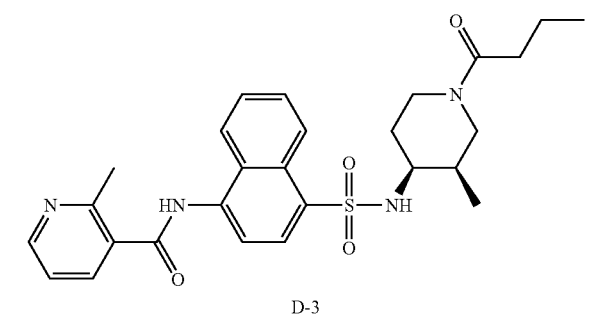

D-3

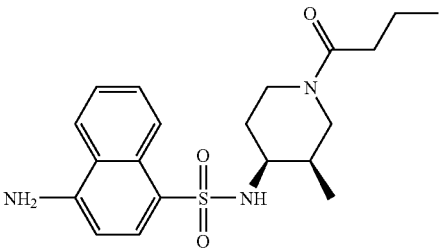

(±)-(cis)-4-Amino-naphthalene-1-sulfonic acid (1-butyryl-3-methyl-piperidin-4-yl)-amide (D-1)

(±)-cis-N-[4-(1-Benzyl-3-methyl-piperidin-4-ylsulfamoyl)-naphthalen-1-yl]-2-methyl-benzamide (18) was prepared as described previously according to the general procedure in Scheme 3, substituting 1-benzyl-3-methyl-piperidin-4-ylamine for p-anisidine. (±)-(cis)4-(1,3-Dioxo-1,3-dihydro-isoindol-2-yl)-naphthalene-1-sulfonic acid (3-methyl-piperidin-4-yl)-amide (C-74) and (±)-(cis)4-(1,3-dioxo-1,3-dihydro-isoindol-2-yl)-naphthalene-1-sulfonic acid (1-butyryl-3-methyl-piperidin-4-yl)-amide (C-75) were prepared as described previously according to the general procedure in Scheme 5. The title compound was made following general procedure in Scheme 3, substituting (±)-(cis)-4-(1,3-dioxo-1,3-dihydro-isoindol-2-yl)-naphthalene-1-sulfonic acid (1-butyryl-3-methyl-piperidin-4-yl)-amide (C-75) for 4-(1,3-dioxo-1,3-dihydro-isoindol-2-yl)-naphthalene-1-sulfonic acid (4-methoxy-phenyl)-amide (A-2). $^1$H NMR (300 MHz, MeOD) δ 8.62 (d, 1H), 8.30 (d, 1H), 7.98 (d, 1H), 7.60 (dt, 1H), 7.48 (dt, 1H), 6.70 (d, 1H), 3.66 (m, 1H), 3.42 (m, 1H), 3.28 (m, 5H), 2.25 (m, 2H), 1.67 (m, 1H), 1.50 (m, 2H), 1.30 (m, 2H), 0.88 (t, 3H), 0.64 (m, 3H); LC/MS m/z 391 (M+H)$^+$

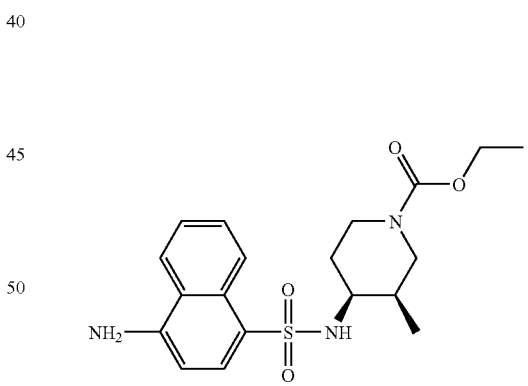

(±)-(cis)-4-(4-Amino-naphthalene-1-sulfonylamino)-3-methyl-piperidine-1-carboxylic acid ethyl ester (D-2)

The title compound was made following general procedure in Scheme 8, substituting ethyl chloroformate for butyryl chloride. $^1$H NMR (300 MHz, MeOD) δ 8.61 (d, 1H), 8.10 (d, 1H), 7.97 (d, 1H), 7.60 (t, 1H), 7.48 (t, 1H), 6.70 (d, 1H), 4.02 (q, 2H), 3.47 (m, 1H), 3.24 (m, 4H), 1.64 (m, 1H), 1.38 (m, 1H), 1.25 (m, 1H), 1.17 (t, 3H), 0.64 (d, 3H); LC/MS m/z 393 (M+H)$^+$

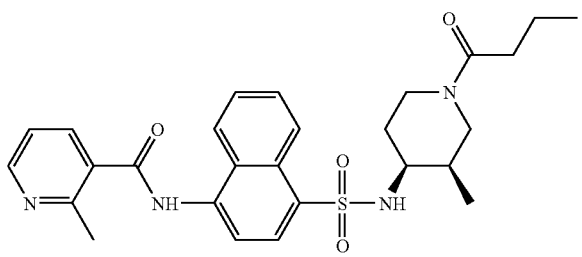

(±)-(cis)-N-[4-(1-Butyryl-3-methyl-piperidin-4-ylsulfamoyl)-naphthalen-1-yl]-2-methyl-nicotinamide (D-3)

To a solution of naphthalenyl amine (D-1) (78 mg, 0.2 mmol) in $CH_2Cl_2$ (3 mL) was added acetyl chloride (20 uL, 0.24 mmol) and $Et_3N$ (60 uL, 0.4 mmol). The resultant solution was stirred at 25° C. overnight. The solvent was removed in vacuo and the residue was purified using HPLC to give the title compound. $^1$H NMR (300 MHz, MeOD) δ 8.84 (d, 1H), 8.57 (dd, 1H), 8.31 (d, 1H), 8.24 (d, 1H), 8.11 (m, 1H), 7.98 (m, 1H), 7.72 (m, 2H), 7.43 (dd, 1H), 3.40 (m, 5H), 2.75 (s, 3H), 2.25 (m, 2H), 1.50 (m, 5H), 0.90 (t, 3H), 0.65 (dd, 3H); LC/MS m/z 510 (M+H)$^+$

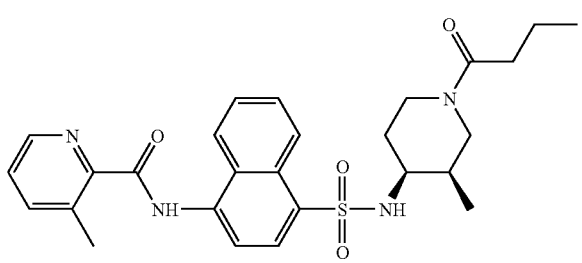

(±)-(cis)-3-Methyl-pyridine-2-carboxylic acid [4-(1-butyryl-3-methyl-piperidin-4-ylsulfamoyl)-naphthalen-1-yl]-amide (D-4)

The title compound was made following general procedure in Scheme 8, substituting 3-methyl-pyridine-2-carbonyl chloride for 2-methyl-nicotinoyl chloride. $^1$H NMR (300 MHz, MeOD) δ 8.83 (m, 1H), 8.59 (d, 1H), 8.28 (m, 3H), 7.74 (m, 3H), 7.53 (dd, 1H), 3.40 (m, 5H), 2.75 (s, 3H), 2.25 (m, 2H), 1.50 (m, 5H), 0.95 (t, 3H), 0.80 (dd, 3H); LC/MS m/z 510 (M+H)$^+$

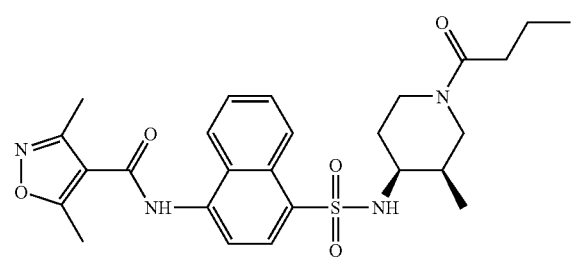

(±)-(cis)-3,5-Dimethyl-isoxazole-4-carboxylic acid [4-(1-butyryl-3-methyl-piperidin-4-ylsulfamoyl)-naphthalen-1-yl]-amide (D)-5)

The title compound was made following general procedure in Scheme 8, substituting 3,5-dimethyl-isoxazole-4-carbonyl chloride for 2-methyl-nicotinoyl chloride. $^1$H NMR (300 MHz, MeOD) δ 8.82 (d, 1H1), 8.28 (d, 1H1), 8.18 (d, 1H1), 7.93 (d, 1H1), 7.71 (m, 211), 3.34 (m, 5H), 2.70 (s, 3H), 2.47 (s, 3H), 2.25 (m, 211), 1.50 (m, 5H), 0.89 (t, 3H), 0.63 (dd, 3H); LC/MS m/z 514 (M+H)$^+$

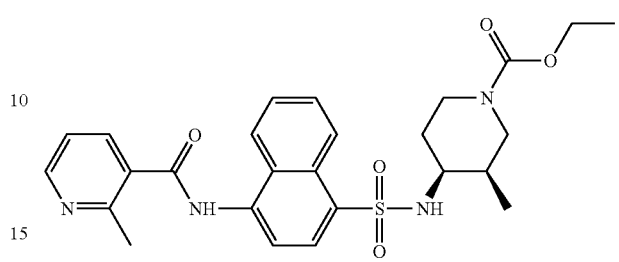

(±)-(cis)-3-Methyl-4-{4-[(2-methyl-pyridine-3-carbonyl)-amino]-naphthalene-1-sulfonylamino}-piperidine-1-carboxylic acid ethyl ester (D-6)

The title compound was made following general procedure in Scheme 8, substituting (±)-(cis)4-(4-amino-naphthalene-1-sulfonylamino)-3-methyl-piperidine-1-carboxylic acid ethyl ester (D-2) for (±)-(cis)-4-amino-naphthalene-1-sulfonic acid (1-butyryl-3-methyl-piperidin-4-yl)-amide (D-1). $^1$H NMR (300 MHz, MeOD) δ 8.83 (d, 1H), 8.56 (dd, 1H), 8.31 (d, 1H), 8.23 (d, 1H), 8.12 (d, 1H), 7.97 (d, lH),7.71 (m, 2H), 7.43 (dd, 1H), 4.03 (q, 2H), 3.48 (m, 1H), 3.28 (m, 4H), 2.75 (s, 3H), 1.68 (m, 1H), 1.40 (m, 1H), 1.29 (m, 1H), 1.18 (t, 3H), 0.64 (d, 3H); LC/MS m/z 512 (M+H)$^+$

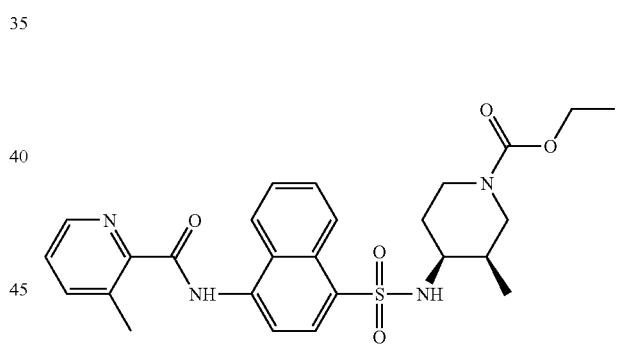

(±)-(cis)-3-Methyl-4-{4-[(3-methyl-pyridine-2-carbonyl)-amino]-naphthalene-1-sulfonylamino}-piperidine-1-carboxylic acid ethyl ester (D-7)

The title compound was made following general procedure in Scheme 8, substituting (±)-(cis)4-(4-amino-naphthalene-1-sulfonylamino)-3-methyl-piperidine-1-carboxylic acid ethyl ester (D-2) for (±)-(cis)4-amino-naphthalene-1-sulfonic acid (1-butyryl-3-methyl-piperidin-4-yl)-amide (D-1), and substituting 3-methyl-pyridine-2-carbonyl chloride for 2-methyl-nicotinoyl chloride. $^1$H NMR (300 MHz, MeOD) δ 8.82 (m, 1H), 8.56 (d, 1H), 8.28 (m, 1H), 8.18 (m, 1H), 7.74 (m, 3H), 7.59 (dd, 1H), 4.02 (q, 2H), 3.48 (m, 1H), 3.28 (m, 4H), 2.73 (s, 3H), 1.68 (m, 1H), 1.40 (m, 1H), 1.28 (m, 1H), 1.17 (t, 3H), 0.63 (d, 3H); LC/MS m/z 512 (M+H)$^+$

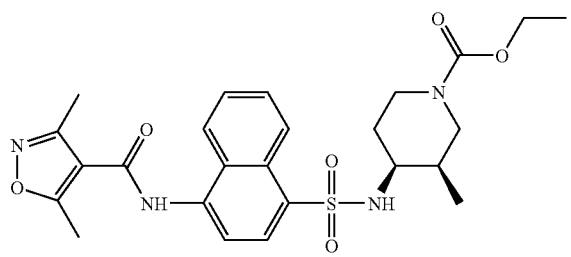

(±)-cis-4-{4-[(3,5-Dimethyl-isoxazole-4-carbonyl)-amino]-naphthalene-1-sulfonylamino}-3-methyl-piperidine-1-carboxylic acid ethyl ester (D-8)

The title compound was made following general procedure in Scheme 8, substituting (±)-(cis)4-(4-amino-naphthalene-1-sulfonylamino)-3-methyl-piperidine-1-carboxylic acid ethyl ester (D-2) for (±)-(cis)-4-amino-naphthalene-1-sulfonic acid (1-butyryl-3-methyl-piperidin-4-yl)-amide (D-1) and substituting 3,5-dimethyl-isoxazole-4-carbonyl chloride for 2-methyl-nicotinoyl chloride. $^1$H NMR (300 MHz, MeOD) δ 8.82 (d, 1H), 8.27 (d, 1H), 8.18 (d, 1H), 7.93 (d, 1H), 7.71 (m, 2H), 4.03 (q, 2H), 3.30 (m, 5H), 2.70 (s, 3H), 2.47 (s, 3H), 1.68 (m, 1H), 1.40 (m, 1H), 1.28 (m, 1H), 1.18 (t, 3H), 0.64 (d, 3H); LC/MS m/z 516 (M+H)$^+$

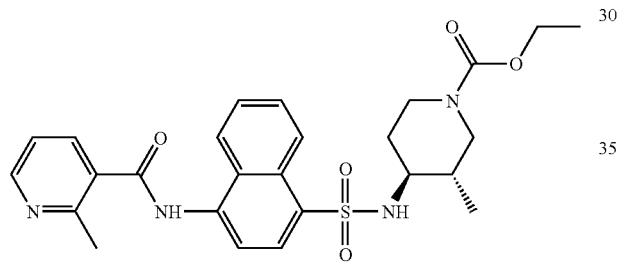

(±)-(trans)-3-Methyl-4-{4-[(2-methyl-pyridine-3-carbonyl)-amino]-naphthalene-1-sulfonylamino}-piperidine-1-carboxylic acid ethyl ester (D-9)

The title compound was made following general procedure in Scheme 8, substituting (±)-(trans)-4-(4-aamino-naphthalene-1-sulfonylamino)-3-methyl-piperidine-1-carboxylic acid ethyl ester for (±)-(cis)-4-amino-naphthalene-1-sulfonic acid (1-butyryl-3-methyl-piperidin-4-yl)-amide (D-1). $^1$H NMR (300 MHz, MeOD) δ 8.78 (d, 1H), 8.58 (dd, 1H), 8.32 (d, 1H), 8.23 (d, 1H), 8.12 (d, 1H), 7.98 (d, 1H), 7.72 (m, 2H), 7.44 (dd, 1H), 4.04 (q, 2H), 3.88 (m, 2H), 3.28 (m, 1H), 2.82 (m, 1H), 2.75 (s, 3H), 2.65 (m, 1H), 2.38 (s, br, 1H), 1.40 (m, 2H), 1.18 (t, 3H), 0.57 (d, 3H); LC/MS m/z 512 (M+H)$^+$

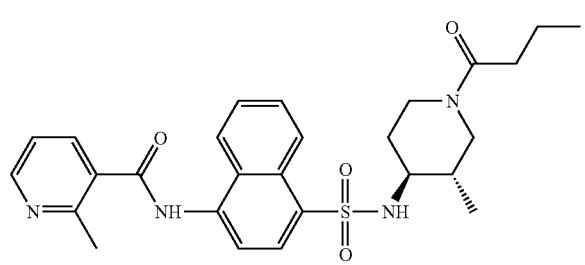

(±)-(trans)-N-[4-(1-Butyryl-3-methyl-piperidin-4-ylsulfamoyl)-naphthalen-1-yl]-2-methyl-nicotinamide (D-10)

The title compound was made following general procedure in Scheme 8, substituting (±)-(trans)-4-amino-naphthalene-1-sulfonic acid (1-butyryl-3-methyl-piperidin-4-yl)-amide for (±)-(cis)-4-amino-naphthalene-1-sulfonic acid (1-butyryl-3-methyl-piperidin-4-yl)-amide (D-1). $^1$H NMR (300 MHz, MeOD) δ 8.78 (d, 1H), 8.57 (dd, 1H), 8.31 (d, 1H), 8.23 (d, 1H), 8.12 (d, 1H), 7.98 (d, 1H), 7.72 (m, 2H), 7.42 (dd, 1H), 4.28 (t, 1H), 3.72 (m, 1H), 2.90 (m, 1H), 2.74 (s, 3H), 2.56 (m, 1H), 2.23 (m, 3H), 1.53 (m, 3H), 1.28 (m, 2H), 0.89 (m, 3H), 0.61 (dd, 3H); LC/MS m/z 510 (M+H)$^+$ Scheme 9

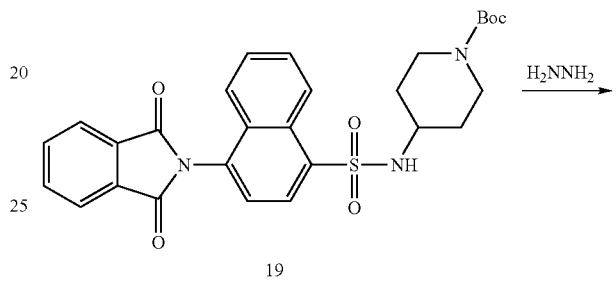

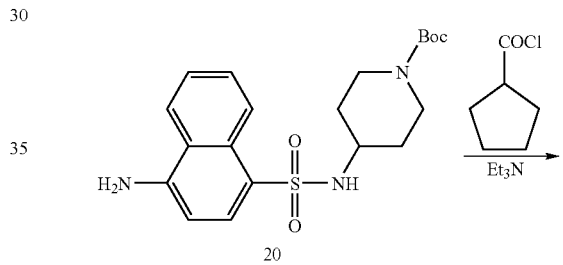

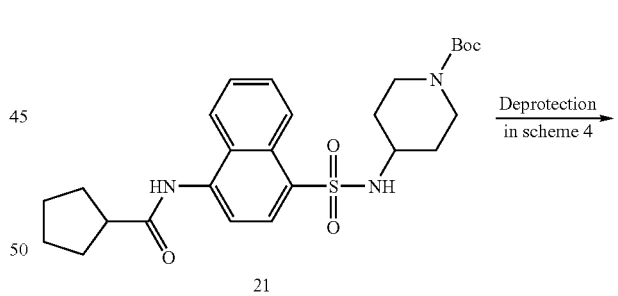

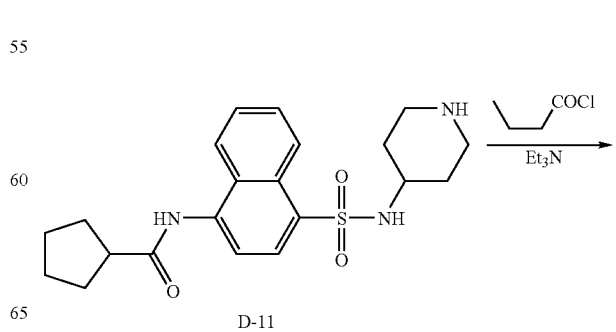

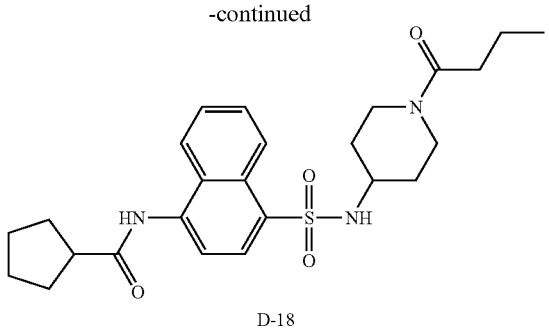

D-18

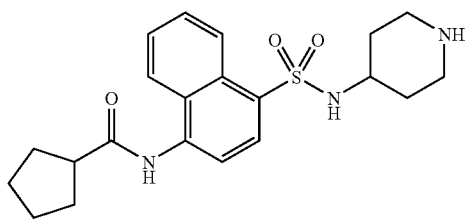

Cyclopentanecarboxylic acid [4-(piperidin-4-ylsulfamoyl)-naphthalen-1-yl]-amide (D-11)

4-[4-(1,3-Dioxo-1,3-dihydro-isoindol-2-yl)-naphthalene-1-sulfonylamino]-piperidine-1-carboxylic acid tert-butyl ester (19) was prepared according to the general procedure in Scheme 3, substituting 4-amino-piperidine-1-carboxylic acid tert-butyl ester for p-anisidine.

4-(4-Amino-naphthalene-1-sulfonylamino)-piperidine-1-carboxylic acid tert-butyl ester (20) was prepared according to the general procedure in Scheme 3 substituting 4-[4-(1,3-dioxo-1,3-dihydro-isoindol-2-yl)-naphthalene-1-sulfonylamino]-piperidine-1-carboxylic acid tert-butyl ester for 4-(1,3-dioxo-1,3-dihydro-isoindol-2-yl)-naphthalene-1-sulfonic acid (4-methoxyphenyl)-amide.

4-[4-(Cyclopentanecarbonyl-amino)-naphthalene-1-sulfonylaamino]-piperidine-1-carboxylic acid tert-butyl ester (21) was prepared according to the general procedure in Scheme 3, substituting cyclopentanecarbonyl chloride for acetyl chloride.

The title compound (D-11) was prepared according to Scheme 9 by following the general deprotection strategy in Scheme 4-1. $^1$H NMR (300 MHz, DMSO) δ 10.15 (s, 1H), 8.66 (m, 1H), 8.58 (m, 1H), 8.41 (m, 1H), 8.26 (m, 2H), 8.12 (d, 1H), 7.94 (d, 1H), 7.71 (m, 2H), 3.11 (m, 3H), 2.82 (m, 2H), 1.94 (m, 2H), 1.86-1.40 (m, 1OH). LC/MS m/z 400 (M−H)$^-$, 402 (M+H)$^+$

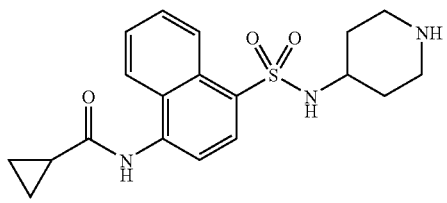

Cyclopropanecarboxylic acid [4-(piperidin-4-ylsulfamoyl)-naphthalen-1-yl]-amide (D-12

The title compound was made following the general procedure in Scheme 9, substituting cyclopropanecarbonyl chloride for cyclopentanecarbonyl chloride. $^1$H NMR (300 MHz, DMSO) δ 10.49 (s, 1H), 8.67 (m, 1H), 8.54 (m, 1H), 8.39 (m, 1H), 8.26 (d, 1H), 8.11 (d, 1H), 8.01 (d, 1H), 7.73 (m, 2H), 3.56 (s, 1H), 3.05 (m, 2H), 2.79 (m, 2H), 2.19 (m, 1H), 1.60 (m, 2H), 1.50 (m, 2H), 0.87 (d, 4H). LC/MS m/z 372 (M−H)$^-$, 374 (M+H)$^+$

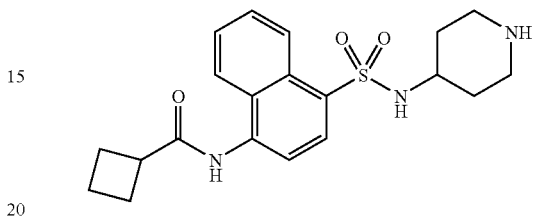

Cyclobutanecarboxylic acid [4-(piperidin-4-ylsulfamoyl)-naphthalen-1-yl]-amide (D-13)

The title compound was made following the general procedure in Scheme 9, substituting cyclobutanecarbonyl chloride for cyclopentanecarbonyl chloride. $^1$H NMR (300 MHz, DMSO) δ 9.98 (s, 1H), 8.62 (d, 1H), 8.21 (d, 1H), 8.12 (d, 1H), 7.99 (d, 1H), 7.95 (d, 1H), 7.70 (m, 2H), 3.59 (d, 2H), 3.51 (t, 1H), 3.13 (m, 1H), 2.67 (m, 2H), 2.32-2.16 (m, 4H), 1.99 (m, 1H), 1.84 (m, 1H), 1.37 (d, 2H), 1.10 (m, 2H). LC/MS m/z 386 (M−H)$^-$, 388 (M+H)$^+$

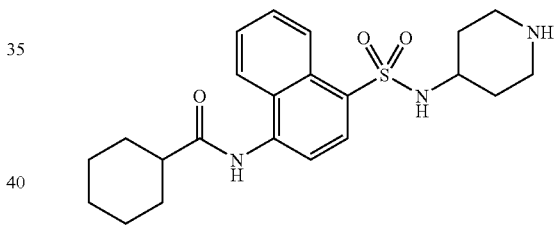

Cyclohexanecarboxylic acid [4-(piperidin-4-ylsulfamoyl)-naphthalen-1-yl]-amide (D-14)

The title compound was made following the general procedure in Scheme 9, substituting cyclohexanecarbonyl chloride for cyclopentanecarbonyl chloride. $^1$H NMR (300 MHz, DMSO) δ 10.07 (s, 1H), 8.64 (dd, 1H), 8.25 (m,4 H), 8.12 (d, 1H), 7.96 (d, 1H), 7.72 (m, 2H), 3.06 (m, 2H), 2.81 (m, 2H), 2.66 (m, 2H), 1.91 (d, 2H), 1.78 (d, 2H), 1.61 (m, 3H), 1.49 (m, 4H), 1.31 (m, 2H). LC/MS m/z 415 (M−H)$^-$, 417 (M+H)$^+$

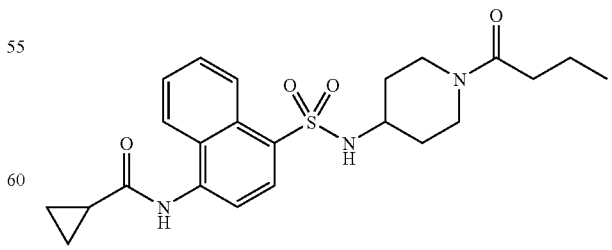

Cyclopropanecarboxylic acid [4-(1-butyryl-piperidin-4-ylsulfamoyl)-naphthalen-1-yl]-amide (D-15)

The title compound was made following the general procedure in Scheme 9, substituting cyclopropanecarbonyl chloride for cyclopentanecarbonyl chloride. $^1$H NMR (300 MHz, DMSO) δ 10.43 (s, 1H), 8.64 (m, 1H), 8.33 (m, 1H), 8.13 (m, 1H), 8.02 (d, 1H), 7.97 (m, 2H), 3.98 (d, 1H), 3.59 (m, 1H), 3.19 (m, 1H), 2.90 (t, 1H), 2.61 (m, 1H), 2.13 (m, 3H), 1.40 (m, 4H), 1.16 (m, 2H), 0.84 (d, 4H), 0.80 (t, 3H). LC/MS m/z 442 (M−H)$^−$, 444 (M+H)$^+$

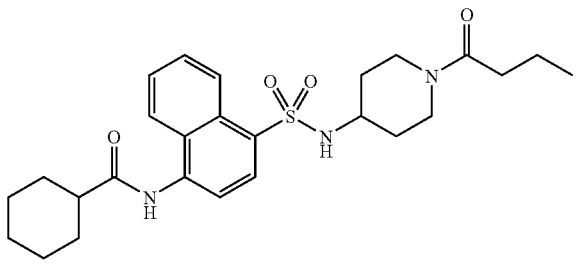

Cyclohexanecarboxylic acid [4-(1-butyryl-piperidin-4-yl-sulfamoyl)-naphthalen-1-yl]-amide (D-16)

The title compound was made following the general procedure in Scheme 9, substituting cyclohexanecarbonyl chloride for cyclopentanecarbonyl chloride. $^1$H NMR (300 MHz, DMSO) δ 10.05 (s, 1H), 8.64 (dd, 1H), 8.25 (dd, 1H), 8.13 (d, 1H), 8.03 (d, 1H), 7.91 (d, 1H), 7.71 (m, 2H), 3.98 (d, 1H), 3.59 (d, 1H), 3.18 (m, 1H), 2.91 (t, 1H), 2.61 (t, 1H), 2.16 (t, 2H), 1.90 (d, 2H), 1.77 (m, 2H), 1.67 (m, 2H), 1.49-1.20 (m, 9H), 0.81 (t, 3H). LC/MS m/z 529 (M−H)$^−$, 531 (M+H)$^+$

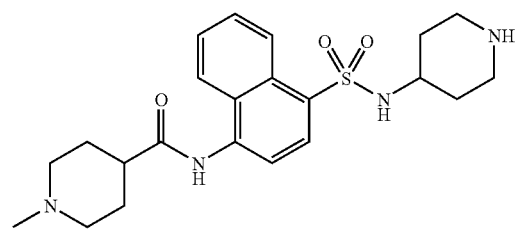

1-Methyl-piperidine-4-carboxylic acid [4-(piperidin-4-yl-sulfamoyl)-naphthalen-1-yl]-amide (D-17)

The title compound was made following general procedure in Scheme 9, substituting 1-methyl-piperidine-4-carbonyl chloride (prepared in situ from the corresponding acid using oxalyl chloride) for cyclopentanecarbonyl chloride. $^1$H NMR (300 MHz, DMSO) δ 10.39 (s, 1H), 8.64 (dd, 1H), 8.29 (dd, 1H), 8.14 (d, 1H), 8.05 (d, 1H), 7.89 (d, 1H), 7.72 (m, 2H), 3.62 (d, 2H), 3.40 (m, 2H), 3.15 (m, 1H), 2.95 (m, 2H), 2.78-2.67 (m, 6H), 2.09 (m, 2H), 2.00 (m, 2H), 1.84 (m, 1H), 1.39 (m, 1H), 1.18 (m, 2H). LC/MS m/z 384 (M−H)$^−$, 386 (M+H)$^+$ Cyclopentanecarboxylic acid [4-(1-butyryl-piperidin-4-ylsulfamoyl)-naphthalen-1-yl]-amide (D-18)

The title compound was made following the general procedure in Scheme 9. $^1$H NMR (300 MHz, DMSO) δ 10.12 (s, 1H), 8.66 (m, 1H), 8.28 (m, 1H), 8.13 (d, 1H), 7.95 (d, 1H), 7.71 (m, 2H), 3.98 (d, 1H), 3.59 (d, 11H), 3.19 (m, 1H), 3.09 (m, 1H), 2.90 (m, 1H), 2.57 (m, 1H), 2.16 (t, 2H), 1.94 (m, 2H), 1.81 (m, 2H), 1.71 (m, 2H), 1.62 (m, 2H), 1.42 (m, 4H), 1.16 (m, 2H), 0.81 (t, 3H). LC/MS m/z 471 (M−H)$^−$, 473 (M+H)$^+$

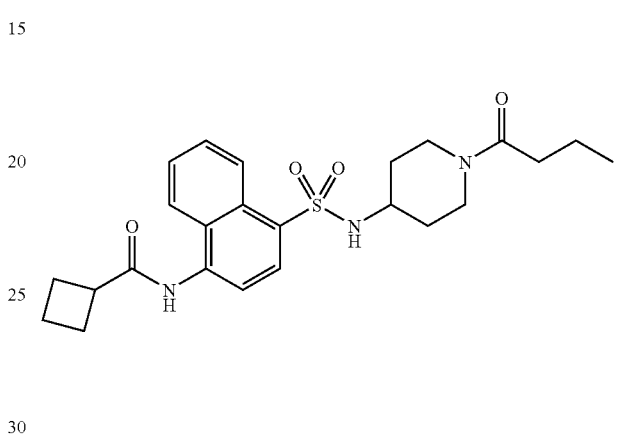

Cyclobutanecarboxylic acid [4-(1-butyryl-piperidin-4-yl-sulfamoyl)-naphthalen-1-yl]-amide (D-19)

The title compound was made following the general procedure in Scheme 9, substituting cyclobutanecarbonyl chloride for cyclopentanecarbonyl chloride. $^1$H NM (300 MHz, DMSO) δ 9.98 (s, 1H), 8.62 (d, 1H), 8.21 (d, 1H), 8.12 (d, 1H), 7.99 (d, 1H), 7.95 (d, 1H), 7.70 (m, 2H), 3.59 (d, 2H), 3.51 (t, 1H), 3.13 (m, 1H), 2.67 (m, 2H), 2.32-2.16 (m, 4H), 2.16 (t, 2H), 1.99 (m, 1H), 1.84 (m, 1H), 1.42 (m, 2H), 1.37 (d, 2H), 1.10 (m, 2H), 0.81 (t, 3H). LC/MS m/z 457 (M−H)$^−$, 459 (M+H)$^+$

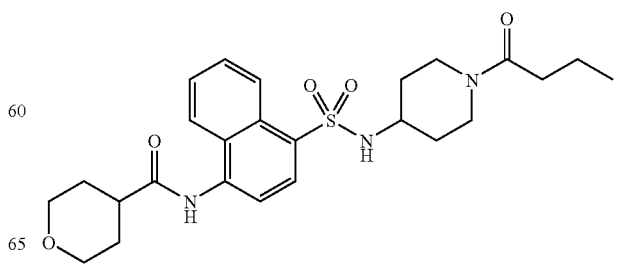

Tetrahydro-pyran-4-carboxylic acid [4-(1-butyryl-piperidin-4-ylsulfamoyl)-naphthalen-1-yl]-amide (D-20)

The title compound was made following the general procedure in Scheme 9, substituting tetrahydro-pyran-4-carbonyl chloride (prepared in situ from the corresponding acid using oxalyl chloride) for cyclopentanecarbonyl chloride. LC/MS m/z 488 (M+H)+

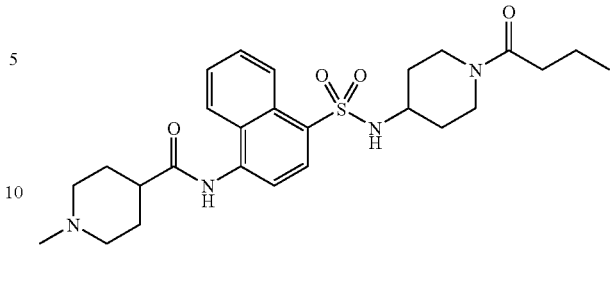

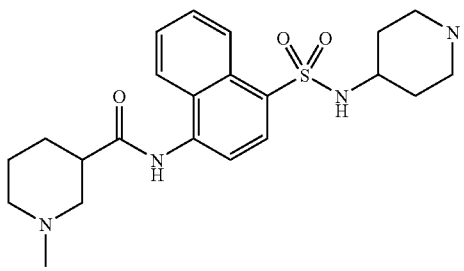

1-Methyl-piperidine-3-carboxylic acid [4-(piperidin-4-ylsulfamoyl)-naphthalen-1-yl]-amide (D-22)

The title compound was made following the general procedure in Scheme 9, substituting 1-methyl-piperidine-3-carbonyl chloride (prepared in situ from the corresponding acid using oxalyl chloride) for cyclopentanecarbonyl chloride. LC/MS m/z 431 (M+H)+.

1-Methyl-piperidine-4-carboxylic acid [4-(1-butyryl-piperidin-4-ylsulfamoyl)-naphthalen-1-yl]-amide (D-24)

The title compound was made following the general procedure in Scheme 9, substituting 1-methyl-piperidine-4-carbonyl chloride (prepared in situ from the corresponding acid using oxalyl chloride) for cyclopentanecarbonyl chloride. $^1$H NMR (300 MHz, DMSO) δ 10.39 (s, 1H), 8.64 (dd, 1H), 8.29 (dd, 1H), 8.14 (d, 1H), 8.05 (d, 1H), 7.891 (d, 1H), 7.72 (m, 2H), 3.62 (d, 2H), 3.40 (m, 2H), 3.15 (m, 1H), 2.95 (m, 2H), 2.78-2.67 (m, 6H), 2.17 (t, 2H), 2.09 (m, 2H), 2.0 (m, 2H), 1.84 (m, 1H), 1.43 (m, 2H), 1.39 (m, 1H), 1.18 (m, 2H), 0.82 (t, 3H). LC/MS m/z 501 (M+H)+

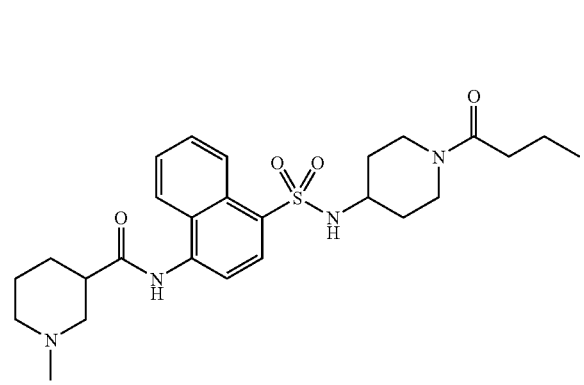

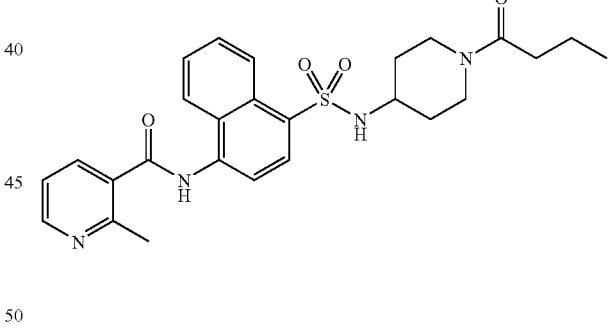

1-Methyl-piperidine-3-carboxylic acid [4-(1-butyryl-piperidin-4-ylsulfamoyl)-naphthalen-1-yl]-ainde (D-23)

The title compound was made following the general procedure in Scheme 9, substituting 1-methyl-piperidine-3-carbonyl chloride (prepared in situ from the corresponding acid using oxalyl chloride) for cyclopentanecarbonyl chloride. LC/MS m/z 501 (M+H)+.

N-[4-(1-Butyryl-piperidin-4-ylsulfamoyl)-naphthalen-1-yl]-2-methyl-nicotinamide (D-25)

The title compound was prepared following the general procedure in Scheme 5, beginning with 4-[(2-methyl-pyridine-3-carbonyl)-amino]-naphthalene-1-sulfonyl chloride, and substituting butyryl chloride and triethylamine for 2-isocyanato-propane. $^1$H NM (300 MHz, DMSO) δ 10.76 (s, 1H), 8.68 (d, 1H), 8.59 (d, 1H), 8.31 (d, 1H), 8.24 (d, 1H), 8.10 (d, 1H), 8.04 (d, 1H), 7.98 (d, 1H), 7.73 (m, 2H), 7.41 (m, 1H), 4.00 (d, 1H), 3.61 (d, 1H), 3.23 (m, 1H), 2.93 (t, 1H), 2.66 (s, 3H), 2.59 (m, 1H), 2.17 (t, 2H), 1.48 (m, 2H), 1.43 (m, 2H), 1.19 (m, 2H), 0.82 (m, 2H). LC/MS m/z 494 (M−H)−, 496 (M+H)

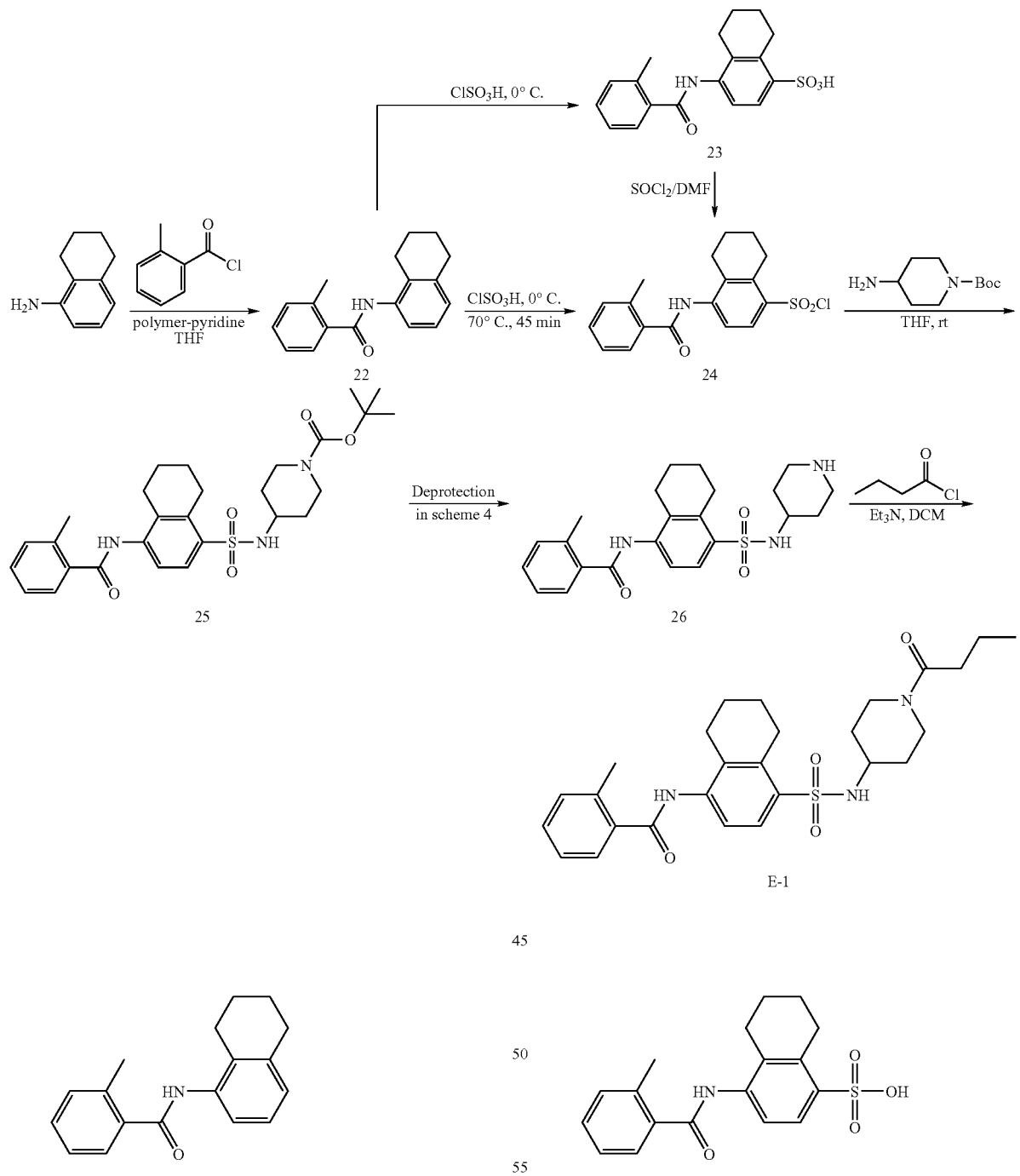

Scheme 10

2-Methyl-N-(5,6,7,8-tetrahydro-naphthalen-1-yl)-benzamide (22)

To a 25° C. solution of aniline (1 eq) in anhydrous THF (2 nL per inmol aniline), was added polymer bound pyridine (1.5 eq) followed by acid chloride (1 eq). The mixture was stirred at 25° C. for 12-24 h. The reaction mixture was filtered and the filtrate concentrated in vacuo. Hexane or MeOH was added to the residue and the resulting precipitate was collected by filtration, resulting in a white solid (yield 65%). LC/MS (M+H)+ m/z 266. The crude material was used without further purification.

4-(2-Methyl-benzoylamino)-5,6,7,8-tetrahydro-naphthalene-1-sulfonic acid (23)

To a 0° C. solution of amide (22) in TFA (1 mL per mmol amide), was added chlorosulfonic acid (2 eq) dropwise under nitrogen atmosphere. The temperature was allowed to warm to 25° C. and stirred for 72 hours. The reaction mixture was quenched by pouring into ice water. The desired product was collected via precipitation from either water/methanol, or ethyl acetate/methanol solution, resulting in a white solid (yield 68%). LC/MS (M+H)+ m/z 346, (M−H)− m/z 344. The crude material was used without further purification.

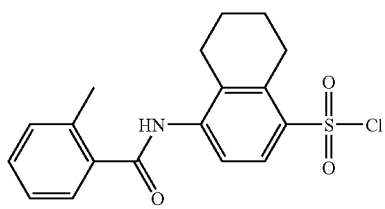

4-(2-Methyl-benzoylamino)-5,6,7,8-tetrahydro-naphthalene-1-sulfonyl chloride (24)

Method A: To a 0C solution of sulfonic acid (23) in DMF (1 ML per mmol acid), was added thionyl chloride (1.1 eq.) dropwise under nitrogen atmosphere. The temperature was allowed to warm to 25° C. and stirred for 18 hours. The reaction mixture was quenched by pouring into ice water and filtered to give the title compound as a white solid.

Method B: To neat amide (22), at 0° C., was added chlorosulfonic acid (5 eq) dropwise. The temperature was allowed to warm to 25° C. and then heated at 70° C. for 45 minutes. After cooling to 25° C., the reaction mixture was poured into ice water, and the resultant precipitate was collected by filtration to give the title sulfonyl chloride as a white solid. The product was used without further purification.

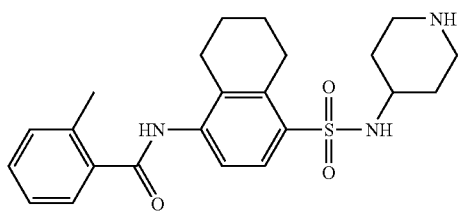

2-Methyl-N-[4-(piperidin-4-ylsulfamoyl)-5,6,7,8-tetrahydro-naphthalen-1-yl]-benzamide (26)

To a 25° C. solution of sulfonyl chloride (24) (1.61 g, 4 mmol) in THF (60 mL) was added 4-amino-piperidine-1-carboxylic acid tert-butyl ester (880 mg, 4.4 mmol), and followed by triethyl amine (668 mg, 6.6 mmol). The resultant solution was stirred at 25° C. for 18 hours. The reaction mixture was filtered and the filtrate was concentrated in vacuo to afford 25. 4 N HCl/Dioxane was added and this mixture was stirred for 2 hours, followed by filtration to collect a light gray solid (1.7 g, yield 75%) as the HCl salt of the title compound. LC/MS (M+H)+ m/z 527.

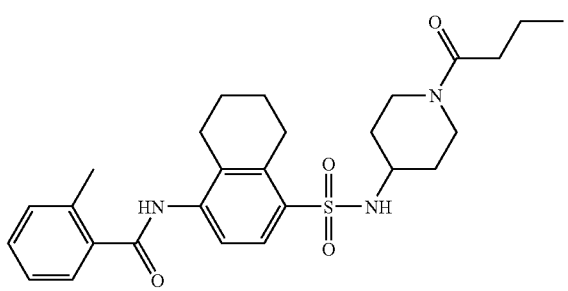

N-[4-(1-Butyryl-piperidin-4-ylsulfamoyl)-5,6,7,8-tetrahydro-naphthalen-1-yl]-2-methyl-benzamide (E-1)

To a 25° C. mixture of sulfonamide (26) (134 mg, 0.29 mmol) in THF (10 mL) was added butyryl chloride (77 mg, 0.725 mmol) and triethylamine (367 mg, 3.625 mmol). The mixture was stirred for 18 hours, followed by filtration to remove the precipitate. The filtrate was concentrated in vacuo and purified via chromatography, resulting in the title compound as white solid (50 mg). $^1$H NMR (300 MHz, MeOD) δ 7.91 (d, 1H), 7.55 (m, 2H), 7.41 (m, 1H), 7.31 (m, 2H), 4.30 (m, 1H), 3.89 (m, 1H), 3.21 (m, 2H), 3.09 (m, 1H), 2.85 (m, 2H), 2.61 (m, 1H), 2.55 (s, 3H), 2.34 (t, 2H), 1.88 (m, 7H), 1.62 (m, 2H), 1.39 (m, 2H), 0.95 (t, 3H) ); LC/MS (M+H)+ m/z 498.

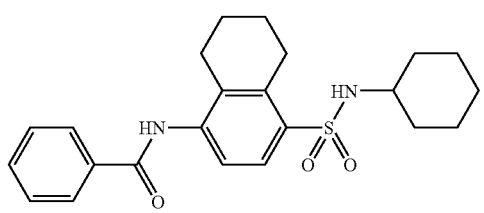

N-(4-Cyclohexylsulfamoyl-5,6,7,8-tetrahydro-naphthalen-1-yl)-benzamide (E-2)

The title compound was made following general procedure in Scheme 10, substituting benzoyl chloride for 2-methyl-benzoyl chloride, and cyclohexylamine for 4-amino-piperidine-1-carboxylic acid tert-butyl ester. $^1$H NMR (300 MHz, CDCl$_3$) δ 8.19 (d, 1H), 7.95 (d, 1H), 7.89 (m, 2H), 7.82 (br s, 1H, NH), 7.53 (m, 3H), 3.90 (m, 1H), 3.20 (t, 2H), 2.72 (t, 2H), 1.52 (m, 14H); LC/MS (M+H)+ m/z 413.

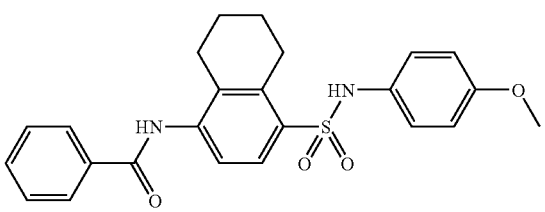

N-[4-(4-Methoxy-phenylsulfamoyl)-5,6,7,8-tetrahydro-naphthalen-1-yl]-benzamide (E-3)

The title compound was made following general procedure in Scheme 10, substituting benzoyl chloride for 2-methyl-benzoyl chloride, and 4-methoxy-phenylamine for 4-amino-piperidine-1-carboxylic acid tert-butyl ester. $^1$H NMR (300 MHz, CDCl$_3$) δ 8.10 (d, 1H), 7.84 (m, 4H), 7.55 (m, 3H), 6.96 (dd, 2H), 6.74 (dd, 2H), 6.64 (br s, 1H, N—H), 3.73 (s, 3H), 3.19 (t, 2H), 2.70 (t, 2H), 1.82 (m, 4H); LC/MS (M+H)+ m/z 437.

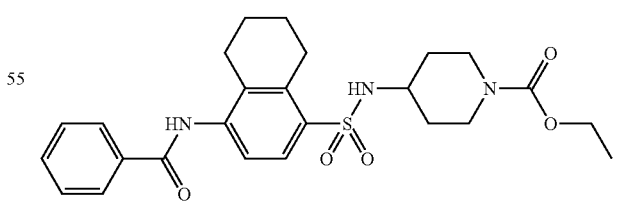

4-(4-Benzoylamino-5,6,7,8-tetrahydro-naphthalene-1-sulfonylamino)-piperidine-1-carboxylic acid ethyl ester (E-4)

The title compound was made following general procedure in Scheme 10, substituting benzoyl chloride for 2-methyl-benzoyl chloride, and ethyl chlorofomate for butyryl chloride. $^1$H NMR (300 MHz, CDCl$_3$) δ 8.15 (d, 1H), 7.94 (d, 1H), 7.89 (m, 2H), 7.53 (m, 3H), 4.70 (m, 1H), 4.08 (q, 2H), 3.92 (m, 2H), 3.32 (m, 1H), 3.15 (m, 2H), 2.76 (m, 4H), 1.80 (m, 4H), 1.36 (m, 3H), 1.22 (t, 3H); LC/MS (M+H)$^+$m/z 486.

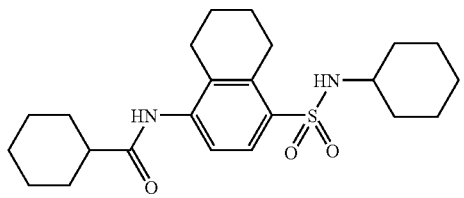

Cyclohexanecarboxylic acid (4-cyclohexylsuffamoyl-5,6,7,8-tetrahydro-naphthalen-1-yl)-amide (E-5)

The title compound was made following general procedure in Scheme 10, substituting cyclohexanecarbonyl chloride for 2-methyl-benzoyl chloride, and cyclohexylamine for 4-amino-piperidine-1-carboxylic acid tert-butyl ester. $^1$H NMR (300 MHz, CDCl$_3$) δ 8.00 (d, 1H), 7.84 (d, 1H), 4.24 (m, 1H), 3.11 (m, 3H), 2.57 (m, 2H), 2.22 (m, 1H), 2.02 (m, 2H), 1.79 (m, 9H), 1.66 (m, 3H), 1.17 (t, 9H); LC/MS (M+H)$^+$ m/z 419.

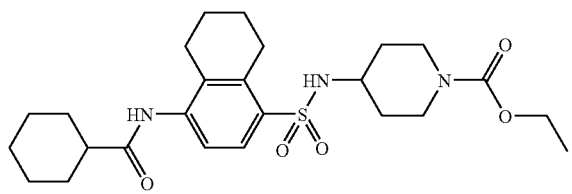

4-(4-(Cyclohexanecarbonyl-amino)-5,6,7,8-tetrahydro-naphthalene-1-sulfonylamino)-piperidine-1-carboxylic acid ethyl ester (E-6)

The title compound was made following general procedure in Scheme 10, substituting cyclohexanecarbonyl chloride for 2-methyl-benzoyl chloride, and ethyl chlorofomate for butyryl chloride. $^1$H NMR (300 MHz, MeOD) δ 7.93 (d, 1H), 7.51 (d, 1H), 4.19 (q, 2H), 4.08 (m, 2H), 3.32 (m, 2H), 3.05 (m, 2H), 2.96 (m, 2H), 2.60 (m, 1H), 1.66 (m, 19H), 1.22 (t, 3H); LC/MS (M+H)$^+$ m/z 492.

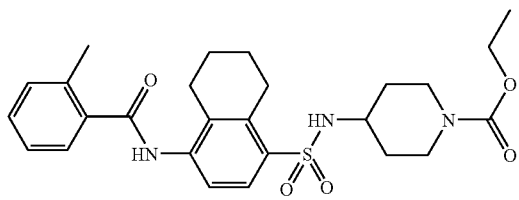

4-[4-(2-Methyl-benzoylamino)-5,6,7,8-tetrahydro-naphthalene-1-sulfonylamino]-piperidine-1-carboxylic acid ethyl ester (E-8)

The title compound was made following general procedure in Scheme 10, substituting ethyl chlorofomate for butyryl chloride. $^1$H NMR (300 MHz, MeOD) δ 7.89 (d, 1H), 7.55 (m, 2H), 7.39 (m, 1H), 7.29 (m, 2H), 4.22 (q, 2H), 3.92 (m, 2H), 3.21 (m, 3H), 2.81 (m, 4H), 2.49(s, 3H), 1.81 (m, 4H), 1.70(m, 2H), 1.39 (m, 2H), 1.21 (t, 3H); LC/MS (M+H)$^+$m/z 500.

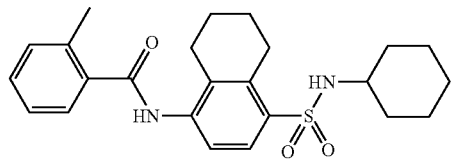

N-(4-Cyclohexylsulfamoyl-5,6,7,8-tetrahydro-naphthalen-1-yl)-2-methyl-benzamide (E-9)

The title compound was made following general procedure in Scheme 10, substituting cyclohexylamine for 4-amino-piperidine-1-carboxylic acid tert-butyl ester. $^1$H NMR (300 MHz, MeOD) δ 7.92 (d, 1H), 7.57 (m, 2H), 7.43 (m, 1H), 7.34 (m, 2H), 3.25 (m, 2H), 3.03 (m, 1H), 2.88 (m, 2H), 2.45 (s, 3H), 1.88 (m, 4H), 1.78 (m, 5H), 1.22 (m, 5H); LC/MS (M+H)$^+$ m/z 427.

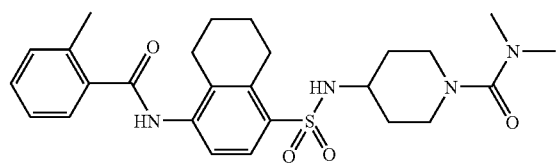

4-[4-(2-Methyl-benzoylamino)-5,6,7,8-tetrahydro-naphthalene-1-sulfonylamino]-piperidine-1-carboxylic acid dimethylamide (E-10)

The title compound was made following general procedure in Scheme 10, substituting dimethylcarbamyl chloride for butyryl chloride. $^1$H NMR (300 MHz, MeOD) δ 7.90 (d, 1H), 7.55 (m, 2H), 7.39 (m, 1H), 7.31 (m, 2H), 3.54 (m, 2H), 3.21 (m, 4H), 2.81 (m, 4H), 2.79 (s, 6H), 2.50 (s, 3H), 1.77(m, 3H), 1.71 (m, 2H), 1.45 (m, 2H) ); LC/MS (M+H)$^+$ m/z 499.

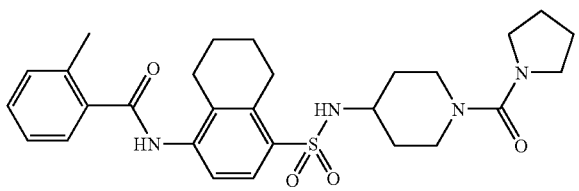

2-Methyl-N-{4-[1-(pyrrolidine-1-carbonyl)-piperidin-4-ylsulfamoyl]-5,6,7,8-tetrahydro-naphthalen-1-yl}-benzamide (E-11)

The title compound was made following general procedure in Scheme 10, substituting pyrrolidine-1-carbonyl chloride for butyryl chloride. $^1$H NMR (300 MHz, MeOD) δ 8.07 (d, 1H), 7.69 (m, 2H), 7.55 (m, 1H), 7.48 (m, 2H), 3.79 (m, 2H), 3.46 (m, 4H), 2.91 (m, 4H), 2.61 (s, 3H), 1.98 (m, 10H), 1.85 (m, 2H), 1.61 (m, 3H) ); LC/MS (M+H)$^+$ m/z 525.

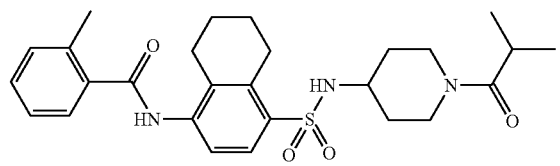

N-[4-(1-Isobutyryl-piperidin-4-ylsulfamoyl)-5,6,7,8-tetrahydro-naphthalen-1-yl]-2-methyl-benzamide (E-12)

The title compound was made following general procedure in Scheme 10, substituting isobutyryl chloride for butyryl chloride. $^1$H NMR (300 MHz, MeOD) δ 7.95 (d, 1H), 7.55 (m, 2H), 7.39 (m, 1H), 7.29 (m, 2H), 4.29 (m, 1H), 3.89 (m, 1H), 3.19 (m, 3H), 2.85 (m, 3H), 2.47 (s, 3H), 1.82 (m, 7H), 1.38 (m, 3H), 1.09 (m, 6H) ); LC/MS (M+H)$^+$ m/z 498.

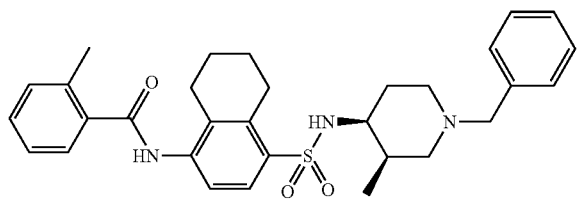

(±)-cis-N-[4-(1-Benzyl-3-methyl-piperidin-4-ylsulfamoyl)-5,6,7,8-tetrahydro-naphthalen-1-yl]-2-methyl-benzamide (E-13)

The title compound was made following general procedure in Scheme 10, substituting 1-benzyl-3-methyl-piperidin-4-ylamine for 4-amino-piperidine-1-carboxylic acid tert-butyl ester. $^1$H NMR (300 MHz, MeOD) δ 7.88 (d, 1H), 7.50 (m, 2H), 7.35 (m, 1H), 7.25 (m, 7H), 3.71 (m, 2H), 3.44 (m, 2H), 3.21 (m, 3H), 2.82 (s, 2H), 2.47 (s, 3H), 2.30 (m, 2H), 1.81 (m, 5H), 1.60 (m, 2H), 0.83 (d, 3H) ); LC/MS (M+H)$^+$ m/z 532.

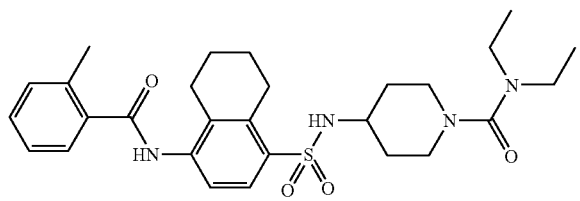

4-[4-(2-Methyl-benzoylamino)-5,6,7,8-tetrahydro-naphthalene-1-sulfonylamino]-piperidine-1-carboxylic acid diethylamide (E-14)

The title compound was made following general procedure in Scheme 10, substituting diethylcarbamyl chloride for butyryl chloride. $^1$H NMR (300 MHz, MeOD) δ 7.90 (d, 1H), 7.51 (m, 2H), 7.39 (m, 1H), 7.31 (m, 2H), 3.50 (m, 2H), 3.20 (m, 4H), 3.18 (q, 4H), 2.80 (m, 4H), 2.50 (s, 3H), 1.85 (m, 3H), 1.73 (m, 2H), 1.49 (m, 2H), 1.11 (t, 6H)); LC/MS (M+H)$^+$ m/z 527.

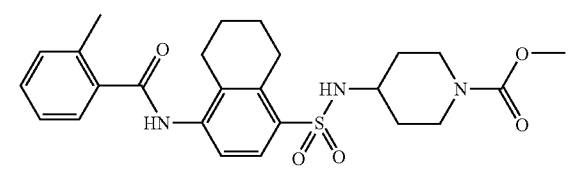

4-[4-(2-Methyl-benzoylamino)-5,6,7,8-tetrahydro-naphthalene-1-sulfonylamino]-piperidine-1-carboxylic acid methyl ester (E-15)

The title compound was made following general procedure in Scheme 10, substituting methyl chlorofomate for butyryl chloride. $^1$H NMR (300 MHz, MeOD) δ 7.90 (d, 1H), 7.55 (m, 2H), 7.39 (m, 1H), 7.31 (m, 2H), 3.92 (m, 2H), 3.63 (s, 3H), 3.20 (m, 4H), 2.85 (m, 4H), 2.50 (s, 3H), 1.85 (m, 3H), 1.72 (m, 2H), 1.41 (m, 2H) ; LC/MS (M+H)$^+$ m/z 486.

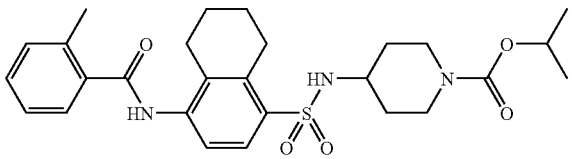

4-[4-(2-Methyl-benzoylamino)-5,6,7,8-tetrahydro-naphthalene-1-sulfonylamino]-piperidine-1-carboxylic acid isopropyl ester (E-16)

The title compound was made following general procedure in Scheme 10, substituting isopropyl chlorofomate chloride for butyryl chloride. $^1$H NMR (300 MHz, MeOD) δ 7.91 (d, 1H), 7.56 (m, 2H), 7.40 (m, 1H), 7.31 (m, 2H), 3.92 (m, 2H), 3.26 (m, 1H), 3.21 (m, 4H), 2.83 (m, 4H), 2.50 (s, 3H), 1.85 (m, 3H), 1.72 (m, 2H), 1.39 (m, 2H), 1.20 (d, 6H) ); LC/MS (M+H)$^+$ m/z 514.

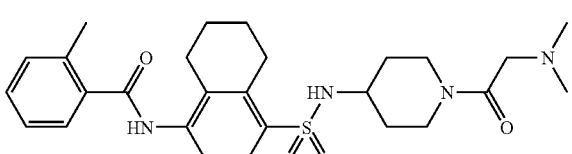

N-{4-[1-(2-Dimethylandno-acetl)-piperidin-4-ylsulfamoyl]-5,6,7,8-tetrahydro-naphthalen-1-yl}-2-methyl-benzamide (E-17)

The title compound was made following general procedure in Scheme 10, substituting dimethylamino-acetyl chloride for butyryl chloride. $^1$H NMR (300 MHz, MeOD) δ 7.91 (d, 1H), 7.56 (m, 2H), 7.40 (m, 1H), 7.31 (m, 2H), 4.28 (m, 1H), 3.93 (d, 2H), 3.66 (m, 1H), 3.25 (m, 4H), 2.80 (m, 4H), 2.72 (s, 6H), 2.51 (s, 3H), 1.85 (m, 5H), 1.45 (m, 2H)); LC/MS (M+H)$^+$ m/z 513.

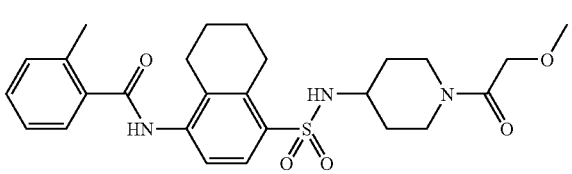

N-{4-[1-(2-Methoxy-acetyl)-piperidin-4-ylsulfamoyl]-5,6,7,8-tetrahydro-naphthalen-1-yl}-2-methyl-benzamide (E-18)

The title compound was made following general procedure in Scheme 10, substituting methoxy-acetyl chloride for butyryl chloride. $^1$H NMR (300 MHz, MeOD) δ 7.92 (d, 1H), 7.56 (m, 2H), 7.41 (m, 1H), 7.35 (m, 2H), 4.25 (m, 1H), 4.12 (d, 2H), 3.73 (m, 1H), 3.36 (s, 3H), 3.26 (m, 4H), 3.02 (m, 1H), 2.80 (m, 3H), 2.49 (s, 3H), 1.84 (m, 5H), 1.40 (m, 2H) ); LC/MS (M+H)$^+$ m/z 500.

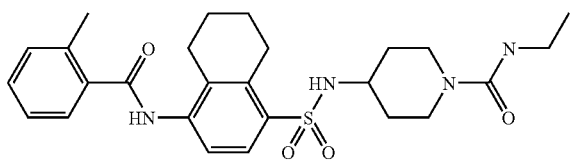

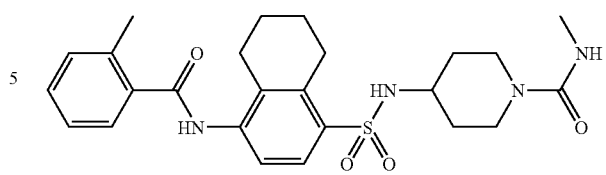

4-[4-(2-Methyl-benzoylamino)-5,6,7,8-tetrahydro-naphthalene-1-sulfonylamino]-piperidine-1-carboxylic acid ethylamide (E-19)

The title compound was made following general procedure in Scheme 10, substituting isocyanato-ethane for butyryl chloride. $^1$H NMR (300 MHz, MeOD) δ 7.90 (d, 1H), 7.55 (m, 2H), 7.41 (m, 1H), 7.31 (m, 2H), 3.83 (m, 2H), 3.24 (m, 4H), 3.14 (q, 2H), 2.79 (m, 4H), 2.50 (s, 3H), 1.84 (m, 3H), 1.70 (m, 2H), 1.38 (m, 2H), 1.07 (t, 3H) ); LC/MS (M+H)$^+$ m/z 499.

4-[4-(2-Methyl-benzoylamino)-5,6,7,8-tetrahydro-naphthalene-1-sulfonylamino]-piperidine-1-carboxylic acid methylamide (E-22)

The title compound was made following general procedure in Scheme 10, substituting isocyanato-methane for butyryl chloride. $^1$H NMR (300 MHz, MeOD) δ 7.93 (d, 1H), 7.59 (m, 2H), 7.43 (m, 1H), 7.36 (m, 2H), 3.88 (m, 2H), 3.29 (m, 4H), 2.83 (m, 4H), 2.71 (s, 3H), 2.54 (s, 3H), 1.88 (m, 3H), 1.73 (m, 2H), 1.41 (m, 2H) ); LC/MS (M+H)$^+$ m/z 486.

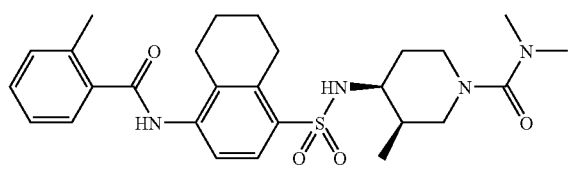

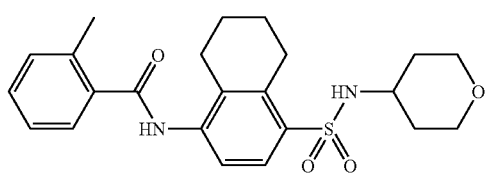

(±)-cis-3-Methyl-4-[4-(2-methyl-benzoylamino)-5,6,7,8-tetrahydro-naphthalene-1-sulfonylamino]-piperidine-1-carboxylic acid dimethylamide (E-20)

The title compound was made following general procedure in Scheme 10, substituting 1-benzyl-3-methyl-piperidin-4-ylamine for 4-amino-piperidine-1-carboxylic acid tert-butyl ester, and dimethylcarbamyl chloride for butyryl chloride. $^1$H NMR (300 MHz, MeOD) δ 7.91 (d, 1H), 7.55 (m, 2H), 7.39 (m, 1H), 7.31 (m, 2H), 3.36 (m, 2H), 3.22 (m, 2H), 3.10 (m, 3H ), 2.82 (m, 2H), 2.80 (s, 6H), 2.49 (s, 3H), 1.85 (m, 5H), 1.65 (m, 1H), 1.51 (m, 1H), 0.82 (d, 3H) ); LC/MS (M+H)$^+$ m/z 513.

2-Methyl-N-[4-(tetrahydro-pyran-4-ylsulfamoyl)-5,6,7,8-tetrahydro-naphthalen-1-yl]-benzamide (E-23)

The title compound was made following general procedure in Scheme 10, substituting tetrahydro-pyran-4-ylamine for 4-amino-piperidine-1-carboxylic acid tert-butyl ester. $^1$H NMR (300 MHz, MeOD) δ 7.91 (d, 1H), 7.54 (m, 2H), 7.39 (m, 1H), 7.32 (m, 2H), 3.84 (m, 2H), 3.29 (m, 6H), 2.83 (m, 2H), 2.51 (s, 3H), 1.88 (m, 3H), 1.69 (m, 2H), 1.54 (m, 2H)); LC/MS (M+H)$^+$ m/z 429.

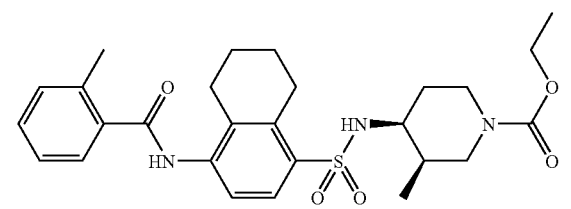

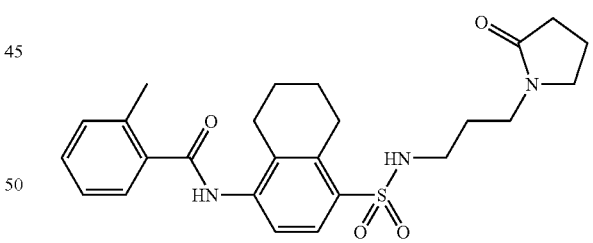

(±)-cis-3-Methyl-4-[4-(2-methyl-benzoylamino)-5,6,7,8-tetrahydro-naphthalene-1-sulfonylamino]-piperidine-1-carboxylic acid ethyl ester (E-21)

The title compound was made following general procedure in Scheme 10, substituting 1-benzyl-3-methyl-piperidin-4-ylamine for 4-amino-piperidine-1-carboxylic acid tert-butyl ester, and ethyl chlorofomate for butyryl chloride. $^1$H NMR (300 MHz, MeOD) δ 7.92 (d, 1H), 7.58 (m, 2H), 7.41 (m, 1H), 7.35 (m, 2H), 4.12 (q, 2H), 3.71 (m, 1H), 3.29 (m, 6H), 2.88 (m, 2H), 2.52 (s, 3H), 1.88 (m, 5H), 1.62 (m, 1H), 1.51 (m, 1H), 1.25 (t, 3H), 0.89 (d, 3H)); LC/MS (M+H)$^+$ m/z 514.

2-Methyl-N-{4-[3-(2-oxo-pyrrolidin-1-yl)-propylsulfamoyl]-5,6,7,8-tetrahydro-naphthalen-1-yl}-benzamide (E-24)

The title compound was made following general procedure in Scheme 10, substituting 1-(3-amino-propyl)-pyrrolidin-2-one for 4-amino-piperidine-1-carboxylic acid tert-butyl ester. $^1$H NMR (300 MHz, MeOD) δ 7.80 (d, 1H), 7.50 (t, 2H), 7.37 (m, 1H), 7.29 (m, 2H), 3.34 (t, 2H), 3.21 (t, 2H), 3.17 (m, 2H), 2.86 (t, 2H), 2.79 (m, 2H), 2.46 (s, 3H), 2.31 (t, 2H), 1.98 (m, 2H), 1.82 (m, 4H), 1.65 (m, 2H) ); LC/MS (M+H)$^+$ m/z 470.

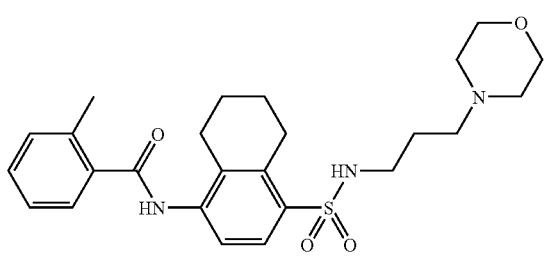

2-Methyl-N-[4-(3-morpholin-4-yl-propylsulfamoyl)-5,6,7,8-tetrahydro-naphthalen-1-yl]-benzamide (E-25)

The title compound was made following general procedure in Scheme 10, substituting 3-morpholin-4-yl-propylamine for 4-amino-piperidine-1-carboxylic acid tert-butyl ester. $^1$H NMR (300 MHz, MeOD) δ 7.83 (d, 1H), 7.54 (t, 2H), 7.41 (m, 1H), 7.31 (m, 2H), 3.74(m, 4H), 3.19 (m, 2H), 2.98 (t, 2H), 2.75 (m, 8H), 2.49 (s, 3H), 1.81 (m, 6H) ); LC/MS (M+H)$^+$ m/z 472.

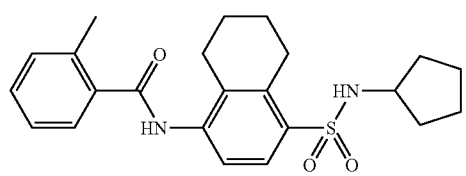

N-(4-Cyclopentylsulfamoyl-5,6,7,8-tetrahydro-naphthalen-1-yl)-2-methyl-benzamide (E-26)

The title compound was made following general procedure in Scheme 10, substituting cyclopentylamine for 4-amino-piperidine-1-carboxylic acid tert-butyl ester. $^1$H NMR (300 MHz, MeOD) δ 7.88 (d, 1H), 7.54 (m, 2H), 7.39 (m, 1H), 7.31 (m, 2H), 3.49 (m, 1H), 3.21 (m, 2H), 2.72 (m, 2H), 2.50 (s, 3H), 1.83 (m, 4H), 1.69 (m, 4H), 1.48 (m, 4H); LC/MS (M+H)$^+$ m/z 413.

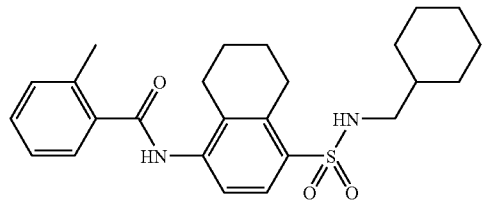

N-[4-(Cyclohexylmethyl-sulfamoyl)-5,6,7,8-tetrahydro-naphthalen-1-yl]-2-methyl-benzamide (E-27)

The title compound was made following general procedure in Scheme 10, substituting C-cyclohexyl-methylamine for 4-amino-piperidine-1-carboxylic acid tert-butyl ester. $^1$H NMR (300 MHz, MeOD) δ 7.82 (d, 1H), 7.54 (m, 2H), 7.39 (m, 1H), 7.31 (m, 2H), 3.21 (m, 2H), 2.83 (m, 2H), 2.69 (d, 2H), 2.49 (s, 3H), 1.83 (m, 3H), 1.69 (m, 6H), 1.39 (m, 1H), 1.19 (m, 3H), 0.85 (m, 2H) ); LC/MS (M+H)$^+$ m/z 441.

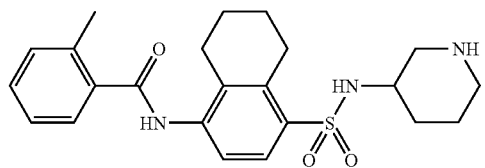

(±)-2-Methyl-N-[4-(piperidin-3-ylsulfamoyl)-5,6,7,8-tetrahydro-naphthalen-1-yl]-benzamide (E-28)

The title compound was made following general procedure in Scheme 10, substituting (R, S)-3-amino-piperidine-1-carboxylic acid tert-butyl ester for 4-amino-piperidine-1-carboxylic acid tert-butyl ester. $^1$H NMR (300 MHz, MeOD) δ 7.91 (d, 1H), 7.57 (m, 2H), 7.41 (m, 1H), 7.33 (m, 2H), 3.23 (m, 4H), 3.11 (m, 1H), 2.85 (m, 2H), 2.70(m, 2H), 2.50 (s, 3H), 1.73 (m, 6H), 1.54 (m, 2H) ); LC/MS (M+H)$^+$ m/z 428.

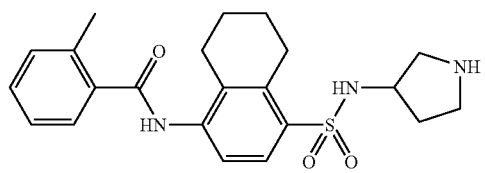

(±)-2-Methyl-N-[4-(pyrrolidin-3-ylsulfamoyl)-5,6,7,8-tetrahydro-naphthalen-1-yl]-benzamide (E-29)

The title compound was made following general procedure in Scheme 10, substituting (R, S)-3-amino-pyrrolidine-1-carboxylic acid tert-butyl ester for 4-amino-piperidine-1-carboxylic acid tert-butyl ester. $^1$H NMR (300 MHz, MeOD) δ 7.89 (d, 1H), 7.57 (m, 2H), 7.41 (m, 1H), 7.33 (m, 2H), 3.81 (m, 1H), 3.22 (m, 7H), 2.84 (m, 2H), 2.50 (s, 3H), 2.09 (m, 1H), 1.83 (m, 4H) ); LC/MS (M+H)$^+$ m/z 414.

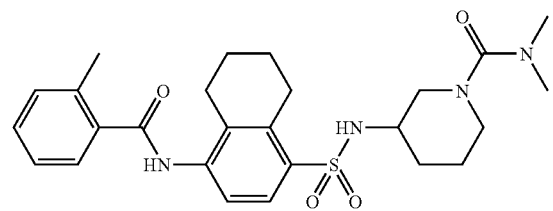

(±)-3-[4-(2-Methyl-benzoylamino)-5,6,7,8-tetrahydro-naphthalene-1-sulfonylamino]-piperidine-1-carboxylic acid dimethylamide (E-30)

The title compound was made following general procedure in Scheme 10, substituting (R, S)-3-amino-piperidine-1-carboxylic acid tert-butyl ester for 4-amino-piperidine-1-carboxylic acid tert-butyl ester, and dimethylcarbamyl chloride for butyryl chloride.

$^1$H NMR (300 MHz, MeOD) δ 7.90 (d, 1H), 7.56 (m, 2H), 7.39 (m, 1H), 7.31 (m, 2H), 3.40 (m, 3H), 3.15 (m, 3H), 2.85 (m, 2H), 2.74 (s, 6H), 2.69(m, 2H), 2.50 (s, 3H), 1.73 (m, 4H), 1.69 (m, 1H), 1.44 (m, 2H) ); LC/MS (M+H)$^+$ m/z 499.

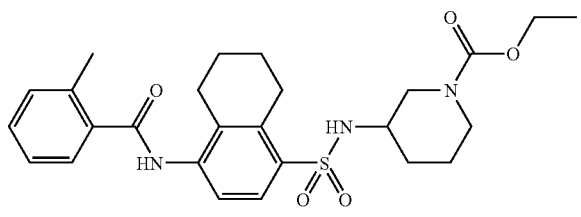

(±)-3-[4-(2-Methyl-benzoylamino)-5,6,7,8-tetrahydro-naphthalene-1-sulfonylamino]-piperidine-1-carboxylic acid ethyl ester (E-31)

The title compound was made following general procedure in Scheme 10, substituting (R, S)-3-amino-piperidine-1-carboxylic acid tert-butyl ester for 4-amino-piperidine-1-carboxylic acid tert-butyl ester, and ethyl chloroformate for butyryl chloride. $^1$H NMR (300 MHz, MeOD) δ 7.92 (d, 1H), 7.59 (m, 2H), 7.42 (m, 1H), 7.34 (m, 2H), 4.09 (q, 2H), 3.91 (m, 1H), 3.79 (m, 1H), 3.24 (m, 2H), 3.09 (m, 2H), 2.85 (m, 4H), 2.51 (s, 3H), 1.86 (m, 4H), 1.71 (m, 1H), 1.42 (m, 2H), 1.23 (t, 3H) ); LC/MS (M+H)$^+$ m/z 500.

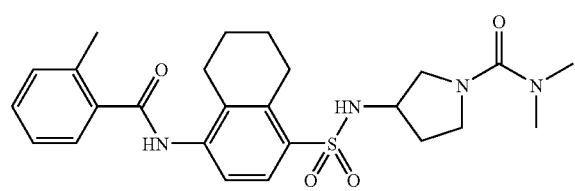

(±)-3-[4-(2-Methyl-benzoylamino)-5,6,7,8-tetrahydro-naphthalene-1-sulfonylamino]-pyrrolidine-1-carboxylic acid dimethylamide (E-32)

The title compound was made following general procedure in Scheme 10, substituting (R,S)-3-amino-pyrrolidine-1-carboxylic acid tert-butyl ester for 4-amino-piperidine-1-carboxylic acid tert-butyl ester, and dimethylcarbamyl chloride for butyryl chloride. $^1$H NMR (300 MHz, MeOD) δ 7.90 (d, 1H), 7.57 (m, 2H), 7.41 (m, 1H), 7.32 (m, 2H), 3.78 (m, 1H), 3.48 (m, 1H), 3.28 (m, 2H), 3.18 (m, 3H), 2.84 (m, 3H), 2.78 (s, 6H), 2.50 (s, 3H), 1.96 (m, 1H), 1.82 (m, 4H) ); LC/MS (M+H)$^+$ m/z 485.

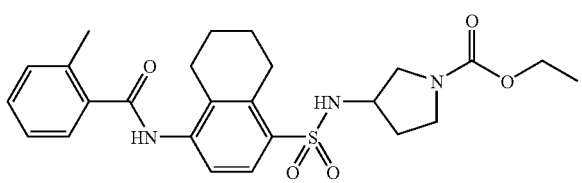

(±)-3-[4-(2-Methyl-benzoylamino)-5,6,7,8-tetrahydro-naphthalene-1-sulfonylamino]-pyrrolidine-1-carboxylic acid ethyl ester (E-33)

The title compound was made following general procedure in Scheme 10, substituting (R, S)-3-amino-pyrrolidine-1-carboxylic acid tert-butyl ester for 4-amino-piperidine-1-carboxylic acid tert-butyl ester, and ethyl chloroformate for butyryl chloride. $^1$H NMR (300 MHz, MeOD) δ 7.89 (d, 1H), 7.55 (m, 2H), 7.39 (m, 1H), 7.30 (m, 2H), 4.09 (m, 2H), 3.79 (m, 1H), 3.41 (m, 3H), 3.18 (m, 4H), 2.82 (m, 2H), 2.50 (s, 3H), 1.99 (m, 1H), 1.89 (m, 4H), 1.22 (m, 3H) ); LC/MS (M+H)$^+$ m/z 486.

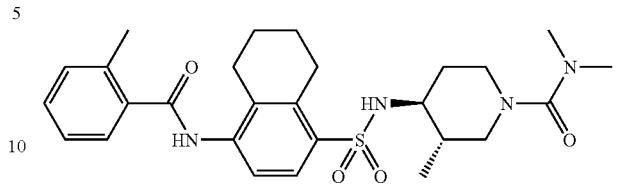

(±)-trans-3-Methyl-4-[4-(2-methyl-benzoylamino)-5,6,7,8-tetrahydro-naphthalene-1-sulfonylamino]-piperidine-1-carboxylic acid dimethylamide (E-34)

The title compound was made following general procedure in Scheme 10, substituting 1-benzyl-3-methyl-piperidin-4-ylamine for 4-amino-piperidine-1-carboxylic acid tert-butyl ester, and dimethylcarbamyl chloride for butyryl chloride. LC/MS (M+H)$^+$ m/z 513.

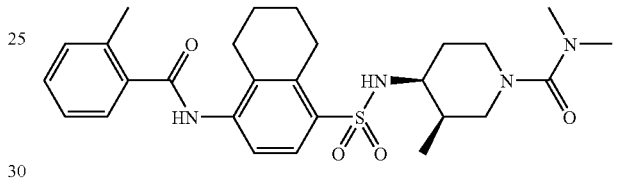

(3R, 4S)-3-Methyl-4-[4-(2-methyl-benzoylamino)-5,6,7,8-tetrahydro-naphthalene-1-sulfonylamino]-piperidine-1-carboxylic acid dimethylamide (E-35)

The title compound was made following general procedure in Scheme 10, substituting 1-benzyl-3-methyl-piperidin-4-ylamine for 4-amino-piperidine-1-carboxylic acid tert-butyl ester, and dimethylcarbamyl chloride for butyryl chloride. Compound E-20 was prepared as described previously, and the enantiomers were separated via chiral HPLC chromatography of E-35; the title compound eluted as peak 1. $^1$H NMR (300 MHz, MeOD) δ 7.90 (d, 1H), 7.55 (m, 2H), 7.39 (m, 1H), 7.31 (m, 2H), 3.36 (m, 2H), 3.22 (m, 2H), 3.10 (m, 3H), 2.82 (m, 2H), 2.80 (s, 6H), 2.49 (s, 3H), 1.85 (m, 4H), 1.65 (m, 1H), 1.49 (m, 1H), 0.83 (d, 3H)); LC/MS (M+H)$^+$ m/z 537.

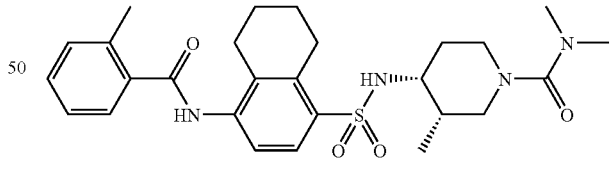

(3S, 4R) -3-Methyl-4-[4-(2-methyl-benzoylamino)-5,6,7,8-tetrahydro-naphthalene-1-sulfonylamino]-piperidine-1-carboxylic acid dimethylamide (E-36)

The title compound was made following general procedure in Scheme 10, substituting 1-benzyl-3-methyl-piperidin-4-ylamine for 4-amino-piperidine-1-carboxylic acid tert-butyl ester, and dimethylcarbamyl chloride for butyryl chloride. Compound E-20 was prepared as described previously, and the enantiomers were separated via chiral HPLC chromatography of E-35; the title compound eluted as peak 2. $^1$H NMR (300 MHz, MeOD) δ 7.90 (d, 1H), 7.55 (m, 2H), 7.39 (m, 1H), 7.31 (m, 2H), 3.36 (m, 2H), 3.22 (m, 2H), 3.10 (m, 3H), 2.82 (m, 2H), 2.80 (s, 6H), 2.49 (s, 3H), 1.85 (m, 4H), 1.65 (m, 1H), 1.49 (m, 1H), 0.83 (d, 3H) ); LC/MS (M+H)+ m/z 513.

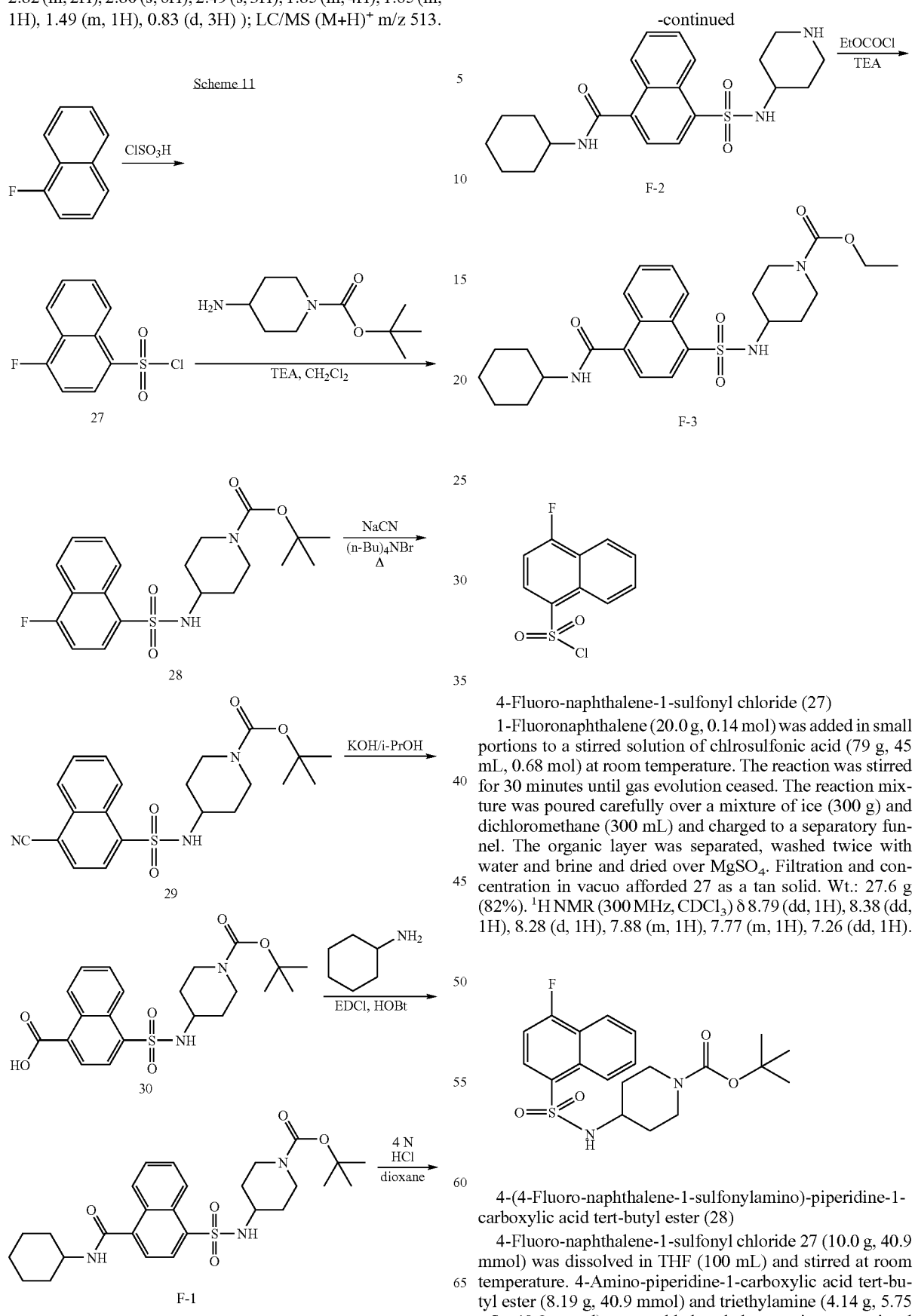

4-Fluoro-naphthalene-1-sulfonyl chloride (27)

1-Fluoronaphthalene (20.0 g, 0.14 mol) was added in small portions to a stirred solution of chlrosulfonic acid (79 g, 45 mL, 0.68 mol) at room temperature. The reaction was stirred for 30 minutes until gas evolution ceased. The reaction mixture was poured carefully over a mixture of ice (300 g) and dichloromethane (300 mL) and charged to a separatory funnel. The organic layer was separated, washed twice with water and brine and dried over MgSO$_4$. Filtration and concentration in vacuo afforded 27 as a tan solid. Wt.: 27.6 g (82%). $^1$H NMR (300 MHz, CDCl$_3$) δ 8.79 (dd, 1H), 8.38 (dd, 1H), 8.28 (d, 1H), 7.88 (m, 1H), 7.77 (m, 1H), 7.26 (dd, 1H).

4-(4-Fluoro-naphthalene-1-sulfonylamino)-piperidine-1-carboxylic acid tert-butyl ester (28)

4-Fluoro-naphthalene-1-sulfonyl chloride 27 (10.0 g, 40.9 mmol) was dissolved in THF (100 mL) and stirred at room temperature. 4-Amino-piperidine-1-carboxylic acid tert-butyl ester (8.19 g, 40.9 mmol) and triethylamine (4.14 g, 5.75 mL, 40.9 mmol) were added and the reaction was stirred overnight at room temperature. The solvent was removed in vacuo. Dichloromethane (250 mL) was added and the solution was charged to a separatory funnel. The organic layer was washed twice with water and brine and dried over MgSO$_4$. Filtration and concentration in vacuo afforded 28 as a yellow foam. Wt.: 15.1 g (90%). $^1$H NMR (300 MHz, CDCl$_3$) δ 8.62 (d, 1H), 8.26 (m, 2H), 7.69 (m, 2H), 7.20 (m, 1H), 4.92 (d, 1H), 3.82 (m, 2H), 3.26 (m, 1H), 2.70 (m, 2H), 1.61 (m, 2H), 1.40 (s, 9H), 1.24 (m, 2H); LC/MS m/z 409 (M+H)$^+$.

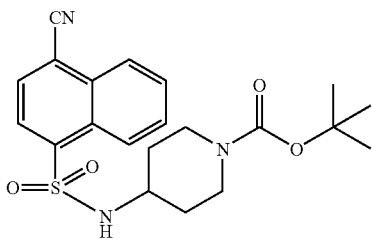

4-(4-Cyano-naphthalene-1-sulfonylamino)-piperidine-1-carboxylic acid tert-butyl ester (29)

4-(4-Fluoro-naphthalene-1-sulfonylamino)-piperidine-1-carboxylic acid tert-butyl ester 28 (2.00 g, 4.9 mmol) was dissolved in DMF (20 mL). Sodium cyanide (1.2 g, 24.5 mmol) and tetra-n-butylammonium bromide (7.9 g, 24.5 mmol) were added and the reaction was heated to 100° C. overnight. The reaction was diluted with dichloromethane (100 mL) and charged to a separatory funnel. The organic layer was washed three times with water, brine and dried over MgSO$_4$. Filtration and concentration in vacuo afforded a dark colored oil. Flash column chromatography (98:2 dichloromethane:methanol) afforded an oil that was rechromatographed (99:1 dichloromethane:methanol) to afford 29 as an orange solid. Wt.: 640 mg (31%). $^1$H NMR (300 MHz, CDCl$_3$) δ 8.71 (m, 1H), 8.40 (m, 1H), 8.34 (d, 1H), 8.00 (d, 1H), 7.83 (m, 2H), 4.80 (d, 1H), 3.87 (m, 2H), 3.32 (m, 1H), 2.61 (m, 2H), 1.63 (m, 2H), 1.38 (s, 9H), 1.27 (m, 2H); LC/MS m/z 414 (M−H)

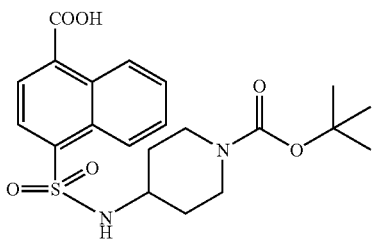

4-(4-Carboxy-naphthalene-1-sulfonylamino)-piperidine-1-carboxylic acid tert-butyl ester (30)

4-(4-Cyano-naphthalene-1-sulfonylamino)-piperidine-1-carboxylic acid tert-butyl ester 29 (0.48 g, 1.15 mmol) was dissolved in a mixture of aqueous potassium hydroxide (20 mL, 1.8N, 36 mmol) and isopropanol (25 mL). The mixture was heated to 75° C. for two days. LC/MS analysis showed a mixture of starting material, carboxylic acid and amide. The isopropanol was removed in vacuo and the aqueous layer was extracted with ethyl acetate and the organic layer discarded. The aqueous layer was acidified to pH 3 and extracted with ethyl acetate. The organic layer washed with water, then brine and dried over MgSO$_4$. Filtration and concentration in vacuo afforded 30 as a tan colored foam. Wt.: 360 mg (72%). $^1$H NMR (300 MHz, CDCl$_3$) δ 9.03 (m, 1H), 8.70 (m, 1H), 8.33 (dd, 2H), 7.74 (m, 2H), 4.78 (d, 1H), 3.85 (m, 2H), 3.31 (m, 1H), 2.71 (m, 2H), 1.62 (m, 2H), 1.40 (s, 9H), 1.27 (m, 2H); LC/MS m/z 433 (M−H)$^−$.

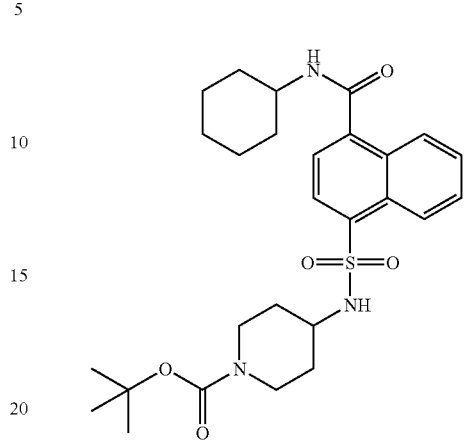

4-(4-Cyclohexylcarbamoyl-naphthalene-1-sulfonylamino)-piperidine-1-carboxylic acid tert-butyl ester (F-1)

4-(4-Carboxy-naphthalene-1-sulfonylamino)-piperidine-1-carboxylic acid tert-butyl ester 5 (400 mg, 0.92 mmol) was dissolved in dichloromethane (5 mL). 1-[3-(Dimethylamino)propyl]-3-ethylcarbodiimide hydrochloride (EDCI) (350 mg, 1.84 mmol), 1-hydroxybenzotriazole (186 mg, 1.38 mmol), triethylamine (280 mg, 0.38 mL, 2.76 mmol) and cyclohexylamine (0.14 g, 0.16 mL, 1.38 mmol) were added and the reaction was stirred overnight at room temperature. The reaction was diluted with dichloromethane (30 mL) and charged to a separatory funnel. The organic layer was washed twice with water and brine and dried over Na$_2$SO$_4$. Filtration and concentration in vacuo afforded a foam that was purified via flash column chromatography (98:2 dichloromethane:methanol) to give the title compound. Wt.: 320 mg (68%). $^1$H NMR (300 MHz, CDCl$_3$) δ 8.61 (m, 1H), 8.31 (m, 1H), 8.26 (d, 1H), 7.68 (m, 2H), 7.59 (d, 1H), 5.91 (d, 1H), 4.64 (d, 1H), 4.12 (m, 1H), 3.82 (m, 2H), 3.22 (m, 1H), 2.68 (m, 2H), 2.13 (m, 2H), 1.79 (m, 2H), 1.57 (m, 6H), 1.38 (s, 9H), 1.27 (m, 4H); LC/MS m/z 516 (M+H)$^+$.

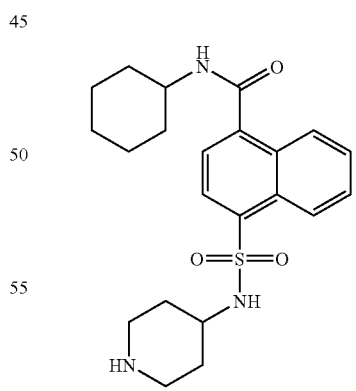

4-(Piperidin-4-ylsulfamoyl)-naphthalene-1-carboxylic acid cyclohexylamide (F-2)

4-(4-Cyclohexylcarbamoyl-naphthalene-1-sulfonylamino)-piperidine-1-carboxylic acid tert-butyl ester F-1 (320 mg, 0.62 mmol) was dissolved in 4N HCl/dioxane (10 mL). The reaction was stirred for 2 hours at room temperature and concentrated in vacuo to afford the title compound as its hydrochloride salt. Wt.: 271 mg (97%) $^1$H NMR (300 MHz, d$^6$-DMSO) δ 8.68 (d, 1H), 8.59 (d, 1H), 8.40 (d, 1H), 8.15 (m, 2H), 7.72 (m, 2H), 7.60 (d, 1H), 3.75 (m, 1H), 3.67 (m, 1H), 3.08 (m, 2H), 2.80 (m, 2H), 2.54 (m, 1H), 1.92 (m, 2H), 1.74 (m, 2H), 1.62 (m, 4H), 1.48 (m, 1H), 1.32 (m, 4H), 1.25 (m, 1H); LC/MS m/z 416 (M+H)$^+$.

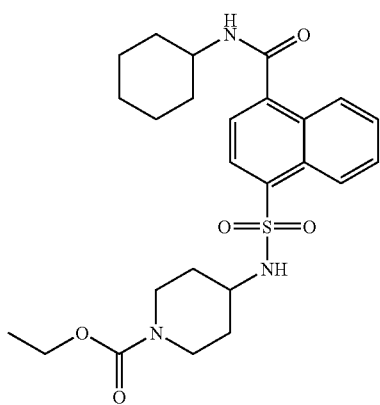

4-(4-Cyclohexylcarbamoyl-naphthalene-1-sulfonylamino)-piperidine-1-carboxylic acid ethyl ester (F-3)

4-(Piperidin-4-ylsulfamoyl)-naphthalene-1-carboxylic acid cyclohexylamide hydrochloride F-2 (87 mg, 0.19 mmol) was dissolved and stirred in dichloromethane (2 mL). Triethylamine (58 mg, 0.08 mL, 0.57 mmol) was added followed by ethyl chloroformate (41 mg, 0.037 mL, 0.39 mmol). The reaction was stirred overnight at room temperature, then charged directly to a flash column. Elution with 99:1 dichloromethane:methanol afforded the titled compound the title compound as a white solid. Wt.: 60 mg (65%). $^1$H NMR (300 MHz, CDCl$_3$) δ 8.59 (m, 1H), 8.28 (m, 1H), 8.19 (d, 1H), 7.64 (m, 2H), 7.54 (d, 1H), 4.10 (m, 1H), 4.03 (q, 2H), 3.80 (m, 2H), 3.64 (m, 1H), 3.18 (m, 1H), 2.68 (m, 2H), 2.12 (m, 2H), 1.79 (m, 2H), 1.68 (m, 1H), 1.58 (m, 2H), 1.47 (m, 2H), 1.24 (m, 6H), 1.18 (t, 3H); LC/MS m/z 488 (M+H)$^+$.

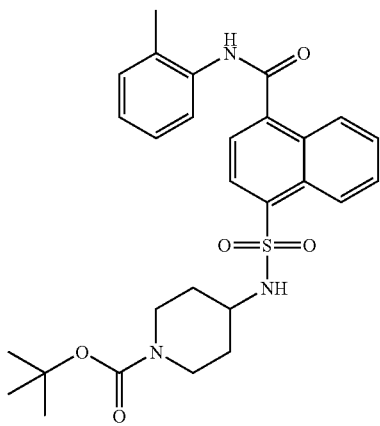

4-(4-o-Tolylcarbamoyl-naphthalene-1-sulfonylamino)-piperidine-1-carboxylic acid tert-butyl ester (F-4)

The titled compound was prepared according to the general procedure in Scheme 11, substituting 2-methylphenylamine for cyclohexylamine. Wt.: 337 mg (70%). $^1$H NMR (300 MHz, CDCl$_3$) δ 8.66 (d, 1H), 8.46 (d, 1H), 8.35 (d, 1H), 8.04 (d, 1H), 7.80 (m, 1H), 7.72 (m, 2H), 7.54 (s, 1H), 7.34 (m, 1H), 7.21 (m, 1H), 4.16 (d, 1H), 3.85 (m, 2H), 3.27 (m, 1H), 2.70 (m, 2H), 2.34 (s, 3H), 2.23 (m, 1H), 1.66 (m, 2H), 1.56 (m, 4H), 1.40 (s, 9H), 1.27 (m, 4H); LC/MS m/z 524 (M+H)$^+$.

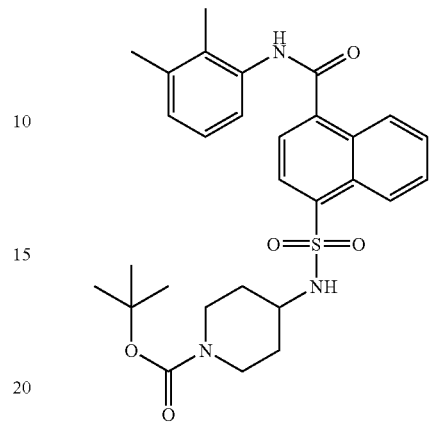

4-[4-(2,3-Dimethyl-phenylcarbamoyl)-naphthalene-1-sulfonylamino]-piperidine-1-carboxylic acid tert-butyl ester (F-13)

The titled compound was prepared according to the general procedure in Scheme 11, substituting 2,3-dimethyl-phenylamine for cyclohexylamine. Wt.: 353 mg (75%). $^1$H NMR (300 MHz, CDCl$_3$) δ 8.66 (m, 1H), 8.47 (d, 1H), 8.35 (d, 1H), 7.81 (d, 1H), 7.72 (m, 2H), 7.54 (s, 1H), 7.22 (m, 1H), 7.13 (m, 1H), 4.63 (d, 1H), 3.86 (m, 2H), 3.27 (m, 1H), 2.70 (m, 2H), 2.35 (s, 3H), 2.24 (s, 3H), 1.64 (m, 2H), 1.34 (m, 2H); LC/MS m/z 537 (M−H)$^−$.

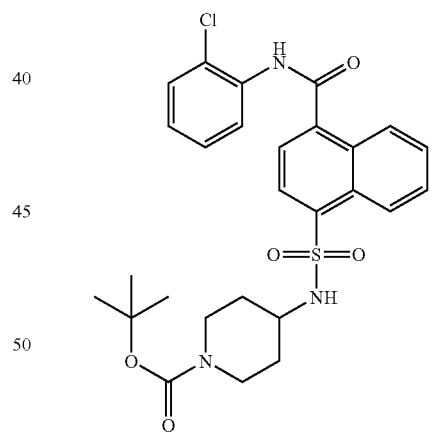

4-[4-(2-Chloro-phenylcarbamoyl)-naphthalene-1-sulfonylamino]-piperidine-1-carboxylic acid tert-butyl ester (F-14)

The titled compound was prepared according to the general procedure in Scheme 11, substituting 2-chloro-phenylamine for cyclohexylamine. Wt.: 329 mg (66%). $^1$H NMR (300 MHz, CDCl$_3$) δ 8.68 (m, 1H), 8.62 (m, 1H), 8.46 (d, 1H), 8.37 (m, 1H), 8.20 (s, 1H), 7.83 (d, 1H), 7.73 (m, 2H), 7.46 (m, 1H), 7.40 (m, 1H), 7.17 (m, 1H), 4.68 (d, 1H), 3.87 (m, 2H), 3.30 (m, 1H), 2.62 (m, 2H), 1.68 (m, 2H), 1.40 (s, 9H), 1.26 (m, 2H); LC/MS m/z 543 (M−H)$^−$.

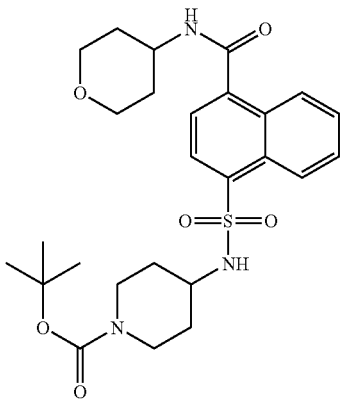

4-[4-(Tetrahydro-pyran-4-ylcarbamoyl)-naphthalene-1-sulfonylamino]-piperidine-1-carboxylic acid tert-butyl ester (F-15)

The title compound was prepared according to the general procedure in Scheme 11, substituting tetrahydro-pyran-4-ylamine for cyclohexylamine. Wt.: 368 mg (77%). $^1$H NMR (300 MHz, CDCl$_3$) δ 8.60 (m, 1H), 8.29 (m, 1H), 8.24 (d, 1H), 7.68 (m, 2H), 7.59 (d, 1H), 6.12 (d, 1H), 4.73 (d, 1H), 4.34 (m, 1H), 4.04 (m, 2H), 3.82 (m, 2H), 3.57 (m, 2H), 3.21 (m, 1H), 2.67 (m, 2H), 2.11 (m, 1H), 1.62 (m, 3H), 1.36 (s, 9H), 1.20 (m, 4H); LC/MS m/z 516 (M−H)$^-$.

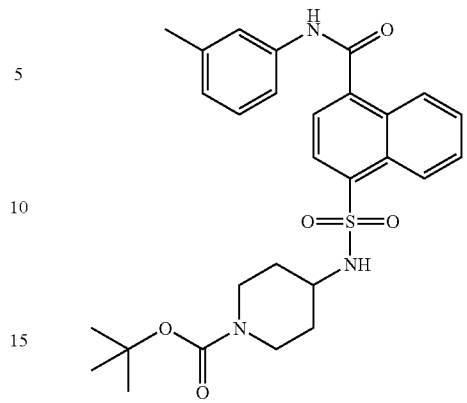

4-(4-m-Tolylcarbamoyl-naphthalene-1-sulfonylamino)-piperidine-1-carboxylic acid tert-butyl ester The title compound was prepared according to the general procedure in Scheme 11, substituting m-tolylamine for cyclohexylamine. Wt.: 61 mg (51%). $^1$H NMR (300 MHz, CDCl$_3$) δ 8.62 (d, 1H), 8.35 (m, 2H), 8.18 (d, 1H), 7.65 (m, 4H), 7.28 (m, 2H), 7.03 (d, 1H), 5.13 (d, 1H), 3.73 (m, 2H), 3.18 (m, 1H), 2.62 (m, 2H), 2.40 (s, 3H), 1.55 (m, 2H), 1.38 (s, 9H), 1.12 (m, 2H); LC/MS m/z 524 (M+H)$^+$.

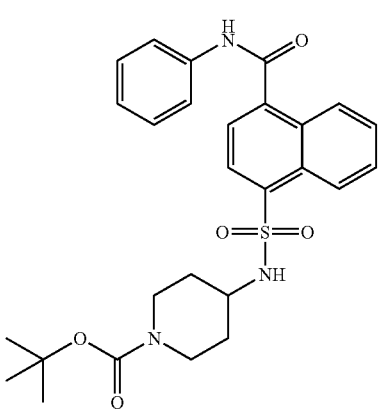

4-(4-Phenylcarbamoyl-naphthalene-1-sulfonylamino)-piperidine-1-carboxylic acid tert-butyl ester The titled compound was prepared according to the general procedure in Scheme 11, substituting phenylamine for cyclohexylamine. Wt.: 66 mg (55%). $^1$H NMR (300 MHz, CDCl$_3$) δ 8.62 (d, 1H), 8.37 (m, 2H), 8.26 (d, 1H), 7.93 (s, 1H), 7.70 (m, 4H), 7.43 (m, 3H), 4.76 (d, 1H), 3.80 (m, 2H), 3.24 (m, 1H), 2.67 (m, 2H), 1.60 (m, 2H), 1.39 (s, 9H), 1.22 (m, 2H); LC/MS m/z 510(M+H)$^+$.

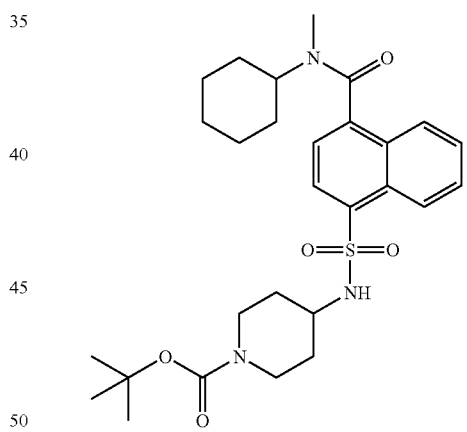

4-[4-(Cyclohexyl-methyl-carbamoyl)-naphthalene-1-sulfonylamino]-piperidine-1-carboxylic acid tert-butyl ester The title compound was prepared according to the general procedure in Scheme 11, substituting cyclohexyl-methyl-amine for cyclohexylamine, and O-(7-azabenzotriazol-1-yl)-N,N,N',N'-tetramethyluronium hexafluorophosphate for EDCI. Wt.: 440 mg (100%). 1H NMR (300 MHz, CDCl$_3$) δ 8.63 (d, 1H), 8.31 (d, 1H), 7.89 (m, 1H), 7.67 (m, 2H), 7.42 (m, 1H), 4.77 (s, 1H), 3.87 (m, 2H), 3.22 (m, 1H), 2.79 (s, 3H), 2.60 (m, 2H), 1.88 (m, 4H), 1.55 (m, 8H), 1.38 (s, 9H), 1.15 (m, 2H); LC/MS m/z 530 (M+H)$^+$.

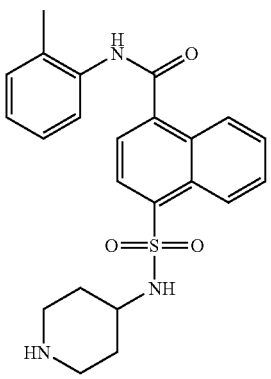

4-(Piperidin-4-ylsulfamoyl)-naphthalene-1-carboxylic acid o-tolylamide (F-5)

The title compound was prepared according to the general procedure in Scheme 11, substituting 4-(4-o-tolylcarbamoyl-naphthalene-1-sulfonylamino)-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 275 mg (97%). $^1$H NMR (300 MHz, d$^6$-DMSO) δ 10.22 (s, 1H), 8.73 (m, 1H), 8.44 (m, 2H), 8.30 (m, 11), 8.24 (m, 1H), 7.88 (d, 1H), 7.77 (m, 2H), 7.52 (d, 1H), 7.28 (m, 1H), 7.22 (m, 1H), 3.11 (m, 2H), 2.83 (m, 2H), 2.53 (m, 1H), 2.32 (s, 3H), 1.67 (m, 2H), 1.51 (m, 2H); LC/MS m/z 424 (M+H)$^+$.

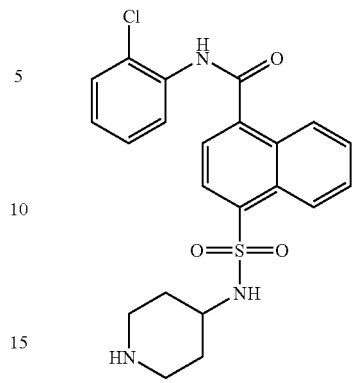

4-(Piperidin-4-ylsulfamoyl)-naphthalene-1-carboxylic acid (2-chloro-phenyl)-amide (F-17)

The title compound was prepared according to the general procedure in Scheme 11, substituting 4-[4-(2-chloro-phenyl-carbamoyl)-naphthalene-1-sulfonylamino]-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 219 mg (98%). $^1$H NMR (300 MHz, d$^6$-DMSO) δ 10.51 (s, 1H), 8.72 (d, 1H), 8.52 (m, 1H), 8.47 (d, 1H), 8.35 (m, 1H), 8.24 (d, 1H), 7.90 (d, 1H), 7.75 (m, 2H), 7.59 (d, 1H), 7.43 (m, 1H), 7.32 (m, 1H), 3.67 (m, 1H), 3.08 (m, 2H), 2.82 (m, 2H), 1.65 (m, 2H), 1.50 (m, 2H); LC/MS m/z 442 (M−H)$^-$.

4-(Piperidin-4-ylsulfamoyl)-naphthalene-1-carboxylic acid (2,3-dimethyl-phenyl)-amide (F-16)

The title compound was prepared according to the general procedure in Scheme 11, substituting 4-[4-(2,3-dimethyl-phenylcarbamoyl)-naphthalene-1-sulfonylamino]-piperidine-1-carboxylic acid tert-butyl ester for 4-(4-cyclohexyl-carbamoyl-naphthalene-1-sulfonylamino)-piperidine-1-carboxylic acid tert-butyl ester. Wt.: 312 mg (99%). $^1$H NMR (300 MHz, d$^6$-DMSO) δ 10.27 (s, 1H), 8.72 (d, 1H), 8.47 (d, 1H), 8.30 (m, 1H), 8.23 (d, 1H), 7.90 (d, 1H), 7.75 (m, 2H), 7.31 (d, 1H), 7.12 (m, 2H), 3.68 (m, 1H), 3.10 (m, 2H), 2.80 (m, 2H), 2.30 (s, 3H), 2.20 (s, 3H), 2.02 (m, 1H), 1.67 (m, 2H), 1.53 (m, 2H); LC/MS m/z 436 (M−H)$^-$.

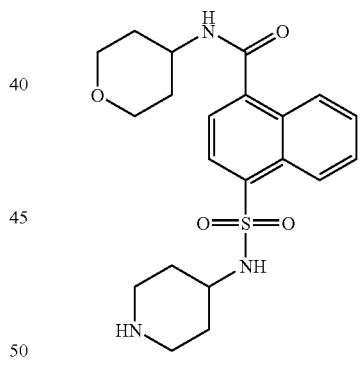

4-(Piperidin-4-ylsulfamoyl)-naphthalene-1-carboxylic acid (tetrahydro-pyran-4-yl)-amide (F-18)

The title compound was prepared according to the general procedure in Scheme 11, substituting 4-[4-(tetrahydro-pyran-4-ylcarbamoyl)-naphthalene-1-sulfonylaamino]-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 321 mg (100%). $^1$H NMR (300 MHz, d$^6$-DMSO) δ 8.69 (m, 2H), 8.42 (m, 2H), 8.15 (m, 1H), 7.72 (m, 2H), 7.63 (d, 1H), 4.08 (m, 1H), 3.87 (m, 2H), 3.42 (m, 2H), 3.08 (m, 2H), 2.80 (m, 2H), 1.86 (m, 2H), 1.64 (m, 4H), 1.51 (m, 4H); LC/MS m/z 416 (M−H)$^-$.

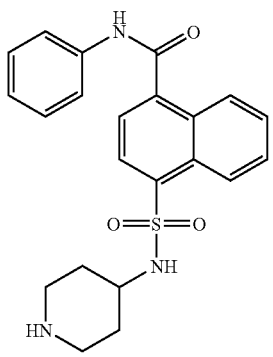

4-(Piperidin-4-ylsulfamoyl)-naphthalene-1-carboxylic acid phenylamide

The title compound was prepared according to the general procedure in Scheme 11, substituting 4-(4-phenylcarbamoyl-naphthalene-1-sulfonylamino)-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 38 mg (67%). LC/MS m/z 410 (M+H)$^+$.

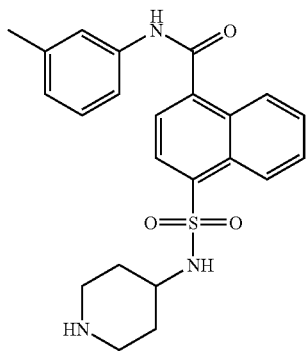

4-(Piperidin-4-ylsulfamoyl)-naphthalene-1-carboxylic acid m-tolylamide

The title compound was prepared according to the general procedure in Scheme 11, substituting 4-(4-m-tolylcarbamoyl-naphthalene-1-sulfonylamino)-piperidine-1-carboxylic acid tert-butyl ester for 4-(4-cyclohexylcarbamoyl-naphthalene-1-sulfonylamino)-piperidine-1-carboxylic acid tert-butyl ester. Wt. 39 mg (75%). LC/MS m/z 424 (M+H)$^+$.

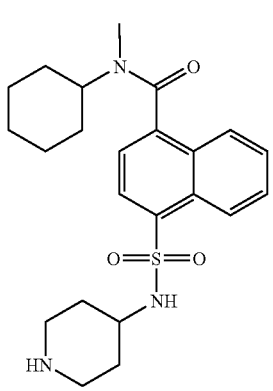

4-(Piperidin-4-ylsulfamoyl)-naphthalene-1-carboxylic acid cyclohexyl-methyl-amide The title compound was prepared according to the general procedure in Scheme 11, substituting 4-[4-(cyclohexyl-methyl-carbamoyl)-naphthalene-1-sulfonylamino]-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 440 mg (100%). LC/MS m/z 424 (M+H)$^+$.

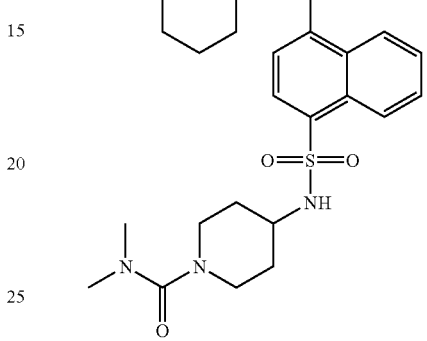

4-(4-Cyclohexylcarbamoyl-naphthalene-1-sulfonylamino)-piperidine-1-carboxylic acid dimethylamide (F-6)

The title compound was prepared according to the general procedure in Scheme 11, substituting dimethylcarbamyl chloride for ethyl chloroformate. Wt.: 56 mg (50%). $^1$H NMR (300 MHz, CDCl$_3$) δ 8.58 (d, 1H), 8.30 (d, 1H), 8.25 (d, 2H), 7.68 (m, 2H), 7.56 (d, 1H), 6.00 (d, 1H), 4.77 (d, 1H), 4.11 (m, 1H), 3.42 (m, 2H), 3.23 (m, 1H), 2.71 (s, 6H), 2.63 (m, 2H), 2.13 (m, 2H), 1.80 (m, 2H), 1.63 (m, 2H), 1.47 (m, 2H), 1.27 (m, 6H); LC/MS m/z 485 (M−H)$^-$.

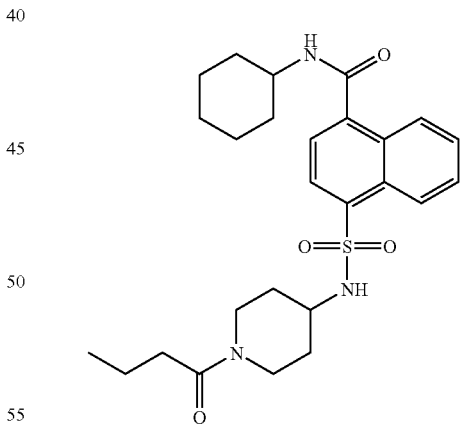

4-(1-Butyryl-piperidin-4-ylsulfamoyl)-naphthalene-1-carboxylic acid cyclohexylainde (F-7)

The title compound was prepared according to the general procedure in Scheme 11, substituting butyryl chloride for ethyl chloroformate. Wt.: 50 mg (47%). $^1$H NMR (300 MHz, CDCl$_3$) δ 8.60 (d, 1H), 8.32 (d, 1H), 8.27 (d, 1H), 7.72 (m, 2H), 7.57 (d, 1H), 6.00 (d, 1H), 4.78 (d, 1H), 4.24 (m, 1H), 4.11 (m, 1H), 3.64 (m, 1H), 3.27 (m, 1H), 2.91 (m, 1H), 2.56 (m, 1H), 2.15 (m, 4H), 1.62 (m, 8H), 1.25 (m, 4H), 0.95 (m, 2H), 0.88 (t, 3H); LC/MS m/z 484 (M−H)$^-$.

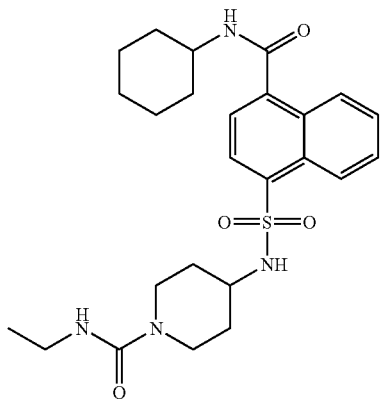

4-(4-Cyclohexylcarbamoyl-naphthalene-1-sulfonylamino)-piperidine-1-carboxylic acid ethylamide (F-8)

The title compound was prepared according to the general procedure in Scheme 11, substituting ethyl isocyanate for ethyl chloroformate. Wt.: 56 mg (49%). $^1$H NMR (300 MHz, CDCl$_3$) δ 8.60 (d, 1H), 8.29 (d, 1H), 8.23 (d, 1H), 7.68 (m, 2H), 7.57 (d, 1H), 6.03 (d, 1H), 4.83 (d, 1H), 4.30 (m, 1H), 4.11 (m, 1H), 3.62 (m, 2H), 3.17 (m, 3H), 2.68 (m, 2H), 2.12 (m, 2H), 1.79 (m, 2H), 1.55 (m, 4H), 1.25 (m, 6H), 1.06 (t, 3H); LC/MS m/z 485 (M−H)$^-$.

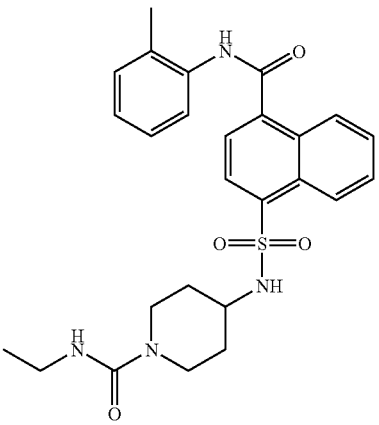

4-(4-o-Tolylcarbamoly-naphthalene-1-sulfonylamino)-piperidine-1-carboxylic acid ethylamide (F-10)

The title compound was prepared according to the general procedure in Scheme 11, substituting 4-(piperidin-4-ylsulfamoyl)-naphthalene-1-carboxylic acid o-tolylamide for 4-(piperidin-4-ylsulfamoyl)-naphthalene-1-carboxylic acid cyclohexylamide, and ethyl isocyanate for ethyl chloroformate. Wt.: 26 mg (47%). $^1$H NMR (300 MHz, CDCl$_3$) δ 8.65 (d, 1H), 8.46 (d, 1H), 8.32 (d, 1H), 8.03 (d, 1H), 7.77 (d, 1H), 7.70 (m, 2H), 7.64 (s, 1H), 7.30 (m, 2H), 7.20 (m, 2H), 4.81 (d, 1H), 4.28 (m, 1H), 3.66 (m, 2H), 3.27 (m, 1H), 3.17 (m, 2H), 2.71 (m, 2H), 2.32 (s, 3H), 1.65 (m, 1H), 1.25 (m, 2H), 1.07 (t, 3H); LC/MS m/z 493 (M−H)$^-$.

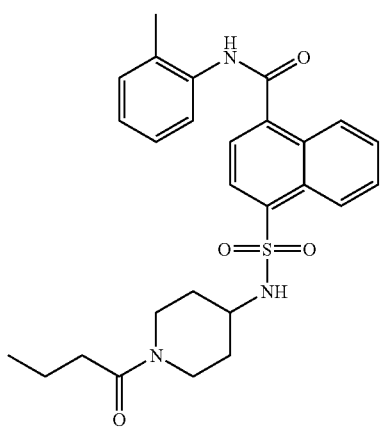

4-(1-Butyryl-piperidin-4-ylsulfamoyl)-naphthalene-1-carboxylic acid o-tolylamide (F-9)

The title compound was prepared according to the general procedure in Scheme 11, substituting 4-(piperidin-4-ylsulfamoyl)-naphthalene-1-carboxylic acid o-tolylamide for 4-(piperidin-4-ylsulfamoyl)-naphthalene-1-carboxylic acid cyclohexylamide, and butyryl chloride for ethyl chloroformate. Wt.: 29 mg (33%). $^1$H NMR (300 MHz, CDCl$_3$) δ 8.66 (d, 1H), 8.45 (d, 1H), 8.34 (d, 1H), 8.04 (d, 1H), 7.78 (d, 1H), 7.71 (m, 2H), 7.60 (s, 1H), 7.30 (m, 2H), 7.20 (m, 2H), 4.75 (d, 1H), 4.29 (d, 1H), 3.66 (d, 1H), 3.31 (m, 1H), 2.95 (m, 1H), 2.60 (m, 1H) 2.34 (s, 3H), 2.20 (m, 2H), 1.70 (m, 2H), 1.23 (m, 3H), 0.89 (t, 3H); LC/MS m/z 492 (M−H)$^-$.

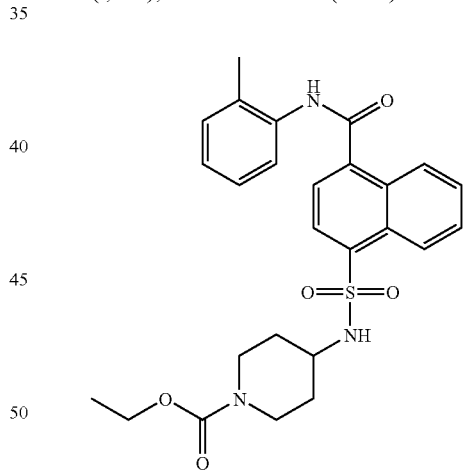

4-(4-o-Tolylcarbamoyl-naphthalene-1-sulfonylamino)-piperidine-1-carboxylic acid ethyl ester (F-11)

The title compound was prepared according to the general procedure in Scheme 11, substituting 4-(piperidin-4-ylsulfamoyl)-naphthalene-1-carboxylic acid o-tolylamide for 4-(piperidin-4-ylsulfamoyl)-naphthalene-1-carboxylic acid cyclohexylamide. Wt.: 60 mg (64%). $^1$H NMR (300 MHz, CDCl$_3$) δ 8.67 (d, 1H), 8.46 (d, 1H), 8.33 (d, 1H), 8.03 (d, 1H), 7.79 (d, 1H), 7.71 (m, 2H), 7.55 (s, 1H), 7.30 (m, 2H), 7.21 (m, 2H), 4.71 (d, 1H), 4.05 (q, 2H), 3.89 (m, 2H), 3.27 (m, 1H), 2.72 (m, 2H), 2.31 (s, 3H), 1.65 (m, 1H), 1.26 (m, 2H), 1.20 (t, 3H); LC/MS m/z 494 (M−H)$^-$.

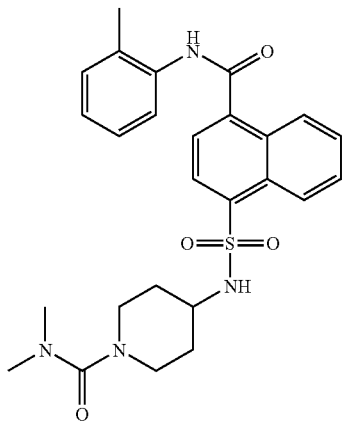

4-(4-o-Tolylcarbamoyl-naphthalene-1-sulfonylamino)-piperidine-1-carboxylic acid dimethylamide (F-12)

The title compound was prepared according to the general procedure in Scheme 11, substituting 4-(piperidin-4-ylsulfamoyl)-naphthalene-1-carboxylic acid o-tolylamide for 4-(piperidin-4-ylsulfamoyl)-naphthalene-1-carboxylic acid cyclohexylamide, and dimethylcarbamyl chloride for ethyl chloroformate. Wt.: 35 mg (64%). $^1$H NMR (300 MHz, CDCl$_3$) δ 8.63 (d, 1H), 8.45 (d, 1H), 8.33 (d, 1H), 8.05 (d, 1H), 7.80 (d, 1H), 7.71 (m, 2H), 7.54 (s, 1H), 7.30 (m, 2H), 7.20 (m, 2H), 4.68 (d, 1H), 3.43 (m, 2H), 3.30 (m, 1H), 2.71 (s, 6H), 2.68 (m, 2H), 2.34 (s, 3H), 1.62 (m, 1H), 1.31 (m, 2H); LC/MS m/z 493 (M−H)$^−$.

4-[4-(2,3Dimethyl-phenylcarbamoyl)-naphthalene-1-sulfonylamino]-piperidine-1-carboxylic acid dimethylamide (F-20)

The title compound was prepared according to the general procedure in Scheme 11, substituting 4-(piperidin-4-ylsulfamoyl)-naphthalene-1-carboxylic acid (2,3-dimethyl-phenyl)-amide for 4-(piperidin-4-ylsulfamoyl)-naphthalene-1-carboxylic acid cyclohexylamide, and dimethycarbamyl chloride for ethyl chloroformate. Wt.: 116 mg (72%). $^1$H NMR (300 MHz, CDCl$_3$) δ 8.60 (m, 1H), 8.40 (m, 1H), 8.20 (m, 2H), 7.72 (d, 1H), 7.63 (m, 2H), 7.35 (d, 1H), 7.16 (m, 1H), 7.09 (m, 1H), 5.42 (d, 1H), 3.32 (m, 2H), 3.15 (m, 1H), 2.67 (s, 6H), 2.55 (m, 2H), 2.33 (s, 3H), 2.22 (s, 3H), 1.52 (m, 2H), 1.23 (m, 2H); LC/MS m/z 509 (M+H)$^+$.

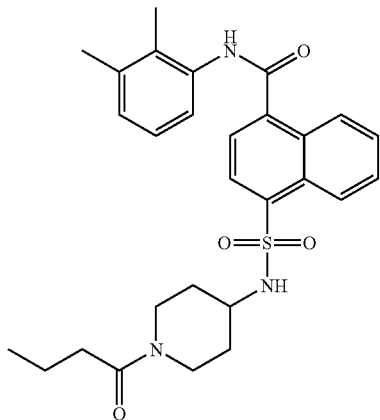

4-(1-Butyryl-piperidin-4-ylsulfamoyl)-naphthalene-1-carboxylic acid (2,3-dimethyl-phenyl)-amide (F-19)

The title compound was prepared according to the general procedure in Scheme 11, substituting 4-(piperidin-4-ylsulfamoyl)-naphthalene-1-carboxylic acid (2,3-dimethyl-phenyl)-amide for 4-(piperidin-4-ylsulfamoyl)-naphthalene-1-carboxylic acid cyclohexylamide, and butyryl chloride for ethyl chloroformate. Wt.: 64 mg (40%). $^1$H NMR (300 MHz, CDCl$_3$) δ 8.63 (m, 2H), 8.40 (m, 1H), 8.30 (s, 1H), 8.22 (d, 1H), 7.72 (d, 1H), 7.68 (m, 1H), 7.60 (d, 1H), 7.18 (m, 1H), 7.10 (m, 1H), 5.57 (d, 1H), 4.02 (m, 1H), 3.55 (m, 1H), 3.28 (m, 1H), 2.85 (m, 1H), 2.49 (m, 1H), 2.31 (s, 3H), 2.23 (s, 3H), 2.09 (2H), 1.63 (m, 2H), 1.50 (m, 2H), 1.20 (m, 1H), 1.03 (m, 1H), 0.84 (t, 3H); LC/MS m/z 508 (M+H)$^+$.

4-[4-(Tetrahydro-pyran-4-ylcarbamoyl)-naphthalene-1-sulfonylamino]-piperidine-1-carboxylic acid dimethylamide (F-21)

The title compound was prepared according to the general procedure in Scheme 11, substituting 4-(piperidin-4-ylsulfamoyl)-naphthalene-1-carboxylic acid (tetrahydro-pyran-4-yl)-amide for 4-(piperidin-4-ylsulfamoyl)-naphthalene-1-carboxylic acid cyclohexylamide, and dimethylcarbamyl chloride for ethyl chloroformate. Wt.: 125 mg (78%). $^1$H NMR (300 MHz, CDCl$_3$) δ 8.8.59 (m, 1H), 8.29 (m, 1H), 8.23 (d, 1H), 7.69 (m, 2H), 7.58 (d, 1H), 6.17 (d, 1H), 4.82 (d, 1H), 4.32 (m, 1H), 4.03 (m, 2H), 3.57 (m, 2H), 3.40 (m, 2H), 3.25 (m, 1H), 2.73 (s, 6H), 2.64 (m, 2H), 2.10 (m, 2H), 1.61 (m, 4H), 1.27 (m, 2H); LC/MS m/z 489 (M+H)$^+$.

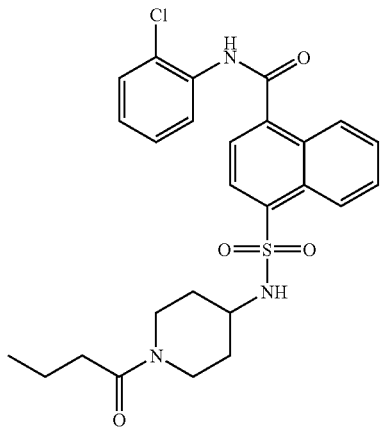

4-(1-Butyryl-piperidin-4-ylsulfamoyl)-naphthalene-1-carboxylic acid (2-chloro-phenyl)-amide (F-22)

The title compound was prepared according to the general procedure in Scheme 11, substituting 4-(piperidin-4-ylsulfamoyl)-naphthalene-1-carboxylic acid (2-chloro-phenyl)-amide for 4-(piperidin-4-ylsulfamoyl)-naphthalene-1-carboxylic acid cyclohexylamide, and butyryl chloride for ethyl chlroformate. Wt.: 21 mg (27%). $^1$H NMR (300 MHz, CDCl$_3$) δ 8.67 (m, 2H), 8.48 (d, 1H), 8.35 (d, 1H), 8.20 (s, 1H), 7.82 (d, 1H), 7.72 (m, 2H), 7.41 (m, 2H), 7.09 (m, 1H), 4.78 (d, 1H), 4.31 (m, 1H), 3.67 (m, 1H), 3.35 (m, 1H), 2.95 (m, 1H), 2.22 (m, 2H), 1.60 (4H), 1.27 (m, 2H), 0.92 (t, 3H); LC/MS m/z 515 (M+H)$^+$.

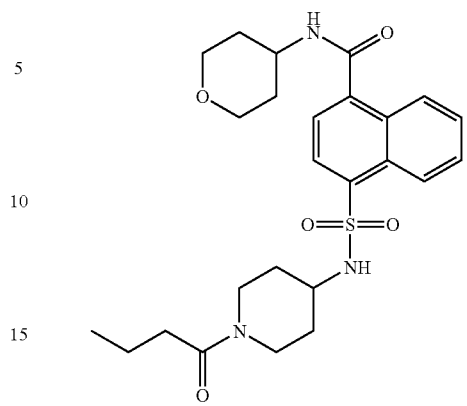

4-(1-Butyryl-piperidin-4-ylsulfamoyl)-naphthalene-1-carboxylic acid (tetrahydro-pyran-4-yl)-amide (F-24)

The title compound was prepared according to the general procedure in Scheme 11, substituting 4-(piperidin-4-ylsulfamoyl)-naphthalene-1-carboxylic acid (tetrahydro-pyran-4-yl)-amide for 4-(piperidin-4-ylsulfamoyl)-naphthalene-1-carboxylic acid cyclohexylamide, and butyryl chloride for ethyl chloroformate. Wt.: 30 mg (19%). $^1$H NMR (300 MHz, CDCl$_3$) δ 8.67 (d, 1H), 8.26 (d, 1H), 8.13 (d, 1H), 7.67 (m, 2H), 7.52 (d, 1H), 6.68 (m, 1H), 5.28 (m, 1H), 4.32 (m, 1H), 4.05 (m, 3H), 3.15 (m, 1H), 2.46 (m, 1H), 2.10 (m, 4H), 1.65 (m, 4H), 1.49 (m, 2H), 1.18 (m, 1H), 9.95 (m, 1H), 0.88 (t, 3H); LC/MS m/z 488 (M+H)$^+$.

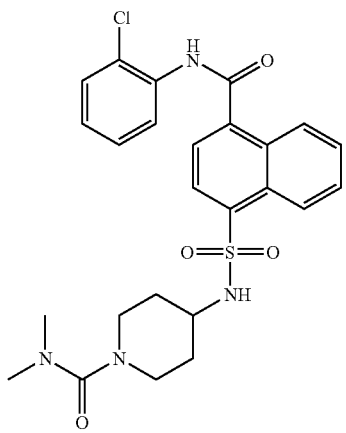

4-[4-(2-Chloro-phenylcarbamoyl)-naphthalene-1-sulfonylamino]-piperidine-1-carboxylic acid dimethylamide (F-23)

The title compound was prepared according to the general procedure in Scheme 11, substituting 4-(piperidin-4-ylsulfamoyl)-naphthalene-1-carboxylic acid (2-chloro-phenyl)-amide for 4-(piperidin-4-ylsulfamoyl)-naphthalene-1-carboxylic acid cyclohexylamide, and dimethylcarbamyl chloride for ethyl chloroformate. Wt.: 28 mg (36%). $^1$H NMR (300 MHz, CDCl$_3$) δ 8.69 (d, 1H), 8.60 (d, 1H), 8.47 (d, 1H), 8.35 (d, 1H), 8.20 (s, 1H), 7.82 (d, 1H), 7.72 (m, 2H), 7.43 (m, 2H), 7.17 (m, 1H), 4.83 (d, 1H), 3.46 (m, 2H), 3.31 (m, 1H), 2.71 (s, 6H), 2.70 (m, 2H), 1.67 (m, 2H), 1.35 (m, 2H); LC/MS m/z 516 (M+H)$^+$.

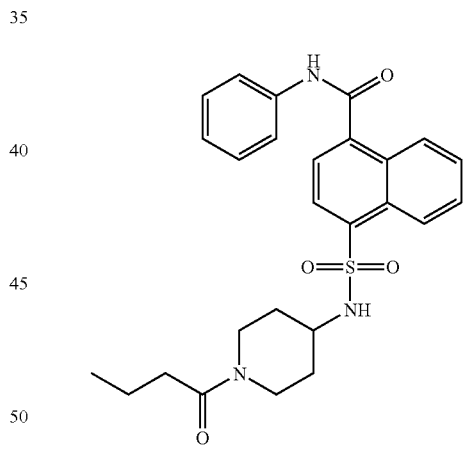

4-(1-Butyryl-piperidin-4-ylsulfamoyl)-naphthalene-1-carboxylic acid phenylamide (F-25)

The title compound was prepared according to the general procedure in Scheme 11, substituting 4-(piperidin-4-ylsulfamoyl)-naphthalene-1-carboxylic acid phenylamide for 4-(piperidin-4-ylsulfamoyl)-naphthalene-1-carboxylic acid cyclohexylamide, and butyryl chloride for ethyl chloroformate. $^1$H NMR (300 MHz, CDCl$_3$) δ 8.87 (s, 1H), 8.67 (m, 1H), 8.36 (m, 2H), 8.25 (d, 1H), 8.08 (m, 2H), 7.87 (d, 1H), 7.78 (d, 1H), 7.70 (m, 1H), 7.63 (m, 1H), 5.50 (d, 1H), 3.95 (m, 1H), 3.55 (m, 1H), 3.26 (m, 1H), 2.88 (m, 1H), 2.48 (m, 1H), 2.13 (m, 2H), 1.66 (m, 2H), 1.48 (m, 3H), 1.19 (m, 1H), 0.88 (t, 3H); LC/MS m/z 480 (M+H)$^+$.

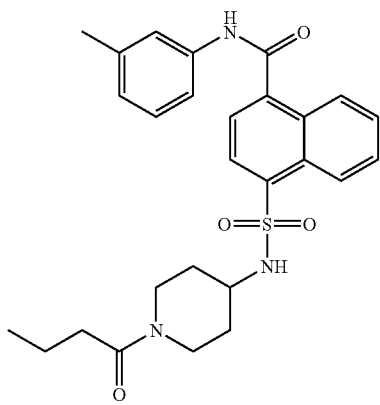

4-(1-Butyryl-piperidin-4-ylsulfamoyl)-naphthalene-1-carboxylic acid m-tolylainde (F-26)

The title compound was prepared according to the general procedure in Scheme 11, substituting 4-(piperidin-4-ylsulfamoyl)-naphthalene-1-carboxylic acid m-tolylamide for 4-(piperidin-4-ylsulfamoyl)-naphthalene-1-carboxylic acid cyclohexylamide, and butyryl chloride for ethyl chloroformate. $^1$H NMR (300 MHz, CDCl$_3$) δ 8.65 (d, 1H), 8.35 (d, 1H), 8.27 (m, 2H), 7.70 (m, 2H), 7.60 (s, 1H), 7.52 (m, 1H), 7.28 (m, 2H), 7.02 (d, 1H), 5.10 (d, 1H), 4.07 (m, 1H), 3.58 (m, 1H), 3.23 (m, 1H), 2.90 (m, 1H), 2.50 (m, 1H), 2.14 (m, 2H), 1.57 (m, 4H), 1.21 (m, 1H), 1.04 (m, 1H), 0.89 (t, 3H); LC/MS m/z 494 (M+H)$^+$.

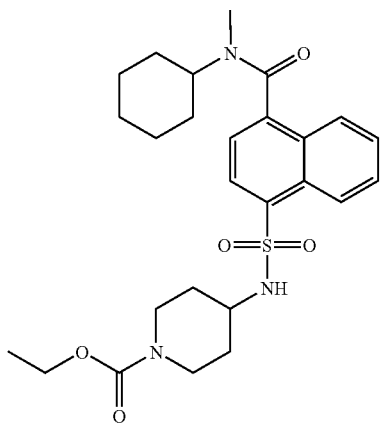

4-[4-(Cyclohexyl-methyl-carbamoyl)-naphthalene-1-sulfonylamino]-piperidine-1-carboxylic acid ethyl ester (F-27)

The title compound was prepared according to the general procedure in Scheme 11, substituting 4-(piperidin-4-ylsulfamoyl)-naphthalene-1-carboxylic acid cyclohexyl-methylamide for 4-(piperidin-4-ylsulfamoyl)-naphthalene-1-carboxylic acid cyclohexylamide. $^1$H NMR (300 MHz, CDCl$_3$) δ 8.61 (d, 1H), 8.29 (d, 1H), 7.88 (m, 1H), 7.65 (m, 2H), 7.42 (m, 1H), 4.83 (m, 1H), 4.72 (m, 1H), 4.05 (q, 2H), 3.88 (m, 2H), 3.25 (m, 1H), 3.05 (m, 1H), 2.80 (s, 3H), 2.74 (m, 1H), 1.90 (m, 4H), 1.54 (m, 8H), 1.20 (t, 3H), 0.85 (m, 2H); LC/MS m/z 502 (M+H)$^+$.

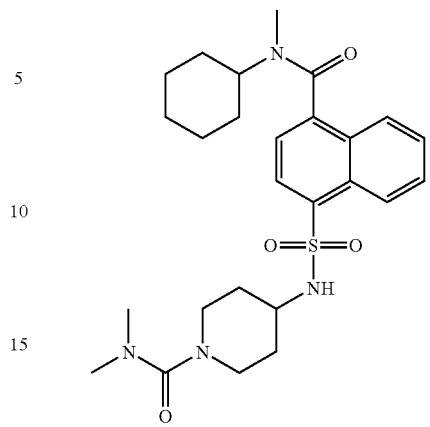

4-[4-(Cyclohexyl-methyl-carbamoyl)-naphthalene-1-sulfonylamino]-piperidine-1-carboxylic acid dimethylamide (F-28)

The title compound was prepared according to the general procedure in Scheme 11, substituting 4-(piperidin-4-ylsulfamoyl)-naphthalene-1-carboxylic acid cyclohexyl-methylamide for 4-(piperidin-4-ylsulfamoyl)-naphthalene-1-carboxylic acid cyclohexylamide, and dimethylcarbamyl chloride for ethyl chloroformate. $^1$H NMR (300 MHz, CDCl$_3$) δ 8.63 (d, 1H), 8.28 (d, 1H), 7.87 (m, 1H), 7.62 (m, 2H), 7.21 (m, 1H), 5.35 (m, 1H), 5.27 (d, 1H), 4.74 (m, 1H), 3.48 (m, 1H), 3.35 (m, 1H), 3.27 (m, 1H), 3.05 (m, 1H), 2.72 (s, 6H), 2.60 (s, 3H), 1.83 (m, 4H), 1.50 (m, 8H), 0.82 (m, 2H); LC/MS m/z 501 (M+H)$^+$.

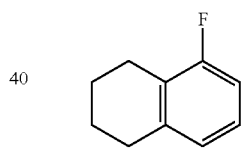

Preparation of 5-fluoro-1,2,3,4-tetrahydro-naphthalene

A modified procedure of Mirsadehgi et al. was used (*J. Org. Chem.* 1989, 54, 3091).

Boron trifluoride etherate (30.0 g, 26.8 mL, 0.21 mol) was dissolved and stirred in dimethoxyethane (50 mL) and cooled to 0° C. A solution of tetrahydro-1-naphthylamine (25 g, 0.17 mol) in dimethoxyethane (75 mL) was added dropwise and the solution was allowed to warm slowly to room temperature over the period of 1 hour. The reaction was cooled to 0° C. and a solution of t-butyl nitrite (18.0 g, 20.7 mL, 0.17 mol) in dimethoxyethane (75 mL) was added dropwise. The reaction was stirred for 2 hours at 0° C. upon which a large quantity of material crystallized. The solvent was removed in vacuo and chlorobenzene (200 mL) was charged to the reaction flask. The flask was stirred vigorously and heated to 135° C. (Caution: N$_2$ evolution) for 1 hour until gas evolution ceased. The flask was cooled to room temperature and the solvent removed in vacuo. Kughelrohr distillation of the residue (1 mm Hg) afforded a yellow liquid. Wt: 14.4 g (56%). $^1$H NM (300 MHz, CDCl$_3$) δ 7.04 (dd, 1H), 6.83 (m, 2H), 2.75 (m, 4H), 1.80 (m, 4H)

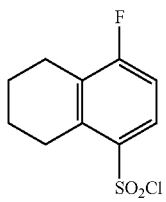

Preparation of 4-fluoro-5,6,7,8-tetrahydro-naphthalene-1-sulfonyl chloride

The compound was prepared according to Scheme 10 in a similar manner to the method for preparing 4-fluoro-naphthalene-1-sulfonyl chloride. Chlorosulfonic acid (2.65 g, 1.5 mL, 22.7 mmol) was stirred in a round-bottom flask cooled by a water bath at room temperature. 5-Fluoro-1,2,3,4-tetrahydro-naphthalene (0.62 g, 4.13 mmol) was added dropwise and the dark mixture was stirred for 30 minutes until gas evolution ceased. The reaction mixture was poured carefully over a mixture of ice (75 g) and dichloromethane (100 mL) and charged to a separatory funnel. The organic layer was separated, washed with brine and dried over MgSO$_4$. Filtration and concentration in vacuo afforded a tan solid. Wt.: 860 mg (86%). $^1$H NMR (300 MHz, CDCl$_3$) δ 7.97 (dd, 1H), 7.02 (t, 1H), 3.27 (m, 2H), 2.80 (m, 2H), 1.86 (m, 4H).

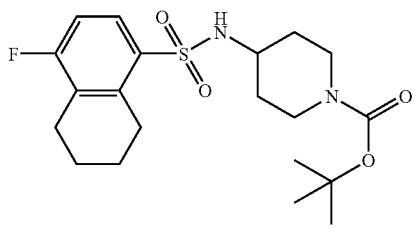

4-(4-Fluoro-5,6,7,8-tetrahydro-naphthalene-1-sulfonylamino)-piperidine-1-carboxylic acid tert-butyl ester 4-Fluoro-5,6,7,8-tetrahydro-naphthalene-1-sulfonyl chloride (860 mg, 3.46 mmol) was dissolved in THF (10 mL). Triethylamine (350 mg, 0.49 mg, 3.46 mmol) was added, followed by 4-amino-piperidine-1-carboxylic acid tert-butyl ester (694 mg, 3.46 mmol). The reaction mixture was stirred overnight at room temperature. The reaction was diluted with dichloromethane (50 mnL) and charged to a separatory funnel. The organic layer was washed with water and brine, then dried over MgSO$_4$. Filtration and concentration in vacuo afforded a yellow foam. Wt.: 1.35 g (95%). $^1$H NMR (300 MHz, CDCl$_3$) δ 7.88 (dd, 1H), 6.95 (t, 1H), 4.47 (d, 1H), 3.93 (m, 2H), 3.27 (m, 1H), 3.11 (m, 2H), 2.76 (m, 4H), 1.81 (m, 6H), 1.44 (s, 9H), 1.32 (m, 2H); LC/MS m/z 411 (M−H)$^-$.

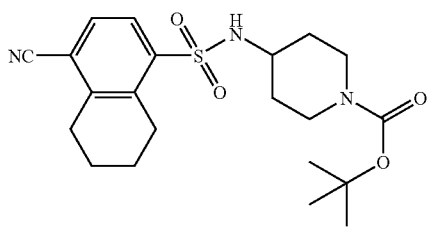

Preparation of 4-(4-Cyano-5,6,7,8-tetrahydro-naphthalene-1-sulfonylamino)-piperidine-1-carboxylic acid tert-butyl ester 4-(4-Fluoro-5,6,7,8-tetrahydro-naphthalene-1-sulfonylamino)-piperidine-1-carboxylic acid tert-butyl ester (970 mg, 2.35 mmol) was dissolved in DMSO (10 mL) and sodium cyanide (577 mg, 11.77 mmol) was added. The mixture was heated overnight at 100° C. An additional 5 equivalents of sodium cyanide (577 mg, 11.77 mmol) were added and the reaction was stirred overnight at 100° C. The reaction was cooled to room temperature and diluted with dichloromethane (100 mL). The mixture was charged to a separatory funnel and extracted three times with water, brine and then dried over MgSO$_4$. Filtration and concentration in vacuo afforded a brown color foam that was triturated with EtOAc to afford a tan solid. Wt.: 550 mg (56%) $^1$H NMR (300 MHz, CDCl$_3$) δ 7.87 (d, 1H), 7.48 (d, 1H), 4.52 (d, 1H), 3.93 (m, 2H), 3.30 (m, 1H), 3.07 (m, 4H), 2.73 (m, 2H), 1.80 (m, 6H), 1.37 (s, 9H), 1.30 (m, 2H); LC/MS m/z 418 (M−H)$^-$.

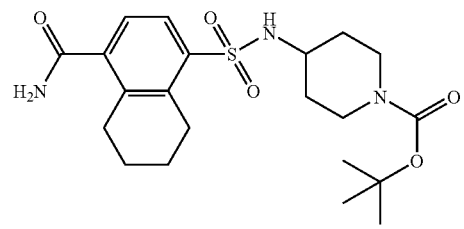

4-(4-Carbamoyl-5,6,1,8-tetrahydro-naphthalene-1-sulfonylamino)-piperidine-1-carboxylic acid tert-butyl ester (F-29) and 4-(4-carboxy-5,6,7,8-tetrahydro-naphthalene-1-sulfonylamino)-piperidine-1-carboxylic acid tert-butyl ester 4-(4-Cyano-5,6,7,8-tetrahydro-naphthalene-1-sulfonylamino)-piperidine-1-carboxylic acid tert-butyl ester (545 mg, 1.30 mmol) was dissolved in a mixture of isopropanol (2 ml) and 2N KOH (4 mL). The reaction was stirred for 5 days at 80° C. The isopropanol was removed in vacuo and the residue was diluted with H$_2$O (20 mL). The mixture was charged to a separatory funnel and extracted three times with dichloromethane. The combined organic layers were washed with brine, dried over MgSO$_4$, and concentrated in vacuo to a white solid that was triturated with dichloromethane to afford 4-(4-carbamoyl-5,6,7,8-tetrahydro-naphthalene-1-sulfonylamino)-piperidine-1-carboxylic acid tert-butyl ester F-29 as a white solid. Wt.: 340 mg (60%). $^1$H NMR (300 MHz, D-DMSO) δ 7.81 (m, 2H), 7.72 (d, 1H), 7.52 (s, 1H), 7.23 (d, 1H), 3.72 (m, 2H), 3.09 (m, 3H), 2.81 (m, 2H), 2.71 (m, 2H), 1.70 (m, 4H), 1.55 (m, 2H), 1.36 (s, 9H), 1.25 (m, 2H); LC/MS m/z 436 (M−H)$^-$. The aqueous extract was acidified to pH 2 with 1N HCl and extracted twice with dichloromethane. The combined organic extracts were washed with brine and dried over MgSO$_4$. Filtration and concentration in vacuo afforded 4-(4-carboxy-5,6,7,8-tetrahydro-naphthalene-1-sulfonylamino)-piperidine-1-carboxylic acid tert-butyl ester as a white solid. Wt.: 76 mg (13%). $^1$H NMR (300 MHz, d$^6$-DMSO) δ 7.72 (d, 1H), 7.33 (s, 1H), 7.23 (d, 1H), 3.72 (m, 2H), 3.09 (m, 3H), 2.81 (m, 2H), 2.71 (m, 2H), 1.70 (m, 4H), 1.55 (m, 2H), 1.36 (s, 9H), 1.25 (m, 2H); LC/MS m/z 437 (M−H)$^-$.

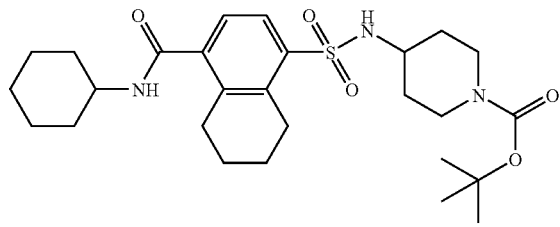

4-[4-(3-Dimethylamino-propylcarbamoyl)-5,6,7,8-tetrahydro-naphthalene-1-sulfonylamino]-piperidine-1-carboxylic acid tert-butyl ester (F-30) and 4-(4-Cyclohexylcarbamoyl-5,6,7,8-tetrahydro-naphthalene-1-sulfonylamino)-piperidine-1-carboxylic acid tert-butyl ester (F-31)

4-(4-Carboxy-5,6,7,8-tetrahydro-naphthalene-1-sulfonylamino)-piperidine-1-carboxylic acid tert-butyl ester (76 mg, 0.17 mmol) was dissolved in dichloromethane (2 mL). 1-[3-(Dimethylamino)propyl]-3-ethylcarbodiimide hydrochloride (32 mg, 0.17 mmol) was added followed by cyclohexylamine (21 mg, 24 ml, 0.21 mmol). The reaction was stirred overnight at room temperature. The reaction was diluted with dichloromethane (15 ml0 and charged to a separatory funnel. The organic layer was washed twice with water, brine and dried over MgSO$_4$. Filtration and concentration in vacuo afforded a clear oil that was subjected to flash column chromatography (96:4 dichloromethane:methanol). Concentration of the more polar fractions afforded 4-[4-(3-dimethylamino-propylcarbamoyl)-5,6,7,8-tetrahydro-naphthalene-1-sulfonylamino]-piperidine-1-carboxylic acid tert-butyl ester (F-30) as a yellow solid. Wt.: 40 mg, (45%). $^1$H NMR (300 MHz, CDCl$_3$) δ 9.05 (s, 1H), 7.98 (d, 1H), 7.31 (d, 1H), 5.02 (d, 1H), 3.96 (m, 3H), 3.37 (m, 2H), 3.20 (m, 2H), 2.83 (m, 4H), 2.70 (s, 6H), 2.13 (m, 2H), 1.97 (m, 2H), 1.83 (m, 4H), 1.42 (s, 9H), 1.32 (m, 4H); LC/MS m/z 523 (M+H)$^+$. Concentration of the less polar fractions afforded 4-(4-cyclohexylcarbamoyl-5,6,7,8-tetrahydro-naphthalene-1-sulfonylamino)-piperidine-1-carboxylic acid tert-butyl ester (F-31) as a clear oil. Wt.: 28 mg (32%) $^1$H NMR (300 MHz, CDCl$_3$) δ 7.87 (d, 1H), 7.20 (d, 1H), 5.73 (d, 1H), 4.38 (d, 1H), 3.91 (m, 3H), 3.22 (m, 1H), 3.12 (m, 2H), 2.89 (m, 2H), 2.73 (m, 2H), 2.03 (m, 2H), 1.78 (m, 8H), 1.74 (m, 2H), 1.43 (s, 9H), 1.27 (m, 6H); LC/MS m/z 518 (M−H)$^−$.

Scheme 12

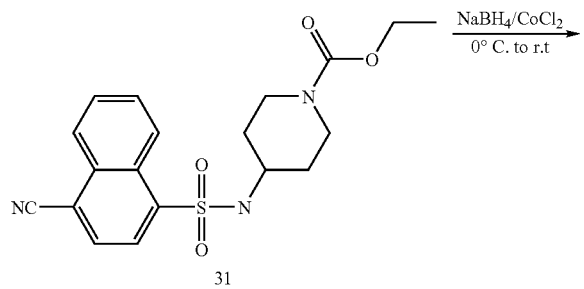

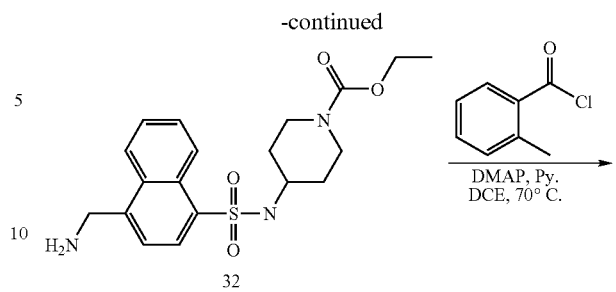

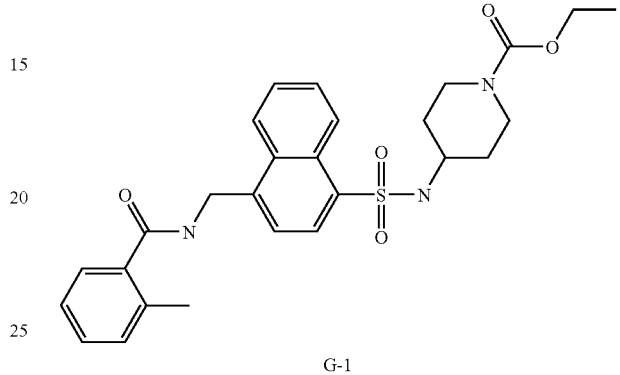

G-1

4-{4-[(2-Methyl-benzoylamino)-methyl]-naphthalene-1-sulfonylamino}-piperidine-1-carboxylic acid ethyl ester (G-1)

4-(4-cyano-naphthalene-1-sulfonylamino)-piperidine-1-carboxylic acid ethyl ester (31) was prepared according to the procedure in Scheme 11, substituting for 4-(4-fluoro-naphthalene-1-sulfonylamino)-piperidine-1-carboxylic acid ethyl ester for 4-(4-fluoro-naphthalene-1-sulfonylamino)-piperidine-1-carboxylic acid tert-butyl ester. To a 0° C. solution of 4-(4-cyano-naphthalene-1-sulfonylamino)-piperidine-1-carboxylic acid ethyl ester (31) (615 mg, 1.59 mmol) in EtOH (10 mL) was added cobalt chloride (207 mg, 1.59 mmol). After stirring at 0° C. for 5 min under argon, sodium borohydride (181 mg, 4.77 mmol) was added into the reaction mixture. The resultant solution was stirred at 0° C. for 30 minutes, and then warmed up to room temperature. After stirring for another 30 min., the resultant mixture was quenched with water. The aqueous layer was extracted with CH$_2$Cl$_2$. The organic extracts were combined, washed with brine and dried over MgSO$_4$. The solution was filtered and concentrated in vacuo to give the crude product. The crude material was purified by Flash column chromatography (CH$_2$Cl$_2$: MeOH) to provide 268 mg (43.0% yield) of 4-(4-aminomethyl-naphthalene-1-sulfonylamino)-piperidine-1-carboxylic acid ethyl ester (32). LC/MS showed m/z: 392 (M+H)$^+$.

To a solution of 4-(4-aminomethyl-naphthalene-1-sulfonylamino)-piperidine-1-carboxylic acid ethyl ester (32) (60 mg, 0.153 mmol) in DCE (5 mL), was added pyridine (62 ul, 0.765 mmol), 2-methyl-benzoyl chloride (22ul, 0.168 mmol) and dimethyl-pyridin-4-yl-amine (4 mg, 0.031 mmol). After stirring at 70° C. overnight, the resultant solution was concentrated in vacuo to give the crude product. Purification using reverse phase HPLC provided the title compound (G-1). LC/MS showed m/z: 510 (M+H)$^+$.

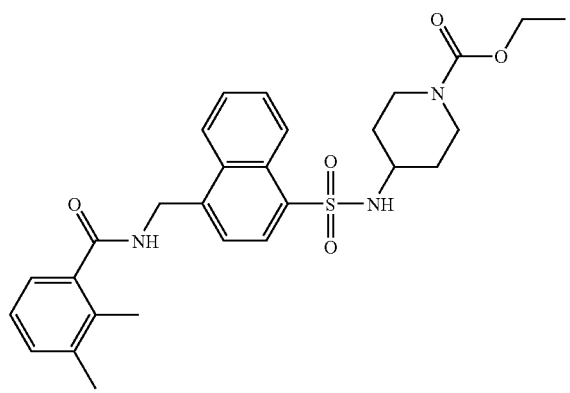

4-{4-[(2,3-Dimethyl-benzoylamino)-methyl]-naphthalene-1-sulfonylamino}-piperidine-1-carboxylic acid ethyl ester (G-2)

The title compound was made following general procedure in scheme 10, substituting 2,3-dimethyl-benzoyl chloride for 2-methyl-benzoyl chloride. $^1$H NMR (300 MHz, CDCl$_3$) δ 8.63 (m, 1H), 8.18 (t, 2H), 7.65 (m, 2H), 7.52 (d, 1H), 7.32 (t, 2H), 7.04 (m, 1H), 6.80 (m, 1H), 5.10 (s, 2H), 4.00 (q, 2H), 3.80 (d, 2H), 3.20 (m, 1H), 2.70 (t, 2H), 2.26 (s, 3H), 2.23 (s, 3H), 1.55 (m, 2H), 1.20 (m, 2H), 1.14 (t, 3H); LC/MS m/z 524 (M+H)$^+$

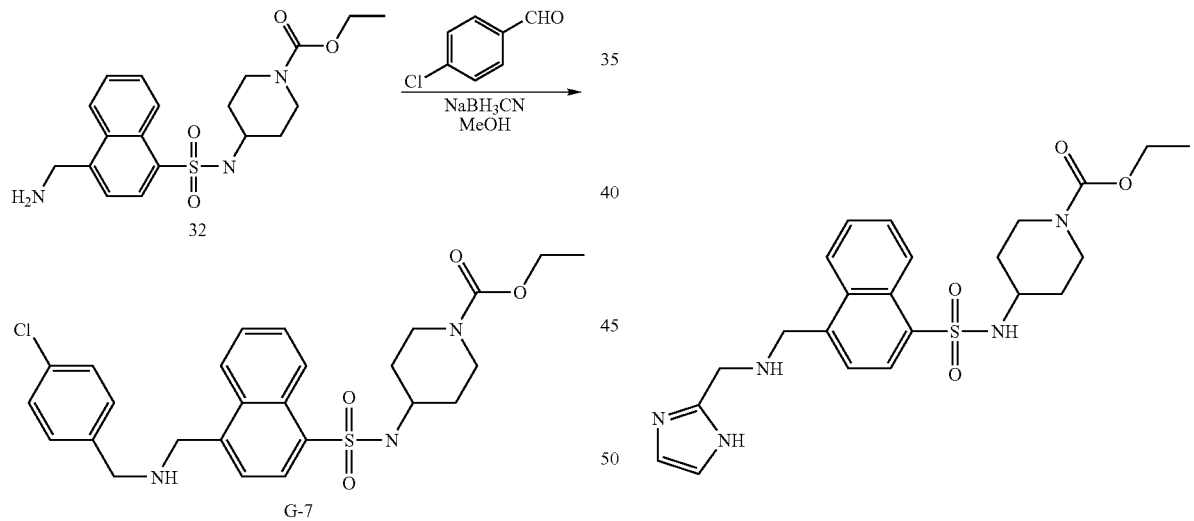

Scheme 13

4-{4-[(4-Chloro-benzylamino)-methyl]-naphthalene-1-sulfonylamino}-piperidine-1-carboxylic acid ethyl ester (G-7)

4-(4-Aminomethyl-naphthalene-1-sulfonylamino)-piperidine-1-carboxylic acid ethyl ester (32) was prepared according to the procedure in Scheme 12. To a 25° C. solution of 4-(4-aminomethyl-naphthalene-1-sulfonylamino)-piperidine-1-carboxylic acid ethyl ester (32) (62 mg, 0.159 mmol) in MeOH (4 mL) was added 4-chloro-benzaldehyde (45 mg, 0.318 mmol) and sodium cyanoborohydride (50 mg, 0.795 mmol). After stirring for 2 h at 25° C., the solution was concentrated in vacuo to give a solid. The resultant solid was purified by reverse phase HPLC providing 4-{4-[(4-chloro-benzylamino)-methyl]-naphthalene-1-sulfonylamino}-piperidine-1-carboxylic acid ethyl ester formate salt (G-7). $^1$H NMR (300 MHz, MeOD) δ 8.76 (m, 1H), 8.38 (s, br, 1H), 8.24 (d, 1H), 8.18 (m, 1H), 7.51 (m, 3H), 7.44 (m, 4H), 4.52 (s, 2H), 4.12 (s, 2H), 4.04 (q, 2H), 3.60 (d, 2H), 3.40 (m, 1H), 2.72 (m, 2H), 1.50 (m, 2H), 1.25 (m, 2H), 1.18 (t, 3H); LC/MS m/z 516 (M+H)$^+$.

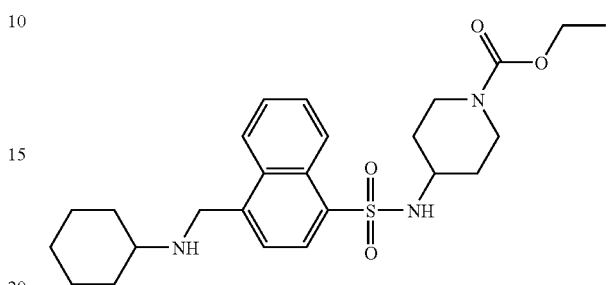

4-(4-Cyclohexylainnomethyl-naphthalene-1-suffonylamino)-piperidine-1-carboxylic acid ethyl ester (G-8)

The title compound was prepared as its formate salt following the general procedure in Scheme 13, substituting cyclohexanone for 4-chloro-benzaldehyde. $^1$H NMR (300 MHz, CDCl$_3$) δ 8.54 (d, 1H), 8.25 (s, br, 1H), 8.17 (s, 1H), 8.04 (t, 2H), 7.70 (d, 1H), 7.57 (m, 2H), 6.15 (d, 1H), 4.48 (s, 2H), 4.04 (q, 2H), 3.80 (d, 2H), 3.25 (s, br, 1H), 3.00 (t, 1H), 2.70 (s, br, 1H), 2.60 (s, 1H), 2.10 (d, 2H), 1.80 (d, 2H), 1.50 (m, 5H), 1.20 (m, 7H); LC/MS m/z 475 (M+H)$^+$

4-(4-{[(lH-Imidazol-2-ylmethyl)-amino]-methyl}-naphthalene-1-sulfonylamino)-piperidine-1-carboxylic acid ethyl ester (G-9)

The title compound was prepared as its formate salt following the general procedure in Scheme 13, substituting 1H-imidazole-2-carbaldehyde for 4-chloro-benzaldehyde. $^1$H NMR (300 MHz, MeOD) δ 8.72 (m, 1H), 8.40 (s, br, 1H), 8.22 (m, 2H), 7.67 (m, 3H), 7.09 (s, 2H), 4.32 (s, 2H), 4.04 (m, 4H), 3.80 (d, 2H), 3.20 (m, 1H), 2.75 (m, 2H), 1.50 (m, 2H), 1.25 (m, 2H), 1.18 (t, 3H); LC/MS m/z 472 (M+H)$^+$

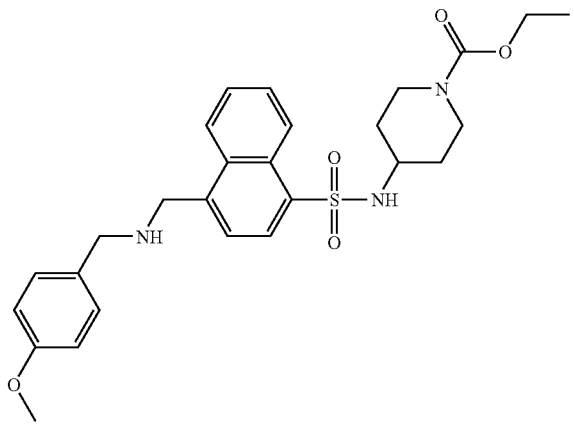

4-{4-[(4-Methoxy-benzylamino)-methyl]-naphthalene-1-sulfonylamino}-piperidine-1-carboxylic acid ethyl ester (G-10)

The title compound was prepared as its formate salt following the general procedure in Scheme 13, substituting 4-methoxy-benzaldehyde for 4-chloro-benzaldehyde. $^1$H NMR (300 MHz, MeOD) δ 8.73 (d, 1H), 8.22 (d, 1H), 8.14 (d, 1H), 7.66 (m, 3H), 7.33 (d, 2H), 6.92 (d, 2H), 4.30 (s, 2H), 4.12 (s, 2H), 4.04 (q, 2H), 3.90 (s, 2H), 3.80 (m, 5H), 3.18 (m, 1H), 2.75 (m, 2H), 1.50 (m, 2H), 1.25 (m, 2H), 1.18 (t, 3H); LC/MS m/z 512 (M+H)$^+$

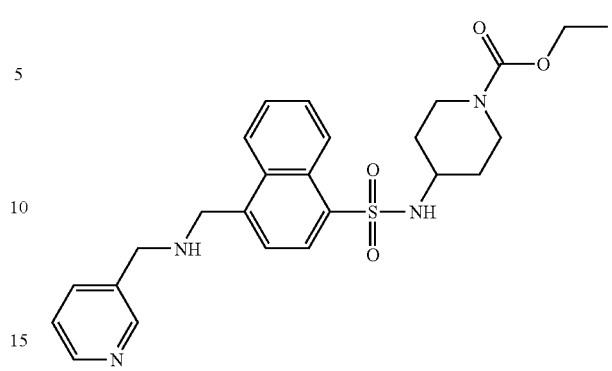

4-(4-{[(Pyridin-3-ylmethyl)-amino]-methyl}-naphthalene-1-sulfonylamino)-piperidine-1-carboxylic acid ethyl ester (G-12)

The title compound was prepared as its formate salt following the general procedure in Scheme 13, substituting pyridine-3-carbaldehyde for 4-chloro-benzaldehyde. $^1$H NMR (300 MHz, MeOD) δ 8.72 (dd, 1H), 8.57 (s, 1H), 8.44 (d, 1H), 8.22 (m, 2H), 7.90 (d, 1H), 7.64 (m, 3H), 7.42 (dd, 1H), 4.30 (s, 2H), 4.05 (q, 2H), 3.95 (s, 2H), 3.68 (d, 2H), 3.18 (m, 1H), 2.75 (m, 2H), 1.50 (m, 2H), 1.25 (m, 2H), 1.18 (t, 3H); LC/MS m/z 483 (M+H)$^+$

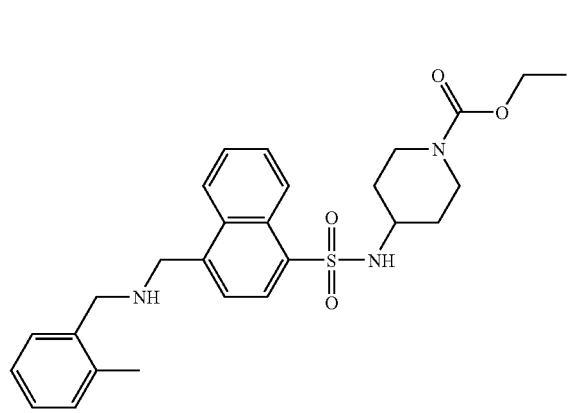

4-{4-[(2-Methyl-benzylamino)-methyl]-naphthalene-1-sulfonylamino}-piperidine-1-carboxylic acid ethyl ester (G-11)

The title compound was prepared as its formate salt following the general procedure in Scheme 13, substituting 2-methyl-benzaldehyde for 4-chloro-benzaldehyde. $^1$H NMR (300 MHz, MeOD) δ 8.76 (d, 1H), 8.22 (m, 2H), 7.70 (m, 3H), 7.38 (m, 1H), 7.21 (m, 3H), 4.51 (s, 2H), 4.05 (m, 4H), 3.80 (d, 2H), 3.20 (m, 1H), 2.75 (m, 2H), 2.30 (s, 3H), 1.50 (m, 2H), 1.25 (m, 2H), 1.18 (t, 3H); LC/MS m/z 496 (M+H)$^+$

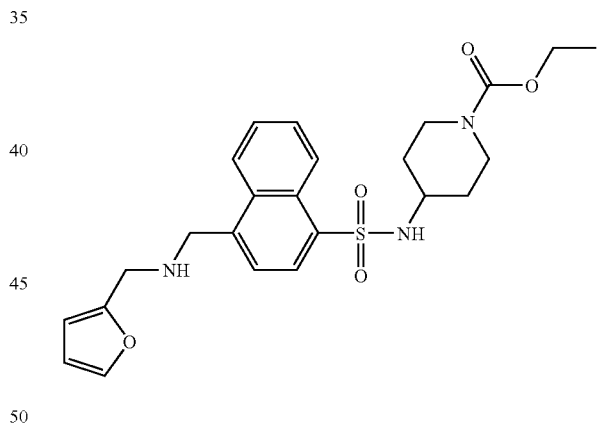

4-(4-{[(Furan-2-ylmethyl)-amino]-methyl}-naphthalene-1-sulfonylamino)-piperidine-1-carboxylic acid ethyl ester (G-13)

The title compound was prepared as its formate salt following the general procedure in Scheme 13, substituting furan-2-carbaldehyde for 4-chloro-benzaldehyde. $^1$H NMR (300 MHz, MeOD) δ 8.72 (dd, 1H), 8.18 (m, 2H), 7.65 (m, 3H), 7.49 (m, 1H), 6.39 (m, 1H), 6.34 (m, 1H), 4.28 (s, 2H), 4.05 (q, 2H), 3.92 (s, 2H), 3.80 (d, 2H), 3.18 (m, 1H), 2.75 (m, 2H), 1.50 (m, 2H), 1.25 (m, 2H), 1.18 (t, 3H); LC/MS m/z 472 (M+H)

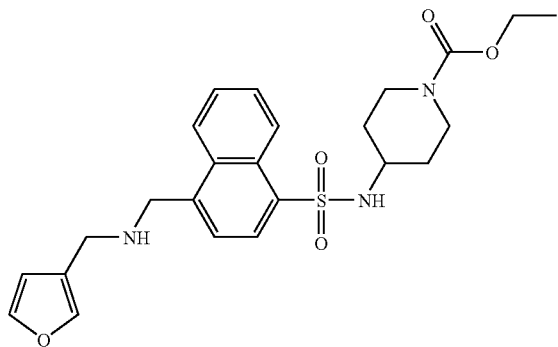

4-(4-{[(Furan-3-ylmethyl)-amino]-methyl}-naphthalene-1-sulfonylamino)-piperidine-1-carboxylic acid ethyl ester (G-14)

The title compound was prepared as its formate salt following the general procedure in Scheme 13, substituting furan-3-carbaldehyde for 4-chloro-benzaldehyde. $^1$H NMR (300 MHz, MeOD) δ 8.76 (m, 1H), 8.22 (m, 2H), 7.64 (m, 5H), 6.56 (m, 1H), 4.42 (s, 2H), 4.05 (q, 2H), 3.95 (s, 2H), 3.80 (d, 2H), 3.20 (m, 1H), 2.75 (m, 2H), 1.50 (m, 2H), 1.25 (m, 2H), 1.18 (t, 3H); LC/MS m/z 472 (M+H)$^+$

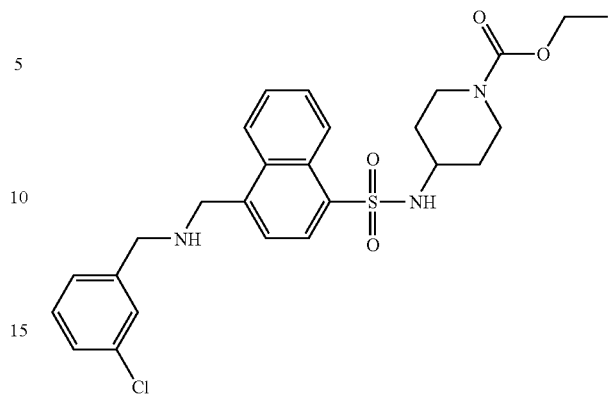

4-{4-[(3-Chloro-benzylamino)-methyl]-naphthalene-1-sulfonylamino}-piperidine-1-carboxylic acid ethyl ester (G-16)

The title compound was prepared as its formate salt following the general procedure in Scheme 13, substituting 3-chloro-benzaldehyde for 4-chloro-benzaldehyde. $^1$H NMR (300 MHz, MeOD) δ 8.72 (d, 1H), 8.20 (m, 2H), 7.66 (m, 3H), 7.45 (s, 1H), 7.30 (m, 3H), 4.25 (s, 2H), 4.05 (q, 2H), 3.90 (s, 2H), 3.78 (d, 2H), 3.20 (m, 1H), 2.75 (m, 2H), 1.50 (m, 2H), 1.25 (m, 2H), 1.17 (t, 3H); LC/MS m/z 516 (M+H)$^+$

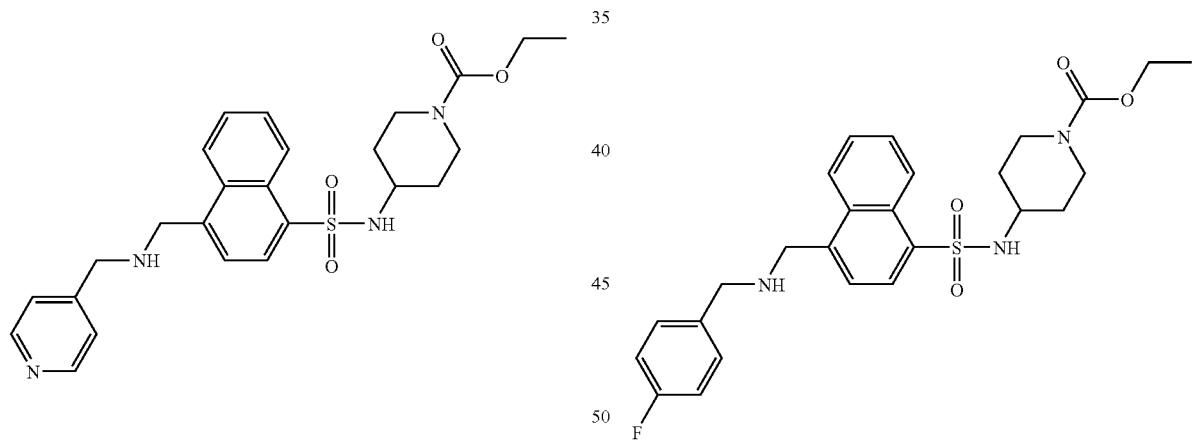

4-(4-{[(Pyridin-4-ylmethyl)-ainno]-methyl}-naphthalene-1-sulfonylamino)-piperidine-1-carboxylic acid ethyl ester (G-15)

The title compound was prepared as its formate salt following the general procedure in Scheme 13, substituting pyridine-4-carbaldehyde for 4-chloro-benzaldehyde. $^1$H NMR (300 MHz, MeOD) δ 8.70 (m, 1H), 8.54 (s, 1H), 8.24 (m, 4H), 7.68 (m, 2H), 7.45 (m, 1H), 7.14 (m, 1H), 4.70 (m, 2H), 4.55 (m, 2H), 4.05 (q, 2H), 3.80 (d, 2H), 3.18 (m, 1H), 2.75 (m, 2H), 1.50 (m, 2H), 1.25 (m, 2H), 1.18 (t, 3H); LC/MS m/z 483 (M+H)$^+$

4-{4-[(4-Fluoro-benzylamino)-methyl]-naphthalene-1-sulfonylamino}-piperidine-1-carboxylic acid ethyl ester (G-17)

The title compound was prepared as its formate salt following the general procedure in Scheme 13, substituting 4-fluoro-benzaldehyde for 4-chloro-benzaldehyde. $^1$H NMR (300 MHz, MeOD) δ 8.72 (d, 1H), 8.19 (m, 2H), 7.66 (m, 3H), 7.40 (m, 2H), 7.06 (m, 2H), 4.25 (s, 2H), 4.05 (q, 2H), 3.85 (s, 2H), 3.78 (d, 2H), 3.18 (m, 1H), 2.75 (m, 2H), 1.50 (m, 2H), 1.25 (m, 2H), 1.17 (t, 3H); LC/MS m/z 500 (M+H)$^+$

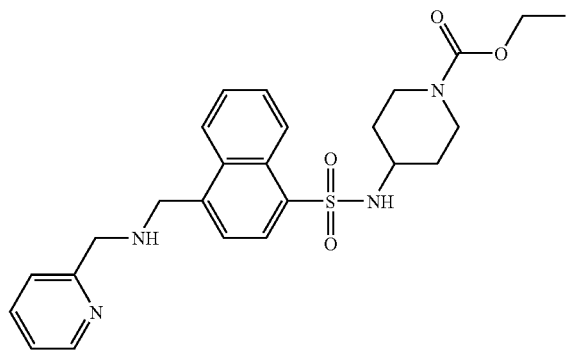

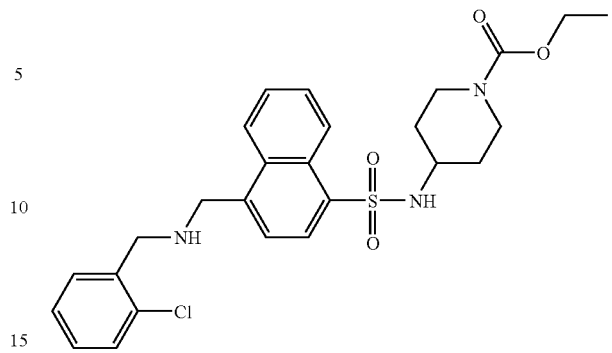

4-(4-{[(Pyridin-2-ylmethyl)-amino]-methyl}-naphthalene-1-sulfonylamino)-piperidine-1-carboxylic acid ethyl ester (G-18)

The title compound was prepared as its formate salt following the general procedure in Scheme 13, substituting pyridine-2-carbaldehyde for 4-chloro-benzaldehyde. $^1$H NMR (300 MHz, MeOD) δ 8.72 (d, 1H), 8.52 (m, 1H), 8.24 (m, 2H), 7.80 (t, 1H), 7.67 (m, 3H), 7.52 (d, 1H), 7.30 (t, 1H), 4.30 (s, 2H), 4.00 (m, 4H), 3.80 (d, 2H), 3.18 (m, 1H), 2.75 (m, 2H), 1.50 (m, 2H), 1.25 (m, 2H), 1.17 (t, 3H); LC/MS m/z 483 (M+H)$^+$ 4-{4-[(2-Chloro-benzylamino)-methyl]-naphthalene-1-sulfonylamino}-piperidine-1-carboxylic acid ethyl ester (G-21)

The title compound was prepared as its formate salt following the general procedure in Scheme 13, substituting 2-chloro-benzaldehyde for 4-chloro-benzaldehyde. $^1$H NMR (300 MHz, MeOD) δ 8.72 (d, 1H), 8.15 (d, 2H), 7.66 (m, 3H), 7.52 (m, 1H), 7.38 (m, 1H), 7.28 (m, 2H), 4.30 (s, 2H), 4.00 (m, 4H), 3.78 (d, 2H), 3.18 (m, 1H), 2.72 (m, 2H), 1.50 (m, 2H), 1.25 (m, 2H), 1.17 (t, 3H); LC/MS m/z 516 (M+H)$^+$

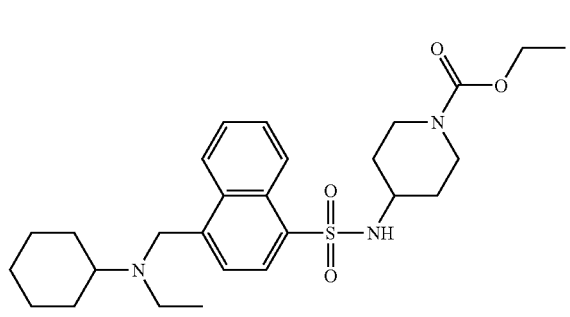

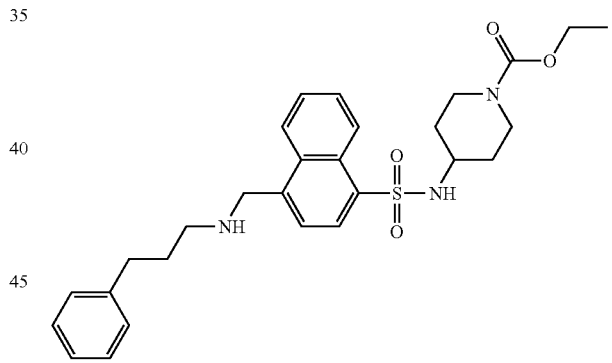

4-{4-[(Cyclohexyl-ethyl-amino)-methyl]-naphthalene-1-sulfonylamino}-piperidine-1-carboxylic acid ethyl ester (G-20)

The title compound was prepared as its formate salt following the general procedure in Scheme 13, substituting acetaldehyde for 4-chloro-benzaldehyde, and substituting 4-(4-cyclohexylaminomethyl-naphthalene-1-sulfonylamino)-piperidine-1-carboxylic acid ethyl ester (G-8) for 4-(4-aminomethyl-naphthalene-1-sulfonylamino)-piperidine-1-carboxylic acid ethyl ester. $^1$H NMR (300 MHz, MeOD) δ 8.79 (m, 1H), 8.36 (m, 2H), 8.27 (dd, 1H), 7.77 (m, 3H), 4.62 (s, 2H), 4.05 (q, 2H), 3.80 (d, 2H), 3.25 (m, 1H), 3.05 (m, 3H), 2.75 (m, 2H), 2.10 (d, 2H), 1.80 (d, 2H), 1.65 (m, 3H), 1.48 (m, 2H), 1.22 (m, 1H); LC/MS m/z 502 (M+H)$^+$ 4-{4-[(3-Phenyl-propylamino)-methyl]-naphthalene-1-sulfonylamino}-piperidine-1-carboxylic acid ethyl ester (G-23)

The title compound was prepared as its formate salt following the general procedure in Scheme 13, substituting 3-phenyl-propionaldehyde for 4-chloro-benzaldehyde. $^1$H NMR (300 MHz, MeOD) δ 8.74 (m, 1H), 8.25 (m, 1H), 8.20 (d, 1H), 7.70 (m, 2H), 7.59 (m, 1H), 7.19 (m, 5H), 4.33 (s, 2H), 4.05 (q, 2H), 3.78 (d, 2H), 3.18 (m, 1H), 2.73 (m, 6H), 1.90 (m, 2H), 1.48 (m, 2H), 1.23 (m, 2H), 1.17 (t, 3H); LC/MS m/z 510 (M+H)$^+$

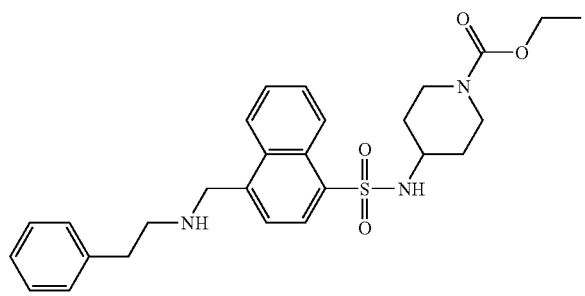

4-[4-(Phenethylamino-methyl)-naphthalene-1-sulfonylamino]-piperidine-1-carboxylic acid ethyl ester (G-24)

The title compound was prepared as its formate salt following the general procedure in Scheme 13, substituting phenyl-acetaldehyde for 4-chloro-benzaldehyde. $^1$H NMR (300 MHz, MeOD) δ 8.74 (m, 1H), 8.19 (m, 2H), 7.67 (m, 2H), 7.59 (m, 1H), 7.22 (m, 5H), 4.35 (s, 2H), 4.05 (q, 2H), 3.78 (d, 2H), 3.18 (m, 1H), 2.92 (m, 4H), 2.62 (m, 2H), 1.90 (m, 2H), 1.48 (m, 2H), 1.25 (m, 2H), 1.17 (t, 3H); LC/MS m/z 496 (M+H)$^+$

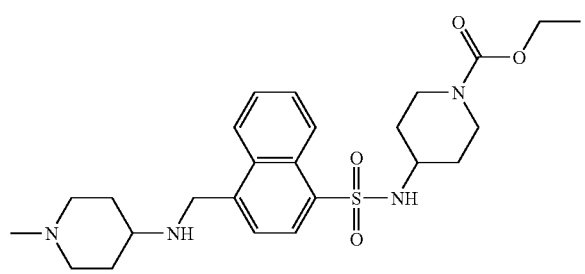

4-{4-[(1-Methyl-piperidin-4-ylamino)-methyl]-naphthalene-1-sulfonylamino}-piperidine-1-carboxylic acid ethyl ester (G-25)

The title compound was prepared as its formate salt following the general procedure in Scheme 13, substituting 1-methyl-piperidin-4-one for 4-chloro-benzaldehyde. $^1$H NMR (300 MHz, CDCl$_3$) δ 8.73 (m, 1H), 8.45 (s, 1H), 8.28 (m, 1H), 8.22 (d, 1H), 7.70 (m, 3H), 4.40 (s, 2H), 4.05 (q, 2H), 3.80 (d, 2H), 3.45 (d, 2H), 3.20 (m, 1H), 3.00 (m, 3H), 2.78 (s, 3H), 2.72 (m, 2H), 2.25 (d, 2H), 1.80 (m, 2H), 1.50 (d, 2H), 1.25 (m, 2H), 1.17 (t, 3H); LC/MS m/z 487 (M+H)$^+$

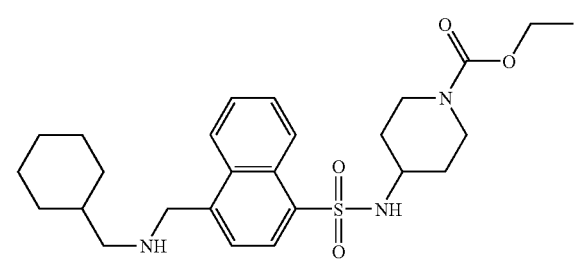

4-{4-[(Cyclohexylmethyl-amino)-methyl]-naphthalene-1-sulfonylamino}-piperidine-1-carboxylic acid ethyl ester (G-27)

The title compound was prepared as its formate salt following the general procedure in Scheme 13, substituting cyclohexanecarbaldehyde for 4-chloro-benzaldehyde. $^1$H NMR (300 MHz, MeOD) δ 8.76 (m, 1H), 8.52 (s, 1H), 8.26 (m, 2H), 7.72 (m, 3H), 4.49 (s, 2H), 4.05 (q, 2H), 3.80 (d, 2H), 3.20 (m, 1H), 2.75 (m, 4H), 1.75 (m, 6H), 1.50 (d, 2H), 1.25 (m, 5H), 1.18 (t, 3H), 1.00 (m, 2H); LC/MS m/z 488 (M+H)$^+$

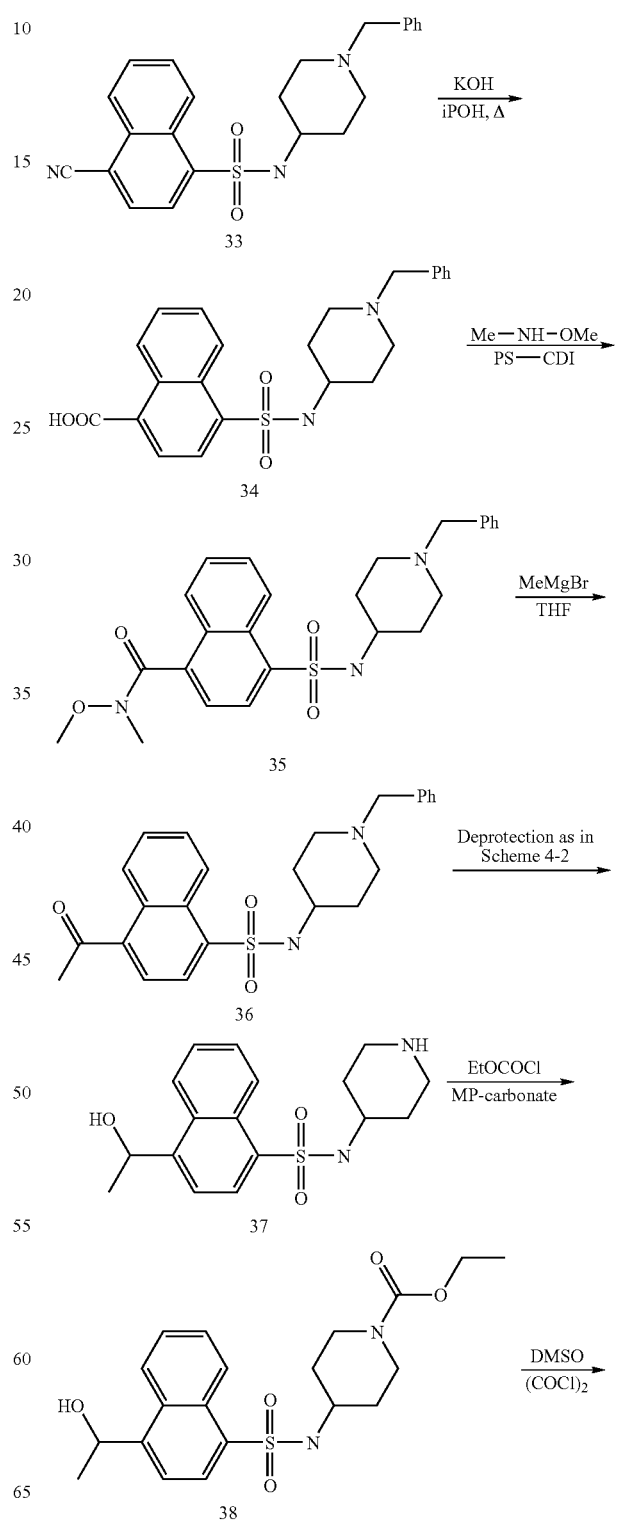

Scheme 14

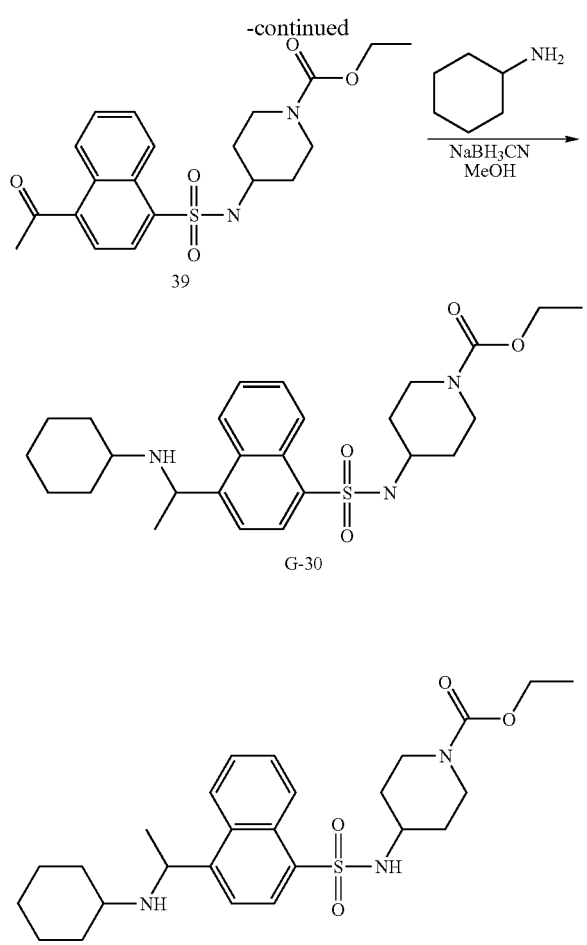

4-[4-(1-Cyclohexylamino-ethyl)-naphthalene-1-sulfonylamino]-piperidine-1-carboxylic acid ethyl ester (G-30)

4-Cyano-naphthalene-1-sulfonic acid (1-benzyl-piperidin-4-yl)-amide (33) was prepared according to the general procedure in Scheme 11, substituting 1-benzyl-piperidin-4-ylamine for 4-amino-piperidine-1-carboxylic acid tert-butyl ester. To a solution of 4-cyano-naphthalene-1-sulfonic acid (1-benzyl-piperidin-4-yl)-amide 33 (3.0 g, 7.43 mmol) in $H_2O$ (70 mL) was added KOH (4.2 g, 75 mmol). After stirring at 100° C. overnight, the resultant mixture became a clear solution. The aqueous layer was washed with $CH_2Cl_2$ twice and acidified to pH 4 by adding hydrochloric acid. After filtration, the resultant solid was dried to give 1.8 g of crude 4-(1-benzyl-piperidin-4-ylsulfamoyl)-naphthalene-1-carboxylic acid 34 in 57% yield. LC/MS showed m/z: 425 $(M+H)^+$. This material was used without further purification.

To a solution of 4-(1-benzyl-piperidin-4-ylsulfamoyl)-naphthalene-1-carboxylic acid 34 (212 mg, 0.5 mmol) in DCE (5 mL), was added O,N-dimethyl-hydroxylamine hydrochloride (59 ul, 0.6 mmol), PS-carbodiimide (1.9 g, 2.5 mmol), triethyl amine (140 uL, 1 mmol) and HOAt (102 mg, 0.75 mmol). After stirring at 50° C. overnight, the resultant solution was filtered and concentrated in vacuo to give the crude product 4-(1-benzyl-piperidin-4-ylsulfamoyl)-naphthalene-1-carboxylic acid methoxy-methyl-amide 35. LC/MS showed m/z: 468 $(M+H)^+$. This material was used without further purification.

To a 0° C. solution of 4-(1-benzyl-piperidin-4-ylsulfamoyl)-naphthalene-1-carboxylic acid methoxy-methyl-amide 35 (200 mg, 0.43 mmol) in THF (5 mL) was slowly added methylmagnesium bromide (5.71 mL, 17.1 mmol, 1M THF solution). After stirring at 25° C. for 4 h, the resultant mixture was quenched with saturated ammonium chloride solution. The aqueous layer was extracted with $CH_2Cl_2$. The organic extracts were combined, washed with brine and dried over $MgSO_4$. The solution was filtered and concentrated in vacuo to give the crude product. The crude material was purified by Flash column chromatography (hexane/EtOAc) to provide 118 mg of 4-acetyl-naphthalene-1-sulfonic acid (1-benzyl-piperidin-4-yl)-amide 36 in 56% overall yield (for two steps).LC/MS showed m/z : 423 $(M+H)^+$.

Following the general procedure in Scheme 4-2, deprotection of 4-acetyl-naphthalene-1-sulfonic acid (1-benzyl-piperidin-4-yl)-amide 36 occurred concomitant with reduction of the ketone group to afford 4-(1-hydroxy-ethyl)-naphthalene-1-sulfonic acid piperidin-4-ylamide acetic acid salt 37 as product. LC/MS showed mm/z: 334 $(M+H)^+$. This material was used without further purification.

To a solution of 4-(1-hydroxy-ethyl)-naphthalene-1-sulfonic acid piperidin-4-ylamide acetic acid salt 37 (290 mg, 0.74 mmol) in MeOH (10 mL) was added MP-Carbonate (1.45 g, 3.69 mmol, 2.54 mmol/g). After shaking at 25° C. for 1h, the solution was filtered. To the resultant solution was added ethyl chloroformate (120 mg, 1.11 mmol). After stirred for another 2 h at 25° C., the solution was concentrated in vacuo to give a solid. The crude material was purified by Flash column chromatography ($CH_2Cl_2$: MeOH) to provide 4-[4-(1-hydroxy-ethyl)-naphthalene-1-sulfonylamino]-piperidine-1-carboxylic acid ethyl ester 38. LC/MS showed m/z 407 $(M+H)^+$.

To a −78° C. solution of oxalyl dihcloride (85 mg, 0.665 mmol) in $CH_2Cl_2$ (10 mL) was added DMSO (104 mg, 1.33 mmol). After stirred at -78° C. for 10 min, a solution of 4-[4-(1-hydroxy-ethyl)-naphthalene-1-sulfonylamino]-piperidine-1-carboxylic acid ethyl ester 38 (180 mg, 0.443 mmol) in $CH_2Cl_2$ was added into the mixture by dropwise. The resultant mixture was stirred at −78° C. for another 30 min, then was added triethyl amine (224 mg, 2.22 mmol). The reaction mixture was warmed up to room temperature and stirred for 2 h. The resultant mixture was quenched with saturated ammonium chloride solution and the aqueous layer was extracted with $CH_2Cl_2$. The organic extracts were combined, washed with brine and dried over $MgSO_4$. The solution was filtered and concentrated in vacuo to give the crude product. The crude material was purified by Flash column chromatography ($CH_2Cl_2$: MeOH) to provide 45 mg of 4-(4-acetyl-naphthalene-1-sulfonylamino)-piperidine-1-carboxylic acid ethyl ester 39 in 25% yield. LC/MS showed m/z: 409 $(M+H)^+$.

To a 25° C. solution of 4-(4-acetyl-naphthalene-1-sulfonylamino)-piperidine-1-carboxylic acid ethyl ester 39 (45 mg, 0.11 mmol) in MeOH (4 mL) was added cyclohexylamine (31 mg, 0.22 mmol) and sodium cyanoborohydride (34 mg, 0.69 mmol). After stirring for 2 h at 25° C., the solution was concentrated in vacuo to give a solid. The resultant solid was purified by reverse phase HPLC providing the title compound (G-30). $^1$H NMR (300 MHz, MeOD) δ 8.84 (m, 1H), 8.42 (s, br, 1H), 8.35 (m, 2H), 7.82 (m, 3H), 5.55 (d, 1H), 4.02 (q, 2H), 3.80 (d, 2H), 3.22(m, 1H), 3.00 (m, 1H), 2.77(s, br, 2H), 2.19 (d, 1H), 2.05 (d, 1H), 1.78 (m, 4H), 1.50 (m, 5H), 1.24 (m, 9H); LC/MS m/z 488 $(M+H)^+$.

Scheme 15

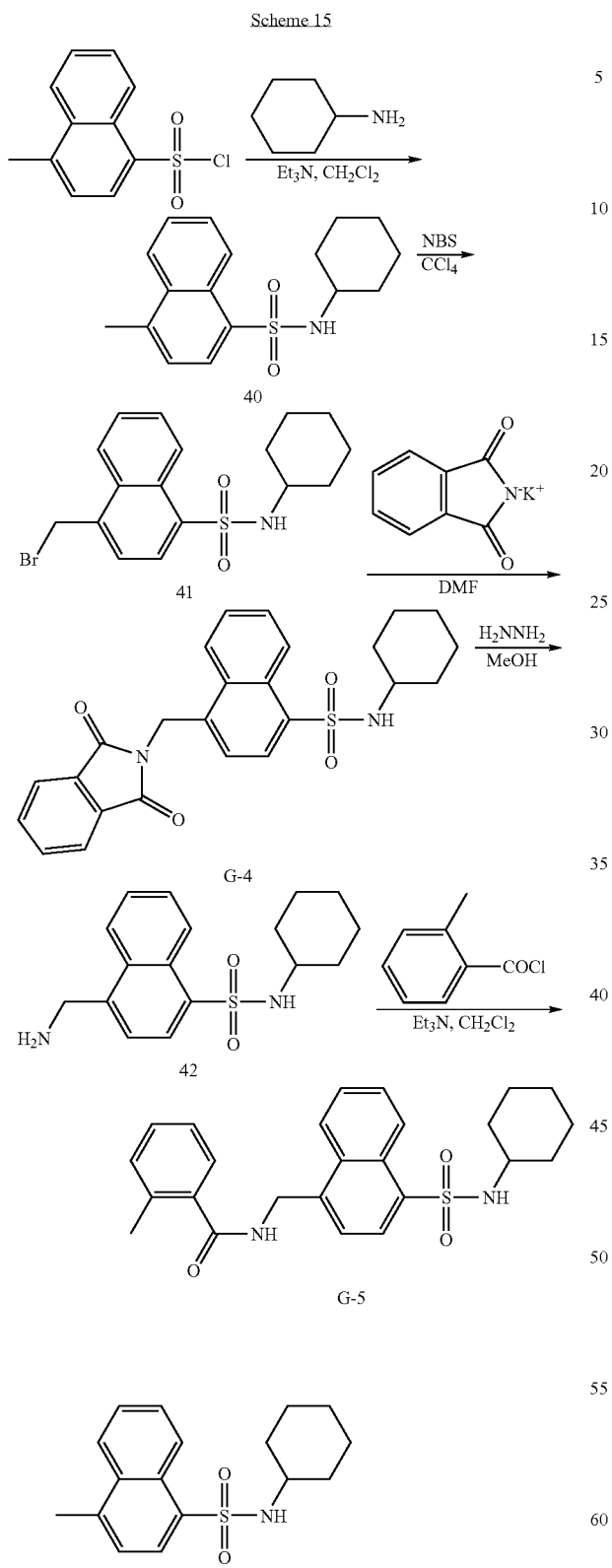

4-Methyl-naphthalene-1-sulfonic acid cyclohexylamide (40)

To a solution of 4-methyl-naphthalene-1-sulfonyl chloride (2.4 g, 10.0 mnmol) in $CH_2Cl_2$ (30 mL), was added cyclo-hexylamine (1.4 g, 11.0 mmol) and triethylamine (2.8 mL, 20.0 mmol) and the resultant solution was stirred at room temperature overnight. The solution was quenched with water and extracted with $CH_2Cl_2$ (3×30 mL). The combined organic layers were dried over $Na_2SO_4$ and concentrated in vacuo. The resulting residue was purified by Flash colunin chromatography (hexane/ethyl acetate, gradient elution) to give the title compound 40 (2.0 g) as a yellow solid. $^1H$ NMR (300 MHz, $CDCl_3$) δ 8.63 (d, 1H), 8.18 (d, 1H1), 8.10 (d, 1H1), 7.64 (m, 2H), 7.38 (d, 1H), 3.08 (m, 1H), 2.76 (s, 3H), 1.52 (m, 5H), 1.09 (m, 5H); LC/MS m/z 304 (M+H)$^+$.

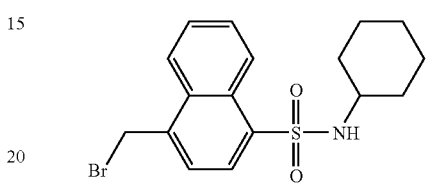

4-Bromomethyl-naphthalene-1-sulfonic acid cyclohexylamide (41)

To a solution of 4-methyl-naphthalene-1-sulfonic acid cyclohexylamide 40 (3.0 g, 10 mmol) in $CCl_4$ (100 mL) was added NBS (2.1 g, 12.0 mmol) and benzoyl peroxide (240 mg, 1.0 mmol), The reaction mixture was heated at reflux overnight. The solid was filtered and the filtrate was concentrated in vacuo. The title compound was a yellow residue (2.5 g, solidified on standing) which was used directly in the next step without further purification. $^1H$ NMR (300 MHz, $CDCl_3$) δ 8.70 (m, 1H), 8.25 (m, 2H), 7.70 (m, 2H), 7.60 (d, 1H), 4.94 (s, 2H), 4.58 (m, 1H); 3.15 (m, 1H), 1.55 (m, 5H), 1.05 (m, 5H); LC/MS m/z 356 (M+H)$^+$ 382.

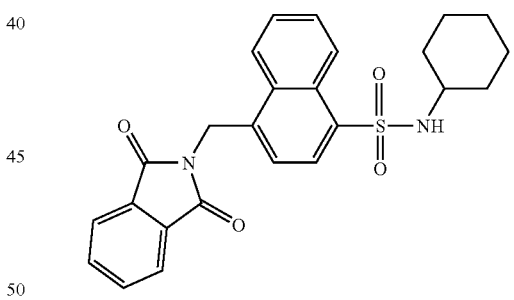

4-(1,3-Dioxo-1,3-dihydro-isoindol-2-ylmethyl)-naphthalene-1-sulfonic acid cyclohexylamide (G-4)

To a solution of 4-bromomethyl-naphthalene-1-sulfonic acid cyclohexylamide 41 (150 mg, 0.39 mmol) in DMF (5 mL) was added potassium phthalimide (109 mg, 0.58 mmol). The resultant solution was stirred at room temperature and then heated to 100° C. for 3 hr. The reaction was quenched with water and extracted with $CH_2Cl_2$. The organic layers were dried and concentrated in vacuo. HPLC purification of the residue gave the title compound (G-4) (63 mg) as white foam. $^1H$ NMR (300 MHz, MeOD) δ 8.67 (d, 1H), 8.42 (d, 1H), 8.22 (d, 1H), 7.88 (m, 23H), 7.76 (m, 4H), 5.48 (s, 2H), 4.48 (d, 1H), 3.12 (d, 1H), 1.58 (m, 6H), 1.10 (m, 4H); LC/MS m/z 449 (M+H)$^+$.

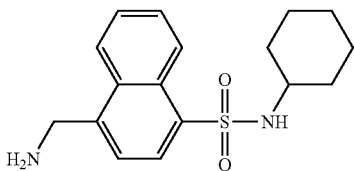

4-Aminomethyl-naphthalene-1-sulfonic acid cyclohexylamide (42)

To a solution of 4-(1,3-dioxo-1,3-dihydro-isoindol-2-ylmethyl)-naphthalene-1-sulfonic acid cyclohexylamide (G-4) (1.6 g, 3.57 mmol) in methanol (30 mL) was added hydrazine (2 mL). The resultant solution was stirred at room temperature overnight. A precipitate was formed and filtered. The solid was further washed with small amount of methanol. The filtrate was collected and solvent was removed in vacuo. Flash chromatography of the residue with Flash column (MeOH/$CH_2Cl_2$: 5-10%) gave the title compound (42) as white solid (0.7 g). $^1$H NMR (300 MHz, DMSO) δ 8.68 (d, 1H), 8.24 (d, 1H), 8.13 (d, 1H), 7.60 (m, 3H), 5.00 (s, 1H), 4.39 (s, 2H), 3.10 (s, 1H), 2.03 (m, 2H), 1.59 (m, 4H), 1.08 (m, 4H); LC/MS m/z 319 (M+H)$^+$.

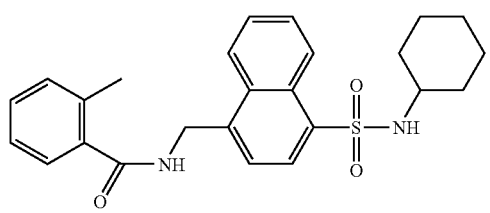

N-(4-Cyclohexylsulfamoyl-naphthalen-1-ylmethyl)-2-methyl-benzamide (G-5)

To a solution of naphthalenyl methylamine 42 (100 mg, 0.32 mmol) in DMF (2 mL) was added o-tolylchloride (49 μL, 0.38 mmol) and triethylamine (88 μL, 0.63 mmol). The resultant solution was stirred at room temperature overnight. The solvent was removed in vacuo and the residue was purified using HPLC to give the title compound (G-5) (30 mg) as pale yellow solid. $^1$H NMR (300 MHz, MeOD) δ 8.78 (d, 1H), 8.34 (d, 1H), 8.20 (d, 1H), 7.72 (m, 2H), 7.63 (d, 1H), 7.35 (d, 1H), 7.30 (d, 1H), 7.20 (d, 1H), 5.07 (s, 2H), 2.95 (s, 1H), 2.34 (s, 3H), 1.55 (m, 51), 1.05 (m, 5H),; LC/MS m/z 437 (M+H)$^+$.

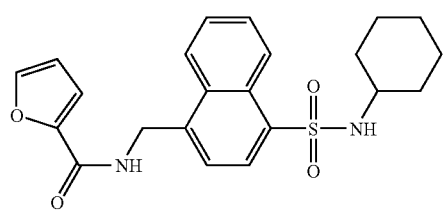

Furan-2-carboxylic acid (4-cyclohexylsulfamoyl-naphthalen-1-ylmethyl)-amide (G-6)

The title compound was made following general procedure in Scheme 15, substituting furan-2-carboxylic chloride for o-tolyl chloride. $^1$H NMR (300 MHz, MeOD) δ 8.76 (d, 1H), 8.26 (d, 1H), 8.18 (d, 1H), 7.67 (d, 1H), 7.50 (d, 1H), 7.16 (d, 1H), 6.58 (m, 1H), 5.08 (s, 2H), 2.87 (s, IfH), 1.52 (m, 5H), 1.11 (m, 5H),; LC/MS m/z 413 (M+H)$^+$.

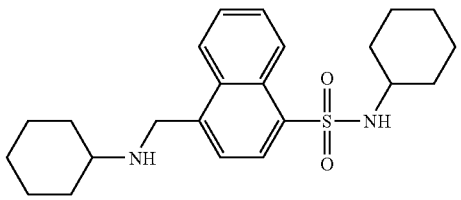

4-Cyclohexylaminomethyl-naphthalene-1-sulfonic acid cyclohexylamide (G-31)

The title compound was prepared according to the general procedure in Scheme 15, substituting cyclohexylamine and potassium carbonate for potassium phthalimide. HPLC purification of the residue gave the title compound (77 mg) as white foam. $^1$H NMR (300 MHz, MeOD) δ 8.80 (m, 1H), 8.37 (s, 1H), 8.26 (d, 2H), 7.78 (m, 3H), 4.79 (s, 2H), 3.36 (m, 1H), 2.96 (m, 1H), 2.30 (m, 2H), 1.90 (m, 2H), 1.72 (m, 1H), 1.48 (m, 10H), 1.10 (m, 2H); LC/MS m/z 401(M+H)$^+$.

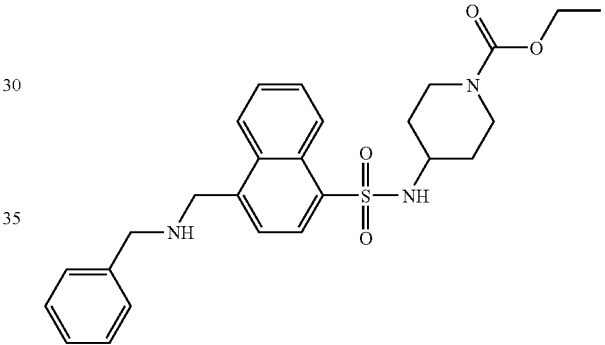

4-[4-(Benzylamino-methyl)-naphthalene-1-sulfonylamino]-piperidine-1-carboxylic acid ethyl ester (G-32)

The intermediate 4-(4-methyl-naphthalene-1-sulfonylamino)-piperidine-1-carboxylic acid tert-butyl ester was prepared according to the general procedure in Scheme 15, substituting 4-amino-piperidine-1-carboxylic acid tert-butyl ester for cyclohexylamine.

The intermediate 4-(4-bromomethyl-naphthalene-1-sulfonylamino)-piperidine-1-carboxylic acid tert-butyl ester was prepared according to the general procedure in Scheme 15 substituting 4-(4-methyl-naphthalene-1-sulfonylamino)-piperidine-1-carboxylic acid tert-butyl ester for 4-methyl-naphthalene-1-sulfonic acid cyclohexylamide (40).

The title compound was prepared according to the general procedure in Scheme 15, substituting phenylamine and potassium carbonate for potassium phthalimide. HPLC purification gave the title compound (15 mg) as a white solid. $^1$H NMR (300 MHz, MeOD) δ 8.73 (d, 1H), 8.29 (s, 1H), 8.22 (m, 1H), 8.04 (m, 1H), 7.68 (m, 3H), 7.20 (m, 2H), 4.59 (s, 2H), 4.23 (s, 2H), 3.97 (AB q, 2H), 3.67 (m, 2H), 3.16 (m, 1H),2.70 (m, 2H), 1.44 (m, 2H), 1.22 (m, 2H), 1.13 (t, 3H); LC/MS m/z 482 (M+H)$^+$.

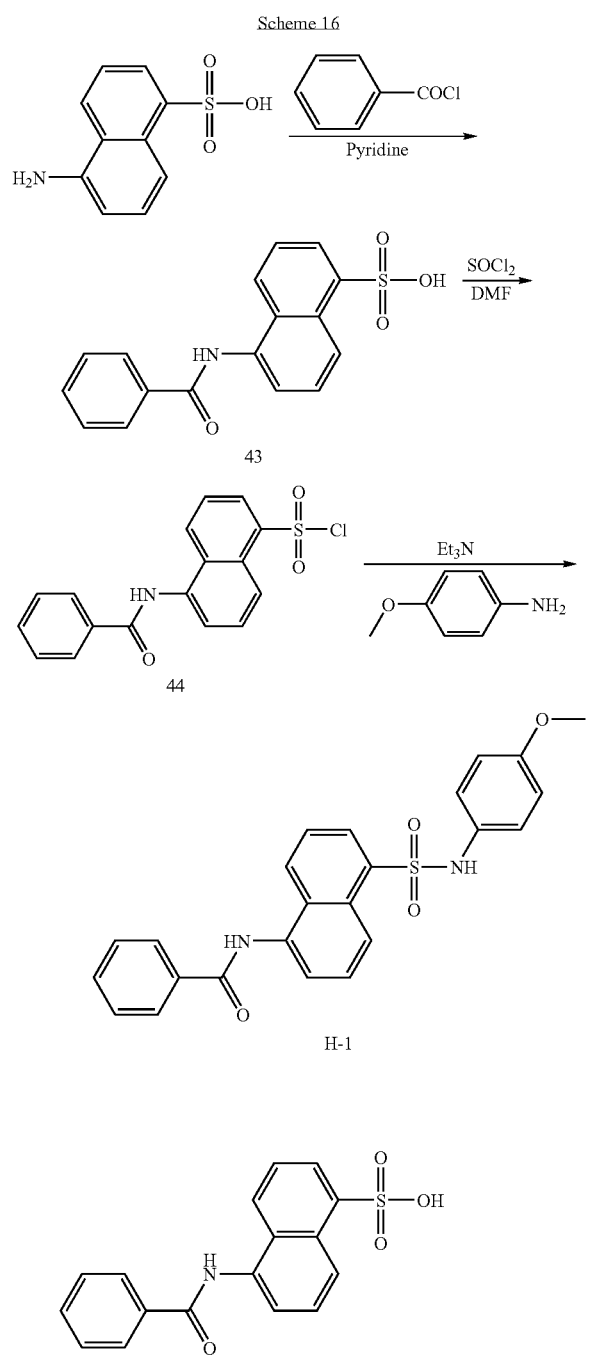

5-Benzoylamino-napthalene-1-sulfonic acid (43)

To an ice cooled solution of 1-naphthylamine-5-sulfonic acid (2 g, 8.9 mmol) in dichloromethane (5 mL), was added triethylamine (1.87 mL, 13.4 mmol). Benzoyl chloride (1.14 ml, 9.85 mmol) was added and the resultant solution was stirred at room temperature overnight. The reaction mixture was quenched by pouring into ice water, and the product was extracted into ethyl acetate. The organic extracts were washed with brine, dried over MgSO$_4$, filtered and concentrated to provide crude intermediate 43 as a white solid that was used without further purification.

5-Benzoylamino-naphthalene-1-sulfonyl chloride (44)

To an ice-cooled solution of 5-benzoylamino-napthalene-1-sulfonic acid (1.5 g, 3.51 mmol) in dichloromethane (5 ml), was added thionyl chloride (0.359 ml, 4.92 mmol). The resultant solution was allowed to warm to room temperature and stirred for 3 hours. The reaction mixture was quenched by pouring into ice water and extracting with ethyl acetate. The organic extracts were washed with brine, dried over MgSO$_4$ and concentrated to provide the crude intermediate 44 as a yellow oil that was used without further purification.

N-[5-(4-Methoxy-phenyl sulfamoyl)-naphthalen-1-yl]-benzamide (H-1)

To a solution of 5-benzoylamino-naphthalene-1-sulfonyl chloride 44 (0.1 g, 0.29 mmol) in dichloromethane (0.5 mL) was added triethylamine (0.06 ml, 0.43 mmol) and p-anisidine (0.05 g, 0.3 mmol). The resultant solution stirred at room temperature for 3 hours. The reaction mixture was quenched with water and the compound extracted into ethyl acetate. The organic extracts were washed with brine, dried over MgSO$_4$, filtered and concentrated to provide the crude product as a yellow oil. $^1$H NMR (300 MHz, DMSO) δ 8.65 (d, 1H), 8.19 (d, 1H), 8.06 (m, 3H), 7.70 (m, 2H), 7.54 (m, 2H), 6.84 (d, 2H), 6.69 (d, 2H), 3.56 (s, 3H); LC/MS (M+H)$^+$ m/z 433.

N-[5-(4-Ethyl-phenylsulfamoyl)-naphthalen-1-yl]-benzamide (H-2)

The title compound was made following the general procedure in Scheme 16, substituting p-ethylaniline for p-anisidine. $^1$H NMR (300 MHz, MeOD) δ 8.76 (d, 1H), 8.20 (t, 2H), 8.04 (d, 2H), 7.72 (m, 2H), 7.56 (m, 4H), 6.90 (m, 4H), 2.45 (m, 2H), 1.07 (m, 3H); LC/MS (M+H)+ m/z 431.

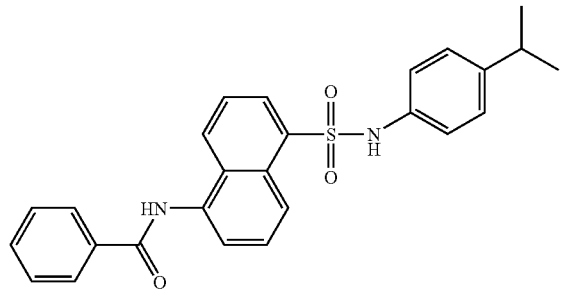

N-[5-(Isopropyl-phenylsulfamoyl)-naphthalen-1-yl]-benzamide (H-3)

The title compound was made following the general procedure in Scheme 16, substituting p-isopropylaniline for p-anisidine. $^1$H NMR (300 MHz, MeOD) δ 8.75 (m,1H), 8.21 (m, 2H), 8.04 (d, 2H), 7.6 (m, 7H), 6.92 (m, 3H), 2.72 (m, 1H), 1.24 (d, 1H), 1.09 (d, 6H); LC/MS (M+H)+ m/z 445.

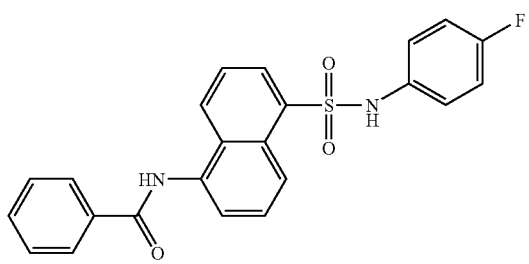

N-[5-(4-Fluoro-phenylsulfamoyl)-naphthalen-1-yl]-benzamide (H-4)

The title compound was made following the general procedure in Scheme 16, substituting p-fluoroaniline for p-anisidine. $^1$H NMR (300 MHz, DMSO) δ 10.62 (s, 1H), 10.50 (s, 1H), 8.61 (d, 1H), 8.23 (d, 1H), 8.14 (d, 1H), 8.04 (s, 1H), 8.02 (s, 1H), 7.72 (m, 2H), 7.55 (m, 4H), 6.98 (s, 2H), 6.95 (s, 2H); LC/MS (M+H)+ m/z 421.

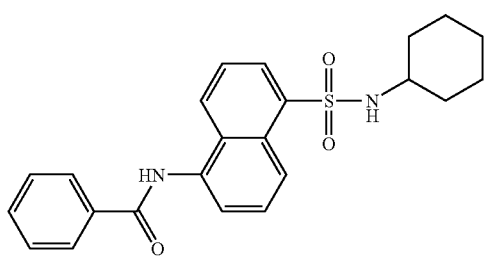

N-(5-Cyclohexylsulfamoyl-naphthalen-1-yl)-benzamide (H-5)

The title compound was made following the general procedure in Scheme 16, substituting cyclohexylamine for p-anisidine. $^1$H NMR (300 MHz, CDCl$_3$) δ 8.50 (d, 1H), 8.13 (t, 2H), 7.96 (d, 2H), 7.66 (d, 1H), 7.52 (t, 1H), 7.40 (m, 4H), 2.80 (m, 4H), 1.20 (m, 7H); LC/MS (M+H)+ m/z 409.

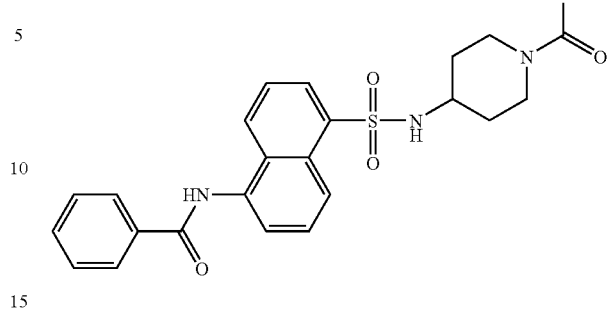

4-(5-Benzoylamino-naphthalene-1-sulfonylamino)-piperidine-1-carboxylic acid ethylester (H-6)

The title compound was made following the general procedure in Scheme 16, substituting 4-amino-piperidine-1-carboxylic acid ethyl ester for p-anisidine. $^1$H NMR (300 MHz, CDCl$_3$) δ 9.40 (s, 1H, N—H), 8.56 (d, 1H), 8.22 (d, 2H), 8.04 (d, 2H), 7.78 (d, 1H), 7.61 (t, 1H), 7.44 (m, 4H), 6.73 (br s, 1H), 3.98 (q, 2H), 3.80 (m, 2H), 3.13 (m, 1H), 2.68 (m, 2H), 1.56 (m, 2H), 1.24 (m, 2H), 1.12 (t, 3H); LC/MS (M+H)+ m/z 482.

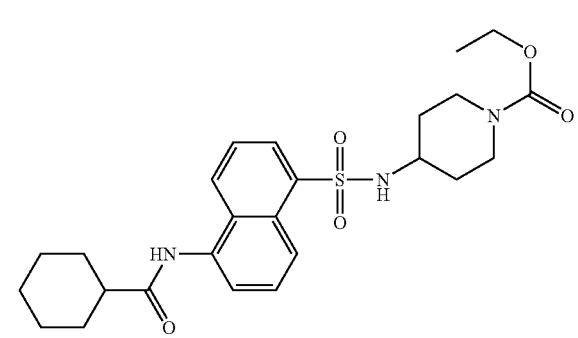

4-[5-(Cyclohexanecarbonyl-amino)-naphthalene-1-sulfonylamino]-piperidine-1-carboxylic acid ethyl ester (H-7)

The title compound was made following the general procedure in Scheme 16, substituting cyclohexane carboxylic acid for benzoyl chloride, and 4-amino-piperidine-1-carboxylic acid ethyl ester for p-anisidine. $^1$H NMR (300 MHz, MeOD) δ 8.64 (d, 1H), 8.28 (m, 2H), 7.66 (m, 3H), 4.06 (q, 2H), 3.80 (m, 2H), 3.22 (m, 1H), 2.78 (m, 2H), 2.60 (m, 2H), 2.06 (m, 2H), 2.90 (m, 2H), 1.56 (m, 1OH), 1.20 (t, 3H); LC/MS (M+H)+ m/z 488.

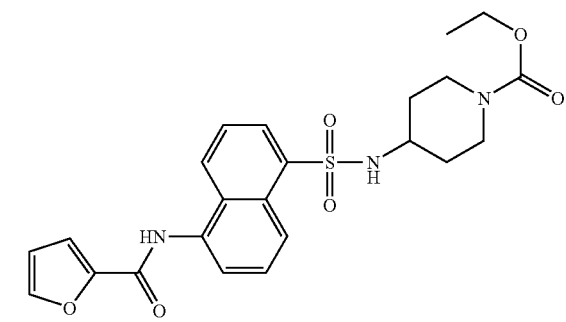

4-{5-[(Furan-2-carbonyl)-amino]-naphthalene-1-sulfonylamino}-piperidine-1-carboxylic acid ethyl ester (H-8)

The title compound was made following the general procedure in Scheme 16, substituting furan-2-carbonyl chloride for benzoyl chloride, and 4-amino-piperidine-1-carboxylic acid ethyl ester for p-anisidine.

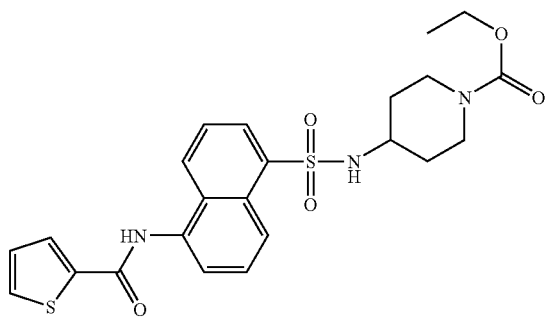

4-15-[(Thiophene-2-carbonyl)-amino]-naphthalene-4-sulfonylamino-4-piperidine-1-carboxylic acid ethyl ester (14-9)

The title compound was made following the general procedure in Scheme 16, substituting thiophene-2-carbonyl chloride for benzoyl chloride, and 4-amino-piperidine-1-carboxylic acid ethyl ester for p-anisidine.

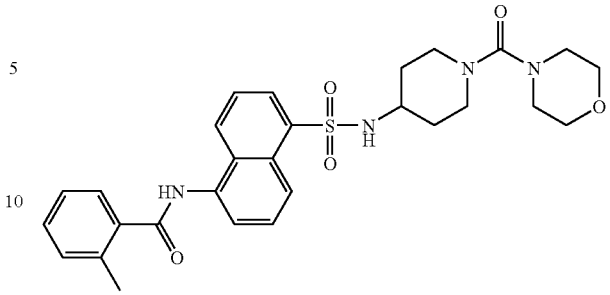

2-Methyl-N-{5-[1-(morpholine-4-carbonyl)-piperidin-4-ylsulfamoyl]-naphthalen-1-yl}-benzamide (H-11)

The title compound was made following the general procedure in Scheme 16, substituting 2-methyl-benzoyl chloride for benzoyl chloride, and 4-amino-piperidine-1-carboxylic acid tert-butyl ester for p-anisidine to give 4-[5-(2-methyl-benzoylamino)-naphthalene-1-sulfonylamino]-piperidine-1-carboxylic acid tert-butyl ester. The crude material was dissolved in 4N HCl/dioxane and stirred for 3 hours at room temperature. Concentration in vacuo afforded 2-methyl-N-[5-(piperidin-4-ylsulfamoyl)-naphthalen-1-yl]-benzamide as its hydrochloride salt which was dissolved in dichloromethane. Triethylamine was added followed by morpholine. The reaction was stirred overnight at room temperature. The crude reaction mixture was charged to HPLC afforded the title compound.

N-15-[1-(Morpholine-4-carbonyl)-piperidin-4-ylsulfamoyl]-naphthalen-1-yl)-benzamide (H-10)

The title compound was made following the general procedure in Scheme 16, substituting 4-amino-piperidine-1-carboxylic acid tert-butyl ester for p-anisidine to give 4-(5-benzoylamino-naphthalene-1-sulfonylamino)-piperidine-1-carboxylic acid tert-butyl ester. The crude material was dissolved in 4N HCl/dioxane and stirred for 3 hours at room temperature. Concentration in vacuo afforded N-[5-(piperidin-4-ylsulfamoyl)-naphthalen-1-yl]-benzamide as its hydrochloride salt which was directly dissolved in dichloromethane. Triethylamine was added followed by morpholine. The reaction was stirred overnight at room temperature. The crude reaction mixture was charged to HPLC to afford the title compound.

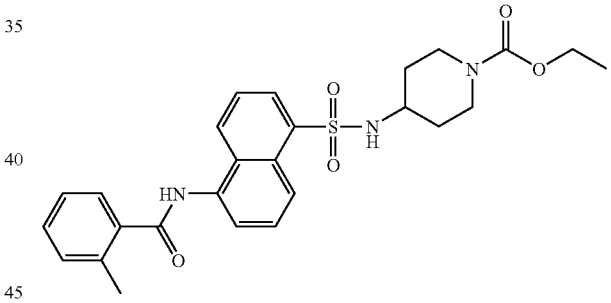

4-[5-(2-Methyl-benzoylamino)-naphthalene-1-sulfonylamino]-piperidine-1-carboxylic acid ethyl ester (H-12)

The title compound was made following the general procedure in Scheme 16, substituting 2-methyl-benzoyl chloride for benzoyl chloride, and 4-amino-piperidine-1-carboxylic acid ethyl ester for p-anisidine.

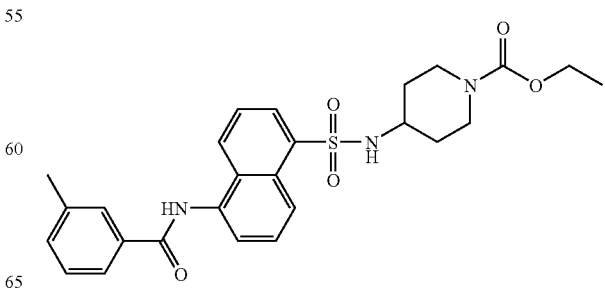

4-[5-(3-Methyl-benzoylamino)-naphthalene-1-sulfonylamino]-piperidine-1-carboxylic acid ethyl ester (H-13)

The title compound was made following the general procedure in Scheme 16, substituting 3-methyl-benzoyl chloride for benzoyl chloride, and 4-amino-piperidine-1-carboxylic acid ethyl ester for p-anisidine.

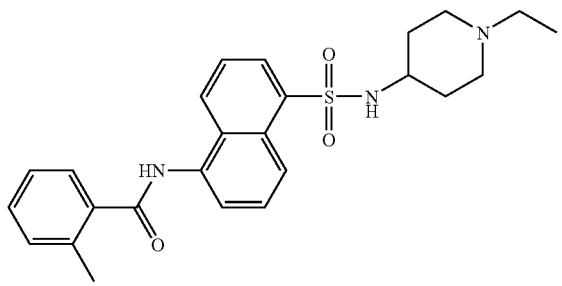

N-[5-(1-Ethyl-piperidin-4-ylsulfamoyl)-naphthalen-1-yl]-2-methyl-benzamide (H-14)

The title compound was made following the general procedure in Scheme 16, substituting 2-methyl-benzoyl chloride for benzoyl chloride, and 4-amino-piperidine-1-carboxylic acid tert-butyl ester for p-anisidine to give 4-[5-(2-methyl-benzoylamino)-naphthalene-1-sulfonylamino]-piperidine-1-carboxylic acid tert-butyl ester. The crude material was dissolved in 4N HCl/dioxane and stirred for 3 hours at room temperature. Concentration in vacuo afforded 2-methyl-N-[5-(piperidin-4-ylsulfamoyl)-naphthalen-1-yl]-benzamide as its hydrochloride salt which was suitable for use without further purification.

To a 25° C. solution of 2-methyl-N-[5-(piperidin-4-ylsulfamoyl)-naphthalen-1-yl]-benzamide in MeOH was added acetyl aldehyde and sodium cyanoborohydride. After stirring for 2 h at 25° C., the solution was concentrated in vacuo. The crude material was purified by reverse phase HPLC to provide the title compound.

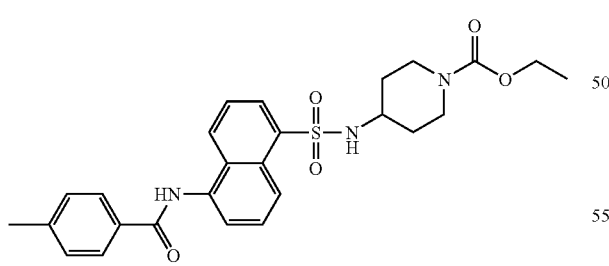

4-[5-(4-Methyl-benzoylamino)-naphthalene-1-sulfonylamino]-piperidine-1-carboxylic acid ethyl ester (H-15)

The title compound was made following the general procedure in Scheme 16, substituting 4-methyl-benzoyl chloride for benzoyl chloride, and 4-amino-piperidine-1-carboxylic acid ethyl ester for p-anisidine.

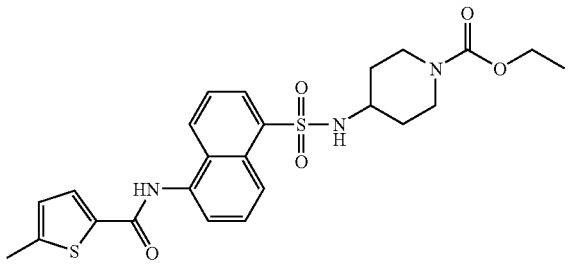

4-{5-[(5-Methyl-thiophene-2-carbonyl)-amino]-naphthalene-1-sulfonylamino}-piperidine-1-carboxylic acid ethyl ester (H-16)

The title compound was made following the general procedure in Scheme 16, substituting 5-methyl-thiophene-2-carbonyl chloride for benzoyl chloride, and 4-amino-piperidine-1-carboxylic acid ethyl ester for p-anisidine.

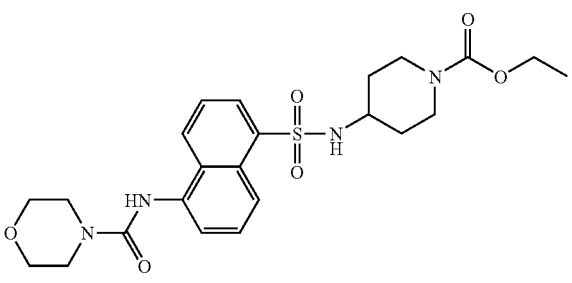

4-{5-[(Morpholine-4-carbonyl)-amino]-naphthalene-1-sulfonylamino}-piperidine-1-carboxylic acid ethyl ester (H-17)

The title compound was made following the general procedure in Scheme 16, substituting morpholine-4-carbonyl chloride for benzoyl chloride, and 4-amino-piperidine-1-carboxylic acid ethyl ester for p-anisidine.

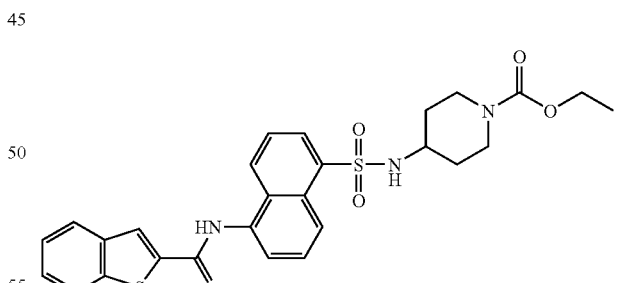

4-{5-[(Benzo[b]thiophene-2-carbonyl)-amino]-naphthalene-1-suffonylamino}-piperidine-1-carboxylic acid ethyl ester (H-18)

The title compound was made following the general procedure in Scheme 16, substituting benzo[b]thiophene-2-carbonyl chloride for benzoyl chloride, and 4-amino-piperidine-1-carboxylic acid ethyl ester for p-anisidine.

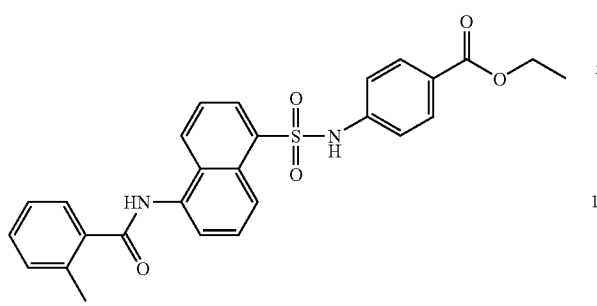

4-[5-(2-Methyl-benzoylamino)-naphthalene-1-sulfonylamino]-benzoic acid ethyl ester (H-19)

The title compound was made following the general procedure in Scheme 16, substituting 2-methyl-benzoyl chloride for benzoyl chloride, and 4-amino-benzoic acid ethyl ester for p-anisidine.

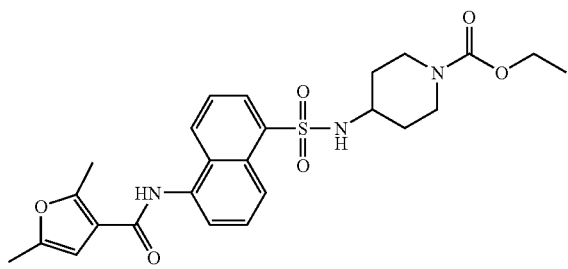

4-{5-[(2,5-Dimethyl-furan-3-carbonyl)-amino]-naphthalene-1-suffonylamino}-piperidine-1-carboxylic acid ethyl ester (H-20)

The title compound was made following the general procedure in Scheme 16, substituting 2,5-dimethyl-furan-3-carbonyl chloride for benzoyl chloride, and 4-amino-piperidine-1-carboxylic acid ethyl ester for p-anisidine.

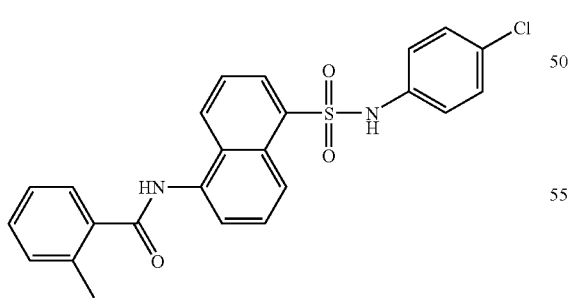

N-[5-(4-Chloro-phenylsulfamoyl)-naphthalen-1-yl]-2-methyl-benzamide (H-21)

The title compound was made following the general procedure in Scheme 16, substituting 2-methyl-benzoyl chloride for benzoyl chloride, and 4-chloro-phenylamine for p-anisidine.

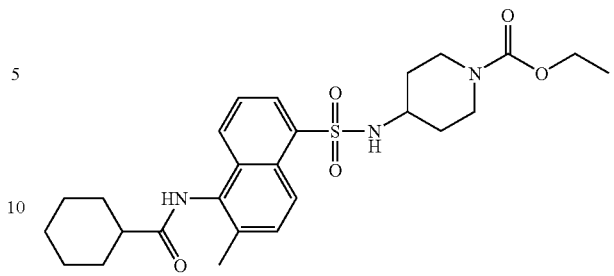

4-[5-(Cyclohexanecarbonyl-amino)-6-methyl-naphthalene-1-sulfonylamino]-piperidine-1-carboxylic acid ethyl ester (H-22)

Compound 5-(cyclohexanecarbonyl-amino)-6-methyl-naphthalene-1-sulfonyl chloride was prepared following general procedure in scheme 10, substituting 2-methyl-naphthalen-1-ylamine for 5,6,7,8-tetrahydro-naphthalen-1-ylarnine, and cyclohexanecarbonyl chloride for 2-methyl-benzoyl chloride.

The title compound was made following the general procedure in Scheme 16, substituting 5-(cyclohexanecarbonylamino)-6-methyl-naphthalene-1-sulfonyl chloride for 5-Benzoylamio-naphthalene-1-sulfonyl chloride (44), and 4-amino-piperidine-1-carboxylic acid ethyl ester for p-anisidine. $^1$H NMR (300 MHz, MeOD) δ 8.59 (d, 1H), 8.19 (m, 2H), 7.61 (m, 2H), 4.02 (q, 2H), 3.81 (m, 2H), 3.21 (m, 1H), 2.78 (m, 2H), 2.62 (m, 1H), 2.40 (s, 3H), 2.09 (m, 2H), 1.92 (m, 2H), 1.50 (m, 10H), 1.21 (t, 3H); LC/MS (M+H)$^+$ m/z 502.

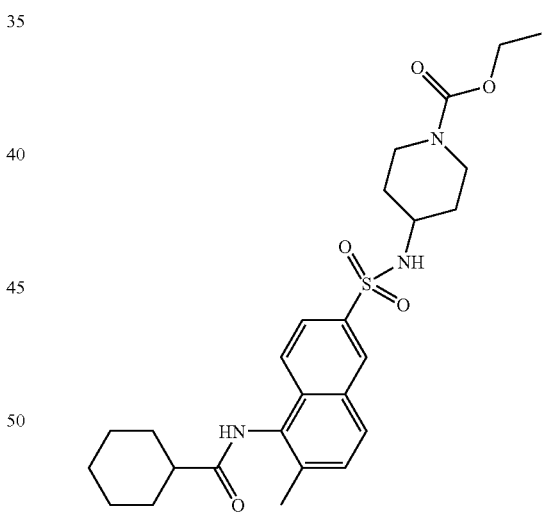

4-[5-(Cyclohexanecarbonyl-amino)-6-methyl-naphthalene-2-sulfonylamino]-piperidine-1-carboxylic acid ethyl ester (H-23)

Compound 5-(Cyclohexanecarbonyl-amino)-6-methyl-naphthalene-2-sulfonyl chloride was prepared following general procedure in scheme 10, substituting 2-methyl-naphthalen-1-ylamine for 5,6,7,8-tetrahydro-naphthalen-1-ylamine, and cyclohexanecarbonyl chloride for 2-methyl-benzoyl chloride.

The title compound was made following the general procedure in Scheme 16, substituting 5-(cyclohexanecarbonylamino)-6-methyl-naphthalene-1-sulfonyl chloride for 5-Benzoylamio-naphthalene-1-sulfonyl chloride (44), and 4-amino-piperidine-1-carboxylic acid ethyl ester for p-anisidine. $^1$H NMR (300 MHz, MeOD) δ 8.41 (s, 1H), 7.90 (m, 3H), 7.59 (m, 1H), 4.04 (q, 2H), 3.88 (m, 2H), 3.25 (m, 1H), 2.83 (m, 2H), 2.65 (m, 1H), 2.40 (s, 3H), 2.11 (m, 2H), 1.94 (m, 2H), 1.50 (m, 10H), 1.21 (t, 3H); LC/MS (M+H)$^+$ m/z 502.

Scheme 17

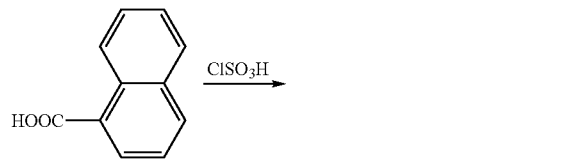

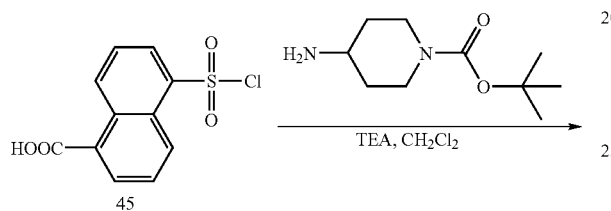

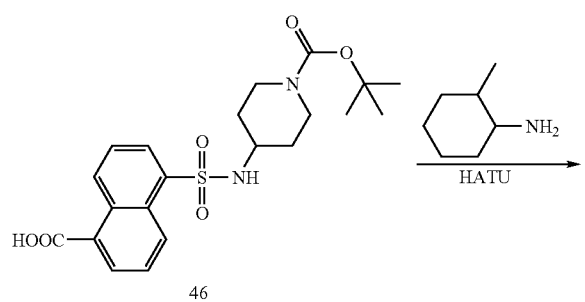

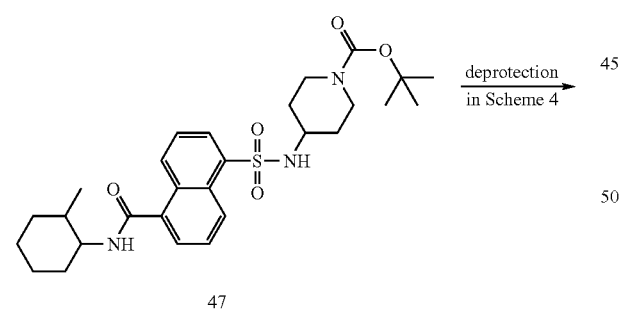

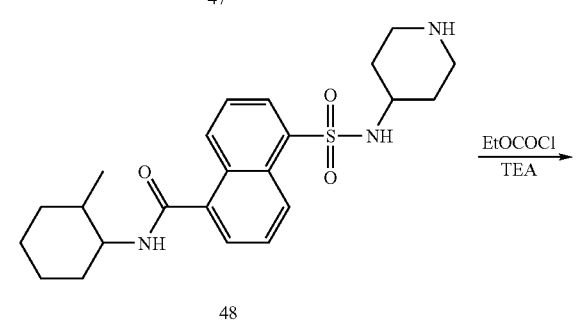

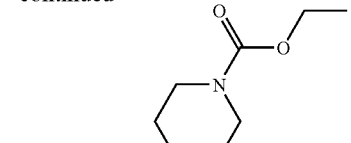

H-24

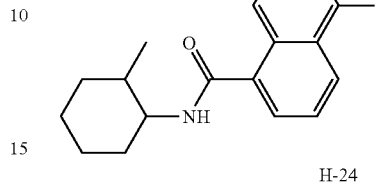

5-Chlorosulfonyl-naphthalene-1-carboxylic acid (45)

The titled compound was prepared using a modified procedure of Reefschlager et al. (see Reefschlager, J., et al., (2000) EP1038868A2). Naphthalene-1-carboxylic acid (6.56 g, 38.1 mmol) was added in small portions to chlorosulfonic acid (22 g, 12.6 mL, 190 mmol) that was cooled in an ice bath. The reaction was stirred overnight at room temperature. The reaction mixture was poured slowly over ice-water (250 mL) and filtered to afford 45 (8.3 g, 80%) as a white solid. $^1$H NMR (300 MHz, d$^6$-DMSO) δ 14.0 (s, 1H), 9.11 (d, 1H), 8.80 (d, 1H), 8.08 (d, 1H), 8.00 (d, 1H), 7.56 (m, 2H).

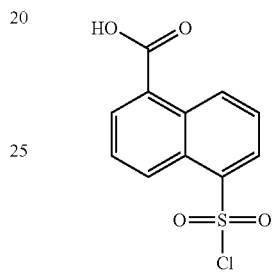

4-(5-Carboxy-naphthalene-1-sulfonylamino)-piperidine-1-carboxylic acid tert-butyl ester (46)

5-Chlorosulfonyl-naphthalene-1-carboxylic acid 45 (2.00 g, 7.39 mmol) was dissolved in dichloromethane (30 mL). Triethylamine (2.24 g, 3.1 mL, 22.2 imnol) was added followed by 4-amino-piperidine-1-carboxylic acid tert-butyl ester (1,63 g, 8.13 mmol). The reaction was stirred overnight at room temperature. The reaction was diluted with dichloromethane (50 mL) and charged to a separatory funnel. The organic layer was washed twice with water and brine and dried over MgSO$_4$. Filtration and concentration in vacuo afforded 46 (3.0 g, 93%) as a yellow foam. $^1$H NMR (300 MHz, d$^6$-DMSO) δ 9.11 (d, 1H), 8.62 (d, 1H), 8.15 (d, 1H), 7.90 (d, 1H), 7.62 (m, 2H), 3.91 (d, 1H), 3.62 (m, 2H), 3.15 (m, 1H), 2.67 (m, 2H), 1.89 (m, 2H), 1.52 (m, 2H), 1.40 (s, 9H); LC/MS m/z 435 (M+H)+.

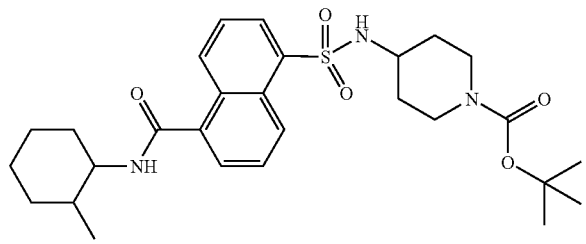

(±)-4-[5-(2-Methyl-cyclohexylcarbamoyl)-naphthalene-1-sulfonylamino]-piperidine-1-carboxylic acid tert-butyl ester (47)

4-(5-Carboxy-naphthalene-1-sulfonylamino)-piperidine-1-carboxylic acid tert-butyl ester 46 (246 mg, 0.57 mmol) was dissolved in dichloromethane (5 mL). O-(7-Azabenzotriazol-1-yl)-N,N,N',N'-tetramethyluronium hexafluorophosphate (HATU) (323 mg, 0.85 mmol) was added followed by diisopropylethyl amine (214 mg, 0.29 mL, 1.66 mmol) and 2-methyl-cyclohexylamine (71 mg, 0.63 mmol). The reaction was stirred overnight at room temperature. The reaction mixture was charged to a flash column. Elution with 99:1 dichloromethane:methanol afforded 47 (380 mg) as a white foam that was contaminated with tetramethylurea, but suitable for use without further purification. $^1$H NMR (300 MHz, CDCl$_3$) (1:1 mixture of diastereomers) δ 8.70 (m, 1H), 8.55 (d, 1H), 8.33 (d. 1H), 7.64 (m, 3H), 5.81 (d, 0.5H), 5.55 (d, 0.5H), 4.66 (d, 1H), 3.82 (m, 2H), 3.00 (m, 2H), 2.70 (m, 2H), 1.80 (m, 2H), 1.40 (s, 9H), 1.23 (m, 5H), 1.11 (d, 1.5F), 0.97 (d, 1.5H); LC/MS m/z 530 (M+H)+.

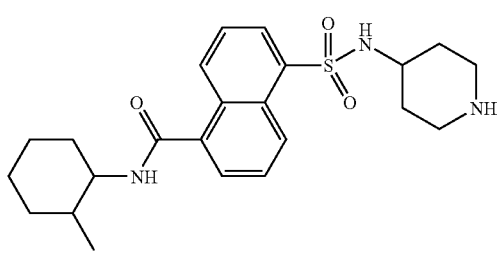

5-(Piperidin-4-ylsulfamoyl)-naphthalene-1-carboxylic acid (2-methyl-cyclohexyl)-amide (48)

4-[5-(2-Methyl-cyclohexylcarbamoyl)-naphthalene-1-sulfonylamino]-piperidine-1-carboxylic acid tert-butyl ester 47 (380 mg) was dissolved in 4N HCl/dioxane (10 mL) and stirred for 3 hours at room temperature. Concentration in vacuo afforded 48 (370 mg) as its hydrochloride salt that was used without further purification. LC/MS m/z 430 (M+H)+.

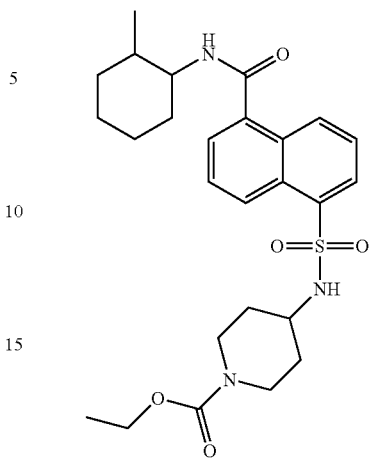

(±)-4-[5-(2-Methyl-cyclohexylcarbamoyl)-naphthalene-1-sulfonylamino]-piperidine-1-carboxylic acid ethyl ester (H-24)

5-(Piperidin-4-ylsulfamoyl)-naphthalene-1-carboxylic acid (2-methyl-cyclohexyl)-amide hydrochloride 48 (190 mg, 0.41 mmol) was dissolved in dichloromethane (1 mL). Triethylamine (0.13 g, 0.18 mL, 1.28 mmol) was added followed by ethyl chloroformate (65 mg, 0.068 mL, 0.60 mmol). The reaction was stirred overnight at room temperature. The crude reaction mixture was charged to a flash column. Elution with 99:1 dichloromethane:methanol afforded H-24 (66 mg, 59%) as a white solid. $^1$H NMR (300 MHz, CDCl$_3$) (1:1 mixture of diastereomers) δ 8.65 (d, 1H), 8.48 (d, 1H), 8.25 (d, 1H), 7.55 (m, 3H), 6.20 (d, 1H), 5.47 (m, 1H), 5.26 (s, 1H), 4.00 (m, 2H), 3.75 (m, 3H), 3.20 (m, 1H), 2.75 (m, 2H), 2.15 (m, 1H), 1.78 (m 3H), 1.57 (m 2H), 1.38 (m, 2H), 1.05 (m, 10H); LC/MS m/z 502 (M+H)+.

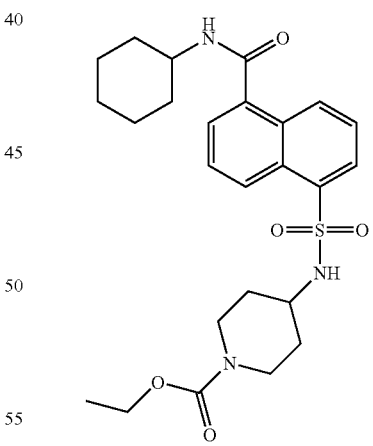

4-(5-Cyclohexylcarbamoyl-naphthalene-1-suffonylamino)-piperidine-1-carboxylic acid ethyl ester (H-25)

The title compound was prepared according to the general procedure in Scheme 17, substituting cyclohexylamine for 2-methyl-cyclohexylamine. Wt.: 17 mg (36%). $^1$H NMR (300 MHz, d$^6$-DMSO) δ 8.70 (d, 1H), 8.52 (d, 1H), 8.36 (d, 1H), 8.18 (d, 1H), 8.12 (d, 1H), 7.66 (m, 3H), 3.94 (q, 2H), 3.83 (m, 1H), 3.67 (m, 2H), 3.17 (m, 2H), 2.74 (m, 2H), 1.92 (m, 2H), 1.75 (m, 2H), 1.60 (m, 2H), 1.44 (m, 2H), 1.33 (m, 2H), 1.21 (m, 2H), 1.10 (t, 3H); LC/MS m/z 488 (M+H)+.

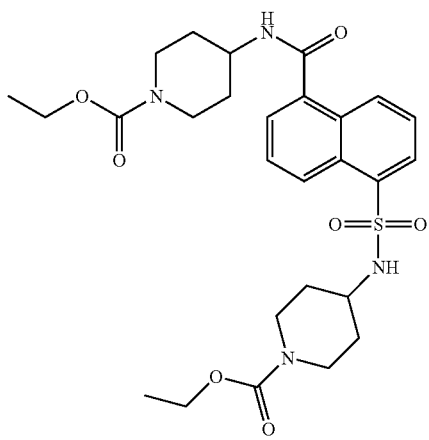

1-(1-Ethoxycarbonyl-piperidin-4-ylsulfamoyl)-naphthalene-5-carboxylic acid-(1-ethoxycarbonyl-piperidin-4-ylcarbamoyl)-amide (H-26)

5-Chlorosulfonyl-naphthalene-1-carboxylic acid 45 (100 mg, 0.37 mmol) was dissolved in dichloromethane (3 mL). Triethylamine (110 mg, 0.15 mL, 1.11 mmol) was added followed by 4-amino-piperidine-1-carboxylic acid ethyl ester (76 mg, 0.44 mmol). The reaction was stirred for 1 hour at room temperature then diluted with dichloromethane (15 mL). The mixture was charged to a separatory funnel and washed with water, brine and dried over $Na_2SO_4$. Flash column chromatography (95:5 dichloromethane:methanol) afforded the title compound as a white solid. Wt.: 20 mg (13%)

$^1$H NMR (300 MHz, $CDCl_3$) δ 8.70 (d, 1H), 8.52 (d, 1H), 8.31 (d, 1H), 7.62 (m, 3H), 6.18 (d, 1H), 4.92 (d, 1H), 4.24 (m, 2H), 4.15 (q, 2H), 4.05 (q, 2H), 3.85 (m, 2H), 3.24 (m, 1H), 2.98 (m, 2H), 2.73 (m, 2H), 2.13 (m, 2H), 1.95 (m, 1H), 1.61 (m, 2H), 1.45 (m, 1H), 1.15 (m, 3H); LC/MS m/z 561 (M+H)$^+$.

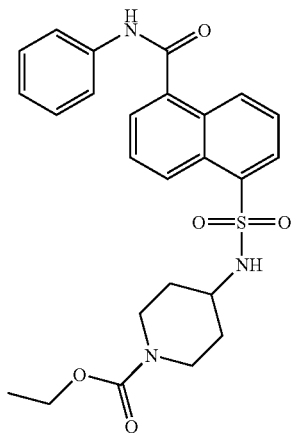

4-(5-Phenylcarbamoyl-naphthalene-1-sulfonylamino)-piperidine-1-carboxylic acid ethyl ester (H-27)

The title compound was prepared according to the general procedure in Scheme 17, substituting phenylamine for 2-methyl-cyclohexylamine. Wt.: 32 mg (47%). $^1$H NMR (300 MHz, $CD_3OD$) δ 8.86 (d, 1H), 8.50 (d, 1H), 8.32 (dd, 1H), 7.87 (dd, 1H), 7.74 (m, 5H), 7.38 (m, 2H), 7.18 (m, 1H), 4.04 (q, 2H), 3.71 (m, 2H), 3.23 (m, 2H), 2.77 (m, 2H, 1.52 (m, 2H), 1.26 (m, 2H), 1.20 (t, 3H); LC/MS m/z 482 (M+H)$^+$.

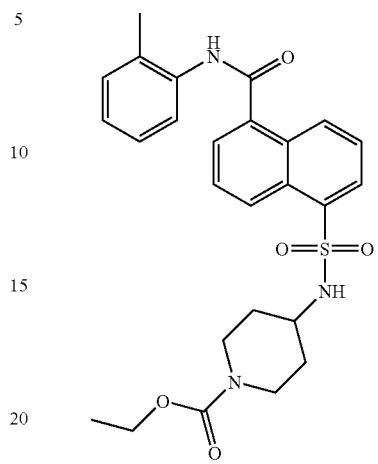

4-(5-o-Tolylcarbamoyl-naphthalene-1-sulfonylamino)-piperidine-1-carboxylic acid ethyl ester (H-28)

The title compound was prepared according to the general procedure in Scheme 17, substituting o-tolylamine for 2-methyl-cyclohexylamine. Wt.: 32 mg (46%). $^1$H NMR (300 MHz, d$^6$-DMSO) δ 10.60 (s, 1H), 8.78 (d, 1H), 8.41 (d, 1H), 8.22 (d, 1H), 8.18 (d, 1H), 7.82 (m, 2H), 7.71 (m, 1H), 7.67 (s, 1H), 7.56 (d, 1H), 7.25 (t, 1H), 6.95 (d, 1H), 3.95 (q, 2H), 3.68 (m, 2H), 3.23 (m, 2H), 2.75 (m, 2H), 2.30 (s, 3H), 1.47 (m, 2H), 1.18 (m, 2H), 1.10 (t, 3H); LC/MS m/z 496 (M+H)$^+$.

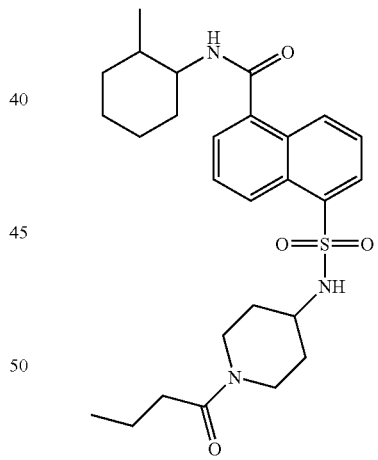

(±)-5-(1-Butyryl-piperidin-4-ylsulfamoyl)-naphthalene-1-carboxylic acid (2-methyl-cyclohexyl)-amide (H-29)

The title compound was prepared according to the general procedure in Scheme 17, substituting butyryl chloride for ethyl chloroformate. Wt.: 63 mg (66%). $^1$H NMR (300 MHz, d$^6$-DMSO) (1:1 mixture of diastereomers) δ 8.72 (d, 1H), 8.47 (d, 1H), 8.33 (m, 1H), 8.15 (m, 2H), 7.68 (m, 3H), 4.00 (m, 1H), 3.56 (m, 1H), 3.26 (m, 1H), 2.87 (m, 1H), 2.52 (m, 1H), 2.13 (m, 2H), 1.90 (m, 1H), 1.68 (m, 2H), 1.39 (m, 6H), 1.28 (m, 2H), 1.13 (m, 2H), 0.95 (m, 4H), 0.75 (m, 5H); LC/MS m/z 500 (M+H)$^+$.

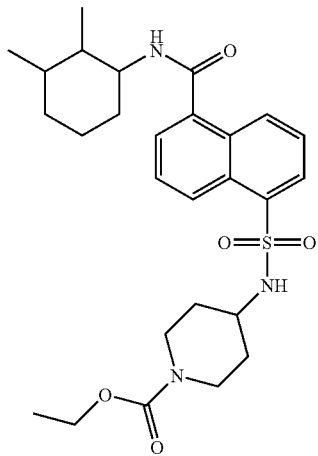

(±)-4-[5-(2,3-Dimethyl-cyclohexylcarbamoyl)-naphthalene-1-sulfonylamino]-piperidine-1-carboxylic acid ethyl ester (H-30)

The title compound was prepared according to the general procedure in Scheme 17, substituting 2,3-dimethyl-cyclohexylamine for 2-methyl-cyclohexylamine. Wt.: 54 mg (24%).

$^1$H NMR (300 MHz, CDCl$_3$) (mixture of four diastereomers) δ 8.70 (d, 1H), 8.55 (d, 1H), 8.33 (d, 1H), 7.64 (m, 3H), 5.96 (m, 1H), 4.67 (m, 1H), 4.05 (m, 3H), 3.87 (m, 2H), 3.25 (m, 1H), 2.72 (m, 2H), 2.23 (m, 1H), 2.03 (m 1H), 1.64 (m, 8H), 1.24 (m, 6H), 1.06 (m, 2H), 0.97 (m, 2H), 0.85 (m, 1H); LC/MS m/z 516 (M+H)$^+$.

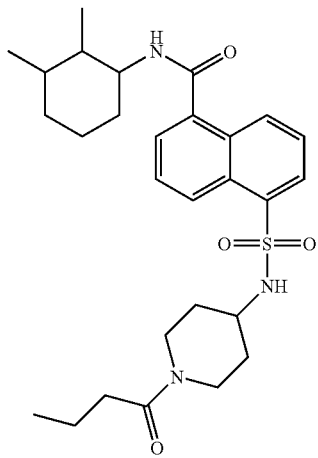

(±)-5-(1-Butyryl-piperidin-4-ylsulfamoyl)-naphthalene-1-carboxylic acid (2,3-dimethyl-cyclohexyl)-amide (H-31)

The title compound was prepared according to the general procedure in Scheme 17, substituting 2,3-dimethyl-cyclohexylamine for 2-methyl-cyclohexylamine, and butyryl chloride for ethyl chloroformate. Wt.: 66 mg (29%) $^1$H NMR (300 MHz, CDCl$_3$) (mixture of four diastereomers) δ 8.70 (d, 1H), 8.55 (d, 1H), 8.33 (d, 1H), 7.66 (m, 3H), 5.96 (m, 1H), 4.73 (m, 1H), 4.27 (m, 1H), 3.63 (m, 1H), 3.27 (m, 2H), 2.94 (m, 1H), 2.58 (m, 1H), 2.18 (m, 2H), 1.60 (m, 12H), 1.15 (m, 4H), 0.93 (m, 7H); LC/MS m/z 514 (M+H)$^+$.

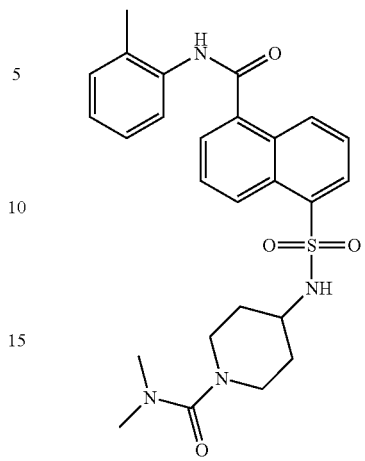

4-(5-o-Tolylcarbamoyl-naphthalene-1-sulfonylamino)-piperidine-1-carboxylic acid dimethylamide (H-32)

The title compound was prepared according to the general procedure in Scheme 17, substituting 2-methyl-phenylamine for 2-methyl-cyclohexylamine, and dimethylcarbamyl chloride for ethyl chloroformate. Wt.: 38 mg (22%). $^1$H NMR (300 MHz, CDCl$_3$) δ 8.77 (d, 1H), 8.67 (d, 1H), 8.35 (d, 1H), 7.97 (d, 1H), 7.85 (d, 1H), 7.68, (m, 3H), 7.25 (m, 3H), 4.95 (d, 1H), 3.46 (m, 2H), 3.29 (m, 1H), 2.69 (m, 2H), 2.54 (s, 3H), 1.62 (m, 2H), 1.33 (m, 2H); LC/MS m/z 495 (M+H)$^+$.

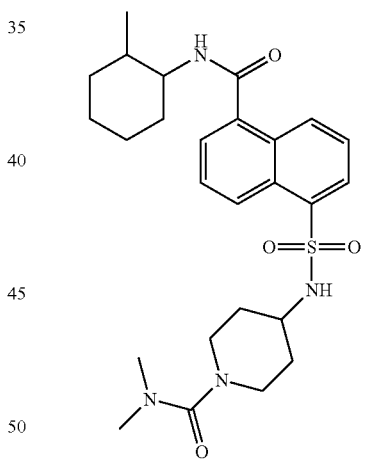

(±)-4-[5-(2-Methyl-cyclohexylcarbamoyl)-naphthalene-1-sulfonylamino]-piperidine-1-carboxylic acid dimethylamide (H-33)

The title compound was prepared according to the general procedure in Scheme 17, substituting dimethylcarbamyl chloride for ethyl chloroformate. Wt.: 20 mg (22%). $^1$H NMR (300 MHz, CDCl$_3$) (1:1 mixture of diastereomers) δ 8.69 (m, 1H), 8.50 (m, 1H), 8.31 (m, 1H), 7.60 (m, 3H), 6.17 (m, 1H), 5.05 (m, 1H), 4.40 (m, 1H), 3.80 (m, 1H), 3.40 (m, 2H), 3.25 (m, 1H), 2.76 (s, 6H), 2.66 (m, 2H), 2.08 (m, 1H), 1.96 (m, 3H), 1.58 (m, 2H), 1.33 (m, 6H), 1.08 (d, 1.5H), 1.02 (d, 1.5H); LC/MS m/z 501 (M+H)$^+$.

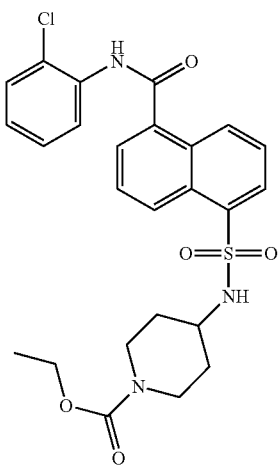

4-[5-(2-chloro-phenylcarbamoyl)-naphthalene-1-sulfonylamino]-piperidine-1-carboxylic acid ethyl ester (H-34)

The title compound was prepared according to the general procedure in Scheme 17, substituting 2-chloro-phenylamine for 2-methyl-cyclohexylamine. Wt.: 36 mg (58%). $^1$H NMR (300 MHz, CDCl$_3$) δ 8.80 (d, 1H), 8.71 (d, 1H), 8.53 (m, 1H), 8.35 (d, 1H), 8.27 (s, 1H), 7.91 (d, 1H), 7.69 (m, 2H), 7.40 (m, 2H), 7.17 (m, 1H), 4.80 (d, 1H), 4.06 (m 2H), 3.90 (m, 2H), 3.31 (m, 1H), 2.74 (m, 2H), 1.80 (m, 2H), 1.22 (m, 2H), 1.20 (t, 311); LC/MS m/z 517 (M+11)$^+$.

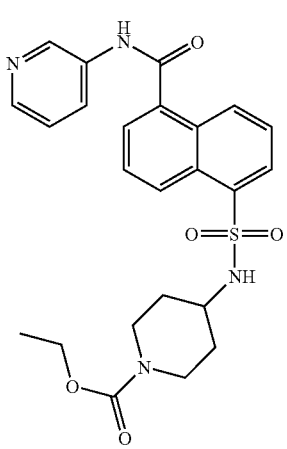

4-[5-(Pyridin-3-ylcarbamoyl)-naphthalene-1-sulfonylamino]-piperidine-1-carboxylic acid ethyl ester (H-35)

The title compound was prepared according to the general procedure in Scheme 17, substituting pyridine-3-ylamine for 2-methyl-cyclohexylamine. Wt.: 20 mg (14%). $^1$H NMR (300 MHz, CDCl$_3$) δ 8.81 (s, 2H), 8.70 (d, 1H), 8.65 (m, 1H), 8.60 (d, 1H), 8.40 (d, 1H), 8.27 (d, 1H), 7.81 (m, 1H), 7.61 (m, 2H), 7.40 (m, 2H), 7.22 (m, 1H), 5.40 (d, 1H), 4.04 (q, 2H), 3.80 (m, 2H), 3.24 (m, 1H), 2.70 (m, 2H), 1.80 (m, 2H), 1.60 (m, 2H), 1.22 (m, 2H), 1.20 (t, 3H); LC/MS m/z 483 (M+H)$^+$.

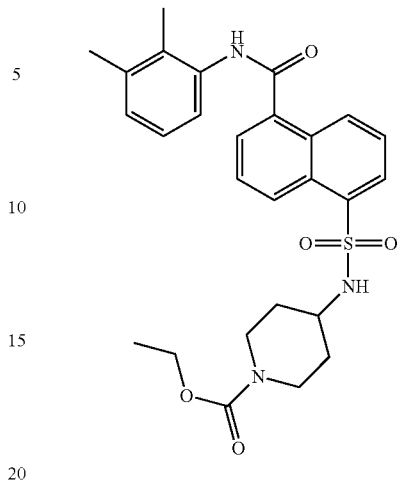

4-[5-(2,3-Dimethyl-phenylcarbamoyl)-naphthalene-1-sulfonylamno]-piperidine-1-carboxylic acid ethyl ester (H-36)

The title compound was prepared according to the general procedure in Scheme 17, substituting 2,3-dimethyl-phenylamine for 2-methyl-cyclohexylamine. Wt.: 86 mg (67%). $^1$H NMR (300 MHz, d$^6$-DMSO) δ 10.18 (s, 1H), 8.77 (d, 1H), 8.51 (d, 1H), 8.23 (d, 1H), 8.17 (d, 1H), 7.93 (d, 1H), 7.82 (d, 1H), 7.72 (m, 1H), 7.30 (d, 1H), 7.12 (m, 2H), 3.94 (q, 2H), 3.68 (m, 2H), 3.20 (m, 1H), 2.76 (m, 2H), 2.32 (s, 3H), 2.20 (s, 3H), 1.45 (m, 2H), 1.18 (m, 2H), 1.04 (t, 3H); LC/MS m/z 510 (M+H)$^+$.

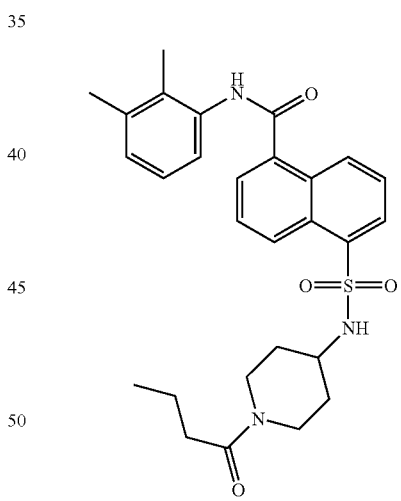

5-(1-Butyryl-piperidin-4-ylsulfamoyl)-naphthalene-1-carboxylic acid (2,3-dimethyl-phenyl)-amide (H-37)

The title compound was prepared according to the general procedure in Scheme 17, substituting 2,3-dimethyl-phenylamine for 2-methyl-cyclohexylamine, and butyryl chloride for ethyl chloroformate. Wt.: 74 mg (58%). $^1$H NMR (300 MHz, d$^6$-DMSO) δ 10.20 (s, 1H), 8.80 (d, 1H), 8.71 (d, 1H), 8.25 (d, 1H), 8.18 (d, 1H), 7.95 (d, 1H), 7.80 (m, 1H), 7.95 (m, 1H), 7.30 (d, 1H), 7.13 (m, 2H), 4.04 (m, 1H), 3.65 (m, 1H), 3.24 (m, 1H), 2.92 (m, 1H), 2.35 (m, 1H), 2.31 (s, 3H) 2.20 (s, 3H), 2.16 (m, 2H), 1.45 (m, 4H), 1.17 (m, 2H), 0.80 (t, 3H); LC/MS m/z 508 (M+H)$^+$.

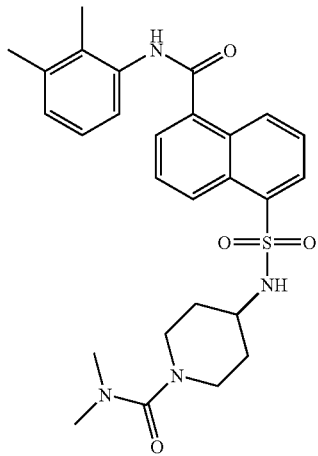

4-[5-(2,3-Dimethyl-phenylcarbamoyl)-naphthalene-1-sulfonylamino]-piperidine-1-carboxylic acid dimethylamide (H-38)

The title compound was prepared according to the general procedure in Scheme 17, substituting 2,3-dimethyl-phenylamine for 2-methyl-cyclohexylamine, and dimethylcarbamyl chloride for ethyl chloroformate. Wt.: 82 mg (64%). $^1$H NMR (300 MHz, d$^6$-DMSO) δ 10.20 (s, 1H), 8.80 (d, 1H), 8.71 (d, 1H), 8.23 (d, 1H), 8.14 (d, 1H), 7.94 (d, 1H), 7.82 (d, 1H), 7.72 (m, 1H), 7.30 (d, 1H), 7.10 (m, 2H), 3.32 (m, 2H), 3.15 (m, 1H), 2.62 (s, 6H), 2.58 (m, 2H), 2.30 (s, 3H), 2.20 (s, 3H), 1.42 (m, 2H), 1.26 (m, 2H); LC/MS m/z 509 (M+H)$^+$.

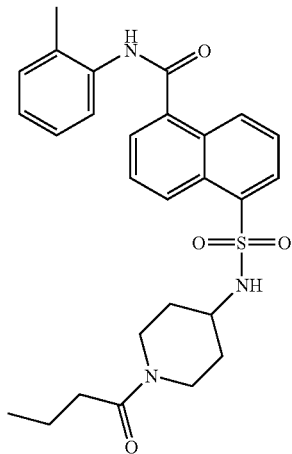

5-(1-Butyryl-piperidin-4-ylsulfamoyl)-naphthalene-1-carboxylic acid o-tolylamide (H-39)

The title compound was prepared according to the general procedure in Scheme 17, substituting 2-methyl-phenylamine for 2-methyl-cyclohexylamine, and butyryl chloride for ethyl chloroformate. Wt.: 38 mg (20%). $^1$H NMR (300 MHz, d$^6$-DMSO) δ 10.15 (s, 1H), 8.80 (d, 1H), 8.72 (d, 1H), 8.22 (d, 1H), 8.15 (m, 1H), 7.95 (m, 2H), 7/77, (m, 2H), 7.52 (d, 1H), 7.23 (m, 3H), 4.03 (m, 1H), 3.63 (m, 1H), 3.25 (m, 1H), 2.96 (m, 1H), 2.55 (m, 1H), 2.31 (s, 3H), 2.14 (m, 2H), 1.43 (m, 41H), 1.16 (m, 2H), 0.80 (t, 3H); LC/MS m/z 494 (M+H)$^+$.

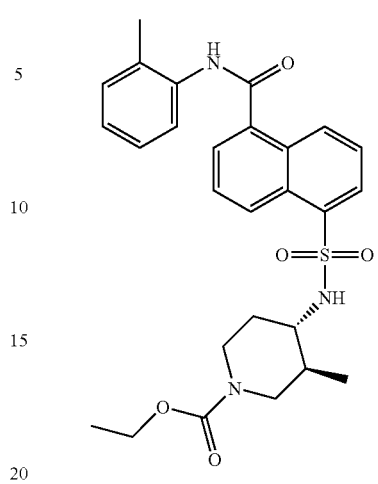

(±)-trans-3-Methyl-4-(5-o-tolylcarbamoyl-naphthalene-1-sulfonylamino)-piperidine-1-carboxylic acid ethyl ester (H-40)

The title compound was prepared according to the general procedure in Scheme 17, substituting (±)-5-(3-methyl-piperidin-4-ylsulfamoyl)-naphthalene-1-carboxylic acid o-tolylamide for 5-(piperidin-4-ylsulfamoyl)-naphthalene-1-carboxylic acid (2-methyl-cyclohexyl)-amide. $^1$H NMR (300 MHz, CDCl$_3$) δ 8.78 (d, 1H), 8.69 (d, 1H), 8.37 (d, 1H), 8.02 (d, 1H), 7.88 (d, 1H), 7.67 (m, 3H), 7.31 (m, 2H), 7.18 (m, 1H), 4.75 (d, 1H), 4.05 (q, 2H), 3.92 (m, 2H), 2.87 (m, 1H), 2.62 (m, 1H), 2.34 (s, 3H), 2.33 (m, 1H), 1.60 (m, 1H), 1.32 (m, 1H), 1.18 (t, 3H), 0.64 (m, 3H); LC/MS m/z 510 (M+H)$^+$.

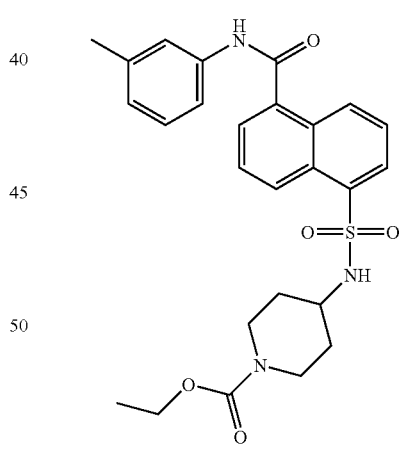

4-(5-m-Tolylcarbamoyl-naphthalene-1-sulfonylamino)-piperidine-1-carboxylic acid ethyl ester (H-41)

The title compound was prepared according to the general procedure in Scheme 17, substituting m-tolylamine for 2-methyl-cyclohexylamine. Wt.: 46 mg (66%). $^1$H NMR (300 MHz, d$^6$-DMSO) δ 10.58 (s, 1H), 8.78 (d, 1H), 8.41 (d, 1H), 8.23 (d, 1H), 8.17 (d, 1H), 7.82 (m, 2H), 7.71 (m, 2H), 7.55 (d, 1H), 7.25 (d, 1H), 6.95 (d, 1H), 3.94 (q, 2H), 3.68 (m, 2H), 3.21 (m, 1H), 2.74 (m, 2H), 2.28 (s, 3H), 1.45 (m, 2H), 1.18 (m, 2H), 1.09 (t, 3H); LC/MS m/z 496 (M+H)$^+$.

Scheme 18

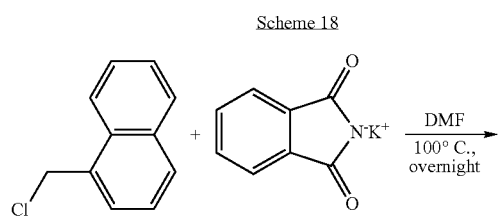

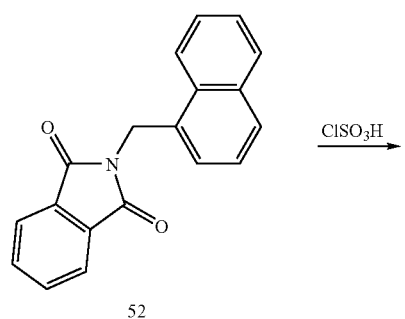

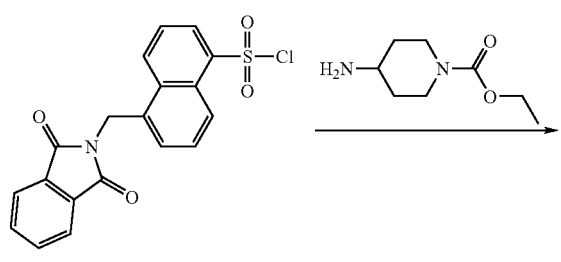

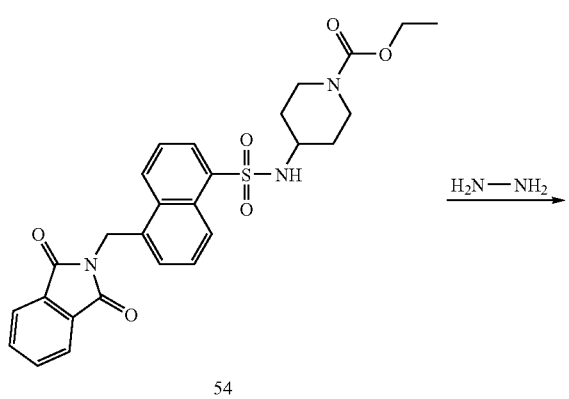

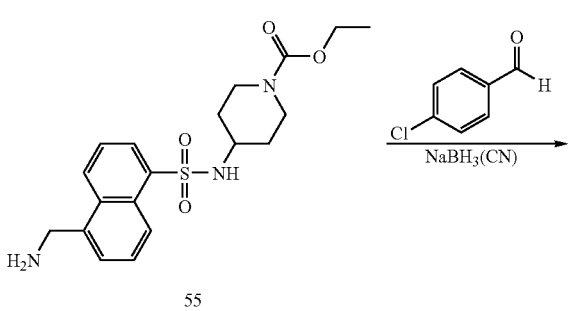

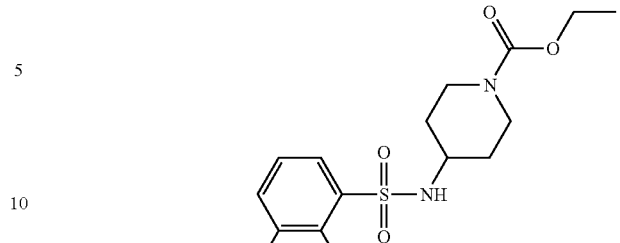

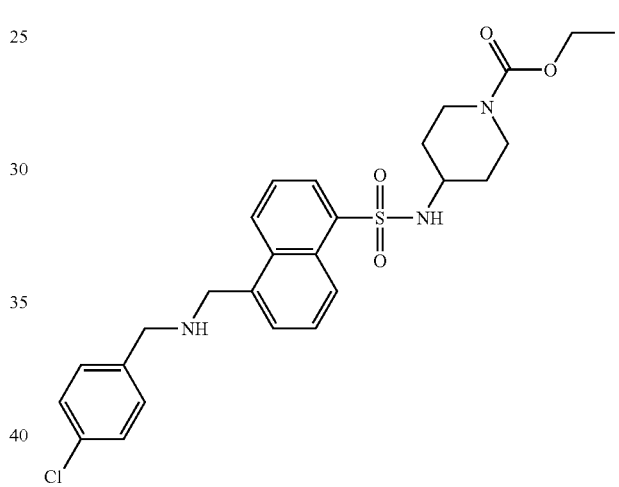

4-{5-[(4-Chloro-benzylamino)-methyl]-naphthalene-1-sulfonylamino}-piperidine-1-carboxylic acid ethyl ester (H-45)

To a solution of 1-chloromethyl-naphthalene (8.83 g, 50 mmol) in DMF (90 mL) was added phthalimide potassium salt (11.1 g, 60 mmol). The resultant solution was stirred at 100° C. overnight. The mixture was poured into ice-cold water and the precipitate was collected, washed with small amount of methanol and dried under vacuo to give 2-naphthalen-1-ylmethyl-isoindole-1,3-dione 52 (14.2 g, 99% yield). This material was used without further purification.

To a 0° C. solution of chlorosulfonic acid (10.8 mL, 160 mmol) was added 2-naphthalen-1-ylmethyl-isoindole-1,3-dione 52 (2.87 g, 10 mmol). The resulting solution was stirred at 25° C. for 2 hr. The mixture was poured into ice; the precipitate was collected and dried in vacuo to give a mixture of 5-(1,3-dioxo-1,3-dihydro-isoindol-2-ylmethyl)-naphthalene-1-sulfonyl chloride 53 and 4-(1,3-dioxo-1,3-dihydro-isoindol-2-ylmethyl)-naphthalene-1-sulfonyl chloride as a byproduct. This material was used without further purification.

To a solution of sulfonyl chlorides 53 (3.86 g, 10 mmol) in dichloromethane (40 mL) was added 4-amino-piperidine-1-carboxylic acid ethyl ester (2.06 g, 12 mmol) and triethyl amine (3.5 mL, 25 mmol). The resulting solution was stirred at 25° C. overnight and quenched with water. The aqueous layer was extracted with CH₂Cl₂. The organic extracts were combined, washed with brine and dried over MgSO₄. The solution was filtered and concentrated in vacuo to give the crude product. The crude material was purified by flash chromatography (hexane:EtOAc) to provide a mixture of 4-[5-(1, 3-dioxo-1,3-dihydro-isoindol-2-ylmethyl)-naphthalene-1-sulfonylamino]-piperidine-1-carboxylic acid ethyl ester 54 and 4-[4-(1,3-dioxo-1,3-dihydro-isoindol-2-ylmethyl)-naphthalene-1-sulfonylamino]-piperidine-1-carboxylic acid ethyl ester as a byproduct.

To a solution of sulfonamide mixtures 54 (3.11 g, 5.97 mmol) in methanol (30 mL) was added hydrazine (3.4 mL). The resulting solution was stirred at 25° C. for 2 hr. The mixture was partitioned between water (20 mL) and CH₂Cl₂ (20 mL). The aqueous layer was re-extracted with CH₂Cl₂. The organic extracts were combined, washed with brine and dried over MgSO₄. The solution was filtered and concentrated in vacuo to give the crude product. The crude material was purified by preparative TLC to provide 4-(5-aminomethyl-naphthalene-1-sulfonylamino)-piperidine-1-carboxylic acid ethyl ester 55 as a white solid.

To a 25° C. solution of 4-(5-aminomethyl-naphthalene-1-sulfonylamino)-piperidine-1-carboxylic acid ethyl ester 55 (62 mg, 0.159 mmol) in MeOH (4 mL) was added 4-chlorobenzaldehyde (45 mg, 0.318 mmol) and sodium cyanoborohydride (50 mg, 0.795 mmol). After stirring for 2 h at 25° C., the solution was concentrated in vacuo and the resultant crude material was purified by reverse phase HPLC to provide the title compound (H-45) as its formate salt. ¹H NMR (300 MHz, MeOD) δ 8.78 (d, 1H), 8.38 (s, 1H), 8.33 (m, 2H), 7.70 (m, 3H), 7.45 (m, 4H), 4.57 (s, 2H), 4.20 (s, 2H), 4.05 (q, 2H), 3.75 (d, 2H), 3.20 (m, 1H), 2.75 (m, 2H), 1.50 (m, 2H), 1.25 (m, 2H), 1.17 (t, 3H); LC/MS m/z 516 (M+H)⁺.

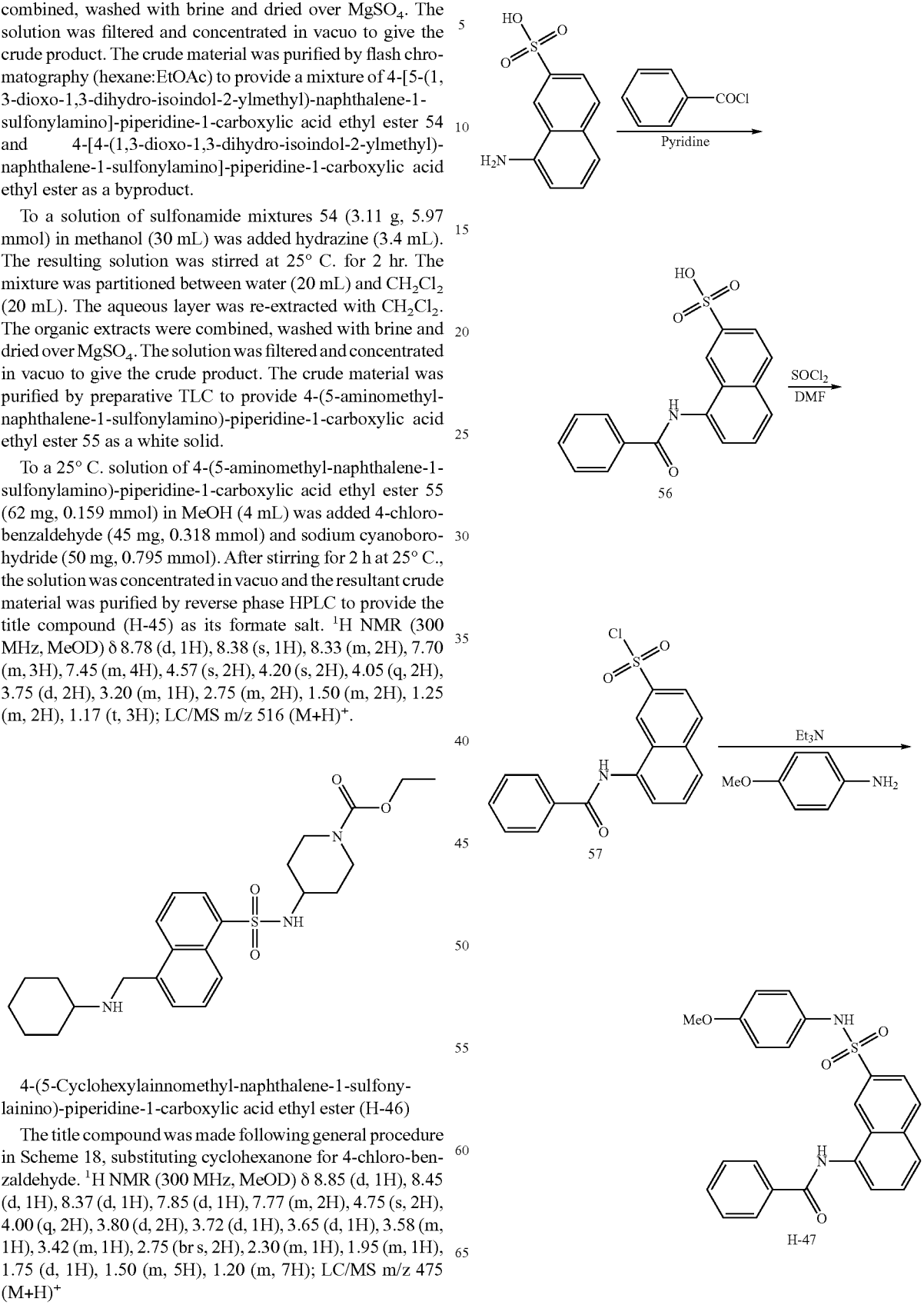

4-(5-Cyclohexylainnomethyl-naphthalene-1-sulfonylainino)-piperidine-1-carboxylic acid ethyl ester (H-46)

The title compound was made following general procedure in Scheme 18, substituting cyclohexanone for 4-chloro-benzaldehyde. ¹H NMR (300 MHz, MeOD) δ 8.85 (d, 1H), 8.45 (d, 1H), 8.37 (d, 1H), 7.85 (d, 1H), 7.77 (m, 2H), 4.75 (s, 2H), 4.00 (q, 2H), 3.80 (d, 2H), 3.72 (d, 1H), 3.65 (d, 1H), 3.58 (m, 1H), 3.42 (m, 1H), 2.75 (br s, 2H), 2.30 (m, 1H), 1.95 (m, 1H), 1.75 (d, 1H), 1.50 (m, 5H), 1.20 (m, 7H); LC/MS m/z 475 (M+H)⁺

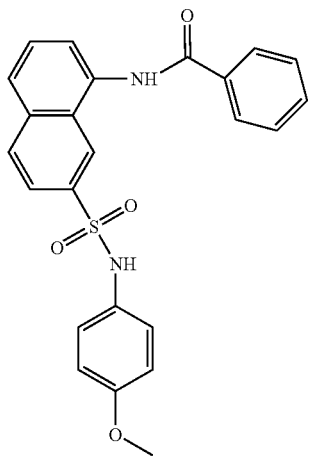

N-[7-(4-Methoxy-phenylsulfamoyl)-naphthalen-1-yl]-benzamide (H-47)

8-Benzoylamino-naphthalene-2-sulfonic acid 56 was prepared following the general procedure in Scheme 16, substituting 8-amino-naphthalene-2-sulfonic acid for 5-amino-naphthalene-1-sulfonic acid.

8-Benzoylamino-naphthalene-2-sulfonyl chloride 57 was prepared following the general procedure in Scheme 16, substituting 8-benzoylamino-naphthalene-2-sulfonic acid for 5-benzoylamino-napthalene-1-sulfonic acid.

The title compound (H-47) was prepared following the general procedure in Scheme 16 substituting 8-benzoylamino-naphthalene-2-sulfonyl chloride for 5-benzoylamino-napthalene-1-sulfonyl chloride. $^1$H NMR (300 MHz, MeOD) δ 8.34 (s, 1H), 8.02 (d, 3H), 7.91 (m, 1H), 7.73 (m, 1H), 7.64 (m, 5H), 6.92 (m, 2H), 6.62 (m, 2H), 3.62 (s, 3H); LC/MS (M+H)$^+$ m/z 433.

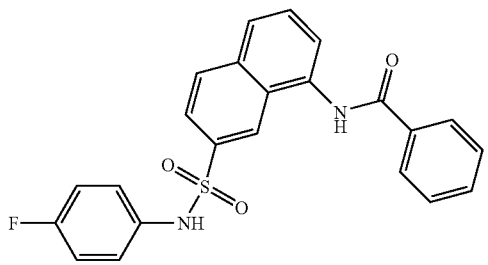

N-[7-(4-Fluoro-phenylsulfamoyl)-naphthalen-1-yl]-benzamide (H-48)

The title compound was made following the general procedure in Scheme 19, substituting p-fluoroaniline for p-anisidine. $^1$H NMR (300 MHz, DMSO) δ 10.60 (s, 1H), 8.37 (s, 1H), 8.08 (m, 3H), 7.93 (d, 1H), 7.68 (m, 6H), 6.96 (m, 4H); LC/MS (M+H)$^+$ m/z 421.

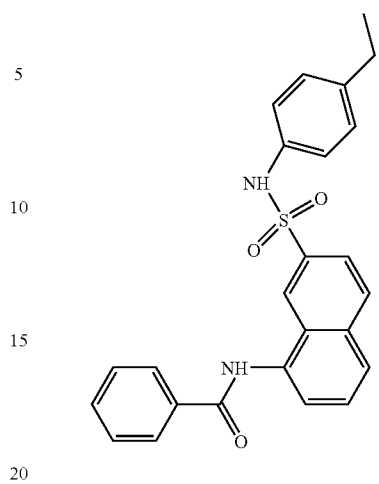

N-[7-(4-Ethyl-phenylsulfamoyl)-naphthalen-1-yl]-benzamide (H-49)

The title compound was made following the general procedure Scheme 19, substituting p-ethylaniline for p-anisidine. $^1$H NMR (300 MHz, DMSO) δ 10.61 (s, 1H), 8.42 (s, 1H), 8.09 (m, 3H), 7.94 (d, 1H), 7.69 (m, 7H), 6.96 (s, 3H), 2.40 (m, 2H), 1.03 (t, 3H); LC/MS (M+H)$^+$ m/z 431.

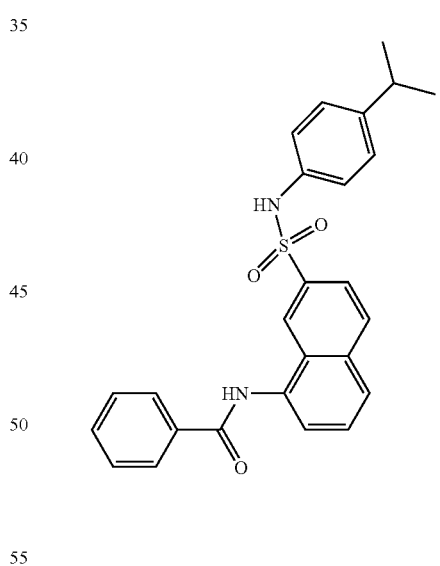

N-[7-(4-Isopropyl-phenylsulfamoyl)-naphthalen-1-yl]-benzamide (H-50)

The title compound was made following the general procedure Scheme 19, substituting p-isopropylaniline for p-anisidine. $^1$H NMR (300 MHz, DMSO) δ 10.63 (s, 1H), 8.44 (s, 1H), 8.10 (m, 3H), 7.94 (d, 1H), 7.69 (m, 6H), 6.99 (s, 4H), 2.69 (m, 1H), 1.23 (s, 3H), 1.05 (d, 6H); LC/MS (M+H)$^+$ m/z 445.

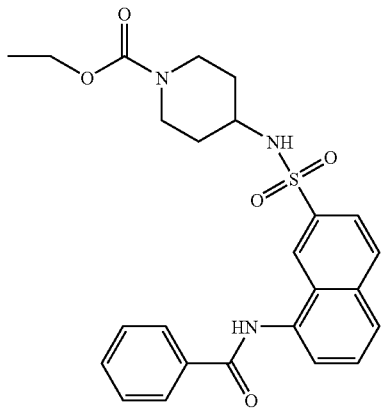

4-(8-Benzoylamno-naphthalene-2-sulfonylamino)-piperidine-1-carboxylic acid ethyl ester (H-51)

The title compound was made following the general procedure Scheme 19, substituting 4-amino-piperidine-1-carboxylic acid ethyl ester for p-anisidine. $^1$H NMR (300 MHz, MeOD) δ 8.47 (s, 1H), 8.06 (m, 3H), 7.94 (d, 1H), 7.86 (m, 1H), 7.62 (m, 5H), 4.00 (q, 2H), 3.80 (d, 2H), 3.20 (m, 1H), 2.76 (m, 2H), 1.61 (m, 2H), 1.25 (m, 2H), 1.16 (m, 3H); LC/MS (M+H)$^+$ m/z 482.

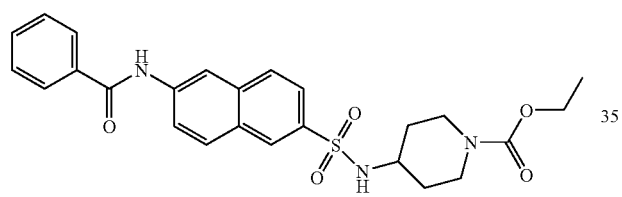

4-(6-Benzoylanno-naphthalene-2-sulfonylamino)-piperidine-1-carboxylic acid ethyl ester (H-52)

The title compound was made following the general procedure in Scheme 16, substituting 6-amino-naphthalene-2-sulfonic acid for 5-amino-naphthalene-1-sulfonic acid, and 4-amino-piperidine-1-carboxylic acid ethyl ester for p-anisidine.

Scheme 20

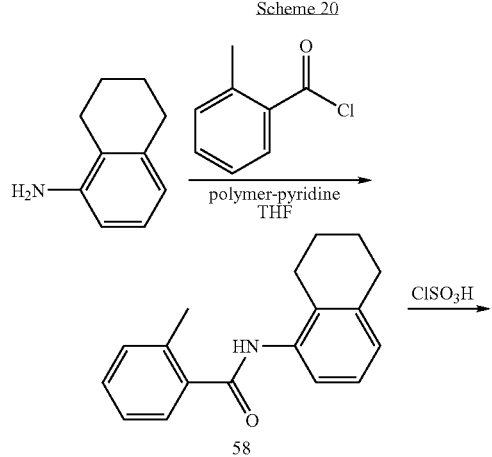

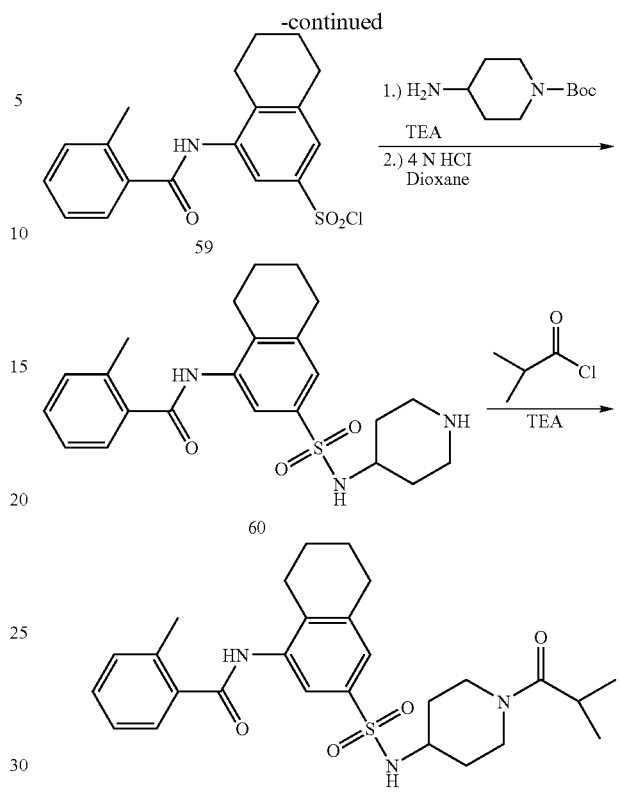

2-Methyl-N-(5,6,7,8-tetrahydro-naphthalen-1-yl)-benzamide (58)

To a 25° C. solution of aniline (1 eq) in anhydrous THF (2 mL per imnol aniline) was added polymer bound pyridine (1.5 eq) followed by 2-methyl-benzoyl chloride (1 eq). The mixture was stirred at 25° C. for 12-24 h. The reaction mixture was filtered and the filtrate concentrated in vacuo. Hexane was added to the residue and the resulting precipitate was collected by filtration, resulting in a white solid (yield 65%). LC/MS (M+H)$^+$ m/z 266. The crude material was used without further purification.

4-(2-Methyl-benzoylamino)-5,6,7,8-tetrahydro-naphthalene-2-sulfonyl chloride (59)

To neat amide (58), at 0° C., was added chlorosulfonic acid (5 eq) dropwise. The temperature was allowed to warm to 25° C. and then heated at 70° C. for 45 minutes. After cooling to 25° C., the reaction mixture was poured into ice water, and the resultant precipitate was collected by filtration to give the title compound as a solid. The product (mixture of regioisomers) was used without further purification.

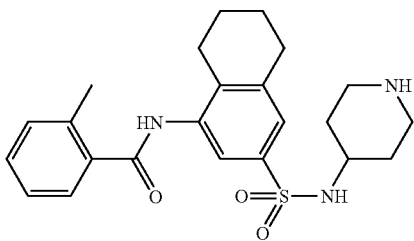

2-Methyl-N-[3-(piperidin-4-ylsulfamoyl)-5,6,7,8-tetrahydro-naphthalen-1-yl]-benzamide (60)

To a 25° C. solution of sulfonyl chloride (59) (1 eq) in anhydrous THF (15 mL per mmol RSO$_2$Cl) was added 4-amino-piperidine-1-carboxylic acid tert-butyl ester (1.1 eq), followed by triethyl amine (1.5 eq). The resultant solution was stirred at 25° C. for 18 hours. The reaction mixture was filtered and the filtrate was concentrated in vacuo. 4 N HCl/Dioxane was added and the reaction was stirred for 2 hours. Filtration afforded a light gray colored solid as the HCl salt of the title compound (in addition to the 1,4 regioisomer). LC/MS (M+H)$^+$ m/z 527.

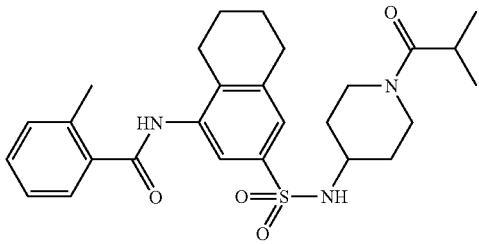

N-[3-(1-Isobutyryl-piperidin-4-ylsulfamoyl)-5,6,7,8-tetrahydro-naphthalen-1-yl]-2-methyl-benzamide (H-53)

To a 25° C. mixture of sulfonamide (60) (185 mg, 0.4 mmol) in THF (10 mL) was added isobutyryl chloride (107 mg, 1 mmol) and triethyl amine (607 mg, 6 mmol). The mixture was stirred for 18 hours, followed by filtration to remove the solid. The filtrate was concentrated in vacuo and purified via chromatography, to afford the title compound as white solid (17 mg).

$^1$H NMR (300 MHz, MeOD) δ 7.81 (s, 1H), 7.53 (m, 2H), 7.38 (m, 1H), 7.31 (m, 2H), 4.28 (m, 1H), 3.90 (m, 1H), 3.19 (m, 1H), 3.09 (m, 1H), 2.83 (m, 6H), 2.55 (s, 3H), 1.85 (m, 7H), 1.38 (m, 2H), 1.04 (m, 6H) ); LC/MS (M+H)$^+$ m/z 498.

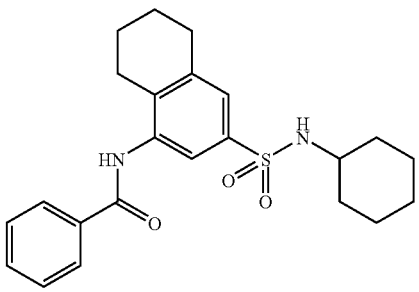

N-(3-Cyclohexylsulfamoyl-5,6,7,8-tetrahydro-naphthalen-1-yl)-benzamide (H-54)

The title compound was made following general procedure in Scheme 20, substituting benzoyl chloride for 2-methyl-benzoyl chloride, and cyclohexylamine for 4-amino-piperidine-1-carboxylic acid tert-butyl ester. $^1$H NMR (300 MHz, CDCl$_3$) δ 8.34 (d, 1H, Ph-H), 7.88 (m, 2H), 7.70 (br s, 1H, N—H), 7.53 (m, 5H), 3.20 (m, 1H), 2.85 (t, 2H), 2.72 (t, 2H), 1.85 (m, 5H,), 1.60 (m, 5H), 1.25 (m, 4H); LC/MS (M+H)$^+$ m/z 413.

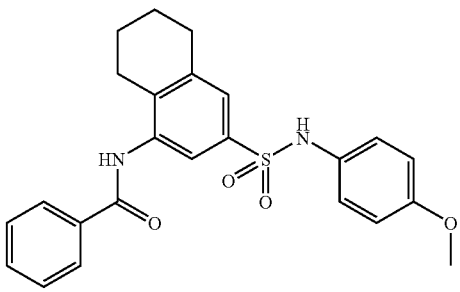

N-[3-(4-Methoxy-phenylsulfamoyl)-5,6,7,8-tetrahydro-naphthalen-1-yl]-benzamide (H-55)

The title compound was made following general procedure in Scheme 20, substituting benzoyl chloride for 2-methyl-benzoyl chloride, and 4-methoxy-phenylamine for 4-amino-piperidine-1-carboxylic acid tert-butyl ester. $^1$H NMR (300 MHz, CDCl$_3$) δ 8.29 (d, 1H), 7.86 (m, 2H), 7.76 (br s, 1H, N—H), 7.55 (m, 3H), 7.20 (d, 1H), 7.06 (dd, 2H), 6.76 (dd, 2H), 6.70 (br s, 1H, N—H), 3.73 (s, 3H), 2.70 (m, 4H), 1.82 (m, 4H); LC/MS (M+H)$^+$ m/z 437.

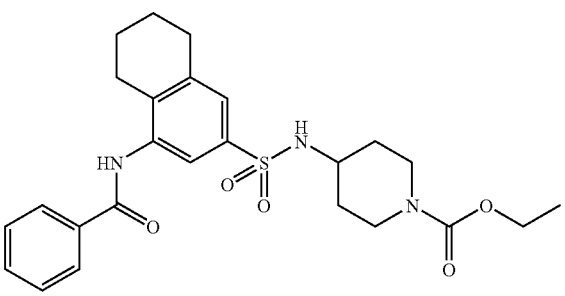

4-(4-Benzoylamino-5,6,7,8-tetrahydro-naphthalene-2-sulfonylamino)-piperidine-1-carboxylic acid ethyl ester (H-56)

The title compound was made following general procedure in Scheme 20, substituting benzoyl chloride for 2-methyl-benzoyl chloride, and 4-amino-piperidine-1-carboxylic acid ethyl ester for 4-amino-piperidine-1-carboxylic acid tert-butyl ester. $^1$H NMR (300 MHz, CDCl$_3$) δ 8.26 (d, 1H), 7.93 (br s, 1H, N—H), 7.86 (m, 2H), 7.50 (m, 4H), 4.08 (q, 2H), 3.92 (m, 2H), 3.32 (m, 1H), 2.82 (m, 6H), 1.90 (m, 6H), 1.36 (m, 2H), 1.24 (t, 3H); LC/MS (M+H)$^+$ m/z 486.

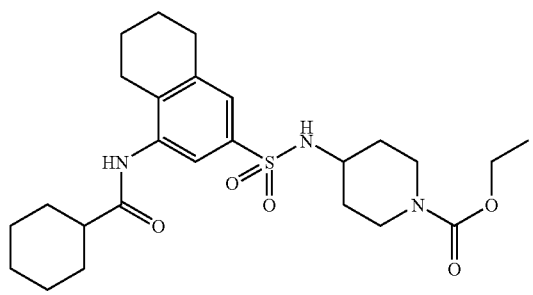

4-[4-(Cyclohexanecarbonyl-amino)-5,6,7,8-tetrahydro-naphthalene-2-sulfonylamino]-piperidine-1-carboxylic acid ethyl ester (H-57)

The title compound was made following general procedure in Scheme 20, substituting cyclohexanecarbonyl chloride for 2-methyl-benzoyl chloride, and 4-amino-piperidine-1-carboxylic acid ethyl ester for 4-amino-piperidine-1-carboxylic acid tert-butyl ester. $^1$H NMR (300 MHz, MeOD) δ 7.74 (s, 1H), 7.53 (s, 1H), 5.65(m, 1H), 4.11 (q, 2H), 3.98 (m, 2H), 3.32 (m, 1H), 2.72 (m, 6H), 1.82 (m, 18H), 1.30 (t, 3H); LC/MS (M+H)$^+$ m/z 492.

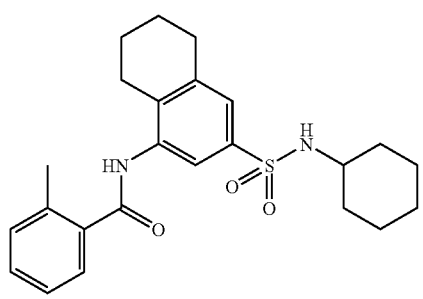

N-(3-Cyclohexylsulfamoyl-5,6,7,8-tetrahydro-naphthalen-1-yl)-2-methyl-benzamide (H-58)

The title compound was made following general procedure in Scheme 20, substituting cyclohexylamine for 4-amino-piperidine-1-carboxylic acid tert-butyl ester. $^1$H NMR (300 MHz, DMSO) δ 9.79 (s, 1H), 7.72 (s, 1H), 7.55(m, 2H), 7.39 (m, 2H), 7.31 (m, 2H), 2.94 (m, 1H), 2.79 (m, 4H), 2.44 (s, 3H), 1.69 (m, 8H), 1.46 (m, 1H), 1.13 (m, 5H); LC/MS (M+H)$^+$ m/z 427.

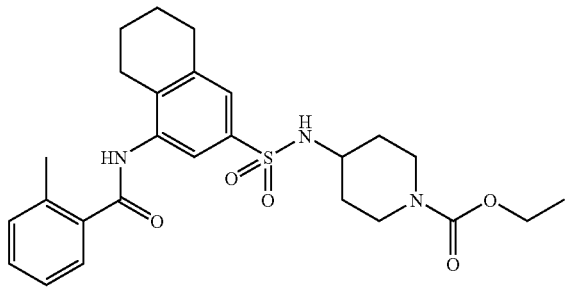

4-[4-(2-Methyl-benzoylamino)-5,6,7,8-tetrahydro-naphthalene-2-sulfonylamino]-piperidine-1-carboxylic acid ethyl ester (H-59)

The title compound was made following general procedure in Scheme 20, substituting 4-amino-piperidine-1-carboxylic acid ethyl ester for 4-amino-piperidine-1-carboxylic acid tert-butyl ester. $^1$H NMR (300 MHz, DMSO) δ 9.82 (s, 1H), 7.77 (m, 2H), 7.53(m, 1H), 7.39 (m, 2H), 7.31 (m, 2H), 3.99 (q, 2H), 3.78 (m, 2H), 3.25 (m, 1H), 2.82 (m, 6H), 2.42 (s, 3H), 1.72 (m, 6H), 1.27 (m, 2H), 1.14 (t, 3H); LC/MS (M+H)$^+$ m/z 500.

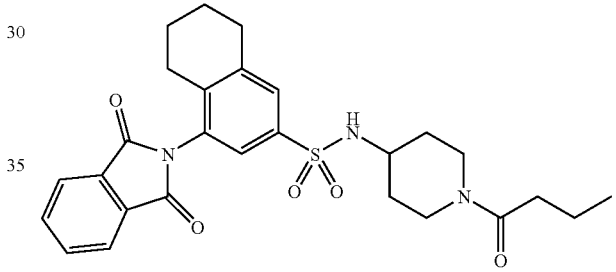

4-(1,3-Dioxo-1,3-dihydro-isoindol-2-yl)-5,6,7,8-tetrahydro-naphthalene-2-sulfonic acid (1-butyryl-piperidin-4-yl)-amide (H-60)

The title compound was prepared following general procedure in Scheme 20, substituting phthaloyl dichloride for 2-methyl-benzoyl chloride and butyryl chloride for isobutyryl chloride. $^1$H NMR (300 MHz, DMSO) δ 7.97 (m, 1H), 7.96 (s, 1H), 7.92 (s, 1H), 7.91 (m, 1H), 7.76 (d, 1H), 7.66 (d, 2H), 4.06 (d, 1H), 3.69 (d, 1H), 3.25 (m, 1H), 3.01 (m, 1H), 2.88 (t, 2H), 2.69 (t, 1H), 2.24 (t, 2H), 1.70 (m, 7H), 1.47 (m, 2H), 1.24 (m, 2H), 0.85 (t, 3H). LC/MS m/z 509 (M−H)$^-$, 511 (M+H)$^+$

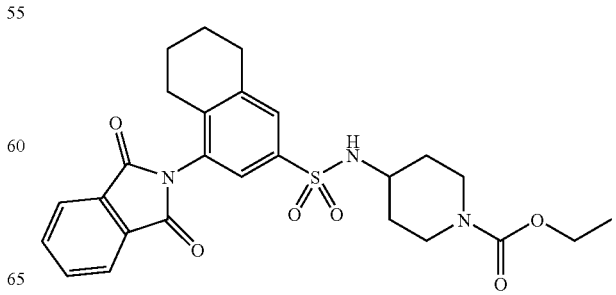

4-[4-(1,3-Dioxo-1,3-dihydro-isoindol-2-yl)-5,6,7,8-tetrahydro-naphthalene-2-sulfonylamino]-piperidine-1-carboxylic acid ethyl ester (H-61)

The title compound was prepared following general procedure in Scheme 20, substituting phthaloyl dichloride for 2-methyl-benzoyl chloride and diethylpyrocarbonate for isobutyryl chloride. $^1$H NMR (300 MHz, DMSO) δ 7.97 (m, 1H), 7.96 (s, 1H), 7.92 (s, 1H), 7.91 (m, 1H), 7.76 (d, 1H), 7.65 (d, 2H), 4.00 (q, 2H), 3.74 (d, 2H), 3.23 (d, 2H), 2.88 (m, 4H), 1.71 (m, 7H), 1.25 (m, 2H), 1.14 (t, 3H). LC/MS m/z 511 (M−H)⁻, 513 (M+H)⁺

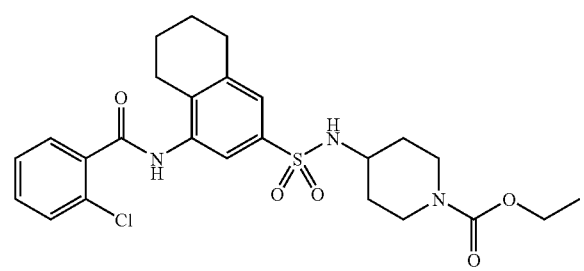

4-[4-(2-Chloro-benzoylamino)-5,6,7,8-tetrahydro-naphthalene-2-sulfonylamino]-piperidine-1-carboxylic acid ethyl ester (H-62)

The title compound was prepared following general procedure in Scheme 20, substituting 2-chloro-benzoyl chloride for 2-methyl-benzoyl chloride and diethylpyrocarbonate for isobutyryl chloride. $^1$H NMR (300 MHz, DMSO) δ 10.04 (s, 1H), 7.81 (s, 1H), 7.77 (s, 1H), 7.63 (dd, 1H), 7.56 (dt, 1H), 7.49 (dt, 2H), 7.43 (s, 1H), 3.97 (q, 2H), 3.72 (d, 2H), 3.19 (m, 1H), 2.82 (m, 4H), 2.76 (m, 2H), 1.75 (d, 4H), 1.73 (m, 2H), 1.27 (m, 2H), 1.14 (t, 3H). LC/MS m/z 519 (M−H)⁻, 520 (M+H)⁺

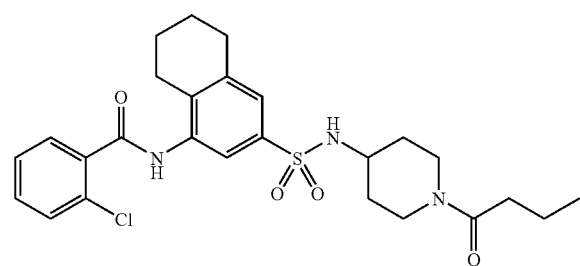

N-[3-(1-Butyryl-piperidin-4-ylsulfamoyl)-5,6,7,8-tetrahydro-naphthalen-1-yl]-2-chloro-benzamide (H-63)

The title compound was prepared following general procedure in Scheme 20, substituting 2-chloro-benzoyl chloride for 2-methyl-benzoyl chloride and butyryl chloride for isobutyryl chloride. $^1$H NMR (300 MHz, DMSO) δ 10.04 (s, 1H), 7.79 (s, 1H), 7.64 (dd, 1H), 7.56 (dt, 1H), 7.49 (dt, 2H), 7.43 (s, 1H), 4.05 (d, 1H), 3.67 (d, 1H), 3.24 (m, 1H), 3.02 (m, 1H), 2.76 (m, 2H), 2.68 (m, 3H), 2.22 (t, 2H), 1.74 (m, 5H), 1.64 (m, 2H), 1.44 (m, 2H), 1.25 (m, 2H), 0.85 (t, 3H). LC/MS m/z 517 (M−H)⁻, 519 (M+H)⁺

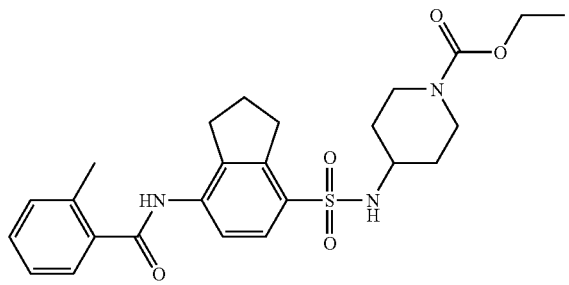

4-[7-(2-Methyl-benzoylamino)-indane-4-sulfonylamino]-piperidine-1-carboxylic acid ethyl ester (H-64)

The title compound was made following general procedure in Scheme 10, substituting indan-4-ylamine for 5,6,7,8-tetrahydro-naphthalen-1-ylamine, and ethyl chloroformate for butyryl chloride. $^1$H NMR (300 MHz, DMSO) δ 7.65 (m, 3H), 7.48 (d, 1H), 7.38 (d, 1H), 7.30 (m, 2H), 3.97 (q, 2H), 3.76 (d, 2H), 3.18 (m, 2H), 2.93 (m, 2H), 2.79 (m, 2H), 2.49 (s, 3H), 2.05 (m, 2H), 1.55 (m, 2H), 1.23 (m, 2H), 1.13 (t, 3H); LC/MS m/z 486 (M+H)⁺.

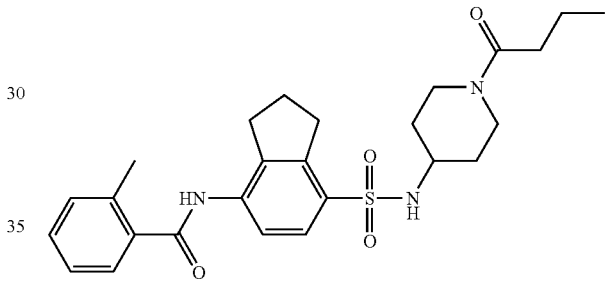

N-[7-(1-Butyryl-piperidin-4-ylsulfamoyl)-indan-4-yl]-2-methyl-benzamide (H-65)

The title compound was made following general procedure in Scheme 10, substituting indan-4-ylamine for 5,6,7,8-tetrahydro-naphthalen-1-ylamine. $^1$H NMR (300 MHz, DMSO) δ 7.66 (m, 3H), 7.44 (d, 1H), 7.40 (m, 1H), 7.29 (m, 2H), 4.10 (d, 1H), 3.68 (d, 1H), 3.17 (m, 3H), 2.92 (m, 3H), 2.60 (t, 2H); 2.41 (s, 3H), 2.16 (m, 2H), 1.55 (m, 1H), 1.47 (m, 2H), 1.23 (m, 2H), 0.84 (t, 6H); LC/MS m/z 482 (M−H)⁻.

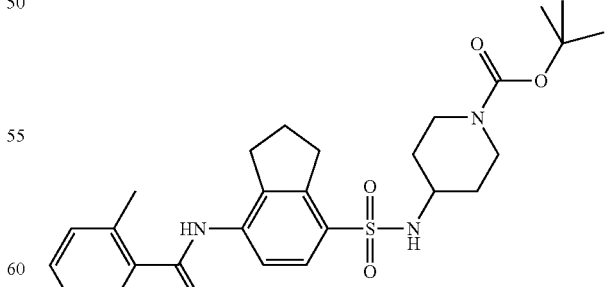

4-[7-(2-Methyl-benzoylamino)-indane-4-sulfonylamino]-piperidine-1-carboxylic acid tert-butyl ester (H-66)

The title compound was made following general procedure in scheme 10, substituting indan-4-ylamine for 5,6,7,8-tetrahydro-naphthalen-1-ylamine. ¹H NMR (300 MHz, CDCl₃) δ 8.24 (d, 1H), 7.79 (d, 1H), 7.50 (d, 1H), 7.38 (m, 2H), 7.27 (m, 2H), 4.59 (d, 1H), 3.90 (d, 2H), 3.28 (m, 3H), 2.80 (m, 3H); 2.53 (s, 3H), 2.20 (m, 2H), 1.75 (d, 2H), 1.42 (s, 9H), 1.35 (m, 2H); LC/MS m/z 514 (M+H)⁺.

rahydro-naphthalen-1-ylamine. ¹H NMR (300 MHz, MeOD) δ 7.73 (m, 2H), 7.51 (d, 1H), 7.30 (m, 3H), 6.41 (m, 1H), 3.83 (d, 2H), 3.19 (m, 2H), 2.96 (t, 2H), 2.77 (t, 2H), 2.48 (s, 3H); 2.16 (m, 2H), 1.64 (m, 2H), 1.33 (m, 2H), 1.06 (t, 3H); LC/MS m/z 485 (M+H)⁺.

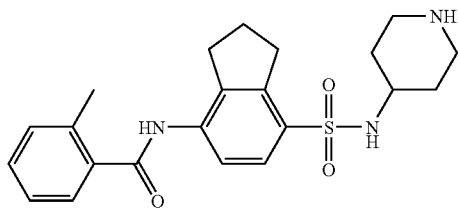

2-Methyl-N-[7-(piperidin-4-ylsulfamoyl)-indan-4-yl]-benzamide (H-67)

The title compound was made following general procedure in Scheme 10, substituting indan-4-ylamine for 5,6,7,8-tetrahydro-naphthalen-1-ylamine. ¹H NMR (300 MHz, DMSO) δ 8.90 (m, 2H), 7.92 (d, 1H), 7.65 (q, 2H), 7.49 (d, 1H), 7.38 (m, 1H), 7.28 (m, 2H), 3.37 (br s, 1H), 3.18 (m, 5H), 2.93 (m, 4H); 2.40 (s, 3H), 2.08 (m, 2H), 1.67 (m, 4H); LC/MS m/z 414 (M+H)⁺.

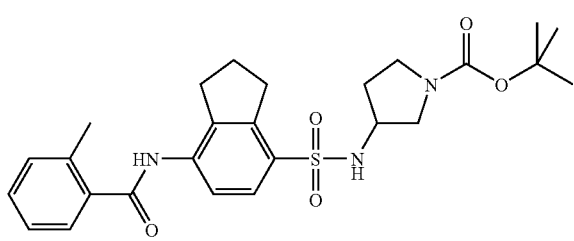

(±)-3-[7-(2-Methyl-benzoylandno)-indane-4-sulfonylamino]-pyrrolidine-1-carboxylic acid tert-butyl ester (H-68)

The title compound was made following general procedure in Scheme 10, substituting indan-4-ylamine for 5,6,7,8-tetrahydro-naphthalen-1-ylamine and 3-amino-pyrrolidine-1-carboxylic acid tert-butyl ester for 4-amino-piperidine-1-carboxylic acid tert-butyl ester. ¹H NMR (300 MHz, MeOD) δ 7.72 (s, 2H), 7.50 (d, 1H), 7.40 (m, 1H), 7.28 (m, 2H), 3.76 (m, 1H), 3.30 (m, 5H), 3.07 (dd, 1H), 2.97 (t, 2H), 2.48 (s, 3H); 2.16 (m, 2H), 1.98 (m, 1H), 1.78 (m, 1H), 1.40 (s, 9H); LC/MS m/z 500 (M+H)⁺.

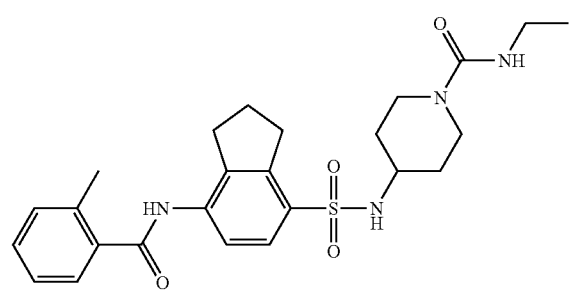

4-[7-(2-Methyl-benzoylamino)-indane-4-sulfonylamino]-piperidine-1-carboxylic acid ethylamide (H-69)

The title compound was made following general procedure in Scheme 10, substituting indan-4-ylamine for 5,6,7,8-tet-

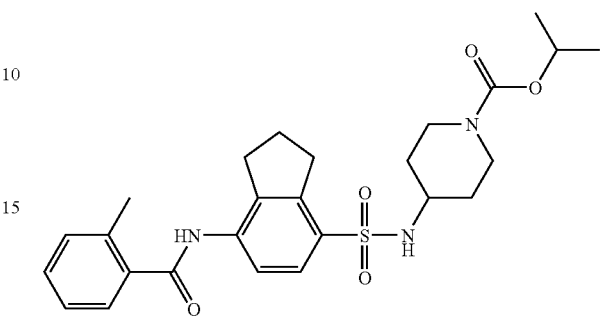

4-[7-(2-Methyl-benzoylamino)-indane-4-sulfonylamino]-piperidine-1-carboxylic acid isopropyl ester (H-70)

The title compound was made following general procedure in Scheme 10, substituting indan-4-ylamine for 5,6,7,8-tetrahydro-naphthalen-1-ylamine and isopropyl chloroformate for butyryl chloride. ¹H NMR (300 MHz, MeOD) δ 7.68 (m, 2H), 7.51 (d, 1H), 7.38 (m, 3H), 3.91 (d, 2H), 2.98 (m, 2H), 2.82 (m, 2H), 2.48 (s, 3H), 2.17 (m, 2H), 1.68 (d, 2H); 1.33 (m, 2H), 1.20 (d, 6H); LC/MS m/z 500 (M+H)⁺.

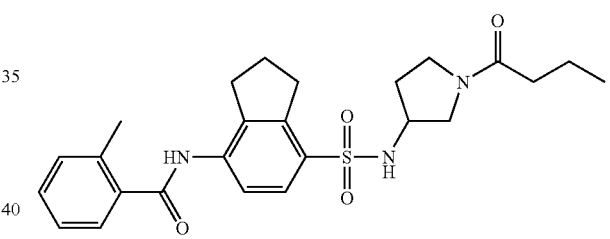

(±)-N-[7-(1-Butyryl-pyrrolidin-3-ylsulfamoyl)-indan-4-yl]-2-methyl-benzamide (H-71)

The title compound was made following general procedure in Scheme 10, substituting indan-4-ylamine for 5,6,7,8-tetrahydro-naphthalen-1-yl amine and 3-amino-pyrrolidine-1-carboxylic acid tert-butyl ester for 4-amino-piperidine-1-carboxylic acid tert-butyl ester ¹H NMR (300 MHz, CDCl₃) δ 8.22 (m, 1H), 7.76 (dd, 1H), 7.49 (m, 2H), 7.39 (m, 1H), 7.28 (m, 2H), 5.32 (dd, 1H), 3.80 (m, 1H), 3.40 (m, 5H), 2.88 (t, 2H); 2.52 (s, 3H), 2.20 (m, 6H), 1.90 (m, H), 1.60 (m, 2H), 0.84 (t, 3H); LC/MS m/z 470 (M+H)⁺.

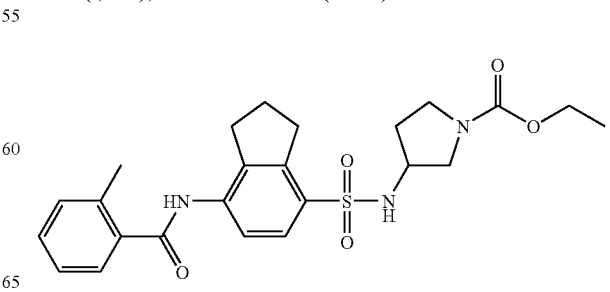

(±)-3-[7-(2-Methyl-benzoylamino)-indane -4-sulfonylamino]-pyrrolidine-1-carboxylic acid ethyl eter (H-72)

The title compound was made following general procedure in Scheme 10, substituting indan-4-ylamine for 5,6,7,8-tetrahydro-naphthalen-1-ylamine, 3-amino-pyrrolidine-1-carboxylic acid tert-butyl ester for 4-amino-piperidine-1-carboxylic acid tert-butyl ester and ethyl chloroformate for butyryl chloride. $^1$H NMR (300 MHz, CDCl$_3$) δ 8.22 (d, 1H), 7.76 (d, 1H), 7.50 (m, 2H), 7.38 (m, 1H), 7.26 (m, 2H), 5.18 (d, 1H), 4.06 (q, 2H), 3.80 (m, 1H), 2.86 (t, 2H); 2.52 (s, 3H), 2.20 (m, 2H), 2.00 (m, 1H), 1.22 (t, 3H); LC/MS m/z 472 (M+H)$^+$.

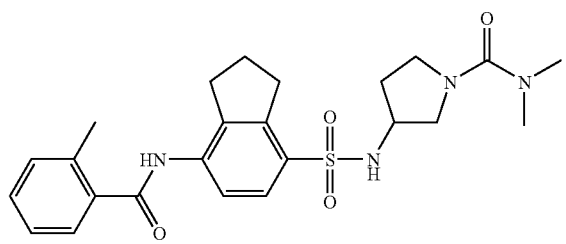

(±)-3-[7-(2-Methyl-benzoylamino)-indane-4-sulfonylamino]-pyrrolidine-1-carboxylic acid dimethylamide (H-73)

The title compound was made following general procedure in Scheme 10, substituting indan-4-ylamine for 5,6,7,8-tetrahydro-naphthalen-1-ylamine, 3-amino-pyrrolidine-1-carboxylic acid tert-butyl ester for 4-amino-piperidine-1-carboxylic acid tert-butyl ester and dimethylcarbamyl chloride for butyryl chloride. $^1$H NMR (300 MHz, CDCl$_3$) δ 8.21 (d, 1H), 7.77 (d, 1H), 7.50 (m, 2H), 7.40 (m, 1H), 7.28 (d, 2H), 5.35 (d, 1H), 3.77 (m, 1H), 3.35 (m, 6H), 2.87 (t, 2H); 2.52 (s, 3H), 2.19 (m, 2H), 1.96 (m, 1H), 1.84 (m, 1H); LC/MS m/z 471 (M+H)$^+$.

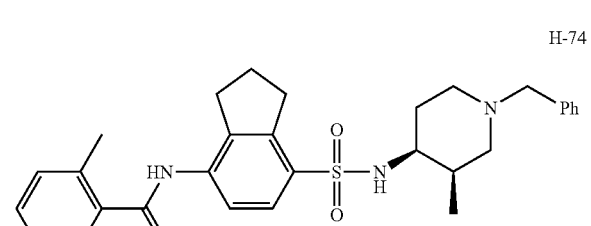

H-74

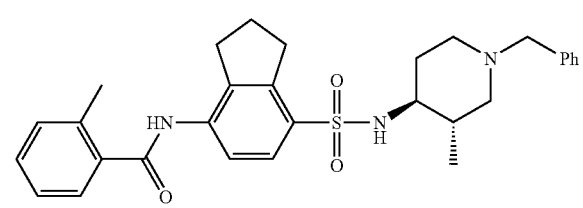

H-75

(±)-cis-N-[7-(1-Benzyl-3-methyl-piperidin-4-ylsulfamoyl)-indan-4-yl]-2-methyl-benzamide (H-74) and (±)-trans-N-[7-(1-Benzyl-3-methyl-piperidin-4-ylsulfamoyl)-indan-4-yl]-2-methyl-benzamide (H-75)

The title compounds were made following general procedure in Scheme 10, substituting indan-4-ylamine for 5,6,7,8-tetrahydro-naphthalen-1-ylamine and (±)4-amino-1-benzyl-3-methyl-piperidine for 4-amino-piperidine-1-carboxylic acid tert-butyl ester. The diastereomers H-74 and H-75 were separated by flash column chromatography. H-74: $^1$H NMR (300 MHz, CDCl$_3$) δ 8.25 (d, 1H), 7.79 (d, 1H), 7.50 (d, 1H), 7.30 (m, 8H), 4.46 (d, 1H), 3.42 (q, 2H), 3.35 (m, 4H), 2.82 (t, 2H), 2.54 (s, 3H), 2.23 (m, 2H), 2.28 (m, 2H), 1.87 (m, 1H), 1.56 (m, 3H), 0.83 (m, 3H); LC/MS m/z 518 (M+H)$^+$.

H-75: $^1$H NMR (300 MHz, CDCl$_3$) δ 8.24 (d, 1H), 7.79 (d, 1H), 7.50 (d, 1H), 7.30 (m, 8H), 4.24 (d, 1H), 3.42 (q, 2H), 3.29 (m, 2H), 2.80 (m, 4H), 2.54 (s, 3H), 2.20 (m, 2H), 1.89 (m, 1H), 1.67 (m, 2H), 1.40 (m, 1H), 0.78 (d, 3H); LC/MS m/z 518 (M+H)$^+$.

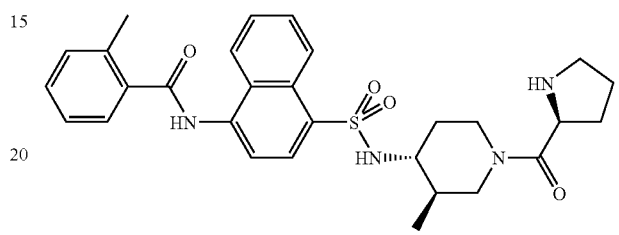

(3R,4R)-2-(S)-Methyl-N-{4-[3-methyl-1-(pyrrolidine-2-carbonyl)-piperidin-4-ylsulfamoyl]-naphthalen-1-yl}-benzamide (J-1)

The title compound was prepared following the general procedure in scheme 6.

$^1$H NMR (300 MHz, MeOD) δ 8.81 (m, 1H), 8.35 (d, 1H), 8.26 (d, 1H), 7.96 (d, 1H), 7.73 (m, 3H), 7.38 (m, 3H), 4.60 (m, 1H), 4.32 (m, 1H), 3.67 (m, 1H), 3.50 (m, 1H), 2.98 (m, 2H), 2.56 (s, 3H), 2.40 (m, 1H), 2.05 (m, 2H), 1.85 (m, 1H), 1.42 (m, 4H), 1.19 (m, 1H), 0.65 (dofd, 3H). LC/MS (M+H)$^+$ m/z 535.

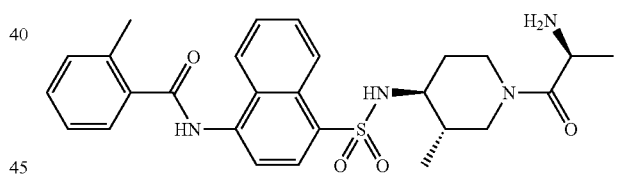

(3S, 4S)-N-{4-[1-(2-(S)-Amino-propionyl)-3-methyl-piperidin-4-ylsulfamoyl]-naphthalen-1-yl}-2-methyl-benzamide (J-2)

The title compound was made following general procedure in scheme 6. $^1$H NMR (300 MHz, MeOD) δ 8.79 (d, 1H), 8.37 (d, 1H), 8.24 (d, 1H), 7.96 (d, 1H), 7.77 (m, 3H), 7.40 (m, 3H), 4.31 (m, 2H), 3.63 (m, 1H), 2.96 (m, 2H ), 2.78 (m, 1H), 2.55 (s, 3H), 2.38 (m, 1H), 1.61 (m, 1H), 1.39 (d, 3H), 1.25 (m, 1H), 0.62 (m, 3H); LC/MS (M+H)$^+$ m/z 509.

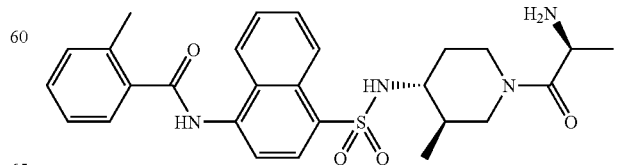

(3R, 4R)-N-{4-[1-(2-(S)-Amino-propionyl)-3-methyl-piperidin-4-ylsulfamoyl]-naphthalen-1-yl}-2-methyl-benzamide (J-3)

The title compound was made following general procedure in scheme 6. ¹H NMR (300 MHz, MeOD) δ 8.79 (d, 1H), 8.37 (d, 1H), 8.24 (d, 1H), 7.96 (d, 1H), 7.77 (m, 3H), 7.40 (m, 3H), 4.31 (m, 2H), 3.63 (m, 1H), 2.96 (m, 2H), 2.78 (m, 1H), 2.55 (s, 3H), 2.38 (m, 1H), 1.61 (m, 1H), 1.39 (m, 3H), 1.25 (m, 1H), 0.62 (m, 3H); LC/MS (M+H)⁺ m/z 509.

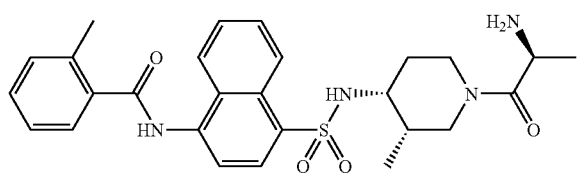

(3S, 4R)-N-{4-[1-(2-(S)-Amino-propionyl)-3-methyl-piperidin-4-ylsulfamoyl]-naphthalen-1-yl}-2-methyl-benzamide (J-4)

The title compound was made following general procedure in scheme 6. ¹H NMR (300 MHz, MeOD) δ 8.79 (d, 1H), 8.37 (d, 1H), 8.24 (d, 1H), 7.96 (d, 1H), 7.77 (m, 3H), 7.40 (m, 3H), 4.31 (m, 1H), 3.82 (m, 1H), 3.43 (m, 2H), 3.05 (m, 1H), 2.55 (s, 3H), 1.81 (m, 1H), 1.39 (d, 6H), 0.63 (m, 3H); LC/MS (M+H)⁺ m/z 509.

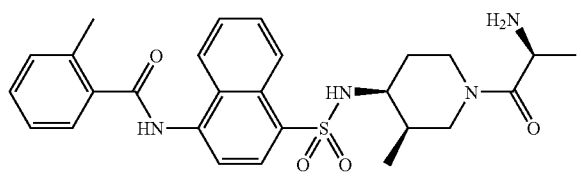

(3R, 4S)-N-{4-[1-(2-(S)-Amino-propionyl)-3-methyl-piperidin-4-ylsulfamoyl]-naphthalen-1-yl}-2-methyl-benzamide (J-5)

The title compound was made following general procedure in scheme 6. ¹H NMR (300 MHz, MeOD) δ 8.79 (d, 1H), 8.37 (d, 1H), 8.24 (d, 1H), 7.96 (d, 1H), 7.77 (m, 3H), 7.40 (m, 3H), 4.31 (m, 1H), 3.52 (m, 3H), 3.21 (m. 1H), 2.55 (s, 3H), 1.81 (m, 1H), 1.61 (m, 1H), 1.39 (m, 5H), 0.66 (m, 3H); LC/MS (M+H)⁺ m/z 509.

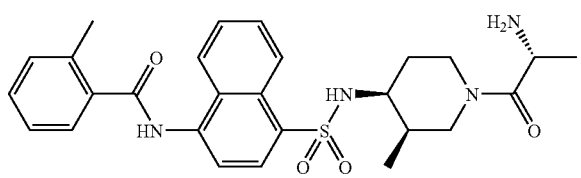

(3R, 4S)-N-{4-[1-(2-(R)-Amno-propionyl)-3-methyl-piperidin-4-ylsulfamoyl]-naphthalen-1-yl}-2-methyl-benzamide (J-6)

The title compound was made following general procedure in scheme 6. ¹H NMR (300 MHz, MeOD) δ 8.81 (m, 1H), 8.37 (d, 1H), 8.24 (d, 1H), 7.95 (d, 1H), 7.71 (m, 3H), 7.40 (m, 3H), 4.21 (m, 1H), 3.40 (m, 4H), 2.55 (s, 3H), 1.81 (m, 1H), 1.39 (m, 6H), 0.66 (m, 3H); LC/MS (M+H)⁺ m/z 509.

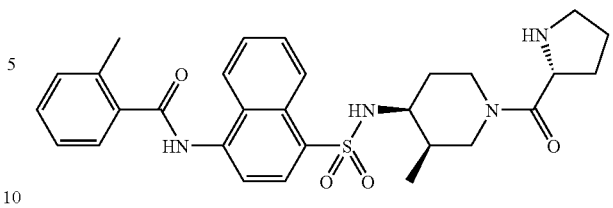

(3R, 4S)-2-Methyl-N-{4-[3-methyl-1-((R) pyrrolidine-2-carbonyl)-piperidin-4-ylsuffamoyl]-naphthalen-1-yl}-benzamide (J-7)

The title compound was prepared following the general procedure in scheme 6.

¹H NMR (300 MHz, MeOD) δ 8.84 (m, 1H), 8.32 (d, 1H), 8.24 (d, 1H), 7.93 (d, 1H), 7.70 (m, 3H), 7.40 (m, 3H), 4.41 (m, 1H), 3.35 (m, 6H), 2.55 (s, 3H), 2.49 (m, 1H), 1.99 (m, 2H), 1.79 (m, 2H), 1.39 (m, 3H), 0.66 (m, 3H); LC/MS (M+H)⁺ m/z 535.

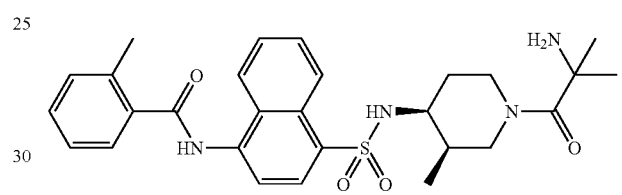

(3R, 4S)-N-{4-[1-(2-Amino-2-methyl-propionyl)-3-methyl-piperidin-4-ylsuffamoyl]-naphthalen-1-yl}-2-methyl-benzamide (J-8)

The title compound was prepared following the general procedure in scheme 6.

¹H NMR (300 MHz, MeOD) δ 8.81 (m, 1H), 8.37 (d, 1H), 8.24 (d, 1H), 7.95 (d, 1H), 7.71 (m, 3H), 7.40 (m, 3H), 3.40 (m, 4H), 2.55 (s, 3H), 1.83 (m, 4H), 1.78 (s, 6H), 0.66 (m, 3H); LC/MS (M+H)⁺ m/z 523.

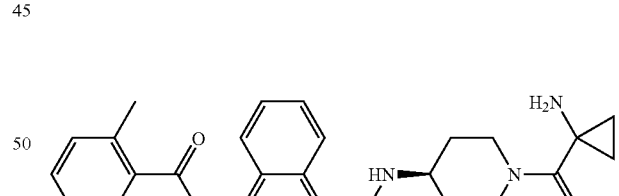

(3R, 4S)-N-{4-[1-(1-Amino-cyclopropanecarbonyl)-3-methyl-piperidin-4-ylsuffamoyl]-naphthalen-1-yl}-2-methyl-benzamide (J-9)

The title compound was prepared following the general procedure in scheme 6.

¹H NMR (300 MHz, MeOD) δ 8.81 (m, 1H), 8.37 (d, 1H), 8.24 (d, 1H), 7.95 (m, 1H), 7.71 (m, 3H), 7.40 (m, 3H), 3.45 (m, 4H), 2.55 (s, 3H), 1.70 (m, 1H), 1.41 (m, 3H), 0.89 (m, 2H), 0.79 (m, 2H), 0.62 (m, 3H); LC/MS (M+H)⁺ m/z 521

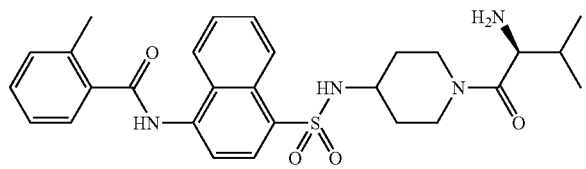

(S)-N-{4-[1-(2-Amino-3-methyl-butyryl)-piperidin-4-yl-sulfamoyl]-naphthalen-1-yl}-2-methyl-benzamide (J-10)

The title compound was prepared following the general procedure in scheme 6.

$^1$H NMR (300 MHz, MeOD) δ 8.75 (d, 1H), 8.35 (d, 1H), 8.21 (d, 1H), 7.91 (d, 1H), 7.71 (m, 3H), 7.40 (m, 3H), 4.20 (m, 2H), 3.69 (m, 1H), 3.38 (m, 1H), 3.10 (m, 1H), 2.81 (m, 1H), 2.55 (s, 3H), 2.05 (m, 1H), 1.69 (m, 2H), 1.32 (m, 2H), 0.95 (m, 6H); LC/MS (M+H)$^+$ m/z 523

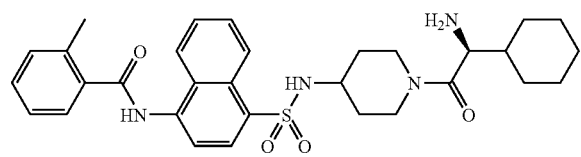

(S)-N-{4-[1-(2-Aniino-2-cyclohexyl-acetyl)-piperidin-4-ylsulfamoyl]-naphthalen-1-yl}-2-methyl-benzainde (J-11)

The title compound was prepared following the general procedure in scheme 6.

$^1$H NMR (300 MHz, MeOD) δ 8.75 (m, 1H), 8.31 (d, 1H), 8.24 (d, 1H), 7.91 (d, 1H), 7.70 (m, 3H), 7.38 (m, 3H), 4.20 (m, 2H), 3.69 (m, 1H), 3.38 (m, 1H), 3.10 (m, 1H), 2.81 (m, 1H), 2.55 (s, 3H), 1.63 (m, 7H), 1.21 (m, 7H); LC/MS (M+H)$^+$ m/z 563

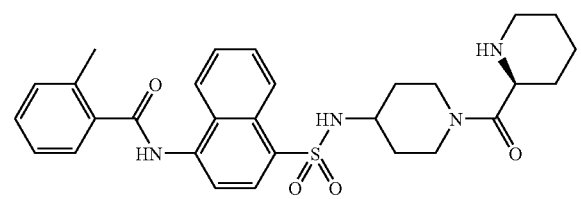

(S)-2-Methyl-N-{4-[1-(piperidine-2-carbonyl)-piperidin-4-ylsulfamoyl]-naphthalen-1-yl}-benzamide (J-12)

The title compound was prepared following the general procedure in scheme 6. $^1$H NMR (300 MHz, MeOD) δ 8.75 (m, 1H), 8.31 (d, 1H), 8.24 (d, 1H), 7.92 (d, 1H), 7.70 (m, 3H), 7.38 (m, 3H), 4.18 (m, 2H), 3.62 (m, 1H), 3.38 (m, 1H), 3.01 (m, 4H), 2.55 (s, 3H), 1.63 (m, 1OH); LC/MS (M+H)$^+$ m/z 535.

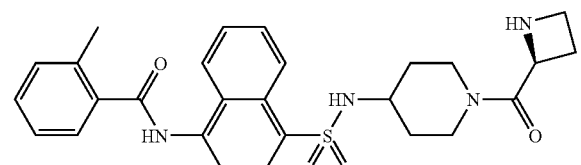

(S)-N-{4-[1-(Azetidine-2-carbonyl)-piperidin-4-ylsulfamoyl]-naphthalen-1-yl}-2-methyl-benzamide (J-13)

The title compound was prepared following the general procedure in scheme 6. $^1$H NMR (300 MHz, MeOD) δ 8.75 (m, 1H), 8.31 (d, 1H), 8.24 (d, 1H), 7.92 (d, 1H), 7.70 (m, 3H), 7.38 (m, 3H), 5.21 (m, 1H), 4.05 (m, 2H), 3.82 (m, 1H), 2.84 (m, 3H), 2.55 (s, 3H), 2.41 (m, 1H), 1.61 (m, 3H), 1.35(H, 3H); LC/MS (M+H)$^+$ m/z 507.

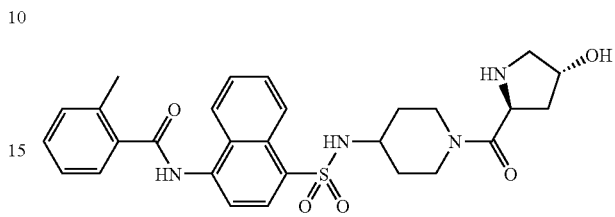

N{4-[1-(4-(R)—Hydroxy-(S)-pyrrolidine-2-carbonyl)-piperidin-4-ylsulfamoyl]-naphthalen-1-yl}-2-methyl-benzamide (J-14)

The title compound was prepared following the general procedure in scheme 6. $^1$H NMR (300 MHz, MeOD) δ 8.75 (m, 1H), 8.31 (d, 1H), 8.24 (d, 1H), 7.92 (d, 1H), 7.70 (m, 3H), 7.38 (m, 3H), 4.65 (m, 1H), 4.50 (m. 1H), 4.15 (m, 1H), 3.62 (m, 1H), 3.40 (m, 2H), 3.21 (m, 1H), 3.10 (m, 1H), 2.82 (m, 1H), 2.55 (s, 3H), 2.35 (m, 1H), 1.89 (m, 1H), 1.65 (m, 2H), 1.30 (m, 2H); LC/MS (M+H)$^+$ m/z 537.

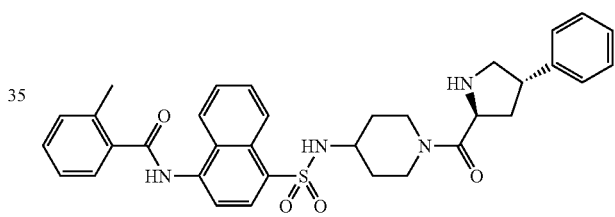

2-Methyl-N-{4-[1-(4-(R)-phenyl-(S)-pyrrolidine-2-carbonyl)-piperidin-4-ylsulfamoyl]-naphthalen-1-yl}-benzamide (J-15)

The title compound was prepared following the general procedure in scheme 6. $^1$H NMR (300 MHz, MeOD) δ 8.75 (m, 1H), 8.31 (d, 1H), 8.21 (m, 1H), 7.92 (d, 1H), 7.68 (m, 3H), 7.30 (m, 8H), 4.79 (m, 1H), 4.20 (m. 1H), 3.75 (m, 1H), 3.61 (m, 1H), 3.38 (m, 3H), 3.10 (m, 1H ), 2.82 (m, 1H), 2.55 (s, 3H), 2.42 (m, 1H), 2.29 (m, 1H), 1.65 (m, 2H), 1.39 (m, 2H); LC/MS (M+H)$^+$ m/z 597.

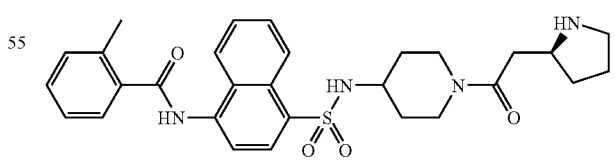

(S)-2-Methyl-N-{4-[1-(2-pyrrolidin-2-yl-acetyl)-piperidin-4-ylsulfamoyl]-4-naphthalen-1-yl}-benzamide (J-16)

The title compound was prepared following the general procedure in scheme 6. $^1$H NMR (300 MHz, MeOD) δ 8.75 (m, 1H), 8.31 (d, 1H), 8.24 (d, 1H), 7.92 (d, 1H), 7.70 (m, 3H), 7.38 (m, 3H), 4.18 (m, 1H), 3.78 (m, 1H), 3.65 (m, 1H), 3.21

(m, 3H), 3.00 (m, 2H), 2.70 (m, 2H ), 2.55 (s, 3H), 2.20 (m, 1H), 2.00 (m, 2H), 1.65 (m, 3H), 1.30 (m, 2H); LC/MS (M+H)⁺ m/z 535.

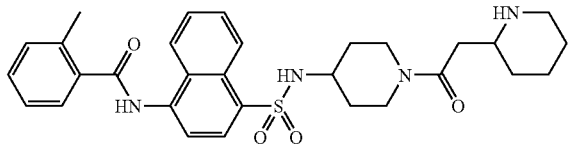

(±)-2-Methyl-N-{4-[1-(2-piperidin-2-yl-acetl)-piperidin-4-ylsulfamoyl]-naphthalen-1-yl}-benzainde (J-17)

The title compound was prepared following the general procedure in scheme 6. $^1$H NMR (300 MHz, MeOD) δ 8.75 (m, 1H), 8.31 (d, 1H), 8.24 (d, 1H), 7.92 (d, 1H), 7.70 (m, 3H), 7.38 (m, 3H ), 4.18 (m, 1H), 3.65 (m. 1H), 3.39 (m, 2H), 3.00 (m, 2H), 2.70 (m, 2H), 2.56 (m, 1H), 2.55 (s, 3H), 1.83 (m, 3H), 1.62 (m, 6H), 1.32 (m, 2H); LC/MS (M+H)⁺ m/z 549.

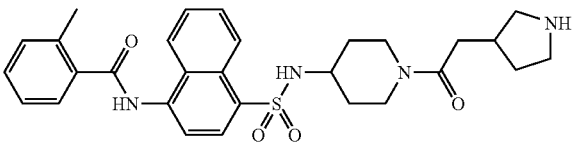

(±)-2-2-Methyl-N-{4-[1-(2-pyrrolidin-3-yl-acetyl)-piperidin-4-ylsulfamoyl]-naphthalen-1-yl}-benzamide (J-18)

The title compound was prepared following the general procedure in scheme 6. $^1$H NMR (300 MHz, MeOD) δ 8.75 (m, 1H), 8.31 (d, 1H), 8.24 (d, 1H), 7.92 (d, 1H), 7.70 (m, 3H), 7.38 (m, 3H ), 4.18 (m, 1H), 3.65 (m. 1H), 3.45 (m, 1H), 3.38 (m, 2H), 3.18 (m, 1H), 3.02 (m, 1H), 2.81 (m, 1H), 2.61 (m, 2H), 2.55 (s, 3H), 2.45 (m, 1H), 2.19 (m, 1H), 1.62 (m, 4H), 1.30 (m, 2H); LC/MS (M+H)⁺ m/z 535.

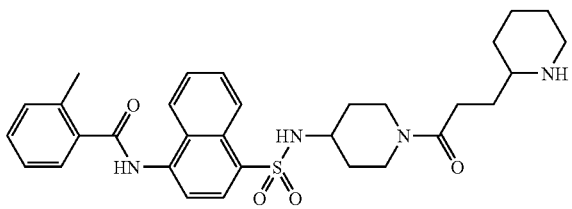

(±)-2-Methyl-N-{4-[1-(3-piperidin-2-yl-propionyl)-piperidin-4-ylsulfamoyl]-naphthalen-1-yl}-benzamiide (J-19)

$^1$H NMR (300 MHz, MeOD) δ 8.75 (m, 1H), 8.31 (d, 1H), 8.24 (d, 1H), 7.92 (d, 1H), 7.70 (m, 3H), 7.38 (m, 3H1), 4.16 (m, 1H), 3.69 (m. 1H), 2.98 (m, 3H), 2.70 (m, 1H), 2.55 (s, 3H), 2.45 (m, 2H), 1.62 (m, 14H); LC/MS (M+H)⁺ m/z 563.

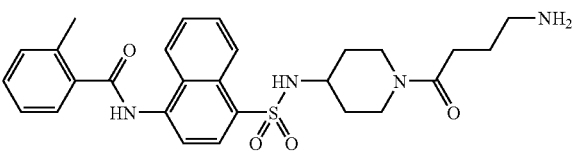

N-{4-[1-(4-Amino-butyryl)-piperidin-4-ylsulfamoyl]-naphthalen-1-yl}-2-methyl-benzamide (J-20)

The title compound was prepared following the general procedure in scheme 6. $^1$H NMR (300 MHz, MeOD) δ 8.75 (m, 1H), 8.31 (m, 1H), 8.24 (m, 1H), 7.89 (m, 1H), 7.68 (m, 3H), 7.38 (m, 3H1), 4.16 (m, 1H), 3.69 (m. 1H), 3.00 (m, 1H), 2.85 (m, 2H), 2.69 (m, 1H), 2.55 (s, 3H), 2.42 (m, 2H), 1.82 (m, 2H), 1.60 (m, 3H), 1.28 (m, 2H); LC/MS (M+H)⁺ m/z 509.

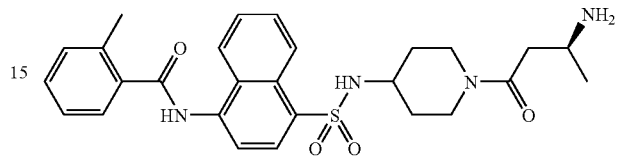

(S)-N-{4-[1-(3-Amino-butyryl)-piperidin-4-ylsulfamoyl]-naphthalen-1-yl}-2-methyl-benzamide (J-21)

The title compound was prepared following the general procedure in scheme 6. $^1$H NMR (300 MHz, MeOD) δ 8.75 (m, 1H), 8.31 (m, 1H), 8.24 (m, 1H), 7.92 (m, 1H), 7.70 (m, 3H), 7.38 (m, 3H ), 4.19 (m, 1H), 3.65 (m. 1H), 3.55 (m, 1H), 3.01 (m, 1H), 2.66 (m, 3H), 2.55 (s, 31H), 2.45 (m, 1H), 1.62 (m, 2H), 1.25 (m, 511); LC/MS (M+H)⁺ m/z 495.

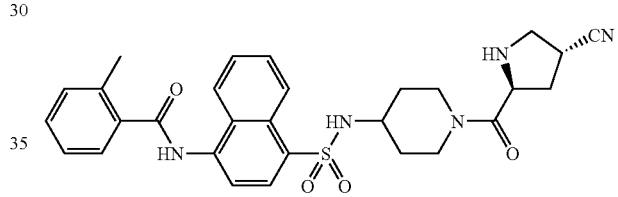

N-{4-[1-(4-(RCyano-pyrrolidine-2-(S)-carbonyl)-piperidin-4-ylsulfamoyl]-naphthalen-1-yl}-2-methyl-benzainde (J-22)

The title compound was prepared following the general procedure in scheme 6. $^1$H NMR (300 MHz, MeOD) δ 8.75 (m, 1H), 8.31 (d, 1H), 8.24 (d, 1H), 7.92 (d, 1H), 7.70 (m, 3H), 7.38 (m, 3H1), 4.15 (m, 1H), 3.96 (m. 1H), 3.68 (m, 2H), 3.40 (m, 2H), 3.10 (m, 2H), 2.75 (m, 1H), 2.55 (s, 3H), 2.45 (m, 1H), 1.89 (m, 1H), 1.61 (m, 2H), 1.28 (m, 2H); LC/MS (M+H)⁺ m/z 546.

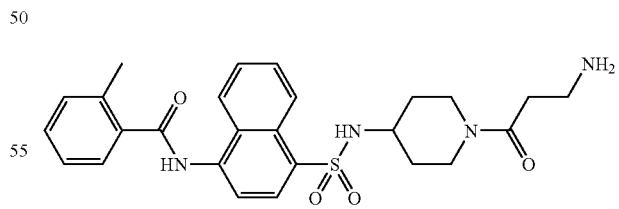

N-{4-[1-(3-Amino-propionyl)-piperidin-4-ylsulfamoyl]-naphthalen-1-yl}-2-methyl-benzamide (J-23)

The title compound was prepared following the general procedure in scheme 6. $^1$H NMR (300 MHz, MeOD) δ 8.75 (m, 1H), 8.31 (d, 1H), 8.24 (d, 1H), 7.92 (d, 1H) 7.70 (m, 3H), 7.38 (m, 3H), 4.19 (m, 1H), 3.65 (m. 1H), 3.05 (m, 3H), 2.71 (m, 1H), 2.62 (m, 3H), 2.55 (s, 3H), 1.62 (m, 2H), 1.29 (m, 2H); LC/MS (M+H)⁺ m/z 495.

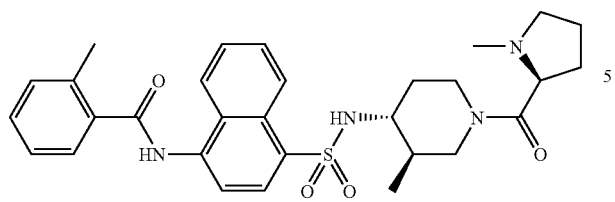

(3R, 4R)-2-Methyl-N-{4-[3-methyl-1-(1-methyl-(S)-pyrrolidine-2-carbonyl)-piperidin-4-ylsulfamoyl]-naphthalen-1-yl}-benzamide (J-24)

¹H NMR (300 MHz, MeOD) δ 8.78 (m, 1H), 8.32 (d, 1H), 8.24 (d, 1H), 7.93 (d, 1H), 7.70 (m, 3H), 7.38 (m, 3H ), 4.30 (m, 2H), 3.59 (m, 2H), 3.01 (m, 2H), 2.78 (d, 3H), 2.55 (s, 3H), 2.41 (m, 2H), 2.12 (m, 1H), 1.84 (m, 2H), 1.59 (m, 1H), 1.32 (m, 3H), 0.66 (m, 3H); LC/MS (M+H)⁺ m/z 549.

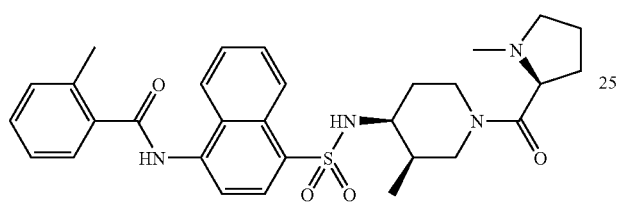

(3R, 4S)-2-Methyl-N-{4-[3-methyl-1-(1-methyl-(S)-pyrrolidine-2-carbonyl)-piperidin-4-ylsulfamoyl]-naphthalen-1-yl}-benzamide (J-25)

The title compound was prepared following the general procedure in scheme 6.

¹H NMR (300 MHz, MeOD) δ 8.82 (d, 1H), 8.32 (d, 1H), 8.24 (d, 1H), 7.93 (d, 1H), 7.70 (m, 3H), 7.38 (m, 3H), 4.33 (m, 1H), 3.62 (m, 1H), 3.45 (m, 3H), 3.25 (m, 1H), 3.08 (m, 1H), 2.80 (d, 3H), 2.55 (s, 3H), 2.49 (m, 1H), 2.12 (m, 1H), 1.84 (m, 3H), 1.45 (m, 3H), 0.66 (m, 3H); LC/MS (M+H)⁺ m/z 549.

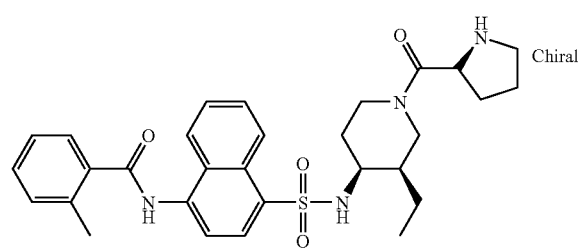

(3R, 4S)-N-{4-[3-Ethyl-1-(pyrrolidine-2-(S)-carbonyl)-piperidin-4-ylsulfamoyl]-naphthalen-1-yl}-2-methyl-benzamide (J-26)

The title compound was prepared as its formate salt following the general procedure in Scheme 6. ¹H NMR (300 MHz, MeOD) δ 8.84 (d, 1H), 8.49 (s, 1H), 8.34 (d, 1H), 8.25 (d, 1H), 7.95 (d, 1H), 7.70 (m, 3H), 7.40 (m, 3H), 4.50 (m, 1H), 3.50 (m, 2H), 3.20 (m, 4H), 2.56 (s, 3H), 2.40 (m, 1H), 2.00 (m, 2H), 1.80 (m, 1H), 1.50 (m, 3H), 1.00 (m, 3H), 0.50 (m, 3H); LC/MS (M+H)⁺ m/z 549.

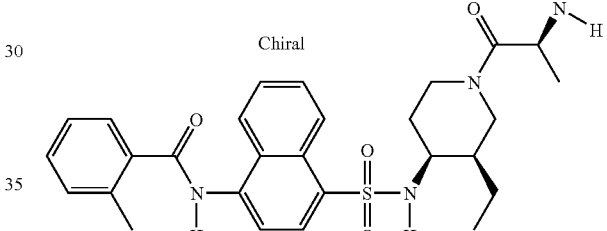

(3S, 4R)-N-{4-[1-(2-(S)-Amino-propionyl)-3-ethyl-piperidin-4-ylsulfamoyl]-naphthalen-1-yl}-2-methyl-benzamide (J-27)

The title compound was prepared as its formate salt following the general procedure in Scheme 6. ¹H NMR (300 MHz, MeOD) δ 8.86 (t, 1H), 8.54 (s, 1H), 8.29 (m, 2H), 7.96 (d, 1H), 7.73 (m, 3H), 7.35 (m, 3H), 4.32 (t, 1H), 3.54 (m, 5H), 2.56 (s, 3H), 1.39 (m, 8H), 0.49 (t, 3H); LC/MS (M+H)⁺ m/z 524.

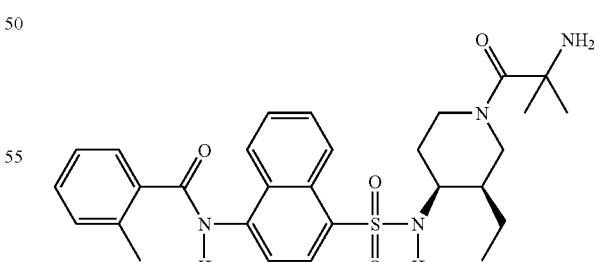

(3R, 4S)-N-{4-[1-(2-(S)-Amino-propionyl)-3-ethyl-piperidin-4-ylsulfamoyl]-naphthalen-1-yl}-2-methyl-benzamide (J-28)

The title compound was prepared as its formate salt following the general procedure in Scheme 6. ¹H NMR (300 MHz, MeOD) δ 8.86 (t, 1H), 8.54 (s, 1H), 8.29 (dd, 2H), 7.96 (d, 1H), 7.73 (m, 3H), 7.35 (m, 3H), 4.32 (t, 1H), 3.54 (m, 5H), 2.56 (s, 3H), 1.39 (m, 8H), 0.49 (t, 3H); LC/MS (M+H)⁺ m/z 524.

(±)-cis-N-{4-[1-(2-Anino-2-methyl-propionyl)-3-ethyl-piperidin-4-ylsulfamoyl]-naphthalen-1-yl}-2-methyl-benzamide (J-29)

The title compound was prepared as its formate salt following the general procedure in Scheme 6. ¹H NMR (300 MHz, MeOD) δ 8.86 (d, 1H), 8.54 (s, 1H), 8.33 (d, 1H), 8.25

(d, 1H), 7.95 (d, 1H), 7.74 (m, 3H), 7.38 (m, 3H), 3.55 (m, 5H), 2.56 (s, 3H), 1.52 (m, 9H), 1.02 (m, 2H), 0.50 (m, 3H); LC/MS (M+H)+ m/z 537.

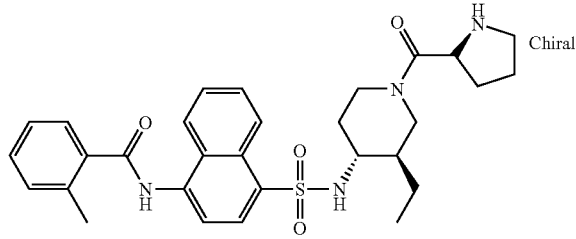

(3R, 4R)-N-{4-[3-Ethyl-1-(pyrrolidine-2-(S)-carbonyl)-piperidin-4-ylsulfamoyl]-naphthalen-1-yl}-2-methyl-benzamide (J-30)

The title compound was prepared as its formate salt following the general procedure in Scheme 6. $^1$H NMR (300 MHz, MeOD) δ 8.78 (m, 1H), 8.52 (s, 1H), 8.33 (d, 1H), 8.25 (d, 1H), 7.94 (d, 1H), 7.70 (m, 3H), 7.40 (m, 3H), 4.40 (m, 2H), 3.65 (m, 1H), 3.05 (m, 3H), 2.70 (m, 1H), 2.56 (s, 3H), 2.40 (m, 2H), 1.98 (m, 2H), 1.90 (m, 1H), 1.50 (m, 2H), 1.25 (m, 2H), 0.95 (m, 1H), 0.65 (m, 3H); LC/MS (M+H)+ m/z 549.

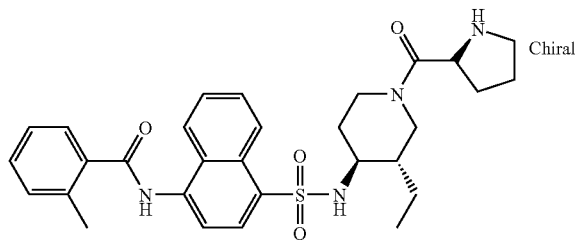

(3S, 4S)-N-{4-[3-Ethyl-1-(pyrrolidine-2-(S)-carbonyl)-piperidin-4-ylsulfamoyl]-naphthalen-1-yl}-2-methyl-benzamide (J-31)

The title compound was prepared as its formate salt following the general procedure in Scheme 6. $^1$H NMR (300 MHz, MeOD) δ 8.78 (d, 1H), 8.53 (s, 1H), 8.33 (d, 1H), 8.25 (d, 1H), 7.94 (d, 1H), 7.70 (m, 3H), 7.40 (m, 3H), 4.30 (m, 2H), 3.60 (m, 1H), 3.05 (m, 3H), 2.80 (m, 1H), 2.56 (s, 3H), 2.40 (m, 2H), 1.95 (m, 2H), 1.75 (m, 2H), 1.50 (m, 1H), 1.25 (m, 2H), 0.95 (m, 1H), 0.65 (m, 3H); LC/MS (M+H)+ m/z 549.

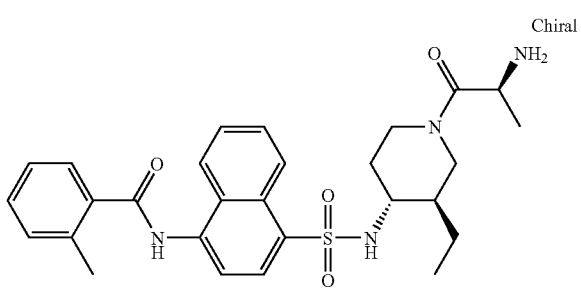

(3R, 4R)-N-{4-[1-(2-(S)-Amino-propionyl)-3-ethyl-piperidin-4-ylsulfamoyl]-naphthalen-1-yl}-2-methyl-benzamide (J-32)

The title compound was prepared as its formate salt following the general procedure in Scheme 6. $^1$H NMR (300 MHz, MeOD) δ 8.78 (d, 1H), 8.51 (s, 1H), 8.33 (d, 1H), 8.25 (d, 1H), 7.94 (d, 1H), 7.70 (m, 3H), 7.40 (m, 3H), 4.25 (m, 2H), 3.70 (m, 1H), 3.05 (m, 2H), 2.56 (s, 3H), 2.45 (m, 1H), 1.40 (m, 7H), 0.95 (m, 1H), 0.65 (m, 3H); LC/MS (M+H)+ m/z 523.

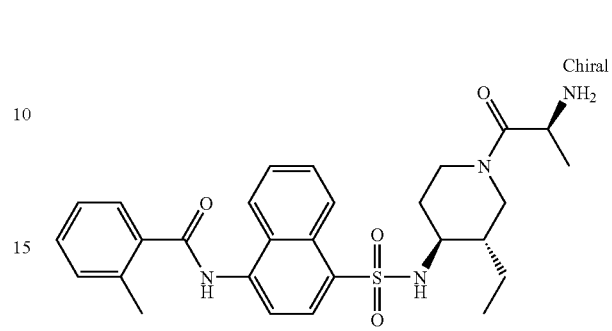

(3S, 4S)-N-{4-[1-(2-(S)-Amino-propionyl)-3-ethyl-piperidin-4-ylsulfamoyl]-naphthalen-1-yl}-2-methyl-benzamide (J-33)

The title compound was prepared as its formate salt following the general procedure in Scheme 6. $^1$H NM (300 MHz, MeOD) δ 8.78 (d, 1H), 8.54 (s, 1H), 8.33 (d, 1H), 8.25 (d, 1H), 7.94 (d, 1H), 7.70 (m, 3H), 7.40 (m, 3H), 4.25 (m, 2H), 3.70 (m, 1H), 3.05 (m, 2H), 2.65 (m, 1H), 2.56 (s, 3H), 1.45 (m, 7H), 0.90 (m, 1H), 0.65 (m, 3H); LC/MS (M+H)+ m/z 523.

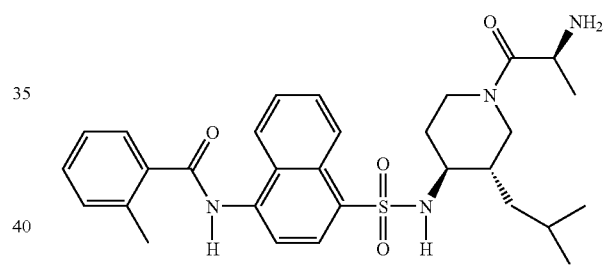

(±)-trans-N-{4-[1-(2-(S)-Amino-propionyl)-3-isobutyl-piperidin-4-ylsulfamoyl]-naphthalen-1-yl}-2-methyl-benzamide (J-34)

The title compound was prepared as its formate salt following the general procedure in Scheme 6. $^1$H NMR (300 MHz, MeOD) δ 8.79 (d, 1H), 8.54 (s, 1H), 8.29 (d, 1H), 8.11 (d, 1H), 7.87 (d, 1H), 7.67 (m, 3H), 7.42 (m, 3H), 4.30 (m, 2H), 3.68 (d, 1H), 3.10 (m, 1H), 2.96 (m, 1H), 2.55 (s, 3H), 2.38 (m, 1H), 1.83 (m, 1H), 1.36 (m, 6H), 0.91 (m, 1H), 0.59 (t, 3H), 0.48 (m, 3H); LC/MS (M+H)+ m/z 551.

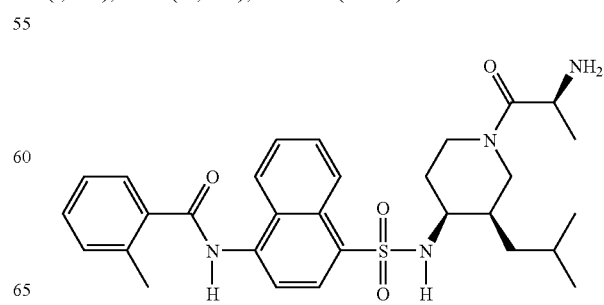

(±)-cis-N-{4-[1-(2-(S)-Ainno-propionyl)-3-isobutyl-piperidin-4-ylsulfamoyl]-naphthalen-1-yl}-2-methyl-benzamide (J-35)

The title compound was prepared as its formate salt following the general procedure in Scheme 6. $^1$H NMR (300 MHz, MeOD) δ 8.87 (d, 1H), 8.54 (s, 1H), 8.33 (d, 1H), 8.25 (d, 1H), 7.95 (d, 1H), 7.74 (m, 3H), 7.38 (m, 3H), 4.33 (m, 1H), 3.50 (m, 3H), 3.27 (m, 1H), 2.56 (s, 3H), 1.58 (m, 3H), 1.41 (t, 3H), 1.15 (m, 1H), 0.61 (m, 6H), 0.34 (m, 3H); LC/MS (M+H)$^+$ m/z 551.

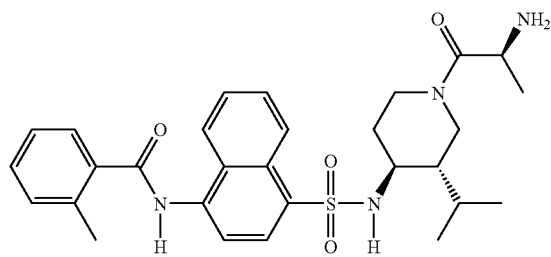

(±)-trans-N-{4-[1-(2-(S)-Amino-propionyl)-3-isopropyl-piperidin-4-ylsulfamoyl]-naphthalen-1-yl}-2-methyl-benzamide (J-36)

The title compound was prepared as its formate salt following the general procedure in Scheme 6. $^1$H NMR (300 MHz, MeOD) δ 8.78 (d, 1H), 8.54 (s, 1H), 8.35 (d, 1H), 8.25 (d, 1H), 7.95 (d, 1H), 7.74 (m, 3H), 7.38 (m, 3H), 4.27 (m, 2H), 3.64 (m, 1H), 3.24 (m, 1H), 3.09 (m, 1H), 2.56 (m, 4H), 1.81 (m, 2H), 1.37 (m, 5H), 0.83 (d, 1H), 0.77 (d, 2H), 0.31 (m, 4H); LC/MS (M+H)$^+$ m/z 538.

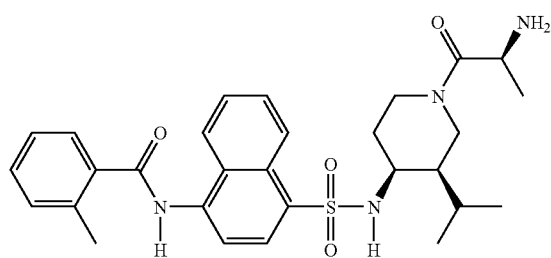

(±)-cis-N-{4-[1-(2-(S)-Andno-propionyl)-3-isopropyl-piperidin-4-ylsulfamoyl]-naphthalen-1-yl}-2-methyl-benzamide (J-37)

The title compound was prepared as its formate salt following the general procedure in Scheme 6. $^1$H NMR (300 MHz, MeOD) δ 8.90 (d, 1H), 8.54 (s, 1H), 8.35 (d, 1H), 8.25 (d, 1H), 7.95 (d, 1H), 7.74 (m, 3H), 7.38 (m, 3H), 4.27 (m, 2H), 3.60 (m, 1H), 3.17 (m, 2H), 2.65 (m, 1H), 2.56 (t, 3H), 1.34 (m, 7H), 0.85 (t, 1H), 0.78 (d, 2H), 0.50 (d, 1H), 0.37 (m, 2H); LC/MS (M+H)$^+$ m/z 538.

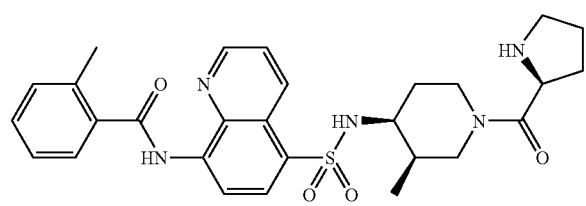

(3R, 4S)-2-Methyl-N-{5-[3-methyl-1-((R) pyrrolidine-2-carbonyl)-piperidin-4-ylsulfamoyl]-quinolin-8-yl}-benzamide (J-38)

The title compound was made following general procedure in scheme 6, substituting 8-(2-methyl-benzoylamino)-quinoline-5-sulfonyl chloride for 4-(2-methyl-benzoylamino)-naphthalene-1-sulfonyl chloride, 1-benzyl-3-methyl-piperidin-4-ylamine for 4-amino-piperidine-1-carboxylic acid tert-butyl ester and Pyrrolidine-1,2-dicarboxylic acid 1-tert-butyl ester for 2-tert-Butoxycarbonylamino-propionic acid. $^1$H NMR (300 MHz, MeOD) δ 9.20 (m, 1H), 8.93 (m, 1H), 8.88 (d, 1H), 8.31 (d, 1H), 7.75 (m, 1H), 7.68 (m, 1H), 7.45 (m, 1H), 7.38 (m, 2H ), 4.52 (m, 1H), 3.47 (m, 3H), 3.25 (m. 3H), 2.55 (s, 3H), 2.40 (m, 1H), 2.00 (m, 2H), 1.80 (m, 2H), 1.61 (m, 1H), 1.43 (m, 2H), 0.62 (m, 3H); LC/MS (M+H)$^+$ m/z 536.

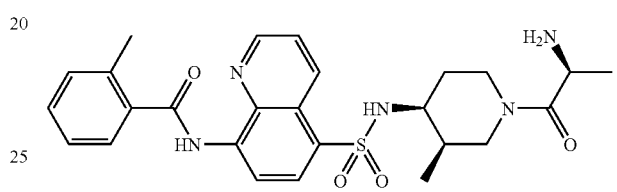

(3R, 4S)-N-{5-[1-(2-(R)-Amino-propionyl)-3-methyl-piperidin-4-ylsulfamoyl]-quinolin-8-yl}-2-methyl-benzamide (J-39)

The title compound was made following general procedure in scheme 6, substituting 8-(2-methyl-benzoylamino)-quinoline-5-sulfonyl chloride for 4-(2-methyl-benzoylamino)-naphthalene-1-sulfonyl chloride and 1-benzyl-3-methyl-piperidin-4-ylamine for 4-amino-piperidine-1-carboxylic acid tert-butyl ester. $^1$H NMR (300 MHz, MeOD) δ 9.20 (m, 1H), 8.93 (m, 1H), 8.88 (d, 1H), 8.31 (d, 1H), 7.75 (m, 1H), 7.68 (m, 1H), 7.45 (m, 1H), 7.38 (m, 2H ), 4.29 (m, 1H), 3.50 (m, 2H), 3.25 (m. 3H), 2.55 (s, 3H), 1.70 (m, 2H), 1.18 (m, 4H), 0.61 (m, 3H); LC/MS (M+H)$^+$ m/z 510.

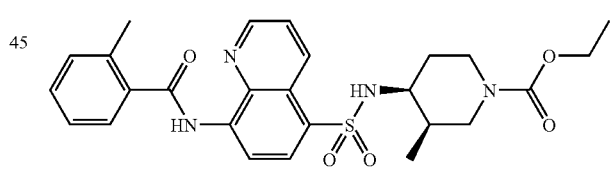

(3R, 4S)-3-Methyl-4-[8-(2-methyl-benzoylamino)-quinoline-5-sulfonylamino]-piperidine-1-carboxylic acid ethyl ester (J-40)

The title compound was made following general procedure in scheme 5, substituting 8-(2-methyl-benzoylamino)-quinoline-5-sulfonyl chloride for 4-(2-methyl-benzoylamino)-naphthalene-1-sulfonyl chloride, 1-benzyl-3-methyl-piperidin-4-ylamine for 4-amino-piperidine-1-carboxylic acid tert-butyl ester and ethyl chloromate for 2-isocyanato-propane. $^1$H NMR (300 MHz, MeOD) δ 9.20 (m, 1H), 8.93 (m, 1H), 8.88 (d, 1H), 8.31 (d, 1H), 7.75 (m, 1H), 7.68 (m, 1H), 7.45 (m, 1H), 7.38 (m, 2H), 4.06 (q, 2H), 3.50 (m, 1H), 3.40 (m. 2H), 3.20 (m, 2H), 2.55 (s, 3H), 1.71 (m, 1H), 1.75 (m, 1H), 1.43 (m, 1H), 1.31 (m, 1H), 1.18 (t, 3H), 0.63 (m, 3H); LC/MS (M+H)$^+$ m/z 511.

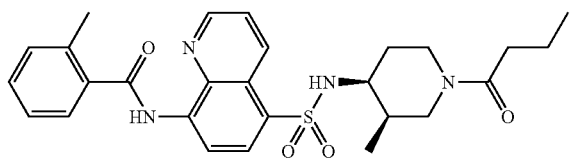

(3R, 4S)-N-[5-(1-Butyryl-3-methyl-piperidin-4-ylsulfamoyl)-quinolin-8-yl]-2-methyl-benzamide (J-41)

The title compound was made following general procedure in scheme 5, substituting 8-(2-methyl-benzoylamino)-quinoline-5-sulfonyl chloride for 4-(2-methyl-benzoylamino)-naphthalene-1-sulfonyl chloride, 1-benzyl-3-methyl-piperidin-4-ylamine for 4-amino-piperidine-1-carboxylic acid tert-butyl ester and butyryl chloride for 2-isocyanato-propane. $^1$H NMR (300 MHz, MeOD) δ 9.20 (m, 1H), 8.93 (m, 1H), 8.88 (d, 1H), 8.31 (d, 1H), 7.75 (m, 1H), 7.68 (m, 1H), 7.45 (m, 1H), 7.38 (m, 2H), 3.70 (m, 1H), 3.43 (m, 2H), 3.25 (m. 1H), 3.11 (m, 1H), 2.55 (s, 3H), 2.28 (m, 2H), 1.75 (m, 2H), 1.51 (q, 2H), 1.39 (m, 2H), 0.90 (t, 3H), 0.67 (d, 1.5H), 0.59 (d, 1.5H); LC/MS (M+H)$^+$ m/z 509.

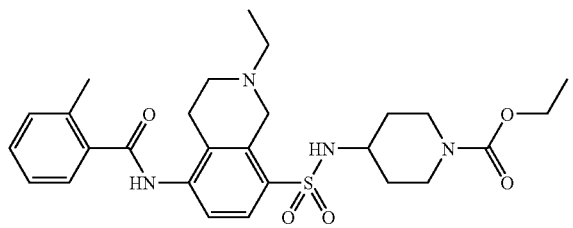

4-[2-Ethyl-5-(2-methyl-benzoylamno)-1,2,3,4-tetrahydro-isoquinoline-8-sulfonylamino]-piperidine-1-carboxylic acid ethyl ester (J-42)

The title compound was made following general procedure in scheme 5, substituting 2-ethyl-5-(2-methyl-benzoylamino)-1,2,3,4-tetrahydro-isoquinoline-8-sulfonyl chloride for 4-(2-methyl-benzoylamino)-naphthalene-1-sulfonyl chloride, and ethyl chloromate for 2-isocyanato-propane. $^1$H NMR (300 MHz, MeOD) δ 7.92 (d, 1H), 7.68 (d, 1H), 7.54 (d, 1H), 7.39 (m, 1H), 7.30 (m, 2H), 4.14 (m, 2H), 4.09 (q, 2H), 3.95 (m, 2H), 2.27 (m, 1H ), 3.01 (m, 2H), 2.87 (m, 4H), 2.70 (q, 2H), 2.50 (s, 3H), 1.79 (m, 2H), 1.41 (m, 2H), 1.23 (m, 6H); LC/MS (M+H)$^+$ m/z 529.

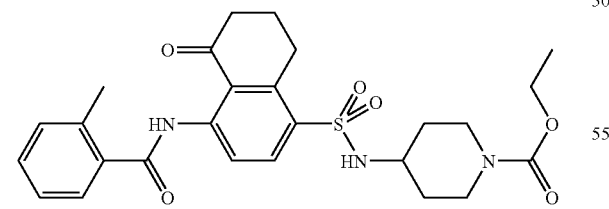

4-[4-(2-Methyl-benzoylamino)-5-oxo-5,6,7,8-tetrahydro-naphthalene-1-sulfonylamino]-piperidine-1-carboxylic acid ethyl ester (J-43)

4-[4-(2-Methyl-benzoylamino)-5,6,7,8-tetrahydro-naphthalene-1-sulfonylamino]-piperidine-1-carboxylic acid ethyl ester (1.12 g, 2.24 mmol) was dissolved in acetone (25 mL) and a 15% aqueous solution of magnesium sulfate(2.5 mL). The solution was cooled in an ice bath and potassium permanganate (1.9 g, 12.3 mmol) was added and the solution was stirred for 15 min at which time the solution was allowed to warm to room temperature and stirred for 3 hr. The solution was concentrated and diluted with 150 mL water. The product was exhaustively extracted from the aqueous layer with methylene chloride. The organic was then washed with brine, dried over anhydrous magnesium sulfate, concentrated and purified on silica (Isco flash column, 0 to 40% ethyl acetate in hexane). The title compound was isolated in 17% yield (200 mg).

$^1$H NMR (300 MHz, CDCl$_3$) δ 1.2 (m, 6H), 1.6 (s,1H), 1.8 (m, 2H), 2.1 (m, 2H), 2.5 (s, 3H), 2.8 (m, 4H), 3.4 (m, 3H), 4.6 (d, 1H), 7.3 (m, 3H), 7.6 (d, 1H), 8.2 (d, 1H), 8.9 (d, 1H), 12.8 (s, 1H). LC/MS (M+H)$^+$ m/z 514.

The following compounds J-44 through J-56 were also prepared according to methods described herein and were further utilized for the preparation of compounds described herein and are useful as inhibitors of CCR8:

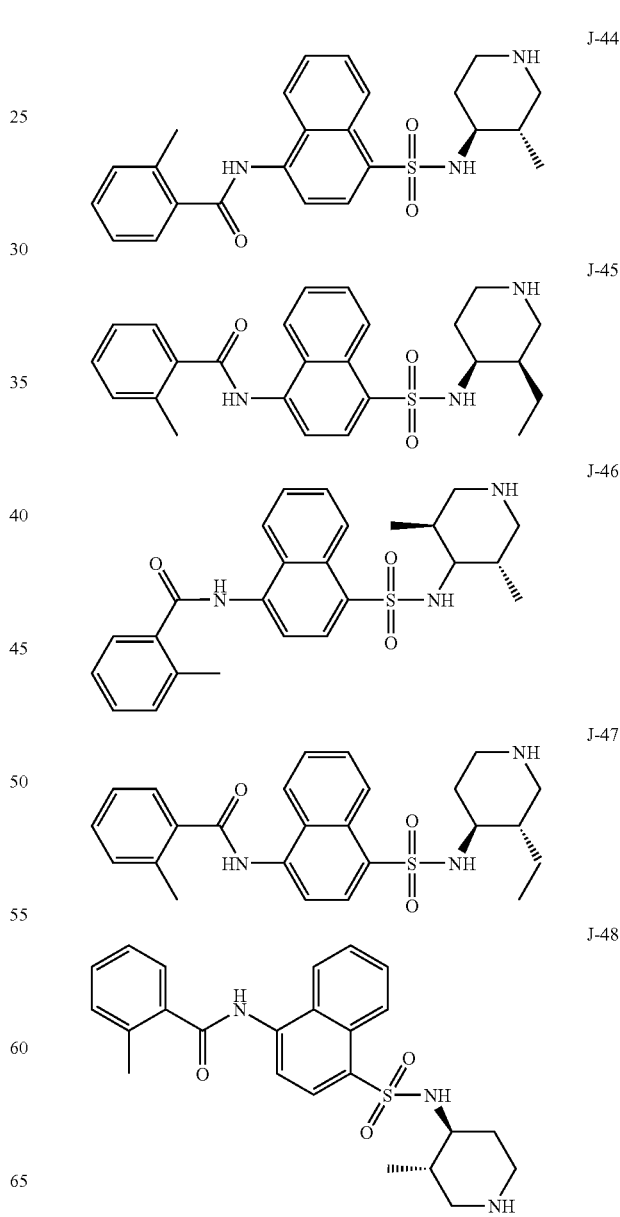

-continued

J-49
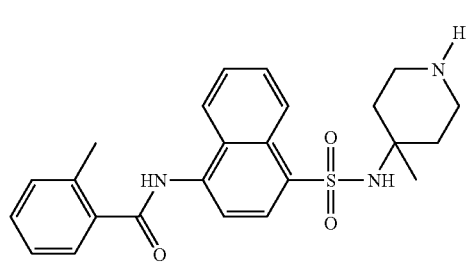

J-50
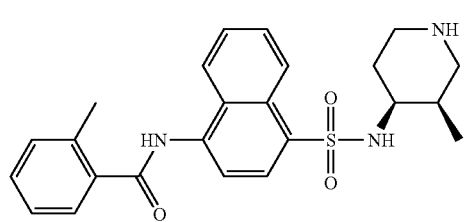

J-51
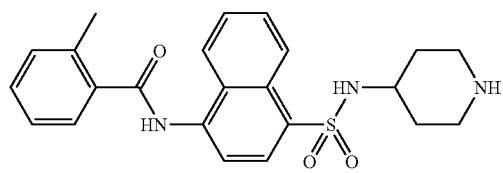

J-52
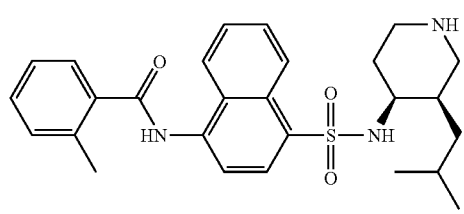

J-53
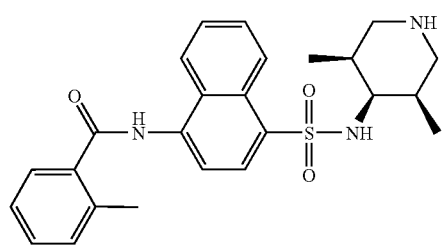

J-54
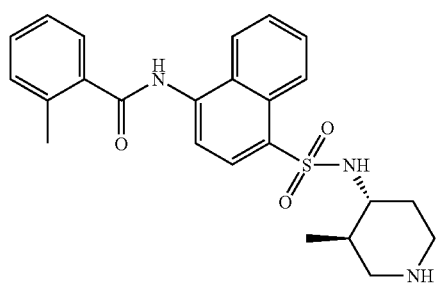

-continued

J-55
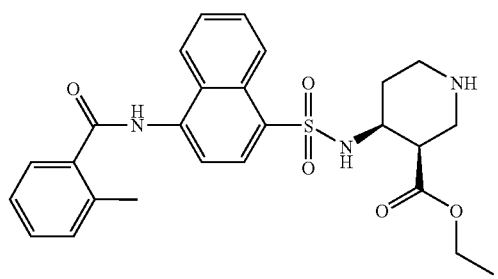

J-56
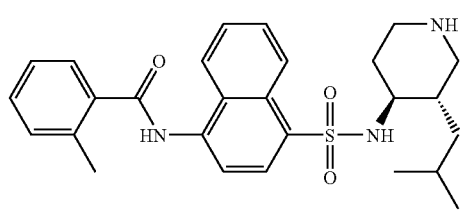

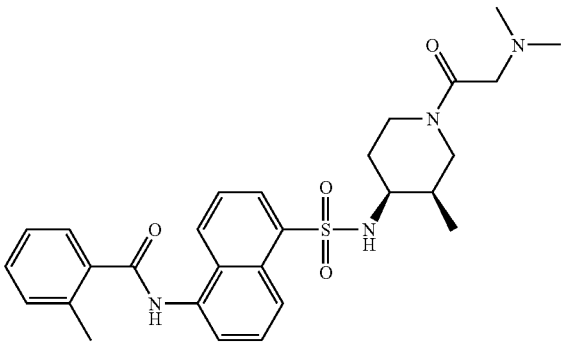

(±)-(cis)-N-{5-[1-(2-Dimethylamino-acetyl)-3-methyl-piperidin-4-ylsulfamoyl]-naphthalen-1-yl}-2-methyl-benzamide (K-1)

The title compound was prepared following the general procedure in Scheme 6. $^1$H NMR (300 MHz, MeOD) δ 8.73 (m, 1H), 8.38 (d, 1H), 8.32 (d, 1H), 7.70 (m, 4H), 7.38 (m, 3H), 3.50 (m, 4H), 3.20 (m, 1H), 2.90 (m, 1H), 2.57 (s, 3H), 2.52 (s, 6H), 1.50 (m, 4H), 0.65 (m, 3H); LC/MS (M+H)$^+$ m/z 523.

Chiral
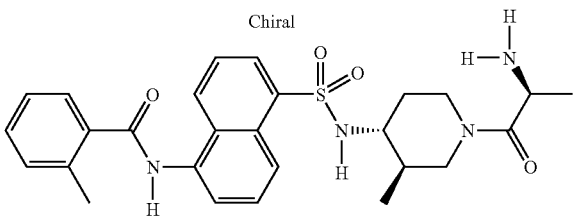

(3R, 4R)-N-{5-[1-(2-(S)-Amino-propionyl)-3-methyl-piperidin-4-ylsulfamoyl]-naphthalen-1-yl}-2-methyl-benzamide (K-2)

The title compound was prepared as its formate salt following the general procedure in Scheme 6. $^1$H NMR (300 MHz, MeOD) δ 8.71 (d, 1H), 8.51 (s, 1H), 8.35 (m, 2H), 7.70

(m, 4H), 7.38 (m, 3H), 4.28 (m, 2H), 3.68 (m, 1H), 2.95 (m, 1H), 2.57 (s, 3H), 2.33 (m, 1H), 1.34 (m, 6H), 0.67 (m, 3H); LC/MS (M+H)⁺ m/z 510.

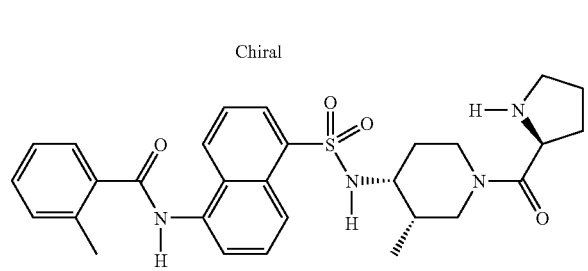

(3S,4R)-2-Methyl-N-{5-[3-methyl-1-(pyrrolidine-2-(S)-carbonyl)-piperidin-4-ylsulfamoyl]-naphthalen-1-yl}-benzamide (K-3)

The title compound was prepared as its formate salt following the general procedure in Scheme 6. ¹H NMR (300 MHz, MeOD) δ 8.76 (d, 1H), 8.54 (s, 1H), 8.35 (m, 2H), 7.68 (m, 4H), 7.38 (m, 3H), 4.49 (m, 1H), 3.48 (m, 2H), 3.26 (m, 1H), 2.57 (s, 3H), 2.40 (m, 2H), 1.91 (m, 5H), 1.47 (m, 3H), 0.76 (m, 3H); LC/MS (M+H)⁺ m/z 536.

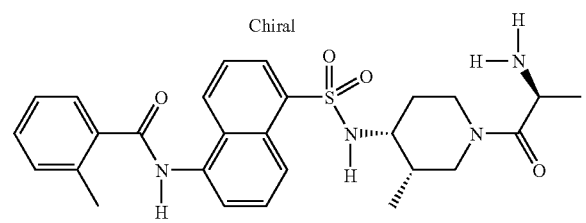

(3S, 4R)N-{5-[1-(2-(S)-Amino-propionyl)-3-methyl-piperidin-4-ylsulfamoyl]-naphthalen-1-yl}-2-methyl-benzamide (K-4)

The title compound was prepared as its formate salt following the general procedure in Scheme 6. ¹H NMR (300 MHz, MeOD) δ 8.78 (d, 1H), 8.50 (s, 1H), 8.35 (m, 2H), 7.71 (m, 4H), 7.38 (m, 3H), 4.28 (m, 1H), 3.44 (m, 3H), 3.26 (m, 1H), 3.08 (m, 1H), 2.57 (s, 3H), 1.79 (m, 1H), 1.37 (m, 5H), 0.71 (m, 3H); LC/MS (M+H)⁺ m/z 510.

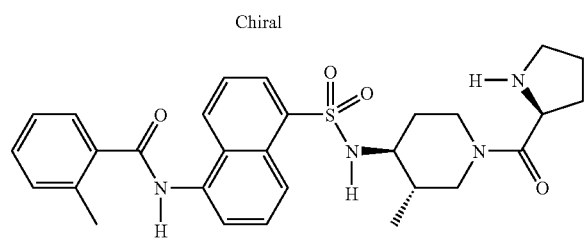

(3S, 4R)-2-Methyl-N-{5-[3-methyl-1-(pyrrolidine-2-(S)-carbonyl)-piperidin-4-ylsulfamoyl]-naphthalen-1-yl}-benzamide (K-5)

The title compound was prepared as its formate salt following the general procedure in Scheme 6. ¹H NMR (300 MHz, MeOD) δ 8.71 (d, 1H), 8.54 (s, 1H), 8.36 (m, 2H), 7.71 (m, 4H), 7.42 (m, 3H), 4.47 (m, 2H), 3.67 (t, 1H), 3.27 (m, 1H), 3.01 (m, 2H), 2.71 (m, 1H), 2.57 (s, 3H), 2.41 (m, 2H), 1.79 (m, 6H), 0.68(t, 3H); LC/MS (M+H)⁺ m/z 535.

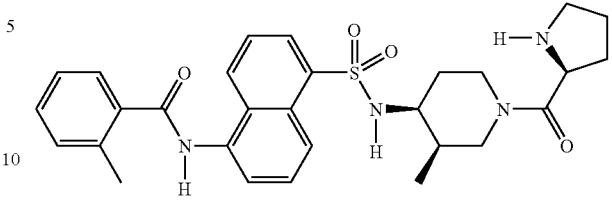

(3R, 4S)-2-Methyl-N-{5-[3-methyl-1-(pyrrolidine-2-(S)-carbonyl)-piperidin-4-ylsulfamoyl]-naphthalen-1-yl}-benzamide (K-6)

The title compound was prepared as its formate salt following the general procedure in Scheme 6. ¹H NMR (300 MHz, MeOD) δ 8.71 (d, 1H), 8.54 (s, 1H), 8.36 (m, 2H), 7.71 (m, 4H), 7.42 (m, 3H), 4.55 (t, 2H), 3.46 (m, 3H), 3.24 (m, 2H), 2.57 (s, 3H), 2.45 (m, 2H), 1.98 (m, 2H), 1.81 (m, 2H), 1.44 (m, 2H), 0.70(t, 3H); LC/MS (M+H)⁺ m/z 535.

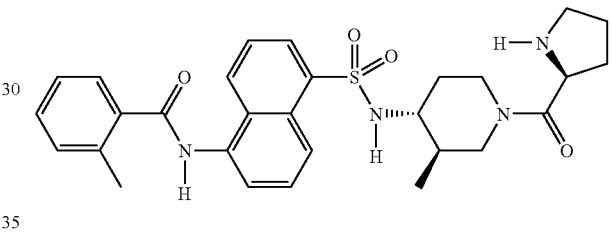

(3R, 4R)-2-Methyl-N-{5-[3-methyl-1-(pyrrolidine-2-(S)-carbonyl)-piperidin-4-ylsulfamoyl]-naphthalen-1-yl}-benzamide (K-7)

The title compound was prepared as its formate salt following the general procedure in Scheme 6. ¹H NMR (300 MHz, MeOD) δ 8.71 (d, 1H), 8.54 (s, 1H), 8.33 (m, 2H), 7.68 (m, 4H), 7.38 (m, 3H), 4.45 (m, 1H), 4.28 (m, 1H), 3.68 (m, 1H), 3.28 (m, 2H), 2.96 (m, 2H), 2.57 (s, 3H), 2.37 (m, 2H), 1.57 (m, 6H), 0.69 (m, 3H); LC/MS (M+H)⁺ m/z 536.

Additional Compounds: The following compounds of the invention are also prepared using the general schemes and experimental procedures described above and herein:

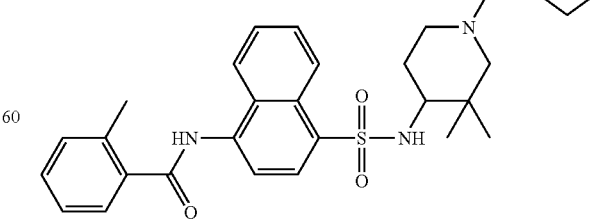

L-1

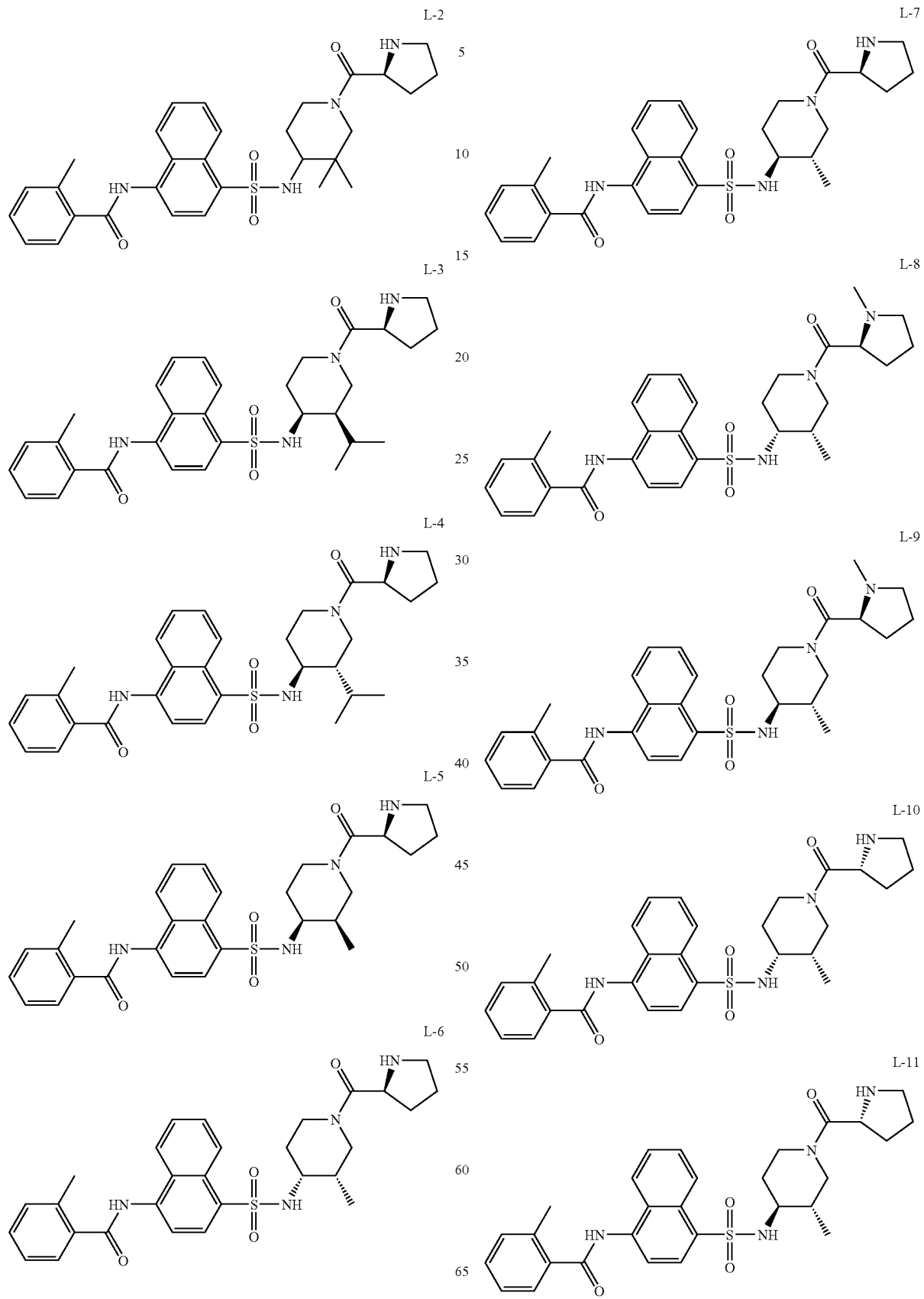

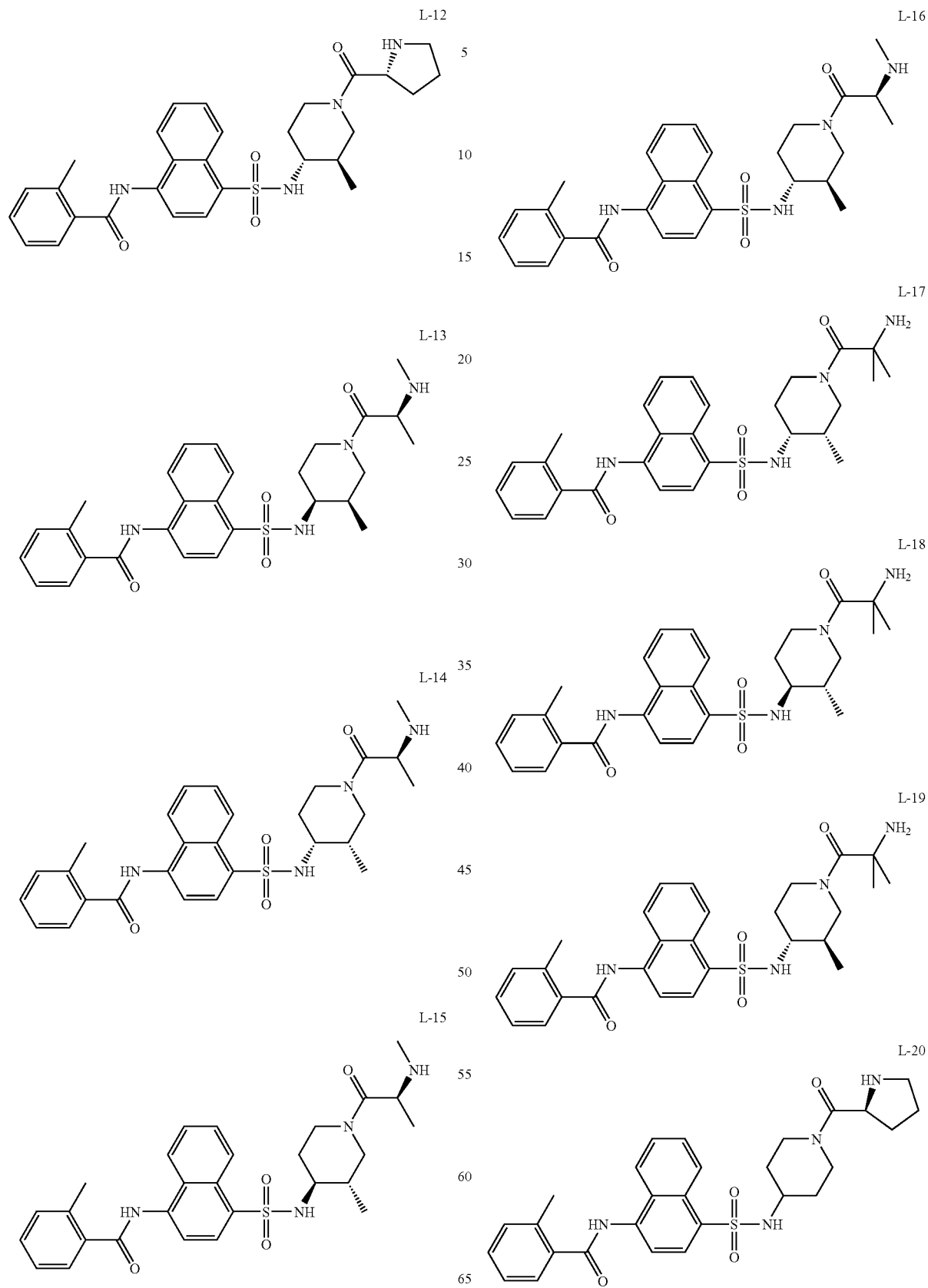

-continued
L-21
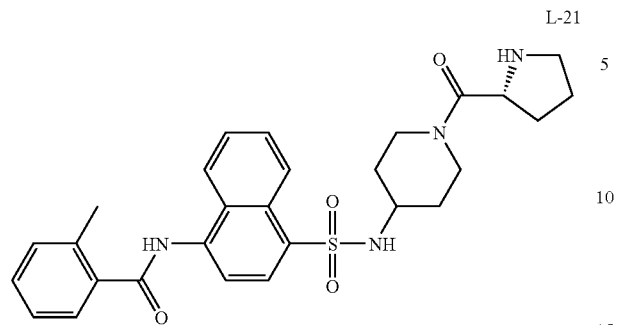
L-22
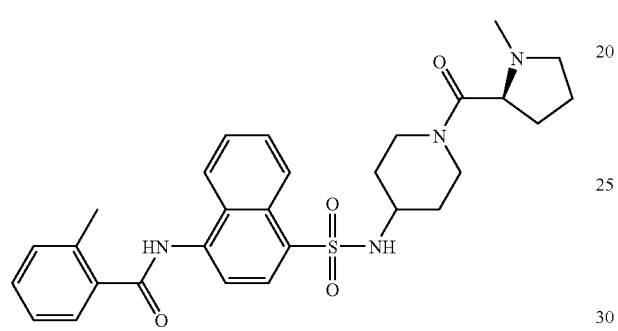
L-23
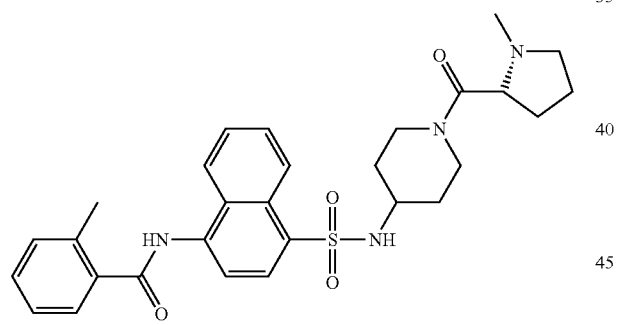
L-24
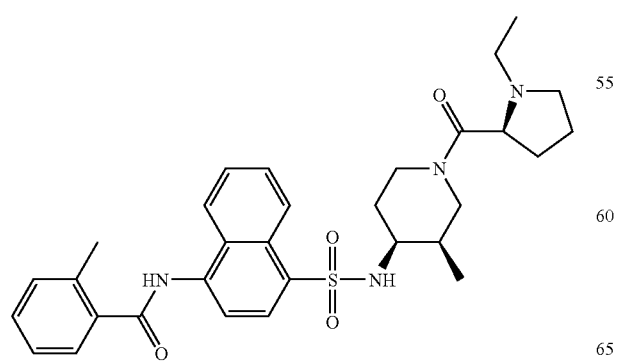
-continued
L-25
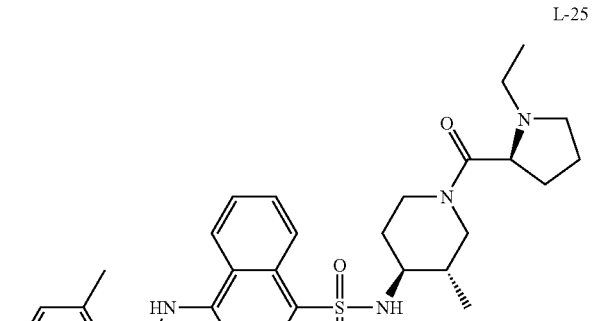
L-26
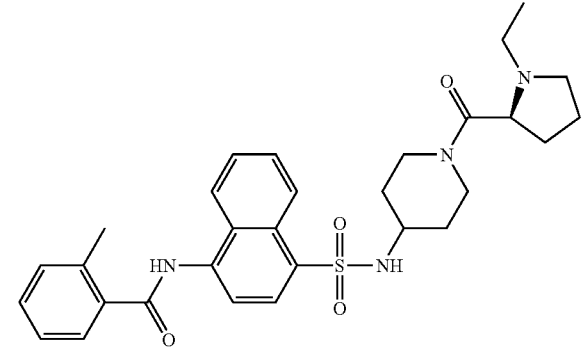
L-27
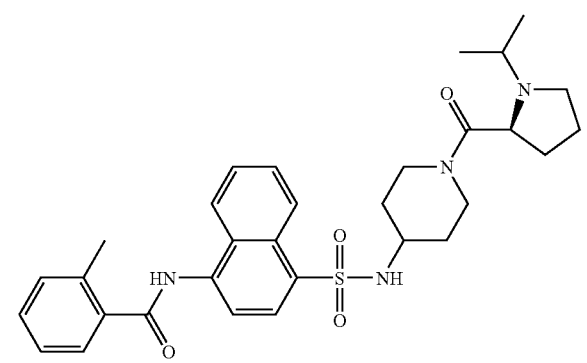
L-28
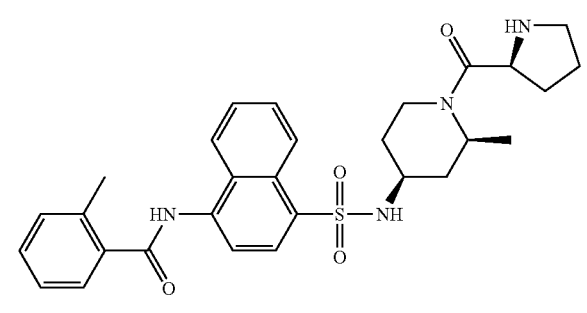

-continued
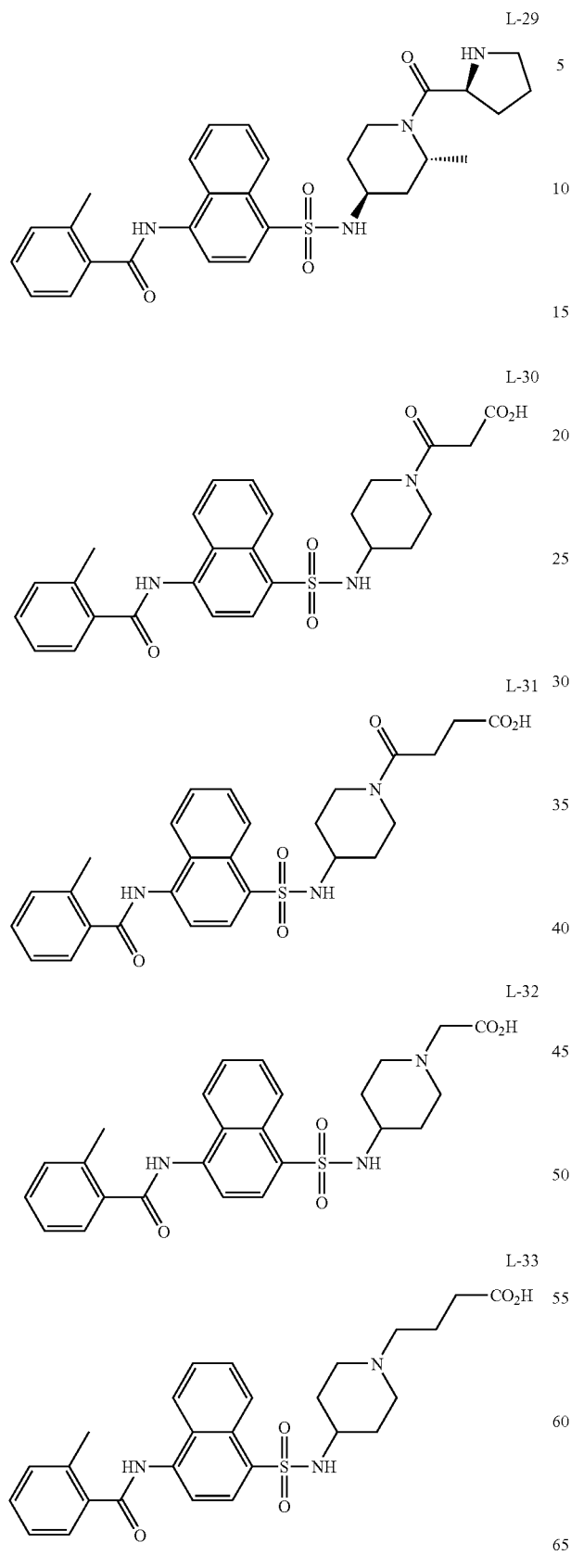
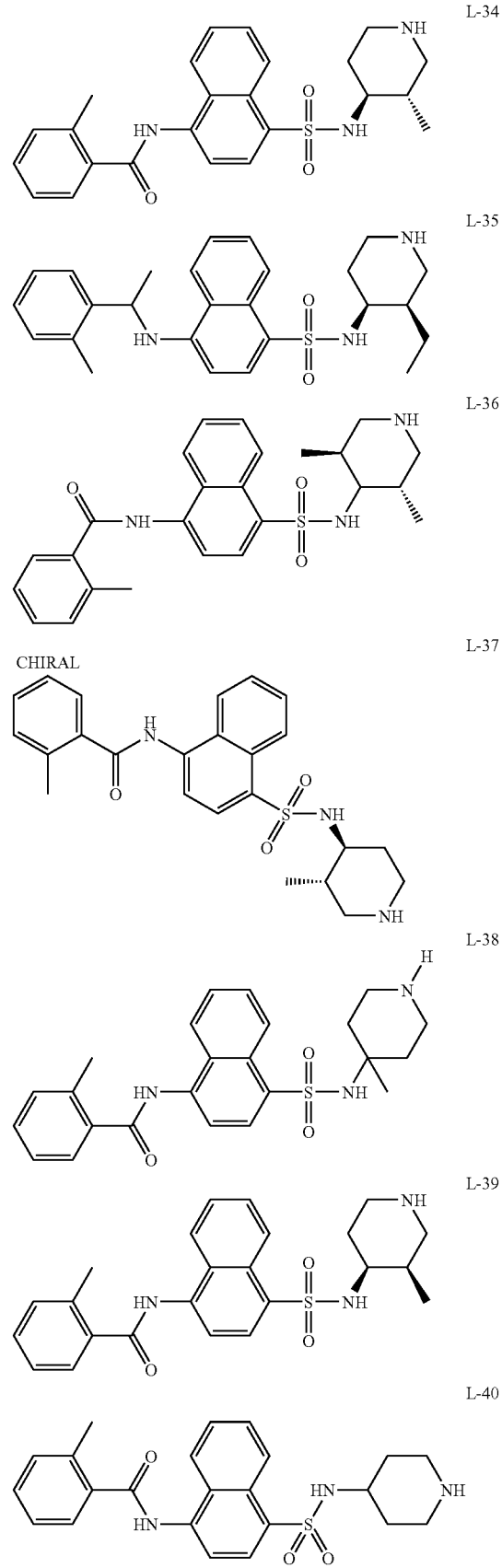

-continued
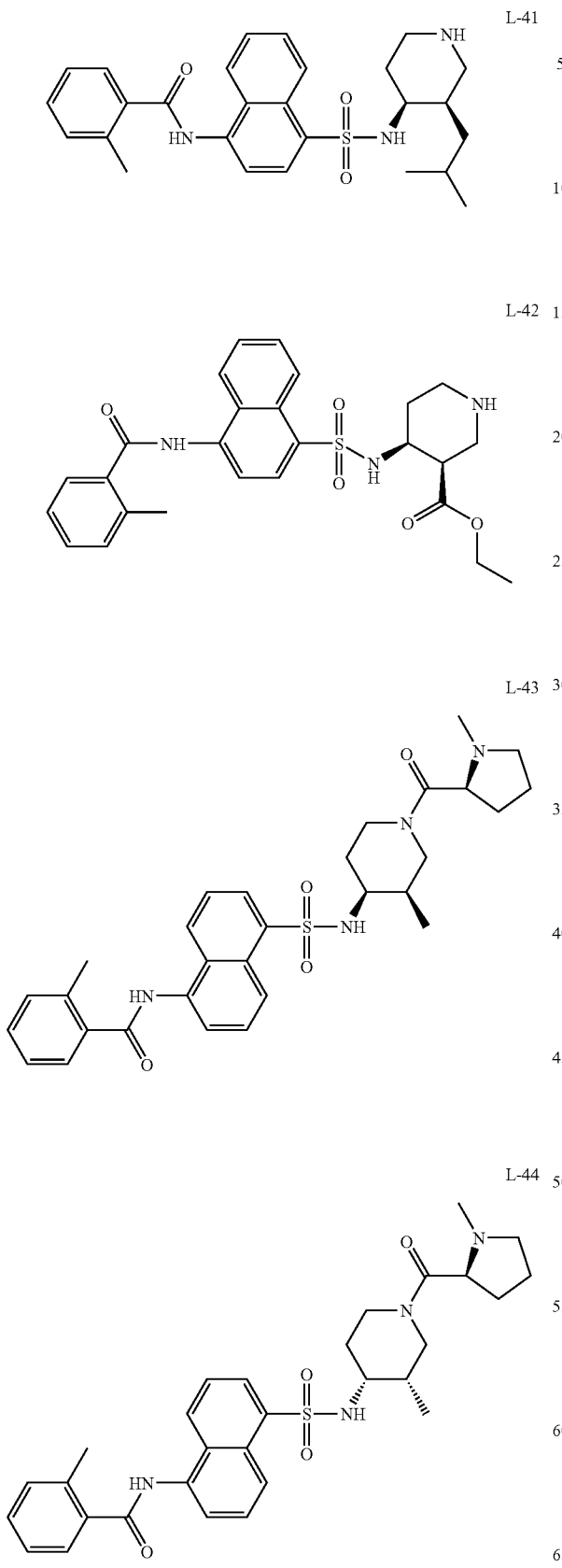
L-41
L-42
L-43
L-44
-continued
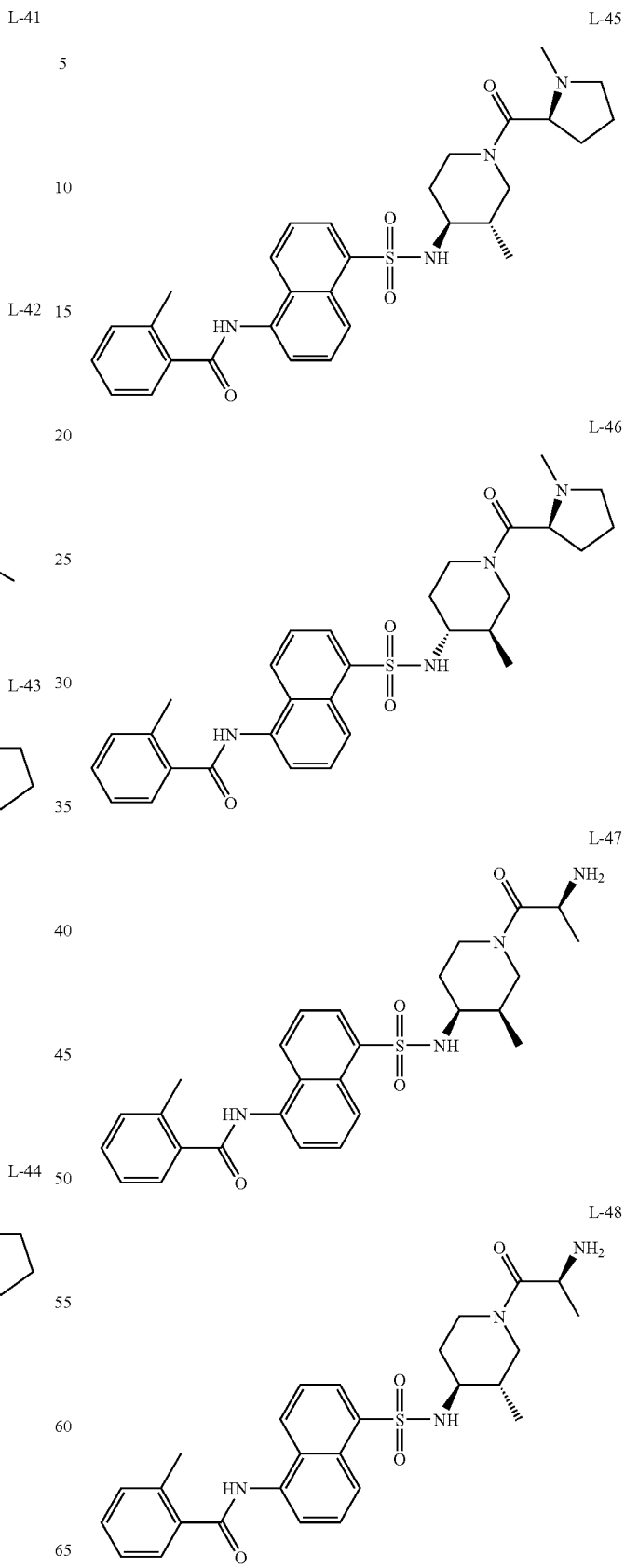
L-45
L-46
L-47
L-48

-continued
L-49
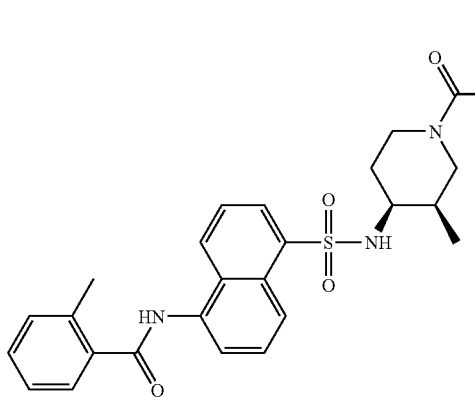
L-50
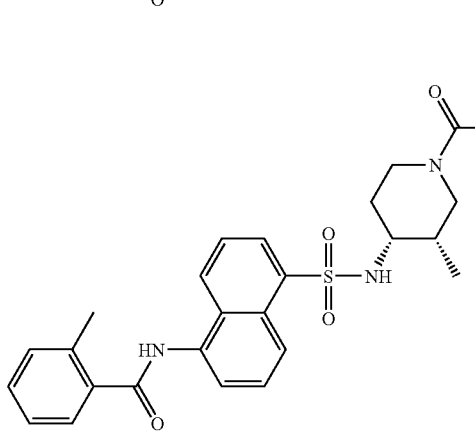
L-51
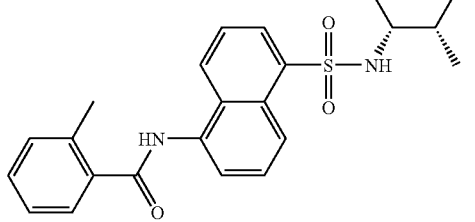
L-52
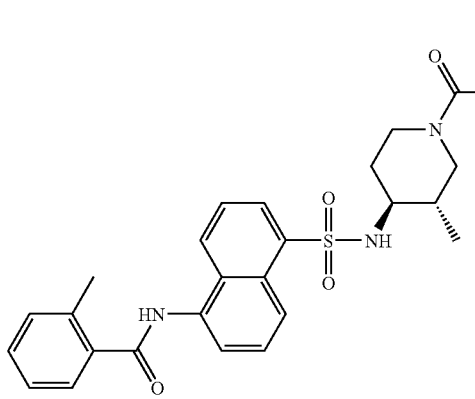
-continued
L-53
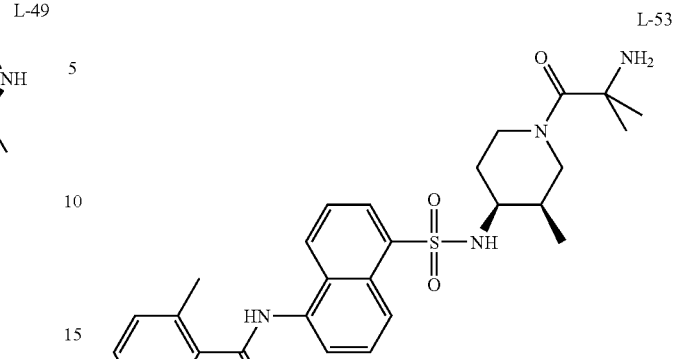
L-54
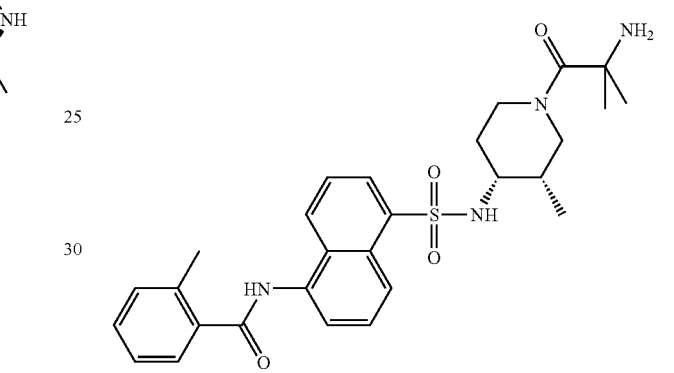
L-55
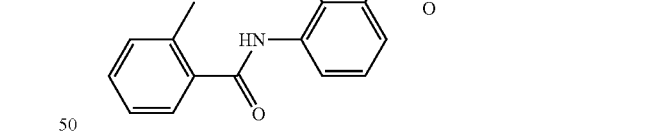
L-56
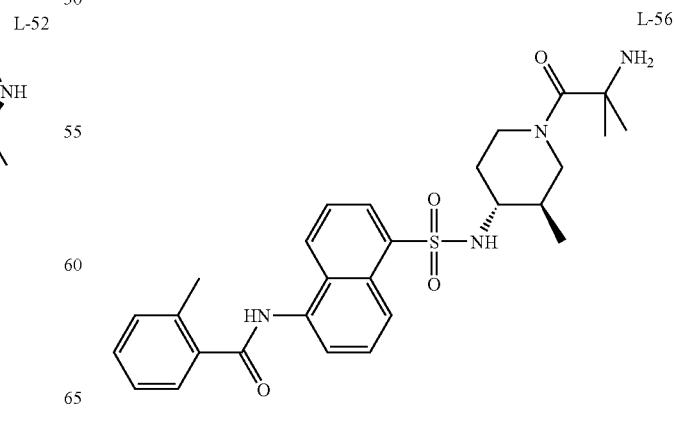

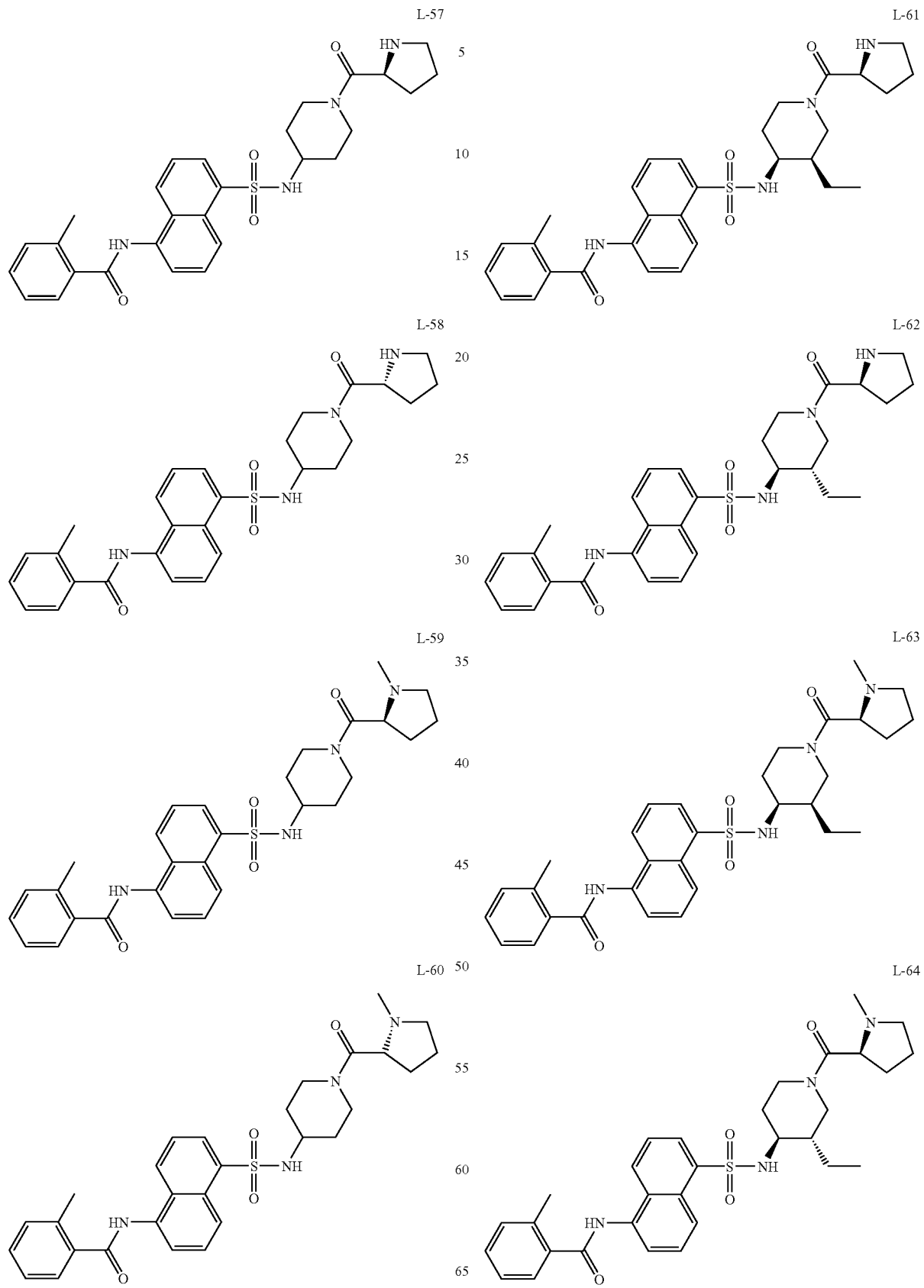

-continued
L-65
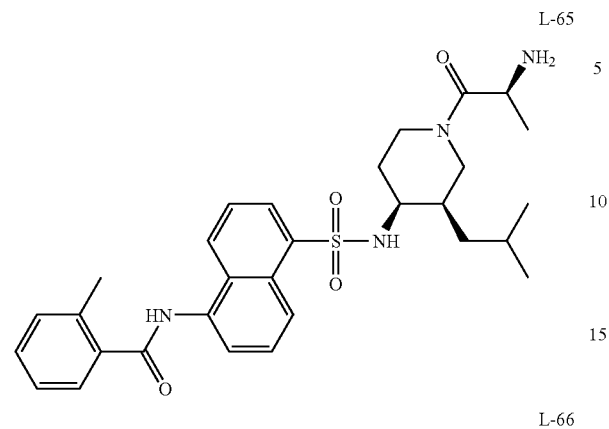
L-66
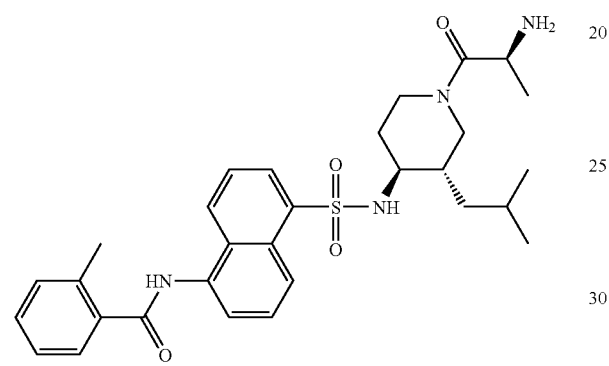
L-67
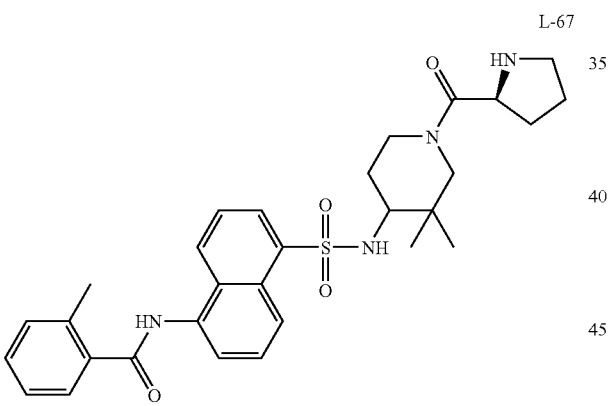
L-68
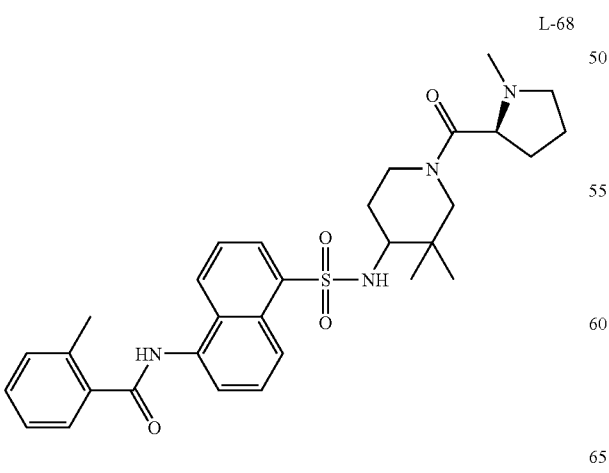
-continued
L-69
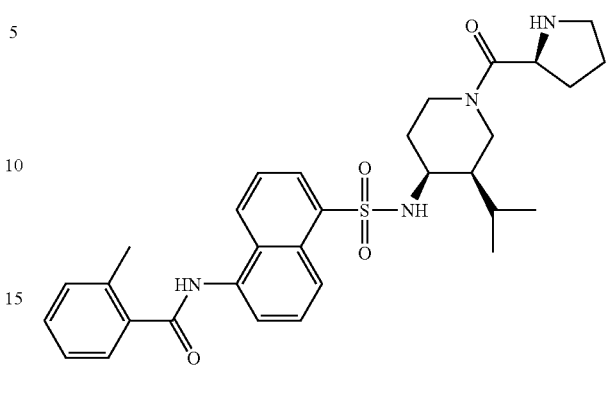
L-70
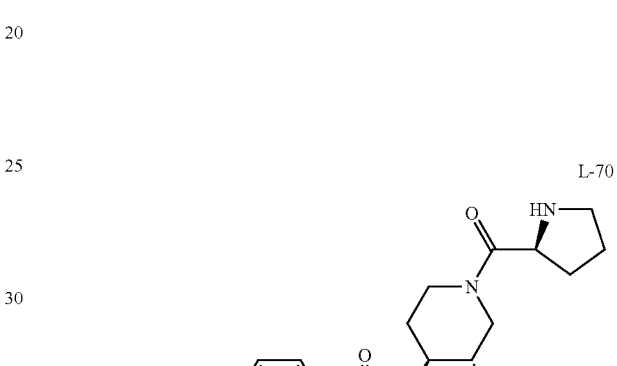
L-71
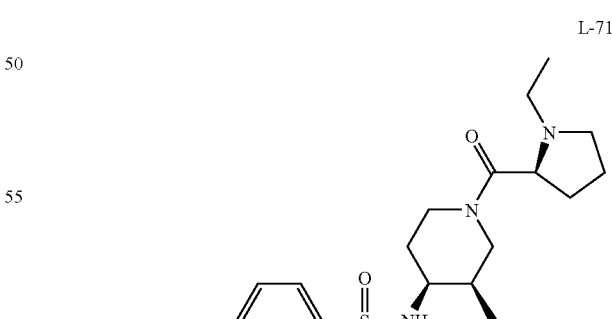

L-72
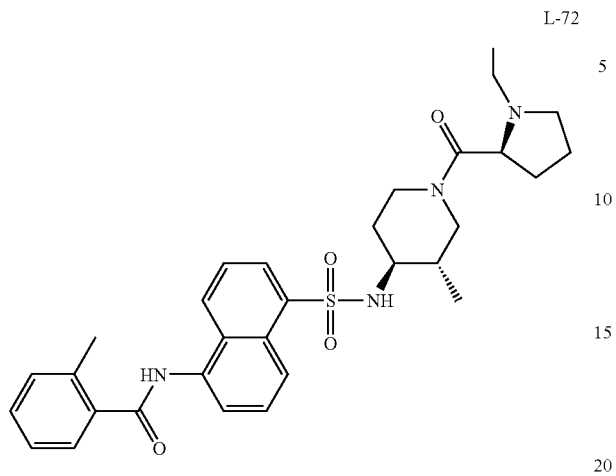
L-75
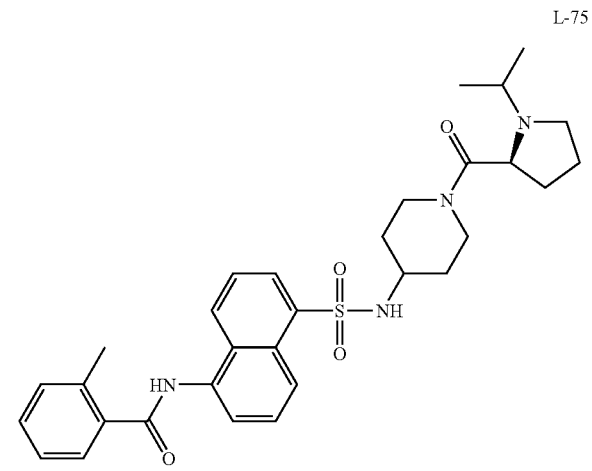
L-73
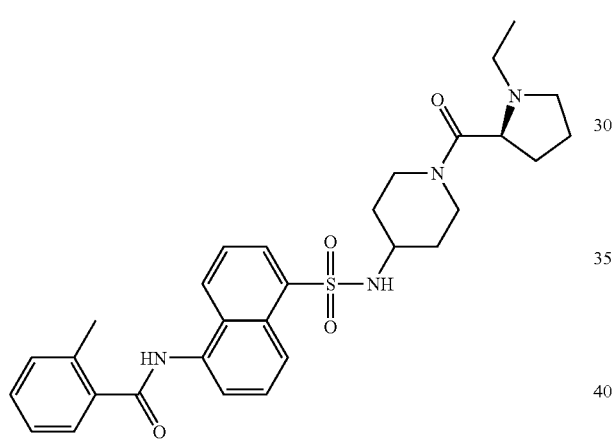
L-76
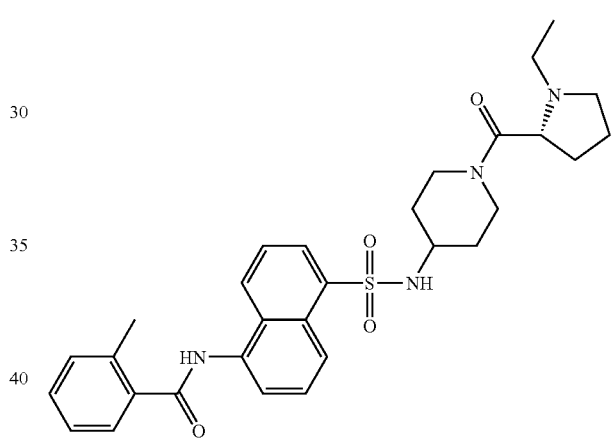
L-74
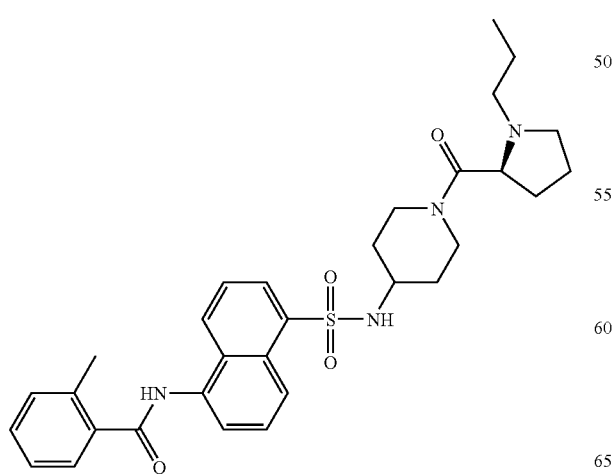
L-77
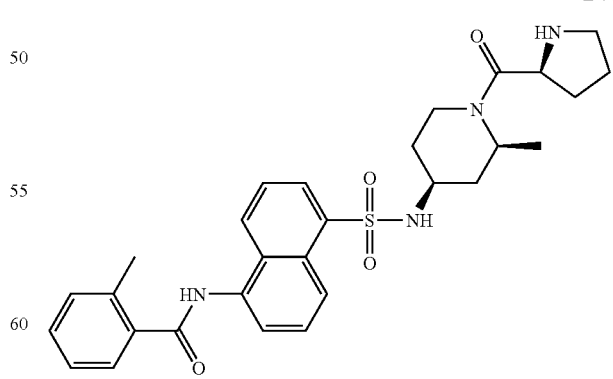

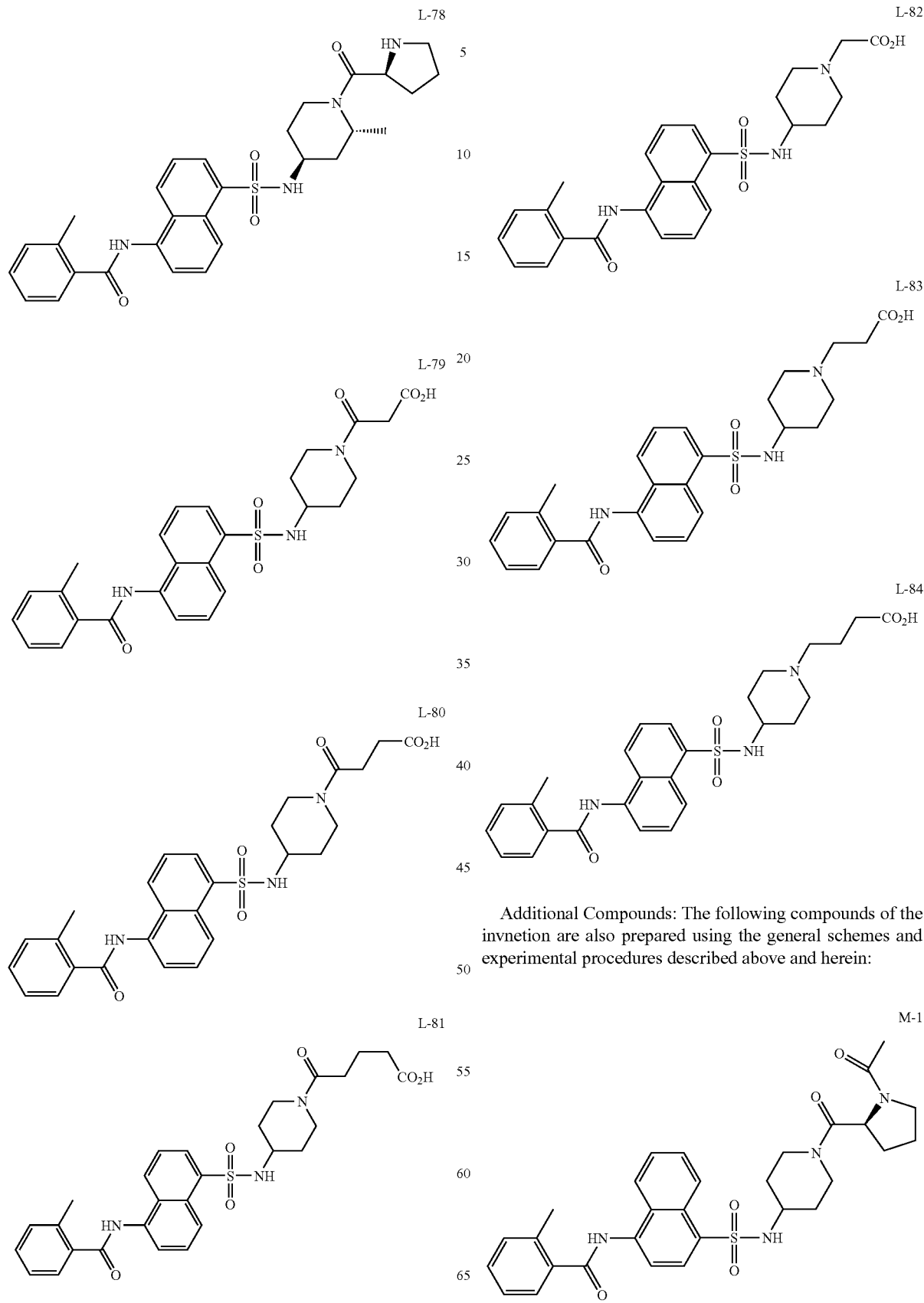
Additional Compounds: The following compounds of the invnetion are also prepared using the general schemes and experimental procedures described above and herein:

-continued
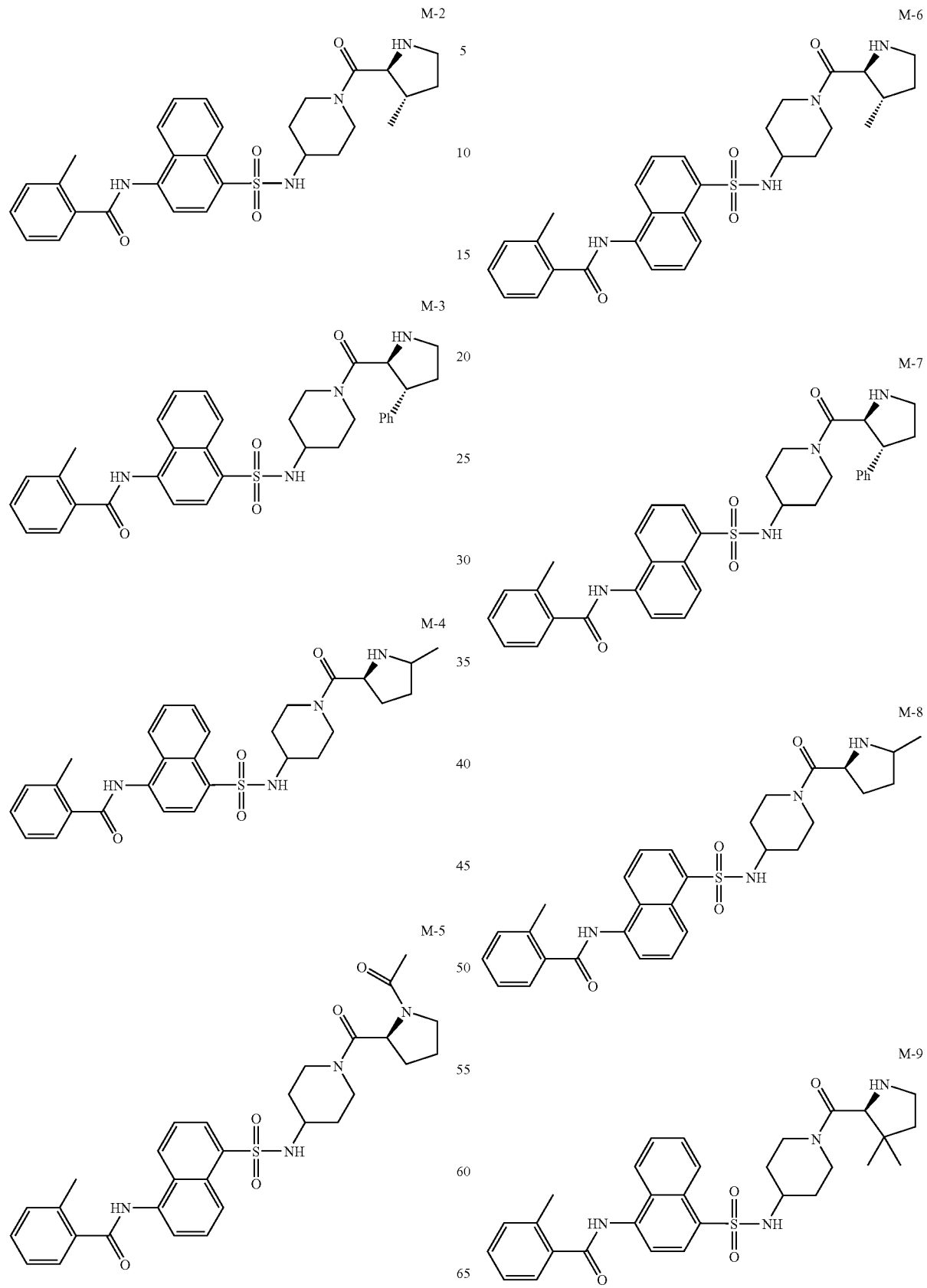

-continued
M-10
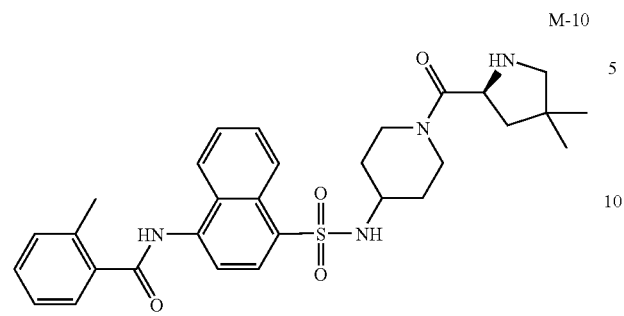
M-11
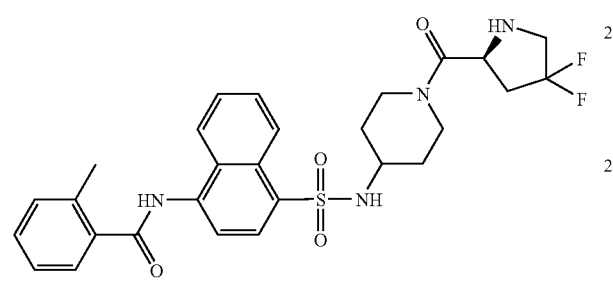
M-12
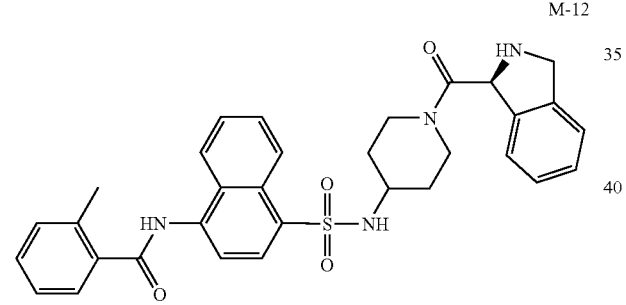
M-13
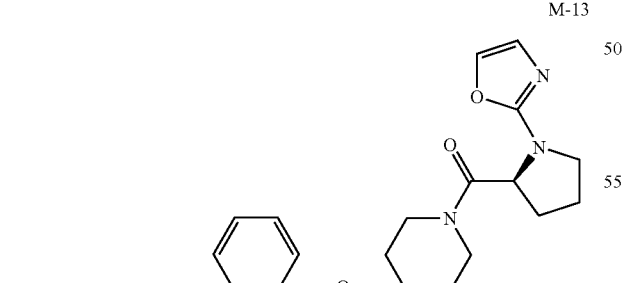
-continued
M-14
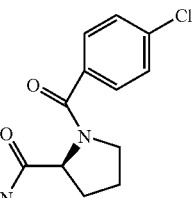
M-15
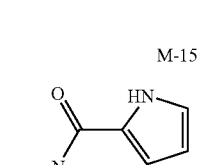
M-16
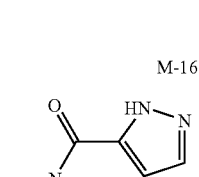
M-17
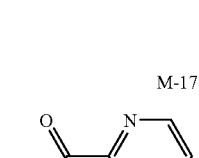
M-18
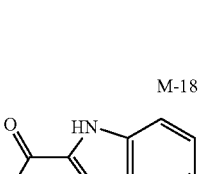

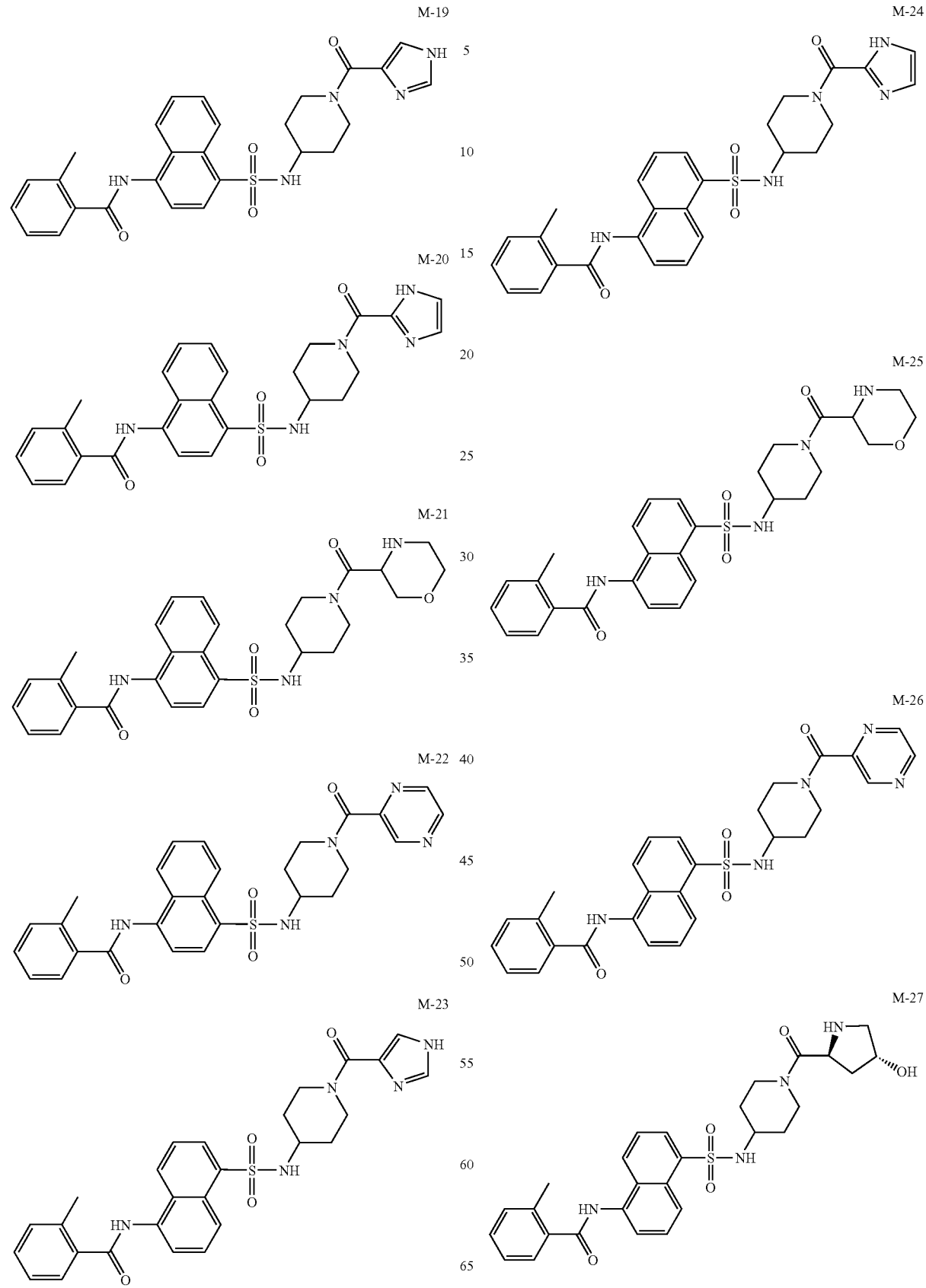

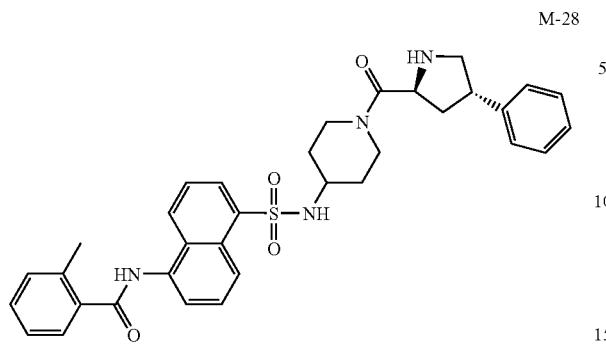
M-28
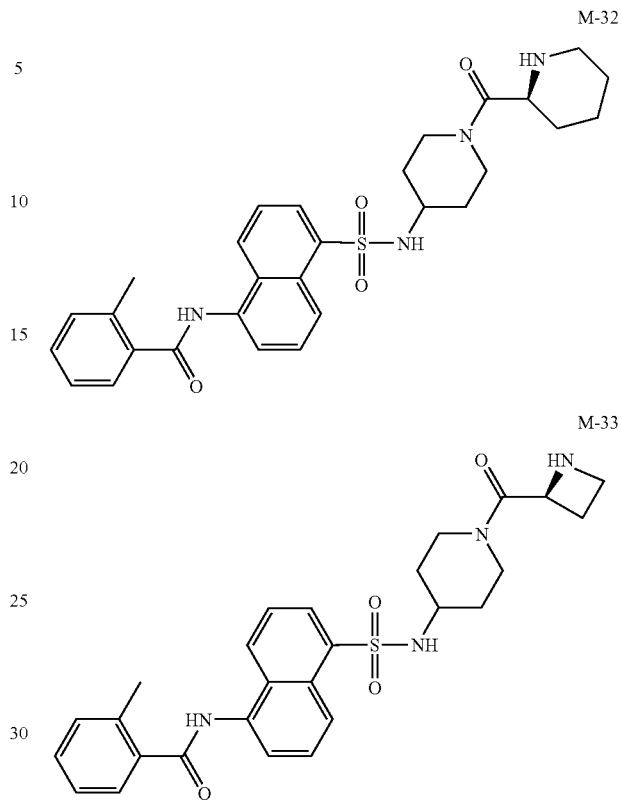
M-32
M-33
M-34
M-35
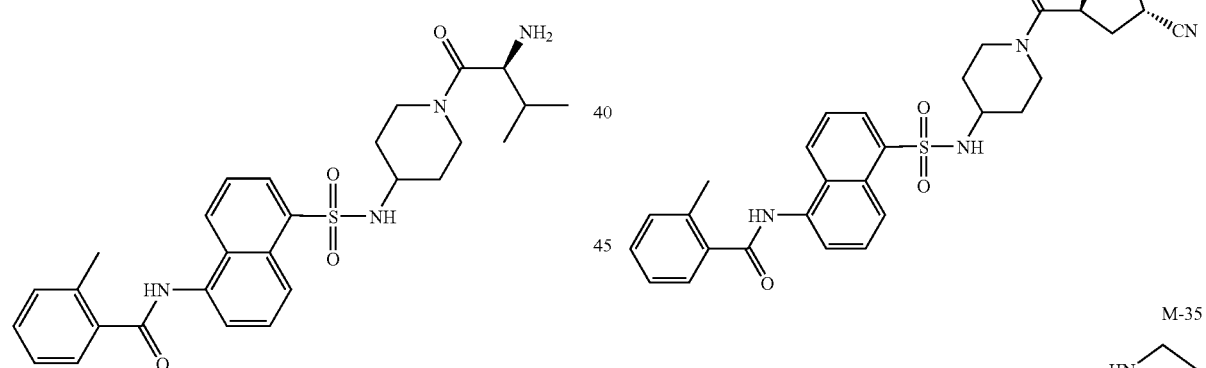
M-29
M-30
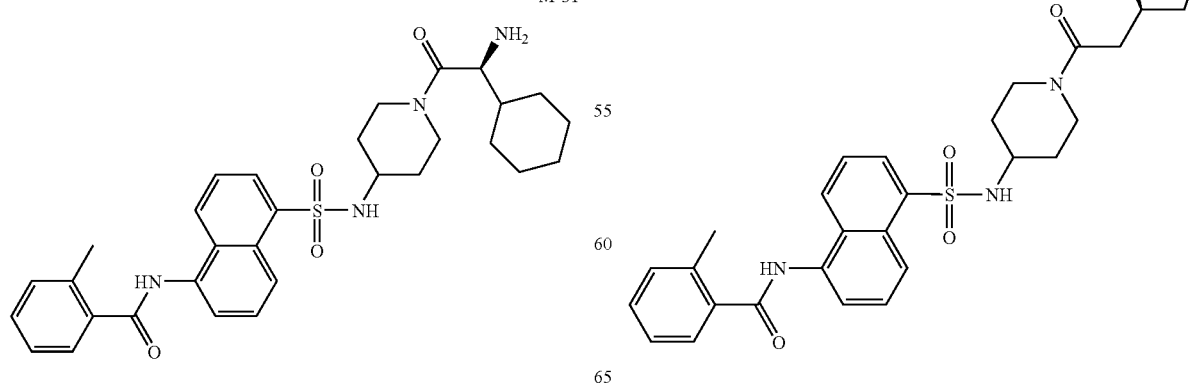
M-31

-continued
M-36
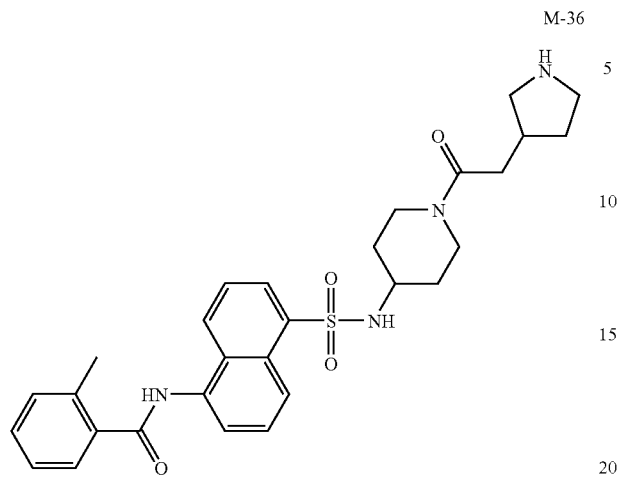
M-37
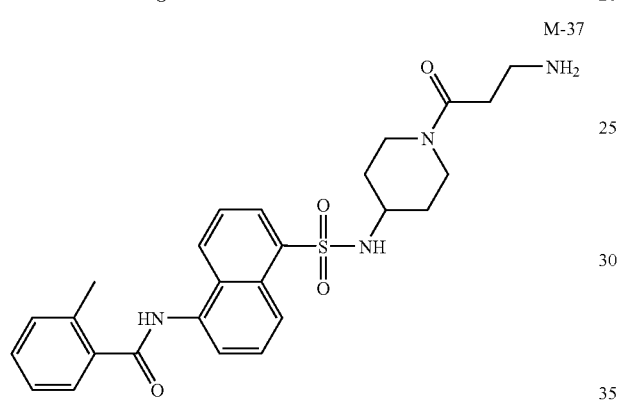
M-38
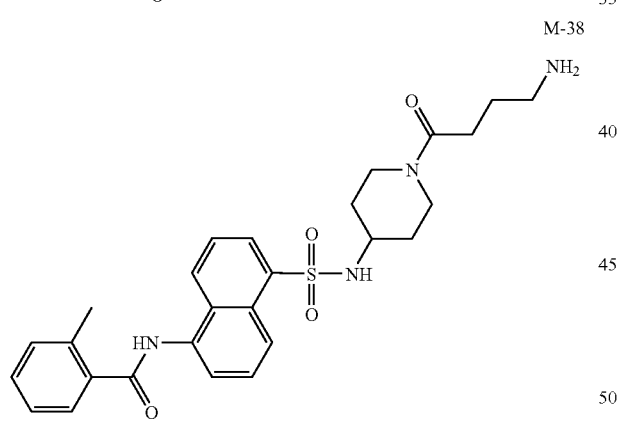
M-39
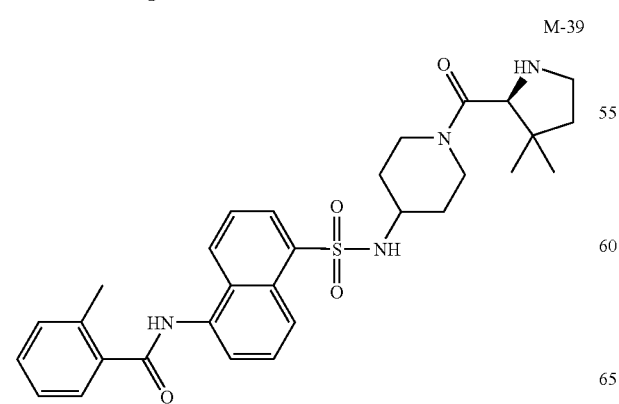
-continued
M-40
M-41
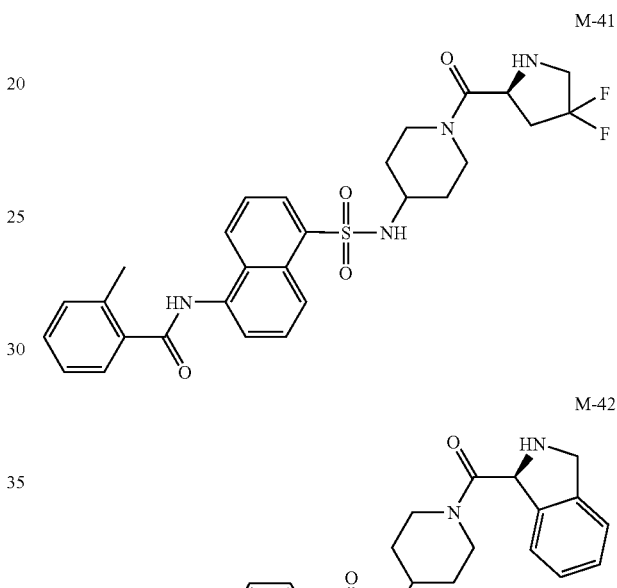
M-42
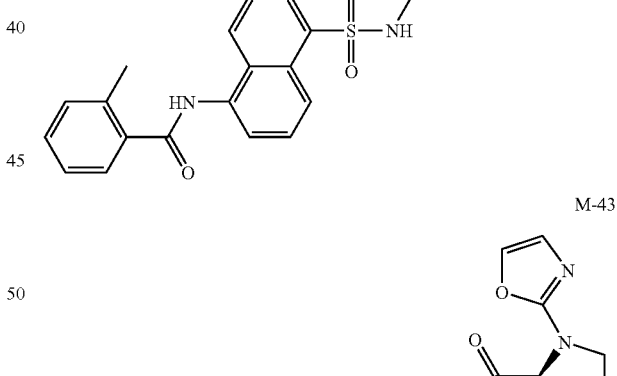
M-43
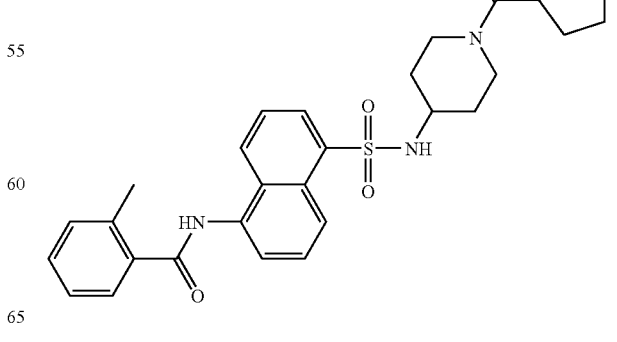

-continued

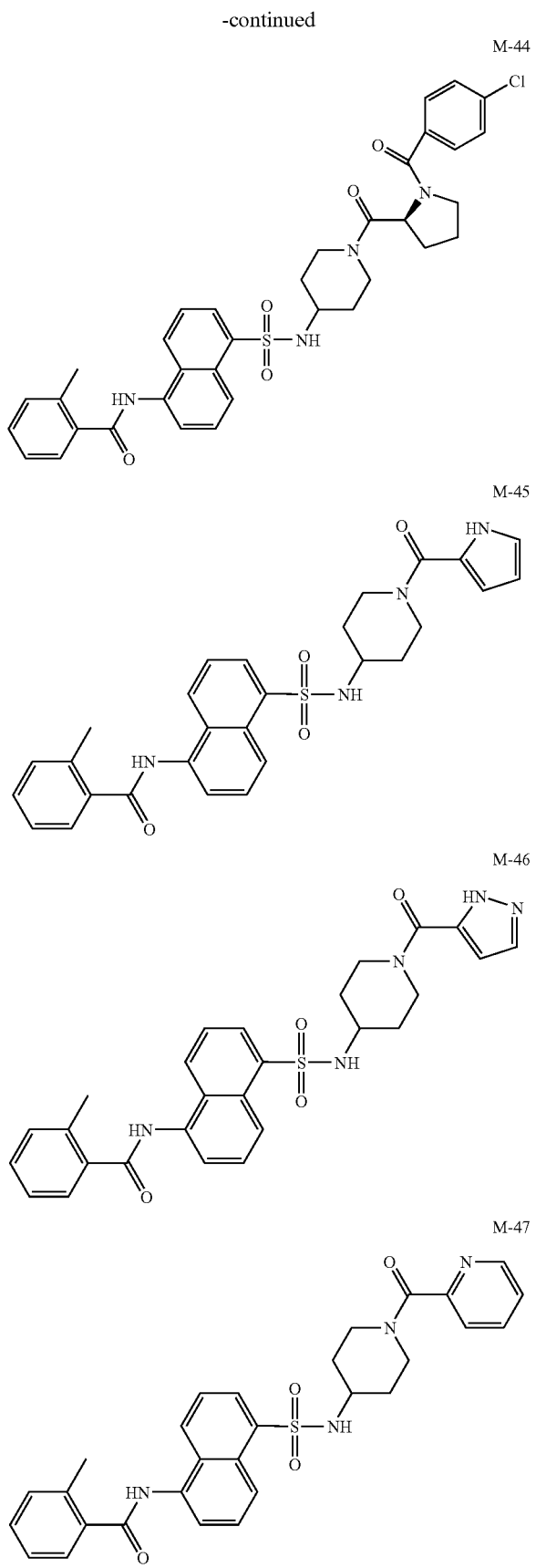

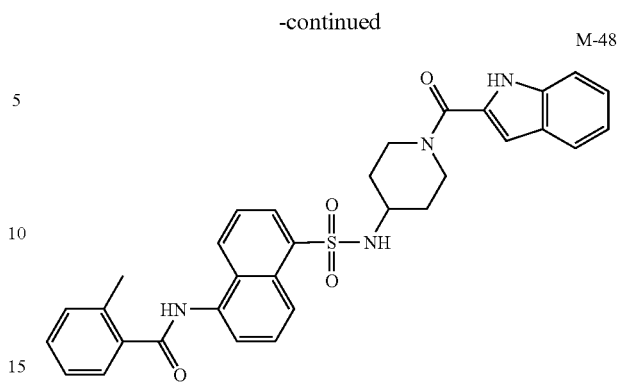

The Sulfonamides Inhibit CCR8:

This whole cell binding screen evaluates the ability of compounds to inhibit biotinlyated human I309 binding to the cloned human CCR8 receptor stably expressed in L1.2 cells. Human CCR8 gene was amplified by PCR using PFU polymerase under standard conditions from human genomic DNA purchased from Stratagene. The PCR primers used were:

The 5' and 3' primers contained flanking enzyme sites (Bam Hi and Not 1,respectively), which were used to subclone the gene into pcDNA3.1. The vector containing the CCR8 gene was sequenced by manual sequencing and matched to the reported hCCR8 sequence. The CCR8 vector was then transfected into L1.2 cells (murine pre-B cells) by electroporation. Positive clones were selected by functional chemotaxis and binding to the ligand I309.

Compounds were screened using the FMAT™ 8100 HTS System (purchased from Applied Biosystems).

A suspension was prepared of L1.2/hCCR8 cells at 4.0× $10^5$ cells/mL in a binding buffer (Buffer consisting of Hanks Balanced Salt Solution (without phenol red), 10 mM HEPES, 0.1% Fatty Acid Free BSA, 0.02% Sodium Azide). A solution of 0.375 nM of Human I-309 (Biotinylated at the C-terminus of the ligand after an additional lysine residue using the Applied Biosystems 433 peptide synthesizer) and 0.375 nM of mouse Cy-5 Mab-α-Biotin (Jackson ImmunoResearch Laboratories, Inc., Code Number 200-172-096) was prepared in binding buffer immediately prior to the assay.

Dilution series of 10 mM stock concentrations of the test compounds were prepared in DMSO and further diluted into binding buffer defined above) to three times the final assay concentration.

10 point concentration response curve is constructed for each compound, starting at 10 µM (final assay concentration in Binding Buffer). 25 µl of each concentration of test were transferred into the appropriate wells of a 384 plate. 25 µl of cold 100 nM I-309 (R and D Systems: Catalog Number 272-I/CF) were then transferred into empty wells to serve as a control for non-specific binding. 25 µl of the 0.375 nM Biotinylated Human I-309/0.375nM Cy5-α-Biotin solution were then transferred into each well of the same 384 well plate, followed by addition of 25 µl of the resuspended cell solution into each well. The components were mixed in wells by covering the plate with aluminum foil and rotating for 0.5 hours. The plates was allowed to incubate at room temperature for approximately 1-2 hours and then read on FMAT™ 8100 HTS System (PMT=490/518 or 537/568, Set threshold=1SD MAT). Average fluorescence reported for each concentration was normalized to percent inhibition based on negative (no inhibitor) and positive (100 nM excess unlabeled I309 (R and D Systems)) controls.

TABLE 1

$K_i$ of compounds to inhibit I-309 binding to CCR8 (μM)

| Cmpd. No. | $K_i$, μM |
|---|---|
| A-1 | <0.5 |
| A-2 | <30 |
| A-3 | <0.5 |
| A-7 | <1 |
| A-9 | <30 |
| A-10 | <1 |
| A-11 | <30 |
| A-13 | <30 |
| A-14 | <0.5 |
| A-16 | <30 |
| A-17 | <0.5 |
| A-18 | <0.5 |
| A-19 | <0.5 |
| A-20 | — |
| A-21 | <1 |
| A-22 | <30 |
| A-23 | <0.5 |
| A-24 | <0.5 |
| A-25 | <0.5 |
| A-26 | <0.5 |
| A-27 | <1 |
| A-28 | <0.5 |
| A-29 | <30 |
| A-30 | <30 |
| A-31 | <0.5 |
| A-32 | <0.5 |
| A-34 | <30 |
| A-35 | <0.5 |
| A-37 | <0.5 |
| A-38 | <0.5 |
| A-40 | <0.5 |
| A-41 | — |
| A-42 | — |
| A-43 | <0.5 |
| A-44 | — |
| A-45 | <30 |
| A-46 | <30 |
| A-47 | <30 |
| A-48 | <30 |
| A-49 | — |
| A-50 | — |
| B-2 | <0.5 |
| B-3 | <30 |
| B-4 | <0.5 |
| B-5 | <1 |
| B-6 | <30 |
| B-7 | <0.5 |
| B-8 | <1 |
| B-9 | <30 |
| B-10 | <30 |
| B-11 | <0.5 |
| B-12 | <0.5 |
| B-13 | <1 |
| B-14 | <0.5 |
| B-15 | <0.5 |
| B-16 | <1 |
| B-17 | <30 |
| B-18 | <30 |
| B-19 | <0.5 |
| B-20 | <1 |
| B-21 | <30 |
| B-22 | <30 |
| B-23 | <30 |
| B-24 | <0.5 |
| B-26 | <0.5 |
| B-27 | <0.5 |
| B-28 | <0.5 |
| B-33 | <30 |
| C-1 | <1 |
| C-2 | <0.5 |
| C-4 | <0.5 |
| C-5 | <0.5 |
| C-7 | <0.5 |
| C-9 | <1 |
| C-10 | <0.5 |
| C-11 | <0.5 |
| C-12 | <0.5 |
| C-13 | <0.5 |
| C-14 | <0.5 |
| C-15 | <0.5 |
| C-16 | <0.5 |
| C-17 | <0.5 |
| C-18 | <0.5 |
| C-19 | <0.5 |
| C-20 | <0.5 |
| C-21 | <0.5 |
| C-22 | <0.5 |
| C-23 | <30 |
| C-24 | <0.5 |
| C-25 | <0.5 |
| C-26 | <0.5 |
| C-27 | <0.5 |
| C-28 | <1 |
| C-29 | <0.5 |
| C-30 | <0.5 |
| C-31 | <0.5 |
| C-32 | <1 |
| C-33 | <1 |
| C-34 | <0.5 |
| C-35 | <0.5 |
| C-36 | <0.5 |
| C-37 | <0.5 |
| C-38 | <0.5 |
| C-39 | <0.5 |
| C-40 | <0.5 |
| C-41 | <0.5 |
| C-42 | <0.5 |
| C-43 | <0.5 |
| C-44 | <1 |
| C-45 | <0.5 |
| C-46 | <0.5 |
| C-47 | <0.5 |
| C-48 | <0.5 |
| C-49 | <0.5 |
| C-50 | <0.5 |
| C-51 | <0.5 |
| C-52 | <0.5 |
| C-53 | <0.5 |
| C-54 | <0.5 |
| C-55 | <0.5 |
| C-56 | <0.5 |
| C-57 | <0.5 |
| C-58 | <0.5 |
| C-59 | <0.5 |
| C-60 | <0.5 |
| C-61 | — |
| C-62 | — |
| C-63 | — |
| C-64 | <0.5 |
| C-65 | <0.5 |
| C-66 | <0.5 |
| C-67 | <0.5 |
| C-68 | <30 |
| C-69 | <1 |
| C-70 | <1 |
| C-71 | <1 |
| C-72 | <1 |
| C-73 | <1 |
| C-74 | <30 |
| C-75 | <0.5 |
| C-76 | <0.5 |
| C-77 | <30 |
| C-78 | <30 |
| C-79 | <30 |
| C-80 | <0.5 |
| C-81 | <0.5 |
| C-82 | <0.5 |
| C-83 | <30 |
| C-84 | — |
| C-85 | — |

TABLE 1-continued

K<sub>i</sub> of compounds to inhibit I-309 binding to CCR8 (μM)

| Cmpd. No. | $K_i$, μM |
|---|---|
| C-86 | — |
| C-87 | — |
| C-88 | — |
| C-89 | — |
| C-90 | — |
| C-91 | — |
| C-92 | — |
| C-93 | — |
| C-94 | — |
| C-95 | — |
| C-96 | — |
| C-97 | — |
| C-98 | <1 |
| C-99 | <0.5 |
| C-100 | <0.5 |
| C-101 | <0.5 |
| C-102 | <0.5 |
| C-103 | <0.5 |
| C-104 | <0.5 |
| C-105 | <0.5 |
| C-106 | <1 |
| C-107 | <30 |
| C-108 | — |
| C-109 | <1 |
| C-110 | <0.5 |
| C-111 | <0.5 |
| C-112 | <1 |
| C-113 | <0.5 |
| C-114 | <0.5 |
| C-115 | <0.5 |
| C-116 | — |
| C-117 | — |
| C-118 | — |
| C-119 | — |
| C-120 | <0.5 |
| C-121 | <0.5 |
| C-122 | <0.5 |
| C-123 | <0.5 |
| C-124 | <0.5 |
| C-125 | <0.5 |
| C-126 | <0.5 |
| C-127 | — |
| C-128 | — |
| C-129 | — |
| C-130 | — |
| C-131 | — |
| C-132 | — |
| C-133 | — |
| C-134 | — |
| C-135 | — |
| C-136 | <0.5 |
| C-137 | <0.5 |
| C-138 | <1 |
| C-139 | <0.5 |
| C-140 | <0.5 |
| C-141 | <1 |
| C-142 | <0.5 |
| C-143 | <30 |
| C-144 | <30 |
| C-145 | <1 |
| C-146 | — |
| C-147 | <0.5 |
| C-148 | <30 |
| D-1 | <30 |
| D-2 | <30 |
| D-3 | <0.5 |
| D-4 | <0.5 |
| D-5 | <0.5 |
| D-6 | <0.5 |
| D-7 | <0.5 |
| D-8 | <0.5 |
| D-9 | <0.5 |
| D-10 | <0.5 |
| D-11 | <30 |
| D-12 | <30 |
| D-13 | <30 |
| D-14 | <0.5 |
| D-15 | <0.5 |
| D-16 | <0.5 |
| D-17 | <30 |
| D-18 | <0.5 |
| D-19 | <0.5 |
| D-20 | <0.5 |
| D-21 | <30 |
| D-22 | <30 |
| D-23 | <30 |
| D-24 | <30 |
| E-1 | <0.5 |
| E-2 | <0.5 |
| E-3 | <0.5 |
| E-4 | <1 |
| E-5 | <0.5 |
| E-6 | <0.5 |
| E-7 | <30 |
| E-8 | <0.5 |
| E-9 | <0.5 |
| E-10 | <0.5 |
| E-11 | <0.5 |
| E-12 | <0.5 |
| E-13 | <1 |
| E-14 | <1 |
| E-15 | <0.5 |
| E-16 | <0.5 |
| E-17 | <0.5 |
| E-18 | <0.5 |
| E-19 | <0.5 |
| E-20 | <0.5 |
| E-21 | <0.5 |
| E-22 | <0.5 |
| E-23 | <0.5 |
| E-24 | <1 |
| E-25 | <30 |
| E-26 | <1 |
| E-27 | <0.5 |
| E-28 | <0.5 |
| E-29 | <0.5 |
| E-30 | <0.5 |
| E-31 | <0.5 |
| E-32 | <0.5 |
| E-33 | <0.5 |
| E-34 | — |
| E-35 | — |
| E-36 | — |
| F-1 | <1 |
| F-2 | <30 |
| F-3 | <0.5 |
| F-4 | <0.5 |
| F-5 | <30 |
| F-6 | <0.5 |
| F-7 | <0.5 |
| F-8 | <0.5 |
| F-9 | <0.5 |
| F-10 | <0.5 |
| F-11 | <0.5 |
| F-12 | <0.5 |
| F-13 | <0.5 |
| F-14 | <1 |
| F-15 | <30 |
| F-16 | <30 |
| F-17 | <30 |
| F-18 | <30 |
| F-19 | <0.5 |
| F-20 | <0.5 |
| F-21 | <0.5 |
| F-22 | <0.5 |
| F-23 | <0.5 |
| F-24 | <1 |
| F-25 | <0.5 |
| F-26 | <0.5 |
| F-27 | <0.5 |

TABLE 1-continued

K$_i$ of compounds to inhibit I-309 binding to CCR8 (μM)

| Cmpd. No. | K$_i$, μM |
|---|---|
| F-28 | <0.5 |
| F-29 | — |
| F-30 | — |
| F-31 | — |
| G-1 | <0.5 |
| G-2 | <0.5 |
| G-4 | <30 |
| G-5 | <1 |
| G-6 | <1 |
| G-7 | <0.5 |
| G-8 | <0.5 |
| G-11 | <0.5 |
| G-9 | <30 |
| G-10 | <0.5 |
| G-12 | <0.5 |
| G-13 | <0.5 |
| G-14 | <0.5 |
| G-15 | <1 |
| G-16 | — |
| G-17 | — |
| G-18 | — |
| G-20 | <0.5 |
| G-21 | <0.5 |
| G-24 | <0.5 |
| G-25 | <30 |
| G-27 | <0.5 |
| G-30 | — |
| G-31 | <0.5 |
| G-32 | <0.5 |
| H-1 | <0.5 |
| H-2 | <30 |
| H-3 | <0.5 |
| H-4 | <30 |
| H-5 | <0.5 |
| H-6 | <0.5 |
| H-7 | <0.5 |
| H-8 | <0.5 |
| H-9 | <1 |
| H-10 | <0.5 |
| H-11 | <0.5 |
| H-12 | <1 |
| H-13 | <30 |
| H-14 | <0.5 |
| H-15 | <1 |
| H-16 | <0.5 |
| H-17 | <1 |
| H-18 | <0.5 |
| H-19 | <30 |
| H-20 | <1 |
| H-21 | <1 |
| H-22 | <1 |
| H-23 | — |
| H-24 | <0.5 |
| H-25 | <1 |
| H-26 | — |
| H-27 | <1 |
| H-28 | <0.5 |
| H-29 | <0.5 |
| H-30 | <0.5 |
| H-31 | <0.5 |
| H-32 | <0.5 |
| H-33 | <0.5 |
| H-34 | <0.5 |
| H-35 | <1 |
| H-36 | <0.5 |
| H-37 | <0.5 |
| H-38 | <0.5 |
| H-39 | <0.5 |
| H-40 | <0.5 |
| H-41 | <30 |
| H-45 | <0.5 |
| H-46 | <0.5 |
| H-47 | <0.5 |
| H-48 | <30 |
| H-49 | <30 |
| H-50 | <30 |
| H-51 | <30 |
| H-52 | — |
| H-53 | <30 |
| H-54 | <0.5 |
| H-55 | <30 |
| H-56 | <0.5 |
| H-57 | <1 |
| H-58 | <1 |
| H-59 | <1 |
| H-60 | <30 |
| H-61 | — |
| H-62 | — |
| H-63 | <30 |
| H-64 | <0.5 |
| H-65 | <0.5 |
| H-66 | <1 |
| H-67 | <1 |
| H-68 | <0.5 |
| H-69 | <0.5 |
| H-70 | <0.5 |
| H-71 | <0.5 |
| H-72 | <0.5 |
| H-73 | <1 |
| H-74 | <1 |
| H-75 | <1 |
| J-1 | <0.5 |
| J-2 | <0.5 |
| J-3 | <0.5 |
| J-4 | <0.5 |
| J-5 | <0.5 |
| J-6 | <0.5 |
| J-7 | <0.5 |
| J-8 | <0.5 |
| J-9 | <0.5 |
| J-10 | — |
| J-11 | — |
| J-12 | — |
| J-13 | — |
| J-14 | — |
| J-15 | — |
| J-16 | — |
| J-17 | — |
| J-18 | — |
| J-19 | — |
| J-20 | — |
| J-21 | — |
| J-22 | — |
| J-23 | — |
| J-24 | — |
| J-25 | — |
| J-26 | — |
| J-27 | — |
| J-28 | — |
| J-29 | — |
| J-30 | <0.5 |
| J-31 | <0.5 |
| J-32 | <0.5 |
| J-33 | <0.5 |
| J-34 | — |
| J-35 | — |
| J-36 | — |
| J-37 | — |
| J-38 | <0.5 |
| J-39 | <0.5 |
| J-40 | <0.5 |
| J-41 | <0.5 |
| J-42 | <0.5 |
| J-43 | <1 |
| J-44 | <0.5 |
| J-45 | <0.5 |
| J-46 | <0.5 |
| J-47 | <0.5 |
| J-48 | <0.5 |
| J-49 | <0.5 |

TABLE 1-continued

K$_i$ of compounds to inhibit I-309 binding to CCR8 (μM)

| Cmpd. No. | K$_i$, μM |
| --- | --- |
| J-50 | <0.5 |
| J-51 | <0.5 |
| J-52 | <0.5 |
| J-53 | <5.0 |
| J-54 | <5.0 |
| J-55 | <5.0 |
| J-56 | <5.0 |
| K-1 | <0.5 |
| K-2 | — |
| K-3 | — |
| K-4 | — |
| K-5 | — |
| K-6 | — |
| K-7 | — |

The invention claimed is:

1. A compound represented by structural formula (I):

$$R^2\!-\!N(X_1)\!-\!Ar\!-\!S(O)_n\!-\!N(R^3)(R^4)$$
$$R^1\!-\!(CH_2)_m\!-\!X\!-\!C(=\!Z)$$
(I)

or a pharmaceutically acceptable salt thereof, wherein:
  X$_1$ is a covalent bond, C=Z is C=O, X is a bond, m is 0, and n is 2, or
  X$_1$ is C=O, C=Z is absent, X is a bond, m is 0, and n is 2;
Ar in Formula (1) is selected from:

A-i

A-ii

R$^1$ is a substituted or unsubstituted aromatic or carbocyclic ring;
R$^2$ is —H or a C$_1$-C$_3$ alkyl group;
R$^3$ is —H;
R$^4$ is a substituted or unsubstituted piperidinyl group;
Ar is optionally substituted at any substitutable carbon or nitrogen atom with p independent occurrences of R$^6$, wherein:
  p is 0, 1, 2, or 3; and
  each occurrence of R$^6$ is independently halogen, —CN, NO$_2$, —R$^7$, or —OR$^7$, wherein each occurrence of R$^7$ is independently hydrogen or a substituted or unsubstituted C$_1$-C$_6$aliphatic group;
wherein:
  a) R$^1$ is optionally substituted at one or more substitutable aromatic or non-aromatic carbon atoms with q occurrences of R$^8$, wherein:
  q is 0, 1, 2, or 3,
  each occurrence of R$^8$ is independently halogen, —R$^{10}$, —OR$^{10}$, —SR$^{10}$, —NO$_2$, —CN, —N(R$^{11}$)$_2$, —NR$^{11}$CO$_2$R$^{10}$, —NR$^{11}$C(O)R$^{10}$, —NR$^{11}$NR$^{11}$C(O)R$^{10}$, —N(R$^{11}$)C(O)N(R$^{11}$)$_2$, —NR$^{11}$NR$^{11}$C(O)N(R$^{11}$)$_2$, —NR$^{11}$NR$^{11}$CO$_2$R$^{10}$, —C(O)C(O)R$^{10}$, —C(O)CH$_2$C(O)R$^{10}$, —CO$_2$R$^{10}$, —C(O)R$^{10}$, —C(O)N(R$^{11}$)$_2$, —OC(O)R$^{10}$, —OC(O)N(R$^{11}$)$_2$, —S(O)$_2$R$^{10}$, —SO$_2$N(R$^{11}$)$_2$, —S(O)R$_{10}$, —NR$^{11}$SO$_2$N(R$^{11}$)$_2$, —NR$^{11}$SO$_2$R$^{10}$, —C(=S)N(R$^{11}$)$_2$, —C(=NH)—N(R$^{11}$)$_2$, -V-R$^{10}$, -V-OH, -V-OR$^{10}$, -V-SH, -V-SR$^{10}$, -V-NO$_2$, -V-CN, -V-N(R$^{11}$)$_2$, -V-NR$^{11}$CO$_2$R$^{10}$, -V-NR$^{11}$C(O)R$^{10}$, -V-NR$^{11}$NR$^{11}$C(O)R$^{10}$, -V-N(R$^{11}$)C(O)N(R$^{11}$)$_2$, -V-NR$^{11}$NR$^{11}$C(O)N(R$^{11}$)$_2$, -V-NR$^{11}$NR$^{11}$CO$_2$R$^{10}$, -V-C(O)C(O)R$^{10}$, -V-C(O)CH$_2$C(O)R$^{10}$, -V-CO$_2$R$^{10}$, -V-C(O)R$^{10}$, -V-C(O)N(R$^{10}$)$_2$, -V-OC(O)R$^{10}$, -V-OC(O)N(R$^{11}$)$_2$, -V-S(O)$_2$R$^{10}$, -V-SO$_2$N(R$^{11}$)$_2$, -V-S(O)R$^{10}$, -V-NR$^{11}$SO$_2$N(R$^{11}$)$_2$, -V-NR$^{11}$SO$_2$R$^{10}$, -V-C(=S)N(R$^{11}$)$_2$ or -V-C(=NH)—N(R$^{11}$)$_2$, or two occurrences of R$^8$, taken together with the atom(s) to which they are bound form a substituted or unsubstituted cycloaliphatic or substituted or unsubstituted non-aromatic heterocyclic ring, and when R$^1$ is a non-aromatic ring, any occurrence of R$^8$ is also selected from: =O, =S, =NNHR*, =NN(R*)$_2$, =NNHC(O)R*, =NNHCO$_2$(alkyl), =NNHSO$_2$ (alkyl), or =NR*;
  V is a substituted or unsubstitutdd C$_1$-C$_6$alkylene group;
  each occurrence of R$^{10}$ is independently hydrogen or a substituted or unsubstituted aliphatic group, a substituted or unsubstituted cycloaliphatic ring, a substituted or unsubstituted non-aromatic heterocyclic ring, or a substituted or unsubstituted aromatic ring;
  each occurrence of R$^{11}$ is independently —R$^{10}$, —CO$_2$R$^{10}$, —SO$_2$R$^{10}$ or —C(O)R$^{10}$, or two occurrences of R$^{11}$, taken together with the nitrogen atom to which they are bound form a substituted or unsubstituted non-aromatic heterocyclic ring;
  each occurrence of R* is independently hydrogen, or a substituted or unsubstituted aliphatic group;
  b) R$^4$ is optionally and independently substituted at one or more substitutable non-aromatic carbon atoms with s occurrences of R$^{13}$, and at one or more substitutable nitrogen atoms with r occurrences of R$^{14}$ wherein:
  s is 0, 1, 2, or 3,
  r is 0 or 1,
  provided that the sum of s and r is not greater than 4,
  each occurrence of R$^{13}$ is independently halogen, —R$^{15}$, —OR$^{15}$, —SR$^{15}$, —NO$_2$, —CN, —N(R$^{16}$)$_2$, —NR$^{16}$CO$_2$R$^{15}$, —NR$^{16}$C(O)R$^{15}$, —NR$^{16}$NR$^{16}$C(O)R$^{15}$, —N(R$^{15}$)C(O)N(R$^{16}$)$_2$, NR$^{16}$NR$^{16}$C(O)N(R$^{16}$)$_2$, —NR$^{16}$NR$^{16}$CO$_2$R$^{15}$, —C(O)C(O)R$^{15}$, —C(O)CH$_2$C(O)R$^{15}$, —CO$_2$R$^{15}$, —C(O)R$^{15}$, —C(O)N(R$^{16}$)$_2$, —OC(O)R$^{15}$, —OC(O)N(R$^{16}$)$_2$, —S(O)$_2$R$^{15}$, —SO$_2$N(R$^{16}$)$_2$, —S(O)R$^{15}$, —NR$^{16}$SO$_2$N(R$^{16}$)$_2$, —NR$^{16}$SO$_2$R$^{15}$, —C(=S)N(R$^{16}$)$_2$, —C(=NH)—N(R$^{16}$)$_2$, -W-R$^{15}$, -W-OH, -W-OR$^{15}$, -W-SH, -W-SR$^{15}$, -W-NO$_2$, -W-CN, -W-N $(R^{16})_2$, -W-NR$^{16}$CO$_2$R$^{15}$, -W-NR$^{16}$C(O)R$^{15}$, -W-NR$^{16}$NR$^{16}$C(O)R$^{15}$, -W-N(R$^{16}$)C(O)N(R$^{16}$)$_2$, -W-NR$^{16}$NR$^{16}$C(O)N(R$^{16}$)$_2$, -W-NR$^{16}$NR$^{16}$CO$_2$R$^{15}$, -W-C(O)C(O)R$^{15}$, -W-C(O)CH$_2$C(O)R$^{15}$, -W-CO$_2$R$^{15}$, -W-C(O)R$^{15}$, -W-C(O)N(R$^{16}$)$_2$, -W-OC(O)R$^{15}$, -W-OC(O)N(R$^{16}$)$_2$, -W-S(O)$_2$R$^{15}$, -W-SO$_2$N(R$^{16}$)$_2$, -W-S(O)R$^{15}$, -W-NR$^{16}$SO$_2$N(R$^{16}$)$_2$, -W-NR$^{16}$SO$_2$R$^{15}$, -W-C(=S)N(R$^{16}$)$_2$, or -W-C(=NH)—N(R$^{16}$)$_2$, or two occurrences of R$^{13}$, taken together with the atom(s) to which they are bound form a substituted or unsubstituted cycloaliphatic or substituted or unsubstituted non-aromatic heterocyclic ring, and when R$^4$ is a non-aromatic ring, any occurrence of R$^{13}$ is also selected from: =O, =S, =NNHR$^+$, =NN(R$^+$)$_2$, =NNHC(O)R$^+$, =NNHCO$_2$(alkyl), =NNHSO$_2$ (alkyl), or =NR$^+$;

W is a substituted or unsubstituted C$_1$-C$_6$alkylene group;

each occurrence of R$^{15}$ is independently hydrogen or substituted or unsubstituted aliphatic group, a substituted or unsubstituted cycloaliphatic, a substituted or unsubstituted non-aromatic heterocyclic ring or a substituted or unsubstituted aromatic ring, each occurrence of R$^{16}$ is independently R$^{15}$, —CO$_2$R$^{15}$, —SO$_2$R$^{15}$ or —C(O)R$^{15}$, or two occurrences of R$^{16}$, taken together with the nitrogen atom, form a substituted or unsubstituted non-aromatic heterocyclic ring;

each occurrence of R$^+$ is independently hydrogen, or a substituted or unsubstituted aliphatic group; and each occurrence of R$^{14}$ is independently —R$^{17}$, -L-N(R$^{17}$)$_2$, —C(O)R$^{17}$, —C(O)-L-R$^{17}$, -L-C(O)R$^7$, —CO$_2$R$^{17}$, -L-CO$_2$R$^{17}$, —C(O)C(O)R$^{17}$, -L-C(O)C(O)R$^{17}$, —C(O)-L-C(O)R$^{17}$, —SO$_2$R$^{17}$, L-SO$_2$R$^{17}$, —SO$_2$N(R$^{17}$)$_2$, -L-SO$_2$N(R$^{17}$)$_2$, —C(=S)N(R$^{17}$)$_2$, —C(=NH)—N(R$^{17}$)$_2$, L-NR$^{17}$SO$_2$R$^{17}$, —C(O)—N(R$^{17}$)$_2$, -L-C(O)—N(R$^{17}$)$_2$, —C(O)-L-N(R$^{17}$)$_2$ or —C(O)-L-OR$^{17}$;

wherein L is a substituted or unsubstituted C$_1$-C$_6$alkylene group; and each occurrence of R$^{17}$ is independently hydrogen, a substituted or unsubstituted group selected from an aliphatic, aromatic, cycloaliphatic, or non-aromatic heterocyclic group, or two occurrences of R$^{17}$, taken together with the nitrogen atom, form a substituted or unsubstituted non-aromatic heterocyclic ring.

2. The compound of claim 1, wherein R$^1$ is a substituted or unsubstituted ring selected from:

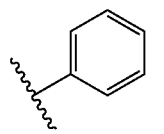

i

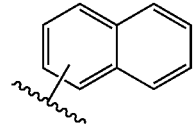

xxiii

-continued

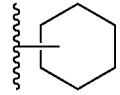

xL

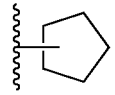

xLvi

xLvii

xLviii

3. The compound of claim 2, wherein R$^1$ is a substituted or unsubstituted phenyl (i).

4. The compound of claim 2, wherein q is 0, 1, or 2 and each occurrence of R$^8$, when present is halogen, —CN, —NO$_2$, —C$_1$-C$_6$alkyl, —OH, —O(C$_1$-C$_6$alkyl), —NH$_2$, —NH(C$_1$-C$_6$alkyl), —N(C$_1$-C$_6$alkyl)$_2$, —SH, —S(C$_1$-C$_6$alkyl), wherein C$_1$-C$_6$alkyl is substituted or unsubstituted.

5. The compound of claim 2, wherein q is 0, 1, or 2 and each occurrence of R$^8$, when present is —Cl, —F, —Br, —CH$_3$, —CH$_2$CH$_3$, —CH$_2$CH$_2$CH$_3$, —OCH$_3$, —OCH$_2$CH$_3$, —OCH$_2$CH$_2$CH$_3$, —CF$_3$, —OCF$_3$, —NO$_2$, or —CN.

6. The compound of claim 2, wherein q is 0.

7. The compound of claim 2, wherein when R$^1$ is phenyl, q is 1 and R$^8$ is substituted in the ortho position of the phenyl ring.

8. The compound of claim 7, wherein R$^8$ is C$_1$-C$_3$alkyl, halogen, or —CN.

9. The compound of claim 2, wherein R$^1$ is phenyl, q is 2 and R$^8$ is substituted at the ortho and meta positions of the phenyl ring.

10. The compound of claim 9, wherein each occurrence of R$^8$ is independently C$_1$-C$_3$alkyl, halogen, or —CN.

11. The compound of claim 1, wherein R$^4$ is a ring selected from:

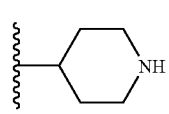

f-i

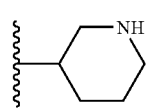

f-ii wherein R$^4$ is substituted at one or more substitutable non-aromatic carbon atoms with s occurrences of R$^{13}$, and at one or more substitutable nitrogen atoms with r occurrences of R$^{14}$.

12. The compound of claim 11, wherein s is 0, 1, or 2, and each occurrence of R$^{13}$ is halogen, —R$^{15}$, —COR$^{15}$, —CO$_2$H, or —CO$_2$R$^{15}$, wherein R$^{15}$ is phenyl or a C$_1$-C$_4$alkyl group optionally substituted with halogen, —OH, O(C$_{1-3}$alkyl), —SH, —S(C$_1$-C$_3$alkyl), NH$_2$, NH(C$_1$-C$_3$alkyl), or —N(C$_1$-C$_3$alkyl)$_2$.

13. The compound of claim 11, wherein s is 0, 1, or 2, and each occurrence of $R^{13}$ is —F, —Cl, —Br, phenyl, —$CH_3$, —$OCH_3$, —$CH_2CH_3$, —$CH(CH_3)_2$, —$CH_2CH(CH_3)_2$, —$OCH_2CH_3$, —$CO_2H$, $CO_2CH_3$, —$CO_2CH_2CH_3$, —OH, —$CH_2OH$, —$CH_2CH_2OH$, or —$CONH_2$, or two occurrences of $R^{13}$, taken together, form a fused 5- or 6-membered cycloaliphatic ring.

14. The compound of claim 11, wherein $R^4$ is a piperidin-4-yl or piperidin-3-yl, that is substituted at one or more substitutable carbon atoms with 1 or 2 occurrences of $R^{13}$, wherein $R^{13}$ is —$CH_3$, —$CH_2CH_3$, —$CH_2CH(CH_3)_2$, —$CH(CH_3)_2$, $CO_2CH_2CH_3$, —$CH_2OH$, or $CONH_2$ or two occurrences of $R^{13}$, taken together, form a fused 5- or 6-membered cycloaliphatic ring.

15. The compound of claim 11, wherein $R^4$ is a piperidinyl-4-yl ring substituted at one or more carbon atoms and has one of the following structures:

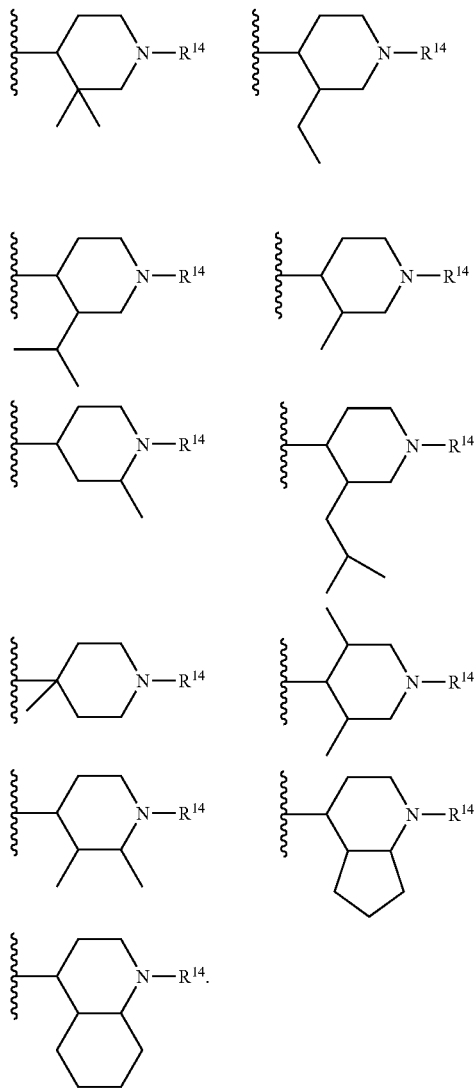

16. The compound of claim 11, wherein $R^4$ is a piperidinyl-4-yl group substituted at one or more carbon atoms and has one of the following structures:

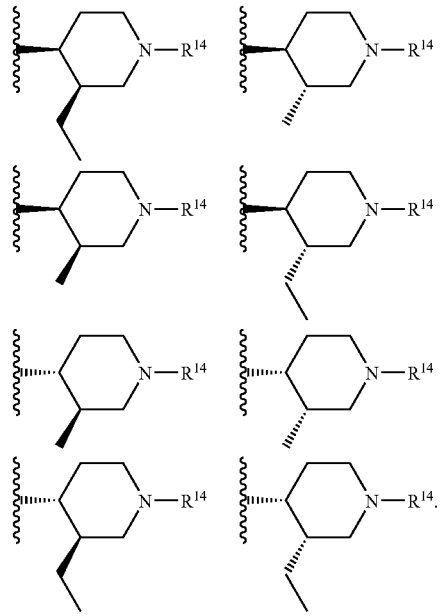

17. The compound of claim 11, wherein L is a substituted or unsubstituted $C_1$-$C_4$alkylene chain.

18. The compound of claim 11, wherein L is —$(CH_2)_x$—$(CR^{17a}R^{17b})_y$—, wherein x is 0, 1, 2, 3, or 4, and y is 0 or 1, provided that the sum of x and y is at least 1, and wherein each occurrence of $R^{17a}$ and $R^{17b}$ is independently hydrogen, substituted or unsubstituted $C_1$-$C_6$alkyl, substituted or unsubstituted Cy, substituted or unsubstituted —($C_1$-$C_6$alkyl)Cy, where Cy is a ring selected from: substituted or unsubstituted $C_3$-$C_6$cycloalkyl, a substituted or unsubstituted 5- or 6-membered heterocyclic ring, a substituted or unsubstituted 5- or 6-membered aromatic ring, or $R^{17a}$ and $R^{17b}$ taken together form a substituted or unsubstituted $C_3$-$C_6$spiro cycloalkyl ring.

19. The compound of claim 18, wherein $R^{17a}$ and $R^{17b}$ are each independently substituted with up to three occurrences of $R^{17c}$, where $R^{17c}$ is halogen, —CN, —$NO_2$, —OH, —O($C_1$-$C_6$alkyl), —SH, —S($C_1$-$C_6$alkyl), —$NH_2$, —NH($C_1$-$C_6$alkyl), —N($C_1$-$C_6$alkyl)$_2$, —CO($C_1$-$C_6$alkyl), —COOH, —COO($C_1$-$C_6$alkyl), —$CONH_2$, —CONH($C_1$-$C_6$alkyl), —CON($C_1$-$C_6$alkyl)$_2$, —NHCO($C_1$-$C_6$alkyl), —NHSO$_2$($C_1$-$C_6$alkyl), —SO$_2$NH$_2$, —SO$_2$NH($C_1$-$C_6$alkyl).

20. The compound of claim 19, wherein one of $R^{17a}$ or $R^{17b}$ is hydrogen and the other is substituted or unsubstituted $C_1$-$C_4$alkyl, or a substituted or unsubstituted ring selected from phenyl, cyclohexyl, imidazolyl, thiazolyl, oxazolyl, pyrrolyl, pyrazolyl, thiophene, furyl, —($C_1$-$C_3$alkyl)phenyl, —($C_1$-$C_3$alkyl)cyclohexyl, —($C_1$-$C_3$alkyl)imidazolyl, —($C_1$-$C_3$alkyl)thiazolyl, —($C_1$-$C_3$alkyl)oxazolyl, —($C_1$-$C_3$alkyl)pyrrolyl, —($C_1$-$C_3$alkyl)pyrazolyl, —($C_1$-$C_3$alkyl) thiophene, or —($C_1$-$C_3$alkyl)furyl.

21. The compound of claim 18, wherein x is 0 or 1 and y is 1, or x is 0 and y is 1.

22. The compound of claim 18, wherein $R^{14}$ is —C(O)—$(CH_2)_x$—$(CR^{17a}R^{17b})_y$$R^{17}$, —C(O)—$(CH_2)_x$—$(CR^{17a}R^{17b})_y$N($R^{17})_2$, —C(O)—$(CH_2)_x$—$(CR^{17a}R^{17b})_y$OR$^{17}$, —C(O)—$(CH_2)_x$—$(CR^{17a}R^{17b})_y$COOR$^{17}$, or —C(O)—$(CH_2)_x$—$(CR^{17a}R^{17b})_y$COR$^{17}$.

23. The compound of claim 11, wherein each occurrence of $R^{17}$ is independently hydrogen, substituted or unsubstituted $C_1$-$C_6$alkyl, or a substituted or unsubstituted ring selected from:
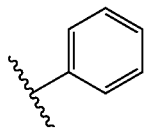
w
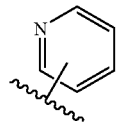
x
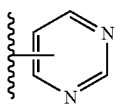
y
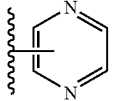
z
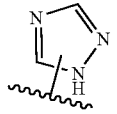
aa
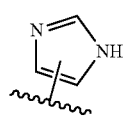
bb
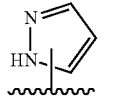
cc
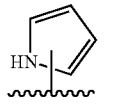
dd
ee
ff
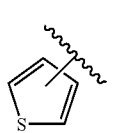
gg
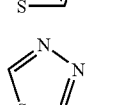
hh
-continued
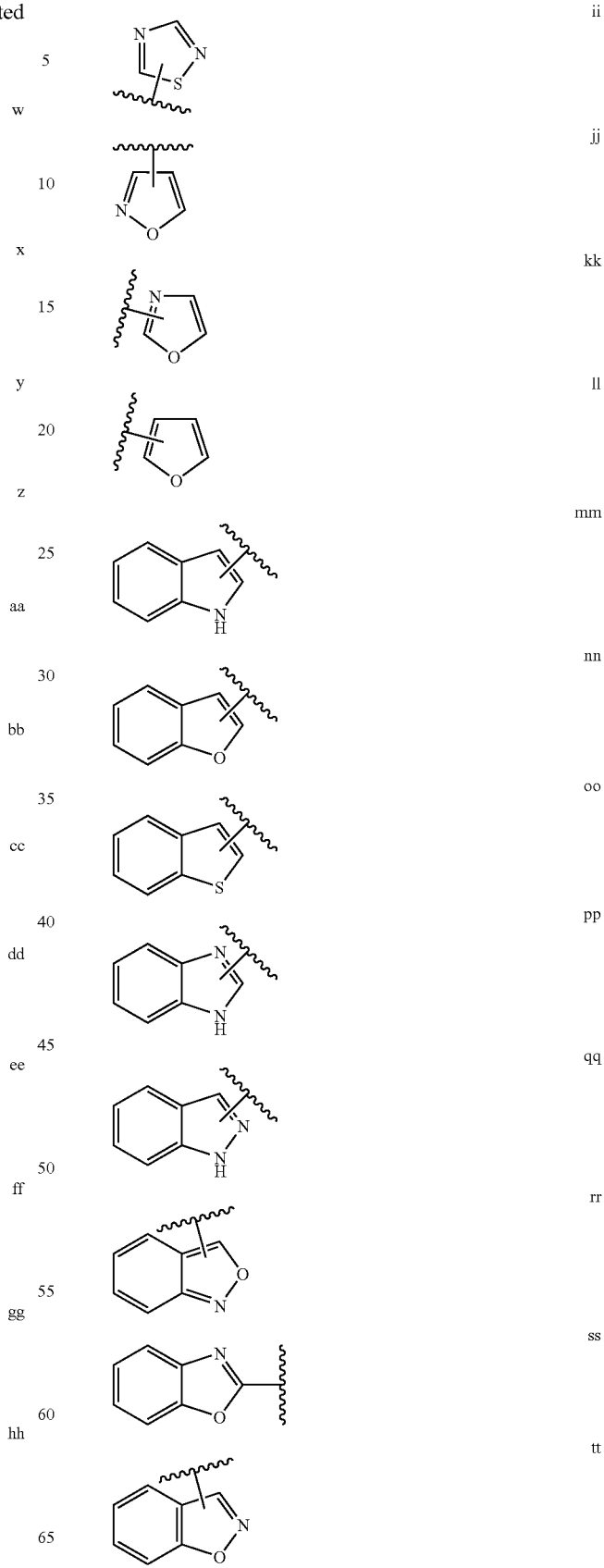

-continued

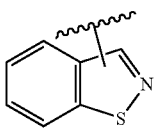

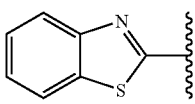

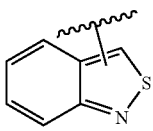

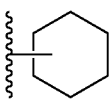

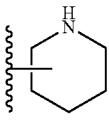

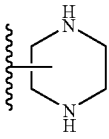

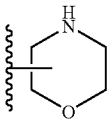

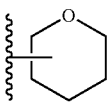

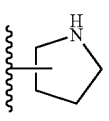

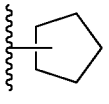

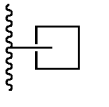

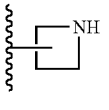

-continued uu

vv ww xx yy zz aaa bbb ccc wherein one or more substitutable carbon atoms of $R^{17}$ are substituted with w occurrences of $R^{18}$, and one or more substitutable nitrogen atoms are substituted with z occurrences of $R^{19}$, wherein w is 0, 1, 2, or 3, z is 0, 1, or 2, $R^{18}$ is halogen, —CN, —NO$_2$, —$R^{20}$, —OR$^{20}$, —SR 2, —N(R$^{20}$)$_2$, —COR$^{20}$, —COOR$^{20}$, —NHCOR$^{20}$, —CON(R$^{20}$)$_2$, —SO$_2$R$^{20}$, —SO$_2$N(R$^{20}$)$_2$, —NHSO$_2$R$^{20}$, and $R^{19}$ is —R$^{20}$, —COR$^{20}$, —COOR$^{20}$, —CON(R$^{20}$)$_2$, —SO$_2$R$^{20}$, —SO$_2$N(R$^2$)$_2$, wherein each occurrence of $R^{20}$ is hydrogen, substituted or unsubstituted C$_1$-C$_6$aliphatic, or is a substituted or unsubstituted ring selected from an aromatic or non-aromatic ring, or two occurrences of $R^{20}$, taken together with the atom(s) to which they are bound form a substituted or unsubstituted fused or spiro aromatic or non-aromatic 5- or 6-membered ring.

24. The compound of claim 23, wherein w is 0, 1, or 2, and each occurrence of $R^{18}$, when present, is halogen, —CN, —NO$_2$, —R$^{20}$, —OR$^{20}$, and z is 0 or 1 and $R^{19}$ is —R$^{20}$ or —COR$^{20}$, wherein each occurrence of $R^{20}$ is independently hydrogen, substituted or unsubstituted C$_1$-C$_4$alkyl, or is a substituted or unsubstituted monocyclic 5- or 6-membered aromatic or non-aromatic ring optionally having 0-3 heteroatoms selected from nitrogen, oxygen, or sulfur, or two occurrences of $R^{20}$, taken together with the atoms to which they are bound form a substituted or unsubstituted 5- or 6-membered fused aromatic or nonaromatic ring.

25. The compound of claim 23, wherein w is 0, 1, or 2, and each occurrence of $R^{18}$, when present, is —CN, —CH$_3$, —CF$_3$, —CH$_2$CH$_3$, —CH$_2$CH$_2$CH$_3$, —CH(CH$_3$)$_2$, —CH$_2$CH(CH$_3$)$_2$, —OH, —OCH$_3$, —OCF$_3$, —OCH$_2$CH$_3$; phenyl, fused phenyl, —F, —Br, or —Cl, and z is 0 or 1 and $R^{18}$ is —CH$_3$, —CH$_2$CH$_3$, —CH$_2$CH$_2$CH$_3$, —CH(CH$_3$)$_2$, —CH$_2$CH$_2$CH$_2$CH$_3$, substituted or unsubstituted phenyl, —COCH$_3$, —COCH$_2$CH$_3$, —CO(substituted or unsubstituted phenyl), isoxazolyl, thiazolyl, pyrrolyl, or pyrazolyl.

26. The compound of claim 1, wherein the compound has one of Structural formulas (XLIV), (XLV), (XLVI), or (XLVII):

ddd eee fff ggg

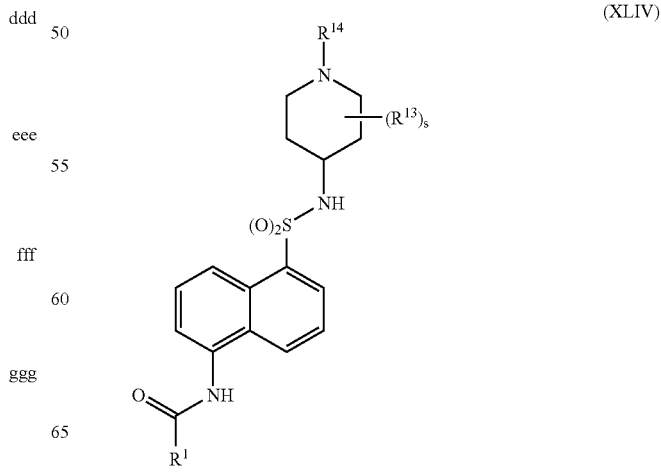

(XLIV)

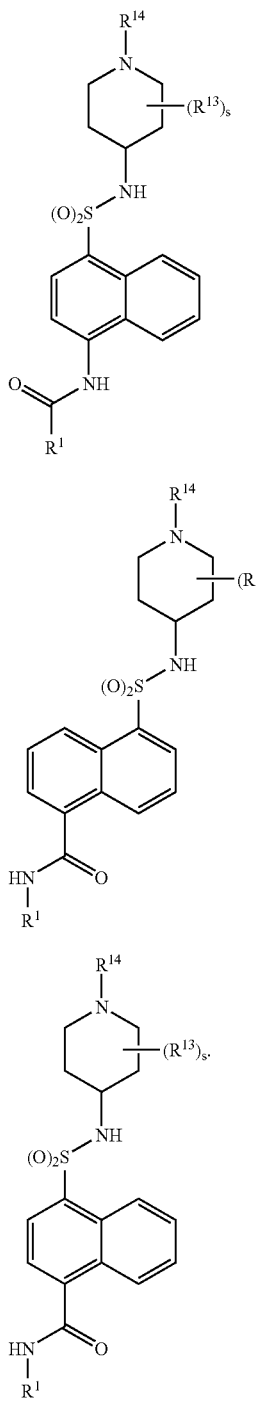

(XLV)

(XLVI)

(XLVII)

27. The compound of claim 26 wherein:

a) $R^1$ is substituted or unsubstituted phenyl (i), cyclohexyl (xL), cyclopentyl (xLvi), cyclobutyl (xLvii), or cyclopropyl (xLviii), wherein q is 0, 1, or 2 and each occurrence of $R^8$, when present is halogen, —CN, —NO$_2$, —C$_1$-C$_6$alkyl, —OH, -O(C$_1$-C$_6$alkyl), —NH$_2$, —NH(C$_1$-C$_6$alkyl), —N(C$_1$-C$_6$alkyl)$_2$, —SH, —S(C$_1$-C$_6$alkyl), wherein C$_1$-C$_6$alkyl is substituted or unsubstituted; and b) s is 0 and the piperidin-4-yl group is not substituted with $R^3$, or s is 1 or 2 and piperidin-4-yl group has one of the following structures:

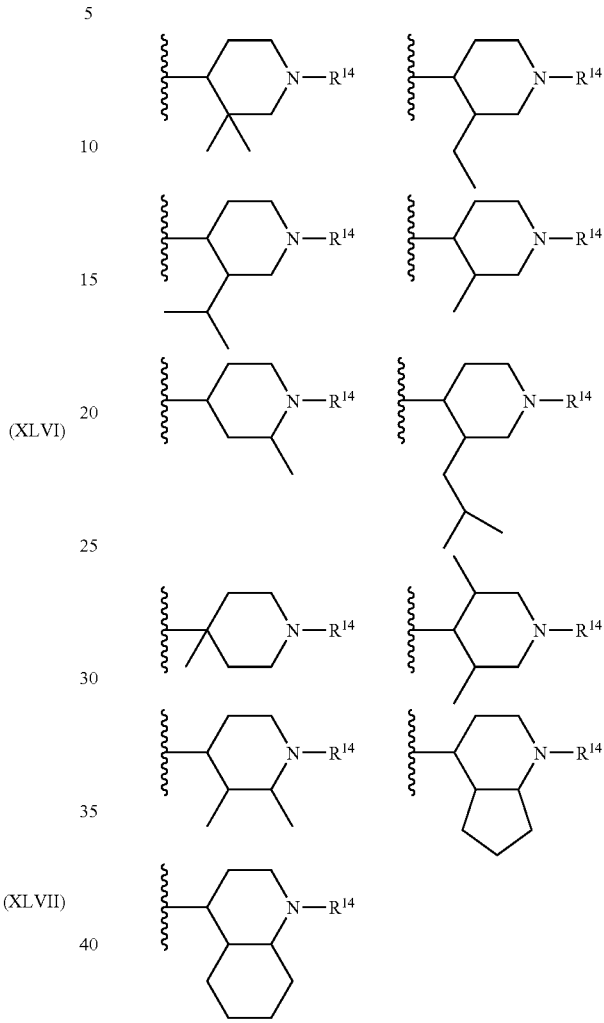

c) $R^{14}$ is —COR$^{17}$, —C(O)—(CH$_2$)$_x$—(CR$^{17a}$R$^{17b}$)$_y$R$^{17}$, —C(O)—(CH$_2$)$_x$—(CR$^{17a}$R$^{17b}$)$_y$N(R$^{17}$)$_2$, —C(O)N(R$^{17}$)$_2$, or —C(O)OR$^{17}$, and x is 0 or 1, and y is 0 or 1; $R^{17a}$ or $R^{17b}$ are each independently selected from hydrogen, substituted or unsubstituted C$_1$-C$_4$alkyl, or a substituted or unsubstituted ring selected from phenyl, cyclohexyl, imidazolyl, thiazolyl, oxazolyl, pyrrolyl, pyrazolyl, thiophene, furyl, —(C$_1$-C$_3$alkyl)phenyl, —(C$_1$-C$_3$alkyl)cyclohexyl, —(C$_1$-C$_3$alkyl)imidazolyl, —(C$_1$-C$_3$alkyl)thiazolyl, —(C$_1$-C$_3$alkyl)oxazolyl, —(C$_1$-C$_3$alkyl)pyrrolyl, —(C$_1$-C$_3$alkyl)pyrazolyl, —(C$_1$-C$_3$alkyl)thiophene, or —(C$_1$-C$_3$alkyl)furyl, wherein $R^{17a}$ and $R^{17b}$ are optionally substituted with up to three occurrences of $R^{17c}$, where $R^{17c}$ is halogen, —CN, —NO$_2$, —OH, —O(C$_1$-C$_6$alkyl), —SH, —S(C$_1$-C$_6$alkyl), —NH$_2$, —NH(C$_1$-C$_6$alkyl), —N(C$_1$-C$_6$alkyl)$_2$, —CO(C$_1$-C$_6$alkyl), —COOH, —COO(C$_1$-C$_6$alkyl), —CONH$_2$, —CONH(C$_1$-C$_6$alkyl), —CON(C$_1$-C$_6$alkyl)$_2$, —NHCO(C$_1$-C$_6$alkyl), —NHSO$_2$(C$_1$-C$_6$alkyl), —SO$_2$NH$_2$, —SO$_2$NH(C$_1$-C$_6$alkyl);

$R^{17}$ is hydrogen, $C_1$-$C_4$alkyl, or is a ring selected from:

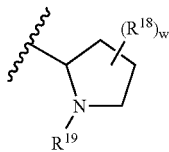 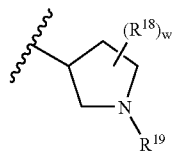

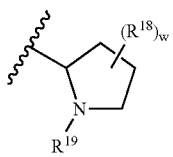 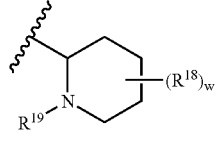

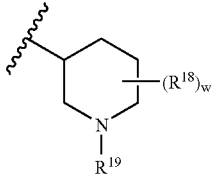 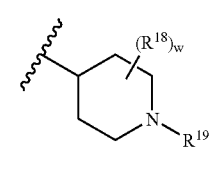

w is 0, 1, or 2, and each occurrence of $R^{18}$, when present, is N, —$CH_3$, —$CF_3$, —$CH_2CH_3$, —$CH_2CH_2CH_3$, —$CH(CH_3)_2$, —$CH_2CH(CH_3)_2$, —OH, —$OCH_3$, —$OCF_3$, —$OCH_2CH_3$, phenyl, fused phenyl, —F, —Br, or —Cl, and z is 0 or 1 and $R^{19}$ is —$CH_3$, —$CH_2CH_3$, —$CH_2CH_2CH_3$, —$CH(CH_3)_2$, —$CH_2CH_2CH_2CH_3$, substituted or unsubstituted phenyl, —$COCH_3$, —$COCH_2CH_3$, —CO(substituted or unsubstituted phenyl), or a substituted or unsubstituted ring selected from isoxazolyl, thiazolyl, pyrrolyl, or pyrazolyl.

28. The compound of claim 27, wherein $R^1$ is substituted or unsubstituted phenyl.

29. The compound of claim 27, wherein $R^1$ is phenyl, q is 1 and $R^8$ is $C_1$-$C_3$alkyl, halogen, or —CN and is substituted in the ortho position of the phenyl ring.

30. The compound of claim 27, wherein $R^1$ is phenyl, q is 2 and each occurrence of $R^8$ is $C_1$-$C_3$alkyl, halogen, or —CN and is substituted at the ortho and meta positions of the phenyl ring.

31. The compound of claim 27, wherein the piperidinyl-4-yl group is substituted at one carbon atom with —$CH_3$ or —$CH_2CH_3$ and has one of the following structures:

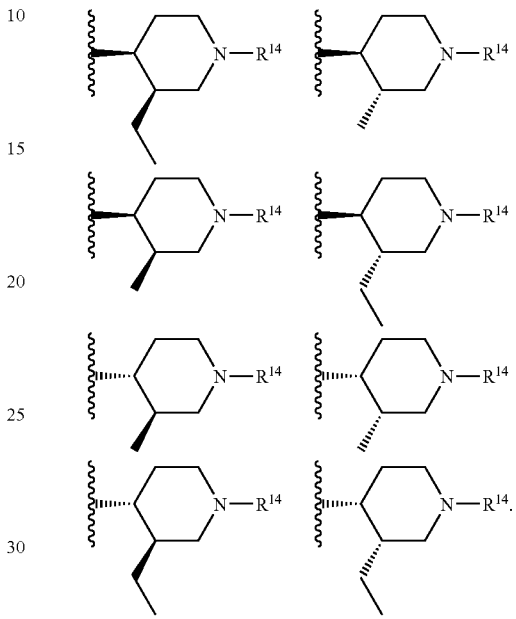

32. A new pharmaceutical composition comprising a pharmaceutically acceptable carrier or diluent and the compound of claim 1 or a pharmaceutically acceptable salt thereof.

\* \* \* \* \*